(12) United States Patent
Bakthavatchalam et al.

(10) Patent No.: US 9,969,687 B2
(45) Date of Patent: May 15, 2018

(54) COMPOUNDS USEFUL AS CCR9 MODULATORS

(71) Applicant: Norgine B.V., Amsterdam Zuid-Ost (NL)

(72) Inventors: Rajagopal Bakthavatchalam, Bangalore (IN); Manas Kumar Basu, Ghaziabad (IN); Ajit Kumar Behera, Dist-nayagarh (IN); Chandregowda Venkateshappa, Bangalore (IN); Christopher Alexander Hewson, Middlesex (GB); Sanjay Venkatachalapathi Kadnur, Bangalore (IN); Sarkis Barret Kalindjian, Middlesex (GB); Bheemashankar Kulkarni, Bangalore (IN); Rohit Saxena, Lucknow (IN); Juluri Suresh, Hyderabad (IN); Vellarkad Viswanathan, Bangalore (IN); Mohd Zainuddin, Kanpur (IN); Akila Parvathy Dharshinis, Thruneveli (IN); Rajenda Kristam, Bangalore (IN)

(73) Assignee: Norgine B.V., Amsterdam Zuid-Ost (NL)

( * ) Notice: Subject to any disclaimer, the term of this patent is extended or adjusted under 35 U.S.C. 154(b) by 0 days. days.

(21) Appl. No.: 15/107,397

(22) PCT Filed: Dec. 22, 2014

(86) PCT No.: PCT/EP2014/078944
§ 371 (c)(1),
(2) Date: Jun. 22, 2016

(87) PCT Pub. No.: WO2015/097121
PCT Pub. Date: Jul. 2, 2015

(65) Prior Publication Data
US 2017/0001959 A1 Jan. 5, 2017

(30) Foreign Application Priority Data
Dec. 23, 2013 (IN) .......................... 5984/CHE/2013

(51) Int. Cl.
| | |
|---|---|
| *C07D 209/50* | (2006.01) |
| *C07D 413/14* | (2006.01) |
| *C07D 401/04* | (2006.01) |
| *C07D 401/06* | (2006.01) |
| *C07D 403/04* | (2006.01) |
| *C07D 403/06* | (2006.01) |
| *C07D 409/04* | (2006.01) |
| *C07D 417/04* | (2006.01) |
| *C07D 405/04* | (2006.01) |
| *C07D 413/12* | (2006.01) |

(52) U.S. Cl.
CPC ......... *C07D 209/50* (2013.01); *C07D 401/04* (2013.01); *C07D 401/06* (2013.01); *C07D 403/04* (2013.01); *C07D 403/06* (2013.01); *C07D 405/04* (2013.01); *C07D 409/04* (2013.01); *C07D 413/12* (2013.01); *C07D 413/14* (2013.01); *C07D 417/04* (2013.01)

(58) Field of Classification Search
CPC .. C07D 209/50; C07D 413/12; C07D 413/14; C07D 401/06; C07D 401/04; C07D 403/04; C07D 403/06; C07D 417/04; C07D 409/04; C07D 405/04
See application file for complete search history.

(56) References Cited

U.S. PATENT DOCUMENTS

| | | |
|---|---|---|
| 5,707,997 A | 1/1998 | Shoji et al. |
| 6,191,131 B1 | 2/2001 | He et al. |
| | (Continued) | |

FOREIGN PATENT DOCUMENTS

| | | |
|---|---|---|
| EP | 0 714 898 A1 | 6/1996 |
| JP | S5340787 A | 4/1978 |
| | (Continued) | |

OTHER PUBLICATIONS

M.M. Ali et al., Synthesis of New fused Isoindolinesdione Derivatives, Al-Azhar Journal of Pharmaceutical Sciences (1994), 14, 100-7.*

(Continued)

*Primary Examiner* — Alexander R Pagano
*Assistant Examiner* — Ebenezer Sackey
(74) *Attorney, Agent, or Firm* — Wolf, Greenfield & Sacks, P.C.

(57) ABSTRACT

The present invention relates to compounds useful as CCR9 modulators, to compositions containing them, to methods of making them, and to methods of using them. In particular, the present invention relates to compounds capable of modulating the function of the CCR9 receptor by acting as partial agonists, antagonists or inverse agonists. Such compounds may be useful to treat, prevent or ameliorate a disease or condition associated with CCR9 activation, including inflammatory and immune disorder diseases or conditions such as inflammatory bowel diseases (IBD).

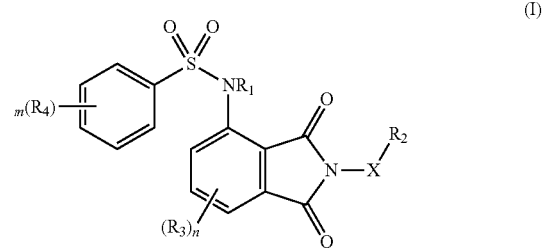

23 Claims, No Drawings

(56) References Cited

U.S. PATENT DOCUMENTS

| | | | |
|---|---|---|---|
| 6,939,885 | B2 | 9/2005 | Ungashe et al. |
| 2004/0171654 | A1 | 9/2004 | Solomon et al. |
| 2005/0227987 | A1* | 10/2005 | Vicker .............. C07D 209/48 514/249 |
| 2006/0281750 | A1 | 12/2006 | James et al. |
| 2007/0082900 | A1 | 4/2007 | Guzi et al. |
| 2008/0132511 | A1* | 6/2008 | Allison .............. C07C 311/21 514/249 |
| 2010/0029753 | A1 | 2/2010 | Anderson et al. |
| 2017/0001959 | A1 | 1/2017 | Bakthavatchalam et al. |

FOREIGN PATENT DOCUMENTS

| | | |
|---|---|---|
| WO | WO 1995/35298 A1 | 12/1995 |
| WO | WO 1998/000401 A1 | 1/1998 |
| WO | WO 2002/096873 A1 | 12/2002 |
| WO | WO 2003/095455 A2 | 11/2003 |
| WO | WO 2003/099276 A1 | 12/2003 |
| WO | WO 2003/099773 A1 | 12/2003 |
| WO | WO 2004/022054 A1 | 3/2004 |
| WO | WO 2004/022560 A1 | 3/2004 |
| WO | WO 2004/026229 A2 | 4/2004 |
| WO | WO 2004/046092 A2 | 6/2004 |
| WO | WO 2004/085384 A2 | 10/2004 |
| WO | WO 2005/112916 A2 | 12/2005 |
| WO | WO 2005/112925 A2 | 12/2005 |
| WO | WO 2005/113513 A2 | 12/2005 |
| WO | WO 2006/019768 A1 | 2/2006 |
| WO | WO 2006/135667 A1 | 12/2006 |
| WO | WO 2006/135795 A1 | 12/2006 |
| WO | WO 2007/038314 A2 | 2/2007 |
| WO | 2007029076 * | 3/2007 |
| WO | WO 2007/029076 A1 | 3/2007 |
| WO | WO 2007/071441 A1 | 6/2007 |
| WO | WO 2007/124355 A2 | 11/2007 |
| WO | 2008/010934 * | 1/2008 |
| WO | WO 2008/008374 A2 | 1/2008 |
| WO | WO 2008/008375 A2 | 1/2008 |
| WO | WO 2008/008431 A2 | 1/2008 |
| WO | WO 2008/010934 A2 | 1/2008 |
| WO | WO 2008/124518 A1 | 10/2008 |
| WO | WO 2008/134553 A1 | 11/2008 |
| WO | WO 2009/023179 A2 | 2/2009 |
| WO | WO 2009/026248 A2 | 2/2009 |
| WO | WO 2009/038847 A1 | 3/2009 |
| WO | WO 2009/070567 A1 | 6/2009 |
| WO | WO 2009/146358 A1 | 12/2009 |
| WO | 2013/130811 * | 9/2013 |

OTHER PUBLICATIONS

International Search Report and Written Opinion, dated Feb. 4, 2015, in connection with Application No. PCT/EP2014/078944.
International Preliminary Report on Patentability, dated Jul. 7, 2016, in connection with Application No. PCT/EP2014/078944.
International Search Report and Written Opinion, dated Feb. 5, 2015, in connection with Application No. PCT/EP2014/078945.
International Preliminary Report on Patentability, dated Jul. 7, 2016, in connection with Application No. PCT/EP2014/078945.
Bouma et al., The immunological and genetic basis of inflammatory bowel disease. Nat Rev Immunol. Jul. 2003;3(7):521-33.
Chu et al., Abstracts of the 63rd Annual Meeting of the American Association for the Study of Liver Diseases. Nov. 9-13, 2012. Boston, Massachusetts, USA. Abstract 1209.
Eksteen et al., Hepatic endothelial CCL25 mediates the recruitment of CCR9+ gut-homing lymphocytes to the liver in primary sclerosing cholangitis. J Exp Med. Dec. 6, 2004;200(11):1511-7. Epub Nov. 22, 2004.
Fusi et al., Expression of chemokine receptors on circulating tumor cells in patients with solid tumors. J Transl Med. Mar. 20, 2012;10:52. doi: 10.1186/1479-5876-10-52.
Gorvin et al., Sulphonamides. Part III. Sulphanilamidocarboxyamides as intestinal antiseptics; the influence of pKa and hydrogen-bonding capacity. J. Chem. Soc., 1949, 3304-3311.
Kalindijian et al., A New Series of Orally Bioavailable Chemokine Receptor 9 (CCR9) Antagonists; Possible Agents for the Treatment of Inflammatory Bowel Disease. J Med Chem. Apr. 14, 2016;59(7):3098-111. doi: 10.1021/acs.jmedchem.5b01840. Epub Mar. 17, 2016.
Kamm, Review article: chronic active disease and maintaining remission in Crohn's disease. Aliment Pharmacol Ther. Oct. 2004;20 Suppl 4:102-5.
Keshav et al., A randomized controlled trial of the efficacy and safety of CCX282-B, an orally-administered blocker of chemokine receptor CCR9, for patients with Crohn's disease. PLoS One. 2013;8(3):e60094. doi: 10.1371/journal.pone.0060094. Epub Mar. 20, 2013.
Keshav et al., Protect-1 study of intestine-specific chemokine receptor antagonist ccx282-B (traficet-EN) in Crohn's Disease. Gut, 2009, 58 (Suppl II): A468.
Koenecke et al., CCR9 and inflammatory bowel disease. Expert Opin Ther Targets. Mar. 2009;13(3):297-306. doi: 10.1517/14728220902762928.
Kunkel et al., Lymphocyte CC chemokine receptor 9 and epithelial thymus-expressed chemokine (TECK) expression distinguish the small intestinal immune compartment: Epithelial expression of tissue-specific chemokines as an organizing principle in regional immunity. J Exp Med. Sep. 4, 2000;192(5):761-8.
Nakamoto et al., CCR9+ macrophages are required for acute liver inflammation in mouse models of hepatitis. Gastroenterology. Feb. 2012;142(2):366-76. doi: 10.1053/j.gastro.2011.10.039. Epub Nov. 10, 2011.
Papadakis et al., CCR9-positive lymphocytes and thymus-expressed chemokine distinguish small bowel from colonic Crohn's disease. Gastroenterology. Aug. 2001;121(2):246-54.
Papadakis et al., The role of thymus-expressed chemokine and its receptor CCR9 on lymphocytes in the regional specialization of the mucosal immune system. J Immunol. Nov. 1, 2000;165(9):5069-76.
Proudfoot et al., Anti-chemokine small molecule drugs: a promising future? Expert Opin Investig Drugs. Mar. 2010;19(3):345-55. doi: 10.1517/13543780903535867.
Qiuping et al., Selectively increased expression and functions of chemokine receptor CCR9 on CD4+ T cells from patients with T-cell lineage acute lymphocytic leukemia. Cancer Res. Oct. 1, 2003;63(19):6469-77.
Rivera-Nieves et al., Antibody blockade of CCL25/CCR9 ameliorates early but not late chronic murine ileitis. Gastroenterology. Nov. 2006;131(5):1518-29. Epub Aug. 16, 2006.
Svensson et al., Involvement of CCR9 at multiple stages of adult T lymphopoiesis. J Leukoc Biol. Jan. 2008;83(1):156-64. Epub Oct. 2, 2007.
Vinader et al., A beginner's guide to chemokines. Future Med Chem. May. 2012;4(7):845-52. doi: 10.4155/fmc.12.49.
Walters et al., Characterization of CCX282-B, an orally bioavailable antagonist of the CCR9 chemokine receptor, for treatment of inflammatory bowel disease. J Pharmacol Exp Ther. Oct. 2010;335(1):61-9. doi: 10.1124/jpet.110.169714. Epub Jul. 21, 2010.
Zaballos et al., Cutting edge: identification of the orphan chemokine receptor GPR-9-6 as CCR9, the receptor for the chemokine TECK. J Immunol. May 15, 1999;162(10):5671-5.
Zabel et al., Human G protein-coupled receptor GPR-9-6/CC chemokine receptor 9 is selectively expressed on intestinal homing T lymphocytes, mucosal lymphocytes, and thymocytes and is required for thymus-expressed chemokine-mediated chemotaxis. J Exp Med. Nov. 1, 1999;190(9):1241-56.
Bian et al., A new series of N2-substituted-5-(p-toluenesulfonylamino)phthalimide analogues as a-glucosidase inhibitors. Bioorganic & Medicinal Chemistry Letters, Apr. 2013;23(7):2022-6. https://doi.org/10.1016/j.bmcl.2013.02.011.

* cited by examiner

COMPOUNDS USEFUL AS CCR9 MODULATORS

RELATED APPLICATIONS

This application is a national stage filing under 35 U.S.C. § 371 of international PCT application, PCT/EP2014/078944, filed Dec. 22, 2014, which claims priority under 35 U.S.C. § 119(a) to Indian Patent Application No. 5984/CHE/2013, filed Dec. 23, 2013.

INTRODUCTION

The present invention relates to compounds useful as CCR9 modulators, to compositions containing them, to methods of making them, and to methods of using them. In particular, the present invention relates to compounds capable of modulating the function of the CCR9 receptor by acting as partial agonists, antagonists or inverse agonists. Such compounds may be useful to treat, prevent or ameliorate a disease or condition associated with CCR9 activation, including inflammatory and immune disorder diseases or conditions such as inflammatory bowel diseases (IBD).

BACKGROUND OF THE INVENTION

Chemokines are a family of structurally related small proteins released from a variety of different cells within the body (reviewed in Vinader et al, 2012, Future Med Chem, 4(7): 845-52). The name derives from their primary ability to induce chemotaxis and thereby attract multiple cells of the immune system to sites of inflammation or as a part of normal immune function homeostasis. Examples of the types of cells attracted by chemokines include monocytes, T and B lymphocytes, dendritic cells, natural killer cells, eosinophils, basophils and neutrophils. Chemokines, in addition to their primary role in inducing chemotaxis, are also able to cause activation of leukocytes at the site of inflammation—for example, but not limited to, causing degranulation of granulocytes, generation of super-oxide anions (oxidative burst) and up-regulation of integrins to cause extravasation. Chemokines initiate their biological activity through binding to and activation of cell surface receptors—chemokine receptors. Chemokine receptors belong to the G-coupled protein receptor (GPCR), 7-trans-membrane (7-TM) superfamily—comprising an extracellular N-terminus with 7 helical trans-membrane domains and an intracellular C-terminus. Traditionally, chemokines are considered to bind to their receptors in the 7-TM region—this binding leading to activation of the receptor and resulting in G-protein activation (and subsequent secondary messenger transmission) by the intracellular portion of the receptor.

CCR9 is a chemokine receptor shown to be expressed on circulating T lymphocytes (Zabel et al, 1999, J Exp Med, 190:1241-56) and, in contrast to the majority of human chemokine receptors, CCR9 currently has only a single ligand identified: CCL25, otherwise known as thymus-expressed chemokine (TECK) (Zabalos et al, 1999, J Immunol, 162: 5671-5). As CCL25 expression is limited to intestinal epithelium and the thymus (Kunkel et al, 2000, J Exp Med, 192(5): 761-8), this interaction has been demonstrated to be the key chemokine receptor involved in targeting of T lymphocytes to the intestine (Papadakis et al, 2000, J Immunol, 165(9): 5069-76). The infiltration of T lymphocytes into tissues has been implicated in a broad range of diseases, including, but not limited to, such diseases as asthma, rheumatoid arthritis and inflammatory bowel disease (IBD). Specific to IBD, it has been observed that CCR9+ CD4 and CD8 T lymphocytes are increased in disease alongside an increased expression of CCL25 that correlates with disease severity (Papadakis et al, 2001, Gastroenterology, 121(2): 246-54). Indeed, disruption of the CCR9/CCL25 interaction by antibody and small molecule antagonists of CCR9 has been demonstrated to be effective in preventing the inflammation observed in small animal models of IBD (Rivera-Nieves et al, 2006, Gastroenterology, 131(5): 1518-29 and Walters et al, 2010, J Pharmacol Exp Ther, 335(1):61-9). In addition to the IBD specific role for CCR9, recent data also implicates the CCR9/CCL25 axis in liver inflammation and fibrosis where increased expression of CCL25 has been observed in the inflamed liver of primary sclerosing cholangitis patients along with a concomitant increase in the numbers of CCR9+ T lymphocytes (Eksteen et al, 2004, J Exp Med, 200(11):1511-7). CCR9+ macrophages have also been observed in in vivo models of liver disease and their function proven with CCL25 neutralising antibodies and CCR9-knockout mice exhibiting a reduction in CCR9+ macrophage number, hepatitis and liver fibrosis (Nakamoto et al, 2012, Gastroenterol, 142:366-76 and Chu et al, 2012, $63^{rd}$ Annual Meeting of the American Association for the Study of Liver Diseases, abstract 1209). Therefore, modulation of the function of CCR9 represents an attractive target for the treatment of inflammatory, immune disorder and other conditions and diseases associated with CCR9 activation, including IBD and liver disease.

In addition to inflammatory conditions, there is increasing evidence for the role of CCR9 in cancer. Certain types of cancer are caused by T lymphocytes expressing CCR9. For example, in thymoma and thymic carcinoma (where cancer cells are found in the thymus), the developing T lymphocytes (thymocytes) are known to express high levels of CCR9 and CCL25 is highly expressed in the thymus itself. In the thymus, there is evidence that the CCR9/CCL25 interaction is important for thymocyte maturation (Svensson et al, 2008, J Leukoc Biol, 83(1): 156-64). In another example, T lymphocytes from acute lymphocytic leukaemia (ALL) patients express high levels of CCR9 (Qiuping et al, 2003, Cancer Res, 63(19): 6469-77). While the role for chemokine receptors is not clear in the pathogenesis of cancer, recent work has indicated that chemokine receptors, including CCR9, are important in metastasis of tumours—with a potential therapeutic role suggested for chemokine receptor antagonists (Fusi et al, 2012, J Transl Med, 10:52). Therefore, blocking the CCR9/CCL25 interaction may help to prevent or treat cancer expansion and/or metastasis.

Inflammatory bowel diseases (IBD) are chronic inflammatory disorders of the gastrointestinal tract in which tissue damage and inflammation lead to long-term, often irreversible impairment of the structure and function of the gastrointestinal tract (Bouma and Strober, 2003, Nat Rev Immunol, 3(7):521-533). Inflammatory bowel diseases may include collagenous colitis, lymphocytic colitis, ischaemic colitis, diversion colitis, Behçet's disease (also known as Behçet's syndrome), indeterminate colitis, ileitis and enteritis but Crohn's disease and ulcerative colitis are the most common forms of IBD. Crohn's disease and ulcerative colitis both involve chronic inflammation and ulceration in the intestines, the result of an abnormal immune response. Chronic and abnormal activation of the immune system leads to tissue destruction in both diseases, although ulcerative colitis is generally limited to the rectum and colon, whereas Crohn's disease (also known as regional ileitis)

extends deeper in the intestinal wall and can involve the entire digestive tract, from the mouth to the anus.

Up to one million Americans have inflammatory bowel disease, according to an estimate by the Crohn's and Colitis Foundation of America. The incidence of IBD is highest in Western countries. In North America and Europe, both ulcerative colitis and Crohn's disease have an estimated prevalence of 10-20 cases per 100,000 populations (Bouma and Strober, 2003).

The primary goal when treating a patient with IBD is to control active disease until a state of remission is obtained; the secondary goal is to maintain this state of remission (Kamm, 2004, Aliment Pharmacol Ther, 20(4):102). Most treatments for IBD are either medical or surgical (typically only used after all medical options have failed). Some of the more common drugs used to treat IBD include 5-aminosalicylic acid (5-ASA) compounds (such as sulfasalazine, mesalamine, and olsazine), immunosuppressants (such as azathioprine, 6-mercaptopurine (6-MP), cyclosporine A and methotrexate), corticosteroids (such as prednisone, methylprednisolone and budesonide), infliximab (an anti-TNFα antibody) and other biologics (such as adilumumab, certolizumab and natalizumab). None of the currently available drugs provides a cure, although they can help to control disease by suppressing destructive immune processes, promoting healing of intestinal tissues and relieving symptoms (diarrhea, abdominal pain and fever).

There is a need to develop alternative drugs for the treatment of IBD, with increased efficacy and/or improved safety profile (such as reduced side effects) and/or improved pharmacokinetic properties. Treatment of IBD includes control or amelioration of the active disease, maintenance of remission and prevention of recurrence.

Various new drugs have been in development, including the aryl sulfonamide compound N-{4-chloro-2-[(1-oxidopyridin-4-yl)carbonyl]phenyl}-4-(1,1-dimethylethyl)-benzenesulfonamide, also known as Vercirnon or GSK1605786 (CAS Registry number 698394-73-9), and Vercirnon sodium. Vercirnon was taken into Phase III clinical development for the treatment of patients with moderate-to-severe Crohn's disease. Vercirnon is the compound claimed in U.S. Pat. No. 6,939,885 (Chemocentryx) and is described as an antagonist of the CCR9 receptor. Various other aryl sulfonamide compounds have also been disclosed as CCR9 antagonists that may be useful for the treatment of CCR9-mediated diseases such as inflammatory and immune disorder conditions and diseases; for example, see the following Chemocentryx patent applications, WO2004/046092 which includes vercirnon, WO2004/085384, WO2005/112916, WO2005/112925, WO2005/113513, WO2008/008374, WO2008/008375, WO2008/008431, WO2008/010934, WO2009/038847; also WO2003/099773 (Millennium Pharmaceuticals), WO2007/071441 (Novartis) and US2010/0029753 (Pfizer).

Thus a number of CCR9-modulating compounds are known and some are being developed for medical uses (see, for example, the review of CCR9 and IBD by Koenecke and Förster, 2009, Expert Opin Ther Targets, 13 (3):297-306, or the review of CCR antagonists by Proudfoot, 2010, Expert Opin Investig Drugs, 19(3): 345-55). Different classes of compounds may have different degrees of potency and selectivity for modulating CCR9. There is a need to develop alternative CCR9 modulators with improved potency and/or beneficial activity profiles and/or beneficial selectivity profiles and/or increased efficacy and/or improved safety profiles (such as reduced side effects) and/or improved pharmacokinetic properties.

We now provide a new class of compounds that are useful as CCR9 modulators and in particular as partial agonists, antagonists or inverse agonists of CCR9. The compounds of the invention may have improved potency and/or beneficial activity profiles and/or beneficial selectivity profiles and/or increased efficacy and/or improved safety profiles (such as reduced side effects) and/or improved pharmacokinetic properties. Some of the preferred compounds may show selectivity for CCR9 over other receptors, such as other chemokine receptors.

Such compounds may be useful to treat, prevent or ameliorate a disease or condition associated with CCR9 activation, including inflammatory and immune disorder diseases or conditions such as inflammatory bowel diseases (IBD).

SUMMARY OF THE INVENTION

The present invention provides a compound of Formula (I) or a salt or solvate thereof, including a solvate of such a salt:

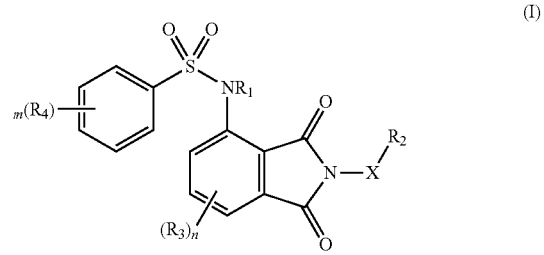

in which:

$R_1$ is selected from hydrogen, methyl, and ethyl;

X is selected from a direct bond and $(CR_5R_6)_p$;

p is 1, 2, 3, 4, or 5;

each $R_5$ is independently selected from hydrogen, methyl, and fluoro;

each $R_6$ is independently selected from hydrogen, methyl, and fluoro;

$R_2$ is selected from hydrogen, optionally substituted aryl, optionally substituted heteroaryl, $C_{3-7}$cycloalkyl, and optionally substituted $C_{3-7}$ heterocycloalkyl;

each $R_3$ is independently selected from halo, cyano (CN), $C_{1-6}$alkyl, methanesulfonyl ($SO_2CH_3$), $C_{1-6}$alkoxy, haloalkyl, haloalkoxy, and $C_{3-7}$cycloalkyl;

n is 0, 1 or 2;

each $R_4$ is $Z_{q_1}B$;

m is 0, 1, 2 or 3;

$q_1$ is 0, 1, 2, 3, 4, 5 or 6;

each Z is independently selected from $CR_7 R_8$, O, C=O, $SO_2$, and $NR_9$;

each $R_7$ is independently selected from hydrogen, methyl, ethyl, and halo;

each $R_8$ is independently selected from hydrogen, methyl, ethyl, and halo;

each $R_9$ is independently selected from hydrogen, methyl, and ethyl;

each B is independently selected from hydrogen, halo, cyano (CN), optionally substituted aryl, optionally substituted heteroaryl, optionally substituted cycloalkyl, and A;

A is

Q is selected from CH$_2$, O, NH, and NCH$_3$;
x is 0, 1, 2, 3 or 4, and y is 1, 2, 3, 4 or 5, the total of x and y being greater or equal to 1 and less than or equal to 5 (1≤x+y≤5).

It will be appreciated that the compounds of the invention may contain one or more asymmetrically substituted carbon atoms. The presence of one or more of these asymmetric centres (chiral centres) in a compound of Formula (I) can give rise to stereoisomers, and in each case the invention is to be understood to extend to all such stereoisomers, including enantiomers and diastereomers, and mixtures thereof (including racemic mixtures thereof).

Where tautomers exist in the compounds of Formula (I), we disclose all individual tautomeric forms and combinations of these as individual specific embodiments of the invention.

In addition, the invention is to be understood to extend to all isomers which are compounds with one or more isotopic substitutions. For example, H may be in any isotopic form, including $^1$H, $^2$H(D) and $^3$H(T); C may be in any isotopic form, including $^{12}$C, $^{13}$C, and $^{14}$C; O may be in any isotopic form, including $^{16}$O and $^{18}$O; and the like.

It will be appreciated that the particular groups or substituents, the number of groups or substituents, and the position of substitution in compounds of Formula (I) are selected so as to avoid sterically undesirable combinations.

When present, each of the R$_3$ and R$_4$ groups may be attached at any suitable position. An R$_3$ group may be para, meta or ortho to the sulfonamide, especially para or meta, and most preferably para. For example, when n is 1 then R$_3$ is most preferably para to the sulfonamide. An R$_4$ group may be para, meta or ortho to the sulfonamide, especially para or meta, and most preferably para. For example, when m is 1, then R$_4$ is preferably meta or para to the sulfonamide, and most preferably para to the sulfonamide; and when m is 2, then most preferably one R$_4$ group is meta to the sulfonamide and the other R$_4$ group is para to the sulfonamide.

Certain compounds of the invention may act as prodrugs, or may be converted into prodrugs by known methods, and in each case the invention is to be understood to extend to all such prodrugs.

Except where otherwise stated, throughout this specification and claims, any of the following groups present in a compound of the invention or in an intermediate used for the preparation of a compound of the invention, is as defined below:

- an alkyl group is any branched or unbranched (straight chain) hydrocarbon, and may for example contain from 1 to 7 carbon atoms, especially from 1 to 6 carbon atoms;
- a cycloalkyl group is any monocyclic saturated hydrocarbon ring structure, and may for example contain from 3 to 7 carbon atoms, especially 3, 4, 5 or 6 carbon atoms;
- a heteroalkyl group is any alkyl group wherein any one or more carbon atoms is replaced by a heteroatom independently selected from N, O, S;
- a heterocycloalkyl group is any cycloalkyl group wherein any one or more carbon atoms is replaced by a heteroatom independently selected from N, O, S;
- an aryl group is any polyunsaturated, aromatic hydrocarbon group having a single ring or multiple rings which are fused together or linked covalently; aryl groups with up to 10 carbon atoms are preferred, particularly a monocyclic aryl group having 6 carbon atoms; examples of aryl groups include phenyl, biphenyl and naphthalene;
- a heteroaryl group is any aryl group wherein any one or more ring carbon atoms is replaced by a heteroatom independently selected from N, O, S; heteroaryl groups with 5 to 10 ring atoms are preferred, particularly a monocyclic heteroaryl group having 5 or 6 ring atoms; examples of heteroaryl groups include pyridyl, pyrazolyl, pyridazinyl, pyrrolyl, oxazolyl, quinolinyl and isoquinolinyl;
- a halo group is any halogen atom, and may for example be fluorine (F), chlorine (Cl) or bromine (Br), and especially fluorine or chlorine;
- a haloalkyl group is any alkyl group substituted with one or more halogen atoms, particularly 1, 2 or 3 halogen atoms, especially fluorine or chlorine;
- an alkoxy group is any Oalkyl group, especially OC$_{1-6}$alkyl;
- a haloalkoxy group is any Ohaloalkyl group, especially OC$_{1-6}$haloalkyl.

Except where otherwise stated, throughout this specification and claims, the phrase "optionally substituted" means unsubstituted or substituted by up to three groups ("optional substituents") independently selected from OH, =O or O$^-$, NO$_2$, CF$_3$, CN, halo (such as Cl or F), CHO, CO$_2$H, C$_{3-7}$cycloalkyl, C$_{1-4}$ alkyl (such as methyl), C$_{1-4}$ alkoxy (such as —O— methyl, —O-ethyl), COC$_{1-4}$ alkyl (such as —(CO)-methyl), COC$_{1-4}$ alkoxy (such as —(CO)—O-methyl), and C$_{1-4}$ haloalkoxy.

Except where otherwise stated, throughout this specification and claims, the term "prodrug" means a compound which, upon administration to the recipient, has very low activity or is inactive in its administered state but is capable of providing (directly or indirectly) an active compound or an active metabolite thereof. A prodrug is converted within the body into its active form which has medical effects.

DETAILED DESCRIPTION OF THE INVENTION

The compounds as defined above are useful as CCR9 modulators and in particular as partial agonists, antagonists or inverse agonists of CCR9. Such compounds may be useful to treat, prevent or ameliorate a disease or condition associated with CCR9 activation, including inflammatory and immune disorder diseases or conditions. Such diseases or conditions include inflammatory bowel diseases (IBD). In particular, the compounds as defined above may be useful to treat, prevent or ameliorate Crohn's disease and/or ulcerative colitis, and most particularly Crohn's disease.

The compounds as defined above are novel. Accordingly, the present invention provides a compound of Formula (I) as defined above or a salt or solvate thereof, including a solvate of such a salt, per se. In particular, the present invention provides a compound of Formula (I) as defined above or a pharmaceutically acceptable salt or solvate thereof, including a solvate of such a salt, per se. Most particularly, the present invention provides a compound of Formula (I) or a pharmaceutically acceptable salt thereof, per se.

In order to use a compound of Formula (I) or a salt or solvate thereof for therapy, it is normally formulated in accordance with standard practice as a composition.

Thus the invention also provides a composition comprising a compound of Formula (I) or a salt or solvate thereof, including a solvate of such a salt, together with an acceptable carrier. In particular, the invention provides a pharmaceutical composition comprising a compound of Formula (I) or a salt or solvate thereof, including a solvate of such a salt, together with a pharmaceutically acceptable carrier.

The invention further provides a compound according to the invention for use in therapy, specifically, for use in the treatment, prevention or amelioration of a disease or condition associated with CCR9 activation, including inflammatory and immune disorder diseases or conditions. Such diseases or conditions include: (1) Inflammatory bowel diseases (IBD) such as Crohn's disease, ulcerative colitis, collagenous colitis, lymphocytic colitis, ischaemic colitis, diversion colitis, Behçet's disease, indeterminate colitis, ileitis and enteritis; (2) allergic diseases such as systemic anaphylaxis or hypersensitivity responses, drug allergies, insect sting allergies and food allergies; (3) immune-mediated food allergies such as Coeliac (Celiac) disease; (4) autoimmune diseases, such as rheumatoid arthritis, fibromyalagia, scleroderma, ankylosing spondylitis, juvenile RA, Still's disease, polyarticular juvenile RA, pauciarticular juvenile RA, polymyalgia rheumatica, psoriatic arthritis, osteoarthritis, polyarticular arthritis, multiple sclerosis, systemic lupus erythematosus, type I diabetes, type II diabetes, glomerulonephritis, and the like; (5) psoriasis and inflammatory dermatoses such as dermatitis, eczema, atopic dermatitis, allergic contact dermatitis, urticaria and pruritus; (6) asthma and respiratory allergic diseases such as allergic asthma, allergic rhinitis, hypersensitivity lung diseases and the like; (7) vaginitis; (8) vasculitis; (9) spondyloarthropathies; (10) scleroderma; (11) graft rejection (including allograft rejection); (12) graft-v-host disease (including both acute and chronic); (13) other diseases in which undesired inflammatory responses are to be inhibited, such as atherosclerosis, myositis, neurodegenerative diseases (such as Alzheimer's disease), encephalitis, meningitis, liver diseases (such as liver inflammation, liver fibrosis, hepatitis, NASH), nephritis, sepsis, sarcoidosis, allergic conjunctivitis, otitis, chronic obstructive pulmonary disease, sinusitis, Behçet's disease and gout; (14) cancers, such as thymoma and thymic carcinoma, and acute lymphocytic leukemia (ALL, also known as acute lymphoblastic leukemia).

In particular, the invention provides a compound according to the invention for use to treat, prevent or ameliorate Crohn's disease and/or ulcerative colitis, and most particularly Crohn's disease.

The invention further provides the use of a compound of the invention for the treatment, prevention or amelioration of diseases or conditions as mentioned above; the use of a compound of the invention for the manufacture of a medicament for the treatment, prevention or amelioration of diseases or conditions as mentioned above; and a method of treating, preventing or ameliorating a disease or condition as mentioned above in a subject, which comprises administering an effective amount of a compound or a composition according to the invention to said subject. The subject to be treated according to the present invention is typically a mammal. The mammal is generally a human but may for example be a commercially reared animal or a companion animal.

A compound of Formula (I) may also be used as an intermediate in a method to synthesise another chemical compound, including but not limited to another compound of Formula (I); as a reagent in an analytical method; as a research tool—for example, as a comparator compound in an assay, or during compound screening to assist in identifying and/or profiling a compound with similar or differing activity in the test conditions applied, or as a control in cell based, in vitro and/or in vivo test assays.

Preferred compounds of Formula (I) include those wherein any one or more of the following apply:

$R_1$ is hydrogen; and/or

X is selected from a direct bond, $CH_2$, and $CH_2CH_2$; especially X is selected from a direct bond and $CH_2$; and/or p is 1, 2, or 3; especially p is 1 or 2; more especially p is 1; and/or $R_2$ is selected from optionally substituted aryl, optionally substituted heteroaryl (particularly $C_{5-6}$ heteroaryl), and optionally substituted $C_{3-7}$ heterocycloalkyl; especially $R_2$ is selected from optionally substituted aryl and optionally substituted heteroaryl; more especially $R_2$ is selected from optionally substituted phenyl, optionally substituted pyridyl, optionally substituted thiophenyl, optionally substituted pyrazolyl, optionally substituted pyridonyl, optionally substituted pyrimidinyl, optionally substituted pyrazinyl, optionally substituted pyridazinyl, optionally substituted imidazolyl, optionally substituted thiazolyl, optionally substituted tetrazolyl, and optionally substituted 1,2,4-triazolyl, including pyridyl, thiophenyl, pyrazolyl, pyrimidinyl, imidazolyl, thiazolyl, tetrazolyl, and 1,2,4-triazolyl; most especially $R_2$ is selected from optionally substituted phenyl, optionally substituted pyridyl, optionally substituted thiophenyl, optionally substituted pyrazolyl, and optionally substituted imidazolyl; preferred optional substituents are selected from OH, =O, O$^-$, $CF_3$, CN, halo (such as Cl or F), $CO_2H$, $C_{1-4}$ alkyl, $C_{1-4}$ alkoxy, $COC_{1-4}$ alkyl (such as acetyl, $CH_3CO$), and $COC_{1-4}$ alkoxy, especially optional substituents are selected from OH, O$^-$, cyano (CN), methyl, ethyl, —O-methyl, —O-ethyl, —(CO)—O-methyl, and —(CO)—O-ethyl; most preferably $R_2$ is selected from cyanophenyl, acetylphenyl, methoxy-phenyl, pyridine N-oxide, methyl-pyridine N-oxide, methoxy-pyridine N-oxide, ethoxy pyridine N-oxide, pyridyl, methoxy-pyridyl, ethoxy-pyridyl, methyl-pyridyl, cyano-pyridyl, thiophenyl, carboxy-thiophenyl, carboxymethyl-thiophenyl, pyrazolyl, methyl-pyrazolyl, imidazolyl, and methyl-imidazolyl; particularly $R_2$ is pyridyl, methyl-pyridyl, methoxy-pyridyl, ethoxy-pyridyl, pyridine N-oxide, methyl-pyridine N-oxide, methoxy-pyridine N-oxide or ethoxy-pyridine N-oxide; and/or each $R_3$ is independently selected from halo, cyano, $C_{1-3}$ alkyl, $C_{1-3}$ alkoxy, $C_{1-3}$haloalkyl, and cyclopropyl; especially each $R_3$ is independently selected from chloro, cyano, methyl, methoxy ($CH_3O$), propoxy particularly isopropoxy (Oisopropyl), trifluoromethyl, and cyclopropyl; especially $R_3$ is chloro or cyano; most especially $R_3$ is chloro; and/or n is 0 or 1; especially n is 1; when n is 1, then the $R_3$ group is preferably para to the sulfonamide; and/or $R_4$ is $Z_{q_1}B$ and $q_1$ is 0, each B is independently selected from halo, CN, optionally substituted aryl, optionally substituted heteroaryl, and A; especially each B is independently selected from halo, optionally substituted $C_{5-6}$ heteroaryl (particularly unsubstituted $C_{5-6}$ heteroaryl), $C_{5-6}$ heterocycloalkyl (where B is A, and the total of x and y is 3 or 4); more especially each B is independently selected from chloro, fluoro, pyridyl, pyrazolyl, oxazolyl, isoxazolyl, imidazolyl, pyrrolyl, $C_{5-6}$ heterocycloalkyl (where B is A, the total of x and y is 3 or 4, and Q is $CH_2$ or O); most especially each B is independently selected from chloro (particularly 4-chloro), fluoro, cyano, pyridyl, pyrazolyl, oxazolyl, isoxazolyl, imidazolyl, pyrrolidinyl, piperidinyl, morpholinyl; particularly each B is independently selected from chloro (particularly 4-chloro), fluoro, cyano, oxazolyl; and/or $R_4$ is $Z_{q1}B$ and $q_1$ is 1, 2 or 3, each Z is independently selected from $C_{1-3}$ alkyl, each B is independently selected from halo, CN, optionally substituted aryl, optionally substituted heteroaryl, and A; especially each B is independently selected from halo, optionally substituted $C_{5-6}$ heteroaryl (particularly unsubstituted $C_{5-6}$ heteroaryl), $C_{5-6}$heterocycloalkyl (where B is A, and the total of x and y is 3 or 4); more especially each B is independently selected from chloro, pyridyl, pyrazolyl, oxazolyl, isoxazolyl, imidazolyl, pyrrolyl, $C_{5-6}$ heterocycloalkyl (where B is A, the total of x and y is 3 or 4, and Q is $CH_2$ or O); most especially each B is independently selected from chloro, pyridyl, pyrazolyl, oxazolyl, isoxazolyl, imidazolyl, pyrrolidinyl, piperidinyl, morpholinyl; and/or $R_4$ is $Z_{q1}B$ and $q_1$ is 1, 2, 3, 4, 5, or 6, particularly $q_1$ is 1, 2, or 4 (most particularly 1 or 2), each Z is independently selected from $CR_7 R_8$, O, C=O, and $SO_2$ (particularly $CR_7 R_8$ and O), each $R_7$ is independently selected from hydrogen, methyl, and halo, each $R_8$ is independently selected from hydrogen, methyl, and halo, B is selected from hydrogen, halo, and cyano (particularly hydrogen and halo); especially each $R_4$ is independently selected from butyl (particularly tert-butyl), propyl (particularly iso-propyl), methyl, $COCH_3$, $C(CH_3)(CH_3)CN$, trifluoromethyl, trifluoromethoxy, difluoromethoxy, methoxy; more especially each $R_4$ is independently selected from butyl (particularly tert-butyl), propyl (particularly iso-propyl), trifluoromethyl, and trifluoromethoxy; most especially each $R_4$ is independently selected from butyl (particularly tert-butyl); and/or m is 1 or 2; especially m is 1; when m is 1, then $R_4$ is preferably meta or para to the sulfonamide, and most preferably para to the sulfonamide; and when m is 2, then most preferably one $R_4$ group is meta to the sulfonamide and the other $R_4$ group is para to the sulfonamide; for example when m is 1, $R_4$ may be tert-butyl, iso-propyl, trifluoromethyl, trifluoromethoxy, difluoromethoxy, or methoxy (especially $R_4$ may be tert-butyl or trifluoromethoxy); for example when m is 2, the two $R_4$ groups may be trifluoromethyl and chloro or the two $R_4$ groups may be trifluoromethyl and fluoro or the two $R_4$ groups may be trifluoromethyl and difluoromethoxy.

Examples of particularly preferred compounds of Formula (I) include those wherein:

$R_1$ is hydrogen; and
X is selected from a direct bond and $CH_2$; and
$R_2$ is selected from optionally substituted pyridyl, optionally substituted phenyl, optionally substituted pyrazolyl, optionally substituted imidazolyl, and optionally substituted thiophenyl (wherein optional substituents are selected from $O^-$, $OCH_3$, $OC_2H_5$, $CH_3$, carboxy, carboxymethyl and CN); and
n is 1 and $R_3$ is chloro or cyano, particularly chloro; and
m is 1 and $R_4$ is tert-butyl.

In preferred compounds of the invention, optionally substituted groups are those that are unsubstituted or substituted by one or two groups independently selected from OH, =O or $O^-$, $NO_2$, $CF_3$, CN, halo (such as Cl or F), CHO, $CO_2H$, $C_{3-7}$cycloalkyl, $C_{1-4}$alkyl (such as methyl, ethyl), $C_{1-4}$alkoxy (such as —O-methyl, —O-ethyl), $COC_{1-4}$alkyl (such as -(CO)-methyl), $COC_{1-4}$ alkoxy (such as —(CO)—O-methyl, —(CO)—O-ethyl), and $C_{1-4}$haloalkoxy. For example, $R_2$ may be optionally substituted pyridyl (including pyridyl; pyridyl substituted by methoxy, ethoxy, methyl or cyano; pyridine N-oxide; pyridine N-oxide substituted by methoxy, ethoxy, methyl or cyano). When $R_2$ is an optionally substituted aryl, each substituent may be ortho, meta or para to the point of attachment to X. When $R_2$ is an optionally substituted heteroaryl, each substituent may be ortho, meta or para to the point of attachment to X, or may be attached to a heteroatom.

Example compounds of Formula (I) include compounds wherein X is a direct bond. Further example compounds of Formula (I) include compounds wherein X is $CH_2$. For compounds of Formula (I), examples of preferred $XR_2$ include those shown below plus $XR_2$ groups wherein the aryl or heteroaryl groups shown below are further optionally substituted:

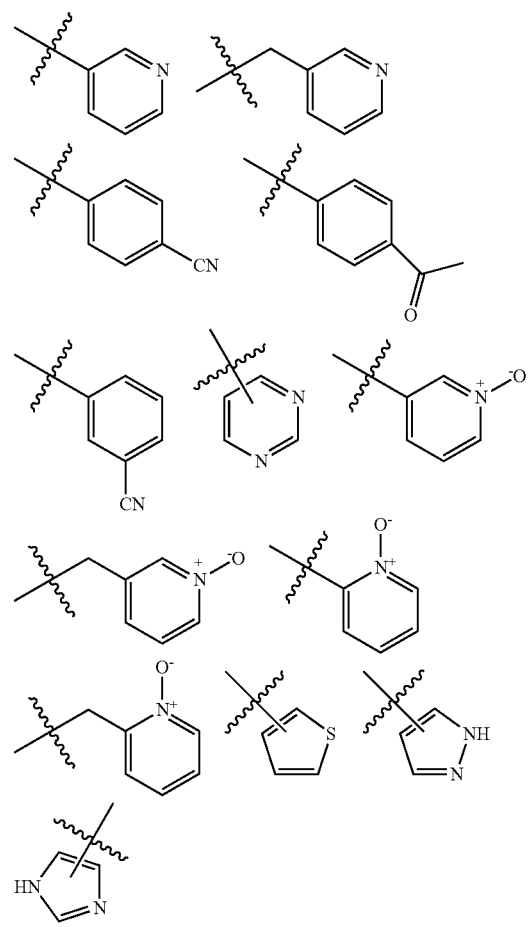

For compounds of Formula (I), when $R_4$ is A (ie $q_1$ is 0 and B is A), $R_4$ is a $C_{3-7}$heterocycloalkyl containing one heteroatom (N) or two heteroatoms (N plus O or N, where the second N may be substituted with methyl). For example, A may be pyrrolidinyl, piperidinyl, or morpholinyl. The group A is attached through any of its carbon or nitrogen atoms, for example as follows:

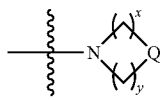

Preferred compounds of Formula (I) include those wherein:
R$_1$ is hydrogen; and
X is CH$_2$; and
R$_2$ is an optionally substituted heteroaryl, particularly unsubstituted heteroaryl, most particularly pyridyl; and
n is 0 (so there is no R$_3$ group present); and
m is 1; and
R$_4$ is trifluoromethoxy.

Examples of such compounds are shown below:

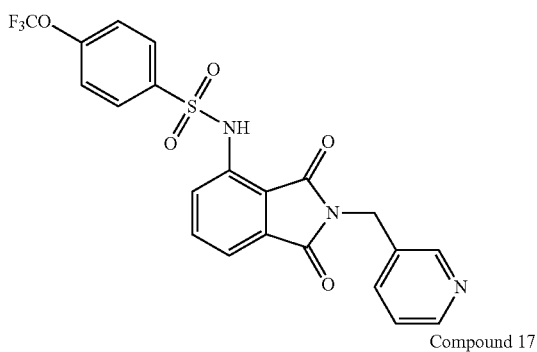

Compound 15

Compound 17

Other preferred compounds of Formula (I) include those wherein:
R$_1$ is hydrogen; and
X is a direct bond; and
R$_2$ is selected from optionally substituted aryl (particularly optionally substituted phenyl) and optionally substituted heteroaryl; for example, R$_2$ is selected from cyanophenyl, acetylphenyl, pyridyl, methyl-pyridyl, methoxy-pyridyl, ethoxy-pyridyl, pyridine N-oxide, methyl-pyridine N-oxide, methoxy-pyridine N-oxide and ethoxy-pyridine N-oxide, thiophenyl, pyrazolyl, pyrimidinyl, and imidazolyl; preferably R$_2$ is selected from cyanophenyl, acetylphenyl, pyridyl, methyl-pyridyl, methoxy-pyridyl, ethoxy-pyridyl, pyridine N-oxide, methyl-pyridine N-oxide, methoxy-pyridine N-oxide and ethoxy-pyridine N-oxide; most preferably R$_2$ is selected from pyridyl, methyl-pyridyl, methoxy-pyridyl, ethoxy-pyridyl, pyridine N-oxide, methyl-pyridine N-oxide, methoxy-pyridine N-oxide and ethoxy-pyridine N-oxide; and
n is 0 (so there is no R$_3$ group present); and
m is 2; and
one R$_4$ group is halo (particularly chloro or fluoro), and the other R$_4$ group is trifluoromethyl.

Examples of such compounds are shown below:

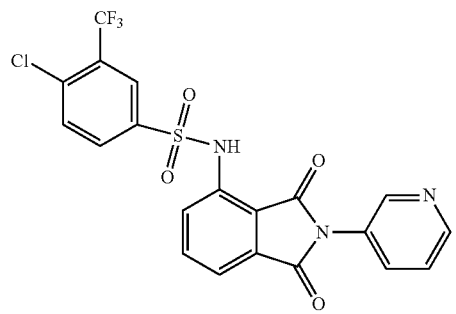

Compound 7

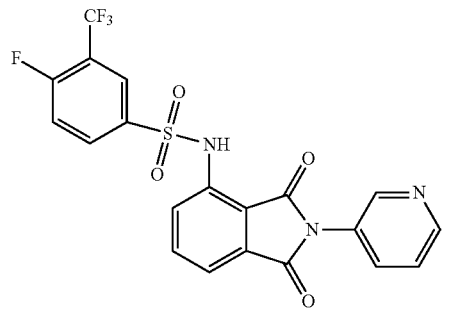

Compound 8

Other preferred compounds of Formula (I) include those wherein:
R$_1$ is hydrogen; and
X is a direct bond; and
R$_2$ is selected from optionally substituted aryl (particularly optionally substituted phenyl) and optionally substituted heteroaryl; for example, R$_2$ is selected from cyanophenyl, acetylphenyl, pyridyl, methyl-pyridyl, methoxy-pyridyl, ethoxy-pyridyl, pyridine N-oxide, methyl-pyridine N-oxide, methoxy-pyridine N-oxide and ethoxy-pyridine N-oxide, thiophenyl, pyrazolyl, pyrimidinyl, and imidazolyl; preferably R$_2$ is selected from cyanophenyl, acetylphenyl, pyridyl, methyl-pyridyl, methoxy-pyridyl, ethoxy-pyridyl, pyridine N-oxide, methyl-pyridine N-oxide, methoxy-pyridine N-oxide and ethoxy-pyridine N-oxide; most preferably R$_2$ is selected from pyridyl, methyl-pyridyl, methoxy-pyridyl, ethoxy-pyridyl, pyridine N-oxide, methyl-pyridine N-oxide, methoxy-pyridine N-oxide and ethoxy-pyridine N-oxide; and
n is 0 (so there is no R$_3$ group present); and
m is 1; and
R$_4$ is butyl (particularly tert-butyl), trifluoromethyl, trifluoromethoxy, or difluoromethoxy; preferably R$_4$ is butyl (particularly tert-butyl), or trifluoromethoxy.

Examples of such compounds are shown below:

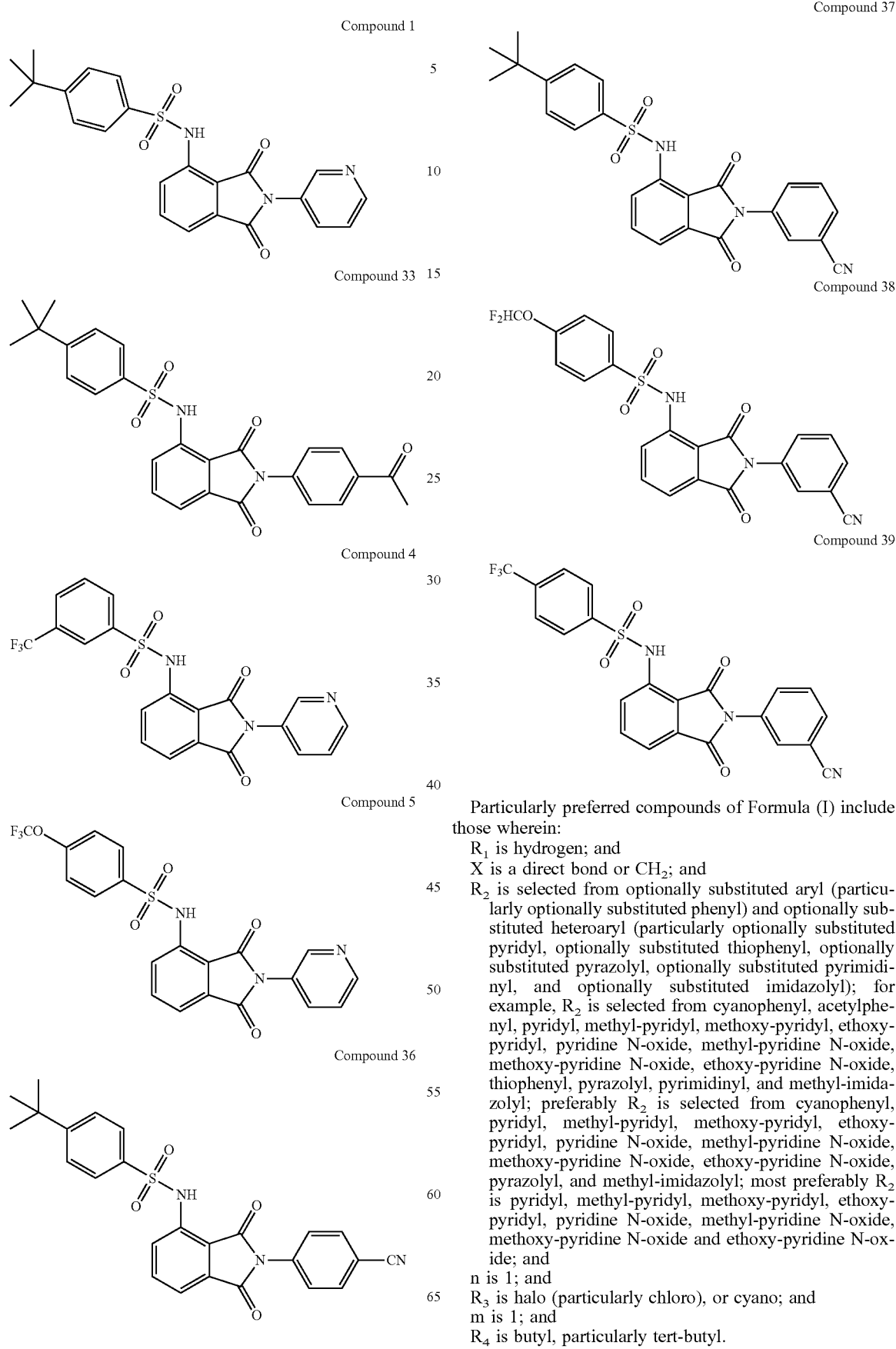

Particularly preferred compounds of Formula (I) include those wherein:

R₁ is hydrogen; and
X is a direct bond or CH₂; and
R₂ is selected from optionally substituted aryl (particularly optionally substituted phenyl) and optionally substituted heteroaryl (particularly optionally substituted pyridyl, optionally substituted thiophenyl, optionally substituted pyrazolyl, optionally substituted pyrimidinyl, and optionally substituted imidazolyl); for example, R₂ is selected from cyanophenyl, acetylphenyl, pyridyl, methyl-pyridyl, methoxy-pyridyl, ethoxy-pyridyl, pyridine N-oxide, methyl-pyridine N-oxide, methoxy-pyridine N-oxide, ethoxy-pyridine N-oxide, thiophenyl, pyrazolyl, pyrimidinyl, and methyl-imidazolyl; preferably R₂ is selected from cyanophenyl, pyridyl, methyl-pyridyl, methoxy-pyridyl, ethoxy-pyridyl, pyridine N-oxide, methyl-pyridine N-oxide, methoxy-pyridine N-oxide, ethoxy-pyridine N-oxide, pyrazolyl, and methyl-imidazolyl; most preferably R₂ is pyridyl, methyl-pyridyl, methoxy-pyridyl, ethoxy-pyridyl, pyridine N-oxide, methyl-pyridine N-oxide, methoxy-pyridine N-oxide and ethoxy-pyridine N-oxide; and
n is 1; and
R₃ is halo (particularly chloro), or cyano; and
m is 1; and
R₄ is butyl, particularly tert-butyl.

Examples of such compounds are shown below:
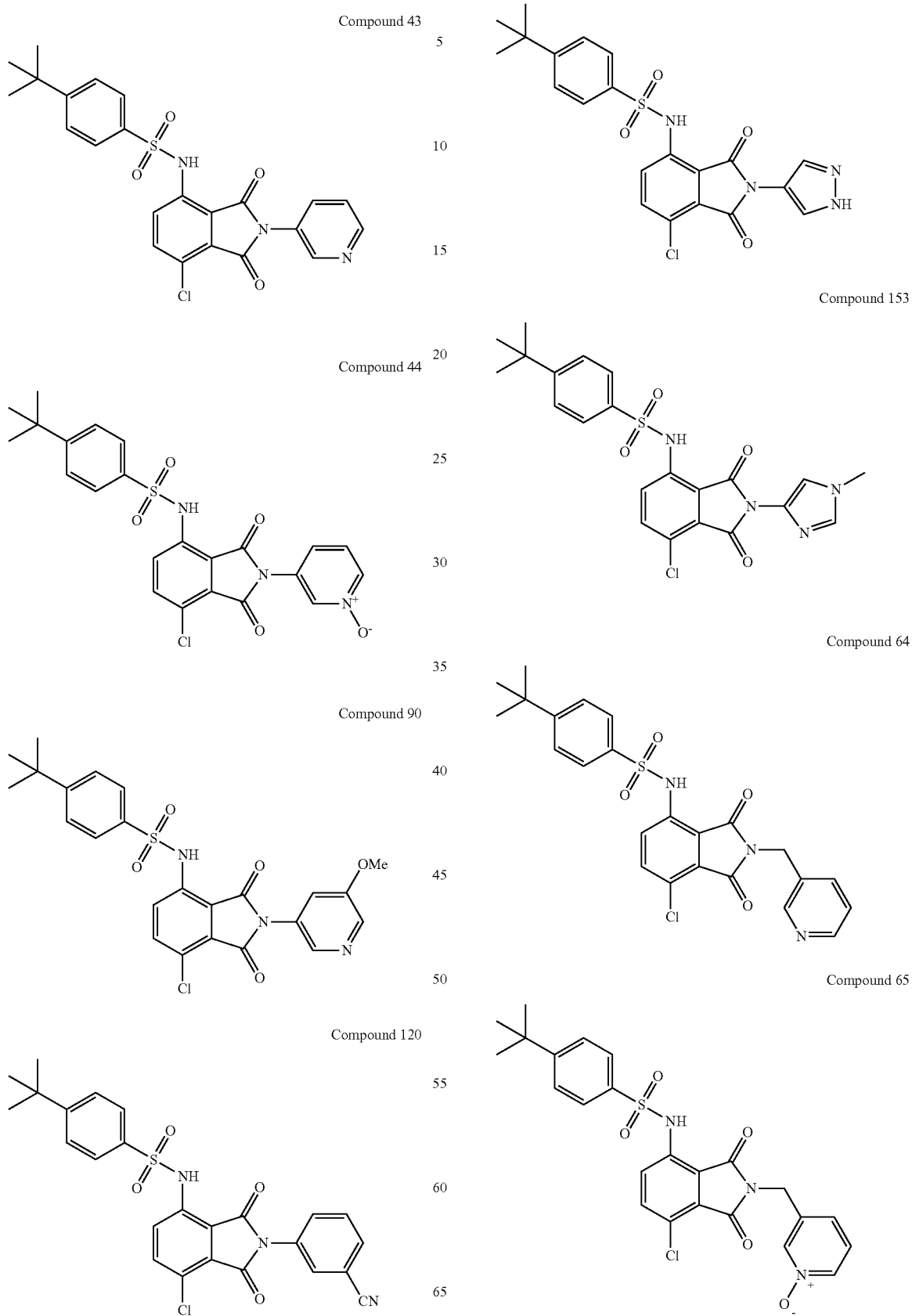

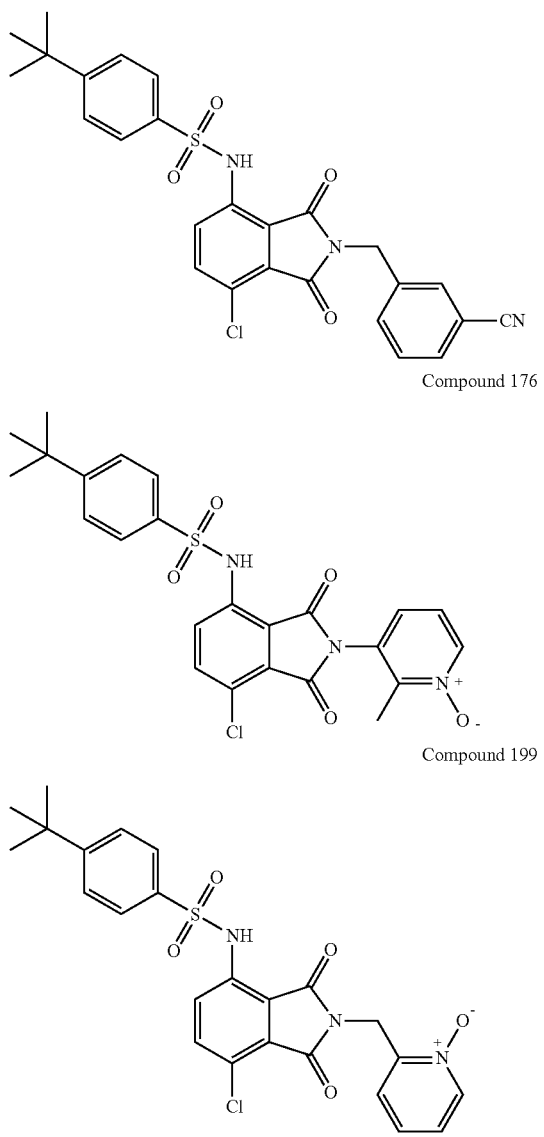

Compound 126

Compound 176

Compound 199

For example, particularly preferred compounds of Formula (I) are those wherein $R_1$ is hydrogen, X is a direct bond or $CH_2$, $R_2$ is a substituted pyridyl (particularly pyridine N-oxide or methyl-pyridine N-oxide), n is 1, $R_3$ is halo (particularly chloro), or cyano, m is 1, and $R_4$ is butyl (particularly tert-butyl). In particular, compounds of Formula (I) are those wherein $R_1$ is hydrogen, X is a direct bond or $CH_2$, $R_2$ is a substituted pyridyl (particularly pyridine N-oxide or methyl-pyridine N-oxide), n is 1, $R_3$ is halo (particularly chloro), m is 1, and $R_4$ is butyl (particularly tert-butyl).

It will be appreciated that, in the compounds described above:

$R_4$ is trifluoromethoxy when $R_4$ is $Z_{q1}B$, $q_1$ is 2, the first Z group is O, the second Z group is $CR_7 R_8$, and each of $R_7$, $R_8$ and B is fluoro;

$R_4$ is trifluoromethyl when $R_4$ is $Z_{q1}B$, $q_1$ is 1, Z is $CR_7 R_8$, and each of $R_7$, $R_8$ and B is fluoro;

$R_4$ is tert-butyl when $R_4$ is $Z_{q1}B$, $q_1$ is 2, the first Z group is $CR_7 R_8$ where each of $R_7$ and $R_5$ is methyl, the second Z group is $CR_7 R_8$ where each of $R_7$ and $R_5$ is hydrogen, and B is hydrogen;

$R_4$ is isopropyl when $R_4$ is $Z_{q1}B$, $q_1$ is 1, the Z group is $CR_7R_8$ where each of $R_7$ and $R_8$ is methyl, and B is hydrogen; or $R_4$ is isopropyl when $R_4$ is $Z_{q1}B$, $q_1$ is 2, the first Z group is $CR_7R_8$ where one of $R_7$ and $R_8$ is methyl and the other is H, the second Z group is $CR_7R_8$ where each of $R_7$ and $R_8$ is hydrogen, and B is hydrogen;

$R_4$ is methyl when $R_4$ is $Z_{q1}B$, q is 1, the Z group is $CR_7R_8$ where each of $R_7$ and $R_8$ is hydrogen, and B is hydrogen;

$R_4$ is difluoromethoxy when $R_4$ is $Z_{q1}B$, $q_1$ is 2, the first Z group is O, the second Z group is $CR_7R_8$, one of $R_7$, $R_8$ and B is hydrogen, and two of $R_7$, $R_8$ and B are fluoro;

$R_4$ is methoxy when $R_4$ is $Z_{q1}B$, $q_1$ is 2, the first Z group is O, the second Z group is $CR_7R_8$ where each of $R_7$ and $R_8$ is hydrogen, and B is hydrogen;

$R_4$ is carboxy-methyl, $(CO)CH_3$ when $R_4$ is $Z_{q1}B$, $q_1$ is 2, the first Z group is CO, the second Z group is $CR_7R_8$ where each of $R_7$ and $R_8$ is hydrogen, and B is hydrogen;

$R_4$ is methyl sulfonyl, $SO_2CH_3$ when $R_4$ is $Z_{q1}B$, $q_1$ is 2, the first Z group is $SO_2$, the second Z group is $CR_7R_8$ where each of $R_7$ and $R_8$ is hydrogen, and B is hydrogen;

$R_4$ is $(CH_2)_3OCH_3$ when $R_4$ is $Z_{q1}B$, $q_1$ is 5, each of the first three Z groups and the fifth Z group is $CR_7R_8$ where each of $R_7$ and $R_8$ is hydrogen, the fourth Z group is O, and B is hydrogen;

$R_4$ is $C(CH_3)(CH_3)CN$ when $R_4$ is $Z_{q1}B$, $q_1$ is 1, the Z group is $CR_7R_8$ where each of $R_7$ and $R_8$ is methyl, and B is cyano.

Specific compounds of the invention include the compounds of Formula (I) listed in Table 1, and any salt or solvate thereof, including a solvate of such a salt:

TABLE 1

| Compound number | Structure |
|---|---|
| 1 | 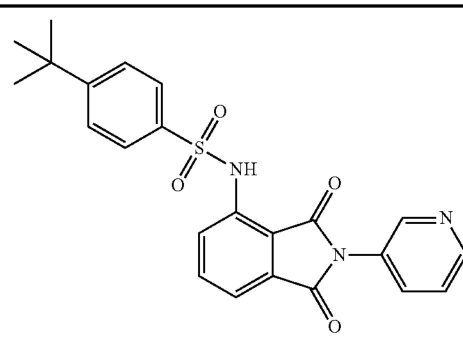 |

TABLE 1-continued
| Compound number | Structure |
|---|---|
| 2 | 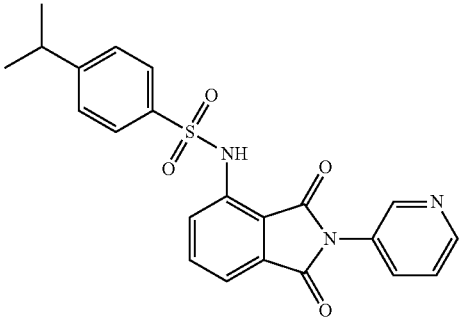 [SMILES: CC(C)c1ccc(S(=O)(=O)Nc2cccc3c2C(=O)N(c2cccnc2)C3=O)cc1] |
| 3 | 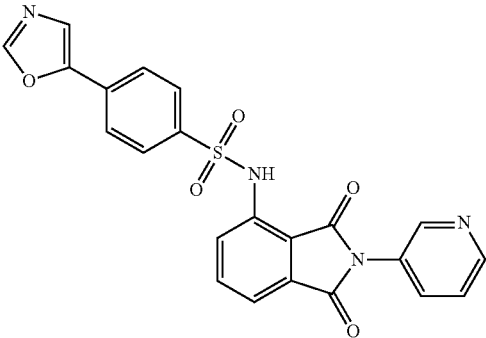 [SMILES: O=C1c2cccc(NS(=O)(=O)c3ccc(-c4cnco4)cc3)c2C(=O)N1c1cccnc1] |
| 4 | 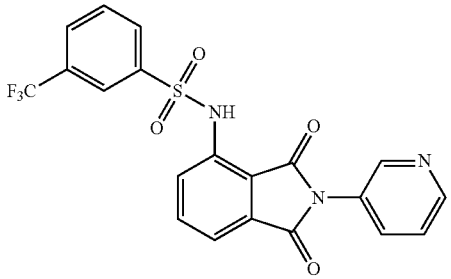 [SMILES: O=C1c2cccc(NS(=O)(=O)c3cccc(C(F)(F)F)c3)c2C(=O)N1c1cccnc1] |
| 5 | 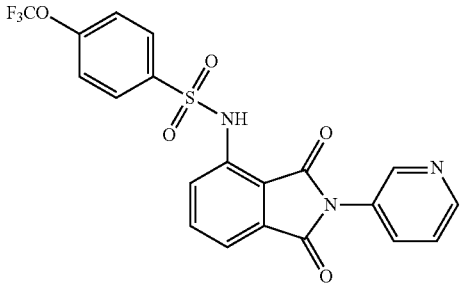 |
| 6 | 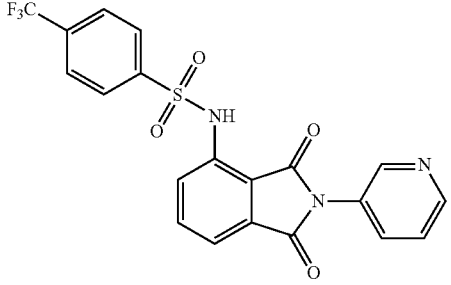 [SMILES: O=C1c2cccc(NS(=O)(=O)c3ccc(C(F)(F)F)cc3)c2C(=O)N1c1cccnc1] |

TABLE 1-continued
| Compound number | Structure |
|---|---|
| 7 | 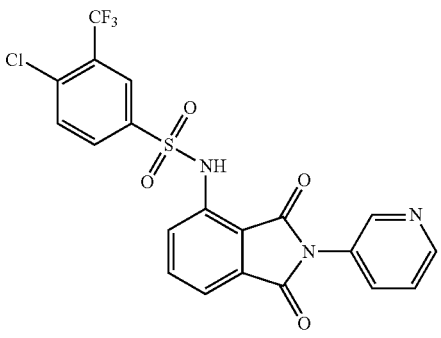 [SMILES: O=C1c2cccc(NS(=O)(=O)c3ccc(Cl)c(C(F)(F)F)c3)c2C(=O)N1c1cccnc1] |
| 8 | 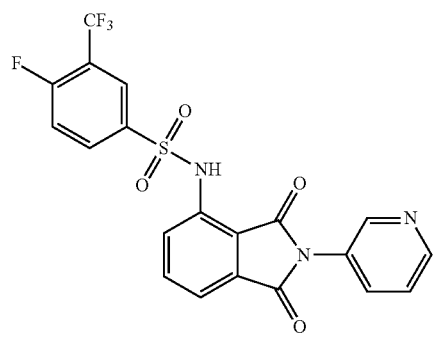 [SMILES: O=C1c2cccc(NS(=O)(=O)c3ccc(F)c(C(F)(F)F)c3)c2C(=O)N1c1cccnc1] |
| 9 | 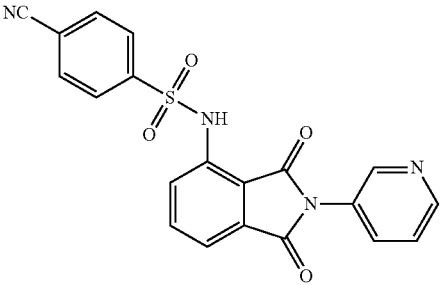 [SMILES: N#Cc1ccc(S(=O)(=O)Nc2cccc3c2C(=O)N(c2cccnc2)C3=O)cc1] |
| 10 | 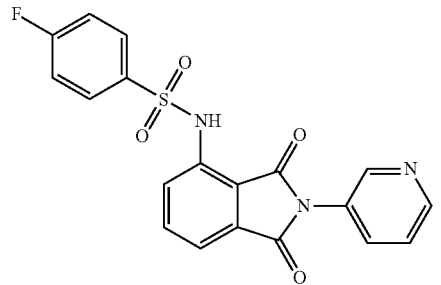 [SMILES: O=C1c2cccc(NS(=O)(=O)c3ccc(F)cc3)c2C(=O)N1c1cccnc1] |
| 11 | 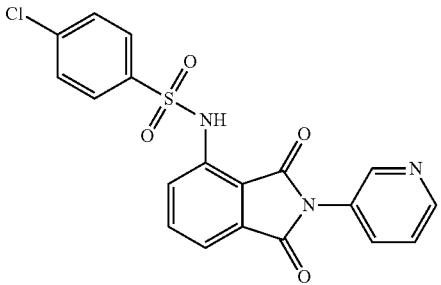 [SMILES: O=C1c2cccc(NS(=O)(=O)c3ccc(Cl)cc3)c2C(=O)N1c1cccnc1] |

TABLE 1-continued

| Compound number | Structure |
|---|---|
| 12 | *4-tert-butylphenyl sulfonamide of 4-amino-N-(pyridin-3-ylmethyl)phthalimide* |
| 13 | *4-(oxazol-5-yl)phenyl sulfonamide of 4-amino-N-(pyridin-3-ylmethyl)phthalimide* |
| 14 | *3-tert-butylphenyl sulfonamide of 4-amino-N-(pyridin-3-ylmethyl)phthalimide* |
| 15 | *4-(trifluoromethoxy)phenyl sulfonamide of 4-amino-N-(pyridin-3-ylmethyl)phthalimide* |

TABLE 1-continued

| Compound number | Structure |
|---|---|
| 16 | 3-(trifluoromethoxy)-N-[1,3-dioxo-2-(pyridin-3-ylmethyl)-2,3-dihydro-1H-isoindol-4-yl]benzenesulfonamide |
| 17 | 2-(trifluoromethoxy)-N-[1,3-dioxo-2-(pyridin-3-ylmethyl)-2,3-dihydro-1H-isoindol-4-yl]benzenesulfonamide |
| 18 | 4-fluoro-3-(trifluoromethyl)-N-[1,3-dioxo-2-(pyridin-3-ylmethyl)-2,3-dihydro-1H-isoindol-4-yl]benzenesulfonamide |
| 19 | 4-(trifluoromethyl)-N-[1,3-dioxo-2-(pyridin-3-ylmethyl)-2,3-dihydro-1H-isoindol-4-yl]benzenesulfonamide |

TABLE 1-continued
| Compound number | Structure |
| --- | --- |
| 20 | 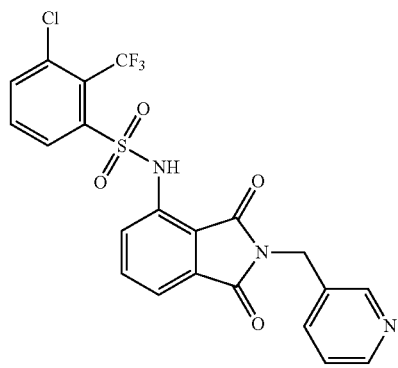 [SMILES: O=C1c2cccc(NS(=O)(=O)c3cccc(Cl)c3C(F)(F)F)c2C(=O)N1Cc1cccnc1] |
| 21 | 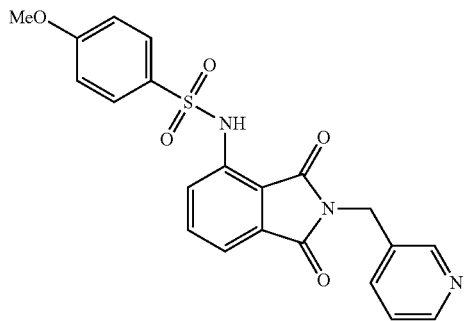 [SMILES: COc1ccc(S(=O)(=O)Nc2cccc3c2C(=O)N(Cc2cccnc2)C3=O)cc1] |
| 22 | 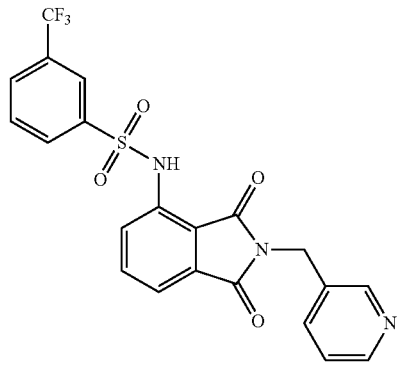 [SMILES: O=C1c2cccc(NS(=O)(=O)c3cccc(C(F)(F)F)c3)c2C(=O)N1Cc1cccnc1] |
| 23 | 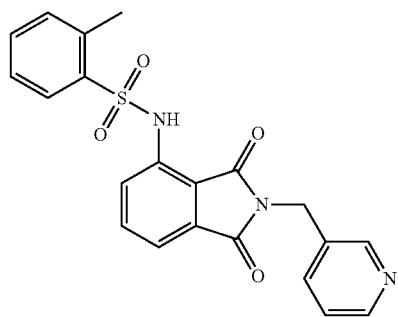 [SMILES: Cc1ccccc1S(=O)(=O)Nc1cccc2c1C(=O)N(Cc1cccnc1)C2=O] |

TABLE 1-continued

| Compound number | Structure |
|---|---|
| 24 | 4-acetyl-N-[2-(pyridin-3-ylmethyl)-1,3-dioxoisoindolin-4-yl]benzenesulfonamide |
| 25 | 4-cyano-N-[2-(pyridin-3-ylmethyl)-1,3-dioxoisoindolin-4-yl]benzenesulfonamide |
| 26 | 2-(trifluoromethyl)-N-[2-(pyridin-3-ylmethyl)-1,3-dioxoisoindolin-4-yl]benzenesulfonamide |
| 27 | 4-methyl-N-[2-(pyridin-3-ylmethyl)-1,3-dioxoisoindolin-4-yl]benzenesulfonamide |

TABLE 1-continued

| Compound number | Structure |
| --- | --- |
| 28 | 3-methoxyphenyl sulfonamide linked to 2-(pyridin-3-ylmethyl)-1,3-dioxoisoindolin-4-yl |
| 29 | 4-(difluoromethoxy)phenyl sulfonamide linked to 2-(pyridin-3-ylmethyl)-1,3-dioxoisoindolin-4-yl |
| 30 | 4-fluorophenyl sulfonamide linked to 2-(pyridin-3-ylmethyl)-1,3-dioxoisoindolin-4-yl |
| 31 | 4-chlorophenyl sulfonamide linked to 2-(pyridin-3-ylmethyl)-1,3-dioxoisoindolin-4-yl |

TABLE 1-continued

| Compound number | Structure |
|---|---|
| 32 | 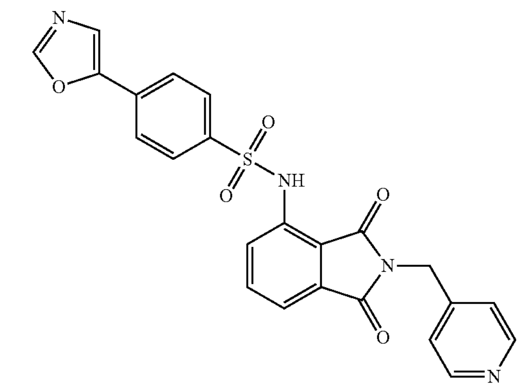 [SMILES: O=C1c2cccc(NS(=O)(=O)c3ccc(-c4cnco4)cc3)c2C(=O)N1Cc1ccncc1] |
| 33 | 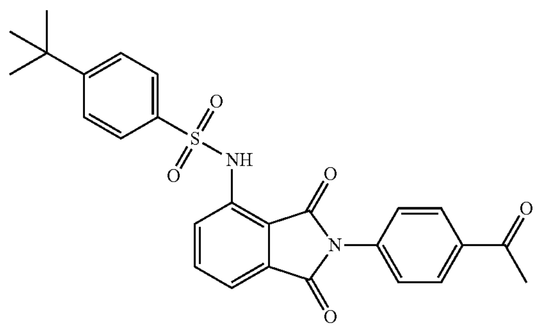 [SMILES: CC(=O)c1ccc(N2C(=O)c3cccc(NS(=O)(=O)c4ccc(C(C)(C)C)cc4)c3C2=O)cc1] |
| 34 | 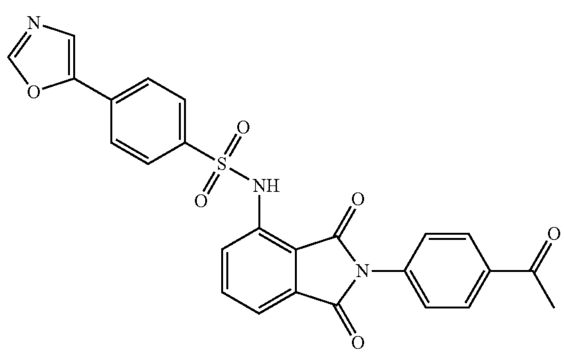 [SMILES: CC(=O)c1ccc(N2C(=O)c3cccc(NS(=O)(=O)c4ccc(-c5cnco5)cc4)c3C2=O)cc1] |
| 35 | 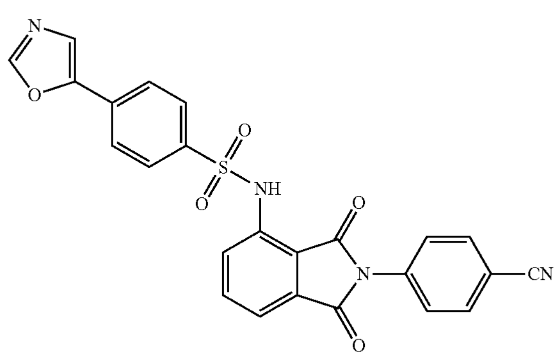 [SMILES: N#Cc1ccc(N2C(=O)c3cccc(NS(=O)(=O)c4ccc(-c5cnco5)cc4)c3C2=O)cc1] |

TABLE 1-continued

| Compound number | Structure |
| --- | --- |
| 36 | 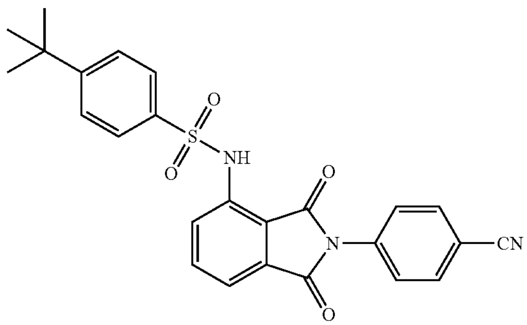 [SMILES: CC(C)(C)c1ccc(S(=O)(=O)Nc2cccc3c2C(=O)N(c2ccc(C#N)cc2)C3=O)cc1] |
| 37 | 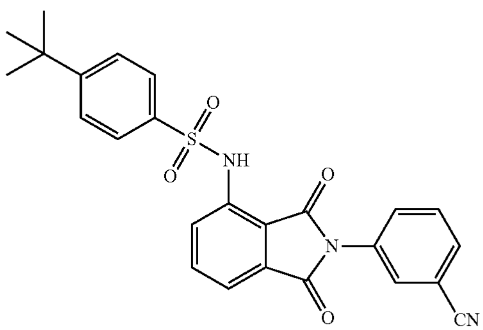 [SMILES: CC(C)(C)c1ccc(S(=O)(=O)Nc2cccc3c2C(=O)N(c2cccc(C#N)c2)C3=O)cc1] |
| 38 | 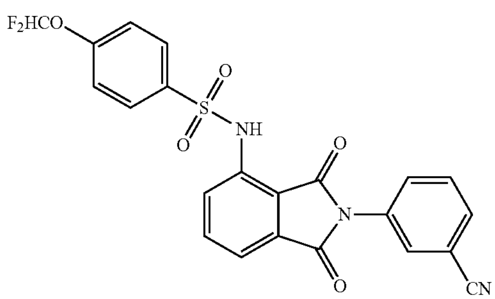 [SMILES: N#Cc1cccc(N2C(=O)c3cccc(NS(=O)(=O)c4ccc(OC(F)F)cc4)c3C2=O)c1] |
| 39 | 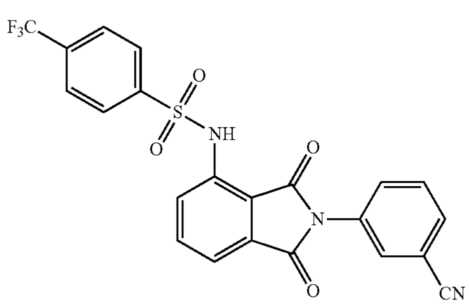 [SMILES: N#Cc1cccc(N2C(=O)c3cccc(NS(=O)(=O)c4ccc(C(F)(F)F)cc4)c3C2=O)c1] |
| 40 | 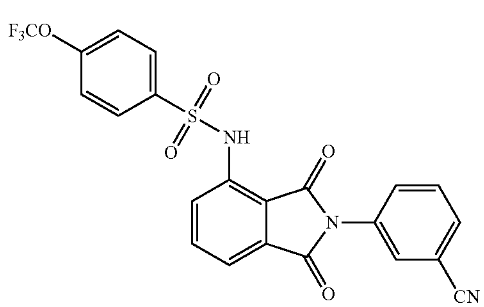 [SMILES: N#Cc1cccc(N2C(=O)c3cccc(NS(=O)(=O)c4ccc(OC(F)(F)F)cc4)c3C2=O)c1] |

TABLE 1-continued

| Compound number | Structure |
|---|---|
| 41 | 4-chloro-3-(trifluoromethyl)-N-[2-(3-cyanophenyl)-1,3-dioxoisoindolin-4-yl]benzenesulfonamide |
| 42 | 4-fluoro-3-(trifluoromethyl)-N-[2-(3-cyanophenyl)-1,3-dioxoisoindolin-4-yl]benzenesulfonamide |
| 43 | 4-tert-butyl-N-[7-chloro-1,3-dioxo-2-(pyridin-3-yl)isoindolin-4-yl]benzenesulfonamide |
| 44 | 4-tert-butyl-N-[7-chloro-1,3-dioxo-2-(1-oxidopyridin-3-yl)isoindolin-4-yl]benzenesulfonamide |

TABLE 1-continued
| Compound number | Structure |
|---|---|
| 45 | 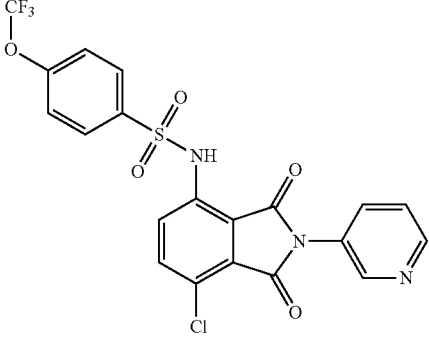 [SMILES: O=C1c2c(Cl)ccc(NS(=O)(=O)c3ccc(OC(F)(F)F)cc3)c2C(=O)N1c1cccnc1] |
| 46 | 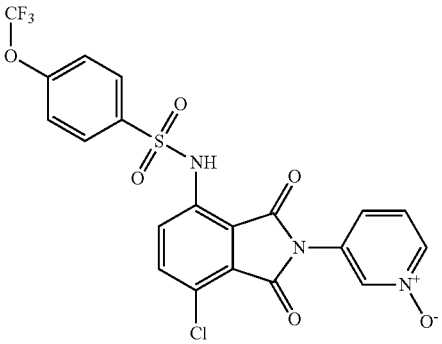 [SMILES: O=C1c2c(Cl)ccc(NS(=O)(=O)c3ccc(OC(F)(F)F)cc3)c2C(=O)N1c1ccc[n+]([O-])c1] |
| 47 | 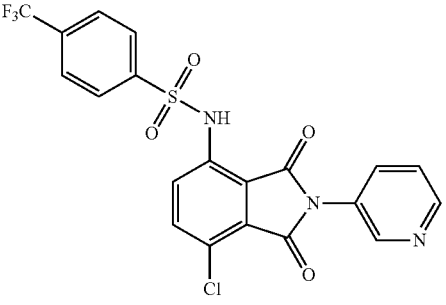 [SMILES: O=C1c2c(Cl)ccc(NS(=O)(=O)c3ccc(C(F)(F)F)cc3)c2C(=O)N1c1cccnc1] |
| 48 | 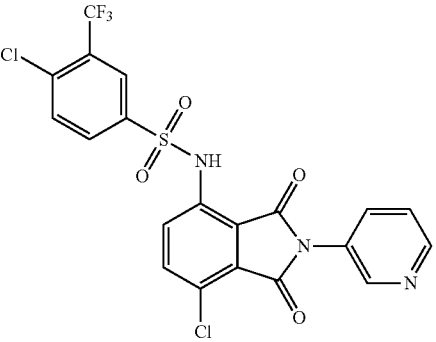 [SMILES: O=C1c2c(Cl)ccc(NS(=O)(=O)c3ccc(Cl)c(C(F)(F)F)c3)c2C(=O)N1c1cccnc1] |

TABLE 1-continued

| Compound number | Structure |
|---|---|
| 49 | (4-(oxazol-5-yl)phenyl)sulfonamide linked to 4-chloro-2-(pyridin-3-yl)isoindoline-1,3-dione |
| 50 | (3-methoxyphenyl)sulfonamide linked to 4-chloro-2-(pyridin-3-yl)isoindoline-1,3-dione |
| 51 | (4-fluorophenyl)sulfonamide linked to 4-chloro-2-(pyridin-3-yl)isoindoline-1,3-dione |
| 52 | (4-(difluoromethoxy)phenyl)sulfonamide linked to 4-chloro-2-(pyridin-3-yl)isoindoline-1,3-dione |

TABLE 1-continued
| Compound number | Structure |
| --- | --- |
| 53 | 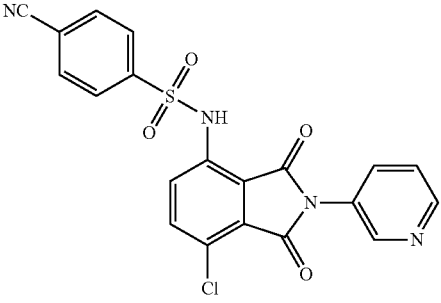 [SMILES: N#Cc1ccc(S(=O)(=O)Nc2ccc(Cl)c3c2C(=O)N(c2cccnc2)C3=O)cc1] |
| 54 | 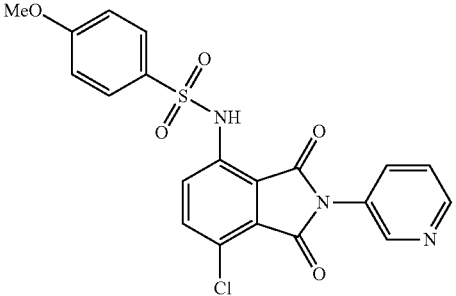 [SMILES: COc1ccc(S(=O)(=O)Nc2ccc(Cl)c3c2C(=O)N(c2cccnc2)C3=O)cc1] |
| 55 | 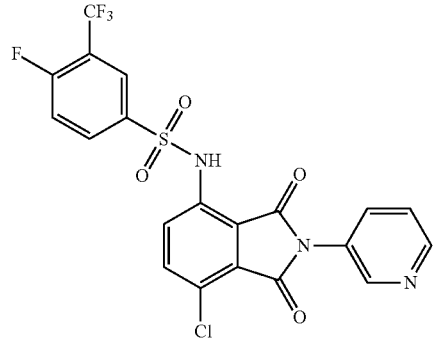 |
| 56 | 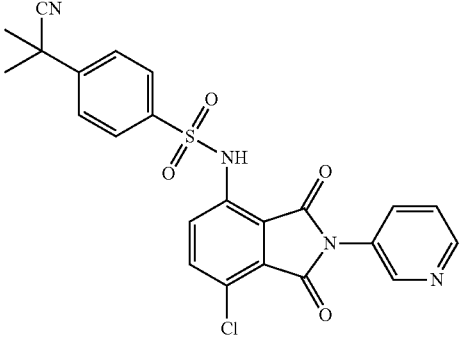 [SMILES: CC(C)(C#N)c1ccc(S(=O)(=O)Nc2ccc(Cl)c3c2C(=O)N(c2cccnc2)C3=O)cc1] |

TABLE 1-continued
| Compound number | Structure |
|---|---|
| 57 | 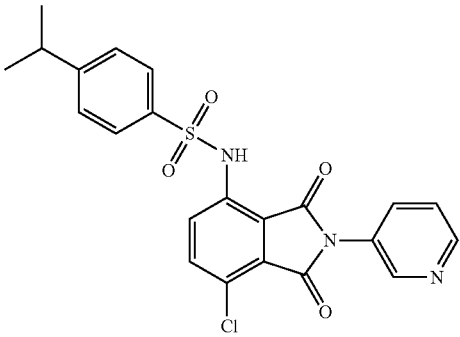 |
| 58 | 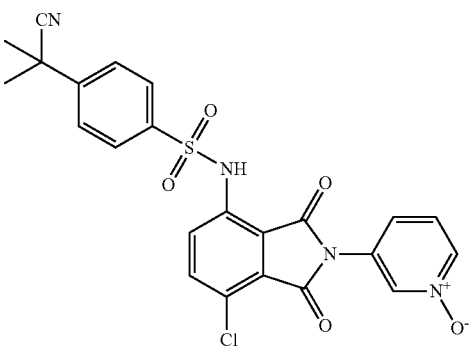 [SMILES: CC(C)(C#N)c1ccc(S(=O)(=O)Nc2ccc(Cl)c3c2C(=O)N(c2ccc[n+]([O-])c2)C3=O)cc1] |
| 59 | 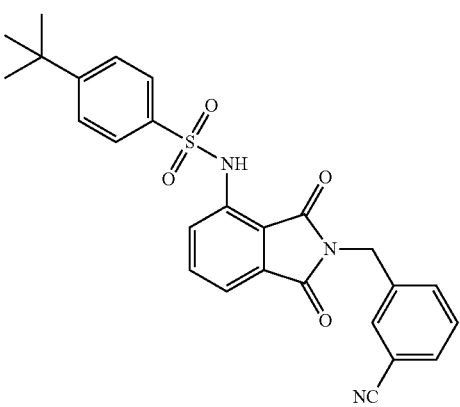 [SMILES: CC(C)(C)c1ccc(S(=O)(=O)Nc2cccc3c2C(=O)N(Cc2cccc(C#N)c2)C3=O)cc1] |
| 60 | 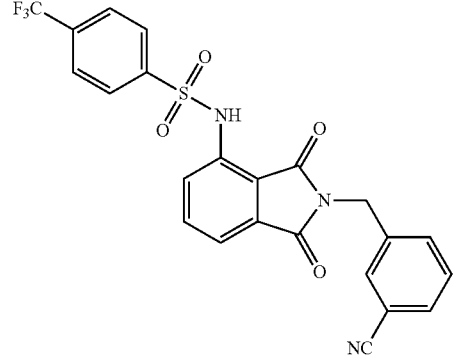 [SMILES: N#Cc1cccc(CN2C(=O)c3cccc(NS(=O)(=O)c4ccc(C(F)(F)F)cc4)c3C2=O)c1] |

TABLE 1-continued
| Compound number | Structure |
| --- | --- |
| 61 | 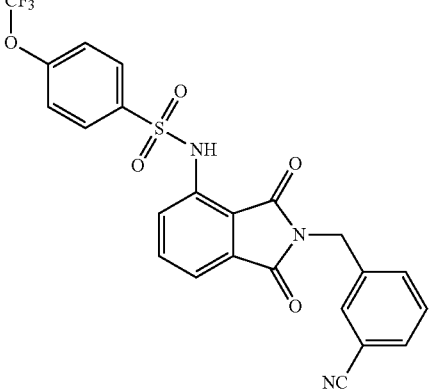 |
| 62 | 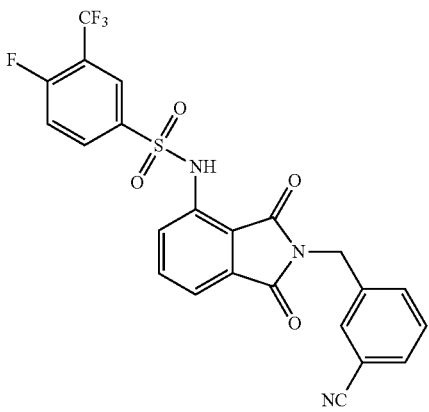 [SMILES: N#Cc1cccc(CN2C(=O)c3cccc(NS(=O)(=O)c4ccc(F)c(C(F)(F)F)c4)c3C2=O)c1] |
| 63 | 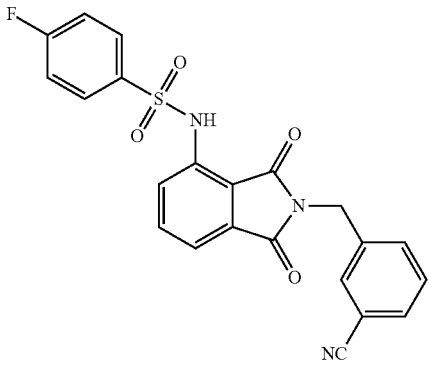 [SMILES: N#Cc1cccc(CN2C(=O)c3cccc(NS(=O)(=O)c4ccc(F)cc4)c3C2=O)c1] |
| 64 | 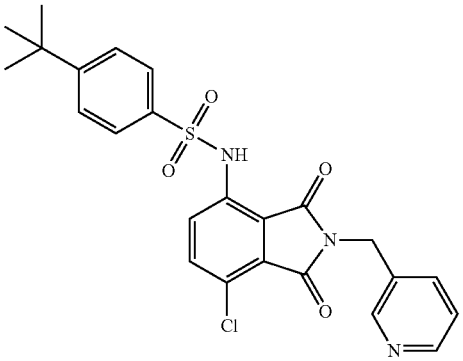 |

TABLE 1-continued

| Compound number | Structure |
|---|---|
| 65 | 4-tert-butyl-N-[7-chloro-2-(1-oxidopyridin-1-ium-3-ylmethyl)-1,3-dioxoisoindolin-4-yl]benzenesulfonamide |
| 66 | 4-(trifluoromethyl)-N-[7-chloro-2-(pyridin-3-ylmethyl)-1,3-dioxoisoindolin-4-yl]benzenesulfonamide |
| 67 | 4-(trifluoromethoxy)-N-[7-chloro-2-(pyridin-3-ylmethyl)-1,3-dioxoisoindolin-4-yl]benzenesulfonamide |
| 68 | 4-(difluoromethoxy)-N-[7-chloro-2-(pyridin-3-ylmethyl)-1,3-dioxoisoindolin-4-yl]benzenesulfonamide |

TABLE 1-continued

| Compound number | Structure |
|---|---|
| 69 | (4-(trifluoromethyl)phenyl)sulfonamide linked to 4-chloro-2-((1-oxidopyridin-1-ium-3-yl)methyl)-1,3-dioxoisoindolin-7-yl) |
| 70 | (4-(trifluoromethoxy)phenyl)sulfonamide linked to 4-chloro-2-((1-oxidopyridin-1-ium-3-yl)methyl)-1,3-dioxoisoindolin-7-yl) |
| 71 | (4-chloro-3-(trifluoromethyl)phenyl)sulfonamide linked to 4-chloro-2-(pyridin-3-ylmethyl)-1,3-dioxoisoindolin-7-yl) |
| 72 | (4-fluoro-3-(trifluoromethyl)phenyl)sulfonamide linked to 4-chloro-2-(pyridin-3-ylmethyl)-1,3-dioxoisoindolin-7-yl) |

TABLE 1-continued

| Compound number | Structure |
|---|---|
| 73 | (4-methoxyphenyl)sulfonyl-NH-[7-chloro-1,3-dioxo-2-(pyridin-3-ylmethyl)isoindolin-4-yl] |
| 74 | (4-fluoro-3-(trifluoromethyl)phenyl)sulfonyl-NH-[7-chloro-1,3-dioxo-2-((1-oxidopyridin-1-ium-3-yl)methyl)isoindolin-4-yl] |
| 75 | (4-chloro-3-(trifluoromethyl)phenyl)sulfonyl-NH-[7-chloro-1,3-dioxo-2-((1-oxidopyridin-1-ium-3-yl)methyl)isoindolin-4-yl] |
| 76 | (3-(trifluoromethyl)phenyl)sulfonyl-NH-[7-chloro-1,3-dioxo-2-(pyridin-3-ylmethyl)isoindolin-4-yl] |

TABLE 1-continued

| Compound number | Structure |
|---|---|
| 77 | (structure) |
| 78 | (structure) |
| 79 | (structure) |
| 80 | (structure) |

TABLE 1-continued

| Compound number | Structure |
|---|---|
| 81 | 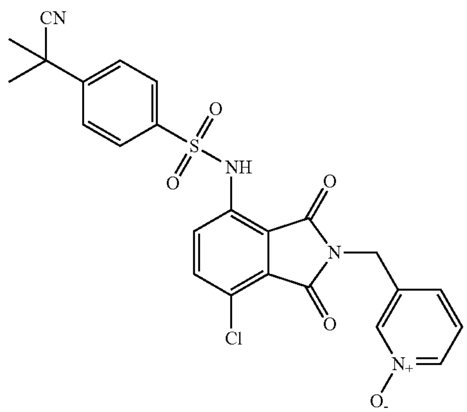 |
| 82 | 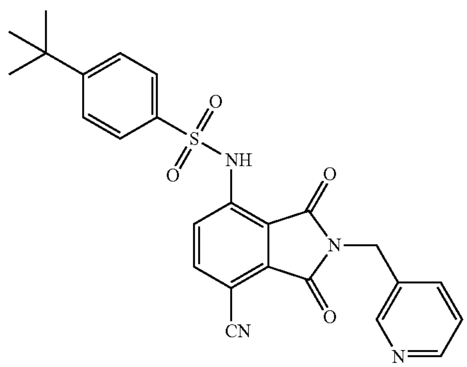 [SMILES: CC(C)(C)c1ccc(S(=O)(=O)Nc2ccc(C#N)c3c2C(=O)N(Cc2cccnc2)C3=O)cc1] |
| 83 | 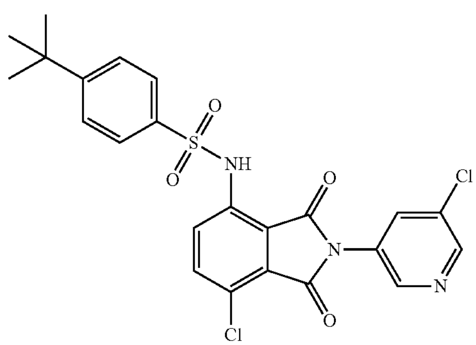 [SMILES: CC(C)(C)c1ccc(S(=O)(=O)Nc2ccc(Cl)c3c2C(=O)N(c2cncc(Cl)c2)C3=O)cc1] |
| 84 | 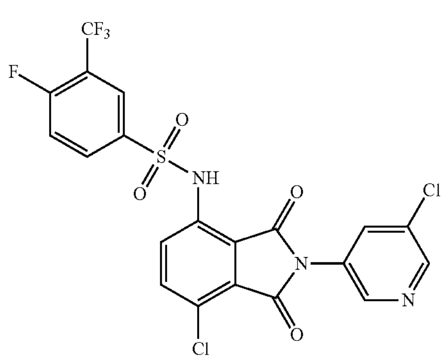 [SMILES: O=C1c2c(Cl)ccc(NS(=O)(=O)c3ccc(F)c(C(F)(F)F)c3)c2C(=O)N1c1cncc(Cl)c1] |

TABLE 1-continued
| Compound number | Structure |
|---|---|
| 85 | 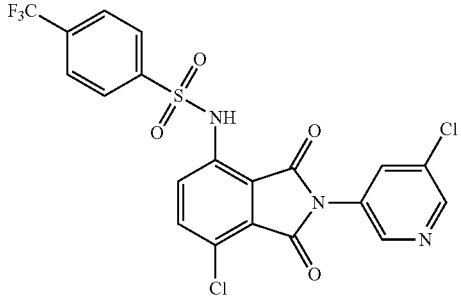 [SMILES: O=C1c2c(Cl)ccc(NS(=O)(=O)c3ccc(C(F)(F)F)cc3)c2C(=O)N1c1cncc(Cl)c1] |
| 86 | 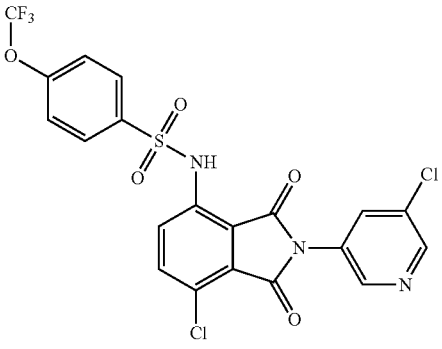 [SMILES: O=C1c2c(Cl)ccc(NS(=O)(=O)c3ccc(OC(F)(F)F)cc3)c2C(=O)N1c1cncc(Cl)c1] |
| 87 | 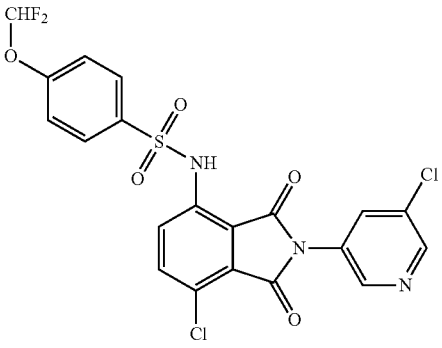 |
| 88 | 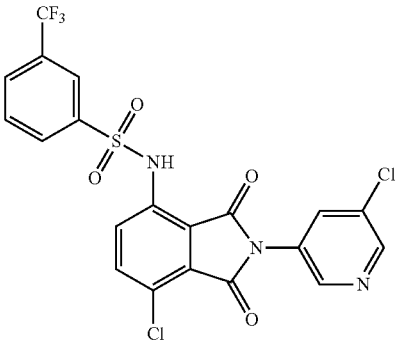 [SMILES: O=C1c2c(Cl)ccc(NS(=O)(=O)c3cccc(C(F)(F)F)c3)c2C(=O)N1c1cncc(Cl)c1] |

TABLE 1-continued
| Compound number | Structure |
|---|---|
| 89 | 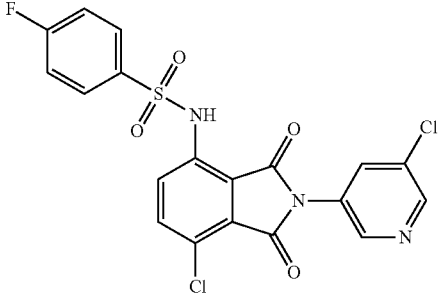 [SMILES: O=C1c2c(Cl)ccc(NS(=O)(=O)c3ccc(F)cc3)c2C(=O)N1c1cncc(Cl)c1] |
| 90 | 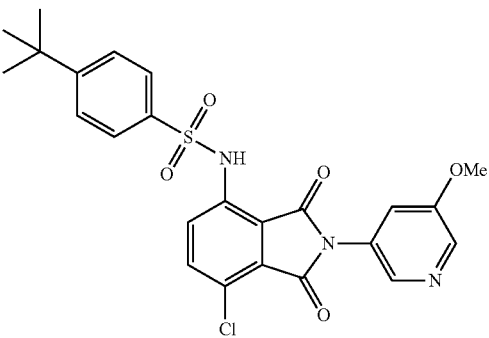 [SMILES: COc1cncc(N2C(=O)c3c(Cl)ccc(NS(=O)(=O)c4ccc(C(C)(C)C)cc4)c3C2=O)c1] |
| 91 | 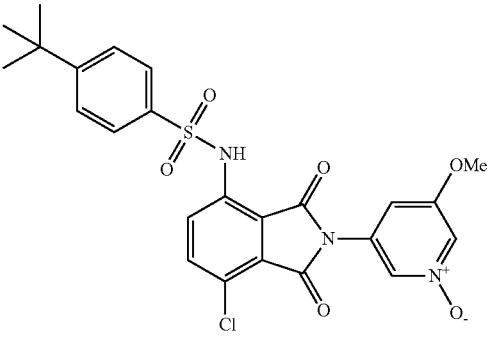 |
| 92 | 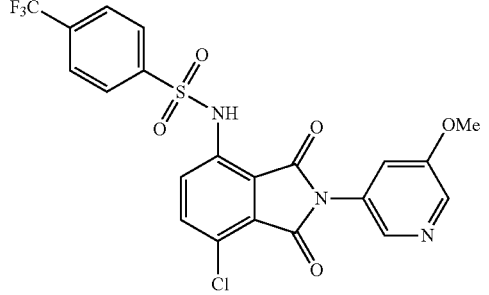 [SMILES: COc1cncc(N2C(=O)c3c(Cl)ccc(NS(=O)(=O)c4ccc(C(F)(F)F)cc4)c3C2=O)c1] |

TABLE 1-continued

| Compound number | Structure |
| --- | --- |
| 93 | (4-chloro-3-(trifluoromethyl)phenyl)sulfonamide linked to 7-chloro-2-(5-methoxypyridin-3-yl)-1,3-dioxoisoindolin-4-yl |
| 94 | (4-(trifluoromethoxy)phenyl)sulfonamide linked to 7-chloro-2-(5-methoxypyridin-3-yl)-1,3-dioxoisoindolin-4-yl |
| 95 | (4-fluoro-3-(trifluoromethyl)phenyl)sulfonamide linked to 7-chloro-2-(5-methoxypyridin-3-yl)-1,3-dioxoisoindolin-4-yl |
| 96 | (4-(oxazol-5-yl)phenyl)sulfonamide linked to 7-chloro-2-(5-methoxypyridin-3-yl)-1,3-dioxoisoindolin-4-yl |

TABLE 1-continued
| Compound number | Structure |
|---|---|
| 97 | 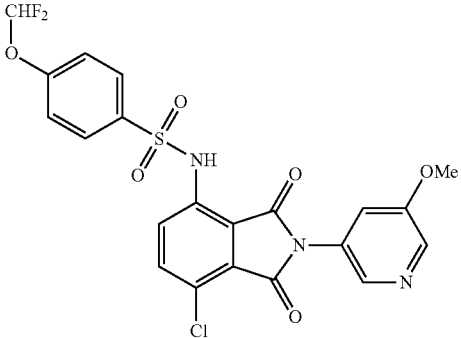 |
| 98 | 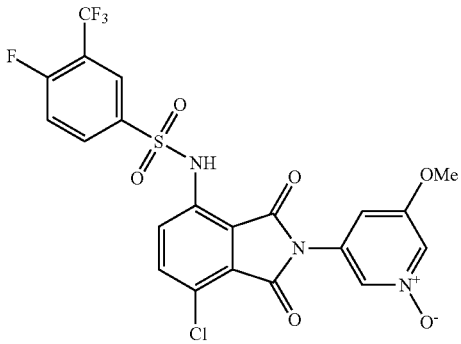 [SMILES: COc1cc(N2C(=O)c3c(Cl)ccc(NS(=O)(=O)c4ccc(F)c(C(F)(F)F)c4)c3C2=O)c[n+]([O-])c1] |
| 99 | 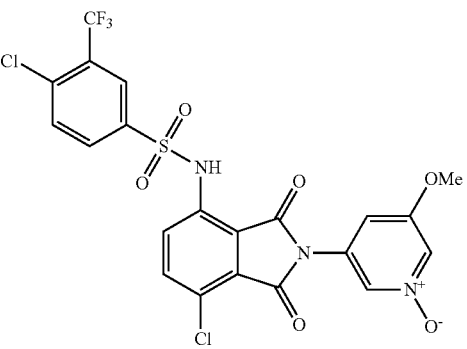 [SMILES: COc1cc(N2C(=O)c3c(Cl)ccc(NS(=O)(=O)c4ccc(Cl)c(C(F)(F)F)c4)c3C2=O)c[n+]([O-])c1] |
| 100 | 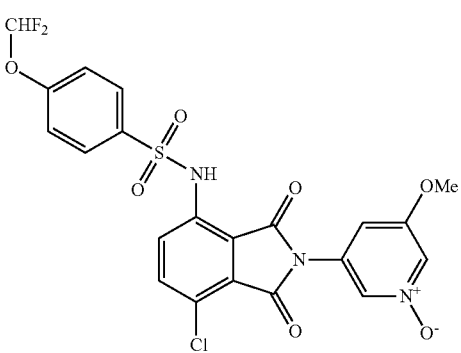 |

TABLE 1-continued

| Compound number | Structure |
|---|---|
| 101 | (4-trifluoromethylphenyl)sulfonyl-NH on chloro-isoindoline-1,3-dione N-substituted with 5-methoxypyridine N-oxide |
| 102 | (4-trifluoromethoxyphenyl)sulfonyl-NH on chloro-isoindoline-1,3-dione N-substituted with 5-methoxypyridine N-oxide |
| 103 | (4-tert-butylphenyl)sulfonyl-NH on chloro-isoindoline-1,3-dione N-substituted with 5-ethoxypyridine |
| 104 | (4-tert-butylphenyl)sulfonyl-NH on chloro-isoindoline-1,3-dione N-substituted with 5-methylpyridine |

TABLE 1-continued

| Compound number | Structure |
| --- | --- |
| 105 | 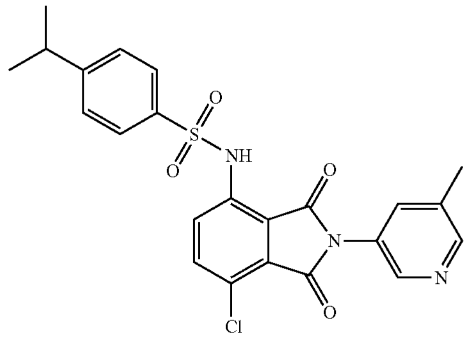 |
| 106 | 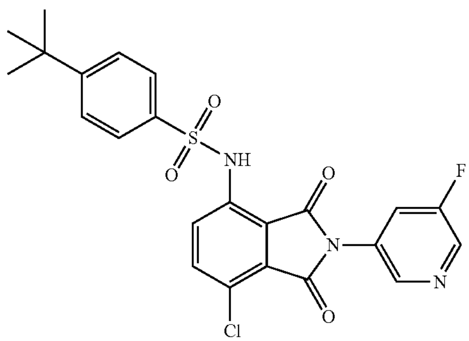 |
| 107 | 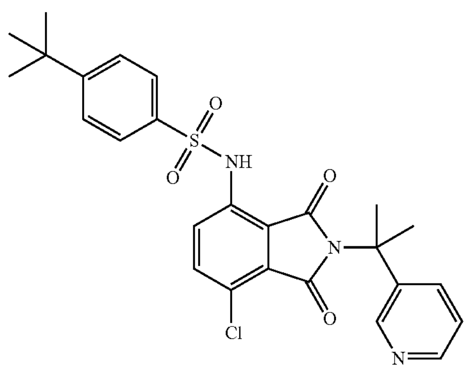 [SMILES: CC(C)(C)c1ccc(S(=O)(=O)Nc2ccc(Cl)c3c2C(=O)N(C(C)(C)c2cccnc2)C3=O)cc1] |
| 108 | 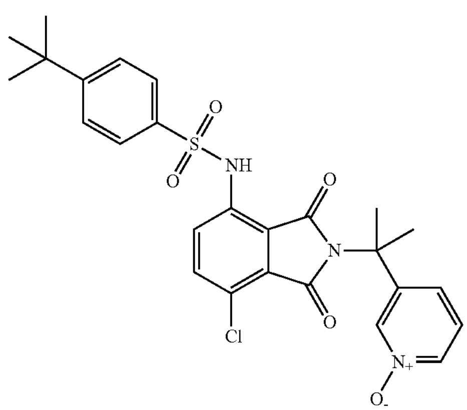 |

TABLE 1-continued
| Compound number | Structure |
|---|---|
| 109 | 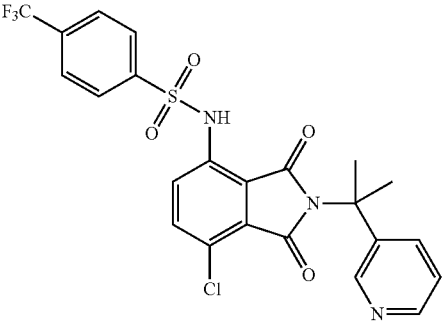 [SMILES: CC(C)(c1cccnc1)N1C(=O)c2c(Cl)ccc(NS(=O)(=O)c3ccc(C(F)(F)F)cc3)c2C1=O] |
| 110 | 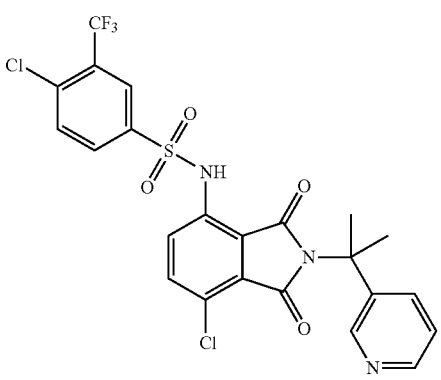 [SMILES: CC(C)(c1cccnc1)N1C(=O)c2c(Cl)ccc(NS(=O)(=O)c3ccc(Cl)c(C(F)(F)F)c3)c2C1=O] |
| 111 | 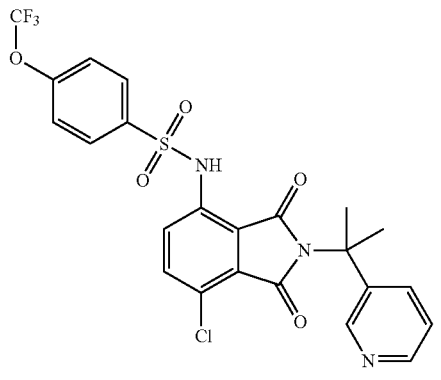 [SMILES: CC(C)(c1cccnc1)N1C(=O)c2c(Cl)ccc(NS(=O)(=O)c3ccc(OC(F)(F)F)cc3)c2C1=O] |
| 112 | 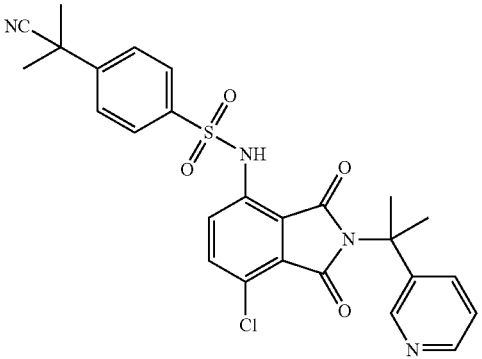 [SMILES: CC(C)(C#N)c1ccc(S(=O)(=O)Nc2ccc(Cl)c3c2C(=O)N(C(C)(C)c2cccnc2)C3=O)cc1] |

TABLE 1-continued
| Compound number | Structure |
|---|---|
| 113 | 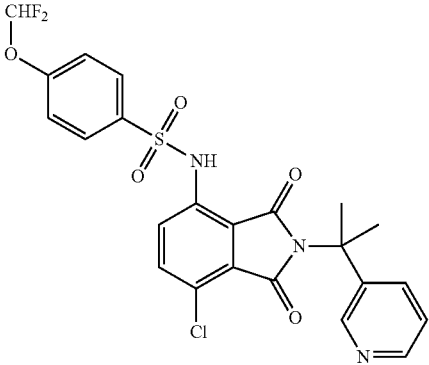 [SMILES: CC(C)(c1cccnc1)N1C(=O)c2c(Cl)ccc(NS(=O)(=O)c3ccc(OC(F)F)cc3)c2C1=O] |
| 114 | 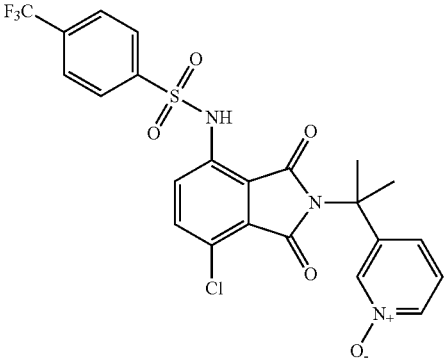 |
| 115 | 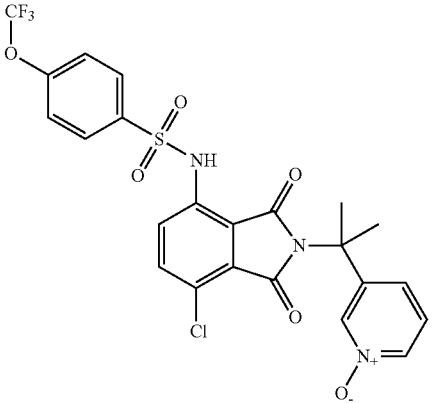 |
| 116 | 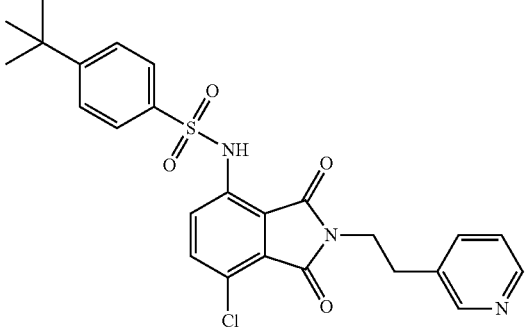 [SMILES: CC(C)(C)c1ccc(S(=O)(=O)Nc2ccc(Cl)c3c2C(=O)N(CCc2cccnc2)C3=O)cc1] |

TABLE 1-continued
| Compound number | Structure |
|---|---|
| 117 | 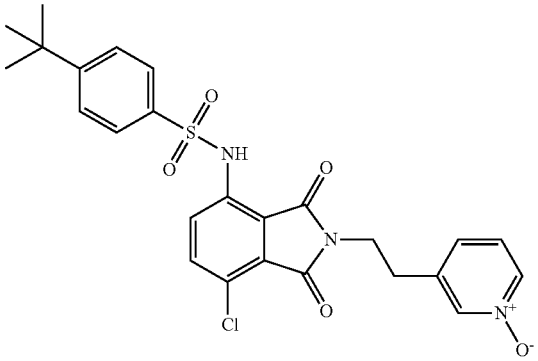 [SMILES: CC(C)(C)c1ccc(S(=O)(=O)Nc2ccc(Cl)c3c2C(=O)N(CCc2ccc[n+]([O-])c2)C3=O)cc1] |
| 118 | 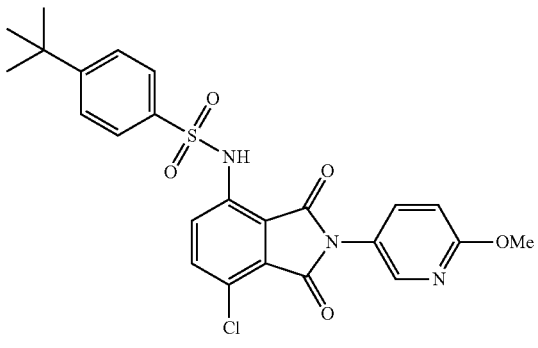 [SMILES: COc1ccc(N2C(=O)c3c(Cl)ccc(NS(=O)(=O)c4ccc(C(C)(C)C)cc4)c3C2=O)cn1] |
| 119 | 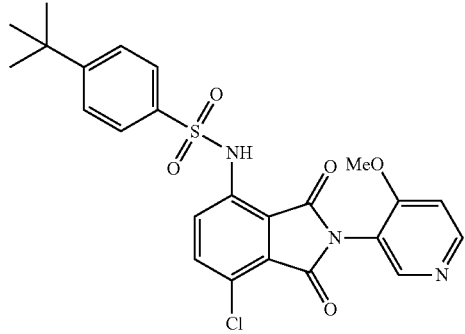 [SMILES: COc1ccncc1N1C(=O)c2c(Cl)ccc(NS(=O)(=O)c3ccc(C(C)(C)C)cc3)c2C1=O] |
| 120 | 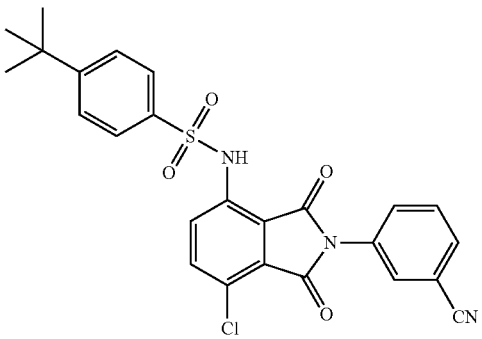 [SMILES: CC(C)(C)c1ccc(S(=O)(=O)Nc2ccc(Cl)c3c2C(=O)N(c2cccc(C#N)c2)C3=O)cc1] |

TABLE 1-continued
| Compound number | Structure |
|---|---|
| 121 | 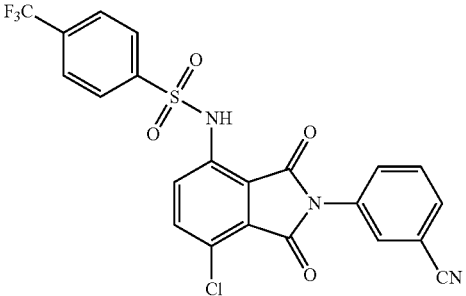 |
| 122 | 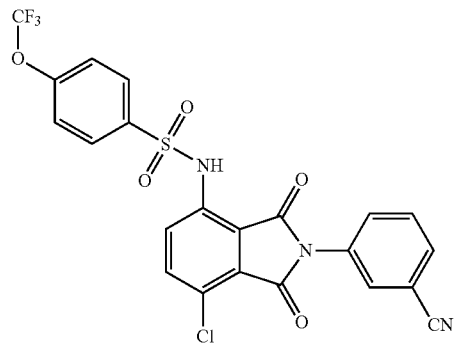 |
| 123 | 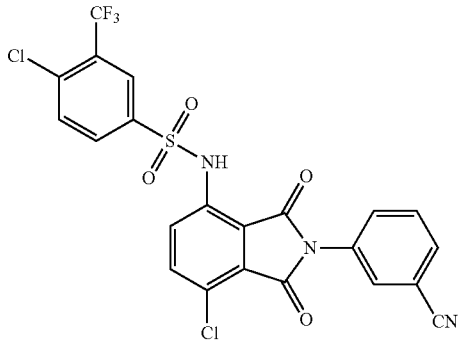 [SMILES: N#Cc1cccc(N2C(=O)c3c(Cl)ccc(NS(=O)(=O)c4ccc(Cl)c(C(F)(F)F)c4)c3C2=O)c1] |
| 124 | 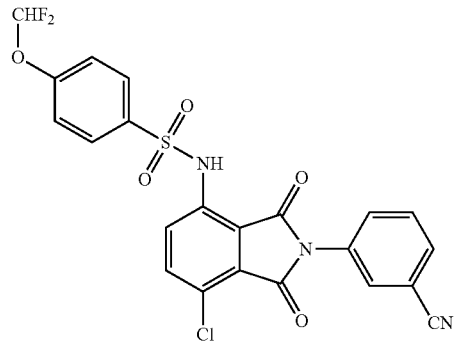 |

TABLE 1-continued
| Compound number | Structure |
|---|---|
| 125 | 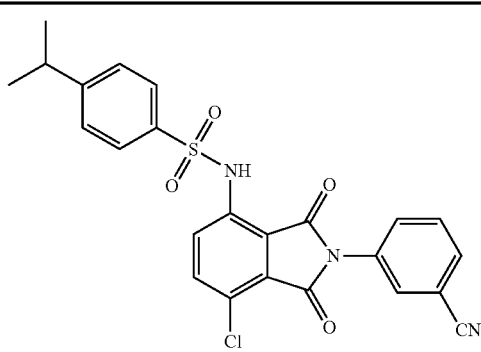 |
| 126 | 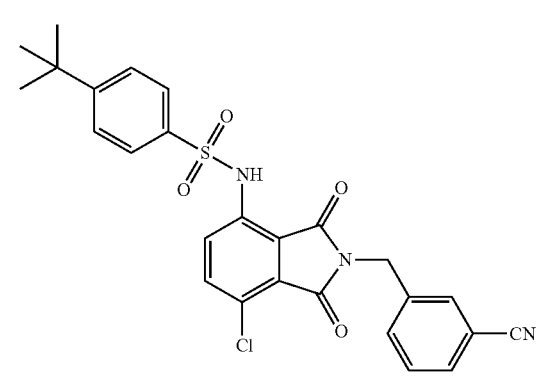 [SMILES: CC(C)(C)c1ccc(S(=O)(=O)Nc2ccc(Cl)c3c2C(=O)N(Cc2cccc(C#N)c2)C3=O)cc1] |
| 127 | 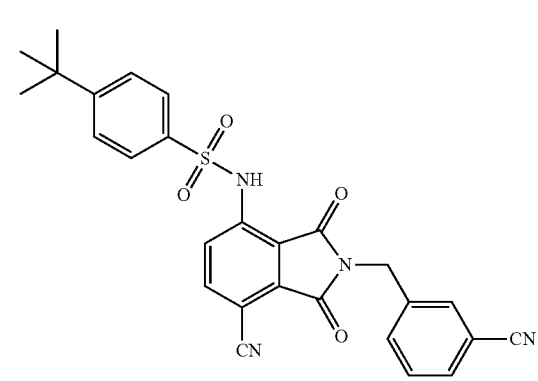 |
| 128 | 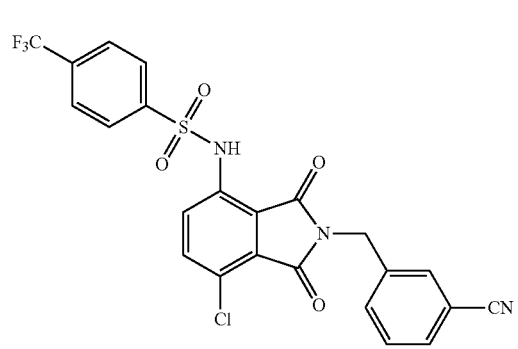 [SMILES: N#Cc1cccc(CN2C(=O)c3c(Cl)ccc(NS(=O)(=O)c4ccc(C(F)(F)F)cc4)c3C2=O)c1] |

TABLE 1-continued
| Compound number | Structure |
|---|---|
| 129 | 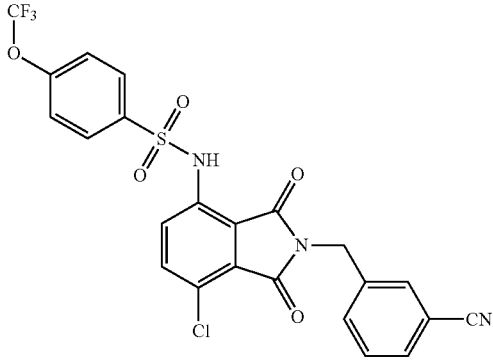 [SMILES: N#Cc1cccc(CN2C(=O)c3c(Cl)ccc(NS(=O)(=O)c4ccc(OC(F)(F)F)cc4)c3C2=O)c1] |
| 130 | 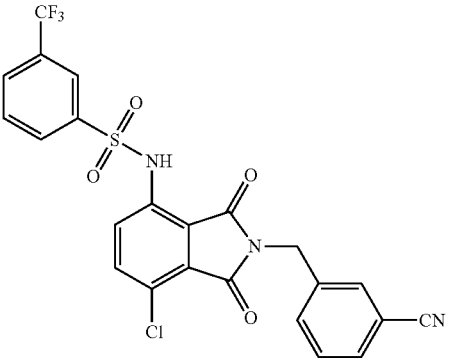 [SMILES: N#Cc1cccc(CN2C(=O)c3c(Cl)ccc(NS(=O)(=O)c4cccc(C(F)(F)F)c4)c3C2=O)c1] |
| 131 | 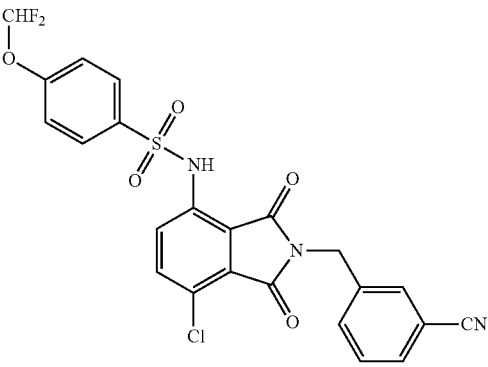 [SMILES: N#Cc1cccc(CN2C(=O)c3c(Cl)ccc(NS(=O)(=O)c4ccc(OC(F)F)cc4)c3C2=O)c1] |
| 132 | 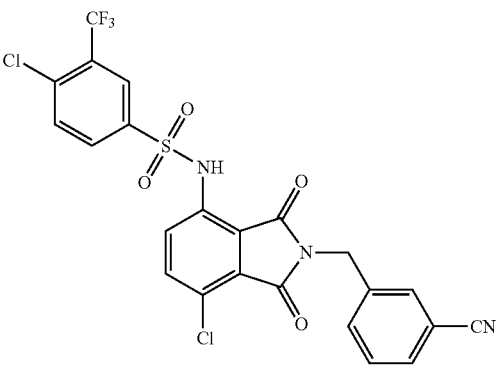 [SMILES: N#Cc1cccc(CN2C(=O)c3c(Cl)ccc(NS(=O)(=O)c4ccc(Cl)c(C(F)(F)F)c4)c3C2=O)c1] |

TABLE 1-continued
| Compound number | Structure |
|---|---|
| 133 | 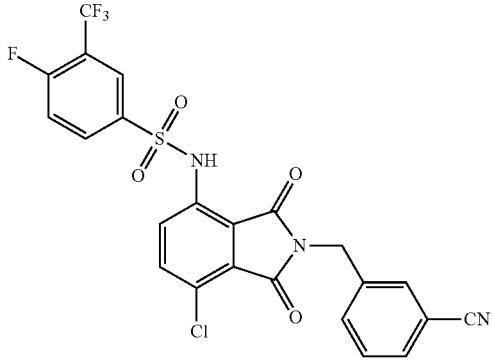 [SMILES: N#Cc1cccc(CN2C(=O)c3c(Cl)ccc(NS(=O)(=O)c4ccc(F)c(C(F)(F)F)c4)c3C2=O)c1] |
| 134 | 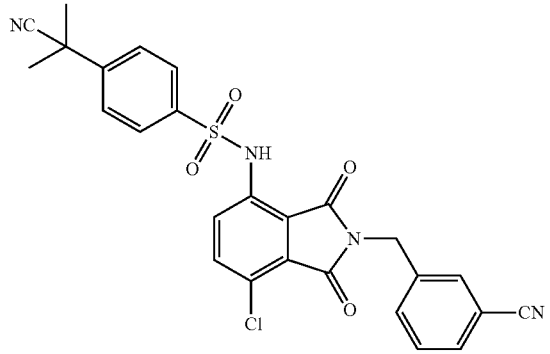 [SMILES: CC(C)(C#N)c1ccc(S(=O)(=O)Nc2ccc(Cl)c3c2C(=O)N(Cc2cccc(C#N)c2)C3=O)cc1] |
| 135 | 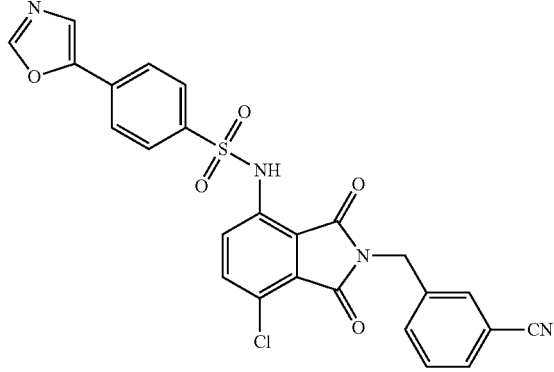 [SMILES: N#Cc1cccc(CN2C(=O)c3c(Cl)ccc(NS(=O)(=O)c4ccc(-c5cnco5)cc4)c3C2=O)c1] |
| 136 | 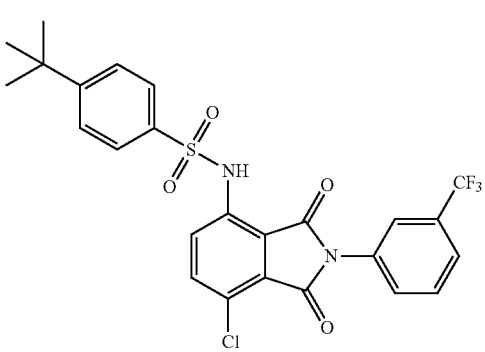 [SMILES: CC(C)(C)c1ccc(S(=O)(=O)Nc2ccc(Cl)c3c2C(=O)N(c2cccc(C(F)(F)F)c2)C3=O)cc1] |

TABLE 1-continued
| Compound number | Structure |
|---|---|
| 137 | 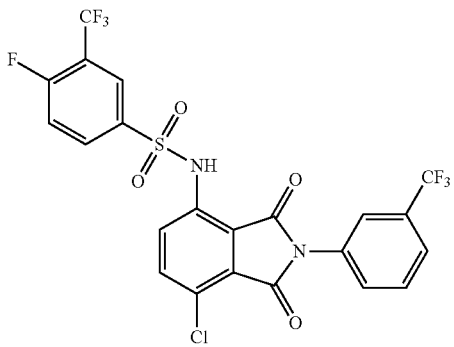 |
| 138 | 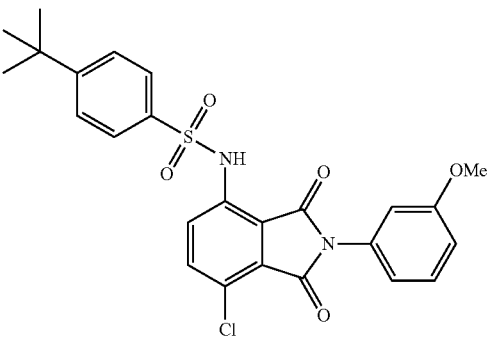 |
| 139 | 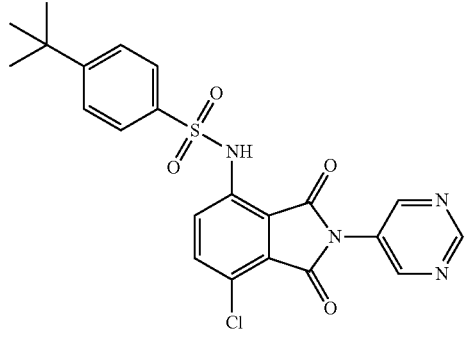 [SMILES: CC(C)(C)c1ccc(S(=O)(=O)Nc2ccc(Cl)c3c2C(=O)N(c2cncnc2)C3=O)cc1] |
| 140 | 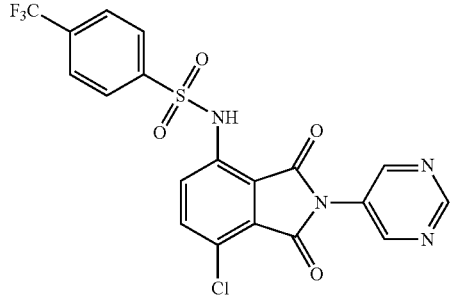 [SMILES: O=C1c2c(Cl)ccc(NS(=O)(=O)c3ccc(C(F)(F)F)cc3)c2C(=O)N1c1cncnc1] |

TABLE 1-continued
| Compound number | Structure |
|---|---|
| 141 | 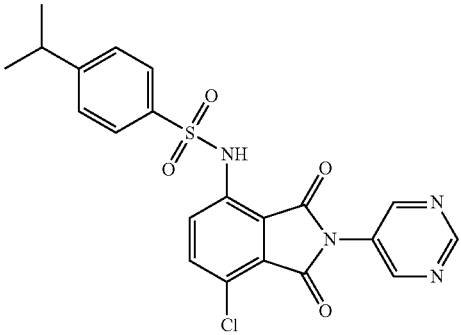 [SMILES: CC(C)c1ccc(S(=O)(=O)Nc2ccc(Cl)c3c2C(=O)N(c2cncnc2)C3=O)cc1] |
| 142 | 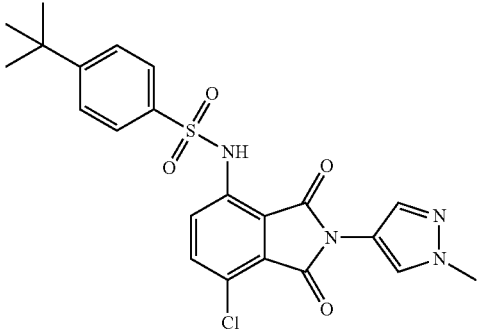 [SMILES: Cn1cc(N2C(=O)c3c(Cl)ccc(NS(=O)(=O)c4ccc(C(C)(C)C)cc4)c3C2=O)cn1] |
| 143 | 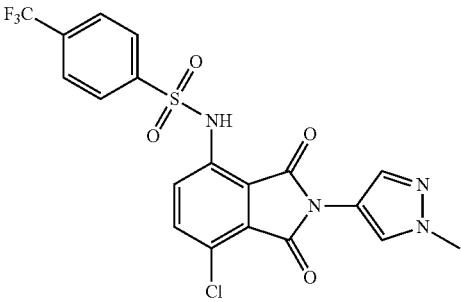 [SMILES: Cn1cc(N2C(=O)c3c(Cl)ccc(NS(=O)(=O)c4ccc(C(F)(F)F)cc4)c3C2=O)cn1] |
| 144 | 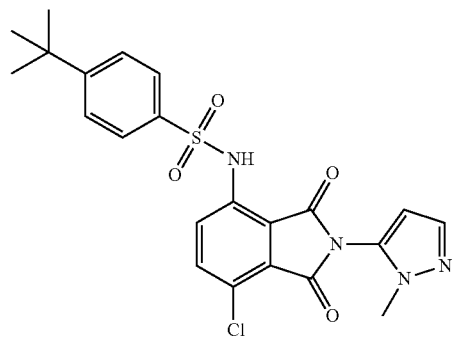 [SMILES: Cn1nccc1N1C(=O)c2c(Cl)ccc(NS(=O)(=O)c3ccc(C(C)(C)C)cc3)c2C1=O] |

TABLE 1-continued
| Compound number | Structure |
|---|---|
| 145 | 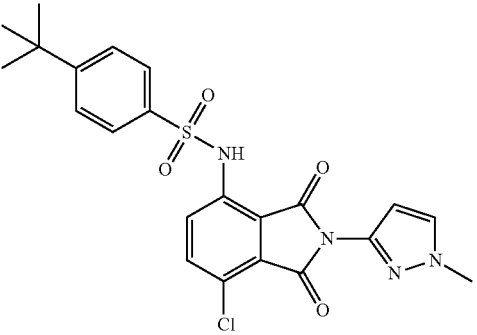 [SMILES: Cn1ccc(N2C(=O)c3c(Cl)ccc(NS(=O)(=O)c4ccc(C(C)(C)C)cc4)c3C2=O)n1] |
| 146 | 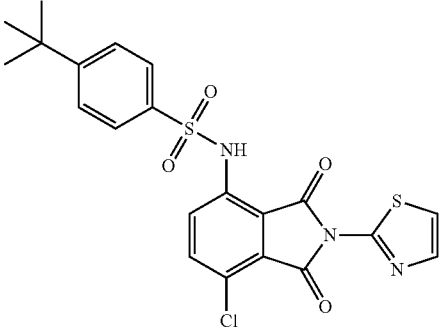 [SMILES: CC(C)(C)c1ccc(S(=O)(=O)Nc2ccc(Cl)c3c2C(=O)N(c2nccs2)C3=O)cc1] |
| 147 | 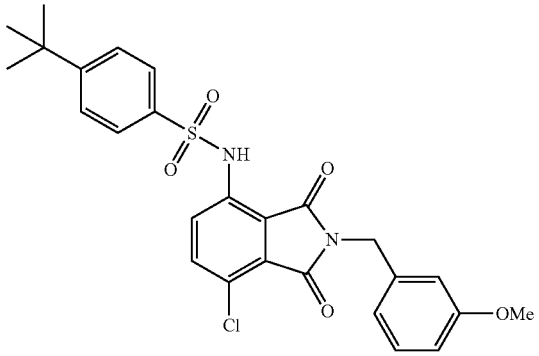 [SMILES: COc1cccc(CN2C(=O)c3c(Cl)ccc(NS(=O)(=O)c4ccc(C(C)(C)C)cc4)c3C2=O)c1] |
| 148 | 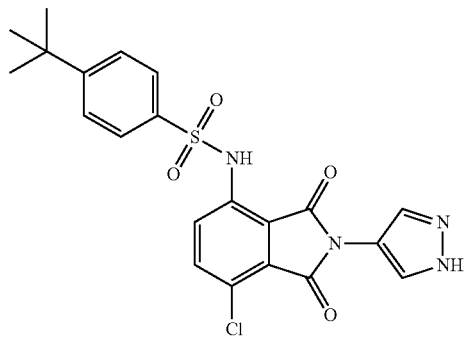 [SMILES: CC(C)(C)c1ccc(S(=O)(=O)Nc2ccc(Cl)c3c2C(=O)N(c2cn[nH]c2)C3=O)cc1] |

TABLE 1-continued
| Compound number | Structure |
|---|---|
| 149 | 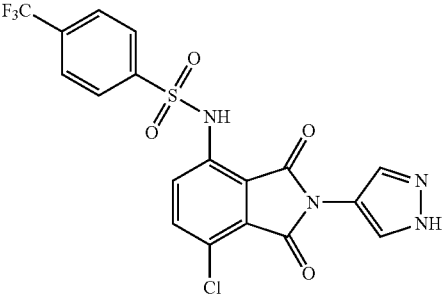 [SMILES: O=C1c2c(Cl)ccc(NS(=O)(=O)c3ccc(C(F)(F)F)cc3)c2C(=O)N1c1cn[nH]c1] |
| 150 | 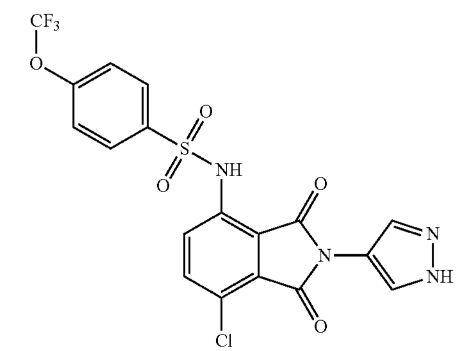 [SMILES: O=C1c2c(Cl)ccc(NS(=O)(=O)c3ccc(OC(F)(F)F)cc3)c2C(=O)N1c1cn[nH]c1] |
| 151 | 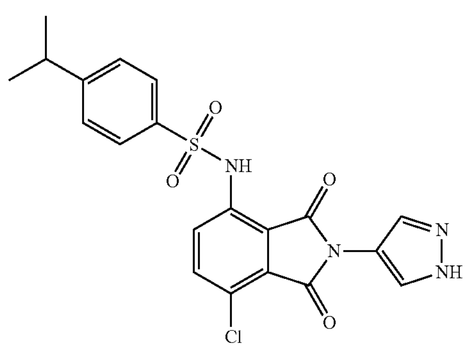 [SMILES: CC(C)c1ccc(S(=O)(=O)Nc2ccc(Cl)c3c2C(=O)N(c2cn[nH]c2)C3=O)cc1] |
| 152 | 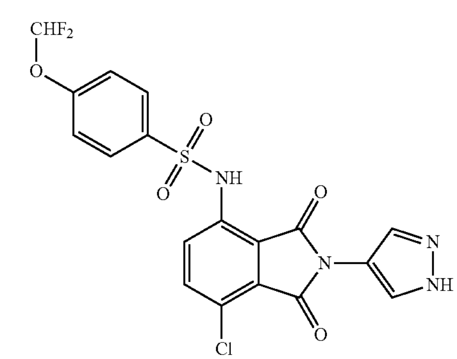 |

TABLE 1-continued

| Compound number | Structure |
|---|---|
| 153 | 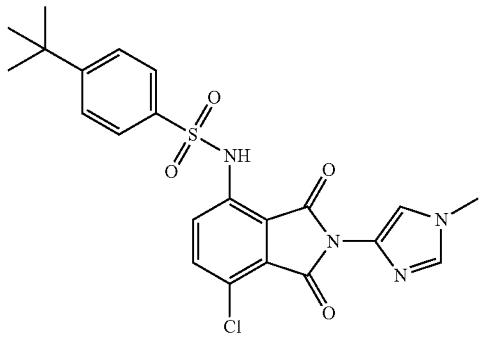 [SMILES: Cn1cnc(N2C(=O)c3c(Cl)ccc(NS(=O)(=O)c4ccc(C(C)(C)C)cc4)c3C2=O)c1] |
| 154 | 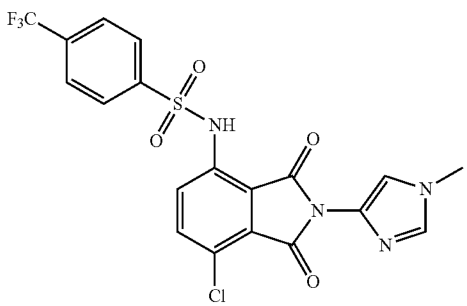 [SMILES: Cn1cnc(N2C(=O)c3c(Cl)ccc(NS(=O)(=O)c4ccc(C(F)(F)F)cc4)c3C2=O)c1] |
| 155 | 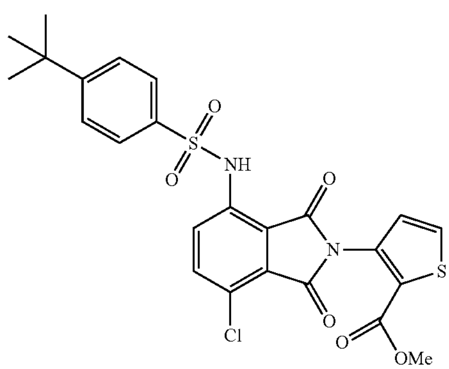 [SMILES: COC(=O)c1sccc1N1C(=O)c2c(Cl)ccc(NS(=O)(=O)c3ccc(C(C)(C)C)cc3)c2C1=O] |
| 156 | 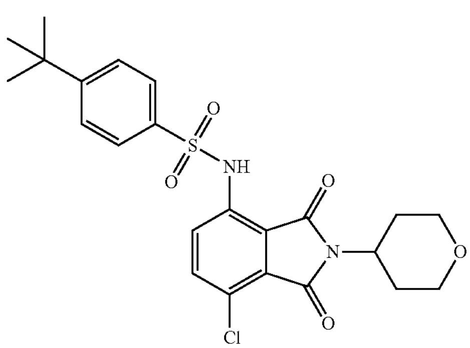 [SMILES: CC(C)(C)c1ccc(S(=O)(=O)Nc2ccc(Cl)c3c2C(=O)N(C2CCOCC2)C3=O)cc1] |

TABLE 1-continued

| Compound number | Structure |
|---|---|
| 157 | 4-tert-butyl-N-(7-methyl-1,3-dioxo-2-(pyridin-3-yl)isoindolin-4-yl)benzenesulfonamide |
| 158 | 4-tert-butyl-N-(7-methyl-1,3-dioxo-2-(1-oxidopyridin-3-yl)isoindolin-4-yl)benzenesulfonamide |
| 159 | N-(7-methyl-1,3-dioxo-2-(pyridin-3-yl)isoindolin-4-yl)-4-(trifluoromethyl)benzenesulfonamide |
| 160 | 4-tert-butyl-N-(7-methyl-1,3-dioxo-2-(pyridin-3-ylmethyl)isoindolin-4-yl)benzenesulfonamide |

TABLE 1-continued
| Compound number | Structure |
|---|---|
| 161 | 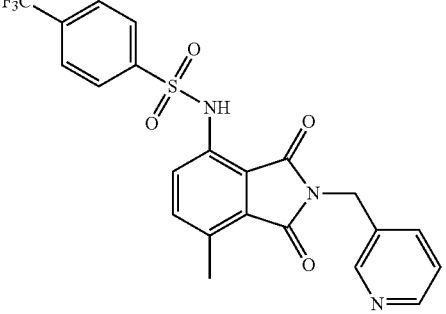 |
| 162 | 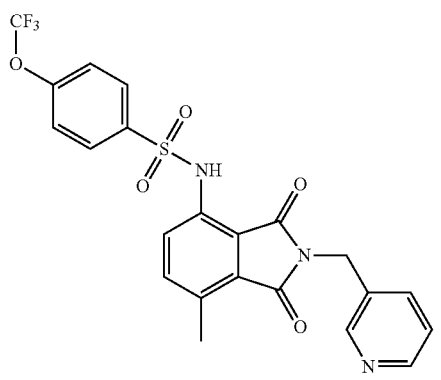 |
| 163 | 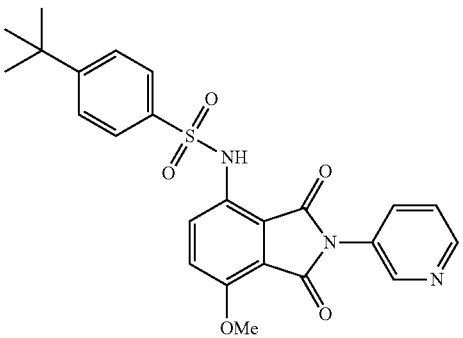 [SMILES: COc1ccc(NS(=O)(=O)c2ccc(C(C)(C)C)cc2)c2c1C(=O)N(c1cccnc1)C2=O] |
| 164 | 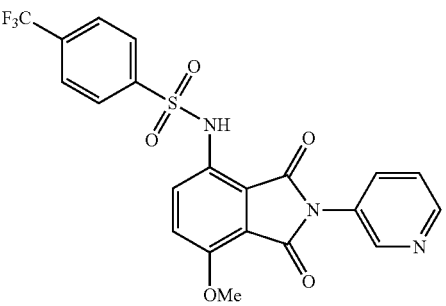 [SMILES: COc1ccc(NS(=O)(=O)c2ccc(C(F)(F)F)cc2)c2c1C(=O)N(c1cccnc1)C2=O] |

TABLE 1-continued
| Compound number | Structure |
|---|---|
| 165 | 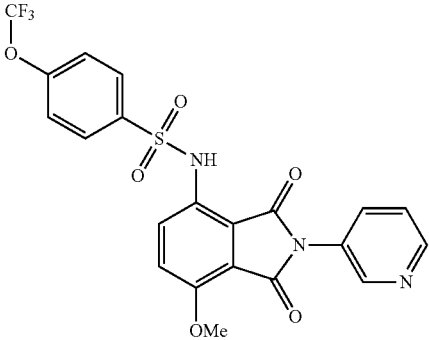 [SMILES: COc1ccc(NS(=O)(=O)c2ccc(OC(F)(F)F)cc2)c2c1C(=O)N(c1cccnc1)C2=O] |
| 166 | 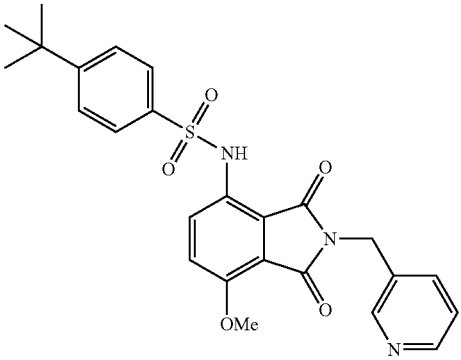 [SMILES: COc1ccc(NS(=O)(=O)c2ccc(C(C)(C)C)cc2)c2c1C(=O)N(Cc1cccnc1)C2=O] |
| 167 | 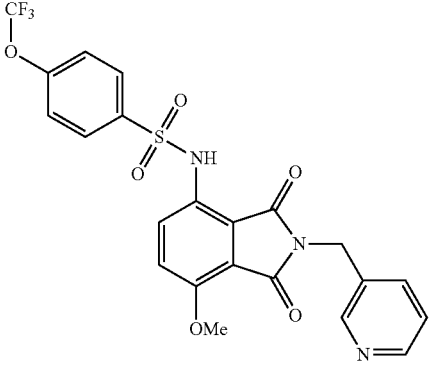 [SMILES: COc1ccc(NS(=O)(=O)c2ccc(OC(F)(F)F)cc2)c2c1C(=O)N(Cc1cccnc1)C2=O] |
| 168 | 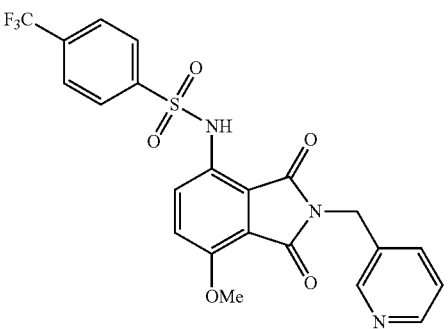 |

TABLE 1-continued
| Compound number | Structure |
|---|---|
| 169 | 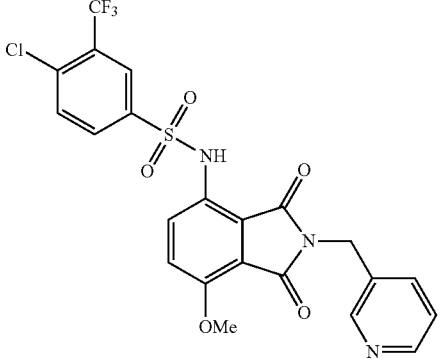 |
| 170 | 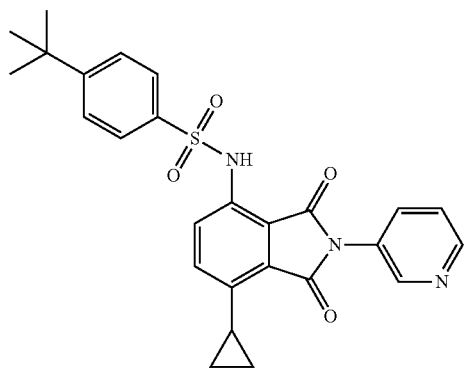 [SMILES: CC(C)(C)c1ccc(S(=O)(=O)Nc2ccc(C3CC3)c3c2C(=O)N(c2cccnc2)C3=O)cc1] |
| 171 | 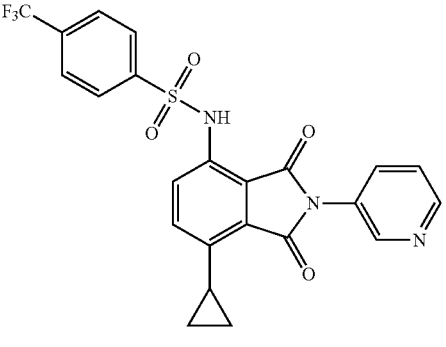 [SMILES: O=C1c2c(NS(=O)(=O)c3ccc(C(F)(F)F)cc3)ccc(C3CC3)c2C(=O)N1c1cccnc1] |
| 172 | 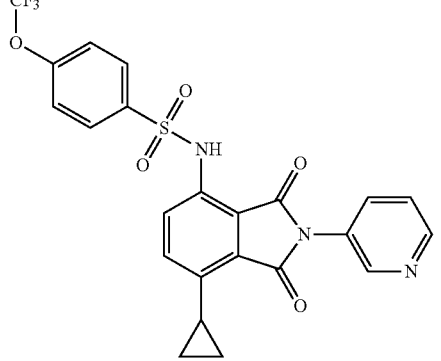 |

TABLE 1-continued
| Compound number | Structure |
|---|---|
| 173 | 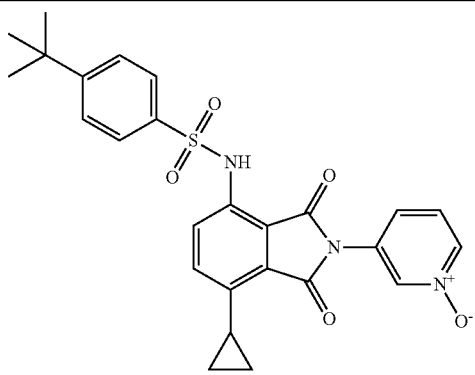 |
| 174 | 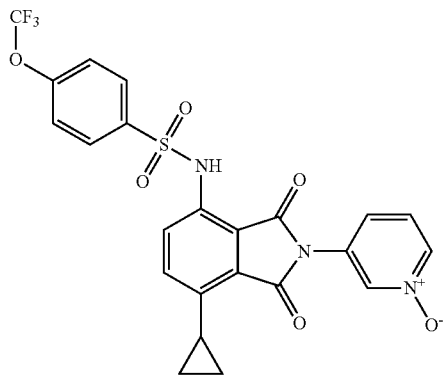 [SMILES: O=C1c2c(NS(=O)(=O)c3ccc(OC(F)(F)F)cc3)ccc(C3CC3)c2C(=O)N1c1ccc[n+]([O-])c1] |
| 175 | 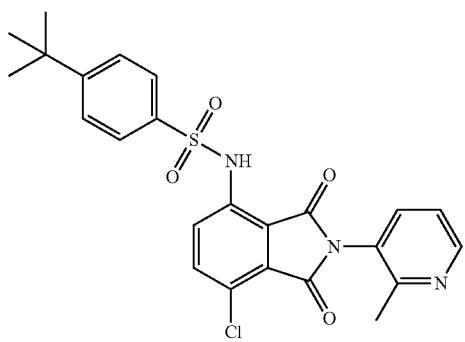 [SMILES: Cc1ncccc1N1C(=O)c2c(Cl)ccc(NS(=O)(=O)c3ccc(C(C)(C)C)cc3)c2C1=O] |
| 176 | 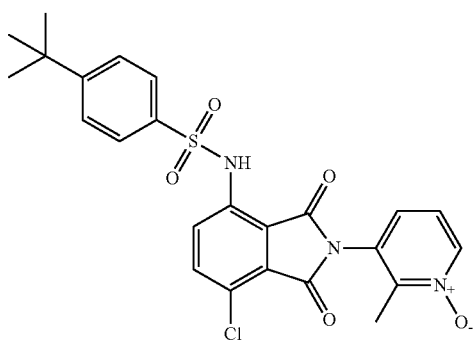 |

TABLE 1-continued
| Compound number | Structure |
|---|---|
| 177 | 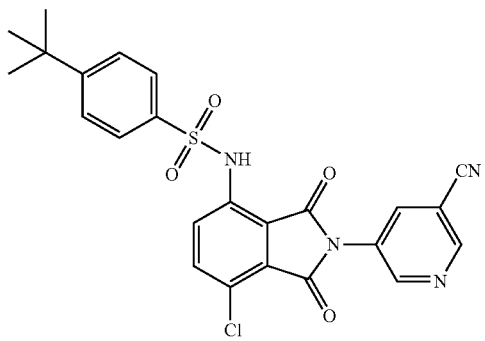 [SMILES: CC(C)(C)c1ccc(S(=O)(=O)Nc2ccc(Cl)c3c2C(=O)N(c2cncc(C#N)c2)C3=O)cc1] |
| 178 | 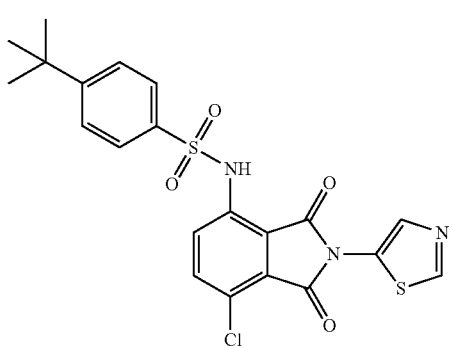 [SMILES: CC(C)(C)c1ccc(S(=O)(=O)Nc2ccc(Cl)c3c2C(=O)N(c2cncs2)C3=O)cc1] |
| 179 | 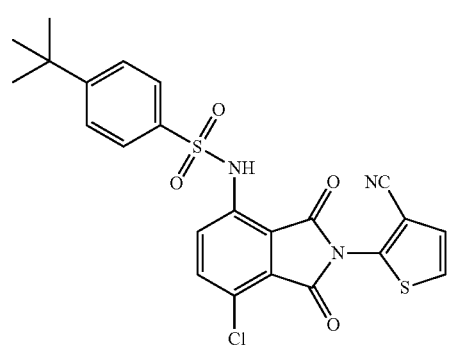 [SMILES: CC(C)(C)c1ccc(S(=O)(=O)Nc2ccc(Cl)c3c2C(=O)N(c2sccc2C#N)C3=O)cc1] |
| 180 | 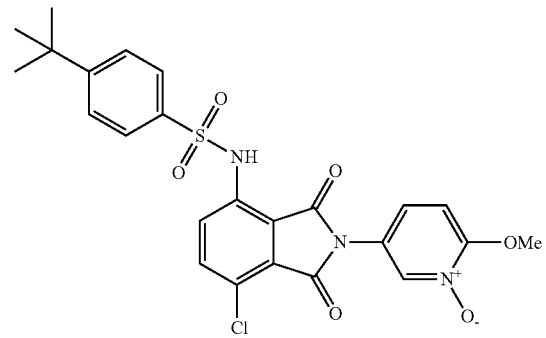 |

TABLE 1-continued

| Compound number | Structure |
|---|---|
| 181 | 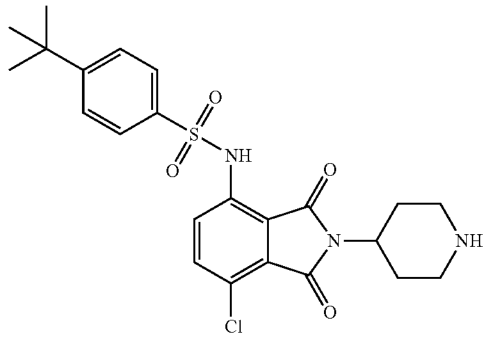 [SMILES: CC(C)(C)c1ccc(S(=O)(=O)Nc2ccc(Cl)c3c2C(=O)N(C2CCNCC2)C3=O)cc1] |
| 182 | 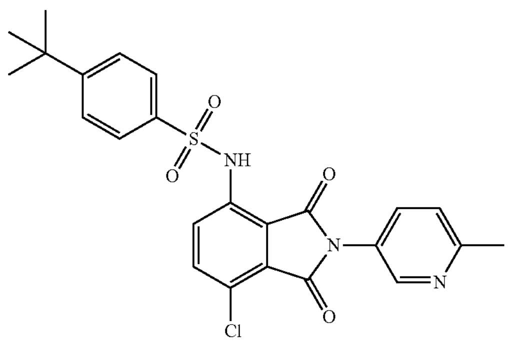 |
| 183 | 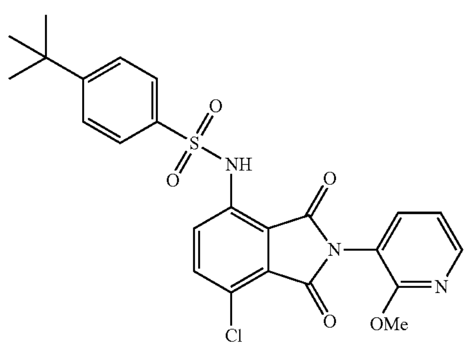 [SMILES: COc1ncccc1N1C(=O)c2c(Cl)ccc(NS(=O)(=O)c3ccc(C(C)(C)C)cc3)c2C1=O] |
| 184 | 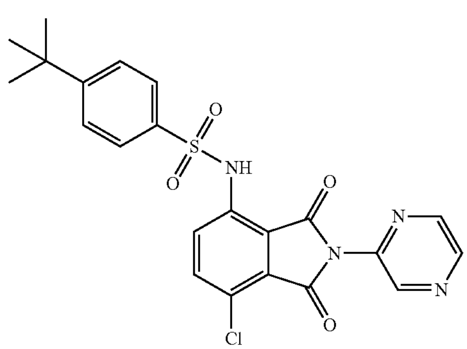 [SMILES: CC(C)(C)c1ccc(S(=O)(=O)Nc2ccc(Cl)c3c2C(=O)N(c2cnccn2)C3=O)cc1] |

TABLE 1-continued
| Compound number | Structure |
|---|---|
| 185 | 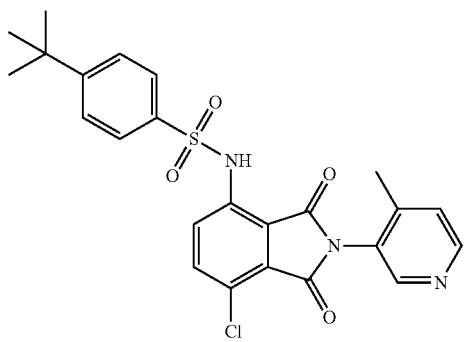 [SMILES: Cc1ccncc1N1C(=O)c2c(Cl)ccc(NS(=O)(=O)c3ccc(C(C)(C)C)cc3)c2C1=O] |
| 186 | 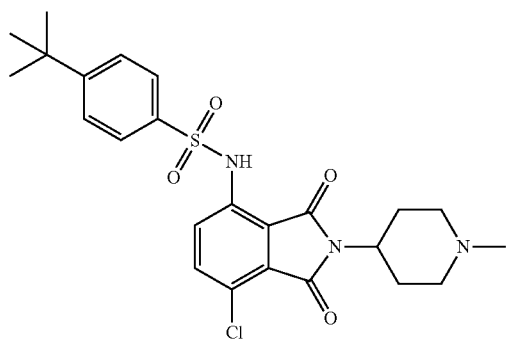 [SMILES: CN1CCC(N2C(=O)c3c(Cl)ccc(NS(=O)(=O)c4ccc(C(C)(C)C)cc4)c3C2=O)CC1] |
| 187 | 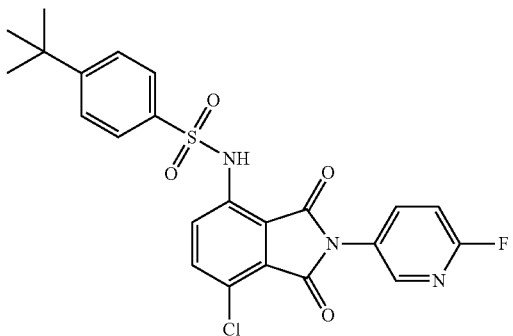 [SMILES: CC(C)(C)c1ccc(S(=O)(=O)Nc2ccc(Cl)c3c2C(=O)N(c2ccc(F)nc2)C3=O)cc1] |
| 188 | 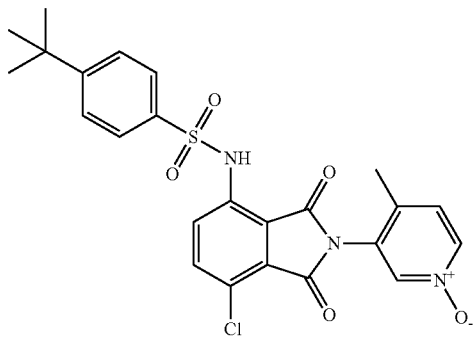 |

TABLE 1-continued

| Compound number | Structure |
|---|---|
| 189 | 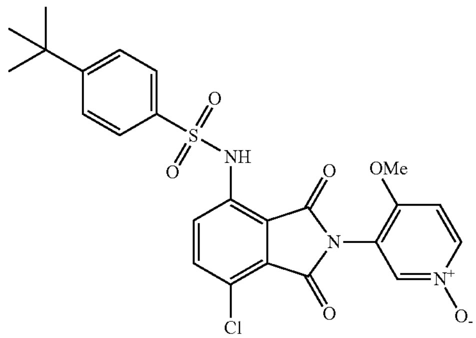 |
| 190 | 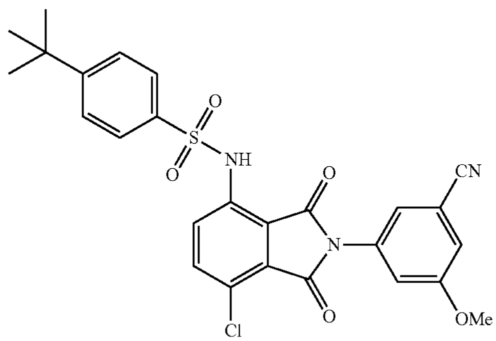 [SMILES: COc1cc(C#N)cc(N2C(=O)c3c(Cl)ccc(NS(=O)(=O)c4ccc(C(C)(C)C)cc4)c3C2=O)c1] |
| 191 | 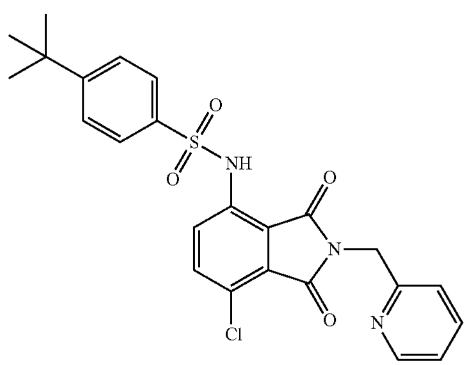 [SMILES: CC(C)(C)c1ccc(S(=O)(=O)Nc2ccc(Cl)c3c2C(=O)N(Cc2ccccn2)C3=O)cc1] |
| 192 | 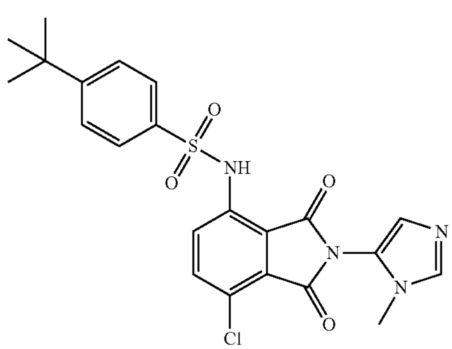 [SMILES: Cn1cncc1N1C(=O)c2c(Cl)ccc(NS(=O)(=O)c3ccc(C(C)(C)C)cc3)c2C1=O] |

TABLE 1-continued
| Compound number | Structure |
|---|---|
| 193 | 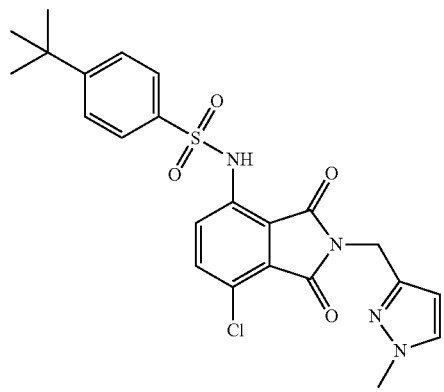 [SMILES: Cn1ccc(CN2C(=O)c3c(Cl)ccc(NS(=O)(=O)c4ccc(C(C)(C)C)cc4)c3C2=O)n1] |
| 194 | 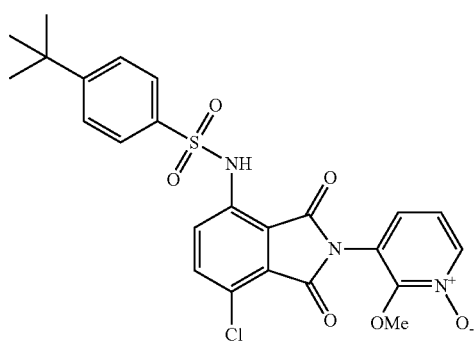 |
| 195 | 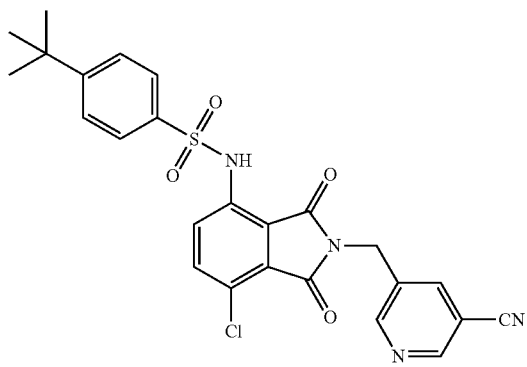 [SMILES: CC(C)(C)c1ccc(S(=O)(=O)Nc2ccc(Cl)c3c2C(=O)N(Cc2cncc(C#N)c2)C3=O)cc1] |
| 196 | 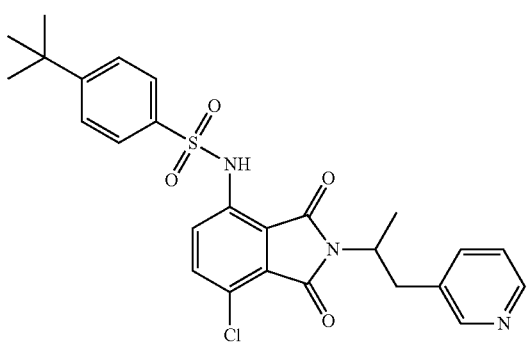 [SMILES: CC(Cc1cccnc1)N1C(=O)c2c(Cl)ccc(NS(=O)(=O)c3ccc(C(C)(C)C)cc3)c2C1=O] |

TABLE 1-continued
| Compound number | Structure |
| --- | --- |
| 197 | 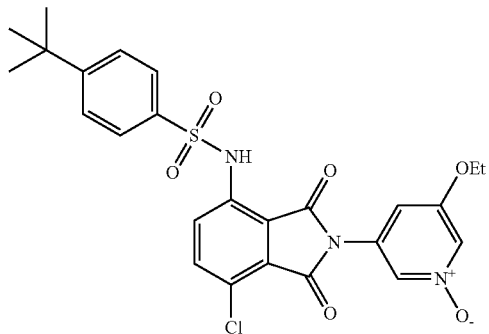 |
| 198 | 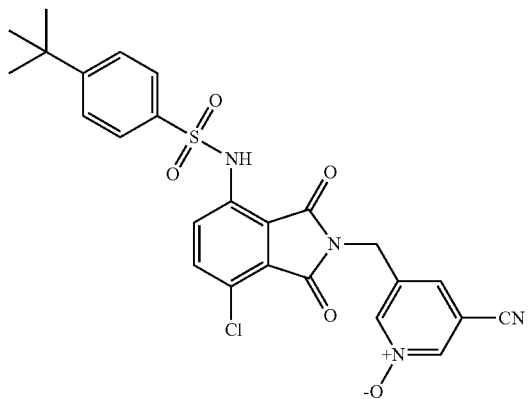 |
| 199 | 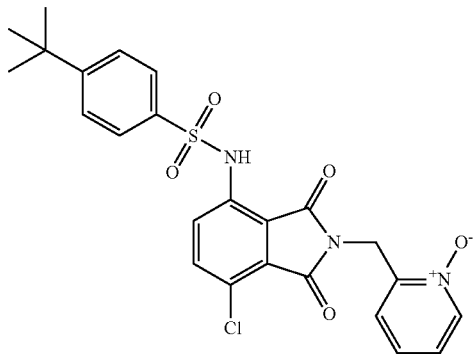 [SMILES: CC(C)(C)c1ccc(S(=O)(=O)Nc2ccc(Cl)c3c2C(=O)N(Cc2cccc[n+]2[O-])C3=O)cc1] |
| 200 | 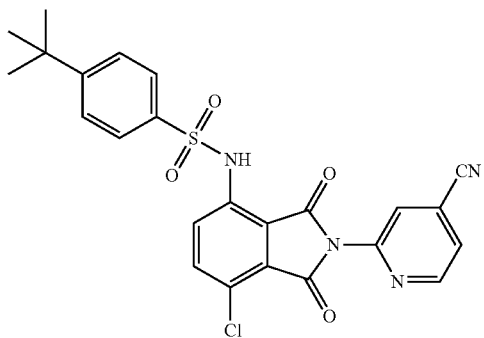 [SMILES: CC(C)(C)c1ccc(S(=O)(=O)Nc2ccc(Cl)c3c2C(=O)N(c2cc(C#N)ccn2)C3=O)cc1] |

TABLE 1-continued
| Compound number | Structure |
|---|---|
| 201 | 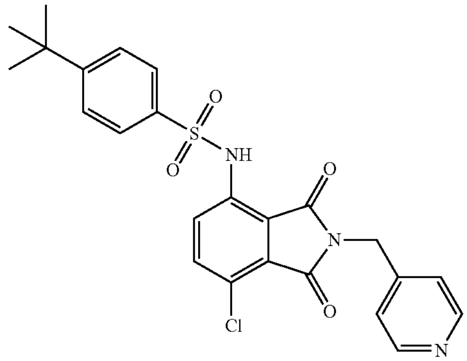 [SMILES: CC(C)(C)c1ccc(S(=O)(=O)Nc2ccc(Cl)c3c2C(=O)N(Cc2ccncc2)C3=O)cc1] |
| 202 | 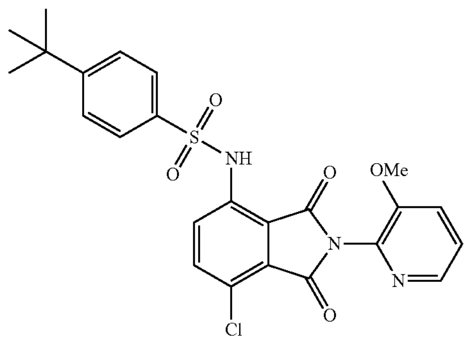 [SMILES: COc1cccnc1N1C(=O)c2c(Cl)ccc(NS(=O)(=O)c3ccc(C(C)(C)C)cc3)c2C1=O] |
| 203 | 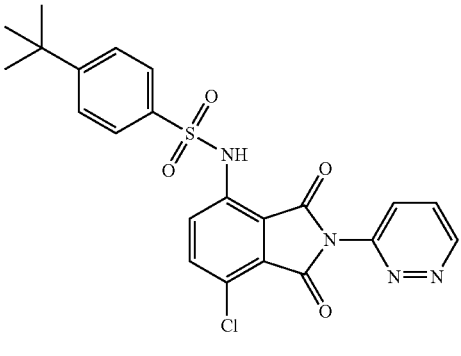 |
| 204 | 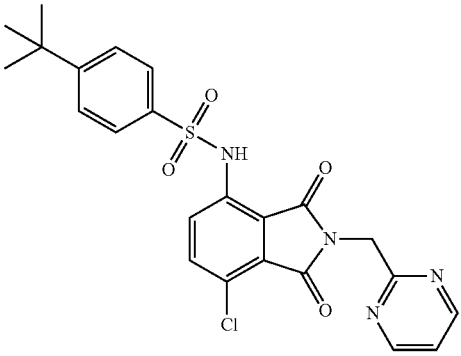 [SMILES: CC(C)(C)c1ccc(S(=O)(=O)Nc2ccc(Cl)c3c2C(=O)N(Cc2ncccn2)C3=O)cc1] |

TABLE 1-continued
| Compound number | Structure |
| --- | --- |
| 205 | 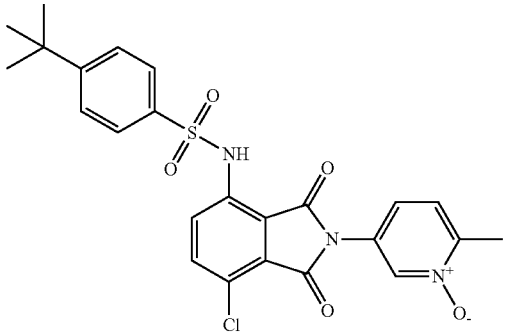 |
| 206 | 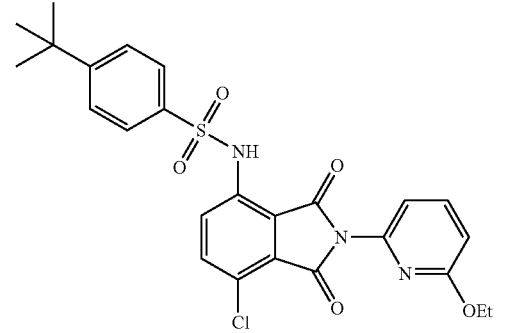 [SMILES: CCOc1cccc(N2C(=O)c3c(Cl)ccc(NS(=O)(=O)c4ccc(C(C)(C)C)cc4)c3C2=O)n1] |
| 207 | 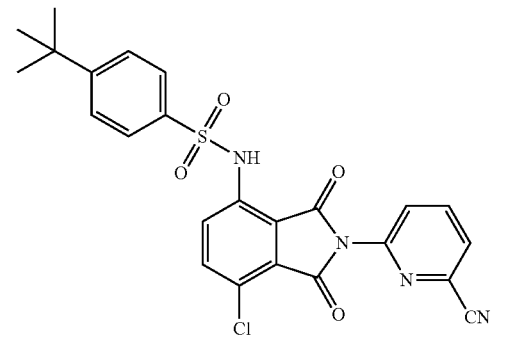 [SMILES: CC(C)(C)c1ccc(S(=O)(=O)Nc2ccc(Cl)c3c2C(=O)N(c2cccc(C#N)n2)C3=O)cc1] |
| 208 | 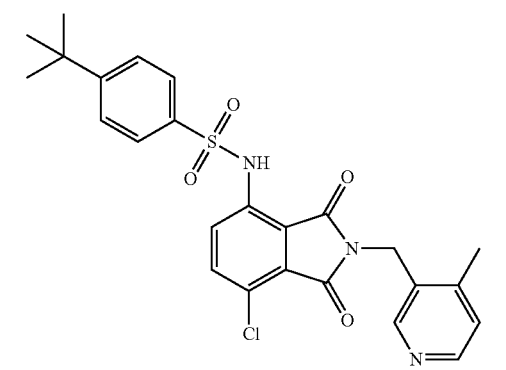 [SMILES: Cc1ccncc1CN1C(=O)c2c(Cl)ccc(NS(=O)(=O)c3ccc(C(C)(C)C)cc3)c2C1=O] |

TABLE 1-continued
| Compound number | Structure |
|---|---|
| 209 | 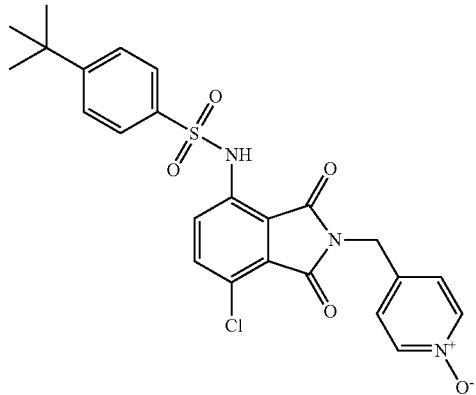 [SMILES: CC(C)(C)c1ccc(S(=O)(=O)Nc2ccc(Cl)c3c2C(=O)N(Cc2cc[n+]([O-])cc2)C3=O)cc1] |
| 210 | 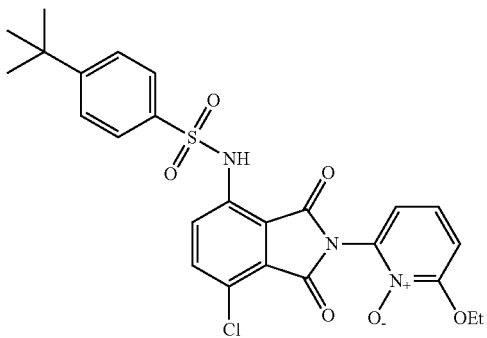 |
| 211 | 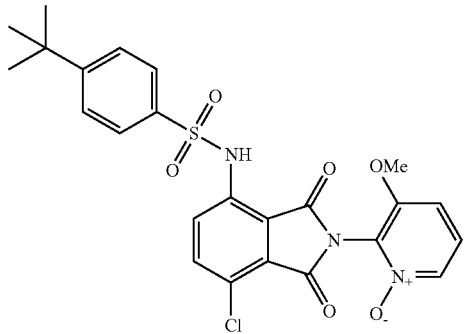 |
| 212 | 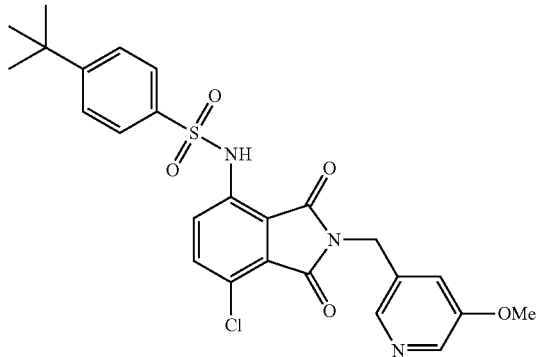 [SMILES: COc1cncc(CN2C(=O)c3c(Cl)ccc(NS(=O)(=O)c4ccc(C(C)(C)C)cc4)c3C2=O)c1] |

TABLE 1-continued
| Compound number | Structure |
|---|---|
| 213 | 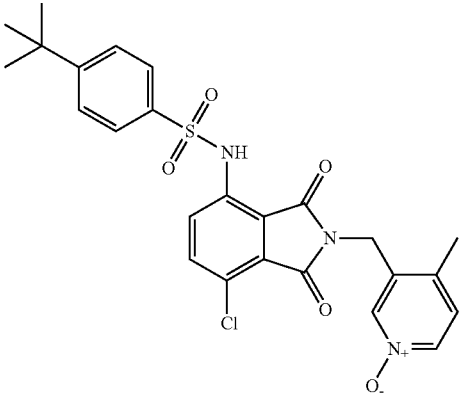 |
| 214 | 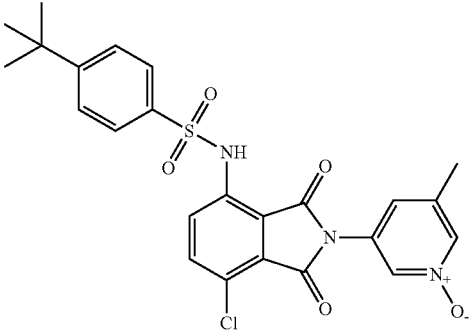 |
| 215 | 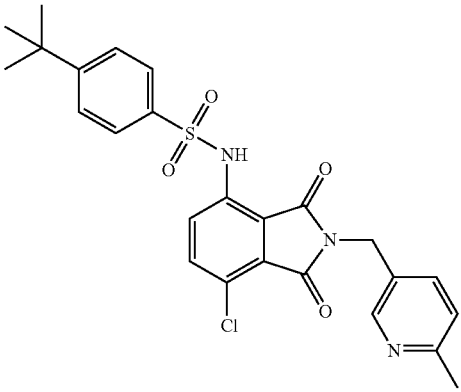 [SMILES: Cc1ccc(CN2C(=O)c3c(Cl)ccc(NS(=O)(=O)c4ccc(C(C)(C)C)cc4)c3C2=O)cn1] |
| 216 | 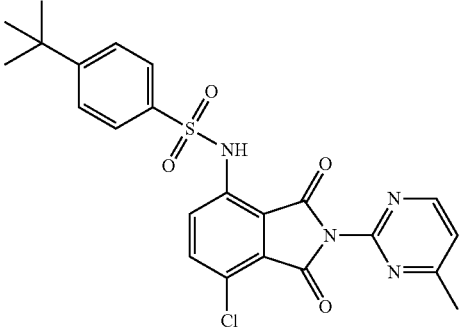 [SMILES: Cc1ccnc(N2C(=O)c3c(Cl)ccc(NS(=O)(=O)c4ccc(C(C)(C)C)cc4)c3C2=O)n1] |

TABLE 1-continued
| Compound number | Structure |
|---|---|
| 217 | 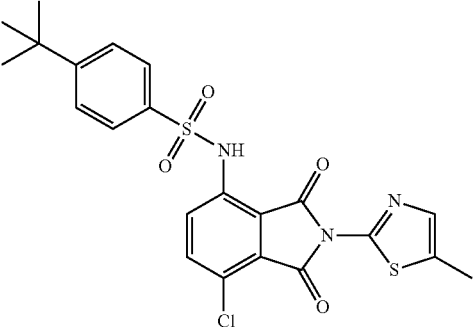 [SMILES: Cc1cnc(N2C(=O)c3c(Cl)ccc(NS(=O)(=O)c4ccc(C(C)(C)C)cc4)c3C2=O)s1] |
| 218 | 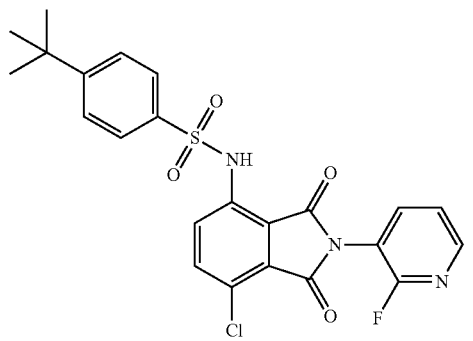 |
| 219 | 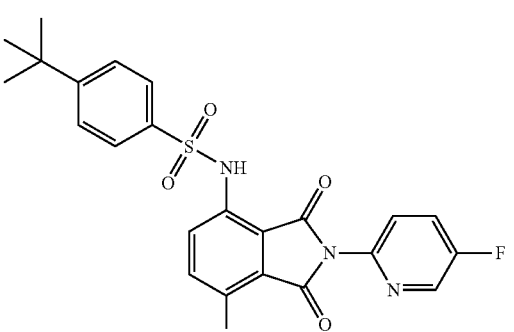 |
| 220 | 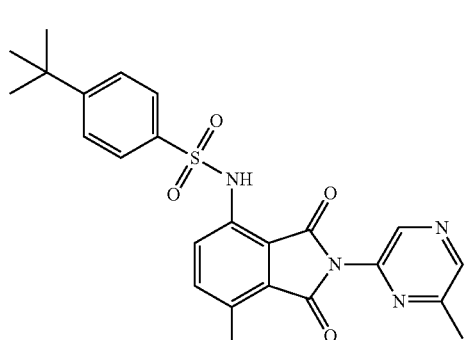 |

TABLE 1-continued
| Compound number | Structure |
|---|---|
| 221 | 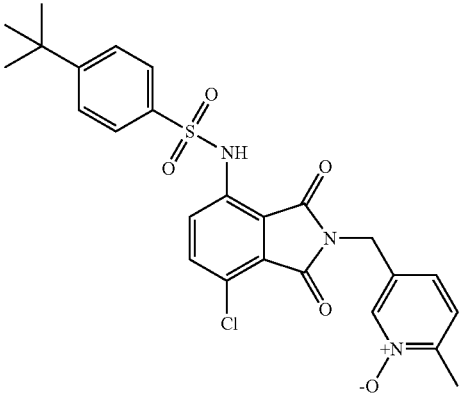 |
| 222 | 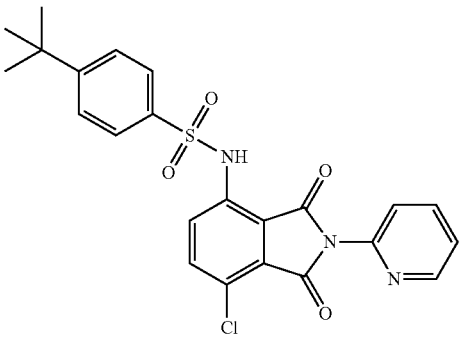 [SMILES: CC(C)(C)c1ccc(S(=O)(=O)Nc2ccc(Cl)c3c2C(=O)N(c2ccccn2)C3=O)cc1] |
| 223 | 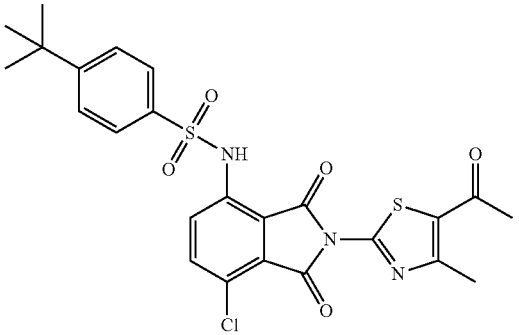 [SMILES: CC(=O)c1sc(N2C(=O)c3c(Cl)ccc(NS(=O)(=O)c4ccc(C(C)(C)C)cc4)c3C2=O)nc1C] |
| 224 | 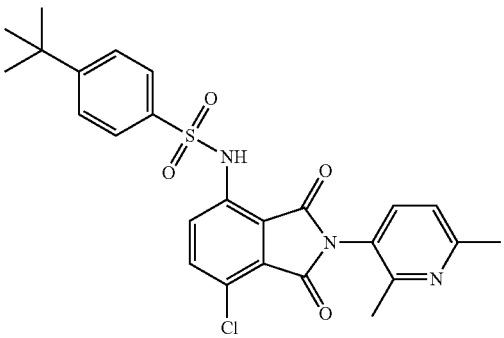 [SMILES: Cc1ccc(N2C(=O)c3c(Cl)ccc(NS(=O)(=O)c4ccc(C(C)(C)C)cc4)c3C2=O)c(C)n1] |

TABLE 1-continued
| Compound number | Structure |
|---|---|
| 225 | 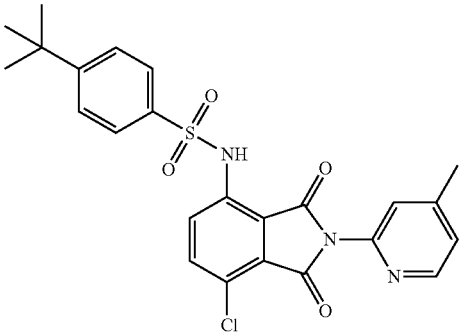 [SMILES: Cc1ccnc(N2C(=O)c3c(Cl)ccc(NS(=O)(=O)c4ccc(C(C)(C)C)cc4)c3C2=O)c1] |
| 226 | 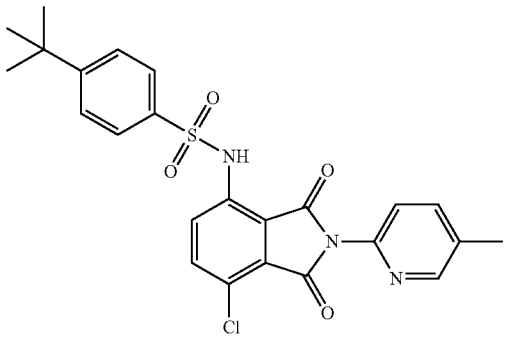 |
| 227 | 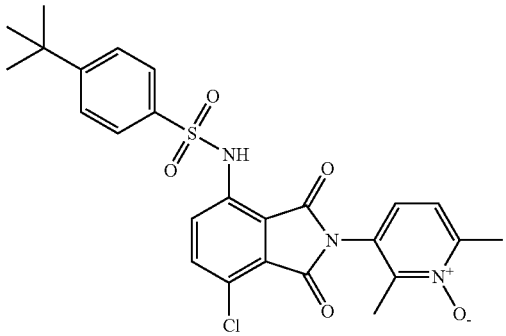 |
| 228 | 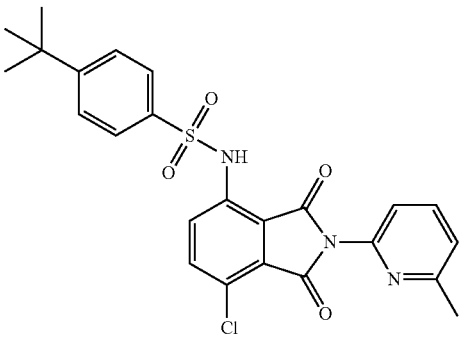 [SMILES: Cc1cccc(N2C(=O)c3c(Cl)ccc(NS(=O)(=O)c4ccc(C(C)(C)C)cc4)c3C2=O)n1] |

TABLE 1-continued
| Compound number | Structure |
|---|---|
| 229 | 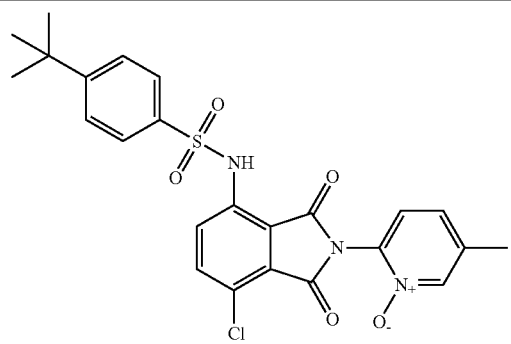 |
| 230 | 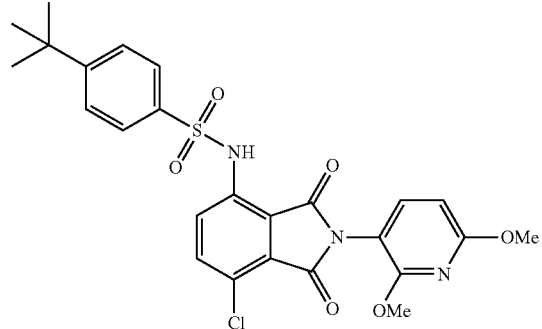 [SMILES: COc1ccc(N2C(=O)c3c(Cl)ccc(NS(=O)(=O)c4ccc(C(C)(C)C)cc4)c3C2=O)c(OC)n1] |
| 231 | 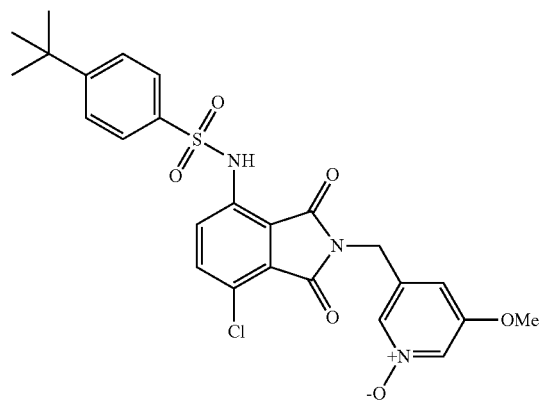 |
| 232 | 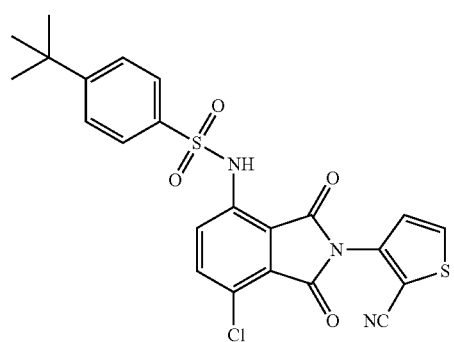 [SMILES: CC(C)(C)c1ccc(S(=O)(=O)Nc2ccc(Cl)c3c2C(=O)N(c2ccsc2C#N)C3=O)cc1] |

133
134
TABLE 1-continued
| Compound number | Structure |
|---|---|
| 233 | 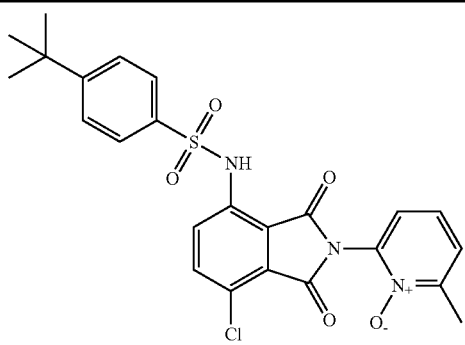 |
| 234 | 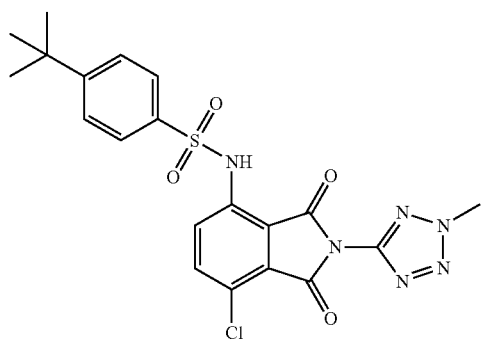 [SMILES: Cn1nnc(N2C(=O)c3c(Cl)ccc(NS(=O)(=O)c4ccc(C(C)(C)C)cc4)c3C2=O)n1] |
| 235 | 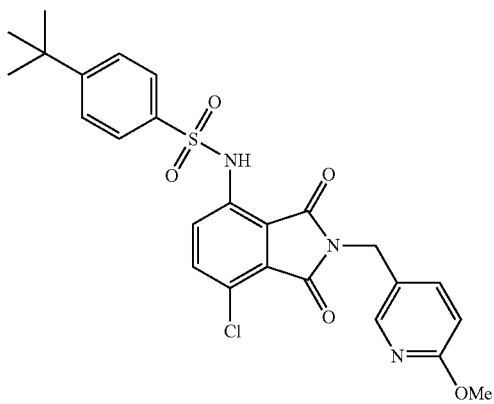 [SMILES: COc1ccc(CN2C(=O)c3c(Cl)ccc(NS(=O)(=O)c4ccc(C(C)(C)C)cc4)c3C2=O)cn1] |
| 236 | 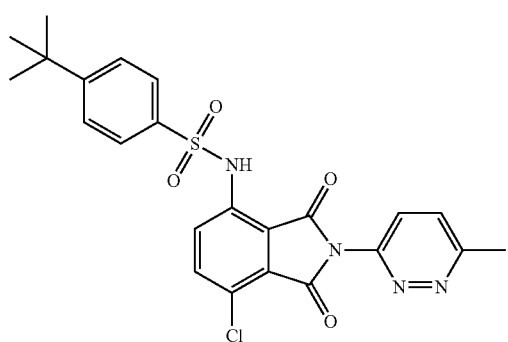 |

TABLE 1-continued

| Compound number | Structure |
| --- | --- |
| 237 | 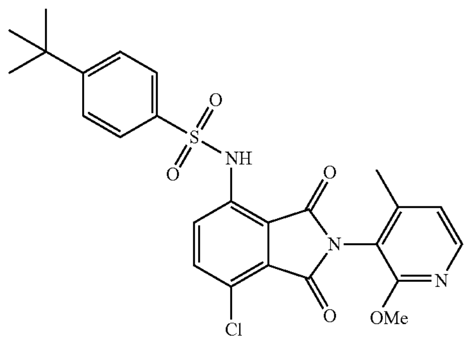 [SMILES: COc1nccc(C)c1N1C(=O)c2c(Cl)ccc(NS(=O)(=O)c3ccc(C(C)(C)C)cc3)c2C1=O] |
| 238 | 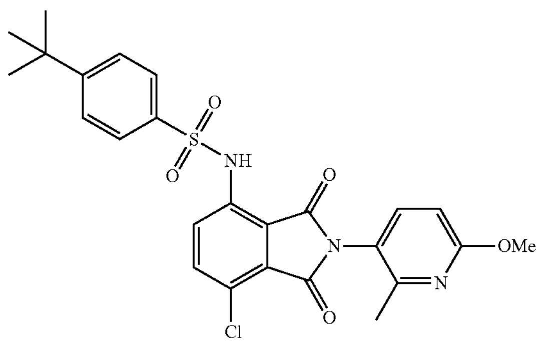 [SMILES: COc1ccc(N2C(=O)c3c(Cl)ccc(NS(=O)(=O)c4ccc(C(C)(C)C)cc4)c3C2=O)c(C)n1] |
| 239 | 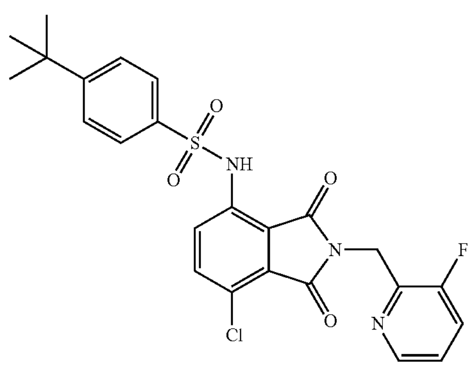 [SMILES: CC(C)(C)c1ccc(S(=O)(=O)Nc2ccc(Cl)c3c2C(=O)N(Cc2ncccc2F)C3=O)cc1] |
| 240 | 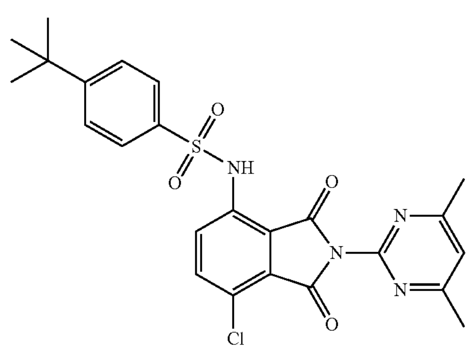 [SMILES: Cc1cc(C)nc(N2C(=O)c3c(Cl)ccc(NS(=O)(=O)c4ccc(C(C)(C)C)cc4)c3C2=O)n1] |

137
TABLE 1-continued
| Compound number | Structure |
|---|---|
| 241 | 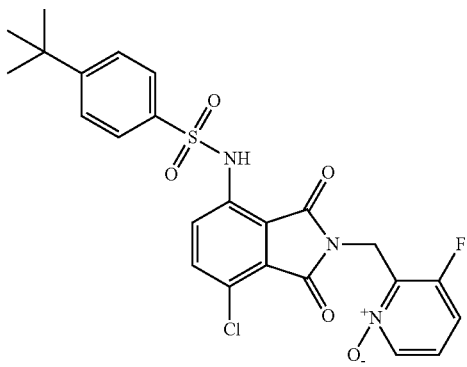 |
| 242 | 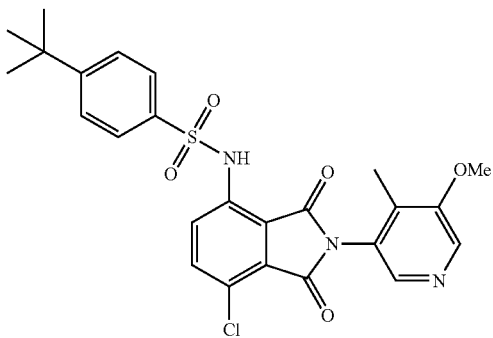 [SMILES: COc1cncc(N2C(=O)c3c(Cl)ccc(NS(=O)(=O)c4ccc(C(C)(C)C)cc4)c3C2=O)c1C] |
| 243 | 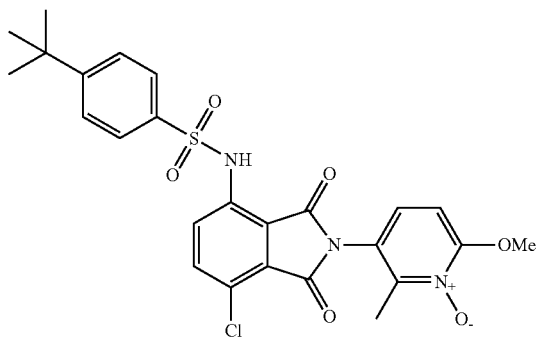 |
| 244 | 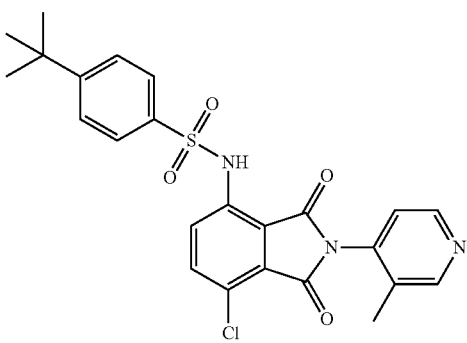 [SMILES: Cc1cnccc1N1C(=O)c2c(Cl)ccc(NS(=O)(=O)c3ccc(C(C)(C)C)cc3)c2C1=O] |

TABLE 1-continued

| Compound number | Structure |
| --- | --- |
| 245 | 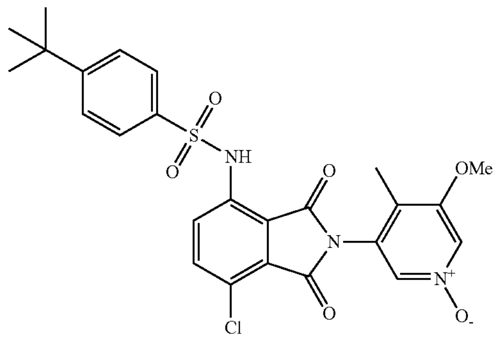 |
| 246 | 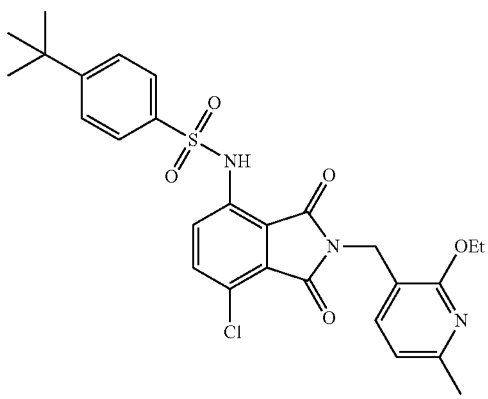 [SMILES: CCOc1nc(C)ccc1CN1C(=O)c2c(Cl)ccc(NS(=O)(=O)c3ccc(C(C)(C)C)cc3)c2C1=O] |
| 247 | 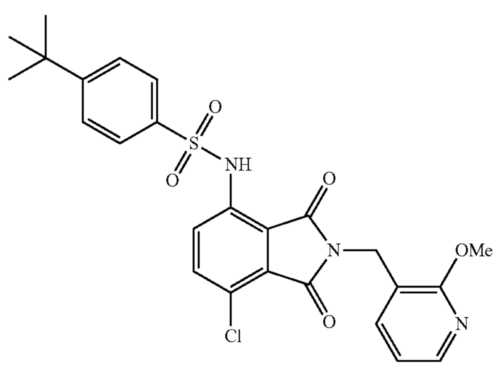 [SMILES: COc1ncccc1CN1C(=O)c2c(Cl)ccc(NS(=O)(=O)c3ccc(C(C)(C)C)cc3)c2C1=O] |
| 248 | 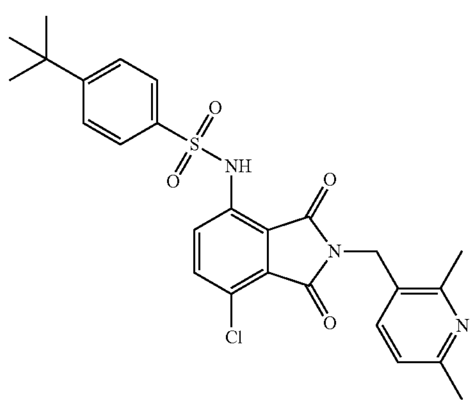 [SMILES: Cc1ccc(CN2C(=O)c3c(Cl)ccc(NS(=O)(=O)c4ccc(C(C)(C)C)cc4)c3C2=O)c(C)n1] |

141
142
TABLE 1-continued

| Compound number | Structure |
|---|---|
| 249 | *(4-tert-butylphenyl)sulfonamide linked to NH of 4-chloro-7-substituted isoindoline-1,3-dione N-substituted with pyrimidin-4-yl)* |
| 250 | *(4-tert-butylphenyl)sulfonamide linked to NH of 4-chloro-7-substituted isoindoline-1,3-dione N-substituted with pyrimidin-2-yl)* |
| 251 | *(4-tert-butylphenyl)sulfonamide linked to NH of 4-chloro-7-substituted isoindoline-1,3-dione N-substituted with (5-methylpyridin-2-yl)methyl)* |
| 252 | *(4-tert-butylphenyl)sulfonamide linked to NH of 4-chloro-7-substituted isoindoline-1,3-dione N-substituted with ((2,6-dimethylpyridin-1-oxide-3-yl)methyl))* |

TABLE 1-continued
| Compound number | Structure |
|---|---|
| 253 | 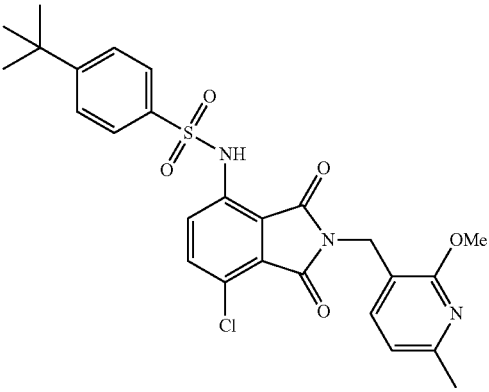 [SMILES: COc1nc(C)ccc1CN1C(=O)c2c(Cl)ccc(NS(=O)(=O)c3ccc(C(C)(C)C)cc3)c2C1=O] |
| 254 | 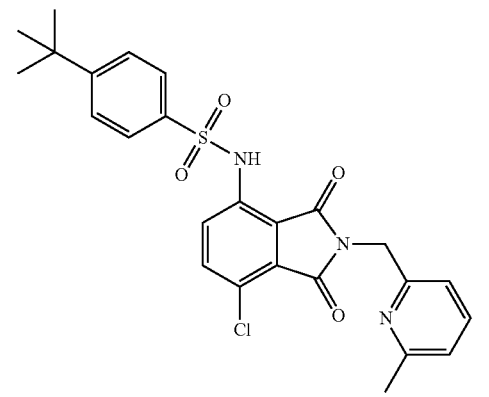 [SMILES: Cc1cccc(CN2C(=O)c3c(Cl)ccc(NS(=O)(=O)c4ccc(C(C)(C)C)cc4)c3C2=O)n1] |
| 255 | 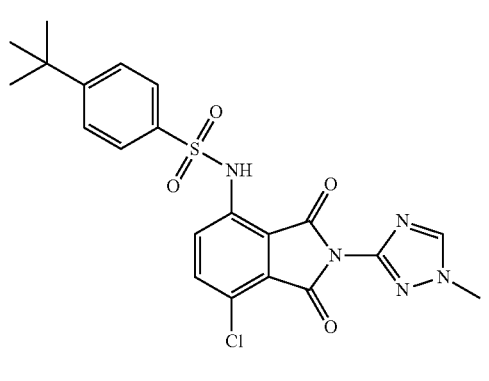 [SMILES: Cn1cnc(N2C(=O)c3c(Cl)ccc(NS(=O)(=O)c4ccc(C(C)(C)C)cc4)c3C2=O)n1] |
| 256 | 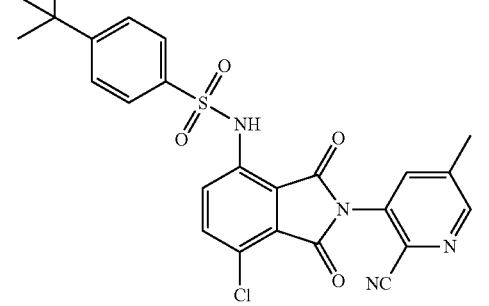 |

TABLE 1-continued

| Compound number | Structure |
|---|---|
| 257 | 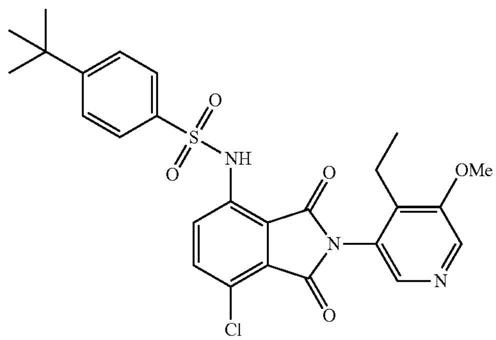 [SMILES: CCc1c(OC)cncc1N1C(=O)c2c(Cl)ccc(NS(=O)(=O)c3ccc(C(C)(C)C)cc3)c2C1=O] |
| 258 | 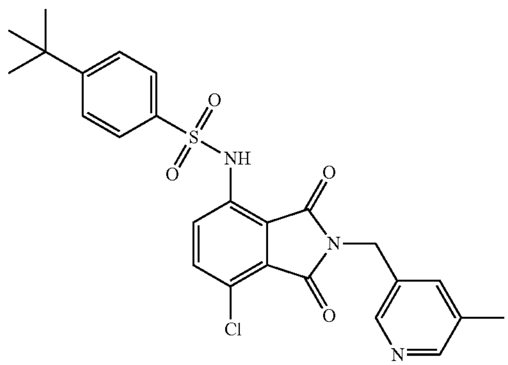 [SMILES: Cc1cncc(CN2C(=O)c3c(Cl)ccc(NS(=O)(=O)c4ccc(C(C)(C)C)cc4)c3C2=O)c1] |
| 259 | 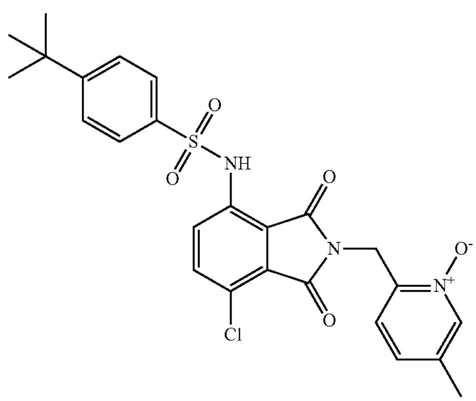 [SMILES: Cc1ccc(CN2C(=O)c3c(Cl)ccc(NS(=O)(=O)c4ccc(C(C)(C)C)cc4)c3C2=O)[n+]([O-])c1] |
| 260 | 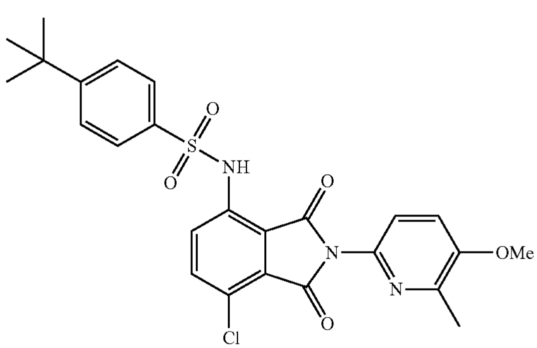 [SMILES: COc1ccc(N2C(=O)c3c(Cl)ccc(NS(=O)(=O)c4ccc(C(C)(C)C)cc4)c3C2=O)nc1C] |

TABLE 1-continued

| Compound number | Structure |
|---|---|
| 261 | 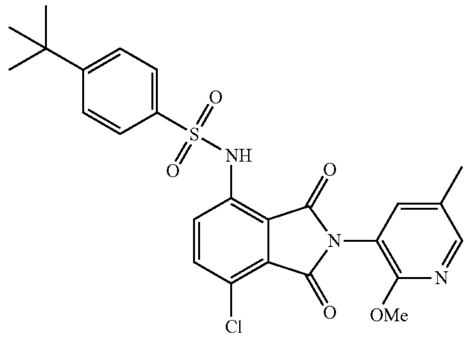 [SMILES: COc1ncc(C)cc1N1C(=O)c2c(Cl)ccc(NS(=O)(=O)c3ccc(C(C)(C)C)cc3)c2C1=O] |
| 262 | 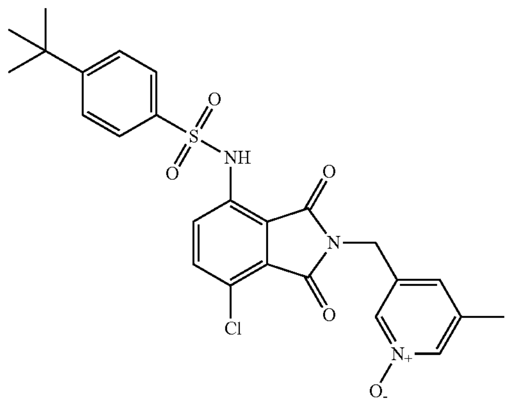 |
| 263 | 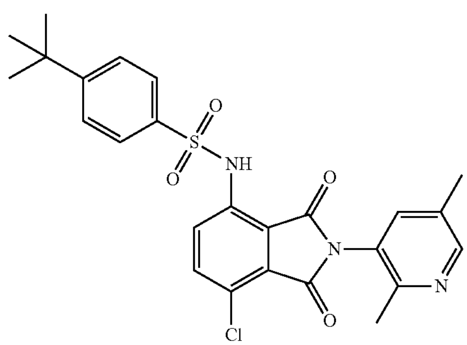 [SMILES: Cc1cnc(C)c(N2C(=O)c3c(Cl)ccc(NS(=O)(=O)c4ccc(C(C)(C)C)cc4)c3C2=O)c1] |
| 264 | 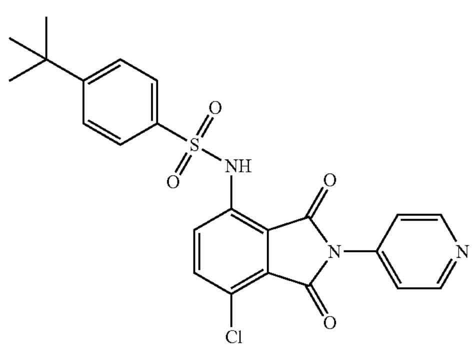 [SMILES: CC(C)(C)c1ccc(S(=O)(=O)Nc2ccc(Cl)c3c2C(=O)N(c2ccncc2)C3=O)cc1] |

TABLE 1-continued
| Compound number | Structure |
|---|---|
| 265 | 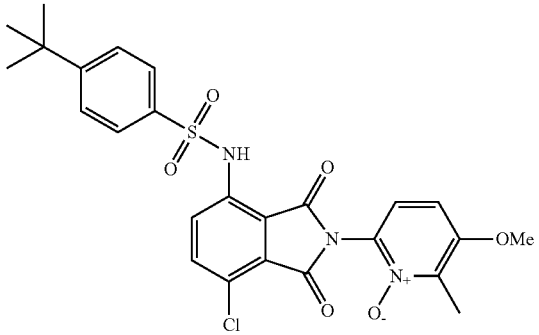 |
| 266 | 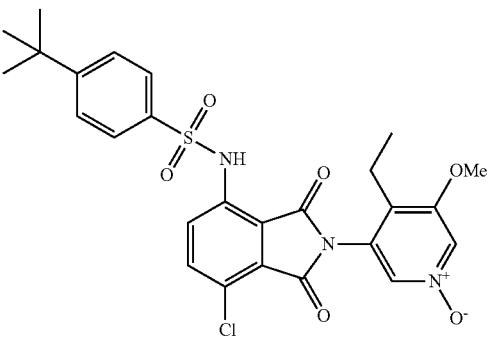 [SMILES: CCc1c(OC)c[n+]([O-])cc1N1C(=O)c2c(Cl)ccc(NS(=O)(=O)c3ccc(C(C)(C)C)cc3)c2C1=O] |
| 267 | 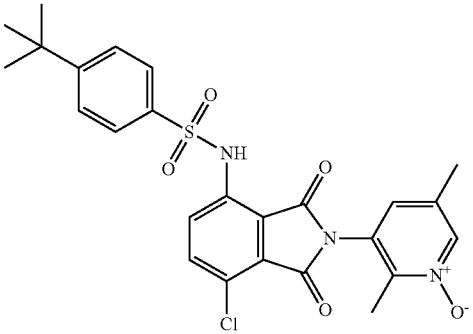 [SMILES: Cc1cc(N2C(=O)c3c(Cl)ccc(NS(=O)(=O)c4ccc(C(C)(C)C)cc4)c3C2=O)c(C)[n+]([O-])c1] |
| 268 | 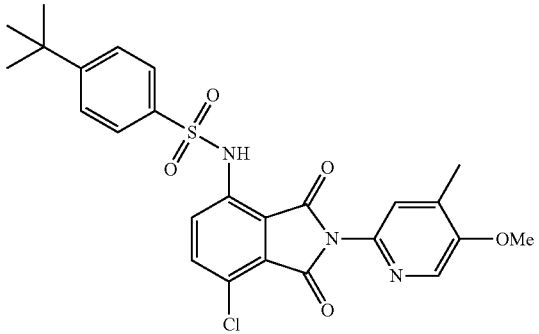 [SMILES: COc1cnc(N2C(=O)c3c(Cl)ccc(NS(=O)(=O)c4ccc(C(C)(C)C)cc4)c3C2=O)cc1C] |

151
TABLE 1-continued
| Compound number | Structure |
|---|---|
| 269 | 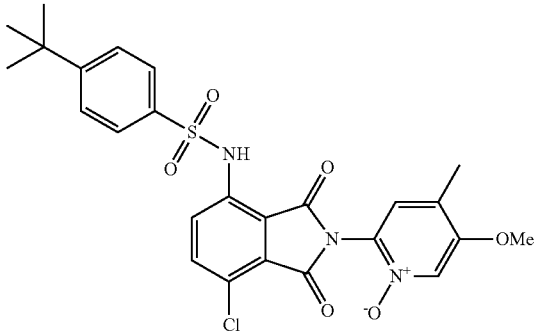 |
| 270 | 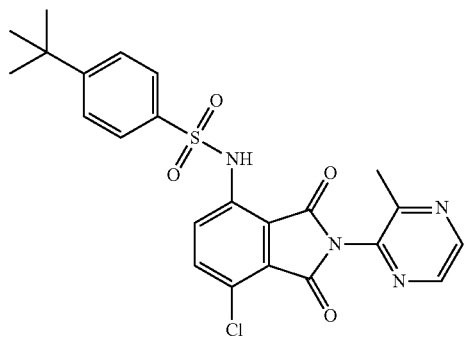 [SMILES: Cc1nccnc1N1C(=O)c2c(Cl)ccc(NS(=O)(=O)c3ccc(C(C)(C)C)cc3)c2C1=O] |
| 271 | 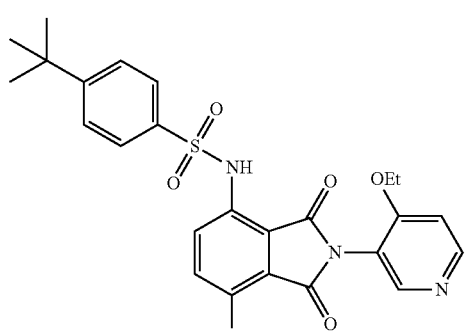 |
| 272 | 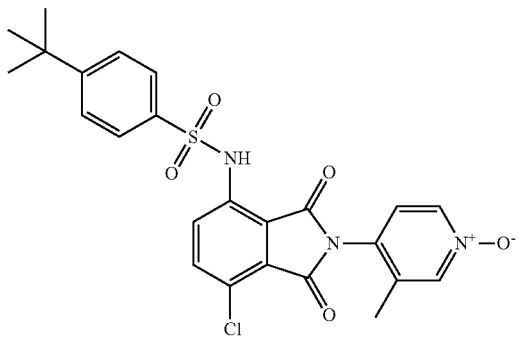 [SMILES: Cc1c[n+]([O-])ccc1N1C(=O)c2c(Cl)ccc(NS(=O)(=O)c3ccc(C(C)(C)C)cc3)c2C1=O] |

TABLE 1-continued
| Compound number | Structure |
|---|---|
| 273 | 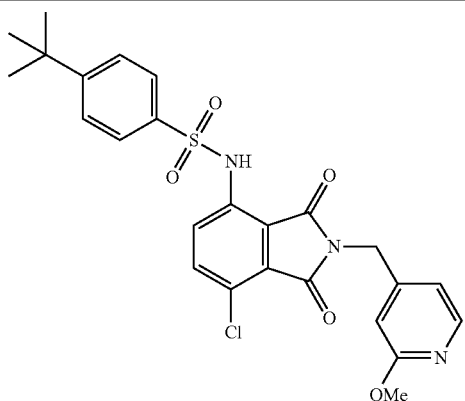 |
| 274 | 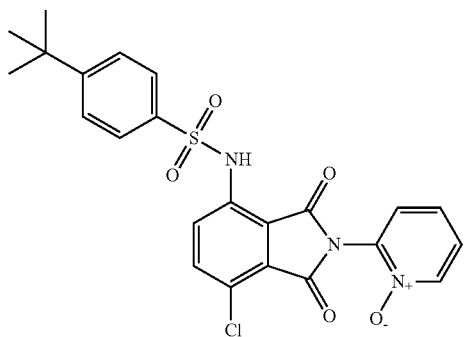 |
| 275 | 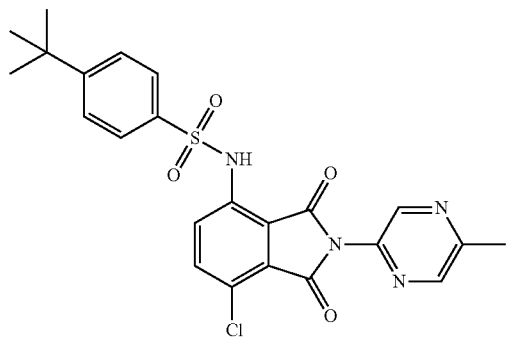 [SMILES: Cc1cnc(N2C(=O)c3c(Cl)ccc(NS(=O)(=O)c4ccc(C(C)(C)C)cc4)c3C2=O)cn1] |
| 276 | 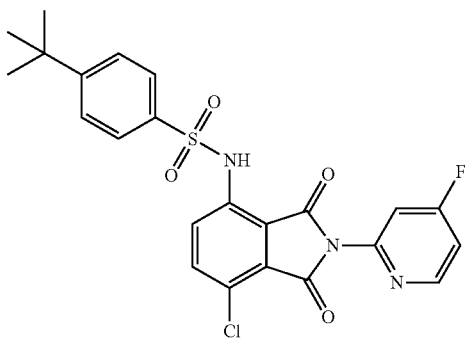 [SMILES: CC(C)(C)c1ccc(S(=O)(=O)Nc2ccc(Cl)c3c2C(=O)N(c2cc(F)ccn2)C3=O)cc1] |

TABLE 1-continued

| Compound number | Structure |
|---|---|
| 277 | 4-tert-butyl-N-(2-(tetrahydro-2H-pyran-4-yl)-1,3-dioxo-7-cyanoisoindolin-4-yl)benzenesulfonamide |
| 278 | 4-tert-butyl-N-(2-(5-methoxypyridin-3-yl)-1,3-dioxo-7-cyanoisoindolin-4-yl)benzenesulfonamide |
| 279 | 4-tert-butyl-N-(2-(pyridin-2-ylmethyl)-1,3-dioxo-7-cyanoisoindolin-4-yl)benzenesulfonamide |
| 280 | 4-tert-butyl-N-(2-((1-oxidopyridin-3-yl)methyl)-1,3-dioxo-7-cyanoisoindolin-4-yl)benzenesulfonamide |

TABLE 1-continued
| Compound number | Structure |
|---|---|
| 281 | 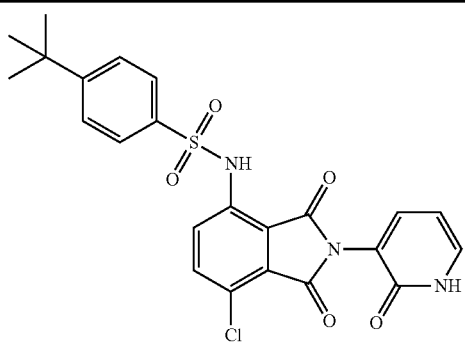 |
| 282 | 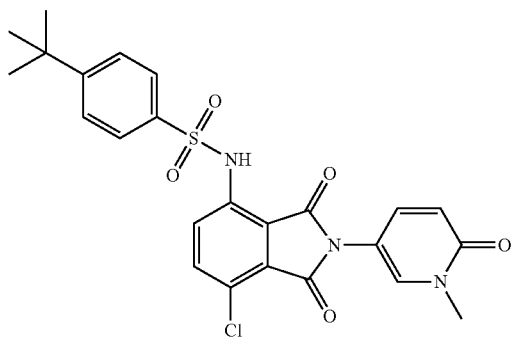 [SMILES: Cn1cc(N2C(=O)c3c(Cl)ccc(NS(=O)(=O)c4ccc(C(C)(C)C)cc4)c3C2=O)ccc1=O] |
| 283 | 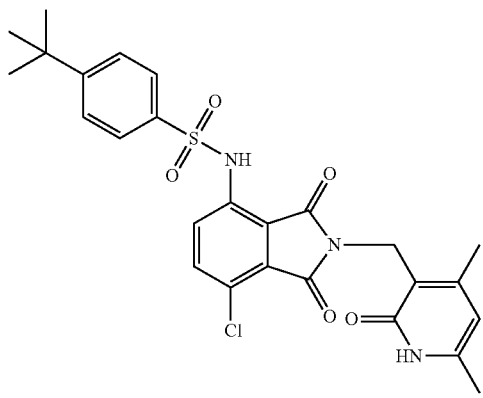 [SMILES: Cc1cc(C)c(CN2C(=O)c3c(Cl)ccc(NS(=O)(=O)c4ccc(C(C)(C)C)cc4)c3C2=O)c(=O)[nH]1] |
| 284 | 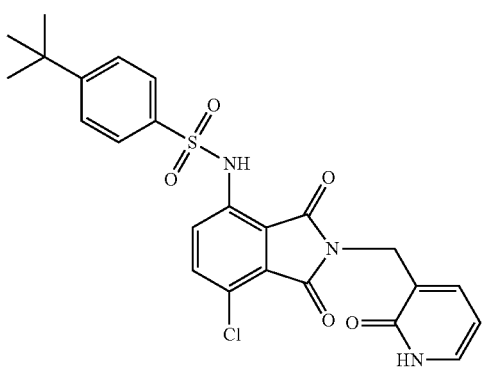 [SMILES: CC(C)(C)c1ccc(S(=O)(=O)Nc2ccc(Cl)c3c2C(=O)N(Cc2ccc[nH]c2=O)C3=O)cc1] |

TABLE 1-continued

| Compound number | Structure |
|---|---|
| 285 | 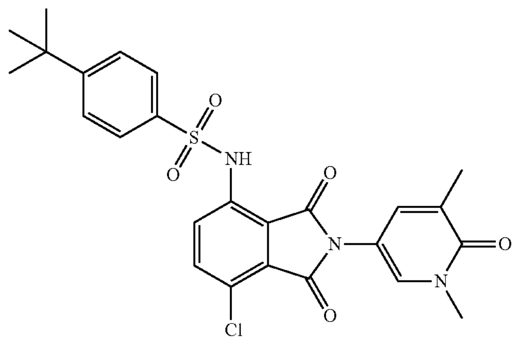 [SMILES: Cc1cc(N2C(=O)c3c(Cl)ccc(NS(=O)(=O)c4ccc(C(C)(C)C)cc4)c3C2=O)cn(C)c1=O] |
| 286 | 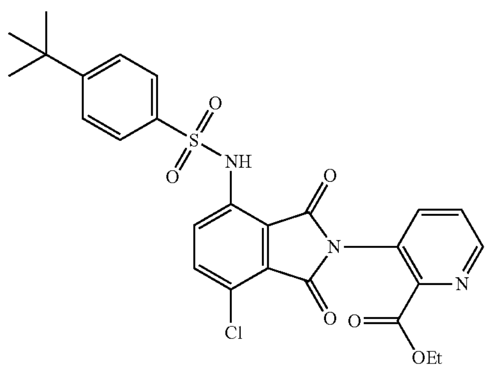 [SMILES: CCOC(=O)c1ncccc1N1C(=O)c2c(Cl)ccc(NS(=O)(=O)c3ccc(C(C)(C)C)cc3)c2C1=O] |
| 287 | 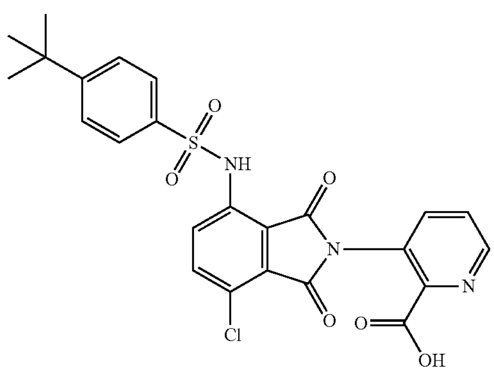 [SMILES: CC(C)(C)c1ccc(S(=O)(=O)Nc2ccc(Cl)c3c2C(=O)N(c2cccnc2C(=O)O)C3=O)cc1] |
| 288 | 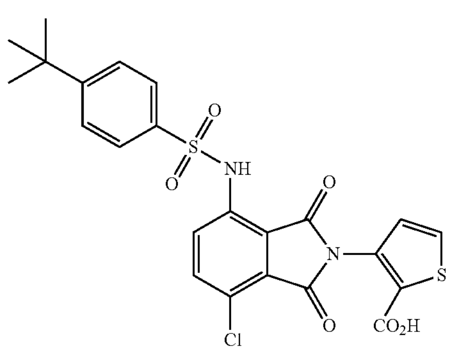 [SMILES: CC(C)(C)c1ccc(S(=O)(=O)Nc2ccc(Cl)c3c2C(=O)N(c2ccsc2C(=O)O)C3=O)cc1] |

TABLE 1-continued

| Compound number | Structure |
|---|---|
| 289 | (structure) |
| 290 | (structure) |
| 291 | (structure) |
| 292 | (structure) |

The compound of Formula (I) may be used as such, or in the form of a salt or solvate thereof, including a solvate of such a salt. Preferably a salt or solvate is one which is pharmaceutically acceptable.

Suitable salts of the compound of Formula (I) include metal salts, for example alkali metal or alkaline earth metal salts, for example sodium, potassium, calcium and magnesium salts; or salts with ammonia, primary, secondary or tertiary amines, or amino acids, for example mono-, di- or tri-alkylamines, hydroxyalkylamines, and nitrogen-containing heterocyclic compounds, for example isopropylamine, trimethylamine, diethylamine, tri(i-propyl)amine, tri(n-propyl)amine, ethanolamine, 2-dimethylaminoethanol, lysine, histidine, arginine, choline, caffeine, glucamine, procaine, hydrabamine, betaine, ethylenediamine, N-alkylglucamines, theobromine, purines, piperazine, piperidine, morpholine, n-alkyl piperidines, etc; or salts such as trifluoroacetic acid (TFA) salt. For example, pharmaceutically acceptable salts of a compound of Formula (I) include acid addition salts such as hydrochloride, hydrobromide, citrate, tartrate and maleate salts and salts formed with phosphoric and sulfuric acid. In another aspect suitable pharmaceutically acceptable salts are base salts such as an alkali metal salt for example sodium or potassium, an alkaline earth metal salt for example calcium or magnesium, or organic amine salt for example triethylamine.

Many organic compounds can form complexes with solvents in which they are reacted or from which they are precipitated or crystallized. These complexes are known as solvates. For example, a complex with water is known as a hydrate. Such solvates form part of the invention.

The compound of Formula (I) or its salt or solvate (including a solvate of such a salt) may itself act as a prodrug, or may be converted into a prodrug by known methods. A further aspect of the invention provides a prodrug of the compound of Formula (I) or its salt or solvate (including a solvate of such a salt). Pharmaceutically acceptable prodrugs are described in T. Higuchi and V. Stella (Prodrugs as novel delivery systems, vol 14 of the ACS Symposium Series), and in Edward B. Roche, ed. (Bioreversible carriers in drug design, American Pharm Assoc and Pergamon Press, 1987), both of which are incorporated herein by reference. In one embodiment, a prodrug is a compound having a group that is cleavable from the molecule to generate a biologically active form. Thus the prodrug may be converted within the body into an active form or an active metabolite or residue thereof, due to the presence of particular enzymes or conditions that cleave the prodrug molecule. The cleavable group within the prodrug may be linked by any suitable bond, such as an ester bond or an amide bond (derived from any suitable amine, for example a mono-, di- or tri-alkylamine, or any of the amines mentioned above). For example, the prodrug may be an in vivo hydrolysable ester, such as an ester of a $CO_2H$ group present in the compound of Formula (I) with any suitable alcohol, for example a $C_{1-6}$ alkanol. Alternatively, it may be an ester of any —OH group present in the compound of Formula (I) with any suitable acid, for example any carboxylic or sulfonic acid. Prodrugs that are in vivo hydrolysable esters of a compound of Formula (I) are pharmaceutically acceptable esters that hydrolyse in the human body to produce the parent compound. Such esters can be identified by administering, for example intravenously, to a test animal, the compound under test and subsequently examining the test animal's body fluids. Suitable in vivo hydrolysable esters for carboxy include methoxymethyl and for hydroxy include formyl and acetyl, especially acetyl.

The present invention also provides a process for the preparation of a compound of Formula (I), which comprises reacting an anhydride (A) with a primary amine (B) to produce a phthalimide (C), reducing the nitro group in the phthalimide (C) to form an aminophthalimide (D), then:
(i) converting the aminophthalimide (D) to a secondary sulfonamide (F) using a sulfonyl chloride (E), and optionally derivatising the secondary sulfonamide (F) to a tertiary sulfonamide (H); or
(ii) converting the aminophthalimide (D) to a secondary amine (G), and converting the secondary amine (G) to a tertiary sulfonamide (H) using a sulfonyl chloride (E); and
(iii) optionally adding appropriate substituents to an $R_2$, $R_3$, or $R_4$ group of the secondary sulfonamide (F) or of the tertiary sulfonamide (H);
as shown in Scheme 1 below, wherein $R_1$, X, $R_2$, $R_3$, n, $R_4$, and m have the meanings given for the general Formula (I) and Z is a halogen, most likely a bromine atom:

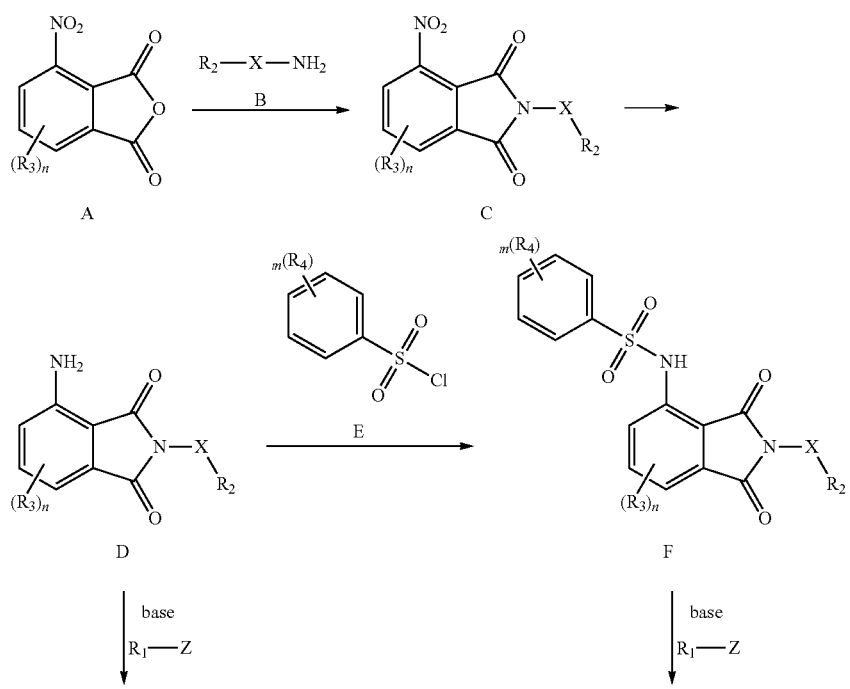

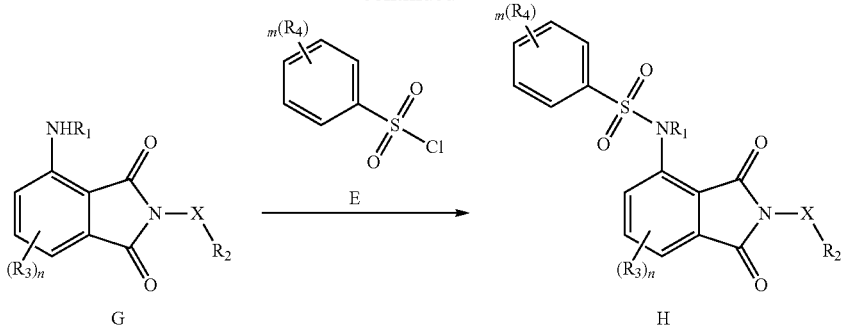

The anhydride A may be reacted with a primary amine of formula B in a solvent such as acetic acid, at an elevated temperature, in order to produce phthalimide C. The nitro group in this molecule is reduced to an amino group using a variety of possible reducing agents including stannous chloride in ethanol, iron powder in acetic acid or by hydrogenation utilizing metal catalysts such as Raney nickel, platinum IV oxide or palladium on carbon.

The aminophthalimide of formula D may either be converted to the secondary sulfonamide F which may then, if desired, be derivatised to the tertiary sulfonamide H or it may first be converted to the secondary amine G, before conversion to the tertiary sulfonamide H. Conversion of the compounds of formula D or G to the compounds of formula F or H respectively may be achieved by the use of a sulfonyl chloride E. This reagent is either used with a base such as pyridine in the presence or absence of a catalytic quantity of an agent such as dimethylaminopyridine and using a solvent such as dichloromethane, or by the use of sodium hydride as base in a dipolar aprotic solvent such as DMF prior to addition of the sulfonyl chloride. Conversion of the compounds of formula D or F to the compounds of formula G or H respectively may be achieved by the use of a base such as sodium hydride followed by the appropriate alkyl halide. In the event that $R_2$ is a pyridine N-oxide, this may be prepared most conveniently from the corresponding pyridine as a final step by treating the pyridine with an oxidizing agent such as meta-chloroperoxybenzoic acid in a solvent such as dichloromethane.

It will be appreciated that many of the relevant starting materials are commercially available or may be made by any convenient method as described in the literature or known to the skilled chemist or described in the Examples herein. For example, compounds of the Formula A

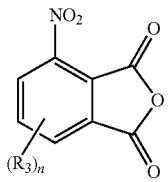

are known or can be prepared by methods analogous to known methods; specific methods are disclosed in the Examples herein.

In a further aspect of the invention, there is provided an intermediate compound for use in the synthesis of a compound of Formula (I). There is further provided the use of an intermediate compound to synthesise a compound of Formula (I). Such intermediate compounds include the intermediate compounds I-CVI disclosed in the Examples herein and listed in Table 2.

TABLE 2

| Intermediate compound number | Disclosed in Example number |
| --- | --- |
| I | 1-6, 8 |
| II | 1, 26, 27 |
| III | 1 |
| IV | 1 |
| V | 1, 2, 4, 6-9, 11-30 |
| VI | 2, 9 |
| VII | 2 |
| VIII | 2 |
| IX | 3 |
| X | 3 |
| XI | 3 |
| XII | 3, 5 |
| XIII | 4 |
| XIV | 4 |
| XV | 4 |
| XVI | 5 |
| XVII | 5 |
| XVIII | 5 |
| XIX | 6, 18 |
| XX | 6 |
| XXI | 6 |
| XXII | 7 |
| XXIII | 7 |
| XXIV | 7, 27 |
| XXV | 7, 9, 11-25, 28-30 |
| XXVI | 7 |
| XXVII | 7, 19 |
| XXVIII | 8 |
| XXIX | 8 |
| XXX | 8 |
| XXXI | 9 |
| XXXII | 9 |
| XXXIII | 11 |
| XXXIV | 11 |
| XXXV | 11 |
| XXXVI | 12 |
| XXXVII | 12 |
| XXXVIII | 12 |
| XXXIX | 13 |
| XL | 13 |
| XLI | 13 |
| XLII | 14 |
| XLIII | 14 |
| XLIV | 14 |
| XLV | 15 |
| XLVI | 15 |
| XLVII | 15 |
| XLVIII | 15 |
| XLIX | 16 |
| L | 16 |
| LI | 16 |
| LII | 17 |
| LIII | 17 |

TABLE 2-continued

| Intermediate compound number | Disclosed in Example number |
| --- | --- |
| LIV | 17 |
| LV | 18 |
| LVI | 18 |
| LVII | 19 |
| LVIII | 19 |
| LIX | 20 |
| LX | 20 |
| LXI | 20 |
| LXII | 21 |
| LXIII | 21 |
| LXIV | 21 |
| LXV | 22 |
| LXVI | 22 |
| LXVII | 22 |
| LXVIII | 22 |
| LXIX | 23 |
| LXX | 23 |
| LXXI | 23 |
| LXXII | 23 |
| LXXIII | 23 |
| LXXIV | 24 |
| LXXV | 24 |
| LXXVI | 24 |
| LXXVII | 25 |
| LXXVIII | 25 |
| LXXIX | 25 |
| LXXX | 26 |
| LXXXI | 26 |
| LXXXII | 26 |
| LXXXIII | 26 |
| LXXXV | 27 |
| LXXXVI | 27 |
| LXXXVII | 27 |
| LXXXVIII | 27 |
| LXXXIX | 27 |
| XC | 27 |
| XCI | 27 |
| XCII | 28 |
| XCIII | 28 |
| XCIV | 28 |
| XCV | 28 |
| XCVI | 28 |
| XCVII | 29 |
| XCVIII | 29 |
| XCIX | 29 |
| CC | 29 |
| CI | 29 |
| CII | 30 |
| CIII | 30 |
| CIV | 30 |
| CV | 30 |
| CVI | 30 |

A resulting compound of the invention may be converted into any other compound of the invention by methods analogous to known methods. For example: a resulting compound of Formula (I) may be converted into a salt or solvate thereof; the oxidation state of an atom in a heterocyclic ring may be increased or decreased by oxidation or reduction using known methods; an ester may be converted to the corresponding acid by hydrolysis (eg using an aqueous hydroxide such as NaOH) or an acid maybe converted to a corresponding metal salt (eg using an aqueous metal hydroxide, such as NaOH to produce the sodium salt). During synthesis of any compound of the invention, protecting groups may be used and removed as desired. Thus in the Scheme above, as well as corresponding to the definitions in Formula I, $R_1$, $R_2$, $R_3$ and $R_4$ can also represent appropriately protected forms of these groups.

The amount of the compound of the invention which is required to achieve a therapeutic effect will, of course, depend upon whether the effect is prophylactic or curative, and will vary with the route of administration, the subject under treatment, and the form of disease being treated. It is generally preferable to use the lowest dose that achieves the desired effect. The compound of the invention may generally be administered at a dose of from 0.1 to 1500 mg/kg per day, preferably 0.1 to 500 mg/kg per day, typically from 0.5 to 20 mg/kg/day, for example about 3 mg/kg/day. Unit dose forms may conveniently contain an amount of compound of the invention which is effective at such dosage or as a multiple of the same, for example units containing 5 mg to 500 mg, usually around 10 mg to 200 mg.

For example, a pharmaceutical composition of this invention may be administered to humans so that, for example, a daily dose of 0.5 to 20 mg/kg body weight (and preferably of 0.5 to 3 mg/kg body weight) is received. This daily dose may be given in divided doses as necessary, the precise amount of the compound received and the route of administration depending on the weight, age and sex of the patient being treated and on the particular disease or condition being treated according to principles known in the art. Typically unit dosage forms may contain about 1 mg to 500 mg of a compound of Formula (I). For example, a unit dosage form containing up to 10 mg/kg may be given twice per day, such as 1.5 mg/kg twice per day or 5 mg/kg twice per day or 10 mg/kg twice per day.

The compound of the present invention may be administered one or more times per day, for example, two or three times per day, or even more often, for example, four or five times per day.

The compounds of this invention may be administered in standard manner for the disease or condition that it is desired to treat. For these purposes the compounds of this invention may be formulated by means known in the art into the required form. While it is possible for the active ingredient to be administered alone, it is preferable for it to be present in a suitable composition formulated as required. Suitable formulations according to the invention include those suitable for oral (including sub-lingual), parenteral (including subcutaneous, intradermal, intramuscular, intravenous, and intraarticular), nasal, inhalation, topical (including dermal, buccal, and sublingual), vaginal and rectal administration. The most suitable route may depend upon, for example, the nature and stage of the condition and disorder of the recipient.

For oral administration, the compounds can be formulated as liquids or solids. Forms suitable for oral administration include for example tablets, capsules, pills, lozenges, granulates, dragees, wafers, aqueous or oily solutions, suspensions, syrups, or emulsions.

Forms suitable for parenteral use include for example sterile aqueous or oily solutions or suspensions or sterile emulsions or infusions.

Forms suitable for nasal administration include for example drops, sprays and aerosols.

Forms suitable for inhalation include for example finely divided powders, aerosols, fine particle dusts or mists which may be generated by means of various types of metered dose pressurized aerosols, nebulizers or insufflators.

Forms suitable for topical administration to the skin include, for example, gels, creams, ointments, emulsions, pastes, foams or adhesive patches. For female patients, the composition may be in a form suitable for intravaginal administration.

Forms suitable for rectal administration include suppositories, rectal capsules and enema solutions.

Forms suitable for transdermal administration generally comprise an adjuvant that enhances the transdermal delivery of the compound of the invention. Suitable adjuvants are known in the art.

A pharmaceutical composition of the present invention may be in unit dosage form. Suitable oral unit dosage forms include those mentioned above. For administration by injection or infusion unit dosage forms include, for example, vials and ampoules. Unit dosage forms for topical administration to the skin include blister packs or sachets, each blister or sachet containing a unit dose of, for example, a gel, cream or ointment, for example, as described above. A metered dosing device may be provided, for example, a pump device, for dosing a predetermined volume of a topical composition, for example, a cream, ointment or gel. A preparation may provide delayed or sustained release, for example a depot preparation or an adhesive patch.

Preferred formulations are those suitable for oral administration, for example in the form of tablets, capsules, pills or the like, or in the form of solutions suitable for injection such as in water for injections BP or aqueous sodium chloride.

To make a composition according to the invention, suitable carriers are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile).

A liquid formulation will generally consist of a suspension or solution of the compound or physiologically acceptable salt in a suitable aqueous or non-aqueous liquid carrier(s), for example water, ethanol, glycerine, polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compositions for oral administration may be designed to protect the active ingredient against degradation as it passes through the alimentary tract, for example by an outer coating of the formulation on a tablet or capsule.

Conveniently the composition is in unit dose form such as a tablet or capsule.

In addition to the compounds of the present invention, the pharmaceutical composition of this invention may also contain, or be co-administered (simultaneously or sequentially) with, one or more pharmacological agents of value in treating one or more diseases or conditions referred to hereinabove. For example, pharmaceutical compositions as described above may also comprise one or more further active ingredients in addition to a compound of the invention, for example, a further active ingredient with efficacy in the treatment or prevention of IBD or of conditions associated with IBD.

The compounds of the invention are compounds which modulate at least one function or characteristic of mammalian CCR9, for example, a human CCR9 protein. The ability of a compound to modulate the function of CCR9 can be demonstrated in a binding assay (such as a ligand binding or agonist binding assay), a migration assay, a signaling assay (such as activation of a mammalian G protein, induction of rapid and transient increase in the concentration of cytosolic free calcium) and/or cellular response assay (such as stimulation of chemotaxis, exocytosis or inflammatory mediator release by leukocytes). In particular, compounds of the invention may be evaluated in one or more of the following assays: (1) human CCR9 FLIPR assay using recombinant cell lines expressing human CCR9 or MOLT-4 cells (for example, identifying active compounds as those having $K_i \leq 10$ μM, preferred compounds as those having $K_i \leq 1$ μM, and most preferred compounds as those having a $K_i \leq 500$ nM); (2) chemotaxis assay using MOLT-4 cells (for example, identifying active compounds as those having $K_i \leq 10$ μM, preferred compounds as those having $K_i \leq 1$ μM, and most preferred compounds as those having a $K_i \leq 500$ nM); (3) chemotaxis assay using mouse and rat thymocytes (for example, identifying active compounds as those having $K_i \leq 1$ μM, preferred compounds as those having $K_i \leq 500$ nM, and most preferred compounds as those having a $K_i \leq 500$ nM).

As previously outlined the compounds of the invention are CCR9 modulators, in particular they are partial agonists, antagonists or inverse agonists of CCR9. Each of the above indications for the compounds of the Formula (I) represents an independent and particular embodiment of the invention. Whilst we do not wish to be bound by theoretical considerations, some of the preferred compounds of the invention may show selective CCR9 modulation for any one of the above indications relative to modulating activity against any other particular receptor, including any other particular chemokine receptor (for example, CCR1, CCR2, CCR3, CCR4, CCR5, CCR6, CCR7, CCR8, CCR10, CXCR1, CXCR2, CXCR3, CXCR4, CXCR5, CXCR6, CXCR7, CX3CR$_1$, XCR1, ChemR23 or CMKLR1); by way of non-limiting example they may show 100-1000 fold selectivity for CCR9 over activity against any other particular chemokine receptor.

The invention will now be illustrated but not limited by the following Examples. Each exemplified compound represents a particular and independent aspect of the invention. Where optically active centres exist in the compounds of Formula (I), we disclose all individual optically active forms and combinations of these as individual specific embodiments of the invention, as well as their corresponding racemates.

Analytical TLC was performed on Merck silica gel 60 F$_{254}$ aluminium-backed plates. Compounds were visualised by UV light and/or stained either with iodine, potassium permanganate or ninhydrin solution. Flash column chromatography was performed on silica gel (100-200 M) or flash chromatography. $^1$H-NMR spectra were recorded on a Bruker Avance-400 MHz spectrometer with a BBO (Broad Band Observe) and BBFO (Broad Band Fluorine Observe) probe. Chemical shifts (d) are expressed in parts per million (ppm) downfield by reference to tetramethylsilane as the internal standard. Splitting patterns are designated as s (singlet), d (doublet), t (triplet), q (quartet), m (multiplet) and bs (broad singlet). Coupling constants (J) are given in hertz (Hz). LC-MS analyses were performed on either an Acquity BEH C-18 column (2.10×100 mm, 1.70 μm) or on a Acquity HSS-T3 column (2.10×100 mm, 1.80 μm) or Zorbax HD C18 (2.1×50 mm, 1.8 μm) using the Electrospray Ionisation (ESI) technique. Purity assessment for final compounds was based on the following 3 LCMS methods. Method 1 consisted of the following: Acquity BEH C-18 column 2.10 mm×100 mm, 1.70 μm. Mobile phase; A, 5 mM ammonium acetate in water; B, acetonitrile; gradient, 90% A to 10% A in 8 min with 10 min run time and a flow rate of 0.3 mL/min. Method 2 consisted of the following: Acquity HSS-T3 column 2.10 mm×100 mm, 1.8 μm. Mobile phase; A, OA % TFA in water; B, acetonitrile; gradient, 90% A to 10% A in 8 min with 10 min run time and a flow rate of 0.3 mL/min. Method 3 consisted of the following: Zorbax HD C18 column 2.10 mm×50 mm, 1.8 μm. Mobile phase; A, 0.01% acetic acid in 95% water and methanol; B, 0.01% acetic acid in 5% water and methanol; gradient, 100% A to 100% B in 4 min with 5 min run time and a flow rate of 0.3 mL/min.

Example 1

Synthesis of Compound 1 [4-tert-Butylphenylsulfonic acid (1,3-dioxo-2-(pyridin-3-yl)-2,3-dihydro-1H-isoindol-4-yl)-amide] and Compounds 2-11

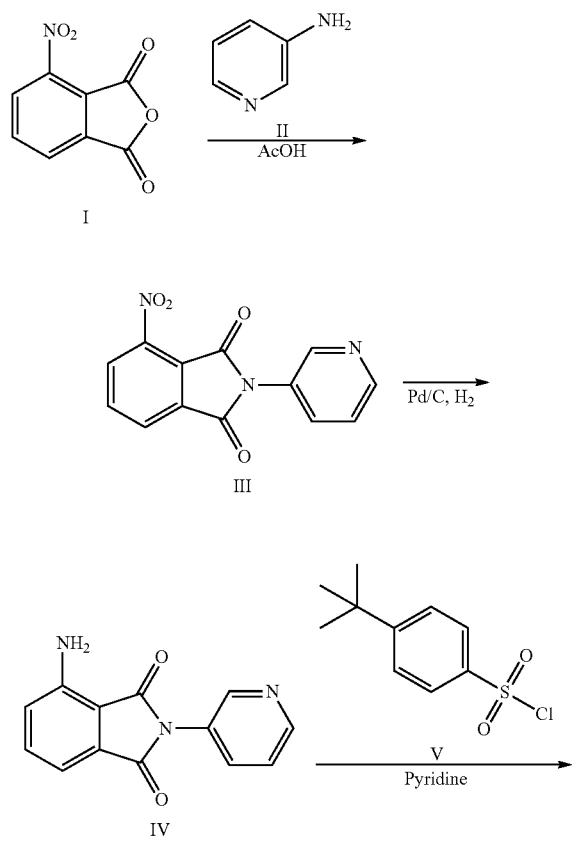

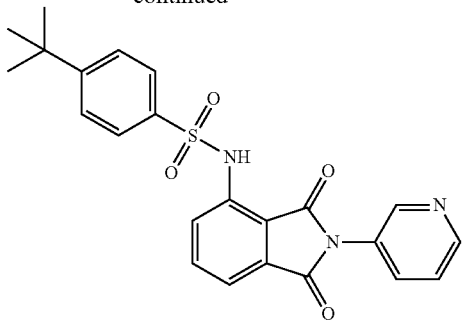

Synthesis of III:

To a stirred solution of I (2.0 g, 10.36 mmol) in acetic acid (28 mL) was added compound II (0.37 g, 3.88 mmol) and the reaction mixture heated to a reflux for 18 hours. The reaction was cooled to room temperature and the acetic acid was removed under reduced pressure to obtain a crude product. This material was suspended in ethanol (5 mL), cooled and filtered to leave crude 4-nitro-2-(pyridin-3-yl)isoindoline-1, 3-dione as a white solid (III; 2.5 g). MS (M+1): 270.1. This was used without further purification in the next step.

Synthesis of IV:

To a solution of crude III (2.0 g) in methanol (100 mL) under nitrogen atmosphere was added 10% Pd/C (0.1 g). The reaction mixture was purged with hydrogen and stirred under hydrogen balloon pressure for 18 hours at room temperature, whereupon the reaction mixture was filtered through a celite bed under a nitrogen atmosphere and the solvent evaporated under reduced pressure to afford crude compound, 4-amino-2-(pyridin-3-yl) isoindoline-1, 3-dione, as a yellow solid (IV; 0.8 g,). MS (M+1): 240.1. The crude was carried forward to next step without purification.

Synthesis of 1; 4-tert-Butylphenylsulfonic acid (1,3-dioxo-2-(pyridin-3-yl)-2,3-dihydro-1H-isoindol-4-yl)-amide A mixture of crude IV (100 mg) and pyridine (2 mL) was cooled to 0° C. tert-Butylbenzenesulfonyl chloride V (274 mg, 1.18 mmol) was added and the mixture stirred for 24 hours at room temperature. The reaction mixture was concentrated and to the residue obtained was added a saturated solution of ammonium chloride and extracted with dichloromethane. The organic layer was washed with brine solution & dried over anhydrous $Na_2SO_4$. This was filtered and the organic solvent was evaporated under reduced pressure to obtain crude compound. The crude material was purified using preparative TLC with 100% ethyl acetate as mobile phase to obtain 4-tert-butylphenylsulfonic acid (1,3-dioxo-2-(pyridin-3-yl)-2,3-dihydro-1H-isoindol-4-yl)-amide as a light yellow solid (1; 30 mg). $^1$H NMR (400 MHz, DMSO-d6): δ 11.28 (bs, 1H), 8.59-8.56 (m, 2H), 7.83 (d, J=8.0 Hz, 2H), 7.76 (d, J=8.0 Hz, 2H), 7.54-7.58 (m, 4H), 7.43 (bs, 1H), 1.24 (s, 9H). MS (M−1): 434.2. (LCMS purity 98.14%, Rt=6.12 min (1)).

The following compounds were prepared in a similar manner using the appropriate sulfonyl chloride in the final step:

| CPD number | Structure | LCMS (M + 1) | Purity (LCMS) | ¹H NMR |
|---|---|---|---|---|
| 2 | 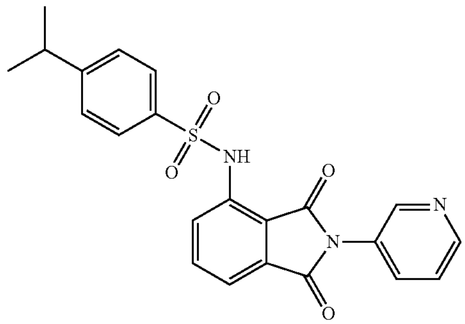 [SMILES: CC(C)c1ccc(S(=O)(=O)Nc2cccc3c2C(=O)N(c2cccnc2)C3=O)cc1] | 422.2 | 97.89%, Rt = 2.51 min (3) | ¹H NMR (400 MHz, DMSO-d6): δ 11.28 (bs, 1H), 8.58 (t, J = 4.8 Hz, 2H), 7.84 (d, J = 8.0 Hz, 2H), 7.78 (d, J = 8.0 Hz, 2H), 7.58-7.44 (m, 5H), 2.94-2.91 (m, 1H), 1.16 (d, 6H). |
| 3 | 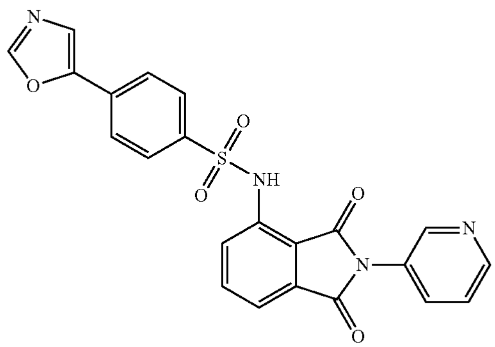 [SMILES: O=C1c2cccc(NS(=O)(=O)c3ccc(-c4cnco4)cc3)c2C(=O)N1c1cccnc1] | 445.2 (M − 1) | 99.99%, Rt = 1.54 min (3) | ¹H NMR (400 MHz, DMSO-d6): δ 8.56 (s, 1H), 8.52 (d, J = 3.6 Hz, 2H), 8.45 (s, 1H), 7.86-7.72 (m, 6H), 7.51-7.48 (m, 2H), 7.31 (s, 1H), 7.07 (d, J = 7.6 Hz, 1H). |
| 4 | 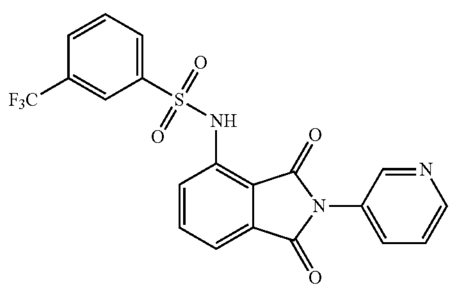 [SMILES: O=C1c2cccc(NS(=O)(=O)c3cccc(C(F)(F)F)c3)c2C(=O)N1c1cccnc1] | 448.1 | 99.99%, Rt = 2.32 min (3) | ¹H NMR (400 MHz, CDCl3): δ 8.74 (s, 1H), 8.63 (d, J = 4.4 Hz, 1H), 8.15 (s, 1H), 8.07 (d, J = 8.0 Hz, 1H), 7.87 (t, J = 8.0 Hz, 2H), 7.80 (d, J = 8.4 Hz, 1H), 7.68 (t, J = 7.2 Hz, 2H), 7.53 (d, J = 8.0 Hz, 1H), 7.45 (q, J = 4.8 Hz, 1H). |
| 5 | 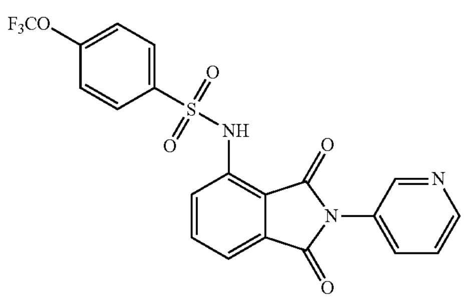 [SMILES: O=C1c2cccc(NS(=O)(=O)c3ccc(OC(F)(F)F)cc3)c2C(=O)N1c1cccnc1] | 464.1 | 99.99%, Rt = 2.37 min (3) | ¹H NMR (400 MHz, DMSO-d6): δ 11.42 (s, 1H), 8.59 (m, 2H), 8.0 (d, J = 8.8 Hz, 2H), 7.88 (d, J = 8.4 Hz, 1H), 7.84 (d, J = 8.0 Hz, 1H), 7.60 (d, J = 7.2 Hz, 3H), 7.54 (m, 2H). |
| 6 | 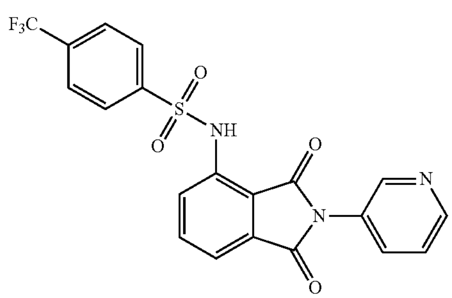 [SMILES: O=C1c2cccc(NS(=O)(=O)c3ccc(C(F)(F)F)cc3)c2C(=O)N1c1cccnc1] | 448.1 | 97.23%, Rt = 2.29 min (3) | ¹H NMR (400 MHz, DMSO-d6): δ 11.51 (s, 1H), 8.60 (s, 1H), 8.58 (d, J = 4.4 Hz, 1H), 8.08 (d, J = 8.4 Hz, 2H), 8.00 (d, J = 8.4 Hz, 2H), 7.89 (d, J = 8.0 Hz, 1H), 7.84 (d, J = 8.4 Hz, 1H) 7.61 (1H, s), 7.56 (2H, m). |

-continued
| CPD number | Structure | LCMS (M + 1) | Purity (LCMS) | ¹H NMR |
|---|---|---|---|---|
| 7 | 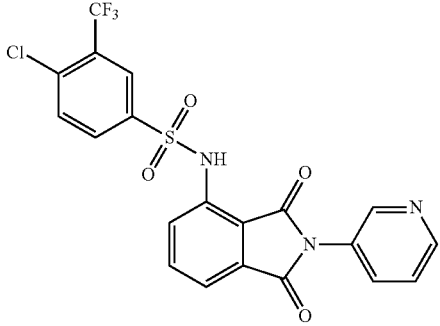 [SMILES: O=C1c2cccc(NS(=O)(=O)c3ccc(Cl)c(C(F)(F)F)c3)c2C(=O)N1c1cccnc1] | 482.0 | 98.48%, Rt = 2.46 min (3) | ¹H NMR (400 MHz, DMSO-d6): δ 11.47 (bs, 1H), 8.60 (s, 1H), 8.59 (d, J = 4.4 Hz, 1H), 8.22 (s, 1H), 8.11 (d, J = 7.6 Hz, 1H), 7.97 (d, J = 8.4 Hz, 1H), 7.89 (d, J = 7.6 Hz, 1H), 7.85 (d, J = 8.0 Hz, 1H), 7.56 (m, 3H). |
| 8 | 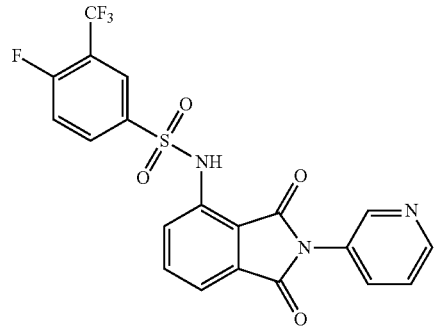 [SMILES: O=C1c2cccc(NS(=O)(=O)c3ccc(F)c(C(F)(F)F)c3)c2C(=O)N1c1cccnc1] | 466.1 | 96.15%, Rt = 5.52 min (1) | ¹H NMR (400 MHz, DMSO-d6): δ 10.62 (bs, 1H), 8.64-8.60 (m, 2H), 8.42-8.42 (m, 1H), 8.37-8.34 (m, 1H), 7.86-7.78 (m, 3H), 7.76-7.73 (m, 1H), 7.65-7.63 (m, 1H), 7.61-7.58 (m, 1H). |
| 9 | 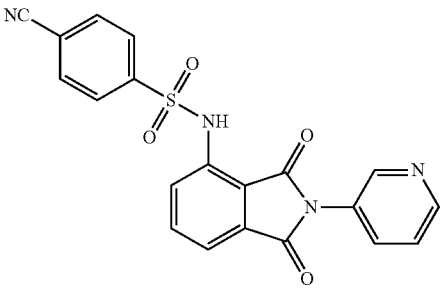 [SMILES: N#Cc1ccc(S(=O)(=O)Nc2cccc3c2C(=O)N(c2cccnc2)C3=O)cc1] | 405.1 | 98.98%, Rt = 5.39 min (1) | ¹H NMR (400 MHz, DMSO-d6): δ 10.53 (bs, 1H), 8.63-8.60 (m, 2H), 8.14-8.08 (m, 4H), 7.86-7.83 (m, 1H), 7.81-7.79 (m, 1H), 7.72-7.70 (m, 1H), 7.61-7.57 (m, 2H). |
| 10 | 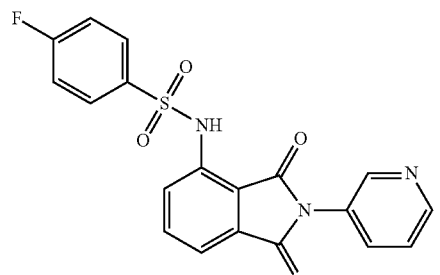 | 398.05 | 96.25% Rt = 5.04 min (1) | ¹H NMR (400 MHz, DMSO-d6): δ 10.15 (bs, 1H), 8.62 (s, 2H), 8.09-8.07 (m, 2H), 7.87-7.79 (m, 2H), 7.68-7.66 (m, 3H), 7.48-7.44 (m, 2H) |
| 11 | 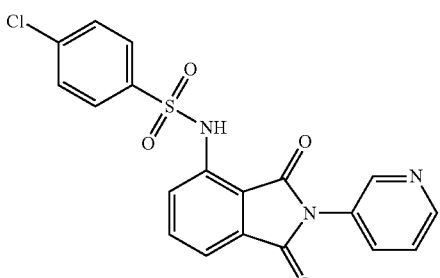 | 414.11 | 97.56% Rt = 5.19 min (1) | ¹H NMR (400 MHz, DMSO-d6): δ 10.24 (bs, 1H), 8.63-8.62 (m, 2H), 8.00-7.98 (d, J = 8.8 Hz, 2H), 7.87-7.80 (m, 2H), 7.71-7.69 (m, 3H), 7.64-7.58 (m, 2 H). |

Example 2

Synthesis of Compound 12 [4-(tert-butyl)-N-(1,3-dioxo-2-(pyridin-3-ylmethyl)isoindolin-4-yl)benzenesulfonamide] and Compounds 13-31

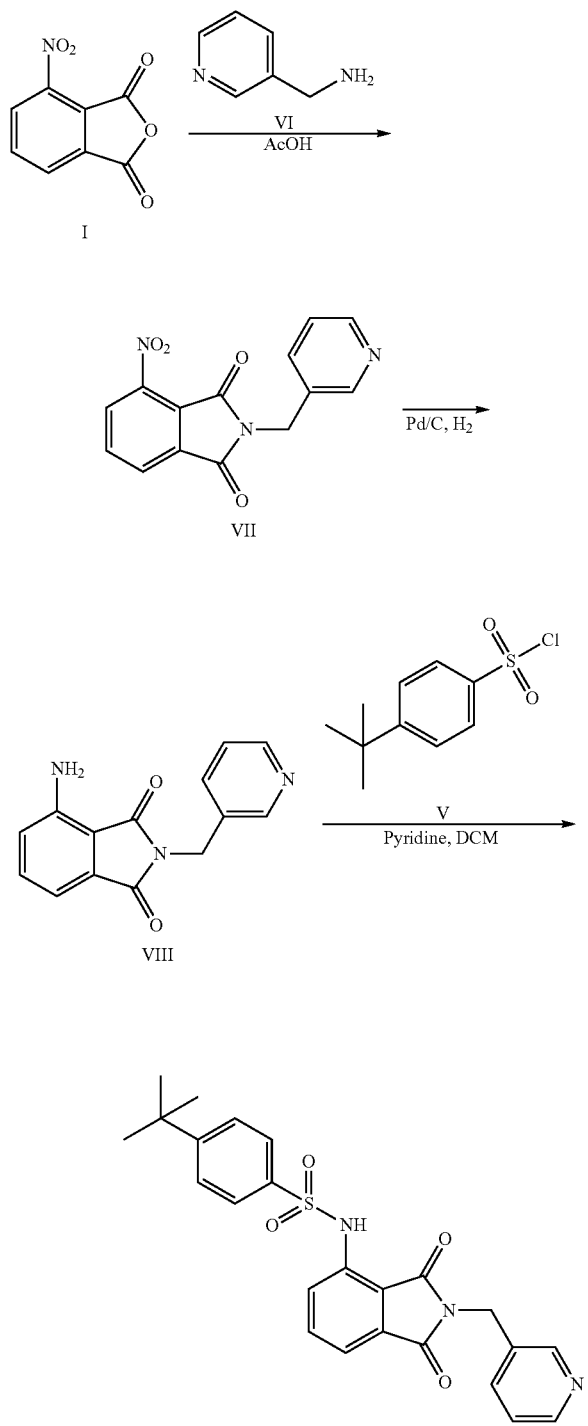

Synthesis of VII:

To a stirred solution of compound I (500 mg, 2.59 mmol) in acetic acid (7 mL) was added compound VI (420 mg, 3.88 mmol) and heated to a reflux for 18 hours. The reaction mixture was cooled to room temperature and the acetic acid was removed under reduced pressure to obtain a crude product. This material was suspended in ethanol (5 mL), cooled and filtered to obtain 4-nitro-2-(pyridin-3-ylmethyl)-isoindole-1,3-dione as a yellow solid (VII; 400 mg). $^1$H NMR (400 MHz, CDCl$_3$): δ 8.57 (1H, s), 8.46 (d, J=4.0 Hz, 1H), 8.27 (d, J=8.0 Hz, 1H), 8.17 (d, J=7.2 Hz, 1H), 8.04 (t, J=7.8 Hz, 1H), 7.74 (d, J=8.0 Hz, 1H), 7.31-7.36 (m, 1H), 4.81 (s, 2H).

Synthesis of VIII:

To a solution of VII (400 mg) in methanol (80 mL) under nitrogen atmosphere was added 10% Pd/C (100 mg). The reaction mixture was purged with hydrogen and stirred under hydrogen balloon pressure for 18 hours at room temperature and then filtered through a celite bed under a nitrogen atmosphere and evaporated under reduced pressure to afford compound 4-amino-2-(pyridin-3-ylmethyl)-isoindole-1,3-dione as a yellow solid (VIII; 380 mg). MS (M+1): 254.5

Synthesis of 12; 4-(tert-butyl)-N-(1,3-dioxo-2-(pyridin-3-ylmethyl)isoindolin-4-yl)benzene sulfonamide To a mixture of compound VIII (50 mg, 0.19 mmol) in dichloromethane (2 mL) was added pyridine (2 mL) and this solution was cooled to 0° C., compound V (96 mg, 0.39 mmol) was added and the solution was stirred for 24 hours at room temperature. The reaction mixture was concentrated under reduced pressure and diluted with saturated ammonium chloride solution and extracted with dichloromethane (2×10 mL). The organic layer was washed with brine solution, dried over anhydrous Na$_2$SO$_4$ and evaporated under reduced pressure to afford the crude compound which was purified by preparative HPLC to obtain 4-(tert-butyl)-N-(1,3-dioxo-2-(pyridin-3-ylmethyl)isoindolin-4-yl)benzene sulfonamide as a white solid (12; 50 mg, 56.8% yield). $^1$H NMR (400 MHz, DMSO-d6): δ 9.82 (bs, 1H), 8.58 (s, 1H), 8.51 (d, J=4.0 Hz, 1H), 7.89 (d, J=8.8 Hz, 2H), 7.71-7.78 (m, 2H), 7.59 (d, J=8.4 Hz, 3H), 7.54 (d, J=7.2 Hz, 1H), 7.39-7.42 (m, 1H), 4.76 (s, 2H), 1.24 (s, 9H). MS (M+1): 450.2. (LCMS Purity 98.25%, Rt=2.56 min (3)).

The following compounds were prepared in a similar manner using the appropriate sulfonyl chloride in the final step:

| Cmpd number | Structure | LCMS (M + 1) | Purity (LCMS) | ¹H NMR |
|---|---|---|---|---|
| 13 | 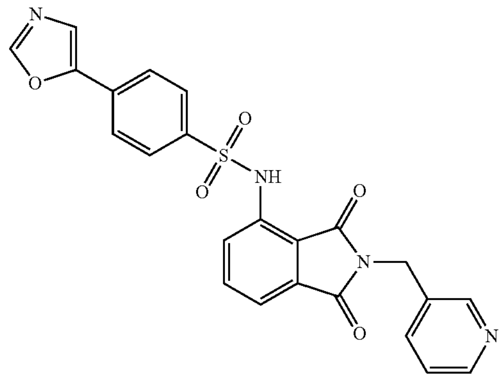 [SMILES: O=C1c2cccc(NS(=O)(=O)c3ccc(-c4cnco4)cc3)c2C(=O)N1Cc1cccnc1] | 461.7 | 99.18%, Rt = 1.99 min (3) | ¹H NMR (400 MHz, DMSO-d6): δ 8.90 (bs, 1H), 8.67 (s, 1H), 8.56 (d, J = 4.8 Hz, 1H), 7.96 (d, J = 8.0 Hz, 3H), 7.89 (d, J = 8.0 Hz, 1H), 7.77 (d, J = 8.0 Hz, 1H), 7.74 (d, J = 8.8 Hz, 2H), 7.63 (t, J = 11.4 Hz, 1H), 7.50 (d, J = 8.8 Hz, 2H), 7.29-7.32 (m, 1H), 4.79 (s, 2H). |
| 14 | 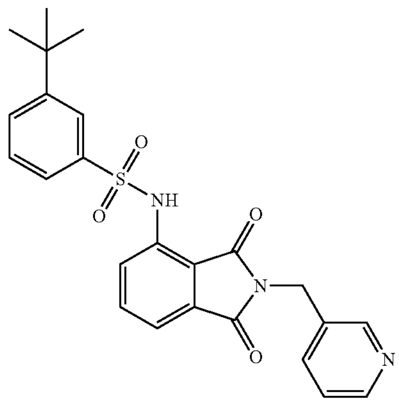 [SMILES: CC(C)(C)c1cccc(S(=O)(=O)Nc2cccc3c2C(=O)N(Cc2cccnc2)C3=O)c1] | 450.23 | 98.65%, Rt = 5.67 min (1) | ¹H NMR (400 MHz, DMSO-d6): δ 9.97 (s, 1H), 8.49 (s, 1H), 7.78-7.71 (m, 3H), 7.69-7.59 (m, 4H), 7.49-7.45 (t, J = 7.8 Hz, 1H), 7.38-7.35 (m, 1H), 4.70 (s, 2H), 1.15 (s, 9H). |
| 15 | 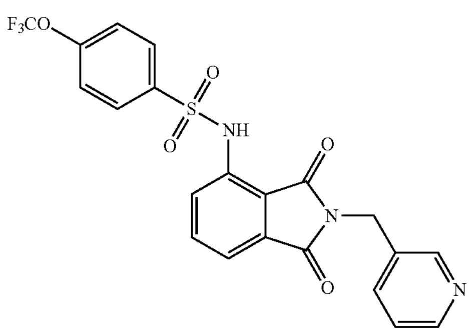 [SMILES: O=C1c2cccc(NS(=O)(=O)c3ccc(OC(F)(F)F)cc3)c2C(=O)N1Cc1cccnc1] | 478.11 | 99.03%, Rt = 5.72 min (1) | ¹H NMR (400 MHz, DMSO-d6): δ 10.26 (bs, 1H), 8.54 (s, 1H), 8.49 (s, 1H), 8.07-8.05 (d, J = 8.4 Hz, 2H), 7.77-7.75 (m, 1H), 7.67-7.55 (m, 5H), 7.36-7.33 (m, 1H), 4.73 (s, 2H). |
| 16 | 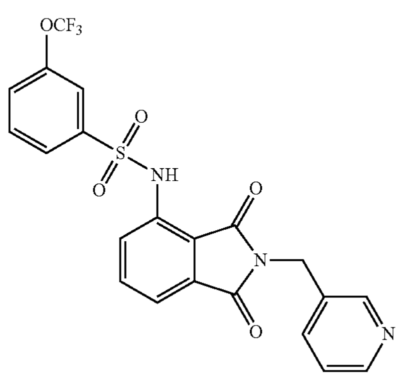 [SMILES: O=C1c2cccc(NS(=O)(=O)c3cccc(OC(F)(F)F)c3)c2C(=O)N1Cc1cccnc1] | 478.14 | 96.82%, Rt = 5.40 min (1) | ¹H NMR (400 MHz, DMSO-d6): δ 10.41 (bs, 1H), 8.51-8.49 (m, 2H), 7.92-7.90 (m, 1H), 7.81 (s, 1H), 7.78-7.74 (m, 1H), 7.72-7.68 (m, 1H), 7.66-7.62 (m, 3H), 7.58-7.56 (m, 2H), 7.38-7.34 (m, 1H), 4.71 (s, 2H). |

| Cmpd number | Structure | LCMS (M + 1) | Purity (LCMS) | ¹H NMR |
|---|---|---|---|---|
| 17 | (2-OCF₃-phenyl)sulfonamide linked to N-(pyridin-3-ylmethyl)phthalimide-4-yl | 478.11 | 98.56%, Rt = 5.74 min (1) | ¹H NMR (400 MHz, DMSO-d6): δ 9.98 (bs, 1H), 8.52-8.50 (m, 2H), 8.08-8.06 (d, J = 7.2 Hz, 1H), 7.78-7.72 (m, 2H), 7.67-7.51 (m, 5H), 7.38-7.35 (m, 1H), 4.74 (s, 2H). |
| 18 | (4-F-3-CF₃-phenyl)sulfonamide linked to N-(pyridin-3-ylmethyl)phthalimide-4-yl | 480.10 | 98.37%, Rt = 5.36 min (1) | ¹H NMR (400 MHz, DMSO-d6): δ 10.55 (bs, 1H), 8.53 (s, 1H), 8.49-8.48 (d, J = 4.0 Hz, 1H), 8.31-8.30 (d, J = 6.4 Hz, 1H), 8.25-8.23 (m, 1H), 8.75-7.55 (m, 5H), 7.36-7.33 (m, 1H), 4.72 (s, 2H). |
| 19 | (4-CF₃-phenyl)sulfonamide linked to N-(pyridin-3-ylmethyl)phthalimide-4-yl | 462.12 | 98.71%, Rt = 5.40 min (1) | ¹H NMR (400 MHz, DMSO-d6): δ 10.43 (bs, 1H), 8.54 (s, 1H), 8.49-8.48 (d, J = 4.4 Hz, 1H), 8.14-8.12 (d, J = 8.4 Hz, 2H), 7.97-7.95 (d, J = 8.4 Hz, 2H), 7.77-7.73 (t, J = 7.8 Hz, 1H), 7.64 (m, 2H), 7.55-7.53 (d, J = 8.4 Hz, 1H), 7.36-7.33 (m, 1H), 4.73 (s, 2H). |
| 20 | (3-Cl-2-CF₃-phenyl)sulfonamide linked to N-(pyridin-3-ylmethyl)phthalimide-4-yl | 493.92 (M − 1) | 99.70%, Rt = 5.50 min (1) | ¹H NMR (400 MHz, DMSO-d6): δ 10.38 (bs, 1H), 8.54 (s, 1H), 8.49-8.48 (d, J = 3.2 Hz, 1H), 8.38 (s, 1H), 8.17-8.15 (d, J = 8.8 Hz, 1H), 7.96-7.92 (m, 1H), 7.78-7.74 (m, 1H), 7.65-7.63 (m, 2H), 7.56-7.54 (m, 1H), 7.36-7.34 (m, 1H), 4.72 (s, 2H). |

-continued

| Cmpd number | Structure | LCMS (M + 1) | Purity (LCMS) | ¹H NMR |
|---|---|---|---|---|
| 21 | MeO-C₆H₄-SO₂-NH-(isoindoline-1,3-dione)-N-CH₂-(3-pyridyl) | 421.98 (M − 1) | 99.44%, Rt = 5.50 min (1) | ¹H NMR (400 MHz, DMSO-d6): δ 9.74 (bs, 1H), 8.54 (s, 1H), 8.49-8.48 (d, J = 3.2 Hz, 1H), 7.89-7.87 (d, J = 8.8 Hz, 2H), 7.74-7.70 (m, 1H), 7.68-7.66 (m, 1H), 7.60-7.53 (m, 2H), 7.36-7.33 (m, 1H), 7.08-7.06 (d, J = 8.8 Hz, 2H), 4.74 (s, 2H), 3.80 (s, 3H). |
| 22 | 3-CF₃-C₆H₄-SO₂-NH-(isoindoline-1,3-dione)-N-CH₂-(3-pyridyl) | 462.09 | 98.44%, Rt = 5.50 min (1) | ¹H NMR (400 MHz, DMSO-d6): δ 10.48 (bs, 1H), 8.50 (s, 1H), 8.49-8.48 (d, J = 1.2 Hz, 1H), 8.20 (s, 1H), 8.18-8.16 (d, J = 8.0 Hz, 1H), 8.02-8.0 (d, J = 8.0 Hz, 1H), 7.81-7.74 (m, 2H), 7.64-7.61 (m, 2H), 7.58-7.56 (d, J = 8.0 Hz, 1H), 7.38-7.34 (m, 1H), 4.71 (s, 2H). |
| 23 | 2-Me-C₆H₄-SO₂-NH-(isoindoline-1,3-dione)-N-CH₂-(3-pyridyl) | 408.11 | 99.78%, Rt = 5.82 min (1) | ¹H NMR (400 MHz, DMSO-d6): δ 9.78 (bs, 1H), 8.54 (s, 1H), 8.49-8.48 (d, J = 4.0 Hz, 1H), 7.94-7.92 (d, J = 8.4 Hz, 1H), 7.73-7.67 (m, 2H), 7.61-7.53 (m, 3H), 7.45-7.37 (m, 3H), 4.74 (s, 2H), 2.62 (s, 3H). |
| 24 | 4-Acetyl-C₆H₄-SO₂-NH-(isoindoline-1,3-dione)-N-CH₂-(3-pyridyl) | 436.09 | 98.38%, Rt = 4.93 min (1) | ¹H NMR (400 MHz, DMSO-d6): δ 10.29 (bs, 1H), 8.51-8.48 (m, 2H), 8.10-8.04 (m, 4H), 7.76-7.72 (m, 1H), 7.66-7.64 (m, 1H), 7.61-7.55 (m, 2H), 7.35-7.32 (m, 1H), 4.73 (s, 2H), 2.60 (s, 3H). |

-continued

| Cmpd number | Structure | LCMS (M + 1) | Purity (LCMS) | ¹H NMR |
|---|---|---|---|---|
| 25 | 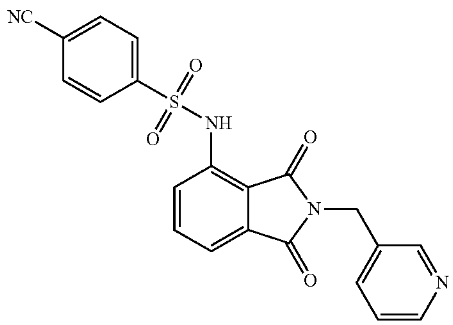 [SMILES: N#Cc1ccc(S(=O)(=O)Nc2cccc3c2C(=O)N(Cc2cccnc2)C3=O)cc1] | 419.10 | 99.19%, Rt = 4.92 min (1) | ¹H NMR (400 MHz, DMSO-d6): δ 10.52 (bs, 1H), 8.53 (s, 1H), 8.50-8.49 (m, 1H), 8.09-8.04 (m, 4H), 7.77-7.73 (m, 1H), 7.64-7.62 (m, 2H), 7.55-7.53 (d, J = 8.0 Hz, 1H), 7.38-7.35 (m, 1H), 4.73 (s, 2H). |
| 26 | 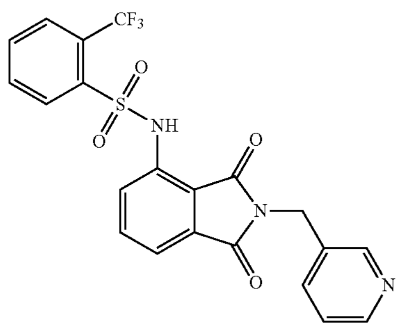 [SMILES: O=C1c2cccc(NS(=O)(=O)c3ccccc3C(F)(F)F)c2C(=O)N1Cc1cccnc1] | 462.13 | 99.39%, Rt = 5.66 min (1) | ¹H NMR (400 MHz, DMSO-d6): δ 10.04 (bs, 1H), 8.54-8.50 (m, 2H), 8.22-8.21 (d, J = 9.6 Hz, 1H), 8.03-8.02 (d, J = 9.6 Hz, 1H), 7.88-7.84 (m, 2H), 7.77-7.73 (m, 1H), 7.68-7.66 (m, 1H), 7.61-7.57 (m, 2H), 7.38-7.35 (m, 1H), 4.74 (s, 2H). |
| 27 | 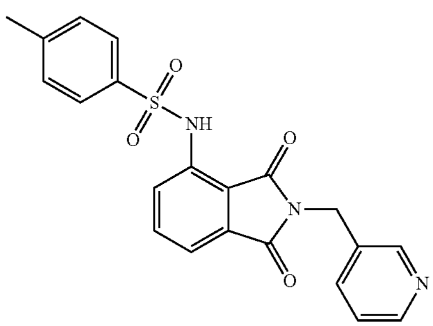 [SMILES: Cc1ccc(S(=O)(=O)Nc2cccc3c2C(=O)N(Cc2cccnc2)C3=O)cc1] | 408.08 | 99.19%, Rt = 5.93 min (1) | ¹H NMR (400 MHz, DMSO-d6): δ 9.85 (bs, 1H), 8.53 (s, 1H), 8.49 (m, 1H), 7.83-7.81 (d, J = 8.4 Hz, 2H), 7.74-7.67 (m, 2H), 7.58-7.54 (m, 2H), 7.37-7.34 (m, 3H), 4.74 (s, 2H), 2.34 (s, 3H). |
| 28 | 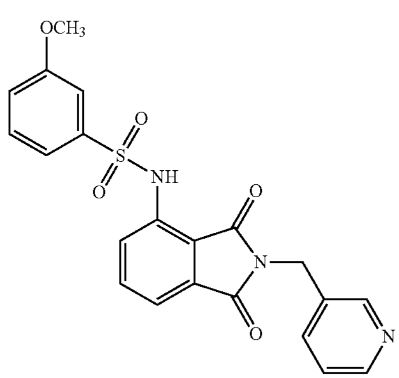 | 424.09 | 99.19%, Rt = 5.60 min (1) | ¹H NMR (400 MHz, DMSO-d6): δ 10.06 (bs, 1H), 8.54 (s, 1H), 8.50-8.49 (m, 1H), 7.75-7.71 (m, 1H), 7.67-7.65 (m, 1H), 7.58-7.55 (m, 2H), 7.49-7.45 (m, 3H), 7.38-7.35 (m, 1H), 7.21-7.19 (m, 1H), 4.74 (s, 2H), 3.76 (s, 3H). |

-continued

| Cmpd number | Structure | LCMS (M + 1) | Purity (LCMS) | ¹H NMR |
|---|---|---|---|---|
| 29 | F₂HCO-C₆H₄-SO₂-NH-(isoindoline-1,3-dione)-N-CH₂-(pyridin-3-yl) | 460.18 | 99.36%, Rt = 5.34 min (1) | ¹H NMR (400 MHz, DMSO-d6): δ 10.05 (bs, 1H), 8.64 (s, 1H), 8.58-8.57 (d, J = 4.0 Hz, 1H), 8.03-8.01 (d, J = 8.8 Hz, 2H), 7.90-7.88 (m, 1H), 7.76-7.72 (t, J = 7.8 Hz, 1H), 7.60-7.09 (m, 6H), 4.80 (s, 2H). |
| 30 | F-C₆H₄-SO₂-NH-(isoindoline-1,3-dione)-N-CH₂-(pyridin-3-yl) | 412.20 | 98.72% Rt = 5.19 min (1) | ¹H NMR (400 MHz, DMSO-d6): δ 10.08 (bs, 1H), 8.54 (s, 1H), 8.49 (m, 1H), 7.99 (m, 2H), 7.76-7.72 (t, J = 7.6 Hz 1H), 7.66-7.63 (d, J = 8.4 Hz, 1H), 7.60-7.56 (m, 2H), 7.42-7.35 (m, 3 H), 4.73 (s, 2 H). |
| 31 | Cl-C₆H₄-SO₂-NH-(isoindoline-1,3-dione)-N-CH₂-(pyridin-3-yl) | 428.08 | 98.83% Rt = 5.41 min (1) | ¹H NMR (400 MHz, DMSO-d6): δ 10.19 (bs, 1H), 8.55 (s, 1H), 8.49 (s, 1H), 7.94-7.90 (d, J = 8.8 Hz, 2H), 7.76-7.72 (m, 1H), 7.66-7.64 (m, 3H), 7.61-7.59 (m, 1H), 7.56-7.54 (m, 1H), 7.38-7.34 (m, 1H), 4.74 (s, 2H). |

Example 3

Synthesis of Compound 32 [N-(1,3-dioxo-2-(pyridin-4-ylmethyl)isoindolin-4-yl)-4-(oxazol-5-yl)benzenesulfonamide]

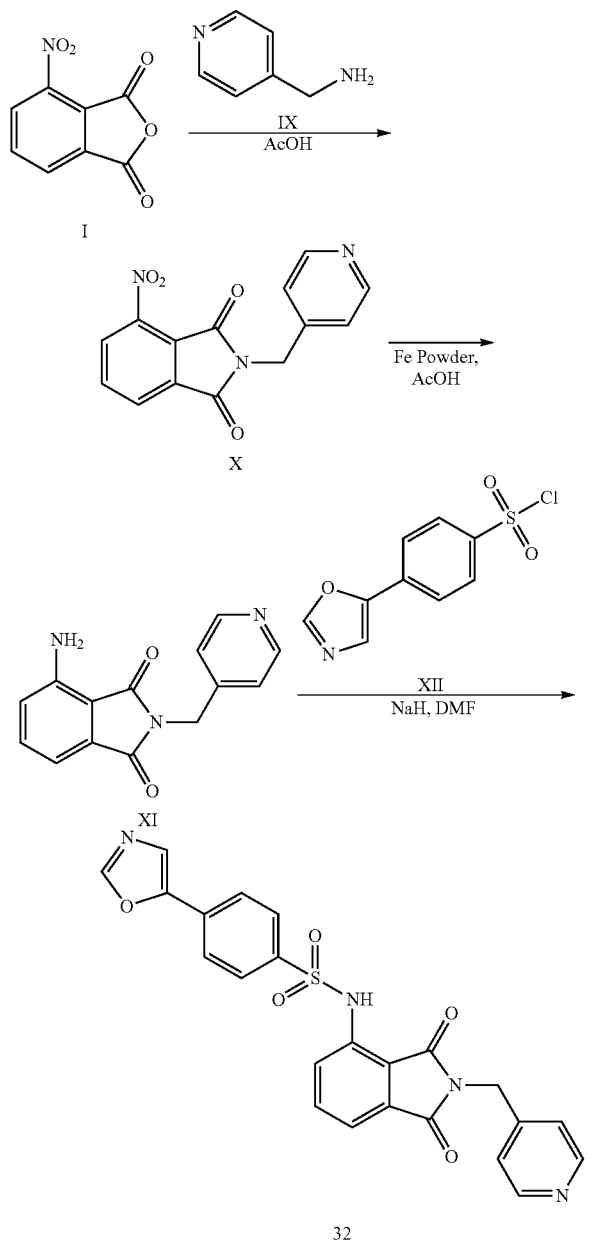

Synthesis of X:

To a stirred solution of compound I (500 mg, 2.59 mmol) in acetic acid (7 mL) was added compound IX (419 mg, 3.88 mmol) and the reaction heated to a reflux for 18 hours. The reaction mixture was cooled to room temperature and the acetic acid removed under reduced pressure to obtain a crude product which was purified by suspension in ethanol (5 mL), cooling and filtration to obtain 4-nitro-2-pyridin-4-ylmethyl-isoindole-1,3-dione as a yellow solid (X; 400 mg). $^1$H NMR (400 MHz, DMSO-d6): δ 8.49 (d, J=5.6 Hz, 2H), 8.29 (d, J=8.4 Hz, 1H), 8.25 (t, J=8.0 Hz, 1H), 8.19 (d, J=8.0 Hz, 1H), 7.34 (d, J=5.2 Hz, 2H), 4.80 (s, 2H).

Synthesis of XI:

To a solution of compound X (400 mg) in acetic acid (10 mL) was added iron powder (40 mg) and the reaction mixture was stirred for 1 hour at room temperature. The acetic acid was removed under reduced pressure to obtain a crude product. The reaction mixture was diluted with water and extracted with dichloromethane. The organic layer was washed with brine solution, dried over anhydrous $Na_2SO_4$ and evaporated under reduced pressure to afford 4-amino-2-pyridin-4-ylmethyl-isoindole-1,3-dione as a light brown solid (XI; 250 mg,). MS (M+1): 254.1

Synthesis of 32; N-(1,3-dioxo-2-(pyridin-4-ylmethyl)isoindolin-4-yl)-4-(oxazol-5-yl)benzenesulfonamide To a mixture of sodium hydride (19 mg, 0.78 mmol) in DMF (2 mL) at 0° C. was added compound XI (50 mg, 0.19 mmol) and this was stirred for 15 minutes at 0° C. To the reaction mixture was further added compound XII (144 mg, 0.59 mmol) and this was stirred for 15 minutes at 0° C. and then allowed to warm to room temperature with constant stirring for 18 hours. The reaction mixture was diluted with water and extracted with dichloromethane. The organic layer was washed with brine solution, dried over anhydrous $Na_2SO_4$ and evaporated under reduced pressure to obtain the crude compound which was purified by preparative TLC using 100% ethyl acetate as mobile phase to afford N-(1,3-dioxo-2-(pyridin-4-ylmethyl)isoindolin-4-yl)-4-(oxazol-5-yl)benzenesulfonamide as a white solid (32; 20 mg, 22.2% yield). $^1$H NMR (400 MHz, CDCl3): δ 8.89 (bs, 1H), 8.55 (d, J=5.6 Hz, 2H), 7.97 (d, J=6.8 Hz, 3H), 7.90 (d, J=8.4 Hz, 1H), 7.74 (d, J=8.4 Hz, 2H), 7.64 (t, J=7.8 Hz, 1H), 7.51-7.48 (m, 2H), 7.25-7.22 (m, 2H), 4.75 (s, 2H). MS (M+1) 461.1 (LCMS Purity 98.57%, Rt=2.39 min (3)).

Example 4

Synthesis of Compound 33 [N-(2-(4-acetylphenyl)-1,3-dioxoisoindolin-4-yl)-4-(tert-butyl)benzenesulfonamide] and Compound 34

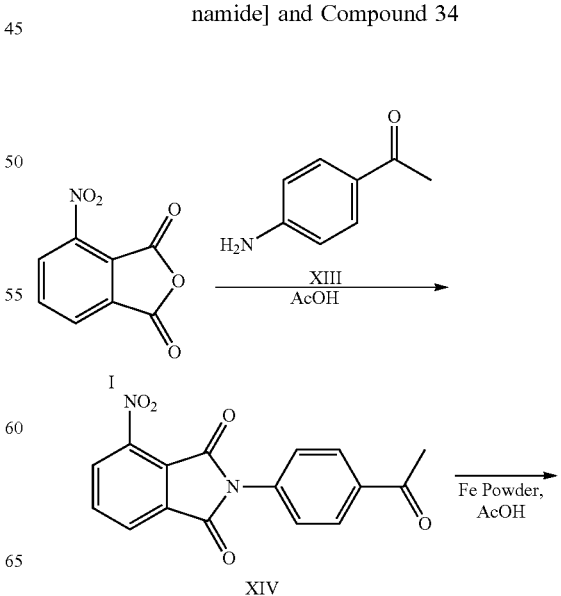

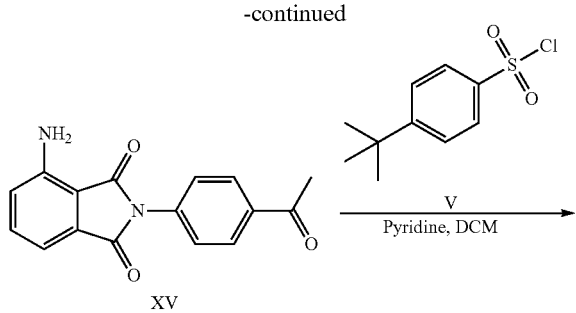

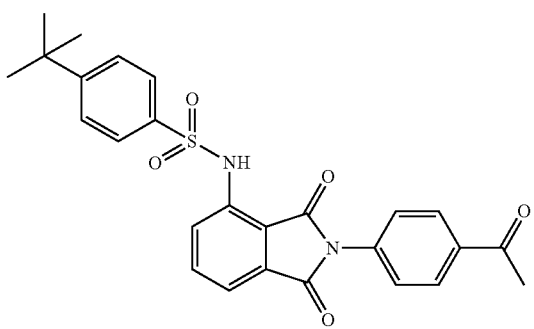

was washed with brine solution, dried over anhydrous Na$_2$SO$_4$ and the organic solvent was evaporated under reduced pressure to afford 2-(4-acetyl-phenyl)-4-amino-isoindoline-1,3-dione as a yellow solid (XV; 250 mg). MS (M+1): 281.1

Synthesis of 33; N-(2-(4-acetylphenyl)-1,3-dioxoisoindolin-4-yl)-4-(tert-butyl)benzenesulfonamide To a stirred mixture of compound XV (100 mg, 0.418 mmol) in dichloromethane (2 mL) was added pyridine (2 mL) at 0° C., followed by compound V (200 mg, 1.25 mmol). The reaction mixture was stirred for 24 hours at room temperature. The reaction mixture was concentrated under reduced pressure and diluted using saturated ammonium chloride solution and extracted with dichloromethane. The organic layer was washed with brine solution, dried over anhydrous Na$_2$SO$_4$ and the organic solvent was evaporated under reduced pressure to obtain crude compound. Crude material was purified by preparative TLC using 100% ethyl acetate as mobile phase to afford N-(2-(4-acetylphenyl)-1,3-dioxoisoindolin-4-yl)-4-(tert-butyl)benzenesulfonamide as a yellow solid (33; 20 mg, 8.4% yield). $^1$H NMR (400 MHz, DMSO-d6): δ 9.85 (bs, 1H), 8.07 (d, J=8.4 Hz, 2H), 7.90 (d, J=8.4 Hz, 2H), 7.76 (bs, 1H), 7.67 (d, J=8.4 Hz, 1H), 7.61-7.54 (m, 5H), 2.61 (s, 3H), 1.26 (s, 9H). MS (M+1) 477.2. (LCMS Purity 98.71%, Rt=2.80 min (3)).

The following compound was also prepared using a similar method and the appropriate sulfonyl chloride in the final step:

| Cmpd number | Structure | LCMS (M + 1) | Purity (LCMS) | $^1$H NMR |
|---|---|---|---|---|
| 34 | (structure shown) | 488.1 | 97.89%, Rt = 2.39 min (3) | $^1$H NMR (400 MHz, CDCl$_3$): δ 8.08 (d, J = 8.0 Hz, 2H), 8.01-7.99 (m, 4H), 7.79-7.79 (m, 3H), 7.61-7.54 (m, 3H), 7.49 (s, 1H), 2.64 (s, 3H). |

Synthesis of XIV:

To a stirred solution of compound I (500 mg, 2.59 mmol) in acetic acid (7 mL) was added compound XIII (525 mg, 3.88 mmol) and the reaction mixture was heated to a reflux for 18 hours. The reaction mixture was cooled to room temperature and acetic acid was removed under reduced pressure to obtain crude product. This was suspended in ethanol (5 mL), cooled and filtered to get pure compound 2-(4-acetyl-phenyl)-4-nitro-isoindoline-1,3-dione as a yellow solid (XIV; 400 mg). $^1$H NMR (400 MHz, DMSO-d6): δ 8.34 (d, J=8.0 Hz, 1H), 8.26 (d, J=7.6 Hz, 1H), 8.13-8.09 (m, 3H), 7.61 (d, J=8.4 Hz, 2H), 2.62 (s, 3H).

Synthesis of XV:

To a solution of compound XIV (400 mg) in acetic acid (30 mL) was added iron powder (50 mg) and the reaction mixture was stirred for 1 hour at room temperature. The acetic acid was removed under reduced pressure to obtain the crude product. The reaction mixture was diluted with water and extracted with dichloromethane. The organic layer Example 5

Synthesis of Compound 35 [N-(2-(4-cyanophenyl)-1,3-dioxoisoindolin-4-yl)-4-(oxazol-5-yl)benzenesulfonamide] and Compound 36

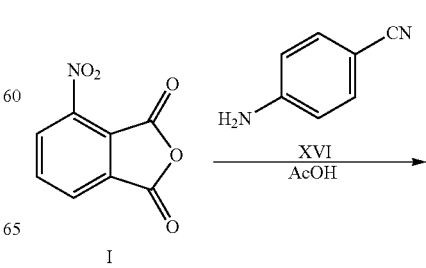

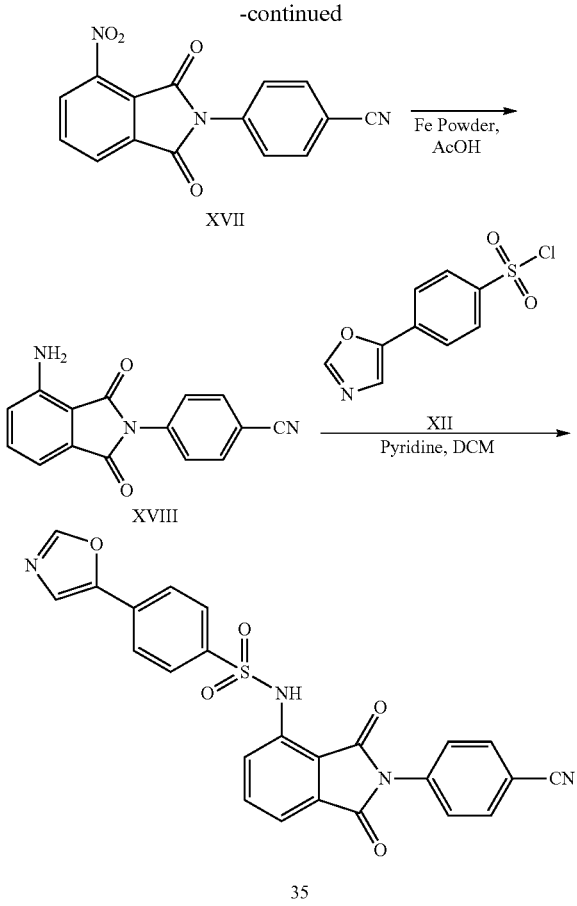

Synthesis of XVII:

To a stirred solution of compound I (500 mg, 2.59 mmol) in acetic acid (7 mL) was added compound XVI (458 mg, 3.88 mmol) and the reaction heated to reflux for 18 hours. The reaction mixture was cooled to room temperature and acetic acid was removed under reduced pressure to obtain the crude product. This material was suspended in ethanol (5 mL), cooled and filtered to leave 4-(4-nitro-1,3-dioxo-1,3-dihydro-isoindolin-2-yl)-benzonitrile as a yellow solid (XVII; 400 mg). $^1$H NMR (400 MHz, DMSO-d6): δ 7.67 (d, J=8.4 Hz, 2H), 8.07 (d, J=8.4 Hz, 2H), 8.12 (t, J=8.0 Hz, 1H), 8.27 (d, J=6.8 Hz, 1H), 8.35 (d, J=8.0 Hz, 1H).

Synthesis of XVIII:

To a solution of compound XVII (400 mg) in acetic acid (10 mL) was added iron powder (100 mg) and the reaction mixture was stirred for 1 hour at room temperature. Acetic acid was removed under reduced pressure to obtain a crude product. The reaction mixture was diluted with water and extracted with dichloromethane. The organic layer was washed with brine solution, dried over anhydrous Na$_2$SO$_4$ and the organic solvent was evaporated under reduced pressure to afford 4-(4-amino-1,3-dioxo-1,3-dihydro-isoindolin-2-yl)-benzonitrile as a yellow solid (XVIII; 300 mg). $^1$H NMR (400 MHz, DMSO-d6): δ 6.59 (s, 2H, s), 7.05 (t, J=8.0 Hz, 2H), 7.50 (d, J=7.6 Hz, 1H), 7.66 (d, J=8.4 Hz, 2H), 7.97 (d, J=8.4 Hz, 2H). MS (M+1) 264.07

Synthesis of 35; N-(2-(4-cyanophenyl)-1,3-dioxoisoindolin-4-yl)-4-(oxazol-5-yl)benzene sulfonamide To a mixture of compound XVIII (100 mg, 0.418 mmol) in dichloromethane (2 mL) was added pyridine (2 mL) at 0° C. and then compound XII (200 mg, 1.25 mmol) was introduced. The reaction mixture was stirred for 24 hours at room temperature. This was concentrated under reduced pressure and diluted using saturated ammonium chloride solution and extracted with dichloromethane. The organic layer was washed with brine solution, dried over anhydrous Na$_2$SO$_4$ and evaporated under reduced pressure to obtain the crude compound. This was purified by preparative TLC using 100% ethyl acetate as mobile phase to afford N-(2-(4-cyanophenyl)-1,3-dioxoisoindolin-4-yl)-4-(oxazol-5-yl)benzenesulfonamide as a white solid (35; 60 mg, 33% yield). $^1$H NMR (400 MHz, DMSO-d6): δ 10.09 (s, 1H). 8.51 (s, 1H), 7.96-8.04 (m, 4H), 7.86-7.91 (m, 3H), 7.70-7.74 (m, 1H), 7.62 (t, J=7.6 Hz, 3H), 7.54-7.56 (m, 1H). MS (M+1) 471.1. (LCMS Purity 99.08%, Rt=2.45 min (3)).

The following compound was also prepared using a similar method and the appropriate sulfonyl chloride in the final step:

| Cmpd number | Structure | LCMS (M + 1) | Purity (LCMS) | $^1$H NMR |
|---|---|---|---|---|
| 36 | 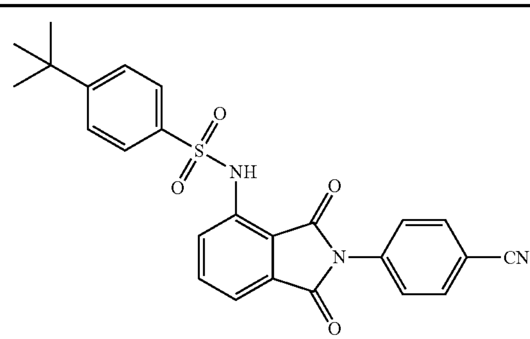 | 460.1 | 98.07%, Rt = 2.66 min (3) | $^1$H NMR (400 MHz, DMSO-d6): δ 9.0 (bs, 1H), 7.98 (d, J = 8.0 Hz, 1H), 7.86 (d, J = 8.0 Hz, 2H), 7.79 (d, J = 8.0 Hz, 2H), 7.69-7.73 (m, 1H), 7.62 (d, J = 12.0 Hz, 2H), 7.58 (d, J = 8.0 Hz, 1H), 7.51 (d, J = 8.0 Hz, 2H), 1.30 (s, 9H). |

Example 6

Synthesis of Compound 37 [4-(tert-butyl)-N-(2-(3-cyanophenyl)-1,3-dioxoisoindolin-4-yl)benzenesulfonamide] and Compounds 38-42

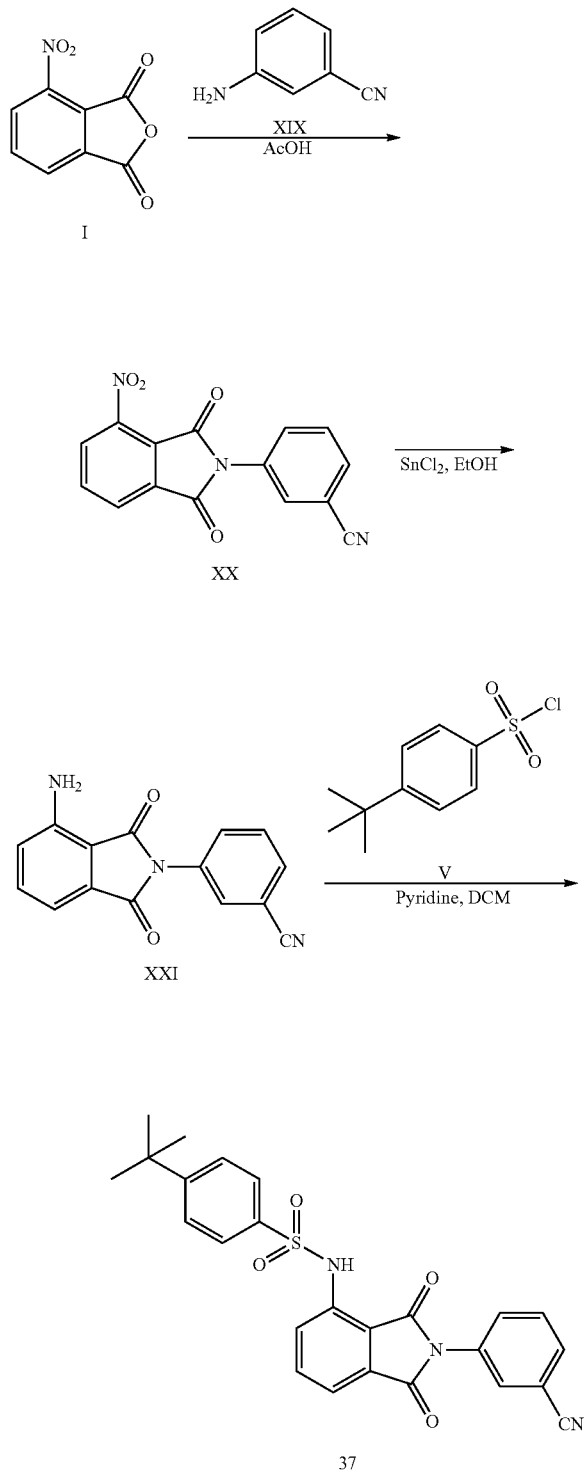

Synthesis of XX:

To a stirred solution of compound I (3 g, 15.54 mmol) in acetic acid (40 mL) was added compound XIX (2.7 g, 23.3 mmol) and the reaction heated to a reflux for 18 hours. The reaction mixture was cooled to room temperature and acetic acid was removed under reduced pressure to obtain a crude product. This was suspended in ethanol, cooled and filtered to afford 3-(4-nitro-1,3-dioxoisoindolin-2-yl)benzonitrile as an off white solid (XX; 3.3 g; 73% yield). $^1$H NMR (400 MHz, DMSO-d6): δ 8.38-8.36 (d, J=8.0 Hz, 1H), 8.31-8.29 (d, J=7.6 Hz, 1H), 8.17-8.13 (t, J=8.0 Hz, 1H), 7.9 (m, 2H), 7.78 (m, 2H).

Synthesis of XXI:

To a stirred solution of compound XX (3.3 g, 11.26 mmol) in ethanol (70 mL) was added tin II chloride powder (27 g, 123 mmol) and the reaction mixture was heated to a reflux for 18 hours. The ethanol was concentrated under reduced pressure to obtain a crude product. The reaction mixture was diluted with water and a saturated solution with sodium bicarbonate and extracted with ethyl acetate. The organic layer was washed with brine solution, dried over anhydrous Na$_2$SO$_4$ and evaporated under reduced pressure to afford 3-(4-amino-1,3-dioxoisoindolin-2-yl)benzonitrile as a yellow solid (XXI; 3 g). MS (M−1): 262.11

Synthesis of 37; 4-(tert-butyl)-N-(2-(3-cyanophenyl)-1,3-dioxoisoindolin-4-yl)benzenesulfonamide To a mixture of compound XXI (150 mg, 0.57 mmol) in pyridine (2 mL) was added 4-tert butylbenzenesulfonyl chloride (V; 264 mg, 1.14 mmol). The reaction mixture was stirred for 2 hours at 100° C. The reaction mixture was cooled and concentrated under reduced pressure and diluted using saturated ammonium chloride solution, which was extracted with dichloromethane. The organic layer was washed with brine solution, dried over anhydrous Na$_2$SO$_4$ and evaporated under reduced pressure to obtain the crude compound, which was purified by column chromatography using 25% ethyl acetate in hexane to afford 4-(tert-butyl)-N-(2-(3-cyanophenyl)-1,3-dioxoisoindolin-4-yl)benzenesulfonamide as an off white solid (37; 130 mg, 50% yield). $^1$H NMR (400 MHz, DMSO-d6): δ 9.91 (bs, 1H), 7.94-7.90 (m, 4H), 7.80-7.62 (m, 7H), 1.27 (s, 9H). MS (M−1) 458.24 (LCMS Purity 96.81%, Rt=6.39 min (1)).

The following compounds were also prepared using a similar method and the appropriate sulfonyl chloride in the final step:

| Cmpd number | Structure | LCMS (M−1) | Purity (LCMS) | ¹H NMR |
|---|---|---|---|---|
| 38 | F₂HCO-C₆H₄-SO₂NH-(isoindoline-1,3-dione)-N-C₆H₄-CN | 468.12 | 96.14%, Rt = 5.66 min (1) | ¹H NMR (400 MHz, DMSO-d6): δ 10.12 (bs, 1H), 8.08-8.05 (d, J = 8.4 Hz, 2H), 7.94-7.90 (m, 2H), 7.81-7.76 (m, 3H), 7.66-7.64 (m, 2H), 7.39-7.22 (m, 3H). |
| 39 | F₃C-C₆H₄-SO₂NH-(isoindoline-1,3-dione)-N-C₆H₄-CN | 470.14 | 99.73%, Rt = 5.55 min (1) | ¹H NMR (400 MHz, DMSO-d6): δ 10.50 (bs, 1H), 8.16-8.14 (d, J = 8.0 Hz, 2H), 8.0-7.98 (d, J = 8.0 Hz, 2H), 7.94-7.92 (m, 1H), 7.86 (s, 1H), 7.82-7.78 (m, 1H), 7.66-7.75 (m, 2H), 7.69-7.68 (m, 1H), 7.64-7.61 (m, 1H). |
| 40 | F₃CO-C₆H₄-SO₂NH-(isoindoline-1,3-dione)-N-C₆H₄-CN | 485.64 | 98.61%, Rt = 5.93 min (1) | ¹H NMR (400 MHz, DMSO-d6): δ 10.29 (bs, 1H), 8.12-8.09 (m, 2H), 7.93 (m, 1H), 7.87-7.83 (m, 2H), 7.76-7.72 (m, 3H), 7.66-7.60 (m, 3H). |
| 41 | 4-Cl-3-CF₃-C₆H₃-SO₂NH-(isoindoline-1,3-dione)-N-C₆H₄-CN | 504.24 | 97.96%, Rt = 5.73 min (1) | ¹H NMR (400 MHz, DMSO-d6): δ 10.71 (bs, 1H), 8.42 (s, 1H), 8.21-8.19 (d, J = 6.8 Hz, 1H), 8.0-7.98 (d, J = 8.4 Hz, 1H), 7.93 (m, 1H), 7.87-7.83 (m, 2H), 7.77 (m, 3H), 7.64-7.62 (d, J = 8.4 Hz, 1H). |
| 42 | 4-F-3-CF₃-C₆H₃-SO₂NH-(isoindoline-1,3-dione)-N-C₆H₄-CN | 488.09 | 99.86%, Rt = 5.66 min (1) | ¹H NMR (400 MHz, DMSO-d6): δ 10.62 (bs, 1H), 8.43-8.42 (m, 1H), 8.35-8.33 (m, 1H), 7.95-7.93 (m, 1H), 7.86-7.76 (m, 5H), 7.73-7.71 (m, 1H), 7.65-7.63 (m, 1H). |

Example 7

Synthesis of Compound 43 [4-(tert-butyl)-N-(7-chloro-1,3-dioxo-2-(pyridin-3-yl)isoindolin-4-yl)benzene sulfonamide]; Compound 44 [3-(4-(4-(tert-butyl)phenyl-sulfonamido)-7-chloro-1,3-dioxoisoindolin-2-yl)pyridine 1-oxide] and Compounds 45-58

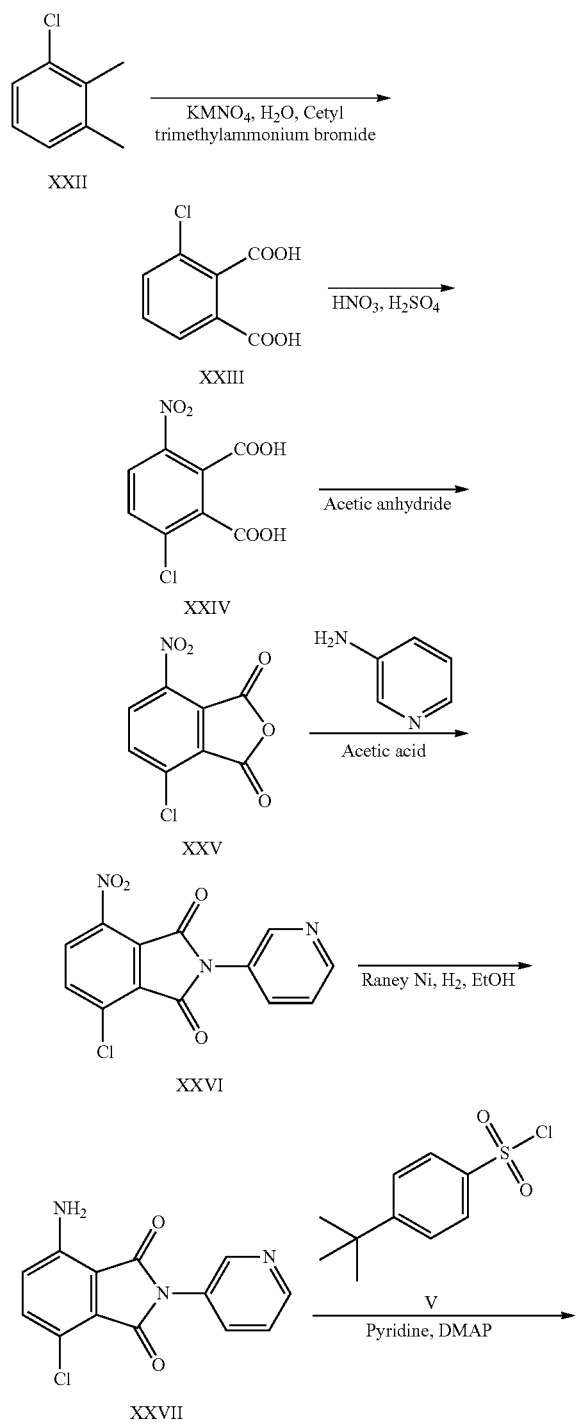

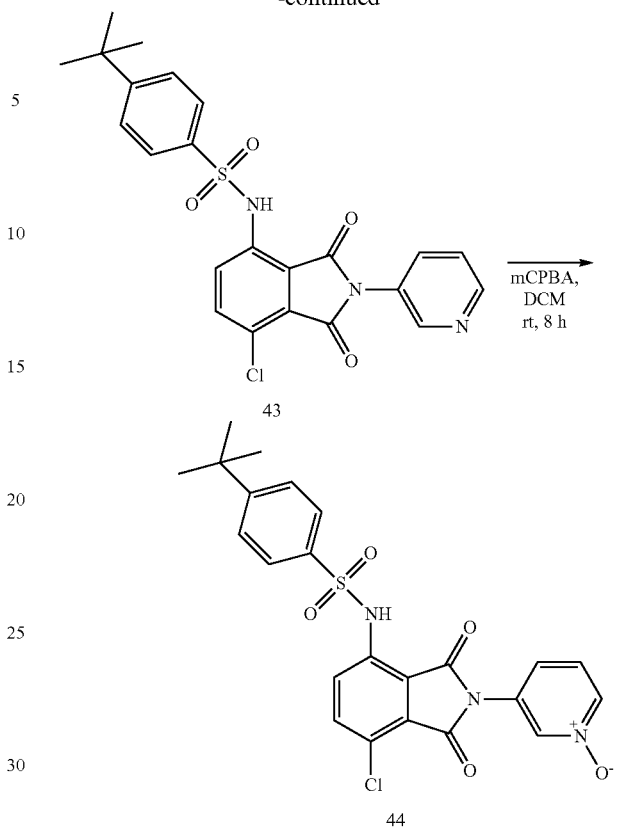

Synthesis of XXIII:

To a stirred solution of compound XXII (10.0 g, 71.4 mmol) in water (125 mL) was added a catalytic amount of cetyl trimethylammonium bromide (0.01 g) and potassium permanganate (45.1 g, 280 mmol). The reaction mixture was heated to a reflux for 5 days. The reaction mass was filtered through a sintered funnel, whereupon the aqueous solution was acidified to pH 1. The aqueous solution was extracted with ethyl acetate. The organic layer was separated, dried using anhydrous $Na_2SO_4$ and concentrated to afford 3-chlorophthalic acid as a yellow solid (XXIII; 5 g, 35% yield). $^1$H NMR (400 MHz, DMSO-d6): δ 13.37 (bs, 2H), 7.90-7.88 (dd, J=7.6 Hz, 1H), 7.77-7.75 (d, J=7.6 Hz, 1H) 7.56-7.52 (t, J=7.8 Hz, 1H). MS (M-1): 198.96

Synthesis of XXIV:

Compound XXIII (5.0 g, 25.1 mmol) was added to a 1:2 solution of nitric acid and sulfuric acid (9 mL) at 0° C. The reaction mixture was stirred at room temperature for 3.5 hours. The reaction mixture was then cooled to 0° C. and crushed ice was added. The solid which precipitated out was filtered to afford 3-chloro-6-nitrophthalic acid as a yellow solid (XXIV; 5 g, 80% yield). $^1$H NMR (400 MHz, DMSO-d6): δ 8.16-8.13 (d, J=8.8 Hz, 1H), 7.93-7.91 (d, J=8.8 Hz, 1H). MS (M-1): 244.06

Synthesis of XXV:

A stirred solution of compound XXIV (5.0 g; 20.3 mmol) in acetic anhydride (60 mL) was heated at 120° C. for 12 hours. The reaction mixture was cooled and diluted with water. The aqueous layer was extracted with ethyl acetate. The organic layer was washed with brine, dried over anhydrous $Na_2SO_4$ and concentrated to afford 4-chloro-7-nitroisobenzofuran-1,3-dione as a yellow solid (XXV; 5 g).

Synthesis of XXVI:

To a stirred solution of compound XXV (5.0 g, 21.1 mmol) in acetic acid (62 mL) was added 2-aminopyridine (3.4 g, 34 mmol) and the reaction mixture heated at a reflux for 18 hours. The reaction mixture was cooled to room temperature and the acetic acid removed under reduced pressure to obtain crude product 4-chloro-7-nitro-2-(pyridin-3-yl)isoindoline-1,3-dione as a yellow solid (XXVI; 4.5 g,). MS (M+1): 304.02, which was used directly in the next step.

Synthesis of XXVII:

To a solution of compound XXVI (4.5 g) in ethanol (100 mL) under nitrogen atmosphere was added Raney nickel. The reaction mixture was purged with hydrogen and stirred under hydrogen balloon pressure for 6 hours at room temperature. The reaction mass was filtered through a celite bed under a nitrogen atmosphere and the solvent evaporated under reduced pressure to afford compound 4-amino-7-chloro-2-(pyridin-3-yl)isoindoline-1,3-dione as a yellow solid (XXVII; 1.3 g). $^1$H NMR (400 MHz, DMSO-d6): δ 8.65 (s, 1H), 8.61-8.59 (d, J=4.8 Hz, 1H), 7.90-7.87 (d, J=4.8 Hz, 1H), 7.59-7.56 (m, 1H), 7.50-7.48 (m, 1H), 7.08-7.04 (m, 1H), 6.74-6.60 (m, 2H). MS (M+1): 274.04

Synthesis of 43; 4-(tert-butyl)-N-(7-chloro-1,3-dioxo-2-(pyridin-3-yl)isoindolin-4-yl)benzenesulfonamide A mixture of compound XXVII (300 mg, 1.09 mmol) and pyridine (3 mL) was cooled to 0° C. and tert-butylbenzenesulfonyl chloride V (1.01 g, 4.1 mmol) was added together with a catalytic quantity of DMAP. The reaction mixture was stirred for 24 hours at 125° C. The reaction mixture was concentrated and to the resultant residue water was added and extracted with dichloromethane. The organic layer was washed with brine solution, dried over anhydrous Na$_2$SO$_4$, filtered and the organic solvent was evaporated under reduced pressure to obtain the crude compound. This was purified by preparative HPLC to afford 4-(tert-butyl)-N-(7-chloro-1,3-dioxo-2-(pyridin-3-yl)isoindolin-4-yl)benzenesulfonamide as a light yellow solid (43; 10 mg,). $^1$H NMR (400 MHz, DMSO-d6): δ 10.0 (bs, 1H), 8.60 (m, 2H), 7.86-7.83 (m, 3H), 7.66-7.64 (m, 2H), 7.59-7.56 (m, 3H), 1.27 (s, 9H). MS (M+1): 470.2 (LCMS Purity 97.52%, Rt=6.17 min (1)).

Synthesis of 44; 3-(4-(4-(tert-butyl)phenylsulfonamido)-7-chloro-1,3-dioxoisoindolin-2-yl)pyridine 1-oxide To a stirred solution of 1-(tert-butyl)-N-(7-chloro-1,3-dioxo-2-(pyridin-3-yl)isoindolin-4-yl)benzenesulfonamide (43; 0.16 g, 0.34 mmol) in dichloromethane (5 mL), was added metachloroperoxybenzoic acid (0.059 g, 0.34 mmol). The reaction was stirred at room temperature for 8 hours whereupon the solvent was concentrated under reduced pressure and the residue diluted with water. The aqueous layer was extracted with dichloromethane. The combined organic layers were washed sequentially with sodium bicarbonate and brine, then dried over anhydrous Na$_2$SO$_4$, filtered and concentrated under vacuum to leave the crude compound which was triturated with hexane ether (1:1) mixture followed by prep TLC purification using 5% methanol in dichloromethane to afford 3-(4-(4-(tert-butyl)phenylsulfonamido)-7-chloro-1,3-dioxoisoindolin-2-yl)pyridine 1-oxide (44; 0.060 g, 36% yield). $^1$H NMR (400 MHz, DMSO-d6): δ 10.06 (bs, 1H), 8.33-8.31 (m, 2H), 7.94-7.92 (m, 2H), 7.83-7.81 (m, 1H), 7.69-7.57 (m, 4H), 7.45-7.43 (d, J=8.0 Hz, 1H), 1.27 (s, 9H). MS (M+1): 486.14. (LCMS purity 96.97%, Rt=5.34 min (1)).

The following compounds were prepared in a similar manner using the appropriate sulfonyl chloride in the penultimate step. This resulted either in the final pyridine compounds, which if required could also be converted into the corresponding pyridine N-oxides using mCPBA:

| Cmpd number | Structure | LCMS (M + 1) | Purity (LCMS) | $^1$H NMR |
|---|---|---|---|---|
| 45 | 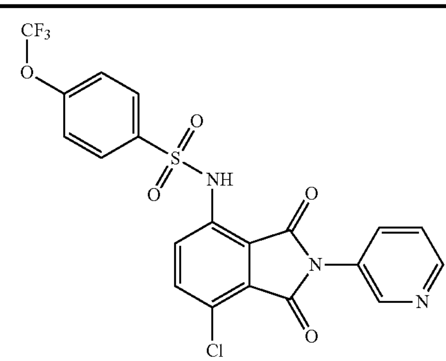 | 498.07 | 97.70% Rt = 5.54 min (1) | $^1$H NMR (400 MHz, DMSO-d6): δ 10.37 (bs, 1H), 8.64-8.63 (d, J = 4 Hz, 1H), 8.59 (s, 1H), 8.11-8.09 (d, J = 8.8 Hz, 2H), 7.85-7.83 (d, J = 8.8 Hz, 2H), 7.65-7.58 (m, 4H). |
| 46 | 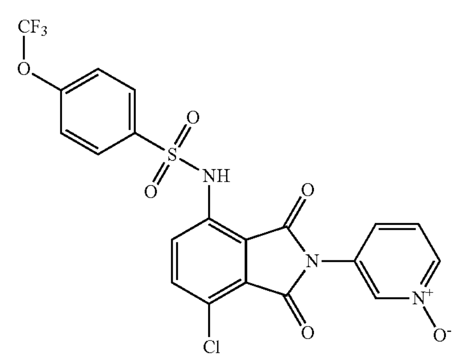 [SMILES: O=C1c2c(Cl)ccc(NS(=O)(=O)c3ccc(OC(F)(F)F)cc3)c2C(=O)N1c1ccc[n+]([O-])c1] | 514.11 | 98.81% Rt = 4.87 (1) | $^1$H NMR (400 MHz, DMSO-d6): δ 10.43 (bs, 1H), 8.32-8.31 (m, 2H), 8.11-8.09 (d, J = 8.8 Hz, 2H), 7.90-7.80 (m, 1H), 7.65-7.57 (m, 4H), 7.43-7.41 (d, J = 8 Hz, 1H) |

-continued

| Cmpd number | Structure | LCMS (M + 1) | Purity (LCMS) | ¹H NMR |
|---|---|---|---|---|
| 47 | 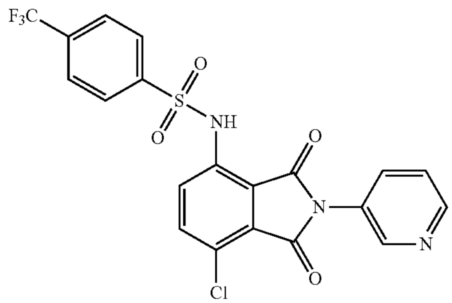 [SMILES: O=C1c2c(Cl)ccc(NS(=O)(=O)c3ccc(C(F)(F)F)cc3)c2C(=O)N1c1cccnc1] | 482.08 | 99.65% Rt = 5.25 min (1) | ¹H NMR (400 MHz, DMSO-d6): δ 10.52 (bs, 1H), 8.63-8.62 (d, J = 3.6 Hz, 1H), 8.58-8.57 (d, J = 2 Hz, 1H), 8.14-8.12 (d, J = 8 Hz, 2H), 7.98-7.96 (d, J = 8 Hz, 2H), 7.83-7.81 (d, J = 8 Hz, 1H), 7.77-7.74 (m, 1H), 7.62-7.57 (m, 2H). |
| 48 | 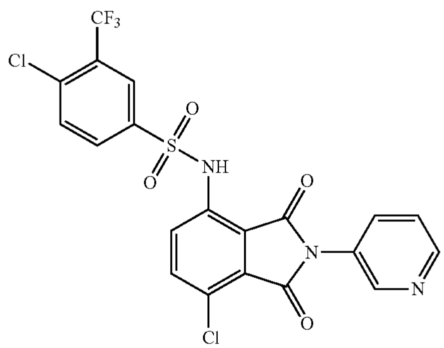 [SMILES: O=C1c2c(Cl)ccc(NS(=O)(=O)c3ccc(Cl)c(C(F)(F)F)c3)c2C(=O)N1c1cccnc1] | 516.06 | 97.50% Rt = 5.48 min (1) | ¹H NMR (400 MHz, DMSO-d6): δ 10.79 (bs, 1H), 8.64-8.63 (d, J = 3.2 Hz, 1H), 8.58 (s, 1H), 8.42 (s, 1H), 8.21-8.19 (d, J = 6.8 Hz, 1H), 7.99-7.97 (d, J = 8.4 Hz, 1H), 7.83-7.81 (d, J = 8.4 Hz, 2H), 7.63-7.58 (m, 2H). |
| 49 | 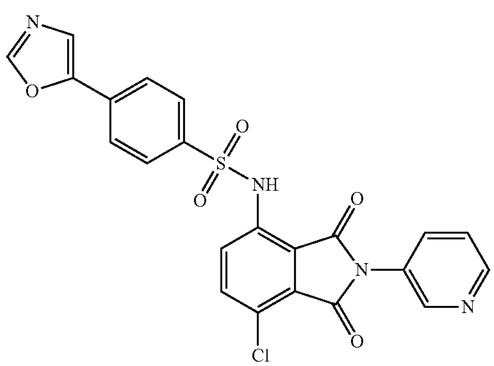 [SMILES: O=C1c2c(Cl)ccc(NS(=O)(=O)c3ccc(-c4cnco4)cc3)c2C(=O)N1c1cccnc1] | 480.81 | 97.92% Rt = 4.76 min (1) | ¹H NMR (400 MHz, DMSO-d6): δ 10.22 (bs, 1H), 8.63-8.62 (d, J = 3.6 Hz, 1H), 8.60-8.59 (d, J = 2 Hz, 1H), 8.56 (s, 1 H), 8.07-8.05 (d, J = 8.4 Hz, 2H), 7.96-7.92 (m, 3H), 7.84-7.81 (m, 2H), 7.67-7.65 (d, J = 8.8 Hz, 1H), 7.59-7.56 (m, 1H). |
| 50 | 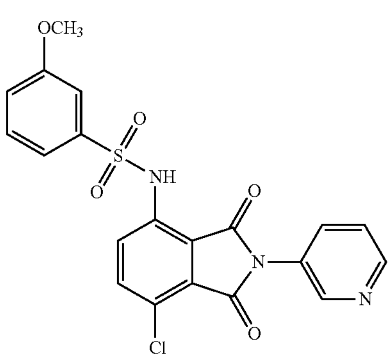 [SMILES: COc1cccc(S(=O)(=O)Nc2ccc(Cl)c3c2C(=O)N(c2cccnc2)C3=O)c1] | 444.09 | 98.76% Rt = 5.25 min (1) | ¹H NMR (400 MHz, DMSO-d6): δ 10.17 (bs, 1H), 8.65-8.62 (m, 2H), 7.88-7.80 (m, 2H), 7.64-7.51 (m, 5H), 7.27-7.25 (d, J = 8 Hz, 1H), 3.80 (s, 3H). |

| Cmpd number | Structure | LCMS (M + 1) | Purity (LCMS) | ¹H NMR |
|---|---|---|---|---|
| 51 | 4-F-C6H4-SO2-NH-[4-position of 4-Cl-2-(pyridin-3-yl)isoindoline-1,3-dione] | 432.03 | 98.57% Rt = 5.05 min (1) | ¹H NMR (400 MHz, DMSO-d6): δ 10.20 (bs, 1H), 8.64-8.63 (d, J = 3.2 Hz, 1H), 8.61 (s, 1H), 8.05 (m, 2H), 7.86-7.80 (m, 2H), 7.65-7.60 (m, 2H), 7.49-7.44 (m, 2H). |
| 52 | 4-(CHF2O)-C6H4-SO2-NH-[4-position of 4-Cl-2-(pyridin-3-yl)isoindoline-1,3-dione] | 480.04 | 99.23% Rt = 5.22 min (1) | ¹H NMR (400 MHz, DMSO-d6): δ 10.17 (bs, 1H), 8.64-8.61 (m, 2H), 8.06-8.04 (d, J = 9.2 Hz, 2H), 7.86-7.80 (m, 2H), 7.66-7.64 (d, J = 8.8 Hz, 1H), 7.59 (m, 1H), 7.40-7.37 (m, 3H). |
| 53 | 4-NC-C6H4-SO2-NH-[4-position of 4-Cl-2-(pyridin-3-yl)isoindoline-1,3-dione] | 439.11 | 98.42% Rt = 4.66 min (1) | ¹H NMR (400 MHz, DMSO-d6): δ 10.63 (bs, 1H), 8.65-8.63 (d, J = 4.8 Hz, 1H), 8.60-8.59 (d, J = 2 Hz, 1H), 8.11 (m, 4H), 7.84-7.81 (m, 2H), 7.62-7.58 (m, 2H). |
| 54 | 4-MeO-C6H4-SO2-NH-[4-position of 4-Cl-2-(pyridin-3-yl)isoindoline-1,3-dione] | 444.16 | 98.28% Rt = 5.39 min (1) | ¹H NMR (400 MHz, DMSO-d6): δ 9.86 (bs, 1H), 8.64-8.62 (m, 2H), 7.94-7.92 (d, J = 8.8 Hz, 2H), 7.87-7.85 (d, J = 7.6 Hz, 1H), 7.82-7.79 (d, J = 9.2 Hz, 1H), 7.68-7.66 (d, J = 8.8 Hz, 1H), 7.61-7.58 (m, 1H), 7.13-7.11 (d, J = 8.4 Hz, 2H), 3.82 (s, 3H), |

| Cmpd number | Structure | LCMS (M + 1) | Purity (LCMS) | ¹H NMR |
|---|---|---|---|---|
| 55 | 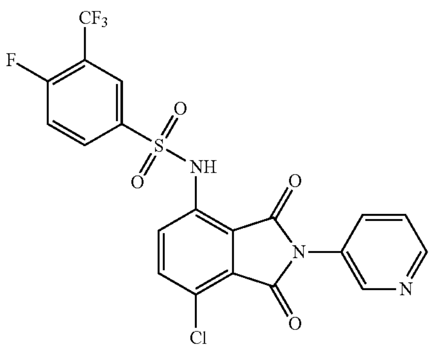 [SMILES: O=C1c2c(Cl)ccc(NS(=O)(=O)c3ccc(F)c(C(F)(F)F)c3)c2C(=O)N1c1cccnc1] | 500.09 | 99.79%, Rt = 5.28 min (1) | ¹H NMR (400 MHz, DMSO-d6): δ 10.72 (bs, 1H), 8.64-8.63 (d, J = 3.6 Hz, 1H), 8.59 (s, 1H), 8.43-8.42 (d, J = 5.3 Hz, 1H), 8.34-8.33 (m, 1H), 7.84-7.76 (m, 3H) 7.64-7.58 (m, 2H). |
| 56 | 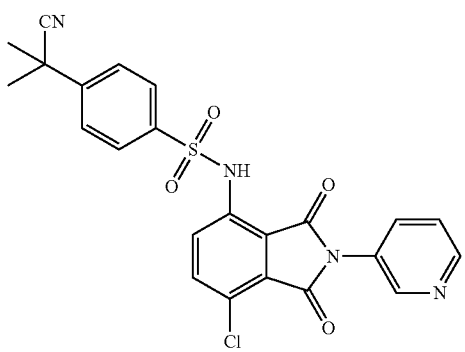 [SMILES: CC(C)(C#N)c1ccc(S(=O)(=O)Nc2ccc(Cl)c3c2C(=O)N(c2cccnc2)C3=O)cc1] | 481.03 | 99.41%, Rt = 5.27 min (1) | ¹H NMR (400 MHz, DMSO-d6): δ 10.41 (bs, 1H), 8.64-8.60 (m, 2H), 8.06-8.04 (d, J = 8.4 Hz, 2H), 7.83-7.82 (m, 2H), 7.78-7.76 (d, J = 8.4 Hz, 2H), 7.67-7.65 (m, 1H), 7.60-7.58 (m, 1H), 1.68 (s, 6H). |
| 57 | 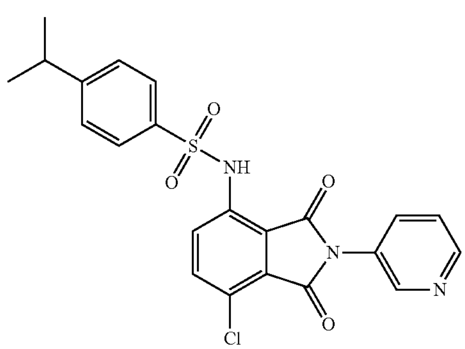 | 456.35 | 99.36%, Rt = 5.94 min (1) | ¹H NMR (400 MHz, DMSO-d6): δ 10.0 (bs, 1H), 8.64-8.63 (d, J = 4.0 Hz, 1H), 8.61 (s, 1H), 7.93-7.91 (d, J = 8.4 Hz, 2H), 7.86-7.82 (m, 2H), 7.69-7.67 (d, J = 8.8 Hz, 1H), 7.60-7.58 (m, 1H), 7.51-7.49 (d, J = 8.4 Hz, 2H), 3.01-2.94 (m, 1H), 1.19-1.18 (d, J = 6.8 Hz, 6H). |
| 58 | 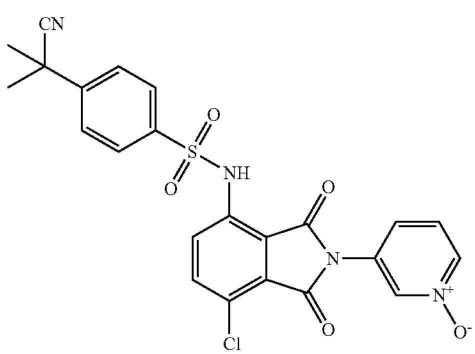 [SMILES: CC(C)(C#N)c1ccc(S(=O)(=O)Nc2ccc(Cl)c3c2C(=O)N(c2ccc[n+]([O-])c2)C3=O)cc1] | 497.36 | 95.01%, Rt = 4.52 min (1) | ¹H NMR (400 MHz, DMSO-d6): δ 10.30 (bs, 1H), 8.32-8.31 (m, 2H), 8.07-8.04 (d, J = 8.4 Hz, 2H), 7.84-7.82 (d, J = 8.4 Hz, 1H), 7.78-7.76 (d, J = 8.4 Hz, 2H), 7.67-7.65 (d, J = 9.2 Hz, 1H), 7.61-7.57 (m, 1H), 7.44-7.42 (d, J = 8.0 Hz, 1H), 1.69 (s, 6H). |

Example 8

Synthesis of 59 [4-(tert-butyl)-N-(2-(3-cyanobenzyl)-1,3-dioxoisoindolin-4-yl)benzene sulfonamide] and Compounds 60-63

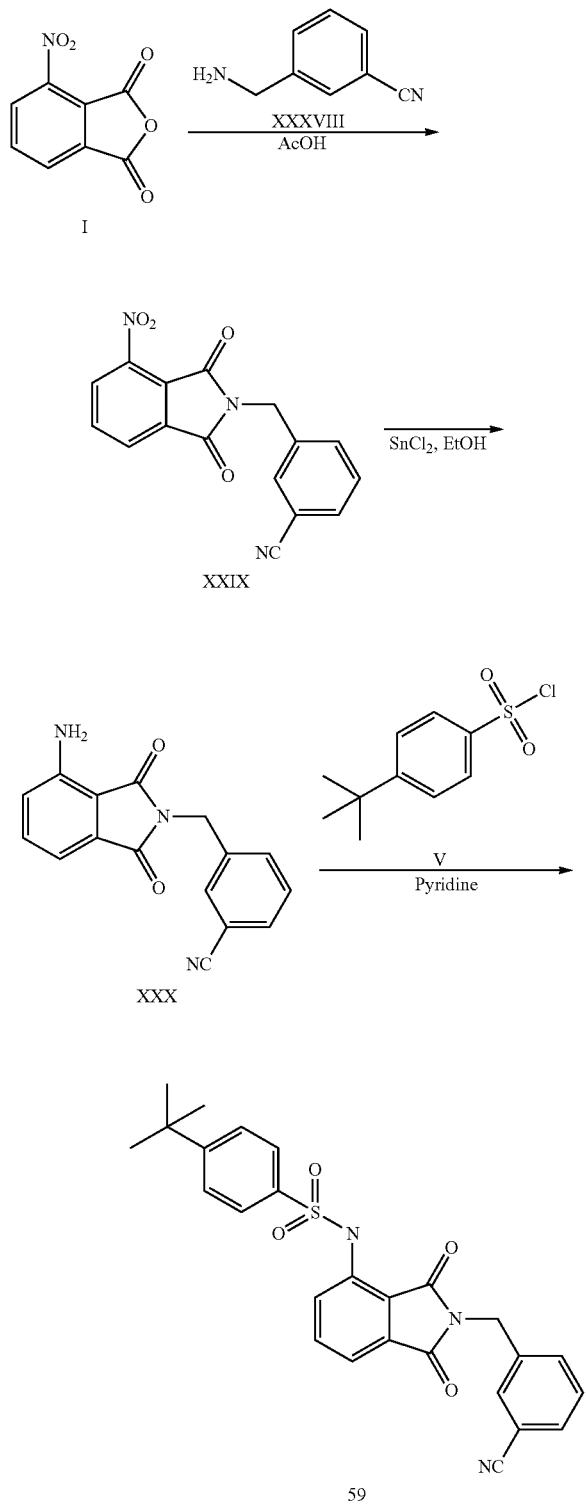

Synthesis of XXIX:

To a stirred solution of compound I (0.5 g, 2.59 mmol) in acetic acid (10 mL) was added compound XXVIII (0.51 g, 3.88 mmol) and the reaction heated at 100° C. for 18 h. The reaction mixture was cooled to room temperature and acetic acid was removed under reduced pressure to obtain a crude product. This was suspended in ethanol, cooled and filtered to afford 3-((4-nitro-1,3-dioxoisoindolin-2-yl)methyl)benzonitrile as an off white solid (XXIX; 0.4 g; 55% yield). $^1$H NMR (400 MHz, DMSO-d6): δ 8.31-8.29 (d, J=8 Hz, 1H), 8.20-8.18 (d, J=7.2 Hz, 1H), 8.08-8.05 (t, J=7.6 Hz, 1H), 7.85 (s, 1H), 7.76-7.70 (m, 2H), 7.57-7.53 (t, J=7.6 Hz, 1H), 4.84 (s, 2H). MS (M+1): 308.00.

Synthesis of XXX:

To a stirred solution of compound XXIX (0.4 g, 1.30 mmol) in ethanol (70 mL) was added stannous chloride powder (0.87 g, 3.9 mmol) and the reaction mixture was heated to a reflux for 18 h. The ethanol was concentrated under reduced pressure to obtain a crude product. The reaction mixture was diluted with water and a saturated solution of sodium bicarbonate and the aqueous layer extracted with ethyl acetate. The organic layer was washed with brine solution, dried over anhydrous Na$_2$SO$_4$ and evaporated under reduced pressure to afford crude 3-((4-amino-1,3-dioxoisoindolin-2-yl)methyl)benzonitrile as a yellow solid (XXX; 0.25 g). MS (M−1): 276.09 which was used in the next step without further purification.

Synthesis of 59: 4-(tert-butyl)-N-(2-(3-cyanobenzyl)-1,3-dioxoisoindolin-4-yl)benzene sulfonamide To a mixture of compound XXX (0.25 g, 0.902 mmol) in pyridine (4 mL) was added 4-tert butylbenzenesulfonyl chloride (V; 0.73 g, 3.15 mmol). The reaction mixture was stirred for 12 h at 100° C. The reaction mixture was cooled and concentrated under reduced pressure and diluted using saturated ammonium chloride solution, which was extracted with dichloromethane. The organic layer was washed with brine solution, dried over anhydrous Na$_2$SO$_4$ and evaporated under reduced pressure to obtain the crude compound, which was purified by column chromatography using 25% ethyl acetate in hexane to afford 4-(tert-butyl)-N-(2-(3-cyanobenzyl)-1,3-dioxoisoindolin-4-yl)benzenesulfonamide as a white solid (59; 0.08 g, 31% yield). $^1$H NMR (400 MHz, DMSO-d6): δ 9.88 (bs, 1H), 7.94-7.92 (d, J=7.2 Hz, 2H), 7.81-7.74 (m, 3H), 7.64-7.54 (m, 6H), 4.77 (s, 2H), 1.26 (s, 9H). MS (M−1): 472.10 (LCMS purity 98.28%, Rt=6.77 min) (1).

The following compounds were also prepared using a similar method and the appropriate sulfonyl chloride in the final step:

| Cpd | Structure | LCMS (M − 1) | Purity (LCMS) | ¹H NMR |
|---|---|---|---|---|
| 60 | 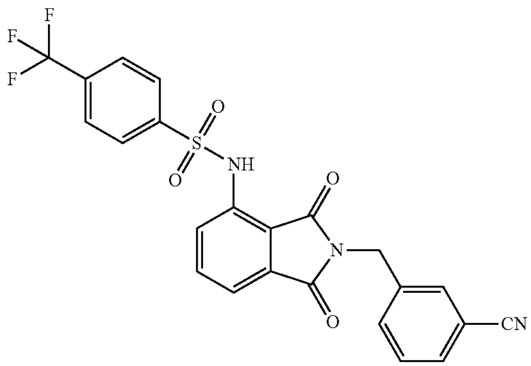 [SMILES: N#Cc1cccc(CN2C(=O)c3cccc(NS(=O)(=O)c4ccc(C(F)(F)F)cc4)c3C2=O)c1] | 484.06 | 98.76%, Rt = 5.90 min (1) | ¹H NMR (400 MHz, DMSO-d6): δ 10.42 (bs, 1H), 8.16-8.14 (d, J = 8 Hz, 2H), 7.98-7.96 (d, J = 8.0 Hz, 2H), 7.92 (s, 1H), 7.76-7.74 (d, J = 6.4 Hz 2H), 7.63-7.60 (m, 2H), 7.57-7.52 (m, 2H), 4.75 (s, 2H). |
| 61 | 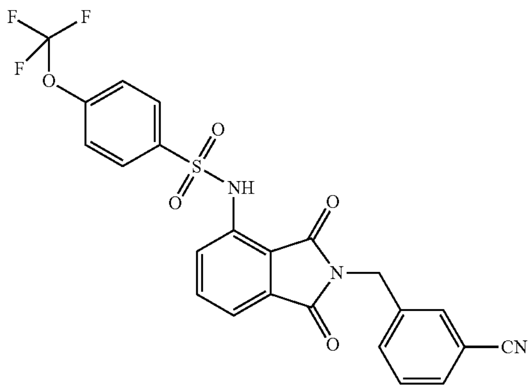 [SMILES: N#Cc1cccc(CN2C(=O)c3cccc(NS(=O)(=O)c4ccc(OC(F)(F)F)cc4)c3C2=O)c1] | 500.15 | 98.23% Rt = 6.18 min (1) | ¹H NMR (400 MHz, DMSO-d6): δ 10.22 (bs, 1H), 8.08-8.06 (d, J = 8.8 Hz, 2H), 7.78-7.73 (m, 3H), 7.62-7.52 (m, 6H), 4.75 (s, 2 H). |
| 62 | 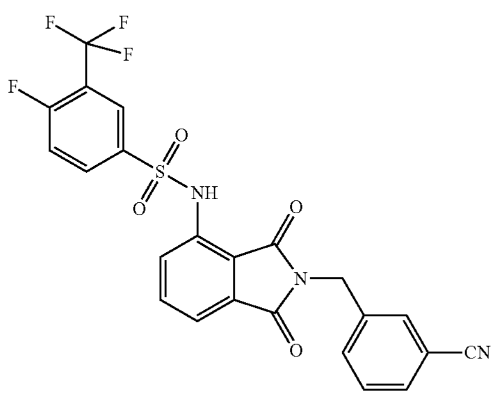 [SMILES: N#Cc1cccc(CN2C(=O)c3cccc(NS(=O)(=O)c4ccc(F)c(C(F)(F)F)c4)c3C2=O)c1] | 502.09 | 99.15% Rt = 5.85 min (1) | ¹H NMR (400 MHz, DMSO-d6): δ 10.53 (bs, 1H), 8.34-8.33 (d, J = 5.6 Hz, 1H), 8.27-8.26 (m, 1H), 7.78-7.68 (m, 4H), 7.65-7.52 (m, 4H), 4.74 (s, 2 H). |
| 63 | 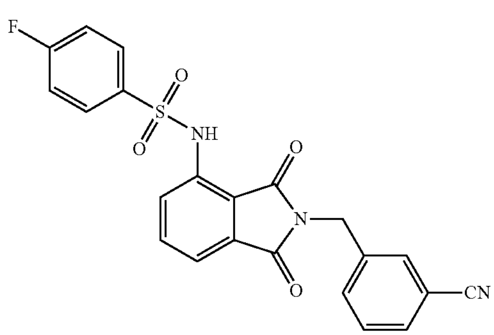 [SMILES: N#Cc1cccc(CN2C(=O)c3cccc(NS(=O)(=O)c4ccc(F)cc4)c3C2=O)c1] | 434.12 | 99.65% Rt = 5.92 min (1) | ¹H NMR (400 MHz, DMSO-d6): δ 10.07 (bs, 1H), 8.02-7.99 (m, 2H), 7.78-7.73 (m, 3H), 7.61-7.52 (m, 4H), 7.43-7.39 (t, J = 8.4 Hz, 2H), 4.76 (s, 2 H). |

Example 9

Synthesis of Compound 64 [4-(tert-butyl)-N-(7-chloro-1,3-dioxo-2-(pyridin-3-ylmethyl) isoindolin-4-yl)benzenesulfonamide]; Compound 65 [3-((4-(4-(tert-butyl)phenylsulfonamido)-7-chloro-1,3-dioxoisoindolin-2-yl)methyl)pyridine 1-oxide]; and Compounds 66-81

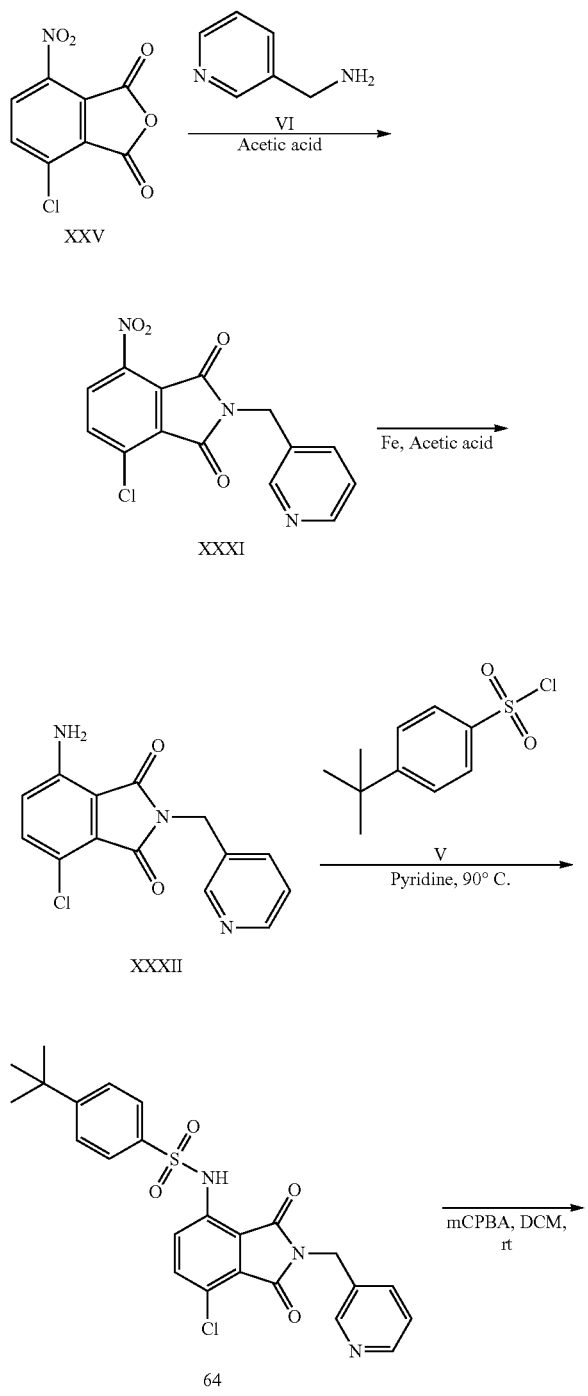

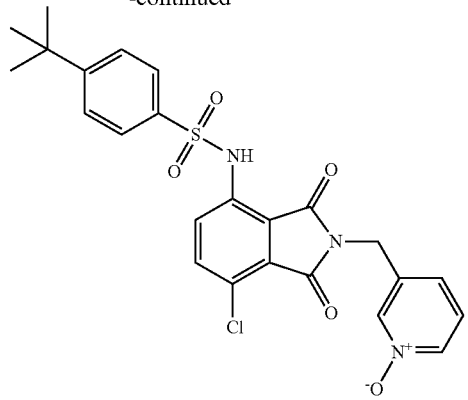

Synthesis of XXXI:

To a stirred solution of compound XXV (5.0 g, 21.1 mmol) in acetic acid (44 mL) was added pyridin-3-ylmethanamine (VI, 7.2 g, 66 mmol) and the reaction mixture heated at 100° C. for 18 h. The reaction mixture was cooled to room temperature and the acetic acid removed under reduced pressure to obtain the crude product which was washed with ethyl acetate to afford 4-chloro-7-nitro-2-(pyridin-3-ylmethyl)isoindoline-1,3-dione as a yellow solid (XXXI; 2 g, 28% yield). $^1$H NMR (400 MHz, DMSO-d6): δ 8.80 (s, 1H), 8.72-8.69 (m, 1H), 8.29-8.27 (d, J=8.4 Hz, 1H), 8.23 (m, 1H), 8.13-8.10 (d, J=8.4 Hz, 1H), 7.74 (m, 1H), 4.91 (s, 2H). MS (M+1): 317.8 (LCMS Purity 94.26%).

Synthesis of XXXII:

To a solution of compound XXXI (2 g, 6 mmol) in acetic acid (30 mL) was added portion wise iron powder (0.5 g, 18 mmol). The reaction mixture was stirred for 5 h at room temperature. The reaction mixture was concentrated under reduced pressure. The crude mass was neutralized with sodium bicarbonate solution with the resulting aqueous layer being extracted with ethyl acetate. The organic solvent was dried, filtered and evaporated under reduced pressure to obtain the crude compound. The crude material was further purified by trituration using acetonitrile and ethyl acetate to afford compound 4-amino-7-chloro-2-(pyridin-3-ylmethyl)isoindoline-1,3-dione as a brown solid (XXXII; 1.2 g, 70% yield). $^1$H NMR (400 MHz, DMSO-d6): δ 8.55 (s, 1H), 8.48 (m, 1H), 7.70-7.68 (d, J=7.6 Hz, 1H), 7.42-7.40 (d, J=8.4 Hz, 1H), 7.35 (m, 1H), 7.0-6.98 (d, J=8.8 Hz, 1H), 6.63 (bs, 2H), 4.72 (s, 2H). MS (M+1): 288.12.

Synthesis of 64; 4-(tert-butyl)-N-(7-chloro-1,3-dioxo-2-(pyridin-3-ylmethyl)isoindolin-4-yl)benzenesulfonamide A mixture of compound XXXII (400 mg, 1.39 mmol) and pyridine (5 mL) was cooled to 0° C. and 4-tert-butylbenzenesulfonyl chloride (V, 0.82 g, 3.53 mmol) was added. The reaction mixture was stirred for 12 h at 80° C. The reaction mixture was concentrated and to the resultant residue, water was added and extracted with dichloromethane. The organic layer was washed with brine solution, dried over anhydrous $Na_2SO_4$, filtered and then evaporated under reduced pressure to obtain the crude compound which was purified by column chromatography using 2% methanol in dichloromethane to afford 4-(tert-butyl)-N-(7-chloro-1,3-dioxo-2-(pyridin-3-ylmethyl)isoindolin-4-yl)benzenesulfonamide as a white solid (64; 0.08 g, 11.8% yield). $^1$H NMR (400 MHz, DMSO-d6): δ 9.92 (bs, 1H), 8.57 (s, 1H), 8.50 (s, 1H), 7.92-7.90 (d, J=8 Hz, 2H), 7.75-7.73 (d, J=9.2 Hz, 2H), 7.62-7.58 (m, 3H), 7.38-7.35 (m, 1H), 4.74 (s, 2H), 1.26 (s, 9H). MS (M+1): 484.10. (LCMS purity 97.90%, Rt=6.38 min(1)).

Synthesis of 65; 3-((4-(4-(tert-butyl)phenylsulfonamido)-7-chloro-1,3-dioxoisoindolin-2-yl)methyl) pyridine 1-oxide To a stirred solution of 4-(tert-butyl)-N-(7-chloro-1,3-dioxo-2-(pyridin-3-ylmethyl)isoindolin-4-yl)benzenesulfonamide (64; 0.065 g, 0.14 mmol) in dichloromethane (5 mL), was added meta-chloroperoxybenzoic acid (0.04 g, 0.14 mmol). The reaction was stirred at RT for 8 h whereupon the solvent was concentrated under reduced pressure and the residue diluted with water. The aqueous layer was extracted with dichloromethane. The combined organic layers were washed sequentially with sodium bicarbonate and brine, then dried over anhydrous $Na_2SO_4$, filtered and concentrated under vacuum to leave the crude compound which was purified by column chromatography using 2% methanol in dichloromethane to afford 3-((4-(4-(tert-butyl)phenylsulfonamido)-7-chloro-1,3-dioxoisoindolin-2-yl)methyl)pyridine 1-oxide (65; 0.012 g, 14% yield). $^1$H NMR (400 MHz, DMSO-d6): δ 9.93 (bs, 1H), 8.26 (s, 1H), 8.14-8.12 (d, J=6 Hz, 1H), 7.93-7.91 (d, J=8 Hz, 2H), 7.75-7.73 (d, J=8.4 Hz, 1H), 7.63-7.58 (m, 3H), 7.38-7.34 (t, J=6.8 Hz, 1H), 7.29-7.27 (d, J=9.2 Hz, 1H), 4.69 (s, 2H), 1.26 (s, 9H). MS (M+1): 500.12. (LCMS purity 98.73%, Rt=5.47 min(1)).

The following compounds were prepared in a similar manner and using the appropriate sulfonyl chloride in the penultimate step. This resulted either in the final pyridine compounds, which if required could also be converted into the corresponding pyridine N-oxides using mCPBA:

| CPD. | Structure | LCMS (M + 1) | Purity (LCMS) | $^1$H NMR |
|---|---|---|---|---|
| 66 | (4-CF$_3$-phenylsulfonamide isoindolinone with pyridinylmethyl) | 495.92 | 99.53% Rt = 5.29 min (1) | $^1$H NMR (400 MHz, DMSO-d6): δ 10.48 (bs, 1H), 8.55 (s, 1H), 8.49-8.48 (d, J = 3.6 Hz, 1H), 8.13-8.11 (d, J = 8.4 Hz, 2H), 7.97-7.95 (d, J = 8.4 Hz, 2H), 7.76-7.31 (d, J = 9.2 Hz, 1H), 7.69-7.67 (d, J = 8 Hz, 1H), 7.55-7.53 (d, J = 8.8 Hz, 1H), 7.36-7.33 (m, 1H), 4.71 (s, 2H). |
| 67 | (4-OCF$_3$-phenylsulfonamide isoindolinone with pyridinylmethyl) | 511.92 | 98.75% Rt = 5.48 min (1) | $^1$H NMR (400 MHz, DMSO-d6): δ 10.30 (bs, 1H), 8.59 (s, 1H), 8.53-8.52 (d, J = 4.4 Hz, 1H), 8.07-8.05 (d, J = 8.4 Hz, 2H), 7.77-7.75 (d, J = 8.4 Hz, 2H), 7.58-7.55 (m, 3H), 7.43-7.40 (m, 1H), 4.74 (s, 2H). |
| 68 | (4-OCHF$_2$-phenylsulfonamide isoindolinone with pyridinylmethyl) | 494.12 | 99.65% Rt = 5.38 min (1) | $^1$H NMR (400 MHz, DMSO-d6): δ 10.10 (bs, 1H), 8.54 (s, 1H), 8.49-8.48 (d, J = 3.6 Hz, 1H), 8.01-7.99 (d, J = 8.8 Hz, 2H), 7.75-7.68 (m, 2H), 7.57-7.55 (d, J = 8.8 Hz, 1H), 7.39-7.21 (m, 4H), 4.73 (s, 2H). |

| CPD. | Structure | LCMS (M + 1) | Purity (LCMS) | ¹H NMR |
|---|---|---|---|---|
| 69 | 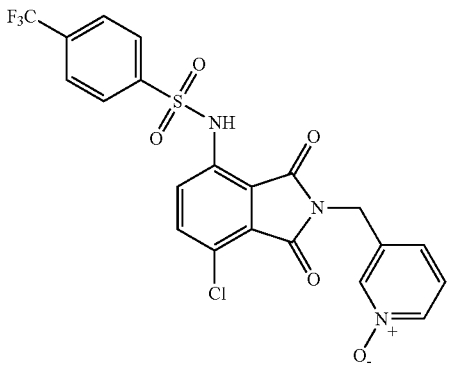 | 512.14 | 96.68% Rt = 4.76 min (1) | ¹H NMR (400 MHz, DMSO-d6): δ 8.19 (s, 1H), 8.12-8.11 (d, J = 6 Hz, 1H), 7.99-7.97 (d, J = 8 Hz, 2H), 7.78-7.76 (d, J = 8.4 Hz, 2H), 7.48-7.46 (d, J = 9.2 Hz, 1H), 7.36-7.32 (m, 1H), 7.25-7.23 (d, J = 9.2 Hz, 1H), 7.20-7.18 (d, J = 8 Hz, 1H), 4.62 (s, 2H). |
| 70 | 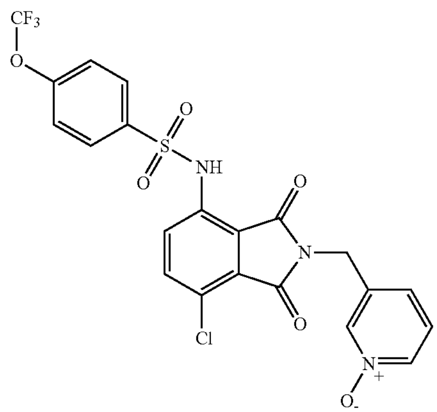 | 528.13 | 99.02% Rt = 4.89 min (1) | ¹H NMR (400 MHz, DMSO-d6): δ 8.21 (s, 1H), 8.13-8.11 (d, J = 6 Hz, 1H), 7.97-7.95 (d, J = 8.4 Hz, 2H), 7.51-7.45 (m, 4H), 7.37-7.33 (m, 1H), 7.22-7.20 (d, J = 7.6 Hz, 1H), 4.64 (s, 2H). |
| 71 | 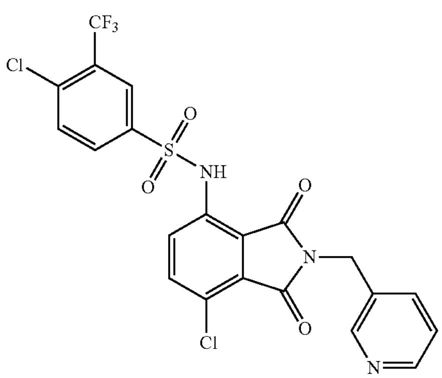 [SMILES: O=C1c2c(Cl)ccc(NS(=O)(=O)c3ccc(Cl)c(C(F)(F)F)c3)c2C(=O)N1Cc1cccnc1] | 530.14 | 99.40%, Rt = 5.42 min (1) | ¹H NMR (400 MHz, DMSO-d6): δ 10.69 (bs, 1H), 8.55 (s, 1H), 8.50-8.49 (d, J = 3.2 Hz, 1H), 8.36 (s, 1H), 8.17-8.15 (d, J = 8 Hz, 1H), 7.93-7.91 (d, J = 8 Hz 1H), 7.74-7.72 (d, J = 8 Hz, 1H) 7.68-7.66 (d, J = 8 Hz, 1H), 7.55-7.53 (d, J = 8 Hz, 1H), 7.38 (t, J = 8 Hz, 1H), 4.71 (s 2H). |
| 72 | 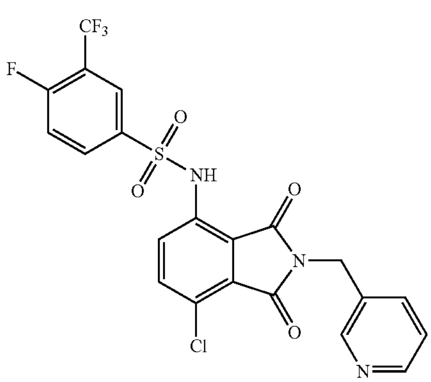 [SMILES: O=C1c2c(Cl)ccc(NS(=O)(=O)c3ccc(F)c(C(F)(F)F)c3)c2C(=O)N1Cc1cccnc1] | 514.23 | 99.24%, Rt = 5.27 min (1) | ¹H NMR (400 MHz, DMSO-d6): δ 10.53 (bs, 1H), 8.54 (s, 1H), 8.50-8.49 (d, J = 4.0 Hz, 1H), 8.34-8.33 (d, J = 6.0 Hz, 1H), 8.26-8.24 (m, 1H), 7.75-7.66 (m, 3H), 7.57-7.55 (d, J = 8.8 Hz, 1H), 7.37-7.34 (m, 1H), 4.71 (s, 2H). |

| CPD. | Structure | LCMS (M + 1) | Purity (LCMS) | ¹H NMR |
|---|---|---|---|---|
| 73 | (4-MeO-C₆H₄-SO₂-NH- attached to 4-position of 7-chloro-2-(pyridin-3-ylmethyl)isoindoline-1,3-dione) | 456.19 (M − 1) | 98.76%, Rt = 5.46 min (1) | ¹H NMR (400 MHz, DMSO-d6): δ 9.80 (bs, 1H), 8.55-8.49 (m, 2H), 7.89-7.87 (m, 2H), 7.73-7.68 (m, 2H), 7.59-7.57 (d, J = 8.8 Hz, 1H), 7.36-7.35 (d, J = 4.8 Hz, 1H), 7.09-7.07 (d, J = 8.0 Hz, 2H), 4.73 (s, 2H), 3.81 (s, 3H). |
| 74 | (4-fluoro-3-(trifluoromethyl)phenylsulfonamide attached to 7-chloro-2-((1-oxidopyridin-3-yl)methyl)isoindoline-1,3-dione) | 530.30 | 97.00%, Rt = 4.84 min (1) | ¹H NMR (400 MHz, DMSO-d6): δ 10.57 (bs, 1H), 8.24-8.21 (m, 3H), 8.13-8.12 (d, J = 6.4 Hz, 1H), 7.63 (t, J = 9.6 Hz, 1H), 7.53-7.51 (m, 2H), 7.34 (t, J = 12 Hz, 1H) 7.21-7.19 (d, J = 8.4 Hz, 1H), 4.65 (s, 2H). |
| 75 | (4-chloro-3-(trifluoromethyl)phenylsulfonamide attached to 7-chloro-2-((1-oxidopyridin-3-yl)methyl)isoindoline-1,3-dione) | 546.30 | 98.08%, Rt = 5.01 min (1) | ¹H NMR (400 MHz, DMSO-d6): δ 8.19 (m, 2H), 8.12-8.11 (d, J = 5.6, 1H), 8.05-8.03 (d, J = 8.0 Hz, 1H), 7.78-7.76 (d, J = 8 Hz, 1H), 7.50-7.48 (d, J = 8.8 Hz, 1H), 7.36-7.27 (m, 2H) 7.19-7.18 (d, J = 7.2 Hz, 1H), 4.63 (s, 2H). |
| 76 | (3-(trifluoromethyl)phenylsulfonamide attached to 7-chloro-2-(pyridin-3-ylmethyl)isoindoline-1,3-dione) | 496.04 | 98.75%, Rt = 5.21 min (1) | ¹H NMR (400 MHz, DMSO-d6): δ 10.62 (bs, 1H), 8.52-8.50 (m, 2H), 8.24 (s, 1H), 8.17-8.15 (d, J = 8.4 Hz, 1H), 8.03-8.01 (d, J = 7.6 Hz, 1H), 7.81-7.74 (m, 2H), 7.66-7.64 (d, J = 7.2 Hz, 1H), 7.56-7.54 (d, J = 8.8 Hz, 1H), 7.38-7.35 (m, 1H), 4.70 (s, 2H). |

| CPD. | Structure | LCMS (M + 1) | Purity (LCMS) | ¹H NMR |
|---|---|---|---|---|
| 77 | 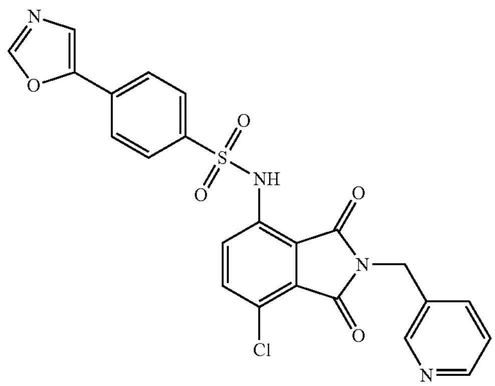 [SMILES: O=C1c2c(Cl)ccc(NS(=O)(=O)c3ccc(-c4cnco4)cc3)c2C(=O)N1Cc1cccnc1] | 495.08 | 98.75%, Rt = 4.83 min (1) | ¹H NMR (400 MHz, DMSO-d6): δ 10.18 (bs, 1H), 8.56 (s, 1H), 8.53 (s, 1H), 8.45-8.44 (d, J = 8.4 Hz, 1H), 8.01-7.99 (d, J = 8.4 Hz, 2H), 7.91-7.89 (m, 3H), 7.76-7.73 (d, J = 8.8 Hz, 1H), 7.66-7.64 (d, J = 8.0 Hz, 1H), 7.59-7.56 (d, J = 8.8 Hz, 1H), 7.30-7.27 (m, 1H), 4.71 (s, 2H). |
| 78 | 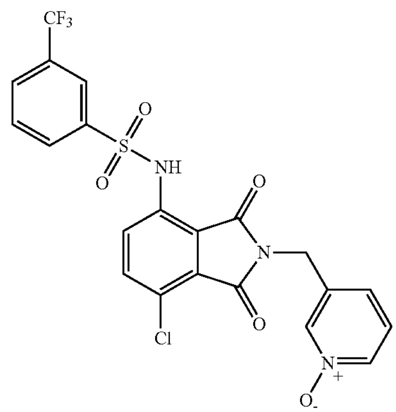 | 510.09 (M − 1) | 97.57%, Rt = 4.77 min (1) | ¹H NMR (400 MHz, DMSO-d6): δ 10.55 (bs, 1H), 8.27 (s, 1H), 8.21-8.14 (m, 3H), 8.06-8.04 (d, J = 8.4 Hz, 1H), 7.85-7.81 (t, J = 7.6 Hz, 1H), 7.77-7.75 (d, J = 8.8 Hz, 1H), 7.56-7.54 (d, J = 8.8 Hz, 1H), 7.39-7.35 (t, J = 7.6 Hz, 1H), 7.23-7.21 (d, J = 7.2 Hz, 1H), 4.66 (s, 2H). |
| 79 | 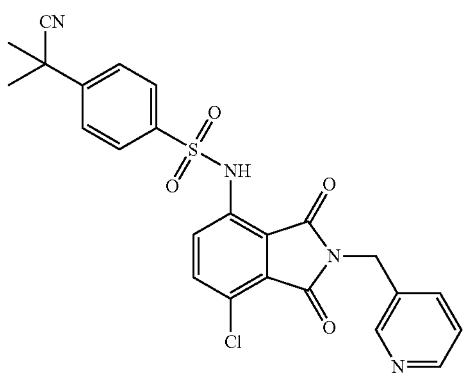 [SMILES: CC(C)(C#N)c1ccc(S(=O)(=O)Nc2ccc(Cl)c3c2C(=O)N(Cc2cccnc2)C3=O)cc1] | 495.05 | 99.37%, Rt = 5.45 min (1) | ¹H NMR (400 MHz, DMSO-d6): δ 10.18 (bs, 1H), 8.56 (s, 1H), 8.49 (s, 1H), 8.04-8.02 (d, J = 8.4 Hz, 2H), 7.75-7.71 (m, 4H), 7.58-7.56 (d, J = 8.8 Hz, 1H), 7.37-7.34 (m, 1H), 4.73 (s, 2H), 1.68 (s, 6H). |
| 80 | 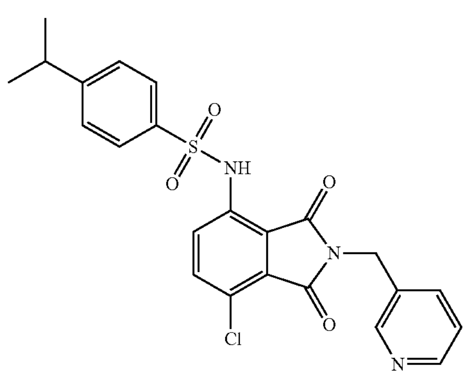 | 470.38 | 99.50%, Rt = 6.11 min (1) | ¹H NMR (400 MHz, DMSO-d6): δ 9.92 (bs, 1H), 8.55 (s, 1H), 8.49-8.48 (d, J = 4.4 Hz, 1H), 7.90-7.88 (d, J = 8.0 Hz, 2H), 7.74-7.70 (m, 2H), 7.59-7.57 (d, J = 9.2 Hz, 1H), 7.47-7.45 (m, 2H), 7.37-7.34 (m, 1H), 4.73 (s, 2H), 2.98-2.90 (m, 1H), 1.18-1.16 (d, J = 6.8 Hz, 6H). |

| CPD. | Structure | LCMS (M + 1) | Purity (LCMS) | ¹H NMR |
|---|---|---|---|---|
| 81 | 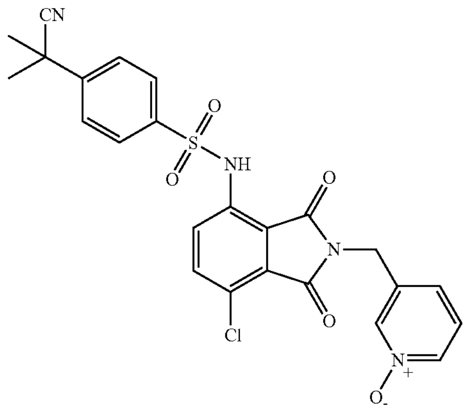 | 511.38 | 99.26%, Rt = 4.52 min (1) | ¹H NMR (400 MHz, DMSO-d6): δ 10.15 (bs, 1H), 8.26 (s, 1H), 8.14-8.12 (d, J = 6.4 Hz, 1H), 8.06-8.04 (d, J = 8.8 Hz, 2H), 7.76-7.73 (m, 3H), 7.58-7.56 (d, J = 8.8 Hz, 1H), 7.38-7.35 (t, J = 8.0 Hz, 1H), 7.28-7.27 (d, J = 7.6 Hz, 1H), 4.69 (s, 2H), 1.68 (s, 6H). |

Example 10

Synthesis of Compound 82 [4-(tert-butyl)-N-(7-cyano-1,3-dioxo-2-(pyridin-3-ylmethyl)isoindolin-4-yl)benzenesulfonamide]

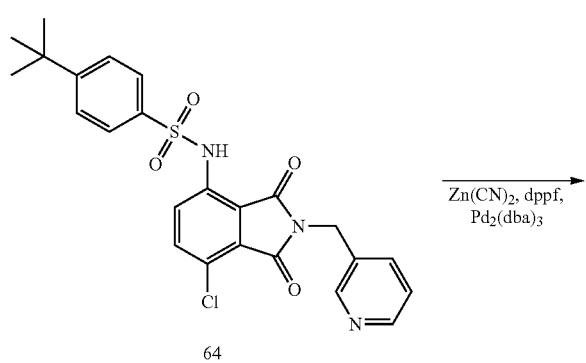

To a stirred solution of 4-(tert-butyl)-N-(7-chloro-1,3-dioxo-2-(pyridin-3-ylmethyl)isoindolin-4-yl)benzenesulfonamide (64; 0.15 g, 0.31 mmol) in dimethylacetamide (4 mL) was added zinc cyanide (0.073 g, 62 mmol) under nitrogen followed by addition of 1,1'-Bis (diphenylphosphino)ferrocene (0.034 g, 0.062 mmol) and Pd2(dba)3 (0.43 g, 0.046 mmol). To the reaction mixture was added zinc dust (0.005 g) and the reaction mixture was purged under nitrogen for 30 minutes. The reaction was heated at 120° C. for 2 h in microwave. The reaction mixture was cooled, filtered and concentrated under reduced pressure. The crude residue was purified by column chromatography using 4% methanol in dichloromethane to afford 4-(tert-butyl)-N-(7-cyano-1,3-dioxo-2-(pyridin-3-ylmethyl)isoindolin-4-yl)benzenesulfonamide (82; 0.02 g, 13.6% yield). ¹H NMR (400 MHz, DMSO-d6): δ 8.70 (s, 1H), 8.61-8.60 (d, J=4.4 Hz, 1H), 8.11-8.09 (d, J=8.8 Hz, 1H), 8.03-7.99 (m, 3H), 7.70-7.64 (m, 3H), 7.58-7.55 (m, 1H), 4.84 (s, 2H), 1.27 (s, 9H). MS (M+1): 475.46. (LCMS purity 99.77%, Rt=5.15 min) (1).

Example 11

Synthesis of Compound 83 [4-(tert-butyl)-N-(7-chloro-2-(5-chloropyridin-3-yl)-1,3-dioxoisoindolin-4-yl)benzenesulfonamide] and Compounds 84-89

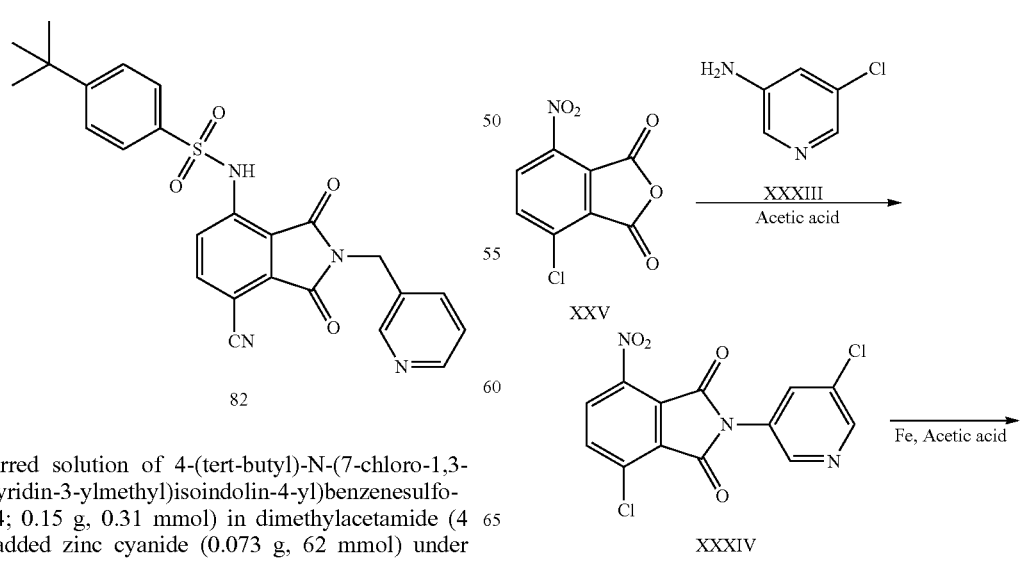

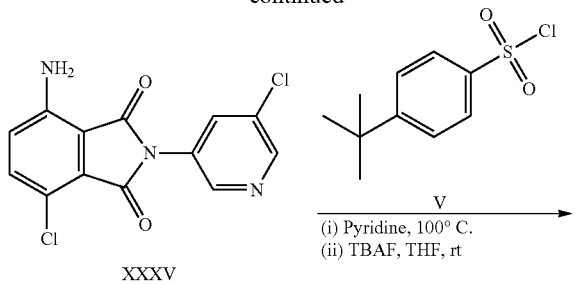

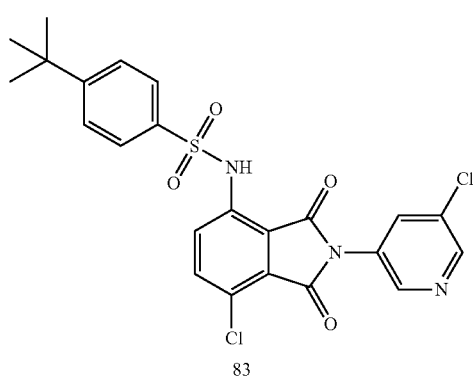

83

Synthesis of XXXIV:

To a stirred solution of compound XXV (3.0 g, 13.2 mmol) in acetic acid (26 mL) was added 5-chloropyridin-3-amine (XXXIII, 5 g, 39 mmol) and the reaction mixture heated at 100° C. for 18 h. The reaction mixture was cooled to room temperature and the acetic acid removed under reduced pressure to obtain the crude product which was washed with ethanol to afford 4-chloro-2-(5-chloropyridin-3-yl)-7-nitroisoindoline-1,3-dione as an off white solid (XXXIV; 4 g, 89% yield). $^1$H NMR (400 MHz, DMSO-d6): δ 8.78 (s, 1H), 8.64 (d, J=1.6 Hz, 1H), 8.40-8.38 (d, J=8.8 Hz, 1H), 8.25-8.22 (d, J=9.2 Hz, 1H), 8.06 (s, 1H).

Synthesis of XXXV:

To a solution of compound XXXIV (4 g, 11.8 mmol) in acetic acid (200 mL) was added iron powder (1.4 g, 23 mmol) in small portions. The reaction mixture was stirred for 5 h at room temperature and then filtered through a celite bed and concentrated under reduced pressure. The crude mass was neutralized by sodium bicarbonate solution. The aqueous layer was extracted with ethyl acetate, which was dried (anhydrous $Na_2SO_4$), filtered and evaporated under reduced pressure to obtain the crude compound. This material was further purified using trituration with acetonitrile and ethyl acetate to afford the compound 4-amino-7-chloro-2-(5-chloropyridin-3-yl)isoindoline-1,3-dione as a yellow solid (XXXV; 3 g, 81% yield). $^1$H NMR (400 MHz, DMSO-d6): δ 8.69-8.66 (m, 2H), 8.10 (s, 1H), 7.52-7.50 (d, J=8.8 Hz, 1H), 7.09-7.07 (d, J=9.2 Hz, 1H), 6.78 (bs, 2H). MS (M+1): 307.98 (LCMS Purity 97.9%).

Synthesis of 83; 4-(tert-butyl)-N-(7-chloro-2-(5-chloropyridin-3-yl)-1,3-dioxoisoindolin-4-yl)benzenesulfonamide A mixture of compound XXXV (300 mg, 0.97 mmol) and pyridine (3 mL) was cooled to 0° C. and added 4-tert-butylbenzenesulfonyl chloride (V, 0.95 g, 2.9 mmol). The reaction mixture was stirred for 12 h at 100° C. The reaction mixture was concentrated and diluted with water. The reaction mixture was extracted with ethyl acetate. The organic layer was washed with brine solution, dried over anhydrous $Na_2SO_4$, filtered and the organic solvent was evaporated under reduced pressure to obtain the crude compound. To the crude compound was added TBAF in THF solution (4 mL) and continued the stirring for 1 h at room temperature. The reaction mixture was concentrated and diluted with ethyl acetate. Washed an organic layer with water, dried over anhydrous $Na_2SO_4$, filtered and the organic solvent was evaporated under reduced pressure to obtain the crude compound which was purified by column chromatography using 40% ethyl acetate in hexane to afford the title compound, 4-(tert-butyl)-N-(7-chloro-2-(5-chloropyridin-3-yl)-1,3-dioxoisoindolin-4-yl)benzenesulfonamide as a yellow solid (83; 0.11 g, 23% yield). $^1$H NMR (400 MHz, DMSO-d6): δ 10.06 (bs, 1H), 8.74 (d, J=2.0 Hz, 1H), 8.61 (d, J=1.6 Hz, 1H), 8.04 (m, 1H), 7.94-7.91 (d, J=8.4 Hz, 2H), 7.87-7.84 (d, J=8.8 Hz, 1H), 7.71-7.69 (d, J=8.8 Hz, 1H), 7.65-7.63 (d, J=8.8 Hz, 2H), 1.27 (s, 9H). MS (M+1): 504.07. (LCMS purity 97.67%, Rt=6.34 min) (1).

The following compounds were also prepared using a similar method and the appropriate sulfonyl chloride in the final step:

| CPD | Structure | LCMS (M + 1) | Purity (LCMS) | $^1$H NMR |
|---|---|---|---|---|
| 84 | ![structure] | 533.83 | 95.92%, Rt = 6.82 min (2) | $^1$H NMR (400 MHz, DMSO-d6): δ 10.78 (bs, 1H), 8.75-8.74 (d, J = 2 Hz, 1H), 8.60-8.59 (d, J = 2.0 Hz, 1H), 8.45-8.44 (d, J = 4.4 Hz, 1H), 8.33-8.31 (m, 1H), 8.01-8.00 (m, 1H), 7.85-7.83 (d, J = 8.8 Hz, 1H), 7.80-7.76 (t, J = 9.6 Hz, 1H), 7.65-7.63 (d, J = 8.8 Hz, 1H). |

-continued

| CPD | Structure | LCMS (M + 1) | Purity (LCMS) | ¹H NMR |
|---|---|---|---|---|
| 85 | 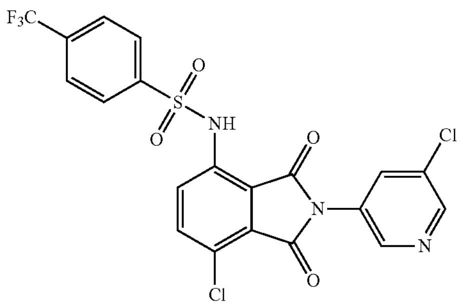 [SMILES: O=C1c2c(Cl)ccc(NS(=O)(=O)c3ccc(C(F)(F)F)cc3)c2C(=O)N1c1cncc(Cl)c1] | 514.11 (M − 1) | 99.16%, Rt = 5.78 min (1) | ¹H NMR (400 MHz, DMSO-d6): δ 10.63 (bs, 1H), 8.74-8.73 (d, J = 2.4 Hz, 1H), 8.58-8.57 (d, J = 1.6 Hz, 1H), 8.15-8.13 (d, J = 8 Hz, 2H), 8.00-7.99 (m, 3H), 7.87-7.84 (d, J = 9.2 Hz, 1H), 7.64-7.62 (d, J = 8.8 Hz, 1H). |
| 86 | 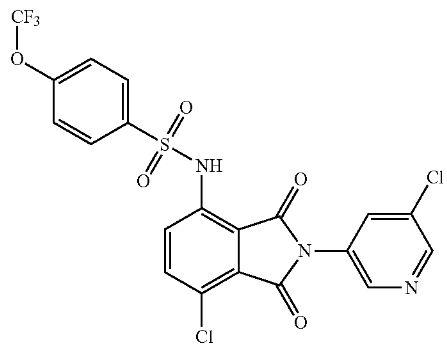 [SMILES: O=C1c2c(Cl)ccc(NS(=O)(=O)c3ccc(OC(F)(F)F)cc3)c2C(=O)N1c1cncc(Cl)c1] | 530.10 (M − 1) | 99.04%, Rt = 5.91 min (1) | ¹H NMR (400 MHz, DMSO-d6): δ 10.45 (bs, 1H), 8.74 (s, 1H), 8.59 (s, 1 H), 8.10-8.08 (d, J = 8.4 Hz, 2H), 8.01 (s, 1H), 7.86-7.84 (d, J = 8 Hz, 1H), 7.66-7.60 (m, 3H). |
| 87 | 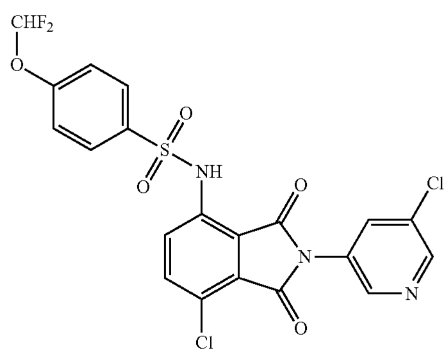 [SMILES: O=C1c2c(Cl)ccc(NS(=O)(=O)c3ccc(OC(F)F)cc3)c2C(=O)N1c1cncc(Cl)c1] | 512.05 (M − 1) | 99.48%, Rt = 5.63 min (1) | ¹H NMR (400 MHz, DMSO-d6): δ 10.25 (bs, 1H), 8.75-8.74 (d, J = 2.4 Hz, 1H), 8.62-8.61 (d, J = 2 Hz, 1H), 8.07-8.03 (m, 3H), 7.85-7.83 (d, J = 8.8 Hz, 1H), 7.67-7.59 (m, 1H), 7.41-7.23 (m, 3H). |
| 88 | 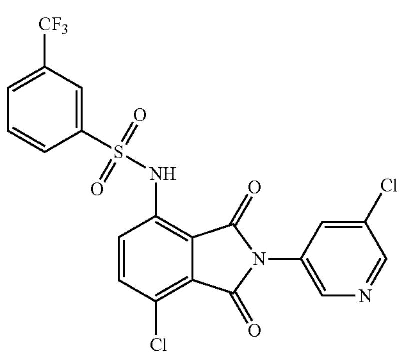 [SMILES: O=C1c2c(Cl)ccc(NS(=O)(=O)c3cccc(C(F)(F)F)c3)c2C(=O)N1c1cncc(Cl)c1] | 516.17 (M + 1) | 95.82%, Rt = 5.56 min (1) | ¹H NMR (400 MHz, DMSO-d6): δ 10.70 (bs, 1H), 8.75-8.74 (d, J = 2.4 Hz, 1H), 8.60-8.59 (d, J = 2 Hz, 1H), 8.39 (s, 1H), 8.28-8.26 (d, J = 8 Hz, 1H), 8.11-8.09 (d, J = 8.4 Hz, 1H), 8.02-8.00 (m, 1H), 7.89-7.83 (m, 2H), 7.64-7.61 (d, J = 9.2 Hz, 1H). |

| CPD | Structure | LCMS (M + 1) | Purity (LCMS) | ¹H NMR |
|---|---|---|---|---|
| 89 | 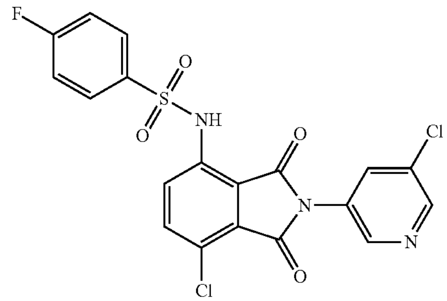 [SMILES: O=C1c2c(Cl)ccc(NS(=O)(=O)c3ccc(F)cc3)c2C(=O)N1c1cncc(Cl)c1] | 464.09 (M − 1) | 99.48%, Rt = 5.50 min (1) | ¹H NMR (400 MHz, DMSO-d6): δ 10.27 (bs, 1H), 8.75-8.74 (d, J = 2 Hz, 1H), 8.62-8.61 (d, J = 1.6 Hz, 1H), 8.08-8.03 (m, 3H), 7.85-7.83 (d, J = 8.8 Hz, 1H), 7.66-7.64 (d, J = 8.8 Hz, 1H), 7.49-7.45 (t, J = 8.8 Hz, 2H). |

Example 12

Synthesis of Compound 90 [4-(tert-butyl)-N-(7-chloro-2-(5-methoxypyridin-3-yl)-1,3-dioxoisoindolin-4-yl)benzenesulfonamide]; Compound 91 [3-(4-(4-(tert-butyl)phenylsulfonamido)-7-chloro-1,3-dioxoisoindolin-2-yl)-5-methoxypyridine 1-oxide] and Compounds 92-103

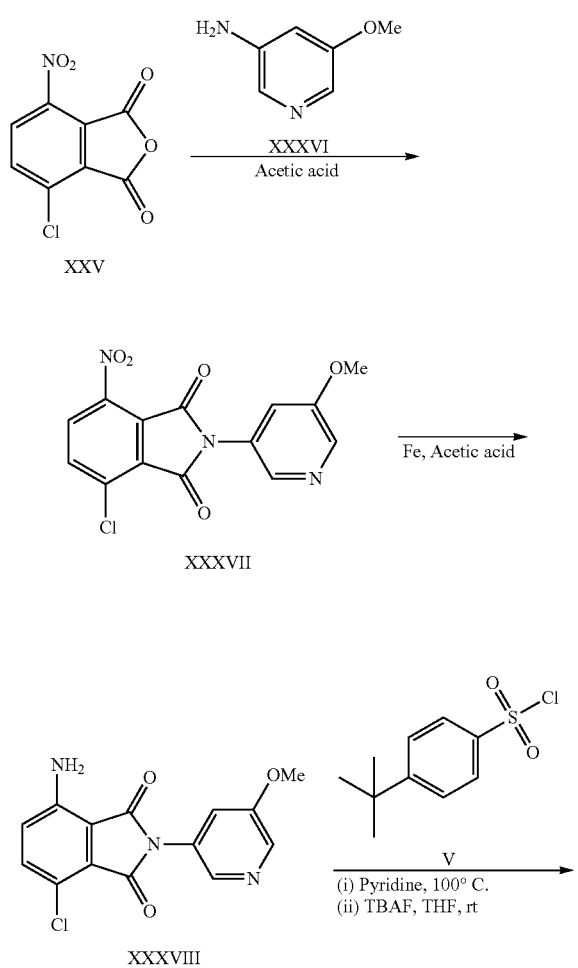

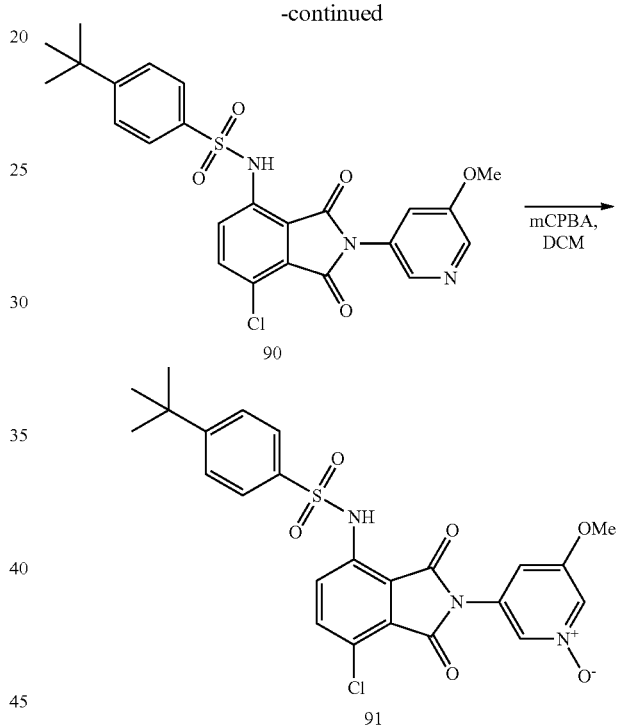

Synthesis of XXXVII:

To a stirred solution of compound XXV (2.0 g, 8.8 mmol) in acetic acid (10 mL) was added 5-methoxypyridin-3-amine (XXXVI, 2.7 g, 22 mmol) and the reaction mixture heated at 120° C. for 18 h. The reaction mixture was cooled to room temperature and the acetic acid removed under reduced pressure to obtain the crude product which was washed with ethanol to afford 4-chloro-2-(5-methoxypyridin-3-yl)-7-nitroisoindoline-1,3-dione as a brown solid (XXXVII; 2.5 g crude). MS (M+1): 333.84. The crude was carried forward to next step without purification.

Synthesis of XXXVIII:

To a solution of compound XXXVII (2.5 g, crude) in acetic acid (10 mL) was added iron powder (2 g) in small portions. The reaction mixture was stirred for 5 h at room temperature. The reaction mixture was filtered through a celite bed and concentrated under reduced pressure. The crude material was neutralized using aqueous sodium bicarbonate solution. The aqueous layer was extracted with ethyl acetate which was dried (anhydrous Na$_2$SO$_4$), filtered and evaporated under reduced pressure to obtain the crude compound. This material was further purified by trituration using acetonitrile and ethyl acetate as solvents to afford compound 4-amino-7-chloro-2-(5-methoxypyridin-3-yl) isoindoline-1,3-dione as a off white solid (XXXVIII; 2 g, 88% yield). $^1$H NMR (400 MHz, DMSO-d6): δ 8.35 (s, 1H), 8.25 (s, 1H), 7.53-7.48 (m, 2H), 7.08 (m, 1H), 6.75 (bs, 2H), 3.85 (s, 3H). MS (M+1): 304.10.

Synthesis of 90; 4-(tert-butyl)-N-(7-chloro-2-(5-methoxypyridin-3-yl)-1,3-dioxoisoindolin-4-yl)benzenesulfonamide A mixture of compound XXXVIII (200 mg, 0.66 mmol) and pyridine (3 mL) was cooled to 0° C. and 4-tert-butylbenzenesulfonyl chloride (V, 0.46 g, 1.98 mmol) was added together with catalytic DMAP (0.040 g, 0.33 mmol). The reaction mixture was stirred for 12 h at 80° C. and then concentrated under vacuum and diluted with water. The aqueous layer was extracted with ethyl acetate which was washed with brine solution, dried over anhydrous Na$_2$SO$_4$, filtered and the organic solvent was evaporated under reduced pressure to obtain the crude compound. To the crude compound was added 1M TBAF in THF solution (2 mL) and the stirring continued for 1 h at room temperature. The reaction mixture was concentrated and diluted with ethyl acetate. This was washed with water, dried over anhydrous Na$_2$SO$_4$, filtered and the organic solvent was evaporated under reduced pressure to obtain the crude compound which was purified by column chromatography using 20% ethyl acetate in hexane to the title compound 4-(tert-butyl)-N-(7-chloro-2-(5-methoxypyridin-3-yl)-1,3-dioxoisoindolin-4-yl)benzenesulfonamide as a yellow solid (90; 0.065 g, 19.7% yield). $^1$H NMR (400 MHz, DMSO-d6): δ 10.03 (bs, 1H), 8.39-8.38 (d, J=2.4 Hz, 1H), 8.22-8.21 (d, J=1.6 Hz, 1H), 7.94-7.92 (d, J=8.4 Hz, 2H), 7.84-7.82 (d, J=9.2 Hz, 1H), 7.69-7.63 (m, 3H), 7.50-7.48 (m, 1H), 3.85 (s, 3H), 1.25 (s, 9H). MS (M−1): 498.20. (LCMS purity 98.37%, Rt=6.20 min) (1).

Synthesis of 91; 3-(4-(4-(tert-butyl)phenylsulfonamido)-7-chloro-1,3-dioxoisoindolin-2-yl)-5-methoxypyridine 1-oxide To a stirred solution of 4-(tert-butyl)-N-(7-chloro-2-(5-methoxypyridin-3-yl)-1,3-dioxoisoindolin-4-yl)benzenesulfonamide (90, 0.1 g, 0.2 mmol) in dichloromethane (4 mL), was added m-chloroperoxybenzoic acid (0.035 g, 0.14 mmol). The reaction was stirred at RT for 5 h whereupon the solvent was concentrated under reduced pressure and the residue diluted with water. The aqueous layer was extracted with dichloromethane. The organic layer was washed sequentially with sodium bicarbonate and brine, then dried over Na$_2$SO$_4$, filtered and concentrated under vacuum to leave the crude compound which was purified by column chromatography using 3% methanol in dichloromethane to afford the title compound 3-(4-(4-(tert-butyl)phenylsulfonamido)-7-chloro-1,3-dioxoisoindolin-2-yl)-5-methoxypyridine 1-oxide (91; 0.05 g, 48% yield). $^1$H NMR (400 MHz, DMSO-d6): δ 10.08 (bs, 1H), 8.20 (s, 1H), 8.01 (s, 1H), 7.94-7.92 (m, 2H), 7.86-7.82 (m, 1H), 7.69-7.63 (m, 3H), 7.15 (s, 1H), 3.85 (s, 3H), 1.27 (s, 9H). MS (M+1): 516.07. (LCMS purity 99.19%, Rt=5.34 min) (1).

The following compounds except 103 were prepared in a similar manner and using the appropriate sulfonyl chloride in the penultimate step. This resulted either in the final pyridine compounds, which if required could also be converted into the corresponding pyridine N-oxides using mCPBA. Compound 103 was prepared using 5-ethoxypyridin-3-amine in the first step described:

| CPD | Structure | LCMS (M + 1) | Purity (LCMS) | $^1$H NMR |
|---|---|---|---|---|
| 92 | 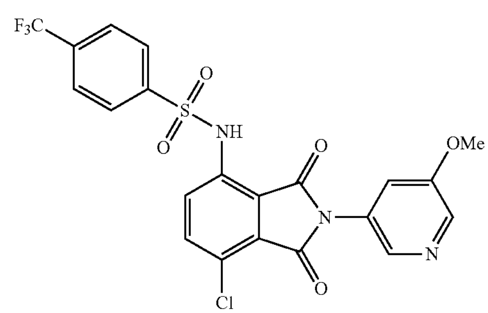 [SMILES: COc1cncc(N2C(=O)c3c(Cl)ccc(NS(=O)(=O)c4ccc(C(F)(F)F)cc4)c3C2=O)c1] | 510.08 (M − 1) | 99.35%, Rt = 5.40 min (1) | $^1$H NMR (400 MHz, DMSO-d6): δ 10.53 (bs, 1H), 8.39-8.38 (d, J = 2.4 Hz, 1H), 8.18-8.17 (m, 3H), 8.02-8.00 (d, J = 8.4 Hz, 2H), 7.85-7.83 (d, J = 8.8 Hz, 1H), 7.63-7.61 (d, J = 8.8 Hz, 1H), 7.46-7.45 (s, 1H), 3.85 (s, 3H). |
| 93 | 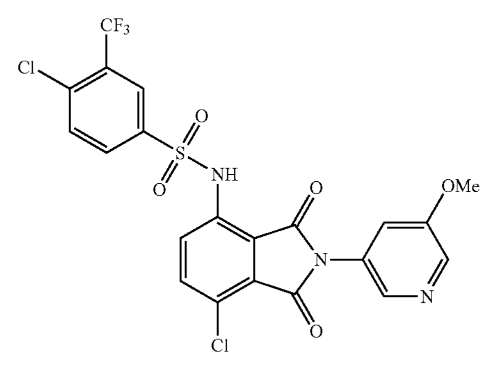 [SMILES: COc1cncc(N2C(=O)c3c(Cl)ccc(NS(=O)(=O)c4ccc(Cl)c(C(F)(F)F)c4)c3C2=O)c1] | 544.08 (M − 1) | 99.43%, Rt = 5.58 min (1) | $^1$H NMR (400 MHz, DMSO-d6): δ 10.79 (bs, 1H), 8.43 (s, 1H), 8.39-8.38 (d, J = 2.4 Hz, 1H), 8.22-8.19 (m, 2H), 8.00-7.98 (d, J = 8.4 Hz, 1H), 7.84-7.81 (d, J = 8.8 Hz, 1H), 7.63-7.61 (d, J = 8.8 Hz, 1H), 7.46-7.45 (m, 1H), 3.85 (s, 3H). |

| CPD | Structure | LCMS (M + 1) | Purity (LCMS) | ¹H NMR |
|---|---|---|---|---|
| 94 | 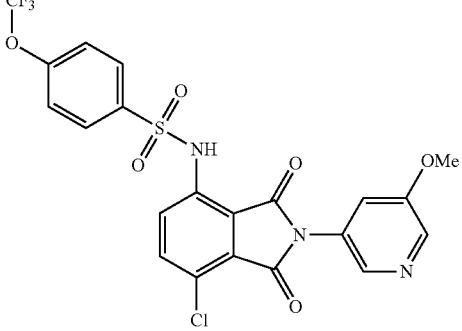 | 528.15 | 99.47%, Rt = 5.56 min (1) | ¹H NMR (400 MHz, DMSO-d6): δ 10.39 (bs, 1H), 8.39-8.38 (d, J = 2.8 Hz, 1H), 8.20-8.19 (d, J = 1.6 Hz, 1H), 8.11-8.09 (d, J = 8.8 Hz, 2H), 7.85-7.83 (d, J = 8.8 Hz, 1H), 7.65-7.60 (m, 3H), 7.47-7.46 (d, J = 2 Hz, 1H), 3.85 (s, 3H). |
| 95 | 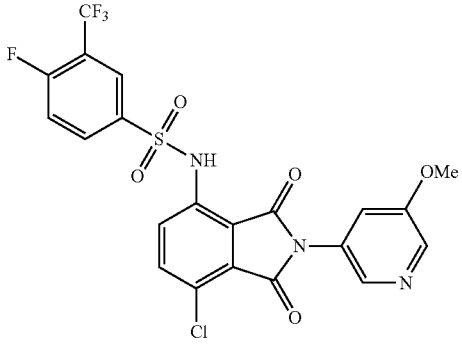 [SMILES: COc1cncc(N2C(=O)c3c(Cl)ccc(NS(=O)(=O)c4ccc(F)c(C(F)(F)F)c4)c3C2=O)c1] | 530.18 | 98.00%, Rt = 5.39 min (1) | ¹H NMR (400 MHz, DMSO-d6): δ 10.69 (bs, 1H), 8.44-8.42 (d, J = 5.2 Hz, 1H), 8.39-8.38 (d, J = 2.8 Hz, 1H), 8.33-8.32 (d, J = 2.8 Hz, 1H), 8.20-8.19 (d, J = 2 Hz, 1H), 7.83-7.76 (m, 2H), 7.64-7.62 (d, J = 8.8 Hz, 1H), 7.47-7.46 (d, J = 2.4 Hz, 1H), 3.85 (s, 3H). |
| 96 | 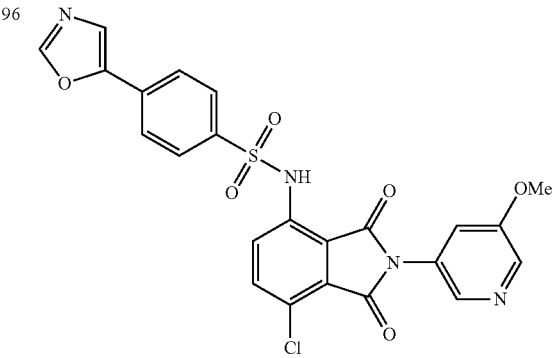 | 511.06 | 96.98%, Rt = 4.88 min (1) | ¹H NMR (400 MHz, DMSO-d6): δ 10.24 (bs, 1H), 8.56 (s, 1H), 8.38 (d, J = 2.8 Hz, 1H), 8.20 (d, J = 1.6 Hz, 1H), 8.07-8.05 (d, J = 8.4 Hz, 2H), 7.96-7.92 (m, 3H), 7.83-7.81 (d, J = 8.0 Hz, 1H), 7.66-7.64 (d, J = 8.8 Hz, 1H), 7.46 (m, 1H), 3.84 (s, 3H). |
| 97 | 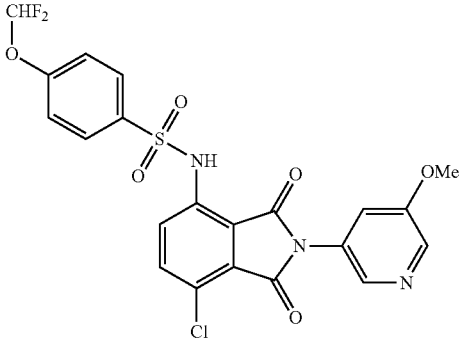 [SMILES: COc1cncc(N2C(=O)c3c(Cl)ccc(NS(=O)(=O)c4ccc(OC(F)F)cc4)c3C2=O)c1] | 510.06 | 98.99%, Rt = 5.33 min (1) | ¹H NMR (400 MHz, DMSO-d6): δ 10.20 (bs, 1H), 8.39 (d, J = 2.8 Hz, 1H), 8.22 (s, 1H), 8.07-8.05 (d, J = 8.8 Hz, 2H), 7.84-7.81 (d, J = 8.8 Hz, 1H), 7.66-7.63 (d, J = 8.8 Hz, 1H), 7.59-7.22 (m, 4H), 3.85 (s, 3H). |

-continued

| CPD | Structure | LCMS (M + 1) | Purity (LCMS) | ¹H NMR |
|---|---|---|---|---|
| 98 | 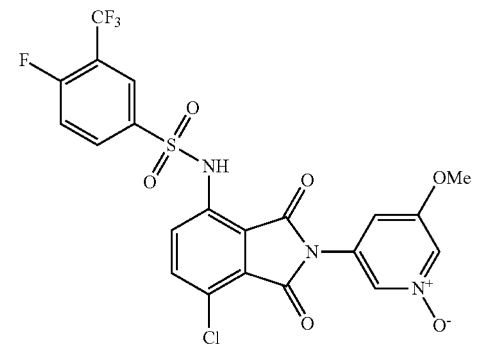 [SMILES: COc1cc(N2C(=O)c3c(Cl)ccc(NS(=O)(=O)c4ccc(F)c(C(F)(F)F)c4)c3C2=O)c[n+]([O-])c1] | 545.99 | 99.31%, Rt 5.05 min (1) | ¹H NMR (400 MHz, DMSO-d6): δ 10.76 (bs, 1H), 8.38-8.30 (m, 2H), 8.18 (s, 1H), 8.01 (s, 1H), 7.75-7.71 (m, 2H), 7.61-7.59 (m, 1H), 7.14 (s, 1H), 3.85 (s, 3H). |
| 99 | 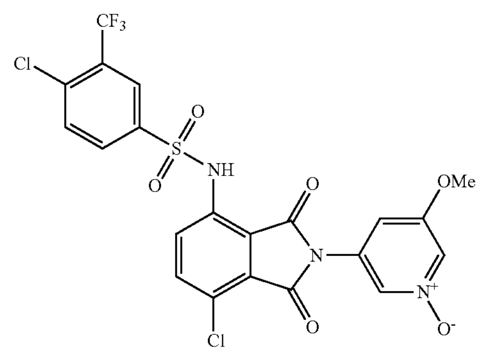 [SMILES: COc1cc(N2C(=O)c3c(Cl)ccc(NS(=O)(=O)c4ccc(Cl)c(C(F)(F)F)c4)c3C2=O)c[n+]([O-])c1] | 561.97 | 99.42%, Rt = 5.23 min (1) | ¹H NMR (400 MHz, DMSO-d6): δ 10.75 (bs, 1H), 8.35 (s, 1H), 8.16 (bs, 2H), 8.02 (s, 1H), 7.92-7.90 (d, J = 8.0 Hz, 1H), 7.66-7.57 (m, 2H), 7.15 (s, 1H), 3.85 (s, 3H). |
| 100 | 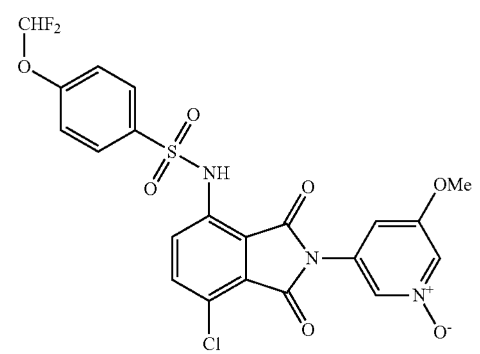 [SMILES: COc1cc(N2C(=O)c3c(Cl)ccc(NS(=O)(=O)c4ccc(OC(F)F)cc4)c3C2=O)c[n+]([O-])c1] | 526.01 | 99.59%, Rt = 4.88 min (1) | ¹H NMR (400 MHz, DMSO-d6): δ 10.27 (bs, 1H), 8.18 (s, 1H), 8.03-8.02 (d, J = 5.6 Hz, 3H), 7.77-7.72 (m, 1H), 7.63-7.61 (d, J = 8.8 Hz, 1H), 7.37-7.34 (m, 2H), 7.22-7.09 (m, 2H), 3.85 (s, 3H). |
| 101 | 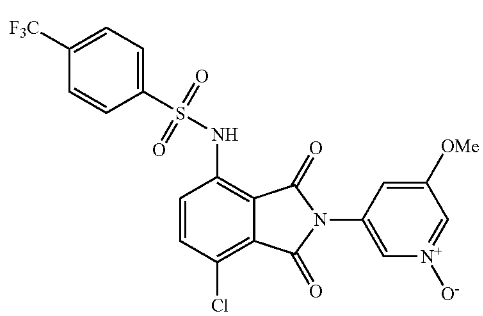 | 528.03 | 98.14%, Rt = 5.96 min (2) | ¹H NMR (400 MHz, DMSO-d6): δ 10.75 (bs, 1H), 8.11 (s, 1H), 8.05 (s, 1H), 8.01-7.99 (d, J = 8.4 Hz, 2H), 7.80-7.78 (d, J = 8.4 Hz, 2H), 7.55-7.53 (d, J = 7.2 Hz, 1H), 7.33-7.30 (d, J = 9.2 Hz, 1H), 7.19 (s, 1H), 3.84 (s, 3H). |

| CPD | Structure | LCMS (M + 1) | Purity (LCMS) | ¹H NMR |
|---|---|---|---|---|
| 102 | 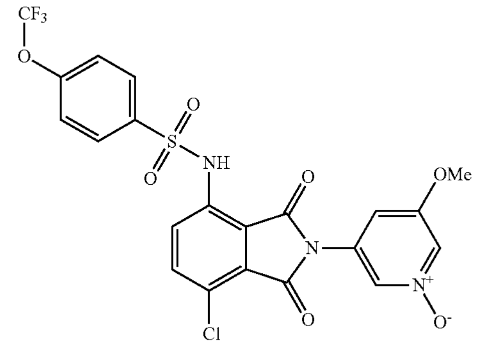 [SMILES: COc1cc(N2C(=O)c3c(Cl)ccc(NS(=O)(=O)c4ccc(OC(F)(F)F)cc4)c3C2=O)c[n+]([O-])c1] | 544.04 | 96.39%, Rt = 6.04 min (2) | ¹H NMR (400 MHz, DMSO-d6): δ 10.46 (bs, 1H), 8.19 (s, 1H), 8.12-8.10 (d, J = 8.8 Hz, 2H), 8.00 (s, 1H), 7.83-7.81 (d, J = 5.2 Hz, 1H), 7.65-7.60 (m, 3H), 7.13 (s, 1H), 3.85 (s, 3H). |
| 103 | 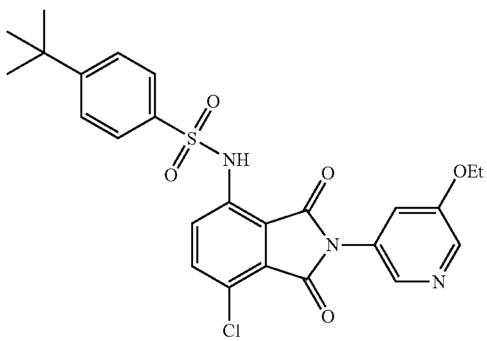 [SMILES: CCOc1cncc(N2C(=O)c3c(Cl)ccc(NS(=O)(=O)c4ccc(C(C)(C)C)cc4)c3C2=O)c1] | 514.47 | 98.16%, Rt = 6.28 min (1) | ¹H NMR (400 MHz, DMSO-d6): δ 10.02 (bs, 1H), 8.36 (s, 1H), 8.19 (s, 1H), 7.93-7.91 (m, 2H), 7.84-7.82 (d, J = 8.8 Hz, 1H), 7.69-7.63 (m, 3H), 7.46 (s, 1H), 4.15-4.10 (q, J = 6.8 Hz, 2H), 1.38-1.34 (t, J = 6.8 Hz, 3H), 1.27 (s, 9H). |

Example 13

Synthesis of Compound 104 [4-(tert-butyl)-N-(7-chloro-2-(5-methylpyridin-3-yl)-1,3-dioxoisoindolin-4-yl)benzenesulfonamide] and Compound 105

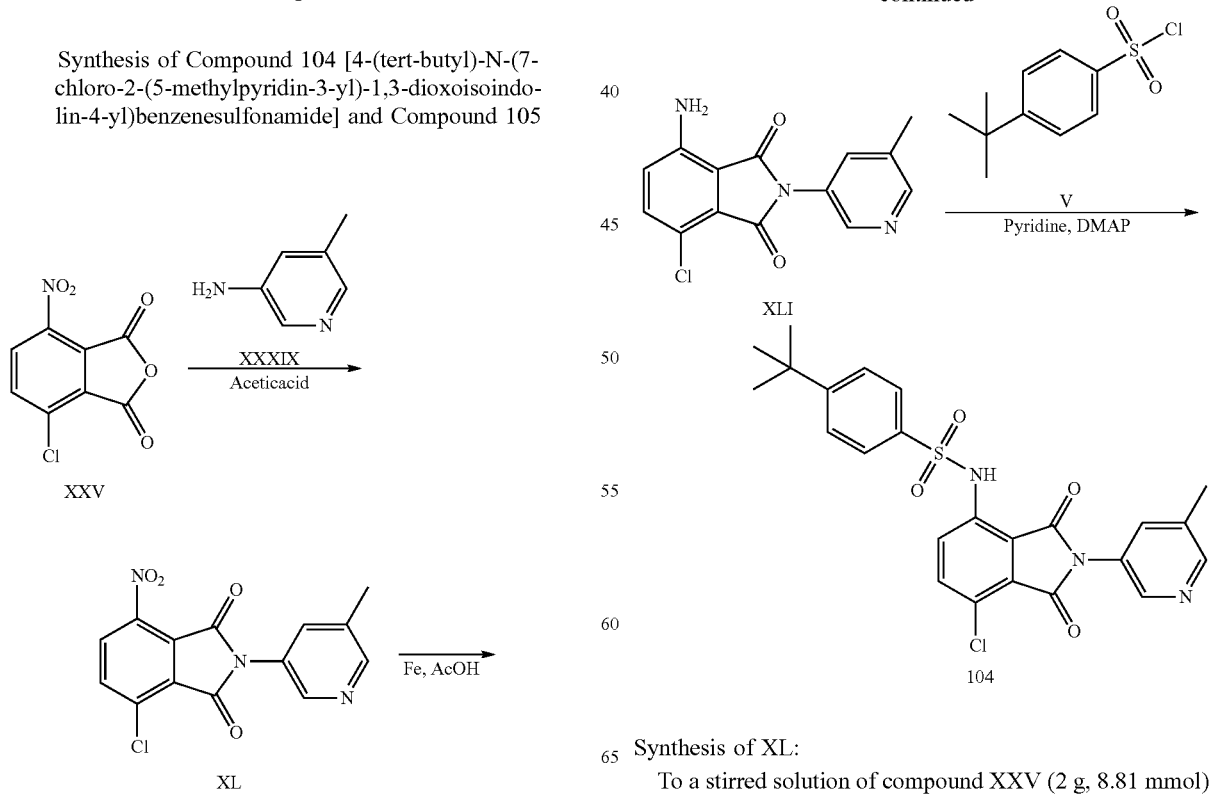

Synthesis of XL:

To a stirred solution of compound XXV (2 g, 8.81 mmol) in acetic acid (18 mL) was added 5-methylpyridin-3-amine (XXXIX, 1.43 g, 13.2 mmol). The reaction mixture was heated at 120° C. for 12 h. On cooling to room temperature, the acetic acid was removed under reduced pressure to obtain the crude product which was washed with ethanol to afford 4-chloro-2-(5-methylpyridin-3-yl)-7-nitroisoindoline-1,3-dione (XL, 1.8 g, 64.5%). ¹H NMR (400 MHz, DMSO-d6): δ 8.63 (s, 1H), 8.52 (m, 1H), 8.20-8.16 (m, 1H), 7.86-7.84 (d, J=8.4 Hz, 1H), 7.70 (m, 1H), 2.3 (s, 3H).

Synthesis of XLI:

To a solution of compound XL (1.8 g, 5.67 mmol) in acetic acid (50 mL) was added iron powder (1 g) in small portions. The reaction mixture was stirred for 12 h at room temperature and then filtered through a celite bed and concentrated under reduced pressure. The crude material was neutralized by addition of sodium bicarbonate solution. The aqueous layer was extracted with ethyl acetate, which was dried (anhydrous $Na_2SO_4$), filtered and evaporated under reduced pressure to afford compound 4-amino-7-chloro-2-(5-methylpyridin-3-yl)isoindoline-1,3-dione as an off white solid (XLI; 1.4 g, 87.5% yield). ¹H NMR (400 MHz, DMSO-d6): δ 8.53-8.44 (m, 2H), 7.70 (s, 1H), 7.50-7.47 (d, J=8.8 Hz, 1H), 7.07-7.05 (d, J=8.8 Hz, 1H), 6.73 (bs, 2H), 2.36 (s, 3H).

Synthesis of 104; 4-(tert-butyl)-N-(7-chloro-2-(5-methylpyridin-3-yl)-1,3-dioxoisoindolin-4-yl)benzenesulfonamide and Compound 105

A mixture of compound XLI (0.3 g, 1.05 mmol) and pyridine (6 mL) was cooled to 0° C. and 4-tert-butylbenzenesulfonyl chloride (V, 0.29 g, 1.25 mmol) was added followed by a catalytic quantity of DMAP (0.034 g, 0.42 mmol). The reaction mixture was heated for 15 h at 80° C. The reaction mixture was concentrated and diluted with water. The reaction mixture was extracted with ethyl acetate. An organic layer was washed with brine solution, dried over anhydrous $Na_2SO_4$, filtered and the organic solvent was evaporated under reduced pressure to obtain the crude compound. The crude compound was purified by column chromatography using 70% ethyl acetate in hexane to afford 4-(tert-butyl)-N-(7-chloro-2-(5-methylpyridin-3-yl)-1,3-dioxoisoindolin-4-yl)benzenesulfonamide as an off white solid (104; 0.2 g, 39.8% yield). ¹H NMR (400 MHz, DMSO-d6): δ 9.97 (bs, 1H), 8.49 (s, 1H), 8.40 (s, 1H), 7.93-7.91 (d, J=8.4 Hz, 2H), 7.84-7.82 (d, J=9.2 Hz, 1H), 7.69-7.63 (m, 4H), 2.37 (s, 3H), 1.27 (s, 9H). MS (M+1): 484.20. (LCMS purity 96.68%, Rt=6.22 min (1)).

The following compound was also prepared using a similar method and the appropriate sulfonyl chloride in the final step:

| CPD | Structure | LCMS (M + 1) | Purity (LCMS) | 1HNMR |
|---|---|---|---|---|
| 105 | 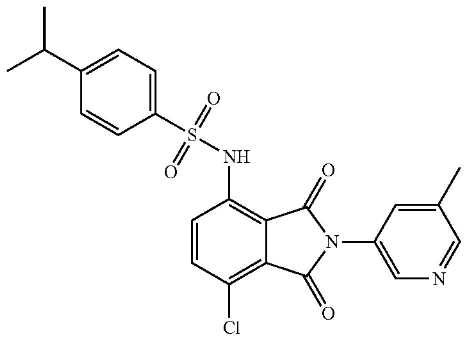 [SMILES: Cc1cncc(N2C(=O)c3c(Cl)ccc(NS(=O)(=O)c4ccc(C(C)C)cc4)c3C2=O)c1] | 470.38 | 98.96%, Rt = 6.05 min (1) | ¹H NMR (400 MHz, DMSO-d6): δ 9.97 (bs, 1H), 8.49 (s, 1H), 8.41 (d, J = 2.0 Hz, 1H), 7.93-7.91 (d, J = 8.4 Hz, 2H), 7.84-7.81 (d, J = 8.8 Hz, 1H), 7.69-7.67 (d, J = 8.8 Hz, 2H), 7.51-7.48 (d, J = 8.4 Hz, 2H), 3.0-2.94 (m, 1H), 2.32 (s, 3H), 1.19-1.18 (d, J = 6.8 Hz, 6H). |

Example 14

Synthesis of Compound 106 [4-(tert-butyl)-N-(7-chloro-2-(5-fluoropyridin-3-yl)-1,3-dioxoisoindolin-4-yl)benzenesulfonamide]

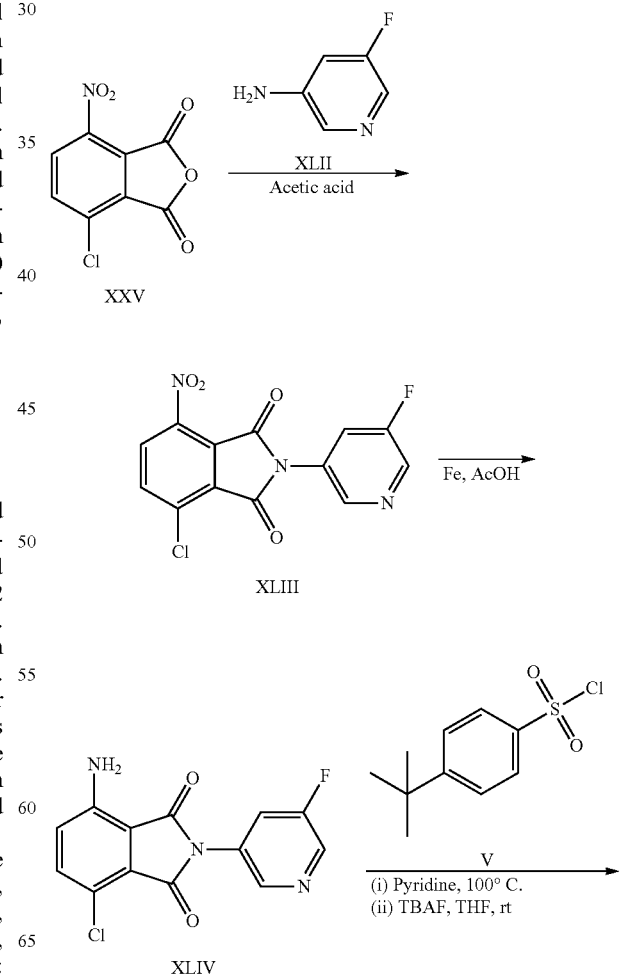

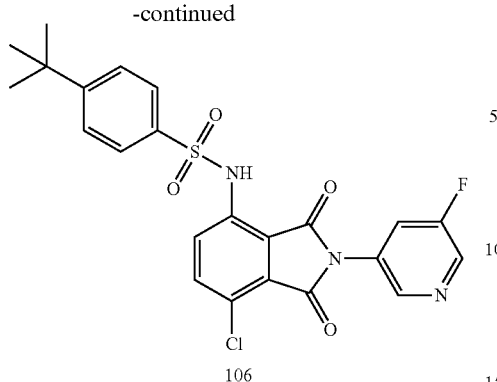

Synthesis of XLIII:

To a stirred solution of compound XXV (0.4 g, 1.7 mmol) in acetic acid (4 mL) was added 5-fluoropyridin-3-amine (XLII, 0.39 g, 3.5 mmol). The reaction mixture was heated at 120° C. for 12 h. The reaction mixture was cooled to room temperature and the acetic acid removed under reduced pressure to obtain the crude product which was washed with ethanol to afford 4-chloro-2-(5-fluoropyridin-3-yl)-7-nitroisoindoline-1,3-dione (XLIII, 0.5 g, 41.6%). MS (M+1): 322.0. (LCMS purity 98.04%).

Synthesis of XLIV:

To a solution of compound XLIII (0.5 g, 1.56 mmol) in acetic acid (10 mL) was added iron powder (0.5 g) in small portions. The reaction mixture was stirred for 12 h at room temperature. The reaction mixture was filtered through a celite bed and concentrated under reduced pressure. The crude mass was neutralized using aqueous sodium bicarbonate solution, whereupon the aqueous layer was extracted with ethyl acetate which was dried (anhydrous $Na_2SO_4$), filtered and evaporated under reduced pressure to obtain the crude compound 4-amino-7-chloro-2-(5-fluoropyridin-3-yl) isoindoline-1,3-dione as a off white solid (XLIV; 0.35 g, 76% yield). MS (M+1): 292.05 which was used without further purification.

Synthesis of 106; 4-(tert-butyl)-N-(7-chloro-2-(5-fluoropyridin-3-yl)-1,3-dioxoisoindolin-4-yl)benzenesulfonamide A mixture of compound XLIV (0.35 g, 1.19 mmol) and pyridine (3 mL) was cooled to 0° C. and 4-tert-butylbenzenesulfonyl chloride (V, 0.56 g, 2.38 mmol) was added. The reaction mixture was stirred for 12 h at 100° C. The reaction mixture was concentrated, diluted with water and extracted with ethyl acetate. The organic layer was washed with brine solution, dried over anhydrous $Na_2SO_4$, filtered and evaporated under reduced pressure to obtain the crude compound. To the crude compound was added 1M TBAF in THF solution (2.4 mL) and this solution was stirred for 1 h at room temperature. The reaction mixture was concentrated and diluted with ethyl acetate. The organic layer was washed with water, dried over anhydrous $Na_2SO_4$, filtered and evaporated under reduced pressure to obtain the crude compound which was purified by column chromatography using 50% ethyl acetate in hexane to afford methyl 4-(tert-butyl)-N-(7-chloro-2-(5-fluoropyridin-3-yl)-1,3-dioxoisoindolin-4-yl)benzenesulfonamide as an off white solid (106; 0.13 g, 22.2% yield). $^1$H NMR (400 MHz, DMSO-d6): δ 10.05 (bs, 1H), 8.71 (d, J=2.4 Hz, 1H), 8.54 (s, 1H), 7.94-7.91 (d, J=8.4 Hz, 2H), 7.87-7.84 (m, 2H), 7.71-7.68 (d, J=9.2 Hz, 1H), 7.65-7.63 (d, J=8.4 Hz, 2H), 1.27 (s, 9H). MS (M+1): 488.07. (LCMS purity 97.48%, Rt=4.60 min) (1).

Example 15

Synthesis of Compound 107 [4-(tert-butyl)-N-(7-chloro-1,3-dioxo-2-(2-(pyridin-3-yl)propan-2-yl) isoindolin-4-yl)benzenesulfonamide]; Compound 108; [3-(2-(4-(4-(tert-butyl)phenylsulfon-amido)-7-chloro-1,3-dioxoisoindolin-2-yl)propan-2-yl)pyridine 1-oxide] and Compounds 109-115

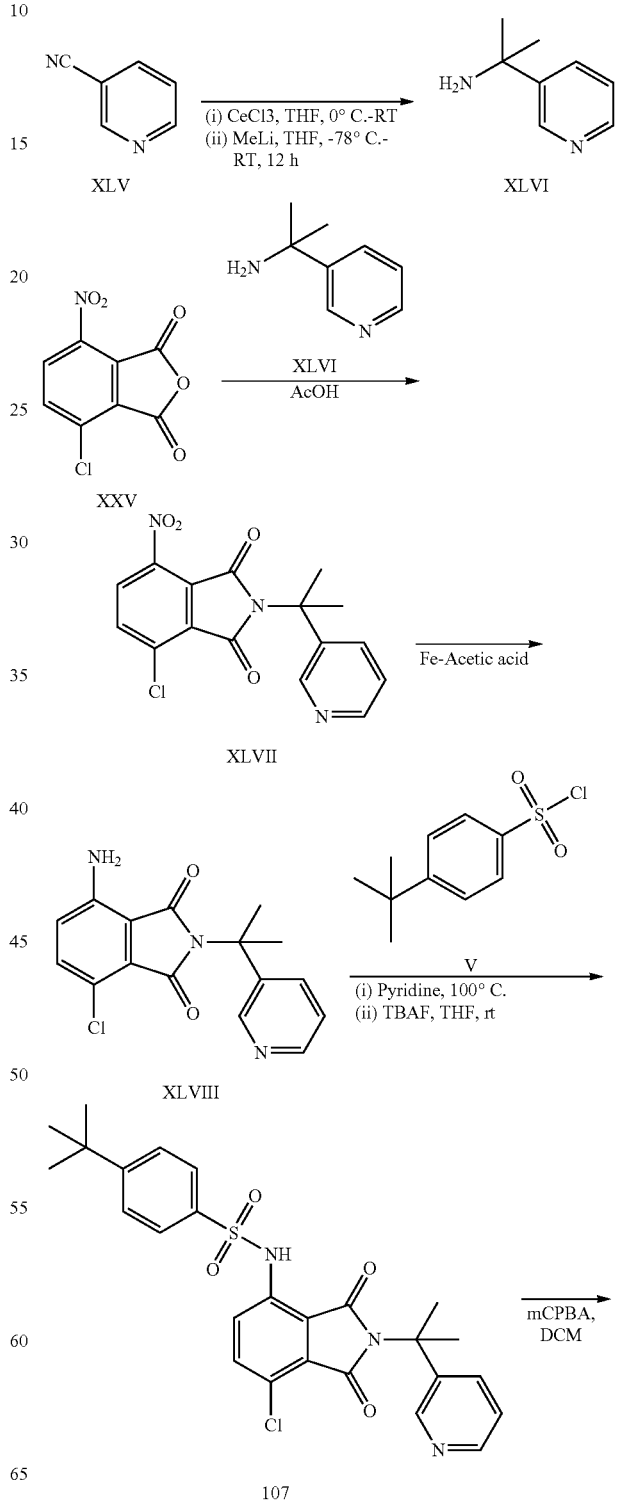

-continued

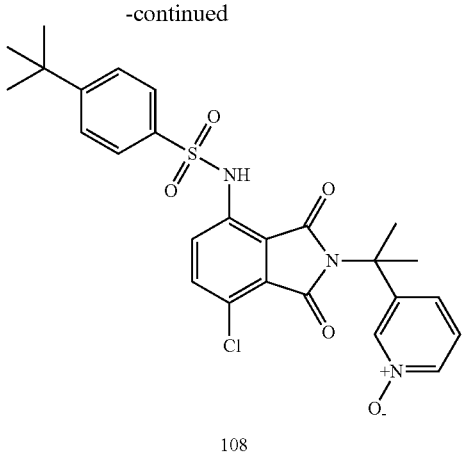

108

Synthesis of XLVI:

Cerium chloride (35.5 g, 144 mmol) was added to dry THF (250 mL). The reaction mixture was stirred at room temperature for 2 h under a nitrogen atmosphere to allow the cerium chloride to form a suspension in the THF solution. This was cooled to −78° C. and then a 1.6 M methyl lithium solution in THF (48 mL, 144 mmol) was added. The reaction mixture was stirred for 30 minutes maintaining the same temperature and then a solution of 3-cyanopyridine (XLV, 5 g, 48 mmol) in THF (50 mL) was added through a cannula. The reaction mixture was allowed to warm to room temperature and stirring continued for 12 h. The reaction mixture was diluted with a saturated aqueous solution of ammonium acetate solution and the stirring continued for a further 1 h at room temperature. The reaction mixture was filtered through a celite bed, concentrated and diluted with water. The resulting aqueous layer was extracted with ethyl acetate and the organic layer was dried (anhydrous $Na_2SO_4$), filtered and evaporated under reduced pressure to obtain the crude compound 2-(pyridin-3-yl)propan-2-amine (XLVI; 2.0 g crude). MS (M+1): 137. The crude material was carried forward to the next step without purification.

Synthesis of XLVII:

To a stirred solution of compound XXV (2.0 g, 8.8 mmol) in acetic acid (50 mL) was added 2-(pyridin-3-yl)propan-2-amine (XLVI, 3.6 g, 26 mmol) and the reaction mixture heated at 120° C. for 18 h. This was then cooled to room temperature and the acetic acid removed under reduced pressure to obtain the crude product which was washed with ethanol to afford 4-chloro-7-nitro-2-(2-(pyridin-3-yl)propan-2-yl)isoindoline-1,3-dione as a yellow solid (XLVII; 1.5 g crude). The crude compound carried forward to next step. MS (M+1): 346.04.

Synthesis of XLVIII:

To a solution of compound XLVII (1.5 g, crude) in acetic acid (30 mL) was added iron powder (1.5 g) in small portions. The reaction mixture was stirred for 5 h at room temperature and then filtered through a celite bed and concentrated under reduced pressure. The crude mass was neutralized using aqueous sodium bicarbonate solution resulting in an aqueous layer which was extracted with ethyl acetate. The organic layer was dried (anhydrous $Na_2SO_4$), filtered and evaporated under reduced pressure to obtain the crude compound. This material was further purified by trituration using acetonitrile and ethyl acetate to afford the compound 4-amino-7-chloro-2-(5-methoxypyridin-3-yl) isoindoline-1,3-dione as a yellow solid (XLVIII; 0.8 g, crude). MS (M+1): 316.

Synthesis of 107; 4-(tert-butyl)-N-(7-chloro-1,3-dioxo-2-(2-(pyridin-3-yl)propan-2-yl)isoindolin-4-yl)benzenesulfonamide A mixture of compound XLVIII (0.4 g, crude) and pyridine (4 mL) was cooled to 0° C. and 4-tert-butylbenzenesulfonyl chloride (V, 0.88 g, 3.8 mmol) was added followed by a catalytic quantity of DMAP (0.07 g, 0.63 mmol). The reaction mixture was stirred for 12 h at 100° C. whereupon the reaction mixture was concentrated at reduced pressure and diluted with water. The aqueous layer was extracted with ethyl acetate. The organic layer was washed with brine solution, dried over anhydrous $Na_2SO_4$, filtered and the organic solvent was evaporated under reduced pressure to obtain the crude compound. To the crude compound was added 1M TBAF in THF solution (2 mL) and stirring was continued for 1 h at room temperature. The reaction mixture was concentrated and diluted with ethyl acetate which was with water, dried over anhydrous $Na_2SO_4$, filtered and evaporated under reduced pressure to obtain the crude compound which was purified by column chromatography using 35% ethyl acetate in hexane to afford the title compound 4-(tert-butyl)-N-(7-chloro-1,3-dioxo-2-(2-(pyridin-3-yl)propan-2-yl)isoindolin-4-yl)benzenesulfonamide as an off white solid (107; 0.065 g, 10% yield). $^1$H NMR (400 MHz, DMSO-d6): δ 9.80 (bs, 1H), 8.63 (s, 1H), 8.44 (m, 1H), 7.89-7.87 (d, J=8.40 Hz, 2H), 7.81-7.79 (d, J=8.40 Hz, 1H), 7.73-7.70 (d, J=8.40 Hz, 1H), 7.63-7.58 (m, 3H), 7.34-7.31 (m, 1H), 1.89 (s, 6H). 1.27 (s, 9H). MS (M+1): 512.14. (LCMS purity 97.95%, Rt=4.36 min (1)).

Synthesis of 108; 3-(2-(4-(4-(tert-butyl)phenylsulfonamido)-7-chloro-1,3-dioxoisoindolin-2-yl)propan-2-yl)pyridine 1-oxide To a stirred solution of 4-(tert-butyl)-N-(7-chloro-1,3-dioxo-2-(2-(pyridin-3-yl)propan-2-yl)isoindolin-4-yl)benzenesulfonamide (107; 0.060 g, 0.11 mmol) in dichloromethane (3 mL), was added metachloroperoxybenzoic acid (0.020 g, 0.11 mmol). The reaction was stirred at room temperature for 8 h whereupon the solvent was concentrated under reduced pressure and the residue diluted with water. The aqueous layer was extracted with dichloromethane. The combined organic layers were washed sequentially with sodium bicarbonate and brine, then dried over $Na_2SO_4$, filtered and concentrated under vacuum to leave the crude compound which was purified by column chromatography using 2% methanol in dichloromethane to afford 3-(2-(4-(4-(tert-butyl)phenylsulfonamido)-7-chloro-1,3-dioxoisoindolin-2-yl)propan-2-yl)pyridine 1-oxide (141; 0.020 g, 32% yield). $^1$H NMR (400 MHz, DMSO-d6): δ 9.81 (bs, 1H), 8.36 (s, 1H), 8.10-8.09 (d, J=5.6 Hz, 1H), 7.91-7.89 (d, J=8.4 Hz, 2H), 7.73-7.71 (d, J=8.8 Hz, 1H), 7.64-7.58 (m, 3H), 7.41-7.32 (m, 2H), 1.85 (s, 6H), 1.27 (s, 9H). MS (M+1): 528.41. (LCMS purity 99.0%, Rt=6.14 min(1)).

The following compounds were prepared in a similar manner and using the appropriate sulfonyl chloride in the penultimate step. This resulted either in the final pyridine compounds, which if required could also be converted into the corresponding pyridine N-oxides using mCPBA:

| CPD | Structure | LCMS (M + 1) | Purity (LCMS) | ¹H NMR |
|---|---|---|---|---|
| 109 | 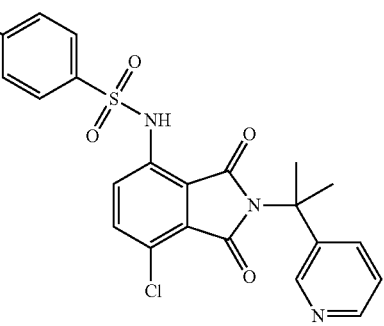 | 524.06 Rt = 6.07 min (1) | 97.23%, | ¹H NMR (400 MHz, DMSO-d6): δ 10.31 (bs, 1H), 8.60 (s, 1H), 8.44-8.43 (d, J = 3.6 Hz, 1H), 8.08-8.06 (d, J = 8.4 Hz, 2H), 7.98-7.96 (d, J = 8.40 Hz, 2H). 7.77-7.73 (m, 2H), 7.57-7.54 (d, J = 8.8 Hz, 1H), 7.33-7.30 (m, 1H), 1.85 (s, 6H). |
| 110 | 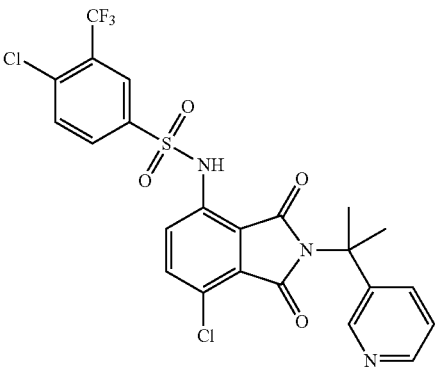 [SMILES: CC(C)(c1cccnc1)N1C(=O)c2c(Cl)ccc(NS(=O)(=O)c3ccc(Cl)c(C(F)(F)F)c3)c2C1=O] | 558.01 Rt = 5.92 min (2) | 98.91%, | ¹H NMR (400 MHz, DMSO-d6): δ 10.59 (bs, 1H), 8.61 (s, 1H), 8.45-8.44 (d, J = 3.6 Hz, 1H), 8.33 (s, 1H), 8.06-8.04 (d, J = 7.2 Hz, 1H), 7.94-7.92 (d, J = 8.4 Hz, 1H), 7.77-7.73 (m, 2H), 7.57-7.55 (d, J = 8.8 Hz, 1H), 7.35-7.32 (m, 1H), 1.86 (s, 6H). |
| 111 | 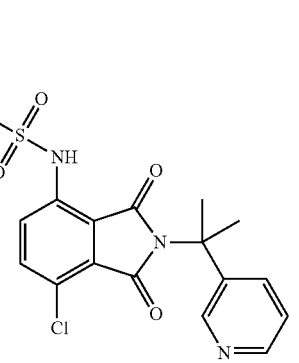 | 540.38 Rt = 6.08 min (1) | 98.48%, | ¹H NMR (400 MHz, DMSO-d6): δ 10.15 (bs, 1H), 8.61 (s, 1H), 8.44-8.43 (d, J = 4.4 Hz, 1H), 8.04-8.02 (d, J = 8.8 Hz, 2H), 7.78-7.72 (m, 2H), 7.59-7.55 (m, 3H), 7.33-7.30 (m, 1H), 1.87 (s, 6H). |
| 112 | 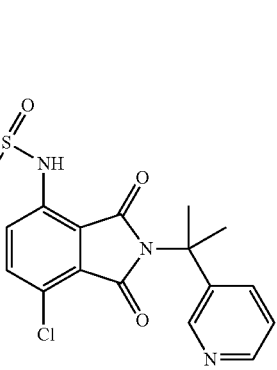 | 523.09 Rt = 5.52 min (2) | 97.12%, | ¹H NMR (400 MHz, DMSO-d6): δ 10.00 (bs, 1H), 8.62- (s, 1H), 8.44-8.43 (d, J = 4.0 Hz, 1H), 8.01-7.98 (d, J = 8.4 Hz, 2H), 7.85-7.70 (m, 4H), 7.59-7.57 (d, J = 8.8 Hz, 1H), 7.34-7.31 (m, 1H), 1.89 (s, 6H), 1.69 (s, 6H). |

| CPD | Structure | LCMS (M + 1) | Purity (LCMS) | ¹H NMR |
|---|---|---|---|---|
| 113 | (4-(difluoromethoxy)phenyl)sulfonamide linked to 7-chloro-2-(2-(pyridin-3-yl)propan-2-yl)isoindoline-1,3-dione | 522.36 | 98.02%, Rt = 6.0 min (1) | ¹H NMR (400 MHz, DMSO-d6): δ 9.96 (bs, 1H), 8.62 (s, 1H), 8.44-8.43 (d, J = 3.6 Hz, 1H), 7.99-7.97 (d, J = 8.8 Hz, 2H), 7.79-7.77 (d, J = 7.6 Hz, 1H), 7.73-7.71 (d, J = 8.4 Hz, 1H), 7.60-7.55 (m, 1H), 7.41-7.23 (m, 4H), 1.89 (s, 6H). |
| 114 | (4-(trifluoromethyl)phenyl)sulfonamide linked to 7-chloro-2-(2-(1-oxidopyridin-3-yl)propan-2-yl)isoindoline-1,3-dione | 538.26 (M − 1) | 99.36%, Rt = 5.18 min (1) | ¹H NMR (400 MHz, DMSO-d6): δ 10.29 (bs, 1H), 8.33 (s, 1H), 8.10-8.08 (m, 3H), 7.99-7.97 (d, J = 8.4 Hz, 2H), 7.75-7.73 (d, J = 8.4 Hz, 1H), 7.57-7.55 (d, J = 8.8 Hz, 1H), 7.36-7.31 (m, 2H), 1.90 (s, 6H). |
| 115 | (4-(trifluoromethoxy)phenyl)sulfonamide linked to 7-chloro-2-(2-(1-oxidopyridin-3-yl)propan-2-yl)isoindoline-1,3-dione | 556.30 | 97.30%, Rt = 5.43 min (1) | ¹H NMR (400 MHz, DMSO-d6): δ 10.13 (bs, 1H), 8.35 (s, 1H), 8.10-8.04 (m, 3H), 7.75-7.72 (d, J = 8.8 Hz, 1H), 7.60-7.55 (m, 3H), 7.38-7.32 (m, 2H), 1.82 (s, 6H). |

Example 16

Synthesis of Compound 116 [4-(tert-butyl)-N-(7-chloro-1,3-dioxo-2-(2-(pyridin-3-yl)ethyl)isoindolin-4-yl)benzenesulfonamide]; and Compound 117 [3-(2-(4-(4-(tert-butyl)phenyl-sulfonamido)-7-chloro-1,3-dioxoisoindolin-2-yl)ethyl)pyridine 1-oxide]

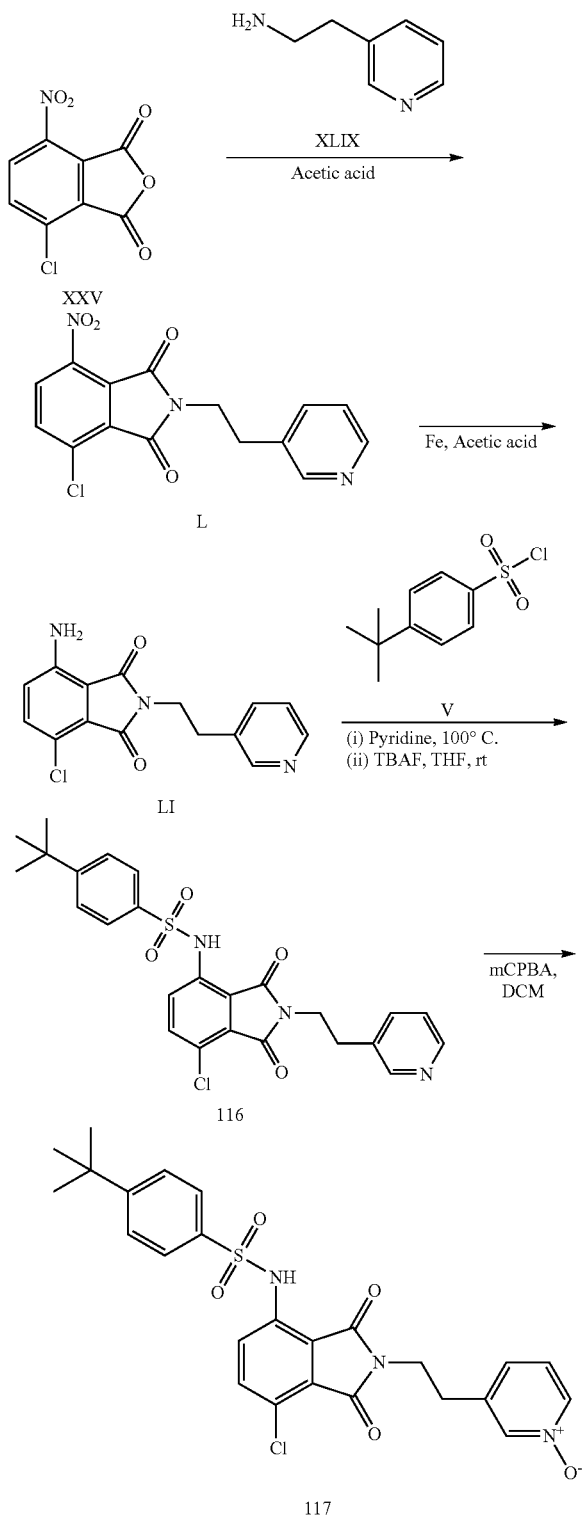

Synthesis of L:

To a stirred solution of compound XXV (1.2 g, 5.28 mmol) in acetic acid (20 mL) was added 2-(pyridin-3-yl)ethylamine (XLIX, 0.71 g, 5.81 mmol) and the reaction mixture heated at 120° C. for 15 h. The reaction mixture was cooled to room temperature and the acetic acid removed under reduced pressure to obtain the crude product. This was washed with ethanol to afford 4-chloro-7-nitro-2-(2-(pyridin-3-yl)ethyl)isoindoline-1,3-dione as a white solid (L; 1.5 g, 86% yield). The crude compound was carried forward to next step. $^1$H NMR (400 MHz, DMSO-d6): δ 8.45 (s, 1H), 8.26-8.24 (d, J=8.8 Hz, 1H), 8.09-8.07 (d, J=8.8 Hz, 1H), 7.71-7.69 (d, J=7.6 Hz, 1H), 7.33-7.30 (m, 1H), 3.83-3.79 (t, J=7.6 Hz, 2H), 2.95-2.91 (t, J=7.6 Hz, 2H). MS (M+1): 332.09 (LCMS Purity 98.15%).

Synthesis of LI:

To a solution of compound L (1 g, 3.01 mmol) in acetic acid (20 mL) was added iron powder (1.5 g) in small portions. The reaction mixture was stirred for 5 h at room temperature. The reaction mixture was filtered through a celite bed and concentrated under reduced pressure. The crude material was neutralized using aqueous sodium bicarbonate solution. The resultant aqueous layer was extracted with ethyl acetate which was dried (anhydrous $Na_2SO_4$), filtered and evaporated under reduced pressure to obtain the crude compound. The material was further purified by trituration using acetonitrile and ethyl acetate to afford 4-amino-7-chloro-2-(2-(pyridin-3-yl)ethyl)isoindoline-1,3-dione as a yellow solid (LI; 0.75 g, 82.4% yield). $^1$H NMR (400 MHz, DMSO-d6): δ 8.40-8.38 (m, 2H), 7.64-7.62 (m, 2H), 7.39-7.37 (d, J=8.8 Hz, 1H), 7.31-7.27 (m, 1H), 6.56 (bs, 2H), 3.77-3.74 (t, J=7.2 Hz, 2H), 2.93-2.90 (t, J=6.8 Hz, 2H). MS (M+1): 302.17 (LCMS purity 97.87%).

Synthesis of 116; 4-(tert-butyl)-N-(7-chloro-1,3-dioxo-2-(2-(pyridin-3-yl)ethyl)isoindolin-4-yl)benzenesulfonamide A mixture of compound LI (1 g, 3.31 mmol) and pyridine (7 mL) was cooled to 0° C. and 4-tert-butylbenzenesulfonyl chloride (V, 2.3 g, 9.89 mmol) was added followed by a catalytic quantity of DMAP (0.040 g, 0.33 mmol). The reaction mixture was stirred for 12 h at 100° C., concentrated and diluted with water. The reaction mixture was extracted with ethyl acetate and the organic layer was washed with brine solution, dried over anhydrous $Na_2SO_4$, filtered and evaporated under reduced pressure to obtain the crude compound. To this material was added 1M TBAF in THF solution (2 mL) and the stirring was continued for 1 h at room temperature. The reaction mixture was concentrated and diluted with ethyl acetate. The organic layer was washed with water, dried over anhydrous $Na_2SO_4$, filtered and evaporated under reduced pressure to obtain the crude compound which was purified by column chromatography using 20% ethyl acetate in hexane to afford the title compound, 4-(tert-butyl)-N-(7-chloro-1,3-dioxo-2-(2-(pyridin-3-yl)ethyl)isoindolin-4-yl)benzenesulfonamide as a off white solid (116; 0.3 g, 18.75% yield). $^1$H NMR (400 MHz, DMSO-d6): δ 9.91 (bs, 1H), 8.41-8.37 (m, 2H), 7.89-7.86 (d, J=8.4 Hz, 2H), 7.73-7.71 (d, J=8.8 Hz, 1H), 7.64-7.58 (m, 4H), 7.30-7.29 (d, J=5.2 Hz, 1H), 3.77-3.74 (t, J=6.4 Hz, 2H), 2.90-2.87 (t, J=6.4 Hz, 2H), 1.26 (s, 9H). MS (M+1): 498.42. (LCMS purity 99.62%, Rt=6.22 min (1)).

Synthesis of 117; 3-(2-(4-(4-(tert-butyl)phenylsulfonamido)-7-chloro-1,3-dioxoisoindolin-2-yl)ethyl)pyridine 1-oxide To a mixture of compound 116 (0.1 g, 0.21 mmol) and dichloromethane (4 mL) was added metachloroperoxybenzoic acid (0.069 g, 0.22 mmol). The reaction was stirred at RT for 5 h whereupon the solvent was concentrated under reduced pressure and the residue diluted with water. The aqueous layer was extracted with dichloromethane. The combined organic layers were washed sequentially with sodium bicarbonate and brine, then dried over $Na_2SO_4$, filtered and concentrated under vacuum to leave the crude compound which was purified by column chromatography using 3% methanol in dichloromethane to afford 3-(2-(4-(4-(tert-butyl)phenylsulfonamido)-7-chloro-1,3-dioxoisoindolin-2-yl)ethyl)pyridine 1-oxide as an off white solid (117; 0.016 g, 15.5% yield). $^1$H NMR (400 MHz, DMSO-d6): δ 9.56 (bs, 1H), 8.17 (s, 1H), 8.07-8.05 (d, J=6.4 Hz, 1H), 7.89-7.87 (m, 2H), 7.73-7.71 (d, J=8.4 Hz, 1H), 7.64-7.58 (m, 3H), 7.30-7.26 (m, 1H), 7.17-7.15 (m, 1H), 3.78-3.74 (t, J=6.8 Hz, 2H), 2.85-2.82 (t, J=6.8 Hz, 2H), 1.27 (s, 9H). MS (M+1): 514.45. (LCMS purity 99.01%).

Example 17

Synthesis of Compound 118 [4-(tert-butyl)-N-(7-chloro-2-(6-methoxypyridin-3-yl)-1,3-dioxoisoindolin-4-yl)benzenesulfonamide] and Compound 119

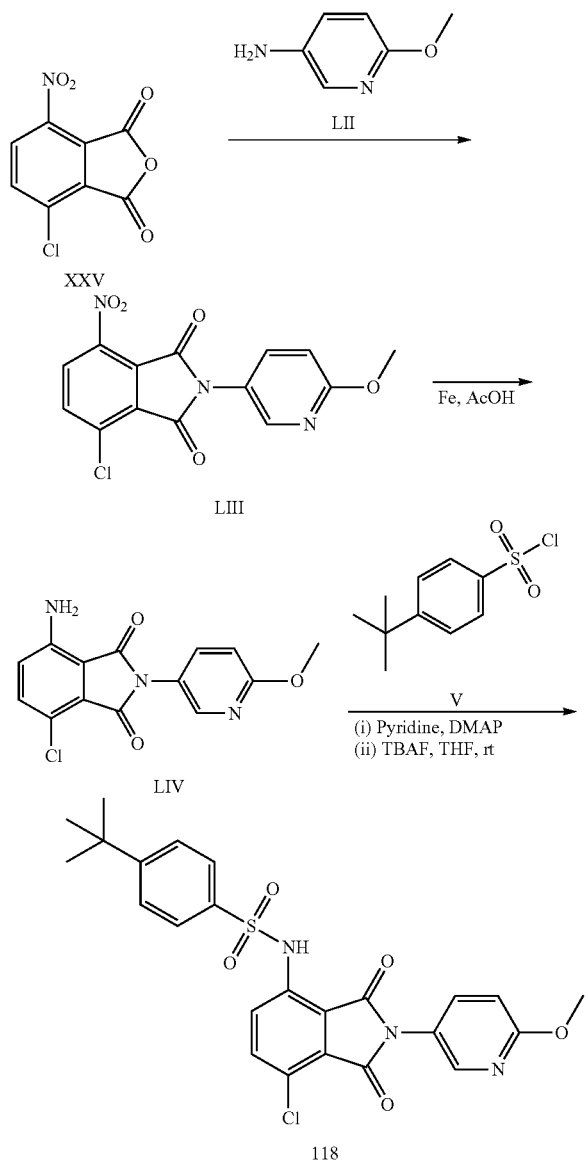

Synthesis of LIII:

To a stirred solution of compound XXV (1.5 g, 6.63 mmol) in acetic acid (10 mL) was added 6-methoxypyridin-3-amine (LII, 0.98 g, 7.96 mmol). The reaction mixture was heated at 100° C. for 12 h. After cooling to room temperature, the acetic acid removed under reduced pressure to obtain the crude product which was washed with ethanol to afford 4-chloro-2-(6-methoxypyridin-3-yl)-7-nitroisoindoline-1,3-dione (LIII, 1.5 g, 68.18%). MS (M+1): 334.06.

Synthesis of LIV:

To a solution of compound LIII (1.5 g, 4.5 mmol) in acetic acid (9 mL) was added iron powder (1.3 g) in small portions. The reaction mixture was stirred for 12 h at room temperature and then filtered through a celite bed and concentrated under reduced pressure. The crude material was neutralized using aqueous sodium bicarbonate solution. The aqueous layer was extracted with ethyl acetate which was dried (anhydrous $Na_2SO_4$), filtered and evaporated under reduced pressure to afford 4-amino-7-chloro-2-(6-methoxypyridin-3-yl)isoindoline-1,3-dione as a greenish coloured solid (LIV; 0.8 g, 58.8% yield). $^1$H NMR (400 MHz, DMSO-d6): δ 8.21 (s, 1H), 7.88-7.87 (d, J=6.4 Hz, 1H), 7.48-7.46 (d, J=8.8 Hz, 1H), 7.07-7.04 (d, J=9.2 Hz, 1H), 6.98-6.96 (d, J=8.8 Hz, 1H), 6.64 (bs, 2H), 3.89 (s, 3H). MS (M+1): 304.14. (LCMS purity 95.16%).

Synthesis of 118; 4-(tert-butyl)-N-(7-chloro-2-(6-methoxypyridin-3-yl)-1,3-dioxoisoindolin-4-yl)benzenesulfonamide A mixture of compound LIV (0.55 g, 1.8 mmol) and pyridine (4 mL) was cooled to 0° C. and 4-tert-butylbenzenesulfonyl chloride (V, 1.47 g, 6.35 mmol) was added together with a catalytic quantity of DMAP. The reaction mixture was heated for 12 h at 100° C. then concentrated and diluted with water. The aqueous layer was extracted with ethyl acetate. The organic layer was washed with brine solution, dried over anhydrous $Na_2SO_4$, filtered and the organic solvent was evaporated under reduced pressure to obtain the crude compound. To this material was added 1M TBAF in THF solution (2 mL) and the stirring continued for 1 h at room temperature. The reaction mixture was concentrated and diluted with ethyl acetate. The organic layer was washed with water, dried over anhydrous $Na_2SO_4$, filtered and the organic solvent was evaporated under reduced pressure to obtain the crude compound which was purified by column chromatography using 40% ethyl acetate in hexane to afford 4-(tert-butyl)-N-(7-chloro-2-(6-methoxypyridin-3-yl)-1,3-dioxoisoindolin-4-yl)benzenesulfonamide as an off white solid (118; 0.5 g, 55.2% yield). $^1$H NMR (400 MHz, DMSO-d6): δ 9.97 (bs, 1H), 8.19-8.18 (s, 1H), 7.94-7.92 (d, J=8.8 Hz, 2H), 7.82-7.80 (d, J=8.8 Hz, 1H), 7.75-7.72 (dd, J=2.8, 2.4 Hz, 1H), 7.68-7.63 (m, 3H), 7.0-6.98 (d, J=8.8 Hz, 1H), 3.90 (s, 3H), 1.27 (s, 9H). MS (M+1): 500.44. (LCMS purity 99.12%, Rt=6.50 min(1)).

The following compound was also prepared using a similar method and appropriate amine in the first step:

| CPD | Structure | LCMS (M + 1) | Purity (LCMS) | 1HNMR |
|---|---|---|---|---|
| 119 | 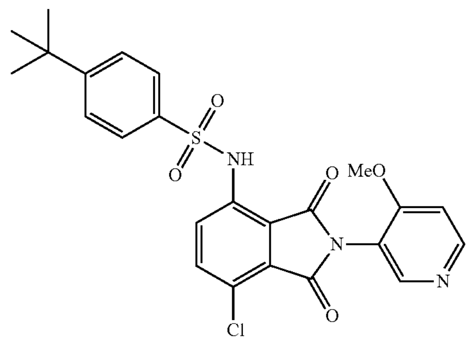 [SMILES: COc1ccncc1N1C(=O)c2c(Cl)ccc(NS(=O)(=O)c3ccc(C(C)(C)C)cc3)c2C1=O] | 500.42 | 99.04%, Rt = 5.91 min (1) | $^1$H NMR (400 MHz, DMSO-d6): δ 10.09 (bs, 1H), 8.59-8.57 (d, J = 6 Hz, 1H), 8.39 (s, 1H), 7.93-7.91 (m, 2H), 7.85-7.82 (d, J = 8.8 Hz, 1H), 7.67-7.62 (m, 3H). 7.31-7.30 (d, J = 5.6 Hz, 1H), 3.84 (s, 3H), 1.28 (s, 9H). |

Example 18

Synthesis of Compound 120 [4-(tert-butyl)-N-(7-chloro-2-(3-cyanophenyl)-1,3-dioxoisoindolin-4-yl)benzenesulfonamidesulfonamide] and Compounds 121-125

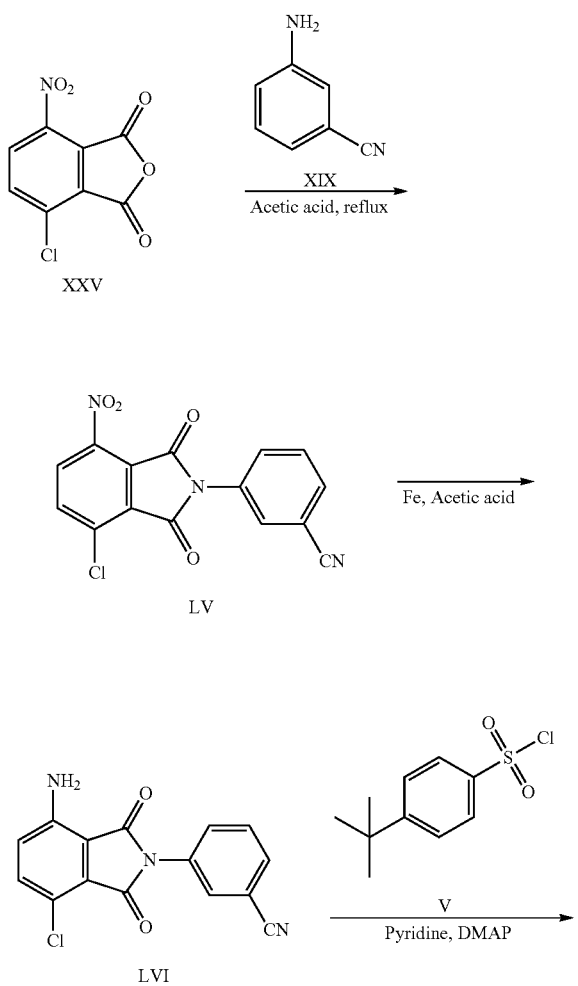

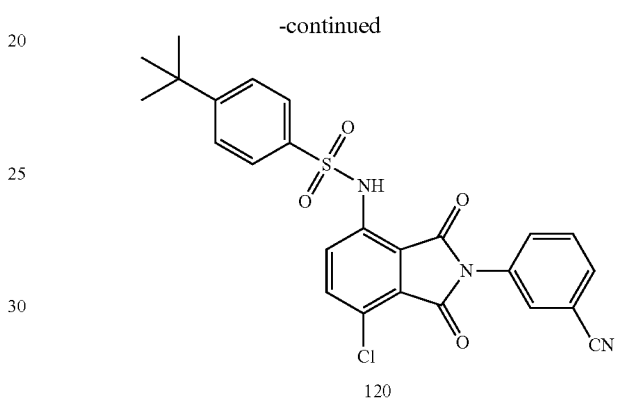

Synthesis of LV:

To a stirred solution of compound XXV (3.0 g, 13 mmol) in acetic acid (65 mL) was added 3-aminobenzonitrile (XIX, 4.6 g, 38 mmol) and the reaction mixture was heated at 100° C. for 18 h. The reaction mixture was cooled to room temperature and the acetic acid removed under reduced pressure to obtain the crude product 3-(4-chloro-7-nitro-1,3-dioxoisoindolin-2-yl)benzonitrile as a brown solid (LV; 3 g,). MS (M+1): 328.02. The crude material was carried forward to next step without purification.

Synthesis of LVI:

To a solution of compound LV (2.5 g, 7.64 mmol) in acetic acid (38 mL) was added iron powder (0.85 g, 15 mmol) and the reaction mixture was stirred for 12 h at room temperature. The acetic acid was removed under reduced pressure to obtain a crude product. The reaction mixture was diluted with water and extracted with dichloromethane. The organic layer was washed with brine solution, dried over anhydrous Na$_2$SO$_4$, filtered and evaporated under reduced pressure before being triturated with tert-butylmethylether to obtain crude product 3-(4-amino-7-chloro-1, 3-dioxoisoindolin-2-yl)benzonitrile as a greenish solid (LVI; 2 g). MS (M+1) 298.07

Synthesis of 120; 4-(tert-butyl)-N-(7-chloro-2-(3-cyanophenyl)-1,3-dioxoisoindolin-4-yl)benzenesulfonamide A mixture of compound LVI (0.5 g, 1.68 mmol) and pyridine (5 mL) was cooled to 0° C. and 4-tert-butylbenzenesulfonyl chloride (V 1.16 g, 5.04 mmol) was added together with a catalytic quantity of DMAP (0.05 g, 0.016 mmol). The reaction mixture was stirred for 24 h at 80° C. The reaction mixture was concentrated and to the resultant residue, water was added and extracted with ethyl acetate. The organic layer was washed with brine solution, dried over anhydrous Na$_2$SO$_4$, filtered and the organic solvent was evaporated under reduced pressure to obtain the crude compound. This was purified by combiflash chromatography using 18% ethyl acetate in hexane as mobile phase to afford 4-(tert-butyl)-N-(7-chloro-2-(3-cyanophenyl)-1,3-dioxoisoindolin-4-1)benzenesulfonamide as a white solid (120, 0.04 g). $^1$H NMR (400 MHz, DMSO-d6): δ 9.99 (bs, 1H), 7.93-7.91 (m, 3H), 7.88 (m, 1H) 7.85-7.82 (m, 1H) 7.78-7.76 (m, 2H), 7.70-7.68 (m, 1H), 7.65-7.63 (m, 2H), 1.27 (s, 9H). MS (M–1): 492.45 (LCMS Purity 98.22%, Rt=6.59 min (1)).

The following compounds were prepared in a similar manner using the appropriate sulfonyl chloride in the final step:

| Cpd | Structure | LCMS (M − 1) | Purity (LCMS) | $^1$H NMR |
|---|---|---|---|---|
| 121 | 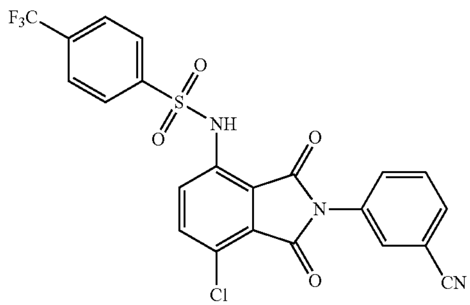 [SMILES: N#Cc1cccc(N2C(=O)c3c(Cl)ccc(NS(=O)(=O)c4ccc(C(F)(F)F)cc4)c3C2=O)c1] | 504.40 | 98.92%, Rt = 5.79 min (1) | $^1$H NMR (400 MHz, DMSO-d6): δ 10.63 (bs, 1H), 8.15-8.13 (d, J = 8.4 Hz, 2H), 8.02-8.00 (d, J = 8.4 Hz, 2H), 7.95-7.94 (d, J = 7.2 Hz, 1H), 7.85-7.83 (d, J = 9.2 Hz, 2H) 7.78-7.72 (m, 2H), 7.64-7.62 (d, J = 8.8 Hz, 1H). |
| 122 | 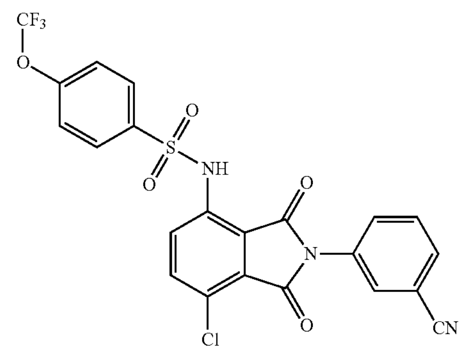 [SMILES: N#Cc1cccc(N2C(=O)c3c(Cl)ccc(NS(=O)(=O)c4ccc(OC(F)(F)F)cc4)c3C2=O)c1] | 520.36 | 99.01%, Rt = 5.78 min (1) | $^1$H NMR (400 MHz, DMSO-d6): δ 10.38 (bs, 1H), 8.10-8.08 (m, 2H), 7.95-7.94 (m, 1H), 7.85-7.83 (m, 2H), 7.79-7.75 (m, 2H), 7.66-7.60 (m, 3H). |
| 123 | 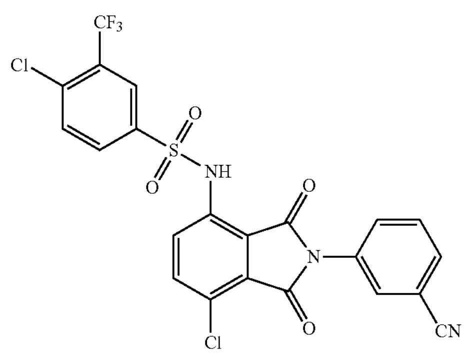 [SMILES: N#Cc1cccc(N2C(=O)c3c(Cl)ccc(NS(=O)(=O)c4ccc(Cl)c(C(F)(F)F)c4)c3C2=O)c1] | 538.31 | 98.74%, Rt = 5.77 min (1) | $^1$H NMR (400 MHz, DMSO-d6): δ 10.86 (bs, 1H), 8.43 (s, 1H) 8.19-8.17 (d, J = 8.0 Hz, 1H), 8.03-7.91 (m, 2H), 7.84-7.82 (m, 2H), 7.77-7.72 (m, 2H), 7.64-7.61 (d, J = 8.8 Hz, 1H). |
| 124 | 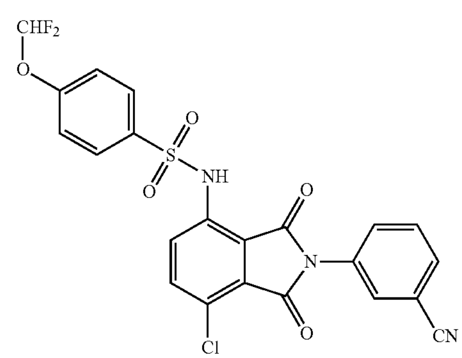 [SMILES: N#Cc1cccc(N2C(=O)c3c(Cl)ccc(NS(=O)(=O)c4ccc(OC(F)F)cc4)c3C2=O)c1] | 501.99 | 99.07%, Rt = 5.68 min (1) | $^1$H NMR (400 MHz, DMSO-d6): δ 10.16 (bs, 1H), 8.07-8.04 (d, J = 8.8 Hz, 2H), 7.96-7.94 (dd, J = 2.8, 2.8 Hz, 1H), 7.87 (s, 1H), 7.84-7.82 (d, J = 8.8 Hz, 1H), 7.77-7.76 (d, J = 9.2 Hz, 2H), 7.67-7.64 (d, J = 9.2 Hz, 1H), 7.59-7.22 (m, 3H). |

| Cpd | Structure | LCMS (M − 1) | Purity (LCMS) | $^1$H NMR |
|---|---|---|---|---|
| 125 | 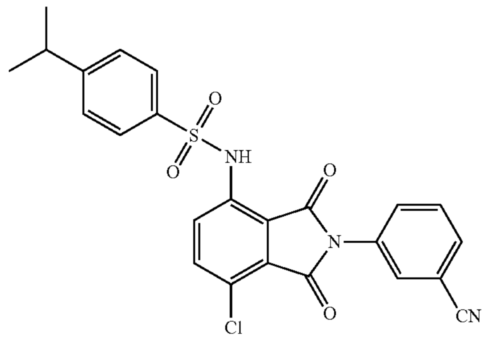 [SMILES: CC(C)c1ccc(S(=O)(=O)Nc2ccc(Cl)c3c2C(=O)N(c2cccc(C#N)c2)C3=O)cc1] | 478.30 | 97.07%, Rt = 6.30 min (1) | $^1$H NMR (400 MHz, DMSO-d6): δ 10.0 (bs, 1H), 7.96-7.91 (m, 3H), 7.88 (d, J = 1.2 Hz, 1H), 7.84-7.82 (d, J = 8.8 Hz, 1H), 7.78-7.77 (m, 2H), 7.69-7.67 (d, J = 8.8 Hz, 1H), 7.51-7.49 (d, J = 8.4 Hz, 2H), 2.99-2.95 (m, 1H), 1.19-1.18 (d, J = 6.8 Hz, 6H). |

Example 19

Synthesis of Compound 126 [4-(tert-butyl)-N-(7-chloro-2-(3-cyanobenzyl)-1,3-dioxoisoindolin-4-yl)benzenesulfonamide]; Compound 127 [4-(tert-butyl)-N-(7-cyano-2-(3-cyanobenzyl)-1,3-dioxoisoindolin-4-yl)benzenesulfonamide] and Compounds 128-135

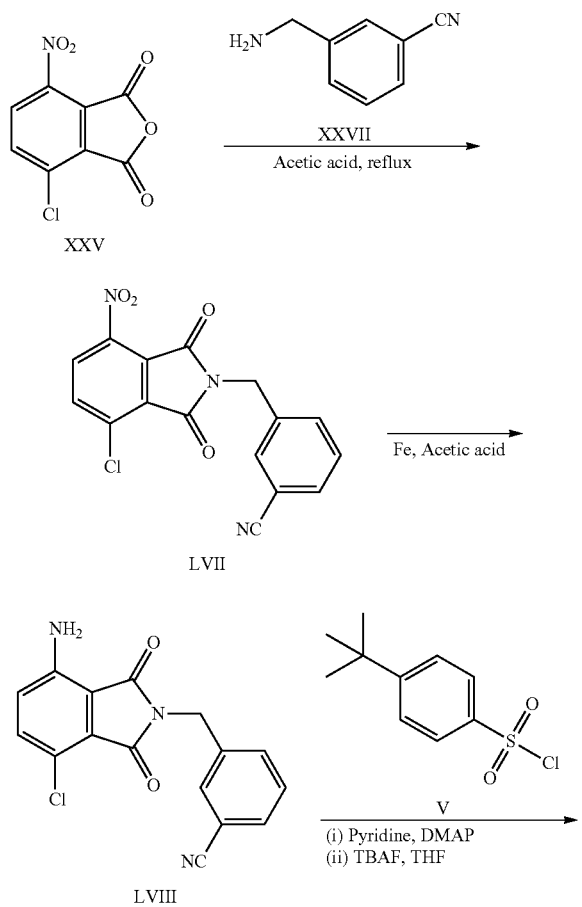

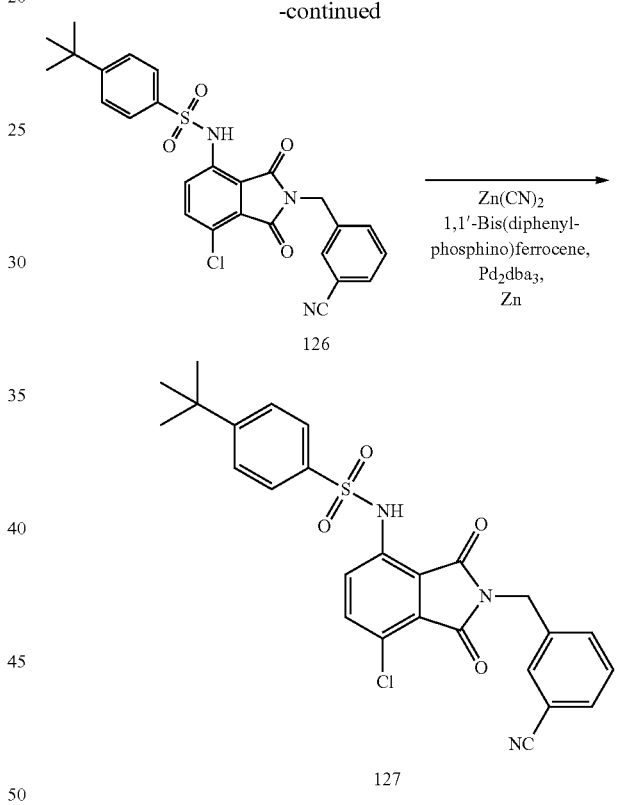

Synthesis of LVII:

To a stirred solution of compound XXV (3.5 g, 15 mmol) in acetic acid (70 mL) was added 3-(aminomethyl)benzonitrile (XXVII, 6.07 g, 46 mmol) and the reaction mixture heated at 100° C. for 18 h. The reaction mixture was cooled to room temperature and the acetic acid removed under reduced pressure to obtain the crude product 3-((4-chloro-7-nitro-1,3-dioxoisoindolin-2-yl)methyl)benzonitrile as a brown solid (LVII; 4.8 g,). $^1$H NMR (400 MHz, DMSO-d6): δ 8.28-8.26 (d, J=8.4 Hz, 1H), 8.12-8.10 (d, J=8.4 Hz, 1H), 7.85 (s, 1H), 7.76-7.72 (m, 2H), 7.58-7.54 (t, J=7.6 Hz, 1H), 4.83 (s, 2H). MS (M+1): 342.02.

Synthesis of LVIII:

To a solution of compound LVII (2.5 g, 7 mmol) in acetic acid (38 mL) was added iron powder (0.85 g, 15 mmol) and the reaction mixture was stirred at room temperature for 12 h. The acetic acid was removed under reduced pressure to obtain the crude product. The reaction mixture was diluted with water and extracted with dichloromethane. The organic layer was washed with brine solution, dried over anhydrous Na$_2$SO$_4$, filtered and concentrated under reduced pressure. This material was triturated with tert-butylmethylether to obtain the crude product 3-((4-amino-7-chloro-1,3-dioxoisoindolin-2-yl)methyl)benzonitrile as a greenish solid (LVIII; 2 g). MS (M+1) 312.

Synthesis of 126; 4-(tert-butyl)-N-(7-chloro-2-(3-cyanobenzyl)-1,3-dioxoisoindolin-4-yl)benzenesulfonamide To a stirred mixture of compound LVIII (0.4 g, 1.28 mmol) in chloroform (10 mL) was added pyridine (3 mL) at 0° C. followed by addition of 4-tert-butylbenzenesulfonyl chloride (V, 0.89 g, 3.84 mmol) and a catalytic quantity of DMAP. The reaction mixture was stirred at 80° C. for 24 h. The reaction mixture was cooled and concentrated at reduced pressure to afford a mixture of the mono and di-substituted sulfonamide product. This was dissolved in THF (15 mL) in presence of 1M TBAF in THF solution (1 mL) and stirred at 90° C. for 5 h. The reaction mixture was concentrated at reduced pressure, diluted with water and the aqueous layer was extracted with ethyl acetate. The combined organic layers were washed with brine, dried over Na$_2$SO$_4$, filtered and concentrated to afford the crude compound, which was purified by column chromatography using 20% ethyl acetate in hexane to afford the title compound 4-(tert-butyl)-N-(7-chloro-2-(3-cyanobenzyl)-1,3-dioxoisoindolin-4-yl)benzenesulfonamide (126; 0.04 g;). $^1$H NMR (400 MHz, DMSO-d6): δ 9.94 (bs, 1H), 7.94-7.92 (d, J=8.4 Hz, 2H), 7.83 (s, 1H), 7.76-7.73 (m, 2H), 7.69-7.67 (m, 1H), 7.63-7.59 (m, 3H), 7.56-7.53 (m, 1H), 4.76 (s, 2H), 1.26 (s, 9H). MS (M−1): 506.40. (LCMS purity 97.23%, Rt=6.64 min (1)).

Synthesis of 127; 4-(tert-butyl)-N-(7-cyano-2-(3-cyanobenzyl)-1,3-dioxoisoindolin-4-yl)benzenesulfonamide To a stirred solution of compound 126 (0.1 g, 0.19 mmol) in dimethylacetamide (10 mL) was added Zn(CN)$_2$ (0.046 g, 0.39 mmol) and the reaction vessel was purged with argon for 20 min. Then 1,1'-Bis(diphenylphosphino)ferrocene (0.021 g, 0.038 mmol), Pd$_2$dba$_3$ (0.026 g, 0.028 mmol) and a catalytic quantity of Zn dust were added. The reaction mixture was stirred at 120° C. for 2 h in microwave reactor. The reaction mixture was cooled and concentrated at reduced pressure, diluted with water and the aqueous layer was extracted with ethyl acetate. The combined organic layers were washed with brine, dried over Na$_2$SO$_4$, filtered and concentrated to afford the crude compound, which was purified by prep HPLC to obtain 4-(tert-butyl)-N-(7-chloro-2-(3-cyanobenzyl)-1,3-dioxoisoindolin-4-yl)benzenesulfonamide, (127; 0.02 g, 20.4% yield). $^1$H NMR (400 MHz, DMSO-d6): δ 8.10-8.07 (d, J=8.0 Hz, 2H), 7.84 (s, 1H), 7.77-7.76 (d, J=8.4 Hz, 1H), 7.72-7.62 (m, 5H), 7.57-7.53 (t, J=8.0 Hz, 1H), 4.79 (s, 2H), 1.27 (s, 9H). MS (M−1): 497.41. (LCMS purity 99.89%, Rt=5.60 min (1)).

The following compounds were prepared in a similar manner using the appropriate sulfonyl chloride in the penultimate step:

| CPD | Structure | LCMS (M − 1) | Purity (LCMS) | $^1$H NMR |
|---|---|---|---|---|
| 128 | 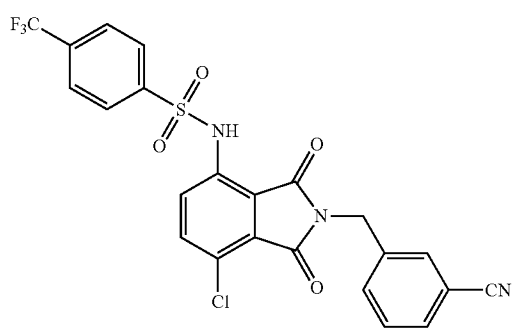 [SMILES: N#Cc1cccc(CN2C(=O)c3c(Cl)ccc(NS(=O)(=O)c4ccc(C(F)(F)F)cc4)c3C2=O)c1] | 518.29 | 99.64%, Rt = 5.82 min (1) | $^1$H NMR (400 MHz, DMSO-d6): δ 10.47 (bs, 1H), 8.14-8.12 (d, J = 8.0 Hz, 2H), 7.97-7.95 (d, J = 8.4 Hz, 2H), 7.80 (s 1H), 7.77-7.54 (m, 2H), 7.64-7.62 (d, J = 8.0 Hz, 1H), 7.56-7.52 (m, 2H), 4.73 (s 2H). |
| 129 | 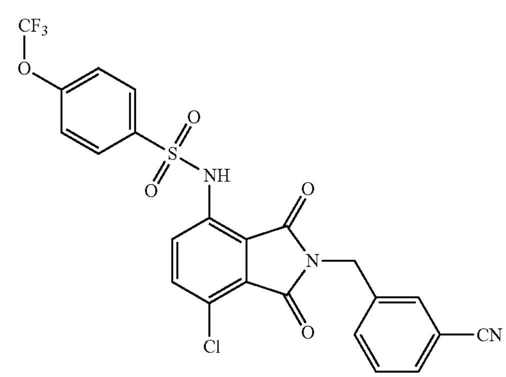 [SMILES: N#Cc1cccc(CN2C(=O)c3c(Cl)ccc(NS(=O)(=O)c4ccc(OC(F)(F)F)cc4)c3C2=O)c1] | 534.31 | 99.17%, Rt = 6.01 min (1) | $^1$H NMR (400 MHz, DMSO-d6): δ 10.29 (bs, 1H), 8.07-8.05 (m, 2H), 7.80-7.75 (m, 3H), 7.65-7.63 (d, J = 7.2 Hz, 1H), 7.58-7.52 (m, 4H), 4.74 (s 2H). |

| CPD | Structure | LCMS (M − 1) | Purity (LCMS) | ¹H NMR |
|---|---|---|---|---|
| 130 | 3-CF₃-C₆H₄-SO₂-NH-[4-chloro-2-(3-cyanobenzyl)-1,3-dioxoisoindolin-7-yl] | 518.04 | 97.74%, Rt = 5.74 min (1) | ¹H NMR (400 MHz, DMSO-d6): δ 10.52 (bs, 1H), 8.28 (s, 1H), 8.20-8.18 (d, J = 8.0 Hz, 1H), 8.03-8.01 (d, J = 8.0 Hz, 1H), 7.83-7.75 (m, 4H), 7.63-7.53 (m, 3H), 4.72 (s 2H). |
| 131 | 4-(OCHF₂)-C₆H₄-SO₂-NH-[4-chloro-2-(3-cyanobenzyl)-1,3-dioxoisoindolin-7-yl] | 515.99 | 98.72%, Rt = 5.90 min (1) | ¹H NMR (400 MHz, DMSO-d6): δ 10.09 (bs, 1H), 8.04-8.02 (d, J = 8.8 Hz, 2H), 7.82 (s, 1H), 7.76-7.73 (m, 2H), 7.66-7.64 (d, J = 7.6 Hz, 1H), 7.58-7.52 (m, 2H), 7.38-7.20 (m, 3H), 4.75 (s, 2H). |
| 132 | 4-Cl-3-CF₃-C₆H₃-SO₂-NH-[4-chloro-2-(3-cyanobenzyl)-1,3-dioxoisoindolin-7-yl] | 552.16 | 99.55%, Rt = 5.89 min (1) | ¹H NMR (400 MHz, DMSO-d6): δ 10.70 (bs, 1H), 8.38 (s, 1H), 8.17-8.15 (d, J = 8.4 Hz, 1H), 7.94-7.92 (d, J = 8.4 Hz, 1H), 7.80-7.74 (m, 3H), 7.64-7.62 (d, J = 7.6 Hz, 1H), 7.56-7.52 (m, 2H), 4.73 (s, 2H). |
| 133 | 4-F-3-CF₃-C₆H₃-SO₂-NH-[4-chloro-2-(3-cyanobenzyl)-1,3-dioxoisoindolin-7-yl] | 536.15 | 99.53%, Rt = 5.78 min (1) | ¹H NMR (400 MHz, DMSO-d6): δ 10.58 (bs, 1H), 8.36-8.35 (d, J = 5.2 Hz, 1H), 8.25 (s, 1H), 7.79-7.68 (m, 4H), 7.63-7.61 (d, J = 7.6 Hz, 1H), 7.58-7.52 (m, 2H), 4.73 (s, 2H). |

-continued
| CPD | Structure | LCMS (M − 1) | Purity (LCMS) | ¹H NMR |
|---|---|---|---|---|
| 134 | 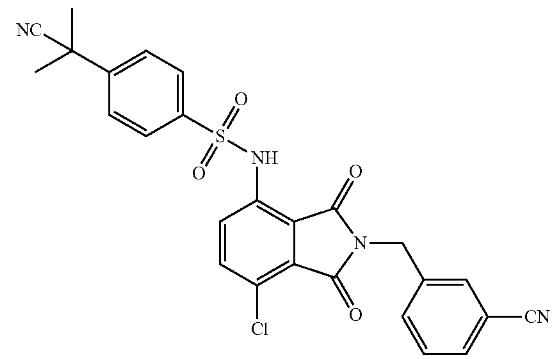 [SMILES: CC(C)(C#N)c1ccc(S(=O)(=O)Nc2ccc(Cl)c3c2C(=O)N(Cc2cccc(C#N)c2)C3=O)cc1] | 517.06 | 99.03%, Rt = 5.83 min (1) | ¹H NMR (400 MHz, DMSO-d6): δ 10.13 (bs, 1H), 8.06-8.04 (m, 2H) 7.83 (s, 1H), 7.76-7.74 (m, 4H). 7.68-7.66 (d, J = 6.8 Hz, 1H) 7.61-7.53 (m, 2H), 4.76 (s, 2H), 1.68 (s, 6H). |
| 135 | 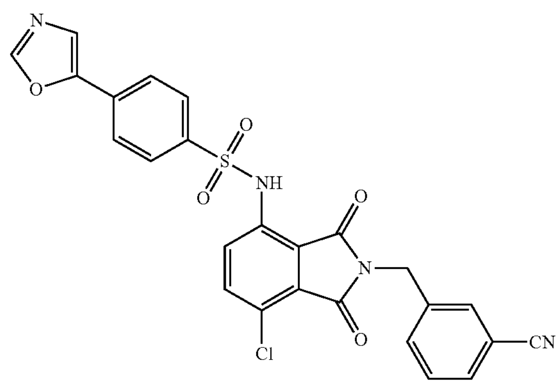 [SMILES: N#Cc1cccc(CN2C(=O)c3c(Cl)ccc(NS(=O)(=O)c4ccc(-c5cnco5)cc4)c3C2=O)c1] | 517.13 | 98.84%, Rt = 5.51 min (1) | ¹H NMR (400 MHz, DMSO-d6): δ 10.15 (bs, 1H), 8.56 (s, 1H), 8.04-8.02 (d, J = 8.4 Hz, 2H), 7.92-7.90 (m, 3H), 7.81 (s, 1H), 7.76-7.71 (t, J = 9.2 Hz, 2H), 7.63-7.57 (m, 2H), 7.52-7.48 (t, J = 7.6 Hz, 1H), 4.74 (s, 2H). |
Example 20
Synthesis of Compound 136 [4-(tert-butyl)-N-(7-chloro-1,3-dioxo-2-(3-(trifluoromethyl)phenyl)isoindolin-4-yl)benzenesulfonamide] and Compounds 137-146
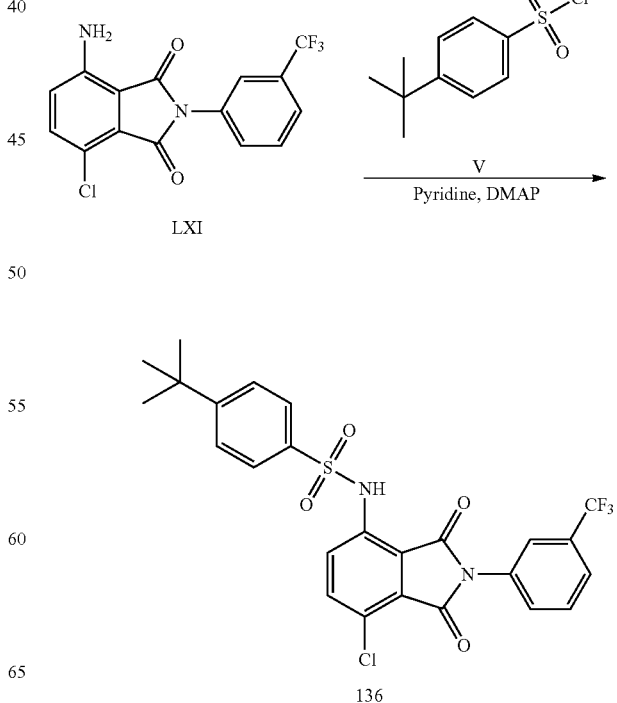

Synthesis of LX:

To a stirred solution of compound XXV (5 g, 22.12 mmol) in acetic acid (100 mL) was added 3-(trifluoromethyl)aniline (LIX, 8.9 g, 55 mmol) and the reaction mixture heated at 100° C. for 12 h. The reaction mixture was cooled to room temperature, diluted and triturated with ethanol to afford 4-chloro-7-nitro-2-(3-(trifluoromethyl)phenyl)isoindoline-1,3-dione (LX, 7.5 g, 91.6%). $^1$H NMR (400 MHz, DMSO-d6): δ 8.36 (m, 1H), 8.21 (m, 2H), 7.85 (m, 1H), 7.54 (m, 1H), 7.38 (m, 1H).

Synthesis of LXI:

To a solution of compound LX (5 g, 13.5 mmol) in acetic acid (100 mL) was added iron powder (5 g) in small portions. The reaction mixture was stirred for 12 h at room temperature. The reaction mixture was filtered through a celite bed and concentrated under reduced pressure. The crude material was neutralized using aqueous sodium bicarbonate solution. The aqueous layer was extracted with ethyl acetate which was dried (anhydrous $Na_2SO_4$), filtered and evaporated under reduced pressure to afford compound 4-amino-7-chloro-2-(3-(trifluoromethyl)phenyl)isoindoline-1,3-dione as a yellow solid (LXI; 4 g, 87% yield). $^1$H NMR (400 MHz, DMSO-d6): δ 7.86 (s, 1H), 7.77 (m, 3H), 7.50-7.48 (d, J=9.2 Hz, 1H), 7.08-7.05 (d, J=8.8 Hz, 1H), 6.73 (bs, 2H).

Synthesis of 136; 4-(tert-butyl)-N-(7-chloro-1,3-dioxo-2-(3-(trifluoromethyl)phenyl) isoindolin-4-yl) benzenesulfonamide A mixture of compound LXI (0.3 g, 0.88 mmol) and pyridine (5 mL) was cooled to 0° C. and 4-tert-butylbenzenesulfonyl chloride (V, 0.62 g, 2.64 mmol) was added followed by catalytic DMAP (0.053 g, 0.44 mmol). The reaction mixture was heated for 15 h at 100° C. The reaction mixture was concentrated and diluted with water and then extracted with ethyl acetate. The organic layer was washed with brine solution, dried over anhydrous $Na_2SO_4$, filtered and the organic solvent was evaporated under reduced pressure to obtain the crude compound. This was purified by column chromatography using 70% ethyl acetate in hexane to afford 4-(tert-butyl)-N-(7-chloro-1,3-dioxo-2-(3-(trifluoromethyl)phenyl)isoindolin-4-yl)benzenesulfonamide as a off white solid (136; 0.25 g, 53% yield). $^1$H NMR (400 MHz, DMSO-d6): δ 9.98 (bs, 1H), 7.94-7.92 (d, J=8.4 Hz, 2H), 7.84-7.74 (m, 5H), 7.70-7.68 (d, J=8.8 Hz, 1H), 7.65-7.63 (d, J=8.4 Hz, 2H), 1.27 (s, 9H). MS (M−1): 535.28. (LCMS purity 99.12%, Rt=6.84 min (1)).

The following compounds were also prepared using a similar method and the appropriate amine in the first step and/or sulfonyl chloride in the final step:

| CPD | Structure | LCMS (M − 1) | Purity (LCMS) | $^1$H NMR |
|---|---|---|---|---|
| 137 | 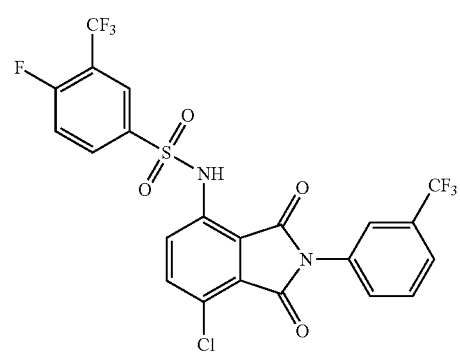 [SMILES: O=C1c2c(Cl)ccc(NS(=O)(=O)c3ccc(F)c(C(F)(F)F)c3)c2C(=O)N1c1cccc(C(F)(F)F)c1] | 565.23 | 97.22%, Rt = 6.06 min (1) | $^1$H NMR (400 MHz, DMSO-d6): δ 10.66 (bs, 1H), 8.42-8.41 (d, J = 8.4 Hz, 1H), 8.32-8.29 (m, 1H), 7.84-7.79 (m, 5H), 7.72 (m, 1H), 7.66-7.63 (d, J = 8.8 Hz, 1H). |
| 138 | 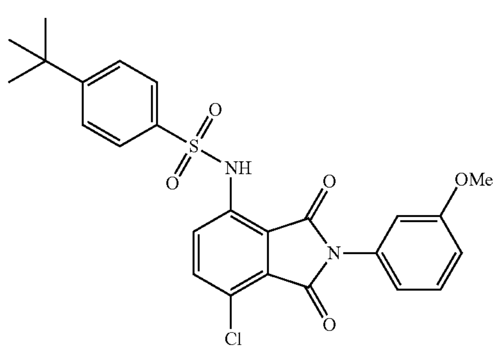 [SMILES: COc1cccc(N2C(=O)c3c(Cl)ccc(NS(=O)(=O)c4ccc(C(C)(C)C)cc4)c3C2=O)c1] | 497.24 | 99.92% Rt = 6.72 min (1) | $^1$H NMR (400 MHz, DMSO-d6): δ 9.92 (bs, 1H), 7.93-7.91 (d, J = 8.0 Hz, 2H), 7.82-7.79 (d, J = 8.8 Hz, 1H), 7.68-7.63 (m, 3H), 7.44-7.41 (t, J = 8.0 Hz, 1H), 7.04-6.94 (m, 3H), 3.77 (s, 3H), 1.27 (s, 9H). |

-continued

| CPD | Structure | LCMS (M − 1) | Purity (LCMS) | ¹H NMR |
|---|---|---|---|---|
| 139 | 4-tert-butylphenyl-SO2-NH-(4-chloro-2-(pyrimidin-5-yl)isoindoline-1,3-dione) | 471.38 (M + 1) | 97.95% Rt = 5.84 min (1) | ¹H NMR (400 MHz, DMSO-d6): δ 10.13 (bs, 1H), 9.26 (s, 1H), 8.91 (s, 2H), 7.94-7.92 (d, J = 8.8 Hz, 2H), 7.87-7.85 (d, J = 8.4 Hz, 1H), 7.70-7.68 (d, J = 8.8 Hz, 1H), 7.65-7.63 (d, J = 8.4 Hz, 2H), 1.27 (s, 9H). |
| 140 | 4-trifluoromethylphenyl-SO2-NH-(4-chloro-2-(pyrimidin-5-yl)isoindoline-1,3-dione) | 481.28 | 98.45%, Rt = 5.13 min (1) | ¹H NMR (400 MHz, DMSO-d6): δ 10.67 (bs, 1H), 9.26 (s, 1H), 8.87 (s, 2H), 8.17-8.15 (d, J = 8.4 Hz, 2H), 8.02-8.0 (d, J = 8.4 Hz, 2H), 7.87-7.85 (d, J = 8.8 Hz, 1H), 7.64-7.62 (d, J = 8.8 Hz, 1H). |
| 141 | 4-isopropylphenyl-SO2-NH-(4-chloro-2-(pyrimidin-5-yl)isoindoline-1,3-dione) | 457.37 | 99.37%, Rt = 5.63 min (1) | ¹H NMR (400 MHz, DMSO-d6): δ 10.10 (bs, 1H), 9.26 (s, 1H), 8.61 (s, 2H), 7.94-7.92 (d, J = 8.0 Hz, 2H), 7.86-7.84 (d, J = 8.8 Hz, 1H), 7.70-7.68 (d, J = 9.2 Hz, 1H), 7.51-7.49 (d, J = 8.4 Hz, 2H), 3.0-2.9 (m, 1H), 1.19-1.18 (d, J = 6.4 Hz, 6H). |
| 142 | 4-tert-butylphenyl-SO2-NH-(4-chloro-2-(1-methyl-1H-pyrazol-4-yl)isoindoline-1,3-dione) | 473.44 (M + 1) | 98.88% Rt = 6.27 min (1) | ¹H NMR (400 MHz, DMSO-d6): δ 9.93 (bs, 1H), 8.07 (s, 1H), 7.92-7.90 (d, J = 8.4 Hz, 2H), 7.78-7.75 (d, J = 8.8 Hz, 1H), 7.72 (s, 1H), 7.64-7.61 (m, 3H), 3.89 (s, 3H), 1.26 (s, 9H). |

-continued

| CPD | Structure | LCMS (M − 1) | Purity (LCMS) | ¹H NMR |
|---|---|---|---|---|
| 143 | 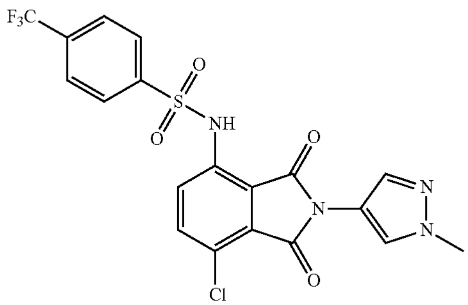 [SMILES: Cn1cc(N2C(=O)c3c(Cl)ccc(NS(=O)(=O)c4ccc(C(F)(F)F)cc4)c3C2=O)cn1] | 485.32 (M + 1) | 99.61%, Rt = 5.35 min (1) | ¹H NMR (400 MHz, DMSO-d6): δ 10.45 (bs, 1H), 8.16-8.14 (d, J = 8.0 Hz, 2H), 8.04 (s, 1H), 8.01-7.99 (d, J = 8.0 Hz, 2H), 7.79-7.76 (d, J = 8.8 Hz, 1H), 7.69 (s, 1H), 7.58-7.56 (d, J = 8.8 Hz, 1H), 3.82 (s, 3H). |
| 144 | 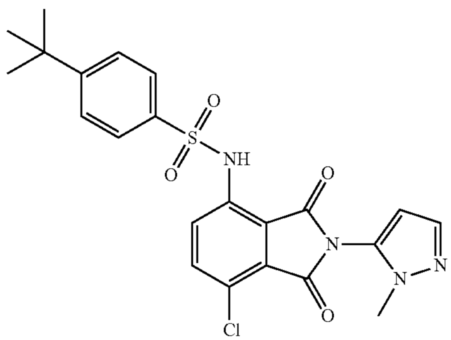 [SMILES: Cn1nccc1N1C(=O)c2c(Cl)ccc(NS(=O)(=O)c3ccc(C(C)(C)C)cc3)c2C1=O] | 473.36 (M + 1) | 99.34% Rt = 5.90 min (1) | ¹H NMR (400 MHz, DMSO-d6): δ 10.04 (bs, 1H), 7.95-7.93 (d, J = 8.4 Hz, 2H), 7.84-7.82 (d, J = 8.8 Hz, 1H), 7.68-7.63 (m, 3H), 7.56 (d, J = 1.6 Hz, 1H), 6.33 (d, J = 1.6 Hz, 1H), 3.68 (s, 3H), 1.27 (s, 9H). |
| 145 | 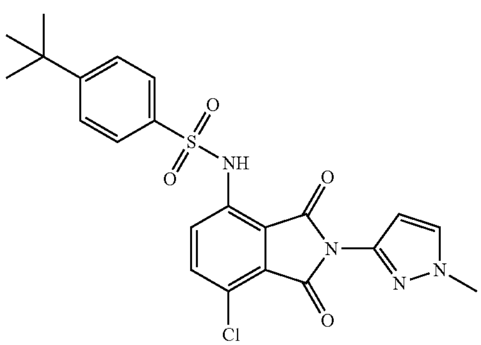 | 473.43 (M + 1) | 97.95% Rt = 6.22 min (1) | ¹H NMR (400 MHz, DMSO-d6): δ 9.93 (bs, 1H), 7.91-7.88 (d, J = 8.4 Hz, 2H), 7.81-7.79 (d, J = 8.4 Hz, 2H), 7.62-7.61 (m, 3H), 6.28 (d, J = 1.6 Hz, 1H), 3.87 (s, 3H), 1.27 (s, 9H). |
| 146 | 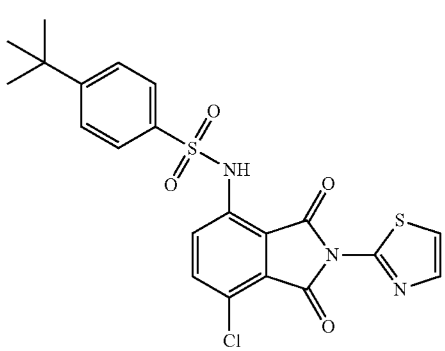 [SMILES: CC(C)(C)c1ccc(S(=O)(=O)Nc2ccc(Cl)c3c2C(=O)N(c2nccs2)C3=O)cc1] | 476.39 (M + 1) | 99.19% Rt = 5.92 min (1) | ¹H NMR (400 MHz, DMSO-d6): δ 10.10 (bs, 1H), 7.93 (d, J = 8.4 Hz, 2H), 7.83-7.80 (m, 3H), 7.68 (d, J = 8.8 Hz, 1H), 7.64-7.62 (d, J = 8.4 Hz, 2H), 1.27 (s, 9H). |

Example 21

Synthesis of Compound 147 [4-(tert-butyl)-N-(7-chloro-2-(3-methoxybenzyl)-1,3-dioxoisoindolin-4-yl)benzenesulfonamide]

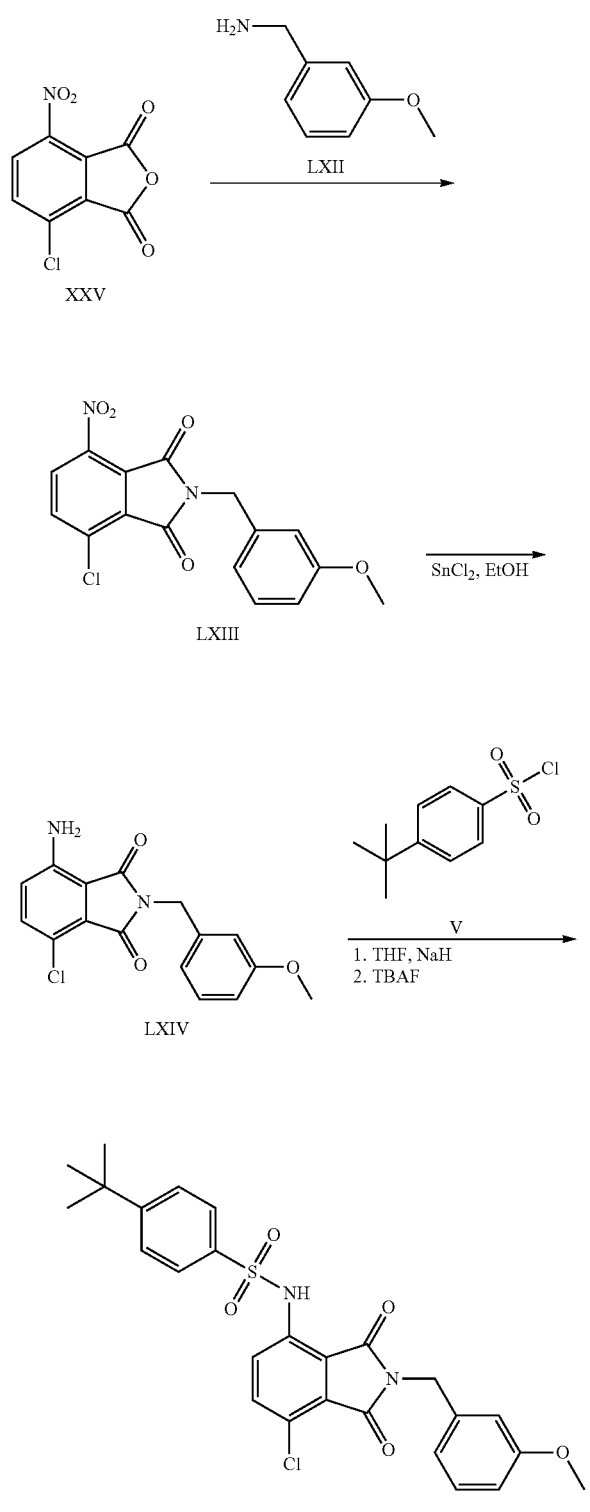

Synthesis of LXIII:

To a stirred solution of compound XXV (1 g, 4.39 mmol) in acetic acid (10 mL) was added (3-methoxyphenyl)methanamine (LXII, 1.2 g, 8.78 mmol). The reaction mixture was heated at 100° C. for 12 h. The reaction mixture was cooled to room temperature and the acetic acid removed under reduced pressure to obtain the crude product. This was washed with ethanol to afford 4-chloro-2-(3-methoxybenzyl)-7-nitroisoindoline-1,3-dione (LXIII, 1 g, 65.7%). $^1$H NMR (400 MHz, DMSO-d6): δ 8.27-8.25 (d, J=8.8 Hz, 1H), 8.10-8.08 (d, J=8.4 Hz, 1H), 7.21-7.23 (t, J=8.0 Hz, 1H), 6.91 (m, 2H), 6.86-6.84 (d, J=8.0 Hz, 1H), 4.7 (s, 2H), 3.7 (s, 3H).

Synthesis of LXIV:

To a solution of compound LXIII (0.6 g, 1.72 mmol) in ethanol (80 mL) was added stannous chloride (0.97 g, 4.3 mmol). The reaction mixture was heated at 90° C. for 12 h. The reaction mixture was filtered through a celite bed and concentrated under reduced pressure. The crude material was diluted with water which was extracted with ethyl acetate. The organic solvent was evaporated under reduced pressure to afford 4-amino-7-chloro-2-(3-methoxybenzyl)isoindoline-1,3-dione as a yellow solid (LXIV; 0.4 g, 73% yield). $^1$H NMR (400 MHz, DMSO-d6): δ 7.42-7.40 (d, J=8.8 Hz, 1H), 7.26-7.24 (t, J=8.4 Hz, 1H), 7.01-6.99 (d, J=9.2 Hz, 1H), 6.84-6.81 (m, 3H), 6.64 (bs, 2H), 4.65 (s, 2H), 3.72 (s, 3H). MS (M-1): 315.25. (LCMS purity 95.34%).

Synthesis of 147; 4-(tert-butyl)-N-(7-chloro-2-(3-methoxybenzyl)-1,3-dioxoisoindolin-4-yl)benzenesulfonamide A mixture of compound LXIV (0.2 g, 0.63 mmol) in THF (4 mL) was cooled to 0° C. and then sodium hydride (0.03 g, 1.26 mmol) was added followed by addition of 4-tert-butylbenzenesulfonyl chloride (16, 0.22 g, 0.91 mmol). The reaction mixture was stirred at room temperature for 4 h. The reaction mixture was diluted with water and the aqueous layer was extracted with ethyl acetate. The organic layer was washed with brine solution, dried over anhydrous Na$_2$SO$_4$, filtered and the organic solvent was evaporated under reduced pressure to obtain the crude compound. To this material was added 1M TBAF in THF solution (1 mL) and the stirring continued for 1 h at room temperature. The reaction mixture was concentrated and diluted with ethyl acetate. The organic layer was washed with water, dried over anhydrous Na$_2$SO$_4$, filtered and the organic solvent was evaporated under reduced pressure to obtain the crude compound which was purified by column chromatography using 15% ethyl acetate in hexane. The title compound 4-(tert-butyl)-N-(7-chloro-2-(3-methoxybenzyl)-1,3-dioxoisoindolin-4-yl)benzenesulfonamide was obtained as a yellow solid (147; 0.1 g, 30.8% yield). $^1$H NMR (400 MHz, DMSO-d6): δ 9.95 (bs, 1H), 7.91-7.89 (d, J=8.0 Hz, 2H), 7.75-7.73 (d, J=9.2 Hz, 1H), 7.62-7.58 (m, 3H), 7.23-7.21 (t, J=7.6 Hz, 1H), 6.86-6.84 (m, 3H), 4.66 (s, 2H), 3.72 (s, 3H), 1.26 (s, 9H). MS (M+1): 511.38. (LCMS purity 98.66%, Rt=6.97 min (1)).

Example 22

Synthesis of Compound 148 [4-(tert-butyl)-N-(7-chloro-1,3-dioxo-2-(1H-pyrazol-4-yl)isoindolin-4-yl)benzenesulfonamide] and Compounds 149-152

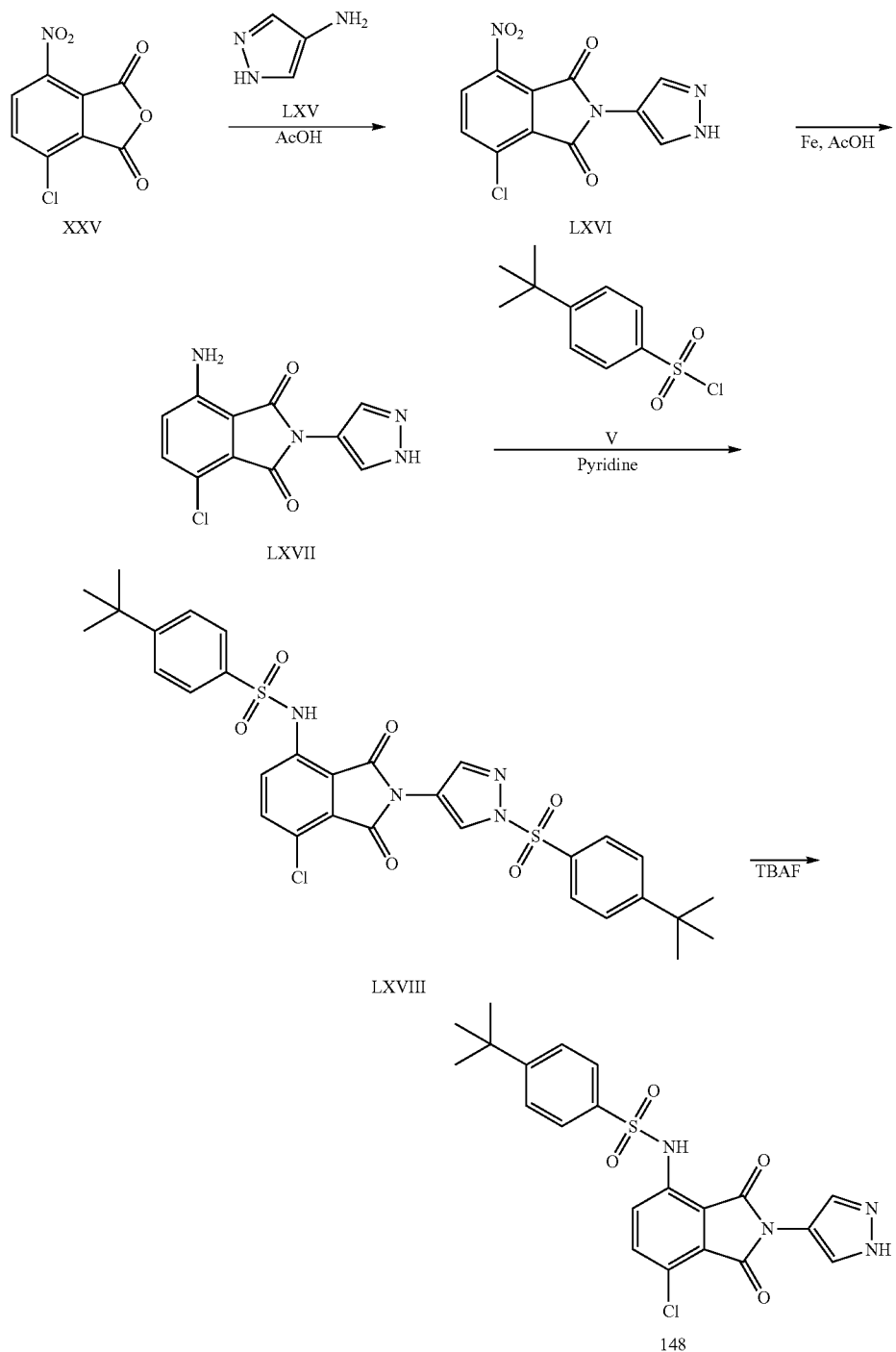

Synthesis of LXVI:

To a stirred solution of compound XXV (2.5 g, 10 mmol) in acetic acid (50 mL) was added 1H-pyrazol-4-amine (LXV; 2.2 g, 20 mmol) and the reaction mixture heated at 100° C. for 18 h. The reaction mixture was cooled to room temperature and the acetic acid removed under reduced pressure to obtain crude product. The crude product was washed with ethanol to afford 4-chloro-7-nitro-2-(1H-pyrazol-4-yl)isoindoline-1,3-dione as a yellow solid (LXVI; 2.5 g, 78% yield). $^1$H NMR (400 MHz, DMSO-d6): v 13.18 (s, 1H), 8.29-8.27 (d, J=8 Hz, 1H), 8.13-8.11 (d, J=8 Hz, 2H), 7.84 (bs, 1H). MS (M+1): 292.93.

Synthesis of LXVII:

To a solution of compound LXVI (2.5 g, crude) in acetic acid (40 mL) was added iron powder (3 g) in small portions. The reaction mixture was stirred for 12 h at room temperature and filtered through a celite bed before being concentrated under reduced pressure. The crude mass was neutralized by aqueous sodium bicarbonate solution. This was extracted with ethyl acetate, which was dried (anhydrous $Na_2SO_4$), filtered and evaporated under reduced pressure to obtain the crude compound. This was purified further by trituration using ethanol to afford compound 4-amino-7-chloro-2-(1H-pyrazol-4-yl)isoindoline-1,3-dione as a yellow solid (LXVII; 2 g, 86% yield). $^1$H NMR (400 MHz, DMSO-d6): δ 13.13 (s, 1H), 7.94 (s, 2H), 7.45-7.42 (d, J=12 Hz, 1H), 7.03-7.01 (d, J=8.8 Hz, 1H), 6.71 (s, 2H). MS (M+1): 263.1

Synthesis LXVIII:

To stirred solution of compound LXVII (0.8 g, 3 mmol) in pyridine (50 mL) was added 4-(tert-butyl)benzene-1-sulfonyl chloride (V, 2.83 g, 12.2 mmol) and heated the reaction mixture for 12 h at 100° C. The reaction mixture was concentrated and then diluted with water. The aqueous layer was extracted with chloroform, which was washed with brine solution and dried over anhydrous $Na_2SO_4$, filtered and evaporated under reduced pressure to obtain crude compound which was partially purified by column chromatography using 50% ethyl acetate in hexane to obtain a mixture of products (4-(tert-butyl)-N-(2-(1-((4-(tert-butyl)phenyl)sulfonyl)-1H-pyrazol-4-yl)-7-chloro-1,3-dioxoisoindolin-4-yl)benzenesulfonamide (LXVII) and material where the sulfonamide bond para to the chloro group had not formed. This mixture was used without further purification.

Synthesis of 148; 4-(tert-butyl)-N-(7-chloro-1,3-dioxo-2-(1H-pyrazol-4-yl)isoindolin-4-yl)benzenesulfonamide To the crude compound LXVII (350 mg), was added 1M TBAF in THF solution (30 mL) and the reaction mixture was stirred for 1 h at room temperature. This was diluted with water and extracted with chloroform. The resulting organic layer was washed with brine solution and dried over anhydrous $Na_2SO_4$, filtered and then evaporated under reduced pressure to afford crude compound which was purified by column chromatography using 60% ethyl acetate in hexane to afford 4-(tert-butyl)-N-(7-chloro-1,3-dioxo-2-(1H-pyrazol-4-yl)isoindolin-4-yl)benzenesulfonamide as a off white solid. (148, 0.015 g). $^1$H NMR (400 MHz, DMSO-d6): δ 13.14 (bs, 1H), 9.96 (s, 1H), 8.07 (s, 1H), 7.94-7.92 (d, J=6.8 Hz, 2H), 7.78-7.76 (m, 2H), 7.64-762 (m, 2H), 1.26 (s, 9H). MS (M−1): 457.04. (LCMS purity 97.12%, Rt=6.12 min (1)).

The following compounds were also prepared using a similar method and the appropriate sulfonyl chloride in the final step:

| CPD | Structure | LCMS (M + 1) | Purity (LCMS) | $^1$H NMR |
|---|---|---|---|---|
| 149 | F3C-phenyl-SO2-NH-(7-chloro isoindoline-1,3-dione-2-yl pyrazole) | 469.33 (M − 1) | 98.58%, Rt = 5.06 min (1) | $^1$H NMR (400 MHz, DMSO-d6): δ 13.14 (bs, 1H), 10.50 (bs, 1H), 8.15-8.13 (d, J = 8.0 Hz, 2H), 8.06-7.71 (m, 5H), 7.58-7.56 (d, J = 8.8 Hz, 1H). |
| 150 | CF3O-phenyl-SO2-NH-(7-chloro isoindoline-1,3-dione-2-yl pyrazole) | 486.97 | 99.17%, Rt = 6.32 min (2) | $^1$H NMR (400 MHz, DMSO-d6): δ 13.14 (bs, 1H), 10.31 (bs, 1H), 8.10-8.07 (d, J = 8.8 Hz, 2H), 7.92-7.77 (m, 3H), 7.61-7.58 (m, 3H). |

| CPD | Structure | LCMS (M + 1) | Purity (LCMS) | $^1$H NMR |
|---|---|---|---|---|
| 151 | 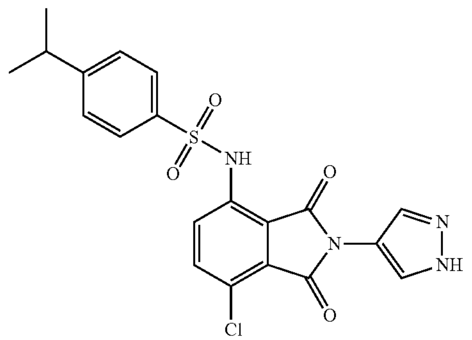 [SMILES: CC(C)c1ccc(S(=O)(=O)Nc2ccc(Cl)c3c2C(=O)N(c2cn[nH]c2)C3=O)cc1] | 443.33 (M − 1) | 98.98%, Rt = 5.78 min (1) | $^1$H NMR (400 MHz, DMSO-d6): δ 13.15 (bs, 1H), 9.94 (bs, 1H), 8.07 (bs, 1H), 7.92-7.89 (d, J = 8.4 Hz, 2H), 7.80 (bs, 1H), 7.77-7.75 (d, J = 8.8 Hz, 1H), 7.63-7.61 (d, J = 8.8 Hz, 1H), 7.49-7.47 (d, J = 8.4 Hz, 2H), 2.99-2.92 (m, 1H), 1.18-1.16 (d, J = 7.2 Hz, 6H). |
| 152 | 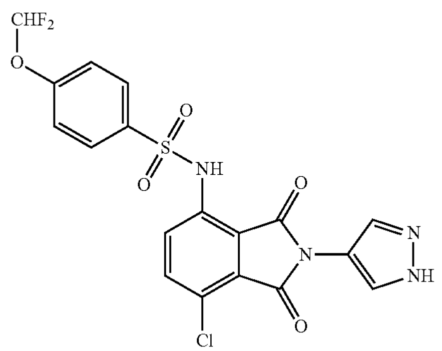 [SMILES: O=C1c2c(Cl)ccc(NS(=O)(=O)c3ccc(OC(F)F)cc3)c2C(=O)N1c1cn[nH]c1] | 467.25 (M − 1) | 98.83%, Rt = 5.09 min (1) | $^1$H NMR (400 MHz, DMSO-d6): δ 13.14 (bs, 1H), 10.12 (bs, 1H), 8.05-8.03 (d, J = 8.4 Hz, 2H), 7.84 (m, 1H), 7.77-7.75 (m, 2H), 7.60-7.58 (d, J = 9.2 Hz, 1H), 7.40-7.36 (m, 2H), 7.21 (m, 1H). |
Example 23
Synthesis of Compound 153 [4-(tert-butyl)-N-(7-chloro-2-(1-methyl-1H-imidazol-4-yl)-1,3-dioxoisoindolin-4-yl)benzenesulfonamide] and Compound 154
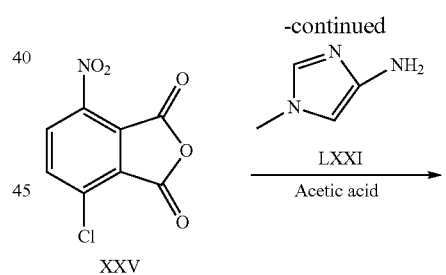
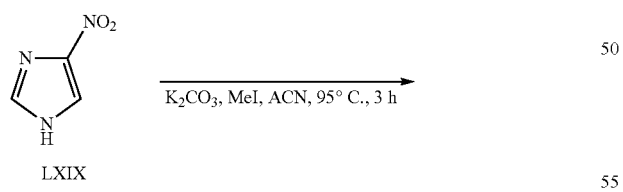
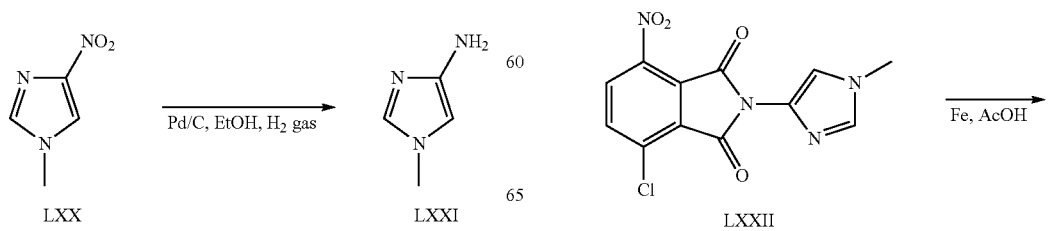

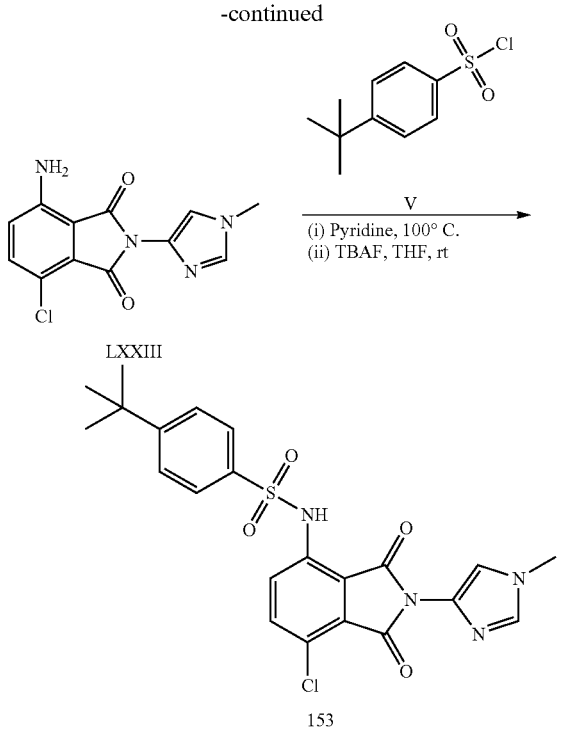

Synthesis of LXX:

To stirred solution of 4-nitro-1H-imidazole (LXIX, 5 g: 44 mmol) in acetonitrile (20 mL) was added $K_2CO_3$ (18.2 g, 137 mmol) at 0° C., followed by addition of methyl iodide (8.9 mL, 57 mmol). The reaction mixture was heated at 95° C. for 3 h. The reaction mixture was concentrated, filtered through a celite bed and diluted with water. The aqueous layer was extracted with chloroform and the separated organic layer was washed with brine solution and dried over anhydrous $Na_2SO_4$ before being filtered and evaporated under reduced pressure to afford 1-methyl-4-nitro-1H-imidazole (LXX, 4 g, 71%). $^1$H NMR (400 MHz, DMSO-d6) δ 8.35 (s, 1H), 7.8 (s, 1H), 3.74 (s, 3H). MS (M+1): 128.

Synthesis of LXXI:

To a stirred solution of compound LXX (4 g, 31 mmol) in ethanol (20 mL) was added 10% Pd—C (catalytic) under nitrogen atmosphere. The reaction mixture was evacuated using high vacuum and stirred in presence of hydrogen gas at balloon pressure at room temperature for 6 h. The reaction mixture was filtered through a celite bed. The organic solvent was evaporated under reduced pressure to afford 1-methyl-1H-imidazol-4-amine (LXXI, 2.5 g) MS (M+1) 98. The crude material was carried forward to next step without purification.

Synthesis of LXXII:

To a stirred solution of compound XXV (3 g, 13.2 mmol) in acetic acid (60 mL) was added 1-methyl-1H-imidazol-4-amine (LXXI, 3.2 g, 33 mmol). The reaction mixture was heated at 100° C. for 12 h. The reaction mixture was cooled to room temperature and the acetic acid removed under reduced pressure to obtain crude product. The crude product was washed with ethanol to afford 4-chloro-2-(1-methyl-1H-imidazol-4-yl)-7-nitroisoindoline-1,3-dione (LXXII, 3 g). MS (M+1): 306.84

Synthesis of LXXIII:

To a solution of compound LXXII (3 g, 98 mmol) in acetic acid (50 mL) was added iron powder (3 g) in small portions. The reaction mixture was stirred for 12 h at room temperature and then filtered through a celite bed and concentrated under reduced pressure. The crude material was neutralized by addition of aqueous sodium bicarbonate solution. The resulting aqueous layer was extracted with ethyl acetate. The layers were separated and the organic layer was dried (anhydrous $Na_2SO_4$), filtered and evaporated under reduced pressure to obtain the crude compound. This was purified using a neutral alumina column and 5% methanol in dichloromethane to afford 4-amino-7-chloro-2-(1-methyl-1H-imidazol-4-yl)isoindoline-1,3-dione as a yellow solid (LXXIII; 0.6 g, 22% yield). MS (M+1): 277.04.

Synthesis of 153; 4-(tert-butyl)-N-(7-chloro-2-(1-methyl-1H-imidazol-4-yl)-1,3-dioxoisoindolin-4-yl)benzenesulfonamide A mixture of compound LXXIII (0.6 g, 2.16 mmol) and pyridine (20 mL) was cooled to 0° C. and 4-tert-butylbenzenesulfonyl chloride (V, 1.2 g, 5.5 mmol) was added. The reaction mixture was stirred for 12 h at 100° C. and then concentrated and diluted with water whereupon it was extracted with ethyl acetate. The organic layer was washed with brine solution, dried over anhydrous $Na_2SO_4$, filtered and the organic solvent evaporated under reduced pressure to obtain the crude compound. To this material was added 1M TBAF in THF solution (25 mL) and the stirring continued for 1 h at room temperature. The reaction mixture was concentrated and diluted with ethyl acetate and the resulting solution was washed with water, dried over anhydrous $Na_2SO_4$, filtered and the organic solvent evaporated under reduced pressure to obtain the crude compound which was purified by column chromatography using 60% ethyl acetate in hexane to afford 4-(tert-butyl)-N-(7-chloro-2-(1-methyl-1H-imidazol-4-yl)-1,3-dioxoisoindolin-4-yl)benzenesulfonamide as an off white solid (153; 0.38 g, 37% yield). $^1$H NMR (400 MHz, DMSO-d6): δ 9.93 (bs, 1H), 7.91-7.89 (d, J=8.0 Hz, 2H), 7.80-7.78 (d, J=8.4 Hz, 1H), 7.65-7.61 (m, 4H), 7.24 (s, 1H), 3.71 (s, 3H), 1.27 (s, 9H). MS (M+1): 473.36. (LCMS purity 99.27%, Rt=5.78 min(2)).

The following compound was also prepared using a similar method and the appropriate sulfonyl chloride in the final step:

| CPD | Structure | LCMS (M + 1) | Purity (LCMS) | 1HNMR |
|---|---|---|---|---|
| 154 | F₃C-[structure] | 485.31 | 97.54%, Rt = 4.97 min (1) | $^1$H NMR (400 MHz, DMSO-d6): δ 10.5 (bs, 1H), 8.15-8.13 (d, J = 8.0 Hz, 2H), 8.0-7.98 (d, J = 8.4 Hz, 2H), 7.81-7.79 (d, J = 8.8 Hz, 1H), 7.66 (s, 1H), 7.60-7.58 (d, J = 8.8 Hz, 1H), 7.21 (s, 1H), 3.71 (s, 3H). |

Example 24

Synthesis of Compound 155 [methyl 3-(4-((4-(tert-butyl)phenyl)sulfonamido)-7-chloro-1,3-dioxo isoindolin-2-yl)thiophene-2-carboxylate]

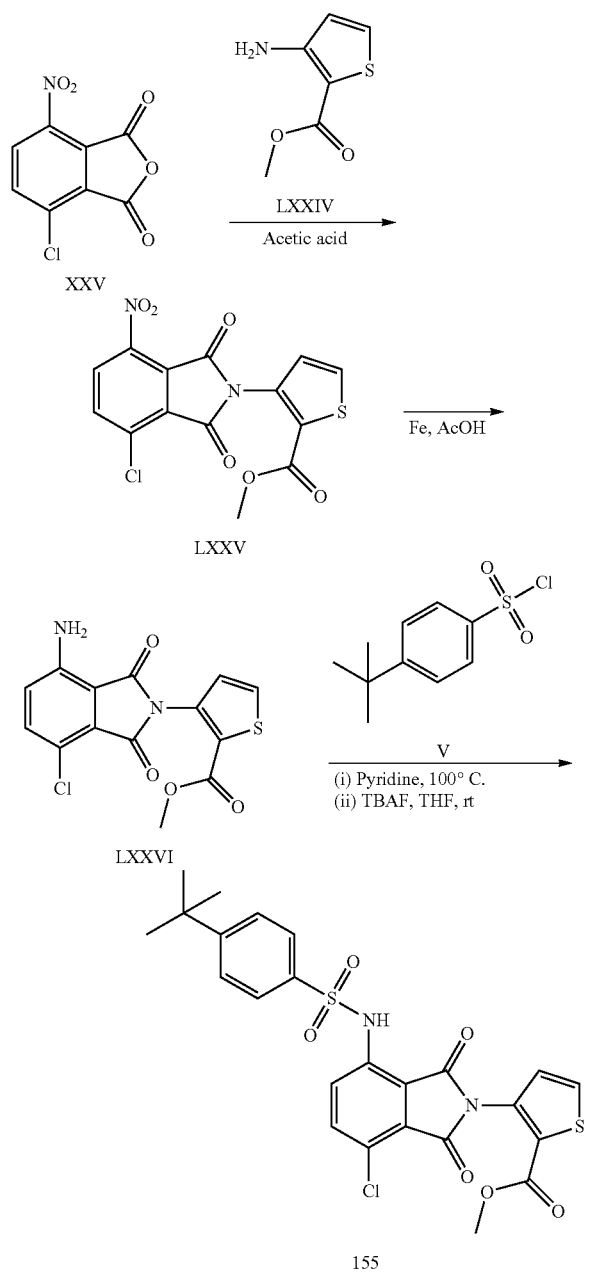

Synthesis of LXXV:

To a stirred solution of compound XXV (0.5 g, 2.2 mmol) in acetic acid (4.5 mL) was added methyl 3-aminothiophene-2-carboxylate (LXXIV, 0.69 g, 4.4 mmol). The reaction mixture was heated at 120° C. for 12 h and after cooling to room temperature, the acetic acid was removed under reduced pressure to obtain the crude product. This was triturated with ethanol to afford methyl 3-(4-chloro-7-nitro-1,3-dioxoisoindolin-2-yl)thiophene-2-carboxylate (LXXV, 0.5 g, crude), which was carried forward to next step without purification.

Synthesis of LXXVI:

To a solution of compound LXXV (0.5 g, crude) in acetic acid (10 mL) was added iron powder (0.5 g) in portions. The reaction mixture was stirred for 12 h at room temperature and then filtered through a celite bed and concentrated under reduced pressure. The crude mass was neutralized using aqueous sodium bicarbonate solution and the aqueous layer was extracted with ethyl acetate. The organic solvent was separated, dried (anhydrous $Na_2SO_4$) filtered and evaporated under reduced pressure to obtain the crude compound methyl 3-(4-amino-7-chloro-1,3-dioxoisoindolin-2-yl)thiophene-2-carboxylate as a greenish solid (LXXVI; 0.35 g, 76% yield). $^1$H NMR (400 MHz, DMSO-d6): ☐ 8.04 (d, J=3.6 Hz, 1H), 7.50-7.48 (d, J=4 Hz, 1H), 7.29-7.28 (d, J=3.6 Hz, 1H), 7.09-7.07 (d, J=8.4 Hz, 1H), 6.74 (bs, 2H), 3.72 (s, 3H).

Synthesis of 155; methyl 3-(4-((4-(tert-butyl)phenyl)sulfonamido)-7-chloro-1,3-dioxoisoindolin-2-yl)thiophene-2-carboxylate A mixture of compound LXXVI (0.35 g, 1.04 mmol) and pyridine (2 mL) was cooled to 0° C. and 4-tert-butylbenzenesulfonyl chloride (V, 0.48 g, 2.08 mmol) was added. The reaction mixture was stirred for 12 h at 100° C. and on cooling was concentrated and diluted with water. The aqueous layer was extracted with ethyl acetate which was washed with brine solution, dried over anhydrous $Na_2SO_4$, filtered and evaporated under reduced pressure to obtain the crude compound. To the crude material was added TBAF in THF solution (2 mL) and the stirring continued for 1 h at room temperature. The reaction mixture was concentrated and diluted with ethyl acetate, which was washed with water, dried over anhydrous $Na_2SO_4$, filtered and evaporated under reduced pressure to leave the crude compound which was purified by column chromatography using 40% ethyl acetate in hexane to afford the title compound methyl 3-(4-((4-(tert-butyl)phenyl)sulfonamido)-7-chloro-1,3-dioxoisoindolin-2-yl)thiophene-2-carboxylate as a off white solid (155; 0.13 g, 24.3% yield). $^1$H NMR (400 MHz, DMSO-d6): δ 10.08 (bs, 1H), 8.08-8.07 (d, J=5.2 Hz, 1H), 7.92-7.90 (d, J=8.8 Hz, 2H), 7.86-7.84 (d, J=8.0 Hz, 1H), 7.70-7.68 (d, J=9.2 Hz, 1H), 7.64-7.62 (d, J=8.4 Hz, 2H), 7.25-7.24 (d, J=4.8 Hz, 1H), 3.70 (s, 3H), 1.27 (s, 9H). MS (M−1): 531.25. (LCMS purity 99.67%, Rt=6.61 min (1)).

Example 25

Synthesis of Compound 156 [4-(tert-butyl)-N-(7-chloro-1,3-dioxo-2-(tetrahydro-2H-pyran-4-yl)isoindolin-4-yl)benzenesulfonamide]

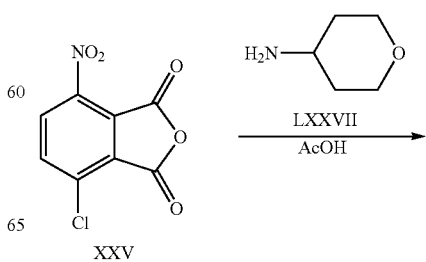

283

-continued

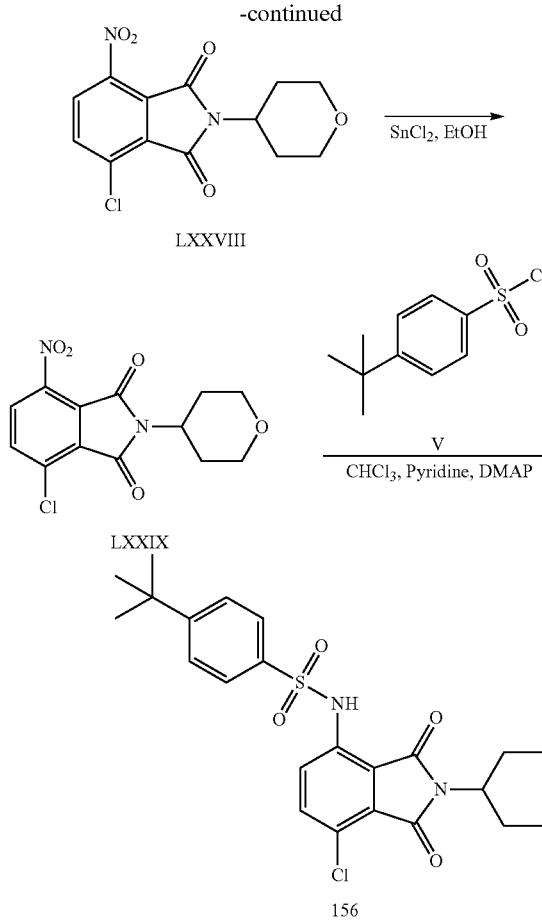

Synthesis of LXXVIII:

To a stirred solution of compound XXV (1 g, 4.40 mmol) in acetic acid (30 mL) was added tetrahydro-2H-pyran-4-amine (LXXVII, 2 g, 19.7 mmol). The reaction mixture was heated at 120° C. for 12 h whereupon it was cooled to room temperature and the acetic acid removed under reduced pressure to obtain crude product. This was triturated with ethanol to afford 4-chloro-7-nitro-2-(tetrahydro-2H-pyran-4-yl)isoindoline-1,3-dione (LXXVIII, 0.7 g). This unpurified material was carried forward to next step without purification.

Synthesis of LXXIX:

To a solution of compound LXXVIII (0.7 g, 2.25 mmol) in ethanol (15 mL) was added stannous chloride (1.27 g, 5.6 mmol). The reaction mixture was heated at 90° C. for 12 h. The reaction mixture was filtered through a celite bed and concentrated under reduced pressure. The crude mass was diluted with water and the aqueous layer was extracted with ethyl acetate. The organic solvent was dried (anhydrous $Na_2SO_4$), filtered and evaporated under reduced pressure to afford 4-amino-7-chloro-2-(tetrahydro-2H-pyran-4-yl)isoindoline-1,3-dione an off-white solid (LXXIX; 0.2 g, 31.7% yield). $^1$H NMR (400 MHz, DMSO-d6): δ 7.40-7.38 (d, J=8.8 Hz, 1H), 6.99-6.96 (d, J=8.8 Hz, 1H), 6.60 (bs, 2H), 4.15 (m, 1H), 3.95-3.92 (m, 2H), 3.40-3.37 (m, 2H), 2.34-2.25 (m, 2H), 1.61-1.57 (m, 2H). MS (M-1): 279.20.

284

Synthesis of 156; 4-(tert-butyl)-N-(7-chloro-1,3-dioxo-2-(tetrahydro-2H-pyran-4-yl)isoindolin-4-yl)benzenesulfonamide Compound LXXIX (0.16 g, 0.57 mmol) was dissolved in a mixture of chloroform (10 mL) and pyridine (15 mL) was cooled to 0° C. and a catalytic quantity of DMAP (0.07 g, 0.057 mmol) was added. To the reaction mixture was further added 4-tert-butylbenzenesulfonyl chloride (V, 0.33 g, 1.43 mmol). The reaction mixture was heated at 100° C. for 12 h before being cooled and then diluted with water. The reaction mixture was extracted with ethyl acetate and the organic layer was washed with brine solution, dried over anhydrous $Na_2SO_4$, filtered and the organic solvent evaporated under reduced pressure to obtain the crude compound. This material was purified by column chromatography using 20% ethyl acetate in hexane to afford 4-(tert-butyl)-N-(7-chloro-1,3-dioxo-2-(tetrahydro-2H-pyran-4-yl)isoindolin-4-yl)benzene-sulfonamide as an off-white solid (156; 0.15 g, 55% yield). $^1$H NMR (400 MHz, DMSO-d6): δ 9.83 (bs, 1H), 7.88-7.86 (d, J=8.4 Hz, 2H), 7.74-7.72 (d, J=8.8 Hz, 1H), 7.63-7.59 (m, 3H), 4.13 (m, 1H), 3.94-3.91 (m, 2H), 3.40 (m, 2H), 2.26-2.18 (m, 2H), 1.59-1.57 (m, 2H), 1.30 (s, 9H). MS (M+1): 477.47. (LCMS purity 96.78%, Rt=6.56 min (1)).

Example 26

Synthesis of Compound 157 [4-(tert-butyl)-N-(7-methyl-1,3-dioxo-2-(pyridin-3-yl)isoindolin-4-yl)benzenesulfonamide]; Compound 158 [3-(4-((4-(tert-butyl)phenyl)sulfonamido)-7-methyl-1,3-dioxoisoindolin-2-yl)pyridine 1-oxide] and Compounds 159-169

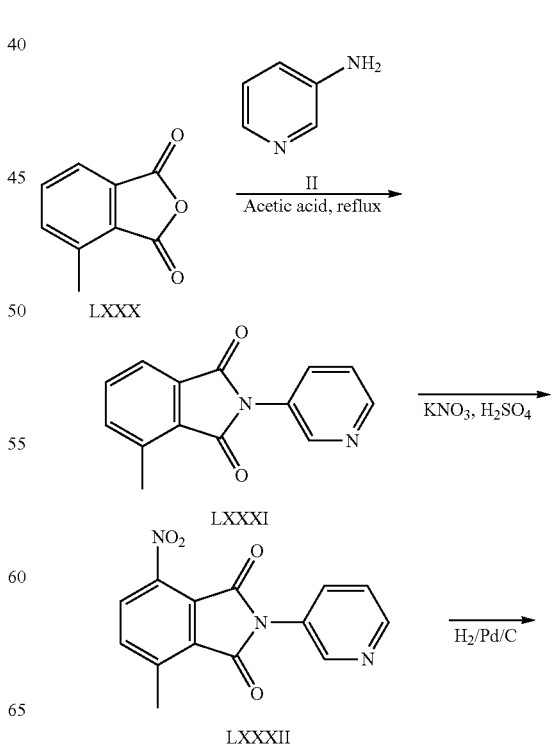

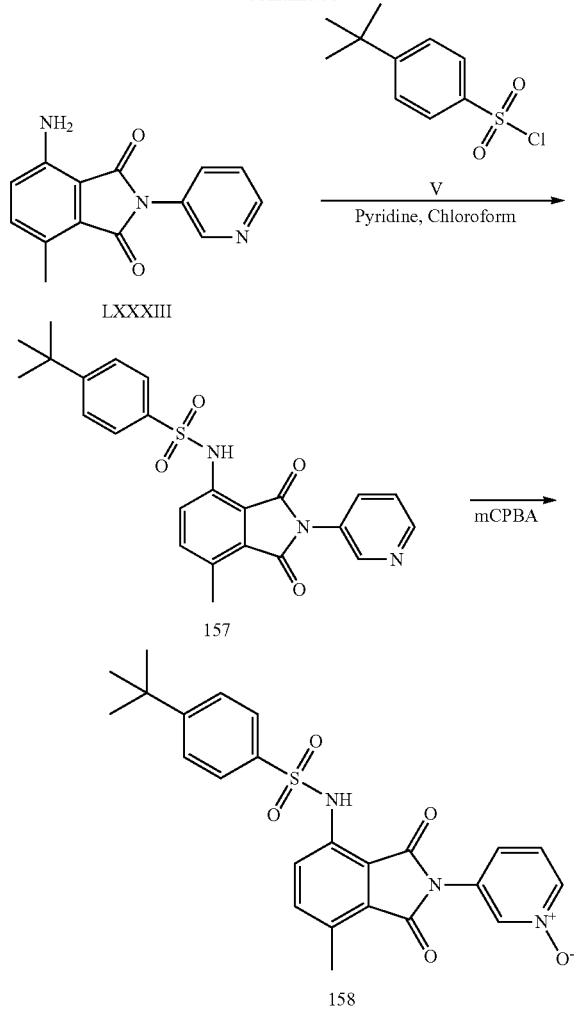

Hz, 1H), 7.81-7.79 (d, J=7.6 Hz, 1H), 7.74-7.72 (d, J=8 Hz, 1H), 7.48-7.45 (m, 1H), 2.86 (s, 3H). MS (M+1): 284.06

Synthesis of LXXXIII:

To a stirred solution of LXXXII, (0.45 g, 1.59 mmol) in methanol (15 mL) and ethyl acetate (2 mL) under a nitrogen atmosphere was added 10% Pd—C (0.1 g). The reaction mixture was purged with nitrogen and stirred under hydrogen balloon pressure for 5 h at room temperature. The reaction mixture was filtered through a celite bed under a nitrogen atmosphere and evaporated under reduced pressure to afford crude compound 4-amino-7-methyl-2-(pyridin-3-yl)isoindoline-1,3-dione as a yellow solid (LXXXIII; 0.35 g). $^1$H NMR (400 MHz, DMSO-d6): δ 8.64-8.63 (d, J=2 Hz, 1H), 8.59-8.58 (d, J=4 Hz, 1H), 7.88-7.86 (d, J=8.4 Hz, 1H), 7.57-7.54 (m, 1H), 7.34-7.32 (d, J=8.4 Hz, 1H), 6.99-6.97 (d, J=8.4 Hz, 1H), 6.45 (bs, 2H), 2.46 (s, 3H). MS (M+1): 254.02.

Synthesis of 157; 4-(tert-butyl)-N-(7-methyl-1,3-dioxo-2-(pyridin-3-yl)isoindolin-4-yl)benzenesulfonamide To a stirred mixture of compound LXXXIII (0.12 g, 0.47 mmol) in chloroform (30 mL) was added pyridine (3 mL) at 0° C. followed by the addition of 4-tert-butylbenzenesulfonyl chloride (V, 0.22 g, 0.94 mmol). The reaction mixture was stirred at 80° C. for 24 h. The reaction mixture was concentrated at reduced pressure and diluted with water. The aqueous layer was extracted with ethyl acetate and the combined organic layers were washed with brine, dried over $Na_2SO_4$, filtered and concentrated to leave the crude compound, which was purified by column chromatography using 30% ethyl acetate in hexane to afford 4-(tert-butyl)-N-(7-methyl-1,3-dioxo-2-(pyridin-3-yl)isoindolin-4-yl)benzenesulfonamide (157; 0.07 g; 33% yield). $^1$H NMR (400 MHz, DMSO-d6): δ 9.76 (bs, 1H), 8.63-8.59 (m, 2H), 7.89-8.83 (m, 3H), 7.63-7.57 (m, 5H), 2.55 (s, 3H), 1.26 (s, 9H). MS (M+1): 450.22. (LCMS purity 99.71%, Rt=4.26 min (1)).

Synthesis of 158; 3-(4-((4-(tert-butyl)phenyl)sulfonamido)-7-methyl-1,3-dioxoisoindolin-2-yl)pyridine 1-oxide To a stirred solution of compound 157 (0.07 g, 0.22 mmol) in dichloromethane (15 mL) was added meta-chloroperoxybenzoic acid (0.057, 0.33 mmol). The reaction mixture was stirred at room temperature for 24 h and then water was added. The layers were separated and the aqueous layer was extracted with ethyl acetate. The organic layer was washed with sodium bicarbonate, dried (anhydrous $Na_2SO_4$) and concentrated. The crude mass was triturated with diethyl ether to afford 3-(4-((4-(tert-butyl)phenyl)sulfonamido)-7-methyl-1,3-dioxoisoindolin-2-yl)pyridine 1-oxide (158; 0.05 g; 50% yield). 1H NMR (400 MHz, DMSO-d6): δ 9.80 (bs, 1H), 8.34 (s, 1H), 8.30-8.29 (d, J=6 Hz, 1H), 7.90-7.88 (d, J=8.4 Hz, 2H), 7.62-7.44 (m, 5H), 7.44-7.42 (d, J=8 Hz, 1H), 2.54 (s, 3H), 1.26 (s, 9H). MS (M−1): 464.03. (LCMS purity 98.14%, Rt=5.76 min(1)).

The following compounds were prepared in a similar manner using the appropriate anhydride and/or amine in the first step and/or sulfonyl chloride instead of 4-tert-butylbenzenesulfonyl chloride V in the penultimate step. Products which are not pyridine N-oxides are not taken through the mCPBA oxidation procedure described in the final step of this example 26

Synthesis of LXXXI:

To a stirred solution of compound LXXX (1 g, 0.006 mol) in acetic acid (10 mL) was added pyridin-3-amine (II, 0.56 g, 0.006 mol) and the reaction mixture heated at 100° C. for 18 h. This was cooled to room temperature and the acetic acid removed under reduced pressure to obtain the crude product 4-methyl-2-(pyridin-3-yl)isoindoline-1,3-dione as a white solid (LXXXI; 1.1 g,). $^1$H NMR (400 MHz, CDCl$_3$): δ 8.78-8.77 (d, J=2 Hz, 1H), 8.63 (d, J=3.6 Hz, 1H), 7.84-7.80 (m, 2H), 7.69-7.65 (t, J=7.6 Hz, 1H), 7.57-7.55 (d, J=8 Hz, 1H), 7.47-7.43 (m, 1H), 2.76 (s, 3H). MS (M+1): 239.02.

Synthesis of LXXXII:

To a stirred solution of KNO$_3$ (1.9 g, 0.018 mol) in concentrated sulfuric acid (22 mL) at 0° C. was added compound LXXXI (0.9 g, 0.003 mol) in sulfuric acid. The reaction mixture was stirred at room temperature for 1 h and then cooled to 0° C. before the addition of crushed ice. The aqueous layer was extracted with ethyl acetate which was washed with brine solution, dried over anhydrous Na$_2$SO$_4$ and evaporated under reduced pressure. The solid crude so obtained was purified by column chromatography using 30% ethyl acetate in hexane to afford 4-methyl-7-nitro-2-(pyridin-3-yl)isoindoline-1,3-dione as a white solid (LXXXII; 0.45 g, 45% yield). $^1$H NMR (400 MHz, CDCl$_3$): δ 8.75 (s, 1H), 8.66-8.65 (d, J=4 Hz, 1H), 8.03-8.01 (d, J=8

| Cpd | Structure | LCMS (M + 1) | Purity (LCMS) | ¹H NMR |
|---|---|---|---|---|
| 159 | 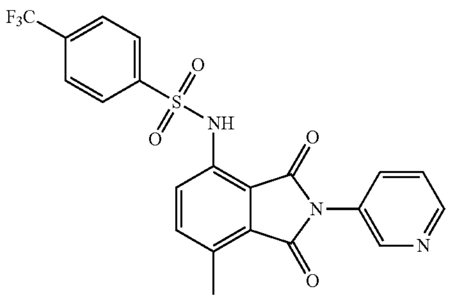 [SMILES: Cc1ccc(NS(=O)(=O)c2ccc(C(F)(F)F)cc2)c2c1C(=O)N(c1cccnc1)C2=O] | 462.14 Rt = 5.83 min (1) | 98.48% | ¹H NMR (400 MHz, DMSO-d6): δ 10.31 (bs, 1H), 8.62-8.61 (d, J = 3.6 Hz, 1H), 8.56-8.55 (d, J = 2 Hz, 1H), 8.12-8.10 (d, J = 8.4 Hz, 2H), 8.00-7.98 (d, J = 8.4 Hz, 2H), 7.81-7.79 (d, J = 8 Hz, 1H), 7.65-7.63 (d, J = 8.8 Hz, 1H), 7.59-7.53 (m, 2H), 2.57 (s, 3H). |
| 160 | 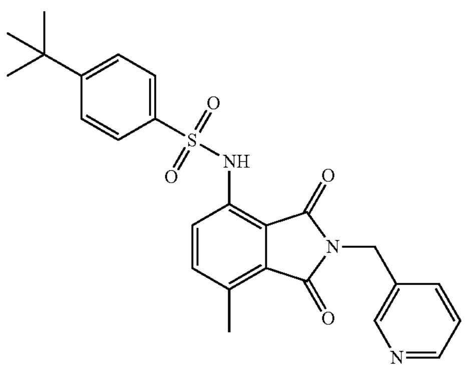 [SMILES: Cc1ccc(NS(=O)(=O)c2ccc(C(C)(C)C)cc2)c2c1C(=O)N(Cc1cccnc1)C2=O] | 464.22 Rt = 6.62 min (1) | 98.68% | ¹H NMR (400 MHz, DMSO-d6): δ 9.72 (bs, 1H), 8.53.-8.48 (m, 2H), 7.87-7.85 (d, J = 8 Hz, 2H), 7.70-7.68 (d, J = 7.6 Hz, 1H), 7.59-7.57 (d, J = 8 Hz, 2H), 7.52-7.51 (m, 2H), 7.35 (m, 1H), 4.72 (s, 2H), 3.32 (s, 3H), 1.25 (s, 9H). |
| 161 | 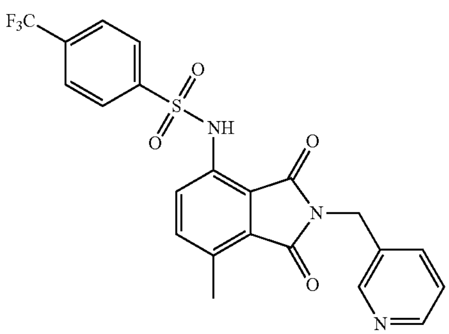 | 475.86 Rt = 5.88 min (1) | 98.91% | 1H NMR (400 MHz, DMSO-d6): δ 10.25 (bs, 1H), 8.52-8.48 (m, 2H), 8.09-8.07 (d, J = 8 Hz, 2H), 7.95-7.93 (d, J = 8 Hz, 2H), 7.63-7.61 (d, J = 8 Hz, 1H), 7.56-7.54 (d, J = 8.4 Hz, 1H), 7.46-7.44 (d, J = 8.4 Hz, 1H), 7.35-7.32 (m, 1H), 4.69 (s, 2H), 2.57 (s, 3H). |
| 162 | 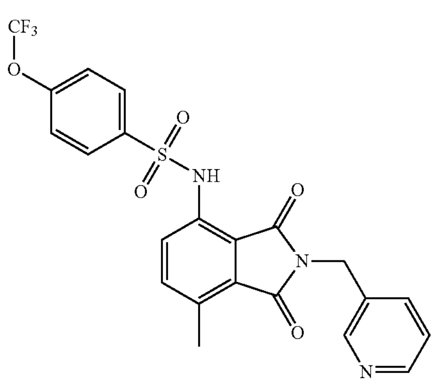 [SMILES: Cc1ccc(NS(=O)(=O)c2ccc(OC(F)(F)F)cc2)c2c1C(=O)N(Cc1cccnc1)C2=O] | 491.94 Rt = 6.07 min (1) | 99.73% | 1H NMR (400 MHz, CDCl3): δ 8.91 (s, 1H), 8.66 (s, 1H), 8.54 (bs, 1H), 7.94-7.92 (d, J = 9.2 Hz, 2H), 7.76-7.74 (d, J = 8.8 Hz, 1H), 7.71-7.69 (d, J = 8 Hz, 1H), 7.39-7.37 (d, J = 8.4 Hz, 1H), 7.28-7.22 (m, 2H), 4.75 (s, 2H), 2.56 (s, 3H). |

| Cpd | Structure | LCMS (M + 1) | Purity (LCMS) | ¹H NMR |
|---|---|---|---|---|
| 163 | 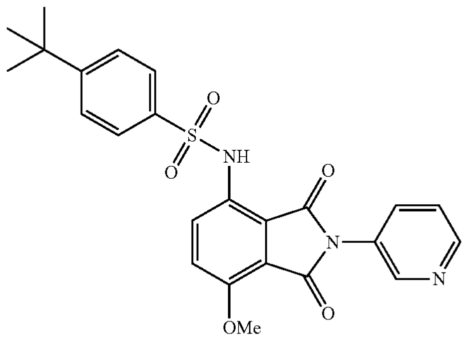 [SMILES: COc1ccc(NS(=O)(=O)c2ccc(C(C)(C)C)cc2)c2c1C(=O)N(c1cccnc1)C2=O] | 466.20 | 98.22% Rt = 6.09 min (1) | ¹H NMR (400 MHz, DMSO-d6-): δ 9.70 (bs, 1H), 8.60-8.59 (d, J = 3.6 Hz, 1H), 8.51 (s, 1H), 7.79-7.74 (m, 3H), 7.68-7.65 (d, J = 9.2 Hz, 1H), 7.60-7.53 (m, 4H), 3.94 (s, 3H), 1.25 (s, 9H). |
| 164 | 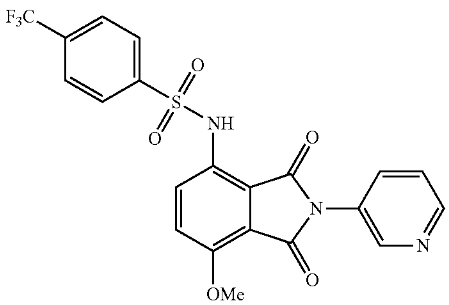 | 478.13 | 99.75% Rt = 5.42 min (1) | ¹H NMR (400 MHz, DMSO-d6-): δ 10.24 (bs, 1H), 8.60-8.59 (dd, J = 1.6 Hz, 3.2 Hz, 1H), 8.47-8.46 (d, J = 2 Hz, 1H), 7.96 (m, 4H), 7.71-7.69 (m, 1H), 7.63-7.60 (d, J = 9.2 Hz, 1H), 7.55-7.53 (m, 2H), 3.95 (s, 3H). |
| 165 | 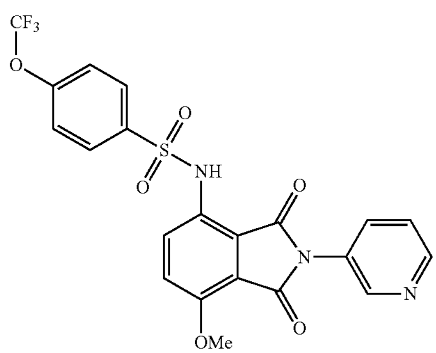 [SMILES: COc1ccc(NS(=O)(=O)c2ccc(OC(F)(F)F)cc2)c2c1C(=O)N(c1cccnc1)C2=O] | 494.17 | 97.42% Rt = 5.63 min (1) | ¹H NMR (400 MHz, DMSO-d6-): δ 10.07 (bs, 1H), 8.63-8.59 (m, 1H), 8.50-8.49 (d, J = 2 Hz, 1H), 7.91-7.90 (d, J = 6.8 Hz, 2H), 7.75-7.73 (m, 1H), 7.64-7.58 (m, 5H), 3.89 (s, 3H). |
| 166 | 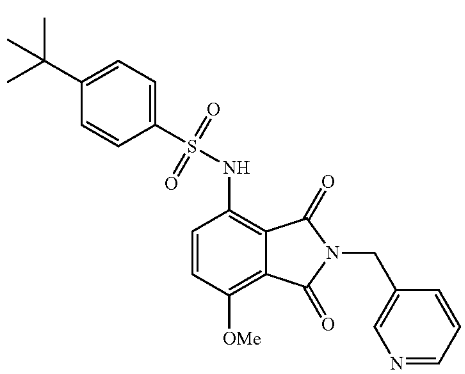 [SMILES: COc1ccc(NS(=O)(=O)c2ccc(C(C)(C)C)cc2)c2c1C(=O)N(Cc1cccnc1)C2=O] | 480.42 | 99.67% Rt = 6.24 min (1) | ¹H NMR (400 MHz, DMSO-d6): δ 9.64 (bs, 1H), 8.48 (m, 2H), 7.76-7.74 (d, J = 8.4 Hz, 2H), 7.65-7.63 (d, J = 8.0 Hz, 1H), 7.58-7.54 (m, 3H), 7.46-7.44 (d, J = 9.6 Hz, 1H) 7.35-7.33 (m, 1H) 4.66 (s, 2H), 3.88 (s, 3H), 1.24 (s, 9H). |

-continued
| Cpd | Structure | LCMS (M + 1) | Purity (LCMS) | ¹H NMR |
|---|---|---|---|---|
| 167 | 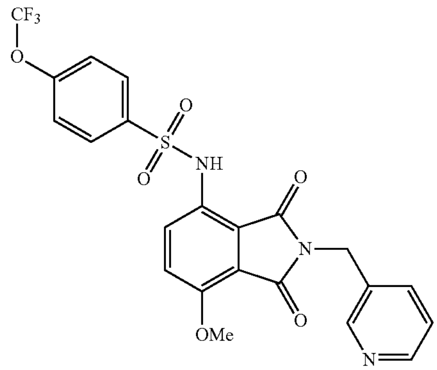 [SMILES: COc1ccc(NS(=O)(=O)c2ccc(OC(F)(F)F)cc2)c2c1C(=O)N(Cc1cccnc1)C2=O] | 508.37 | 98.89%, Rt = 5.81 min (1) | ¹H NMR (400 MHz, DMSO-d6): δ 9.98 (bs, 1H), 8.47 (s, 2H), 7.88-7.85 (d, J = 8.8 Hz, 2H), 7.56-7.46 (m, 5H), 7.34-7.31 (m, 1H), 4.62 (s, 2H), 3.90 (s, 3H). |
| 168 | 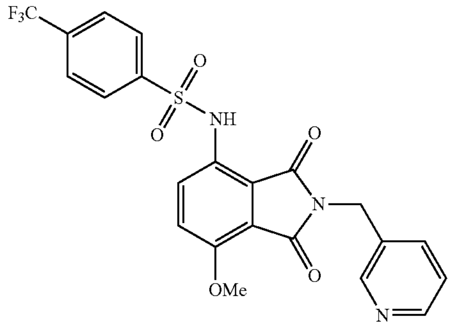 [SMILES: COc1ccc(NS(=O)(=O)c2ccc(C(F)(F)F)cc2)c2c1C(=O)N(Cc1cccnc1)C2=O] | 491.97 | 98.77%, Rt = 5.13 min (2) | ¹H NMR (400 MHz, DMSO-d6): δ 10.18 (bs, 1H), 8.46 (m, 2H), 7.97-7.90 (m, 4H), 7.54-7.52 (m, 2H), 7.48-7.46 (m, 1H), 7.33-7.30 (m, 1H), 4.62 (s, 2H), 3.90 (s, 3H). |
| 169 | 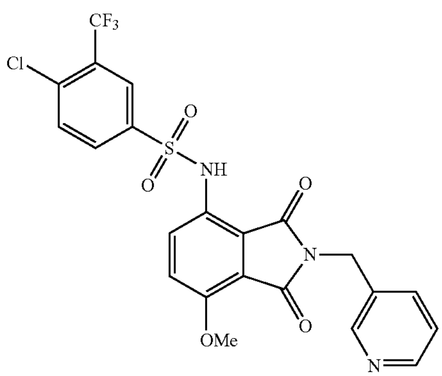 [SMILES: COc1ccc(NS(=O)(=O)c2ccc(Cl)c(C(F)(F)F)c2)c2c1C(=O)N(Cc1cccnc1)C2=O] | 526.21 | 95.53%, Rt = 5.52 min (1) | ¹H NMR (400 MHz, DMSO-d6): δ 10.38 (bs, 1H), 8.47 (m, 2H), 8.16 (s, 1H), 7.92-7.85 (m, 2H), 7.53-7.47 (m, 3H), 7.33 (s, 1H), 4.61 (s, 2H), 3.91 (s, 3H). |
Example 27
Synthesis of Compound 170 [4-(tert-butyl)-N-(7-cyclopropyl-1,3-dioxo-2-(pyridin-3-yl)isoindolin-4-yl)benzenesulfonamide] and Compounds 171-174
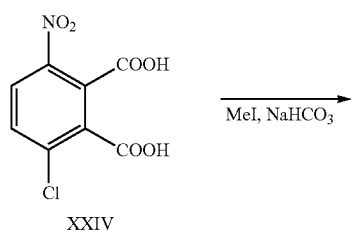
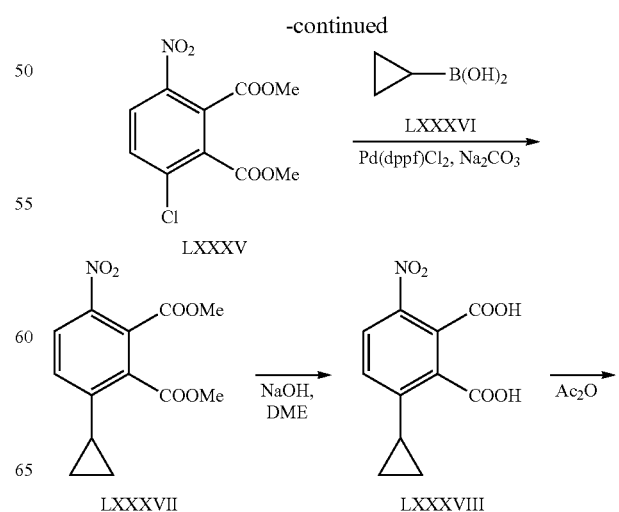

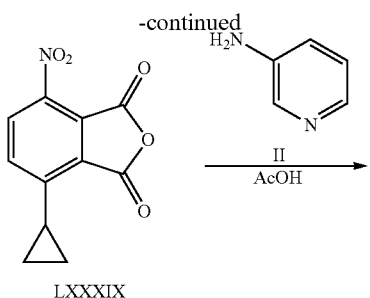
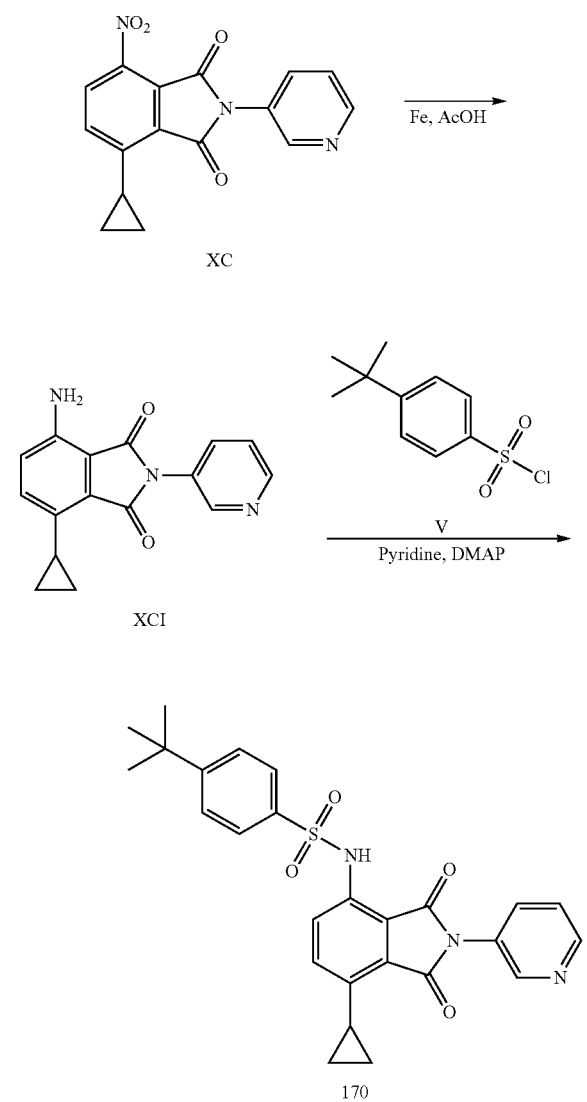

Synthesis of LXXXV:

A stirred solution of 3-chloro-6-nitrophthalic acid (XXIV, 10 g, 36.6 mmol) in DMF (20 mL) was cooled to 0° C. and methyl iodide (13 g, 95 mmol) in DMF solution (16 mL) was added. The reaction mixture was heated at 70° C. for 12 h and on cooling this was diluted with ice cold water. The aqueous layer was extracted with ethyl acetate and the organic layer was dried over anhydrous $Na_2SO_4$, filtered and evaporated under reduced pressure to afford crude compound dimethyl 3-chloro-6-nitrophthalate (LXXXV, 10 g, crude). $^1$H NMR (400 MHz, DMSO-d6): δ 8.08-8.06 (m, 1H), 7.67-7.66 (m, 1H), 3.99 (s, 3H), 3.96 (s, 3H).

Synthesis of LXXXVII:

To a stirred solution of compound LXXXV (10 g, 36 mmol) in dioxane (360 mL) was added cyclopropaneboronic acid (LXXXVI, 6.29 g, 73 mmol). This was followed by a solution of sodium carbonate (11.64 g, 109 mmol) in water (75 mL). The reaction was purged under an argon atmosphere for 30 minutes. The catalyst Pd(dppf)Cl$_2$ (5.9 g, 7.3 mmol) was added to the reaction mixture and the mixture was heated at 120° C. for 12 h. On cooling the solution was filtered through a celite bed. The dioxane was concentrated under reduced pressure and the crude compound was directly purified by column chromatography using 30% ethyl acetate in hexane to afford dimethyl 3-cyclopropyl-6-nitrophthalate (LXXXVII, 2.1 g, 24.5% yield). $^1$H NMR (400 MHz, CDCl$_3$): δ 8.03-8.01 (d, J=8.8 Hz, 1H), 7.15-7.13 (d, J=8.8 Hz, 1H) 3.91 (s, 6H), 2.23 (m, 1H), 1.15-1.13 (m, 2H), 0.82-0.79 (m, 2H).

Synthesis of LXXXVIII:

To a stirred solution of compound LXXXVII (2.1 g, 7.52 mmol) in DME (5 mL) was added a solution of sodium hydroxide (0.6 g, 15.1 mmol) in water (1 mL). The reaction mixture was heated at 70° C. for 48 h. On cooling it was diluted with ice cold water and acidified to pH 2 using 1N HCl solution. The aqueous layer was extracted with ethyl acetate. The organic layer was dried over anhydrous $Na_2SO_4$, filtered and evaporated under reduced pressure to afford 3-cyclopropyl-6-nitrophthalic acid (LXXXVIII, 1.5 g, 80% yield). $^1$H NMR (400 MHz, DMSO-d6): δ 13.9 (bs, 2H), 8.00-7.98 (d, J=8.4 Hz, 1H), 7.25-7.23 (d, J=8.4 Hz, 1H), 2.2 (m, 1H), 1.15 (m, 2H), 0.84 (m, 2H).

Synthesis of LXXXIX:

A stirred solution of compound LXXXVIII (1.5 g; 5.97 mmol) in acetic anhydride (20 mL) was heated at 120° C. for 12 h. The reaction mixture was cooled and diluted with water. The aqueous layer was extracted with ethyl acetate. The organic layer was washed with brine, dried over anhydrous $Na_2SO_4$, filtered and concentrated to afford 4-cyclopropyl-7-nitroisobenzofuran-1,3-dione as an off-white solid (LXXXIX; 1.2 g, 92.3% yield). MS (M−1): 232.20.

Synthesis of XC:

To a stirred solution of compound LXXXIX (1.2 g, 5.15 mmol) in acetic acid (20 mL) was added pyridin-3-amine (II, 0.91 g, 10.3 mmol). The reaction mixture was heated at 120° C. for 12 h. On cooling to room temperature, the acetic acid was removed under reduced pressure to leave the crude product which was triturated with ethanol to afford 4-cyclopropyl-7-nitro-2-(pyridin-3-yl)isoindoline-1,3-dione (XC, 1.2 g, 86%). MS (M−1): 308.99.

Synthesis of XCI:

To a solution of compound XC (1.2 g, 3.88 mmol) in acetic acid (10 mL) was added iron powder (1 g) in small portions. The reaction mixture was stirred for 12 h at room temperature and then filtered through a celite bed and concentrated under reduced pressure. The crude mass was neutralized by aqueous sodium bicarbonate solution. The aqueous layer was extracted with ethyl acetate. The organic solvent which was dried over anhydrous $Na_2SO_4$, filtered and evaporated under reduced pressure to afford 4-amino-7-cyclopropyl-2-(pyridin-3-yl)isoindoline-1,3-dione as an off white solid (XCI; 1 g, 92% yield). $^1$H NMR (400 MHz, DMSO-d6): δ 8.65 (s, 1H), 8.59-8.58 (d, J=4.8 Hz, 1H), 7.90-7.88 (d, J=8.8 Hz, 1H), 7.58-7.55 (m, 1H), 6.98 (m, 2H), 6.44 (bs, 2H), 2.94-2.89 (m, 1H), 1.01-0.97 (m, 2H), 0.77-0.73 (m, 2H).

Synthesis of 170; 4-(tert-butyl)-N-(7-cyclopropyl-1,3-dioxo-2-(pyridin-3-yl)isoindolin-4-yl)benzenesulfonamide A mixture of compound XCI (0.2 g, 0.72 mmol) and pyridine (3 mL) was cooled to 0° C. and 4-tert-butylbenzenesulfonyl chloride (V, 0.33 g, 1.43 mmol) was added followed by DMAP (0.047 g, 0.35 mmol). The reaction mixture was heated for 12 h at 100° C. The reaction mixture was concentrated and diluted with water. The reaction mixture was extracted with ethyl acetate. The organic layer was washed with brine solution, dried over anhydrous Na₂SO₄, filtered and the organic solvent was evaporated under reduced pressure to obtain the crude compound. This was purified by column chromatography using 40% ethyl acetate in hexane to afford 4-(tert-butyl)-N-(7-cyclopropyl-1,3-dioxo-2-(pyridin-3-yl)isoindolin-4-yl)benzene-sulfonamide as an off-white solid (170; 0.08 g, 23.52% yield). $^1$H NMR (400 MHz, DMSO-d6): δ 9.76 (bs, 1H), 8.63-8.61 (m, 2H), 7.87-7.85 (m, 3H), 7.63-7.55 (m, 4H), 7.26-7.24 (d, J=8.8 Hz, 1H), 2.98-2.97 (m, 1H), 1.27 (s, 9H), 1.12 (m, 2H), 0.85 (m, 2H). MS (M+1): 476.11. (LCMS purity 99.32%, Rt=6.73 min (2)).

The following compounds were also prepared using a similar method and the appropriate sulfonyl chloride in the final step described. Conversion to the pyridine N-oxide is achieved by treatment of the corresponding pyridine with mCPBA:

| Cpd | Structure | LCMS (M + 1) | Purity (LCMS) | $^1$H NMR |
|---|---|---|---|---|
| 171 | 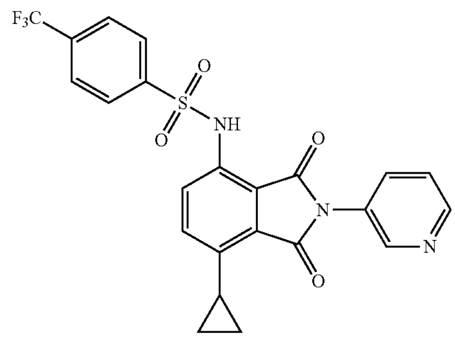 [SMILES: O=C1c2c(NS(=O)(=O)c3ccc(C(F)(F)F)cc3)ccc(C3CC3)c2C(=O)N1c1cccnc1] | 488.36 | 99.57%, Rt = 6.0 min (1) | $^1$H NMR (400 MHz, DMSO-d6): δ 10.31 (bs, 1H), 8.62 (s, 1H), 8.57 (m, 1H), 8.09-8.07 (d, J = 8.0 Hz, 2H), 7.99-7.97 (d, J = 8.4 Hz, 2H), 7.82-7.80 (d, J = 8.4 Hz, 1H), 7.59-7.56 (d, J = 8.8 Hz, 1H), 7.50-7.48 (d. J = 8.8 Hz, 1H) 7.25-7.23 (d, J = 8.8 Hz, 1H), 3.01 (m, 1H), 1.13 (m, 2H), 0.86 (m, 2H). |
| 172 | 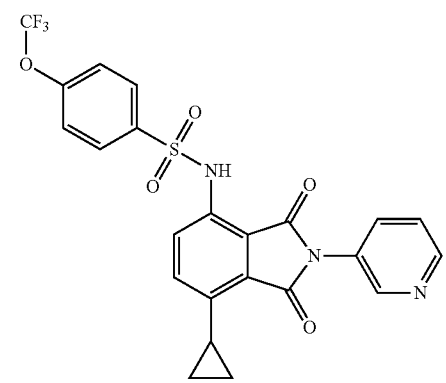 [SMILES: O=C1c2c(NS(=O)(=O)c3ccc(OC(F)(F)F)cc3)ccc(C3CC3)c2C(=O)N1c1cccnc1] | 504.38 | 99.83%, Rt = 6.20 min (1) | $^1$H NMR (400 MHz, DMSO-d6): δ 10.12 (bs, 1H), 8.63-8.59 (m, 2H), 8.04-8.02 (d, J = 8.8 Hz, 2H), 7.84-7.82 (d, J = 8.0 Hz, 1H), 7.60-7.56 (m, 3H), 7.52-7.50 (d, J = 8.8 Hz, 1H), 7.26-7.24 (d, J = 8.8 Hz, 1H), 3.01 (m, 1H), 1.13 (m, 2H), 0.87 (m, 2H). |
| 173 | 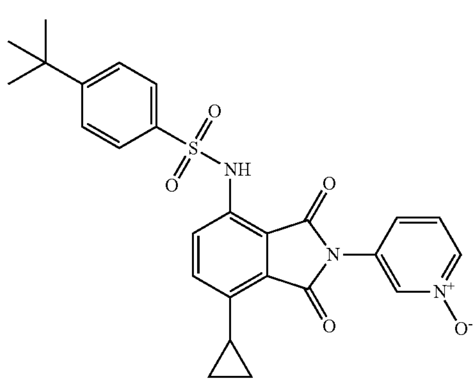 [SMILES: CC(C)(C)c1ccc(S(=O)(=O)Nc2ccc(C3CC3)c3c2C(=O)N(c2ccc[n+]([O-])c2)C3=O)cc1] | 492.39 | 96.98%, Rt = 5.97 min (1) | $^1$H NMR (400 MHz, DMSO-d6): δ 9.82 (bs, 1H), 8.36 (s, 1H), 8.30-8.28 (d, J = 6.4 Hz, 1H), 7.85-7.83 (d, J = 8.4 Hz, 2H), 7.59-7.53 (m, 4H), 7.46-7.44 (d, J = 8.4 Hz, 1H), 7.16 (m, 1H), 2.98-2.92 (m, 1H), 1.27 (s, 9H), 1.10 (m, 2H), 0.87 (s, 2H). |

| Cpd | Structure | LCMS (M + 1) | Purity (LCMS) | ¹H NMR |
|---|---|---|---|---|
| 174 | 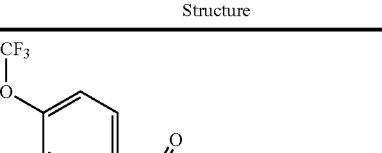 | 518.35 (M − 1) | 98.51%, Rt = 5.31 min (1) | ¹H NMR (400 MHz, DMSO-d6): δ 10.19 (bs, 1H), 8.34 (s, 1H), 8.31-8.30 (d, J = 6.4 Hz, 1H), 8.06-8.02 (d, J = 8.8 Hz, 2H), 7.61-7.56 (m, 3H), 7.51-7.49 (d, J = 8.8 Hz, 1H), 7.43-7.41 (d, J = 8.4 Hz, 1H), 7.26-7.24 (d, J = 8.0 Hz, 1H), 2.99 (m, 1H), 1.13-1.12 (m, 2H), 0.86-0.85 (m, 2H). |
Example 28
Synthesis of Compound 175 [4-(tert-butyl)-N-(7-chloro-2-(2-methylpyridin-3-yl)-1,3-dioxoisoindolin-4-yl)benzenesulfonamide]; Compound 176 [3-(4-(4-(tert-butyl)phenylsulfonamido)-7-chloro-1,3-dioxoisoindolin-2-yl)-2-methylpyridine 1-oxide] and Compounds 177 to 276, and Compounds 277 to 280
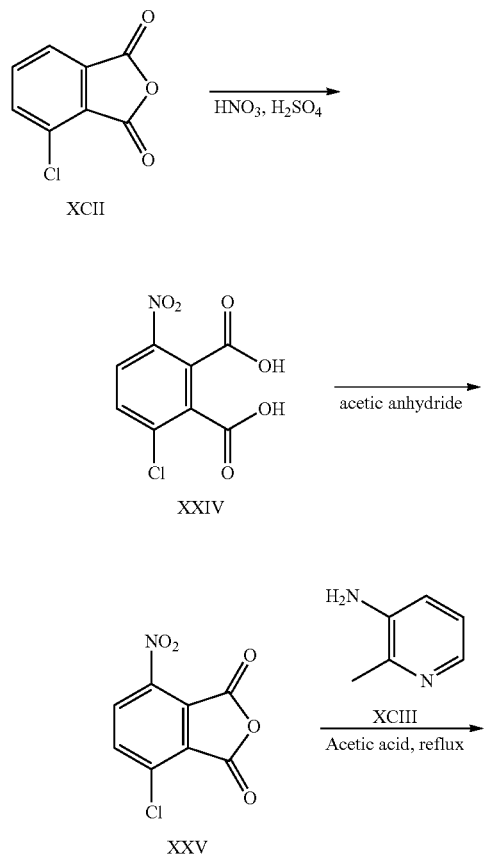
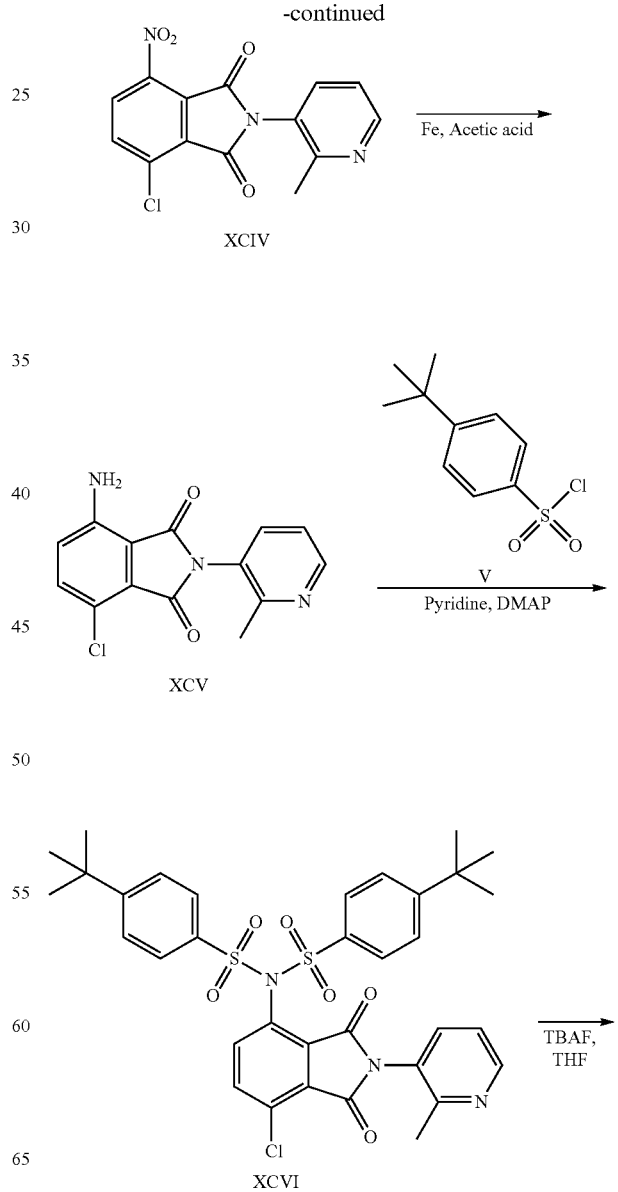

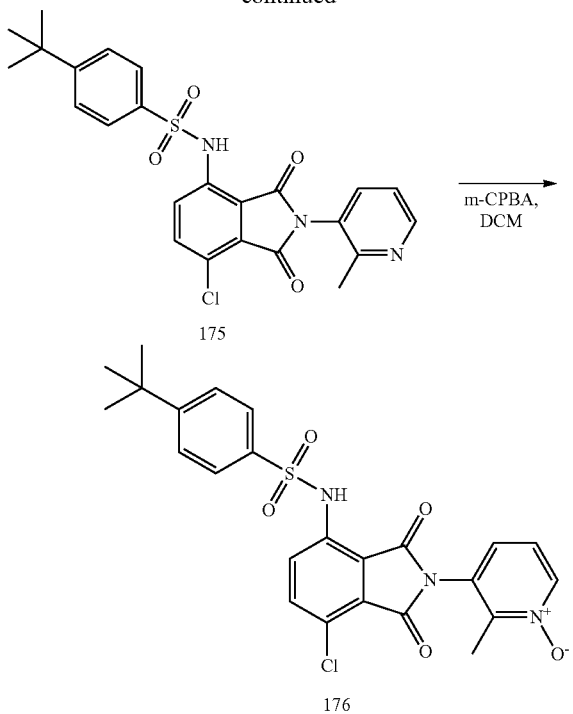

Synthesis of XXIV:

To a stirred solution of nitric acid and sulphuric acid (172 ml: 439 ml) at 0° C. was added portion wise compound XCII (250.0 g, 1.37 mol) and the reaction mixture was stirred at room temperature for 12 h. The reaction mixture was cooled to 0° C. followed by addition of crushed ice. The solid which precipitated out was filtered to afford 3-chloro-6-nitrophthalic acid as a white solid (XXIV; 250.0 g; 74% yield). ¹H NMR (400 MHz, DMSO-d6): δ 14.34 (bs, 2H), 8.16-8.13 (d, J=8.8 Hz, 1H), 7.93-7.91 (d, J=8.8 Hz, 1H). MS (M−1): 243.97.

Synthesis of XXV:

A stirred solution of compound XXIV (250.0 g, 1.02 mol) in acetic anhydride (3.5 L) was heated at 120° C. for 18 h. The reaction mixture was cooled and concentrated under reduced pressure. The crude solid obtained was washed with hexane and triturated with 20% diethyl ether in hexane to afford 4-chloro-7-nitroisobenzofuran-1,3-dione as an off white solid (XXV; 230 g; 99% yield). ¹H NMR (400 MHz, DMSO-d6): δ 8.48-8.46 (d, J=8.8 Hz, 1H), 8.30-8.27 (d, J=8.8 Hz, 1H). MS (M+1): 228.01.

Synthesis of XCIV:

To a stirred solution of compound XXV (230 g, 1.01 mol) in acetic acid (4 L) was added 2-methylpyridin-3-amine (XCIII, 118.15 g, 1.09 mol) and the reaction mixture heated at 120° C. for 4 h. The reaction mixture was cooled to room temperature and the acetic acid removed under reduced pressure. The residual material was washed with hexane to obtain a crude product 4-chloro-2-(2-methylpyridin-3-yl)-7-nitroisoindoline-1,3-dione as a yellow solid (XCIV; 300 g,). MS (M+1): 318.09. The crude material was carried forward to next step without purification.

Synthesis of XCV:

To a solution of compound XCIV (280 g) in acetic acid (10 L) under a nitrogen atmosphere was added iron powder (280 g). The reaction mixture was stirred for 12 h at room temperature. The reaction mixture was filtered through a celite bed followed which was washed with ethyl acetate and the collected filtrate was evaporated under reduced pressure to afford compound 4-amino-7-chloro-2-(2-methylpyridin-3-yl)isoindoline-1,3-dione as a yellow solid (XCV; 220 g; 86% yield). ¹H NMR (400 MHz, DMSO-d6): δ 8.55-8.54 (m, 1H), 7.80-7.78 (d, J=7.6 Hz, 1H), 7.50-7.48 (d, J=8.8 Hz, 1H), 7.41-7.38 (m, 1H), 7.08-7.06 (d, J=8.8 Hz, 1H), 6.73 (s, 2H), 2.34 (s, 3H). MS (M+1): 288.19

Synthesis of 175; 4-(tert-butyl)-N-(7-chloro-2-(2-methylpyridin-3-yl)-1,3-dioxoisoindolin-4-yl)benzenesulfonamide A mixture of compound XCV (210 g, 0.731 mol) in pyridine (4 L) was cooled to 0° C. and 4-(tert-butyl) benzenesulfonyl chloride (V, 509 g, 2.19 mol) was added. The reaction mixture was stirred at 90° C. for 8 h. The reaction mixture was cooled and concentrated under reduced pressure. The reaction mixture was diluted with water and the aqueous layer was extracted with ethyl acetate. The organic layer was separated, washed with brine solution, dried over anhydrous Na₂SO₄, filtered and the concentrated under reduced pressure to obtain the crude compound XCVI. To the crude compound XCVI, was added 1M TBAF in THF solution (4 L) and the resulting mixture stirred for 3 h at room temperature. The reaction mixture was concentrated at reduced pressure and diluted with ethyl acetate. The organic layer was washed with water, dried over anhydrous Na₂SO₄, filtered and evaporated under reduced pressure to obtain the crude compound which was purified by column chromatography using 25% ethyl acetate in hexane to afford the title compound, 4-(tert-butyl)-N-(7-chloro-2-(2-methylpyridin-3-yl)-1,3-dioxoisoindolin-4-yl)benzenesulfonamide as an off white solid (175; 240 g, 68% yield). ¹H NMR (400 MHz, DMSO-d6): δ 10.00 (bs, 1H), 8.57-8.56 (d, J=3.6 Hz, 1H), 7.92-7.90 (d, J=8.4 Hz, 2H), 7.83-7.81 (d, J=8.8 Hz, 1H), 7.78-7.76 (d, J=7.2 Hz, 1H), 7.70-7.67 (d, J=8.8 Hz, 1H), 7.64-7.61 (d, J=8.4 Hz, 2H), 7.43-7.39 (m, 1H), 2.31 (s, 3H), 1.27 (s, 9H). MS (M+1): 484.03. (LCMS purity 99.02%, Rt=6.06 min (1)).

Synthesis of 176; 3-(4-(4-(tert-butyl)phenylsulfonamido)-7-chloro-1,3-dioxoisoindolin-2-yl)-2-methylpyridine 1-oxide To a stirred solution of 4-(tert-butyl)-N-(7-chloro-2-(2-methylpyridin-3-yl)-1,3-dioxoisoindolin-4-yl)benzenesulfonamide (175; 230 g, 0.475 mol) in dichloromethane (3.4 L), was added m-chloroperoxybenzoic acid (81.97 g, 0.475 mol). The reaction mixture was stirred at RT for 8 h whereupon the solvent was concentrated under reduced pressure and the residue was diluted with water. The aqueous layer was extracted with dichloromethane. The combined organic layers were washed sequentially with sodium bicarbonate and brine, then dried over Na₂SO₄, filtered and concentrated under vacuum to leave the crude compound, which was purified by column chromatography using 1% methanol in dichloromethane to afford 3-(4-(4-(tert-butyl)phenylsulfonamido)-7-chloro-1,3-dioxoisoindolin-2-yl)-2-methylpyridine 1-oxide as an off white solid (176; 125 g, 53% yield). ¹H NMR (400 MHz, DMSO-d6): δ 10.04 (bs, 1H), 8.45-8.43 (d, J=5.6 Hz, 1H), 7.93-7.91 (d, J=8.4 Hz, 2H), 7.85-7.83 (d, J=8.8 Hz, 1H), 7.69-7.67 (d, J=8.8 Hz, 1H), 7.64-7.62 (d, J=8.8 Hz, 2H), 7.47-7.40 (m, 2H), 2.20 (s, 3H), 1.27 (s, 9H). MS (M+1): 500.28. (LCMS purity 99.45%, Rt=5.40 min (1)).

The following compounds were prepared essentially in a similar manner as described above using the appropriate amine instead of 2-methylpyridin-3-amine XCIII. The final step described was only carried out only for those compounds where a pyridine-N-oxide was produced:

| S. No. | Structure | LCMS (M + 1) | Purity (LCMS) | 1HNMR |
|---|---|---|---|---|
| 177 | 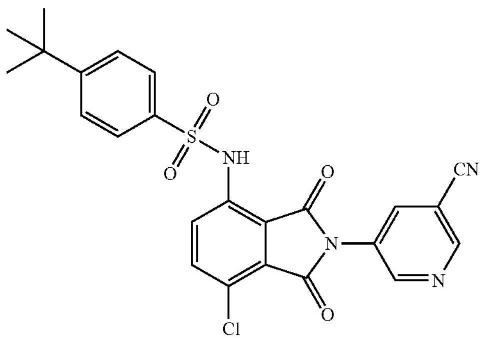 [SMILES: CC(C)(C)c1ccc(S(=O)(=O)Nc2ccc(Cl)c3c2C(=O)N(c2cncc(C#N)c2)C3=O)cc1] | 495.06 | 99.87% Rt = 5.98 min (1) | ¹H NMR (400 MHz, DMSO-d6): δ 10.09 (bs, 1H), 9.12-9.11 (d, J = 1.6 Hz, 1H), 8.93-8.92 (d, J = 2 Hz, 1H), 8.38-8.09 (m, 1H), 7.94-7.92 (d, J = 8.8 Hz, 2H), 7.88-7.86 (d, J = 8.8 Hz, 1H), 7.71-7.69 (d, J = 8.8 Hz, 1H), 7.65-7.63 (d, J = 8.8 Hz, 2H), 1.27 (s, 9H). |
| 178 | 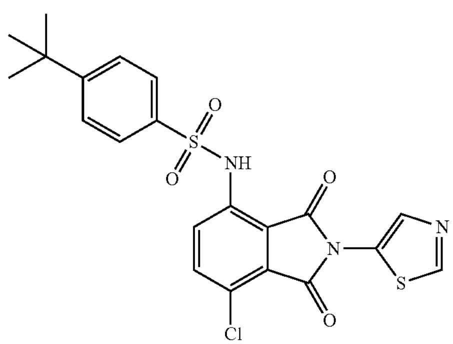 [SMILES: CC(C)(C)c1ccc(S(=O)(=O)Nc2ccc(Cl)c3c2C(=O)N(c2cncs2)C3=O)cc1] | 476.00 | 97.32% Rt = 6.03 min (1) | ¹H NMR (400 MHz, DMSO-d6): δ 10.12 (bs, 1H), 9.06 (s, 1H), 8.21 (s, 1H), 7.94-7.92 (d, J = 8.8 Hz, 2H), 7.83-7.81 (d, J = 8.8 Hz, 1H), 7.66-7.62 (m, 3H), 1.26 (s, 9H). |
| 179 | 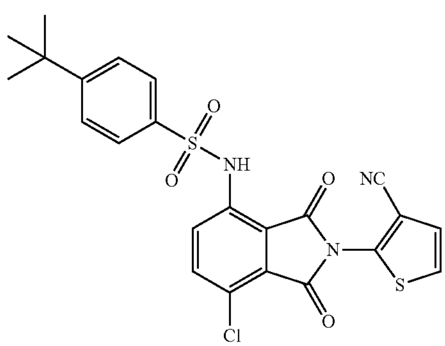 [SMILES: CC(C)(C)c1ccc(S(=O)(=O)Nc2ccc(Cl)c3c2C(=O)N(c2sccc2C#N)C3=O)cc1] | 497.92 (M − 1) | 98.42% Rt = 6.20 min (1) | ¹H NMR (400 MHz, DMSO-d6): δ 10.20 (bs, 1H), 7.89-7.77 (m, 5H), 7.62-7.60 (d, J = 8.4 Hz, 2H), 7.47-7.46 (d, J = 5.2 Hz, 1H), 1.30 (s, 9H). |
| 180 | 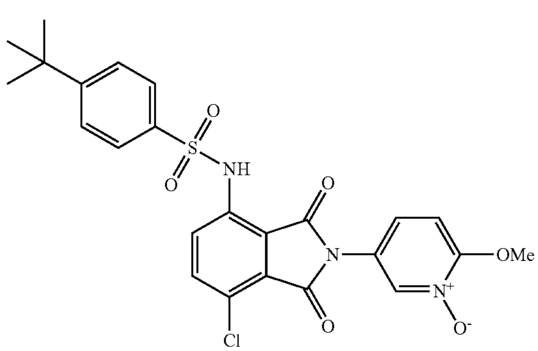 | 516.03 | 97.29% Rt = 5.15 min (1) | ¹H NMR (400 MHz, DMSO-d6): δ 10.04 (bs, 1H), 8.35-8.34 (d, J = 2 Hz, 1H), 7.94-7.92 (d, J = 8 Hz, 2H), 7.80 (m, 1H), 7.68-7.62 (m, 3H), 7.44-7.43 (d, J = 2 Hz, 1H), 7.37-7.35 (d, J = 8.8 Hz, 1H), 4.03 (s, 3H), 1.27 (s, 9H). |

| S. No. | Structure | LCMS (M + 1) | Purity (LCMS) | 1HNMR |
|---|---|---|---|---|
| 181 | 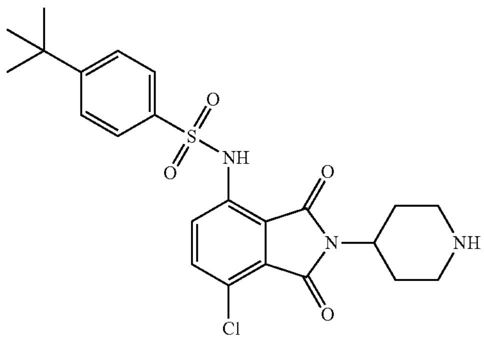 [SMILES: CC(C)(C)c1ccc(S(=O)(=O)Nc2ccc(Cl)c3c2C(=O)N(C2CCNCC2)C3=O)cc1] | 476.09 | 99.78% Rt = 5.79 min (2) | ¹H NMR (400 MHz, DMSO-d6 with TFA): δ 9.65 (bs, 1H), 8.36 (bs, 1H), 7.85-7.83 (d, J = 8.4 Hz, 2H), 7.61 (m, 2H), 7.55-7.53 (d, J = 8.4 Hz, 2H), 4.26 (m, 1H), 3.36 (m, 2H), 3.04 (m, 2H), 2.42 (m, 2H), 1.83 (m, 2H), 1.21 (s, 9H). |
| 182 | 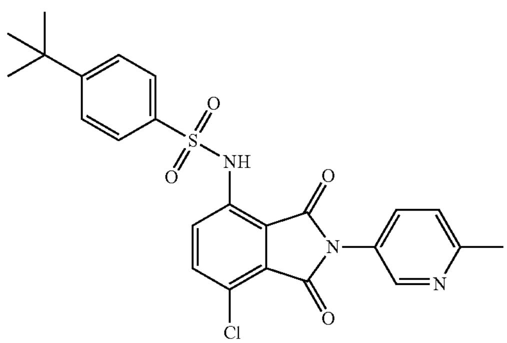 [SMILES: Cc1ccc(N2C(=O)c3c(Cl)ccc(NS(=O)(=O)c4ccc(C(C)(C)C)cc4)c3C2=O)cn1] | 484.06 | 98.42% Rt = 6.21 min (1) | ¹H NMR (400 MHz, DMSO-d6): δ 9.97 (bs, 1H), 8.46-8.45 (d, J = 2 Hz, 1H), 7.93-7.91 (d, J = 8.4 Hz, 2H), 7.82-7.80 (d, J = 8.8 Hz, 1H), 7.72-7.62 (m, 4H), 7.44-7.42 (d, J = 8 Hz, 1H), 2.53 (s, 3H), 1.27 (s, 9H). |
| 183 | 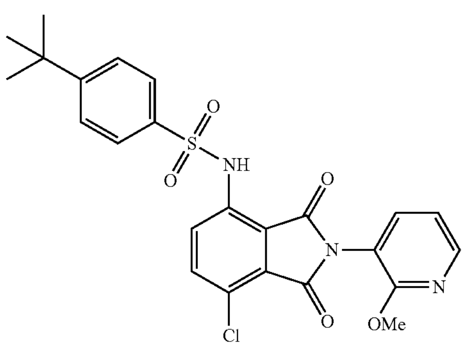 [SMILES: COc1ncccc1N1C(=O)c2c(Cl)ccc(NS(=O)(=O)c3ccc(C(C)(C)C)cc3)c2C1=O] | 500.26 | 99.56% Rt = 6.40 min (1) | ¹H NMR (400 MHz, DMSO-d6): δ 10.09 (bs, 1H), 8.33-8.31 (m, 1H), 7.94-7.92 (d, J = 8.4 Hz, 2H), 7.82-7.80 (m, 2H), 7.67-7.63 (m, 3H), 7.21-7.18 (m, 1H), 3.84 (s, 3H), 1.28 (s, 9H). |
| 184 | 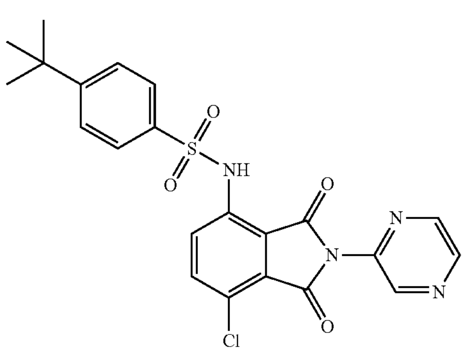 [SMILES: CC(C)(C)c1ccc(S(=O)(=O)Nc2ccc(Cl)c3c2C(=O)N(c2cnccn2)C3=O)cc1] | 471.03 | 98.49% Rt = 5.94 min (1) | ¹H NMR (400 MHz, DMSO-d6): δ 10.09 (bs, 1H), 8.79-8.78 (m, 3H), 7.93-7.91 (d, J = 8.4 Hz, 2H), 7.88-7.85 (d, J = 9.2 Hz, 1H), 7.70-7.68 (d, J = 8.8 Hz, 1H), 7.64-7.62 (d, J = 8.4 Hz, 2H), 1.27 (s, 9H). |

| S. No. | Structure | LCMS (M + 1) | Purity (LCMS) | 1HNMR |
|---|---|---|---|---|
| 185 | 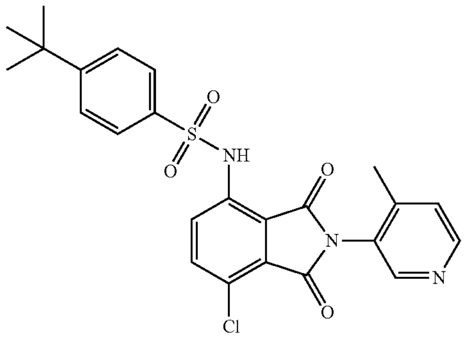 [SMILES: Cc1ccncc1N1C(=O)c2c(Cl)ccc(NS(=O)(=O)c3ccc(C(C)(C)C)cc3)c2C1=O] | 484.06 | 99.08% Rt = 6.13 min (1) | ¹H NMR (400 MHz, DMSO-d6): δ 10.02 (bs, 1H), 8.53-8.52 (d, J = 5.2 Hz, 1H), 8.47 (s, 1H), 7.92-7.90 (d, J = 8.8 Hz, 2H), 7.85-7.83 (d, J = 8.8 Hz, 1H), 7.70-7.68 (d, J = 8.8 Hz, 1H), 7.64-7.62 (d, J = 8.8 Hz, 2H), 7.47-7.46 (d, J = 5.6 Hz, 1H), 2.16 (s, 3H), 1.27 (s, 9H). |
| 186 | 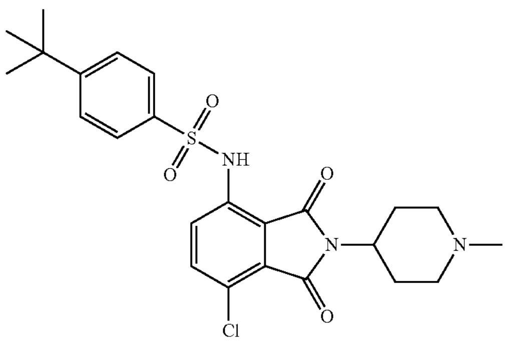 [SMILES: CN1CCC(N2C(=O)c3c(Cl)ccc(NS(=O)(=O)c4ccc(C(C)(C)C)cc4)c3C2=O)CC1] | 490.15 | 98.26% Rt = 5.83 min (1) | ¹H NMR (400 MHz, DMSO-d6): δ 9.54 (bs, 1H), 7.80-7.81 (d, J = 8 Hz, 2H), 7.55-7.45 (m, 4H), 4.15-4.12 (m, 2 H), 3.40-3.30 (m, 2H), 2.98-2.91 (m, 1H), 2.67 (s, 3H), 2.43-2.40 (m, 2H), 1.84-1.80 (m, 2H), 1.27 (s, 9H). |
| 187 | 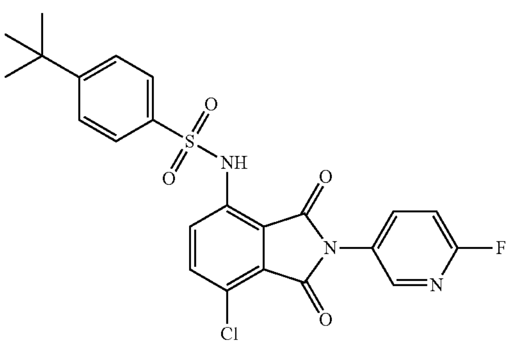 | 488.04 | 98.06% Rt = 6.30 min (1) | ¹H NMR (400 MHz, DMSO-d6): δ 10.03 (bs, 1H), 8.29 (s, 1H), 8.07-8.04 (m, 1H), 7.94-7.92 (d, J = 8.8 Hz, 2H), 7.84-7.82 (d, J = 8.4 Hz, 1H), 7.69-7.67 (d, J = 8.8 Hz, 1H), 7.65-7.63 (d, J = 8 Hz, 2H), 7.43-7.40 (m, 1 H), 2H), 1.27 (s, 9H). |
| 188 | 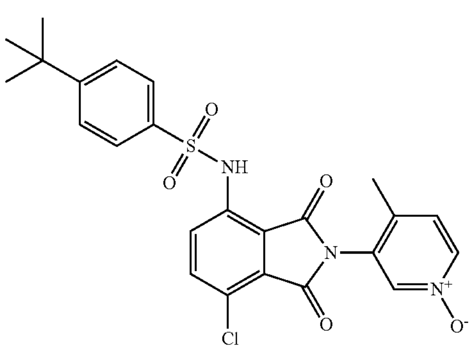 | 500.04 | 96.11% Rt = 5.29 min (1) | ¹H NMR (400 MHz, DMSO-d6): δ 10.08 (bs, 1H), 8.32 (s, 1H), 8.27-8.25 (d, J = 6.4 Hz, 1H), 7.93-7.91 (d, J = 8.4 Hz, 2H), 7.86-7.84 (d, J = 8.8 Hz, 1H), 7.70-7.68 (d, J = 8.8 Hz, 1H), 7.64-7.62 (d, J = 8.4 Hz, 2H), 7.48-7.46 (d, J = 6.4 Hz, 1H), 2.11 (s, 3H), 1.27 (s, 9H). |

| S. No. | Structure | LCMS (M + 1) | Purity (LCMS) | 1HNMR |
|---|---|---|---|---|
| 189 | 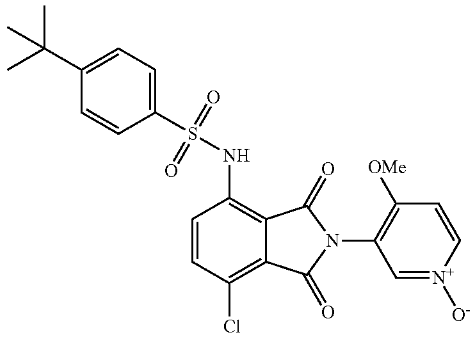 [SMILES: COc1cc[n+]([O-])cc1N1C(=O)c2c(Cl)ccc(NS(=O)(=O)c3ccc(C(C)(C)C)cc3)c2C1=O] | 516.28 | 99.14% Rt = 5.13 min (1) | ¹H NMR (400 MHz, DMSO-d6): δ 10.17 (bs, 1H), 8.35-8.33 (m, 1H), 8.31-8.30 (d, J = 2 Hz, 1H), 7.92-7.90 (d, J = 8 Hz, 2H), 7.80 (m, 1H), 7.66-7.61 (m, 3H), 7.34-7.32 (d, J = 7.2 Hz, 1H), 3.84 (s, 3H), 1.28 (s, 9H). |
| 190 | 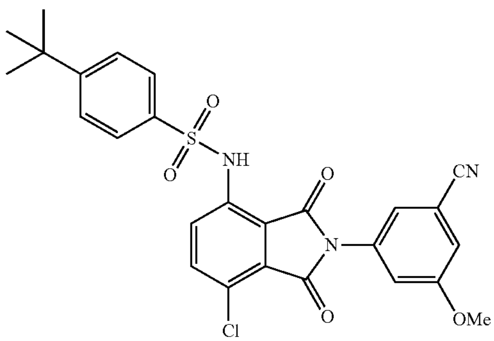 [SMILES: COc1cc(C#N)cc(N2C(=O)c3c(Cl)ccc(NS(=O)(=O)c4ccc(C(C)(C)C)cc4)c3C2=O)c1] | 522.03 (M − 1) | 99.60% Rt = 6.53 min (1) | ¹H NMR (400 MHz, DMSO-d6): δ 10.0 (bs, 1H), 7.89-7.86 (m, 2H), 7.78 (m, 1H), 7.68-7.60 (m, 1H), 7.61-7.56 (m, 3H), 7.45 (m, 1H), 7.37 (m, 1H), 3.85 (s, 3H), 1.27 (s, 9H). |
| 191 | 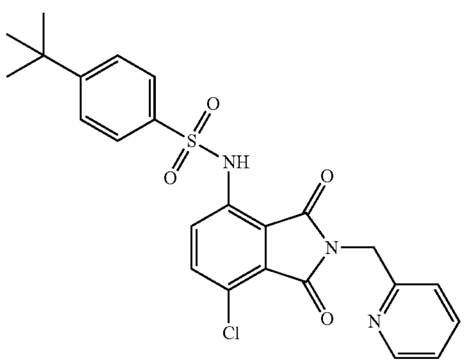 | 484.07 | 99.45% Rt = 6.36 min (1) | ¹H NMR (400 MHz, DMSO-d6): δ 10.00 (bs, 1H), 8.43-8.42 (d, J = 4 Hz, 1H), 7.93-7.90 (d, J = 8.4 Hz, 2H), 7.79-7.75 (m, 2H), 7.63-7.61 (m, 3H), 7.42-7.40 (d, J = 8 Hz, 1H), 7.29-7.26 (m, 1H), 4.84 (s, 2H), 1.27 (s, 9H). |
| 192 | 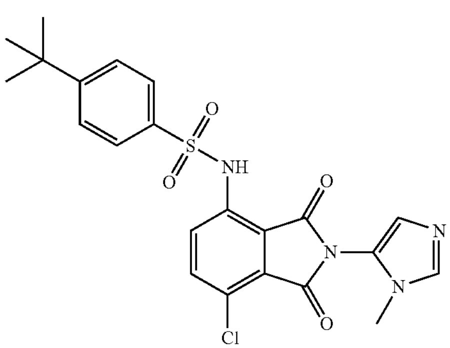 | 473.05 | 96.83% Rt = 5.60 min (1) | ¹H NMR (400 MHz, DMSO-d6): δ 10.15 (bs, 1H), 7.93-7.91 (d, J = 8.8 Hz, 2H), 7.82-7.80 (m, 2H), 7.67-7.61 (m, 3H), 6.97 (s, 1H), 3.38 (s, 3H), 1.27 (s, 9H). |

| S. No. | Structure | LCMS (M + 1) | Purity (LCMS) | 1HNMR |
|---|---|---|---|---|
| 193 | 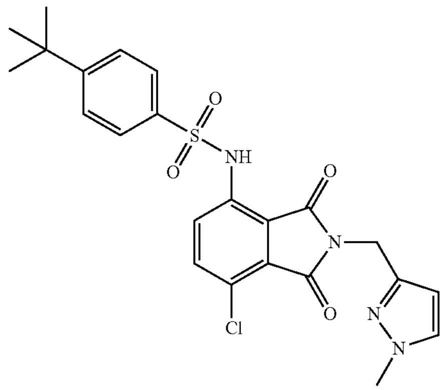 [SMILES: Cn1ccc(CN2C(=O)c3c(Cl)ccc(NS(=O)(=O)c4ccc(C(C)(C)C)cc4)c3C2=O)n1] | 487.10 | 98.75% Rt = 6.89 min (2) | $^1$H NMR (400 MHz, DMSO-d6): δ 9.99 (bs, 1H), 7.91-7.89 (d, J = 7.6 Hz, 2H), 7.74-7.72 (d, J = 8.8 Hz, 1H), 7.62-7.58 (m, 4H), 6.11 (s, 1H), 4.62 (s, 2H), 3.73 (s, 3H), 1.26 (s, 9H). |
| 194 | 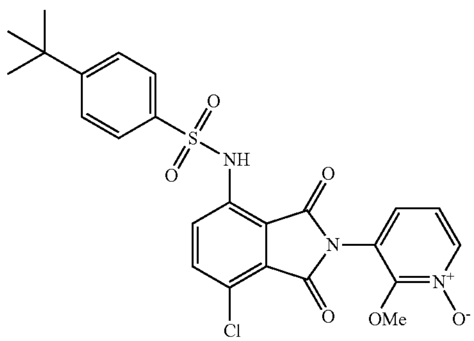 | 516.27 | 98.38% Rt = 5.36 min (1) | $^1$H NMR (400 MHz, DMSO-d6): δ 10.14 (bs, 1H), 8.42-8.41 (d, J = 6.4 Hz, 1H), 7.93-7.91 (d, J = 8.4 Hz, 2H), 7.85-7.84 (d, J = 7.2 Hz, 1H), 7.69-7.62 (m, 3H), 7.47-7.45 (d, J = 8 Hz, 1H), 7.37 (m, 1H), 3.98 (s, 3H), 1.27 (s, 9H). |
| 195 | 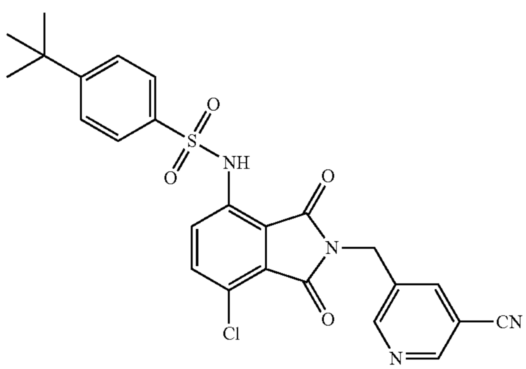 [SMILES: CC(C)(C)c1ccc(S(=O)(=O)Nc2ccc(Cl)c3c2C(=O)N(Cc2cncc(C#N)c2)C3=O)cc1] | 509.12 | 99.14% Rt = 6.92 min (1) | $^1$H NMR (400 MHz, DMSO-d6): δ 9.92 (bs, 1H), 8.94 (s, 1H), 8.88 (s, 1H), 8.30 (s, 1H), 7.94-7.92 (d, J = 8.2 Hz, 2H), 7.75-7.73 (d, J = 8.8 Hz, 1H), 7.63-7.59 (m, 3H), 4.82 (s, 2H), 1.26 (s, 9H). |
| 196 | 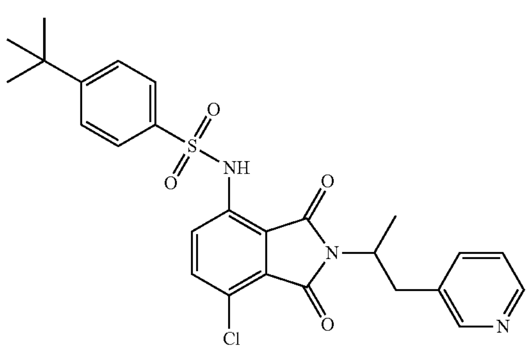 [SMILES: CC(Cc1cccnc1)N1C(=O)c2c(Cl)ccc(NS(=O)(=O)c3ccc(C(C)(C)C)cc3)c2C1=O] | 512.11 | 99.02% Rt = 6.62 min (1) | $^1$H NMR (400 MHz, DMSO-d6): δ 9.91 (bs, 1H), 8.35-8.34 (d, J = 4 Hz, 1H), 8.29 (s, 1H), 7.87-7.85 (d, J = 8 Hz, 2H), 7.71-7.68 (d, J = 8.8 Hz, 1H), 7.63-7.61 (d, J = 8 Hz, 2H), 7.58-7.56 (d, J = 8.8 Hz, 1H), 7.53-7.51 (d, J = 8.8 Hz, 1H), 7.24-7.21 (m, 1H), 4.42 (m, 1H), 3.18-3.12 (m, 1H), 3.05-3.01 (m, 1H), 1.43-1.41 (d, J = 6.8 Hz, 3H), 1.26 (s, 9H). |

| S. No. | Structure | LCMS (M + 1) | Purity (LCMS) | 1HNMR |
|---|---|---|---|---|
| 197 | 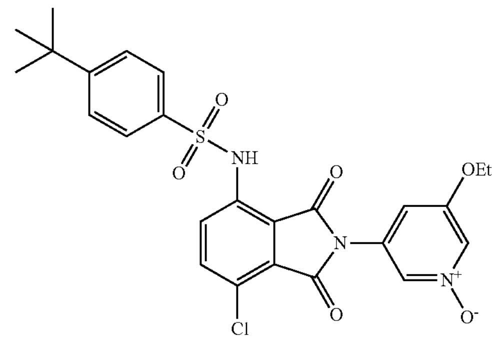 [SMILES: CCOc1cc(N2C(=O)c3c(Cl)ccc(NS(=O)(=O)c4ccc(C(C)(C)C)cc4)c3C2=O)c[n+]([O-])c1] | 530.26 | 99.63% Rt = 5.53 min (1) | ¹H NMR (400 MHz, DMSO-d6): δ 10.08 (bs, 1H), 8.17 (s, 1H), 7.99 (s, 1H), 7.95-7.93 (d, J = 8.4 Hz, 2H), 7.86-7.83 (d, J = 8.8 Hz, 1H), 7.69-7.67 (d, J = 8.8 Hz, 1H), 7.67-7.63 (m, 2H), 7.13-7.12 (m, 1H), 4.15-4.10 (q, J = 7.2 Hz, 6.8 Hz, 2H), 1.35-1.32 (t, 6.8 Hz, 3H), 1.27 (s, 9H). |
| 198 | 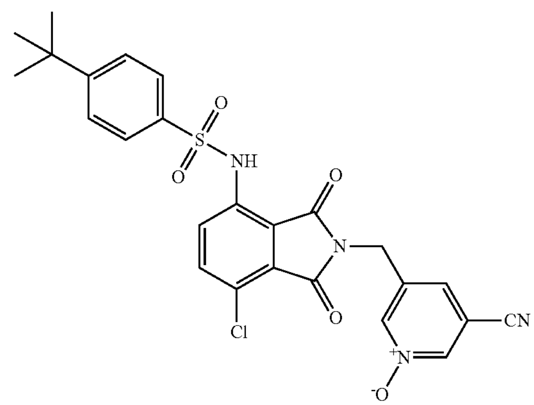 | 525.08 | 98.96% Rt = 6.44 min (2) | ¹H NMR (400 MHz, DMSO-d6): δ 9.91 (bs, 1H), 8.79 (s, 1H), 8.60 (s, 1H), 7.95-7.92 (d, J = 8.4 Hz, 2H), 7.84 (s, 1H), 7.75-7.73 (d, J = 8 Hz, 1H), 7.63-7.59 (m, 3H), 4.73 (s, 2H), 1.27 (s, 9H). |
| 199 | 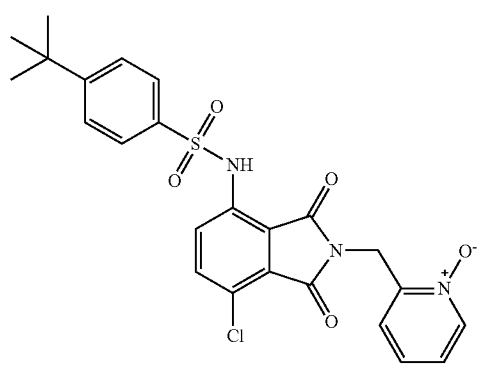 [SMILES: CC(C)(C)c1ccc(S(=O)(=O)Nc2ccc(Cl)c3c2C(=O)N(Cc2cccc[n+]2[O-])C3=O)cc1] | 500.04 | 99.22% Rt = 5.51 min (1) | ¹H NMR (400 MHz, DMSO-d6): δ 9.97 (bs, 1H), 8.34-8.32 (d, J = 6.4 Hz, 1H), 7.95-7.93 (d, J = 8.4 Hz, 2H), 7.78-7.76 (d, J = 8.8 Hz, 1H), 7.64-7.61 (m, 3H), 7.51-7.49 (d, J = 7.2 Hz, 1H), 7.42-7.39 (m, 1H), 7.31-7.28 (m, 1H), 4.77 (s, 2H), 1.27 (s, 9H). |
| 200 | 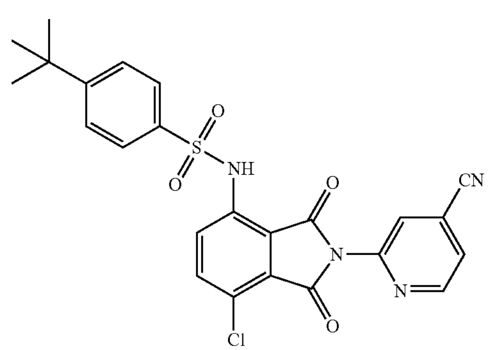 [SMILES: CC(C)(C)c1ccc(S(=O)(=O)Nc2ccc(Cl)c3c2C(=O)N(c2cc(C#N)ccn2)C3=O)cc1] | 495.05 | 96.34% Rt = 6.17 min (1) | ¹H NMR (400 MHz, DMSO-d6): δ 10.07 (bs, 1H), 8.93-8.91 (d, J = 4.8 Hz, 1H), 8.04-8.03 (d, J = 4.8 Hz, 1H), 7.95-7.90 (m, 3H), 7.87-7.85 (d, J = 8.8 Hz, 1H), 7.70-7.68 (d, J = 8.8 Hz, 1H), 7.64-7.62 (d, J = 8.4 Hz, 2H), 1.27 (s, 9H). |

| S. No. | Structure | LCMS (M + 1) | Purity (LCMS) | 1HNMR |
|---|---|---|---|---|
| 201 | 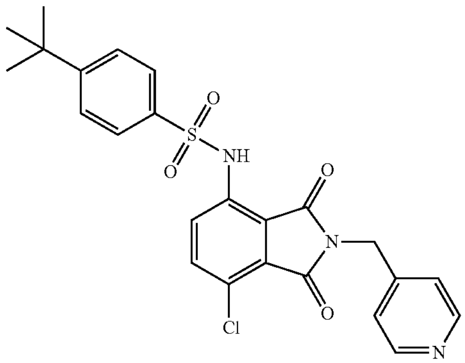 [SMILES: CC(C)(C)c1ccc(S(=O)(=O)Nc2ccc(Cl)c3c2C(=O)N(Cc2ccncc2)C3=O)cc1] | 484.08 | 95.90% Rt = 6.16 min (1) | ¹H NMR (400 MHz, DMSO-d6): δ 9.98 (bs, 1H), 8.51-8.50 (d, J = 5.2 Hz, 2H), 7.93-7.91 (d, J = 8.4 Hz, 2H), 7.77-7.74 (d, J = 8.8 Hz, 1H), 7.63-7.59 (m, 3H), 7.33-7.32 (d, J = 5.2 Hz, 2H), 4.74 (s, 2H), 1.27 (s, 9H). |
| 202 | 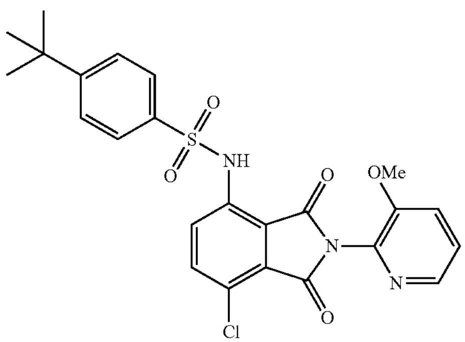 [SMILES: COc1cccnc1N1C(=O)c2c(Cl)ccc(NS(=O)(=O)c3ccc(C(C)(C)C)cc3)c2C1=O] | 500.08 | 98.26% Rt = 6.27 min (1) | ¹H NMR (400 MHz, DMSO-d6): δ 10.10 (bs, 1H), 8.20-8.19 (d, J = 4 Hz, 1H), 7.91-7.84 (m, 3H), 7.76-7.74 (d, J = 8 Hz, 1H), 7.68-7.66 (d, J = 8.4 Hz, 1H), 7.64-7.59 (m, 3H), 3.80 (s, 3H), 1.27 (s, 9H). |
| 203 | 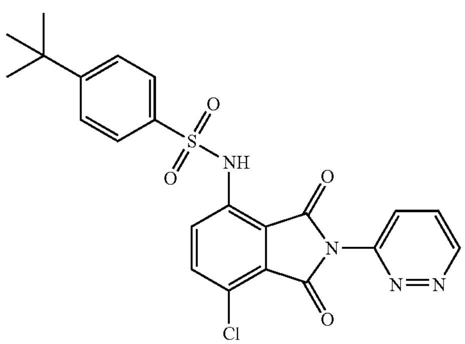 [SMILES: CC(C)(C)c1ccc(S(=O)(=O)Nc2ccc(Cl)c3c2C(=O)N(c2cccnn2)C3=O)cc1] | 471.07 | 99.51% Rt = 5.70 min (1) | ¹H NMR (400 MHz, DMSO-d6): δ 10.10 (bs, 1H), 9.37-9.36 (d, J = 3.6 Hz, 1H), 8.01-7.98 (m, 1H), 7.94-7.92 (d, J = 8.4 Hz, 2H), 7.87-7.85 (d, J = 8.4 Hz, 2H), 7.71-7.68 (d, J = 8.4 Hz, 2H), 7.65-7.63 (d, J = 9.2 Hz, 1H), 7.65-7.63 (d, J = 8 Hz, 2H), 1.27 (s, 9H). |
| 204 | 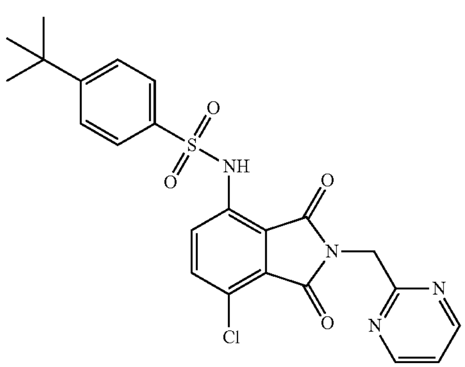 | 485.07 | 99.82% Rt = 6.20 min (1) | ¹H NMR (400 MHz, DMSO-d6): δ 10.06 (bs, 1H), 8.75-8.74 (m, 2H), 7.92-7.90 (d, J = 8.4 Hz, 2H), 7.81-7.79 (d, J = 8.8 Hz, 1H), 7.64-7.61 (m, 3H), 7.45-7.42 (m, 1H), 4.94 (s, 2H), 1.27 (s, 9H). |

| S. No. | Structure | LCMS (M + 1) | Purity (LCMS) | 1HNMR |
|---|---|---|---|---|
| 205 | 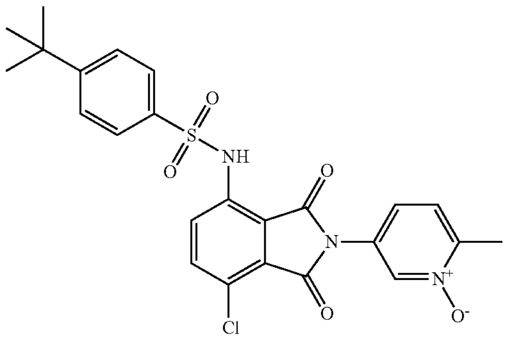 | 500.08 | 99.31% Rt = 5.45 min (1) | ¹H NMR (400 MHz, DMSO-d6): δ 10.04 (bs, 1H), 8.37 (s, 1H), 7.94-7.92 (d, J = 8 Hz, 2H), 7.80 (m, 1H), 7.68-7.62 (m, 4H), 7.36-7.34 (d, J = 8 Hz, 1H), 2.40 (s, 3H), 1.27 (s, 9H). |
| 206 | 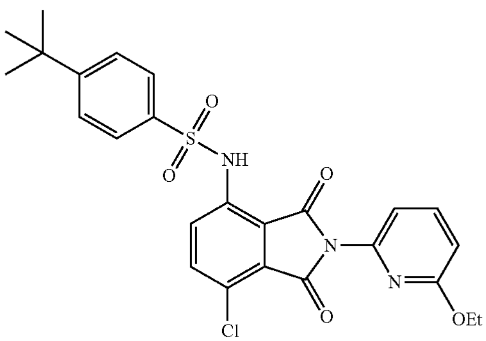 [SMILES: CCOc1cccc(N2C(=O)c3c(Cl)ccc(NS(=O)(=O)c4ccc(C(C)(C)C)cc4)c3C2=O)n1] | 514.05 | 99.53% Rt = 6.71 min (1) | ¹H NMR (400 MHz, DMSO-d6): δ 9.97 (bs, 1H), 8.16-8.15 (d, J = 2 Hz, 1H), 7.94-7.91 (d, J = 8.4 Hz, 2H), 7.82-7.80 (d, J = 9.2 Hz, 1H), 7.73-7.70 (dd, 6.6 Hz, 2.4 Hz, 1H), 7.68-7.63 (m, 3H), 6.97-6.94 (d, J = 8.4 Hz, 1H), 4.37-4.32 (q, J = 6.8 Hz, 7.2 Hz, 2H), 1.36-1.32 (t, J = 6.8 Hz, 3H), 1.27 (s, 9H). |
| 207 | 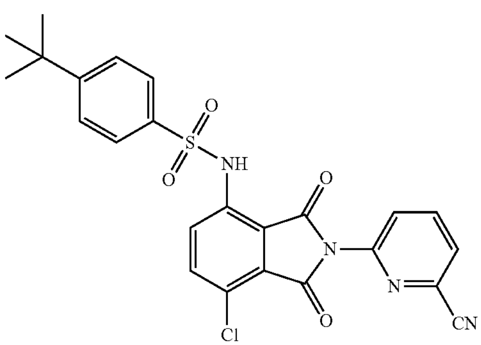 [SMILES: CC(C)(C)c1ccc(S(=O)(=O)Nc2ccc(Cl)c3c2C(=O)N(c2cccc(C#N)n2)C3=O)cc1] | 495.08 | 99.47% Rt = 6.24 min (1) | ¹H NMR (400 MHz, DMSO-d6): δ 10.07 (bs, 1H), 8.35-8.31 (m, 1H), 8.20-8.18 (d, J = 7.2 Hz, 1H), 7.92-7.90 (d, J = 8.4 Hz, 2H), 7.86-7.84 (d, 8.4 Hz, 2H), 7.70-7.68 (d, J = 8.4 Hz, 1H), 7.64-7.62 (d, J = 8.8 Hz, 2H), 1.27 (s, 9H). |
| 208 | 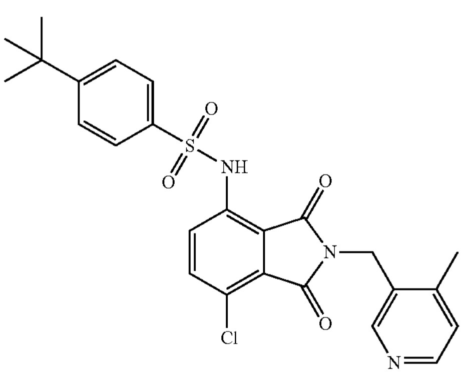 [SMILES: Cc1ccncc1CN1C(=O)c2c(Cl)ccc(NS(=O)(=O)c3ccc(C(C)(C)C)cc3)c2C1=O] | 498.38 | 99.26% Rt = 6.29 min (1) | ¹H NMR (400 MHz, DMSO-d6): δ 9.98 (bs, 1H), 8.41 (s, 1H), 8.35-8.33 (d, J = 5.2 Hz, 1H), 7.91-7.89 (d, J = 8.4 Hz, 2H), 7.74-7.72 (d, J = 9.2 Hz, 1H), 7.62-7.58 (m, 3H), 7.22-7.21 (d, J = 4.8 Hz, 1H), 4.72 (s, 2H), 2.36 (s, 3H), 1.26 (s, 9H). |

| S. No. | Structure | LCMS (M + 1) | Purity (LCMS) | 1HNMR |
|---|---|---|---|---|
| 209 | 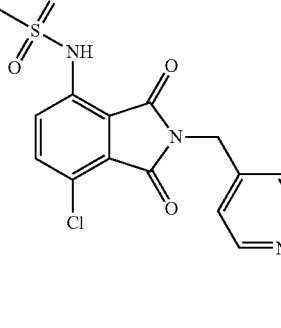 | 500.05 | 95.09% Rt = 5.35 min (1) | $^1$H NMR (400 MHz, DMSO-d6): δ 9.94 (bs, 1H), 8.16-8.14 (d, J = 6.8 Hz, 2H), 7.93-7.91 (d, J = 8.4 Hz, 2H), 7.76-7.74 (d, J = 8.8 Hz, 1H), 7.63-7.58 (m, 3H), 7.37-7.35 (d, J = 6.8 Hz, 2H), 4.68 (s, 2H), 1.26 (s, 9H). |
| 210 | 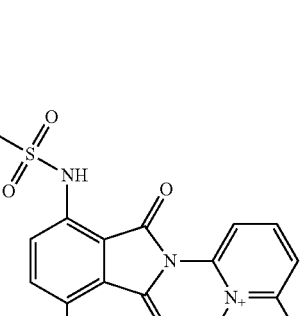 | 530.09 | 97.07% Rt = 5.28 min (1) | $^1$H NMR (400 MHz, DMSO-d6): δ 10.03 (bs, 1H), 8.34-8.33 (d, J = 2 Hz, 1H), 7.95-7.93 (d, J = 8.4 Hz, 2H), 7.83-7.81 (d, J = 8.8 Hz, 1H), 7.68-7.63 (m, 3H), 7.41-7.34 (m, 2H), 4.35-4.30 (q, J = 6.8 Hz, 7.2 Hz, 2H), 1.42-1.39 (t, J = 7.2 Hz, 3H), 1.27 (s, 9H). |
| 211 | 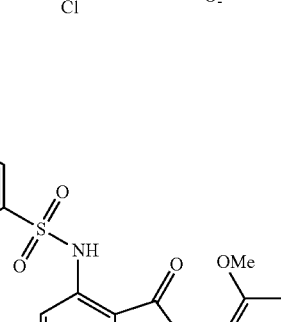 | 516.18 | 99.11% Rt = 6.46 min (2) | $^1$H NMR (400 MHz, DMSO-d6): δ 10.27 (bs, 1H), 8.16-8.15 (d, J = 6 Hz, 1H), 7.92-7.90 (m, 3H), 7.69-7.57 (m, 4H), 7.35-7.33 (d, J = 8.8 Hz, 1H), 3.87 (s, 3H), 1.28 (s, 9H). |
| 212 | 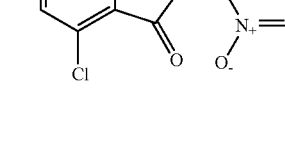 | 514.05 | 99.02% Rt = 6.30 min (1) | $^1$H NMR (400 MHz, DMSO-d6): δ 9.93 (bs, 1H), 8.40 (s, 1H), 8.34 (s, 1H), 7.93-7.91 (d, J = 8.4 Hz, 2H), 7.76-7.74 (d, J = 9.2 Hz, 1H), 7.70 (m, 1H), 7.63-7.61 (m, 3H), 4.81 (s, 2H), 3.88 (s, 3H), 1.26 (s, 9H). |

| S. No. | Structure | LCMS (M + 1) | Purity (LCMS) | 1HNMR |
|---|---|---|---|---|
| 213 | 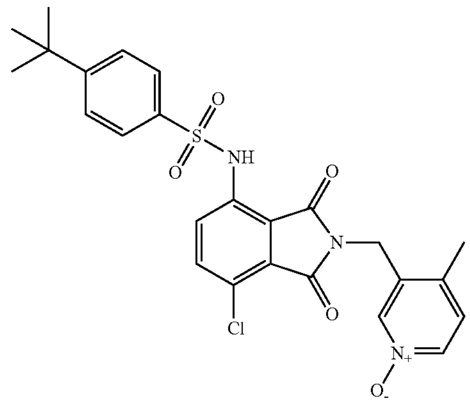 | 514.05 | 98.22% Rt = 5.50 min (1) | ¹H NMR (400 MHz, DMSO-d6): δ 9.93 (bs, 1H), 8.14 (s, 1H), 8.05-8.03 (d, J = 6.8 Hz, 1H), 7.93-7.91 (d, J = 8.8 Hz, 2H), 7.74-7.72 (d, J = 8.8 Hz, 1H), 7.63-7.58 (m, 3H), 7.25-7.23 (d, J = 6.8 Hz, 1H), 4.65 (s, 2H), 2.31 (s, 3H), 1.26 (s, 9H). |
| 214 | 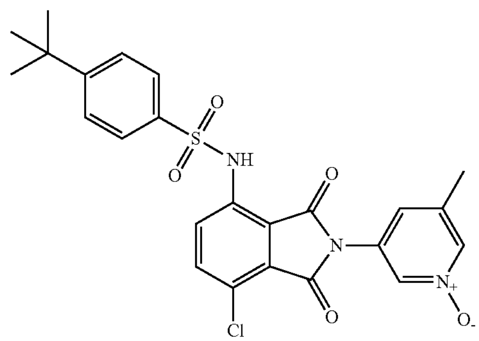 | 500.04 | 97.63% Rt = 6.33 min (2) | ¹H NMR (400 MHz, DMSO-d6): δ 10.05 (bs, 1H), 8.25 (s, 1H), 8.17 (s, 1H), 7.94-7.92 (d, J = 8.4 Hz, 2H), 7.85-7.83 (d, J = 8.8 Hz, 1H), 7.69-7.67 (d, J = 8.8 Hz, 1H), 7.65-7.63 (d, J = 8.4 Hz, 2H), 7.28 (s, 1H), 2.31 (s, 3H), 1.27 (S, 9H). |
| 215 | 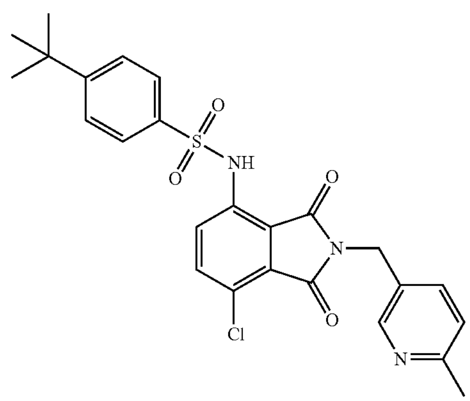 [SMILES: Cc1ccc(CN2C(=O)c3c(Cl)ccc(NS(=O)(=O)c4ccc(C(C)(C)C)cc4)c3C2=O)cn1] | 498.07 | 99.77% Rt = 6.34 min (1) | ¹H NMR (400 MHz, DMSO-d6): δ 9.94 (bs, 1H), 8.41 (s, 1H), 7.90-7.88 (d, J = 8.8 Hz, 2H), 7.73-7.71 (d, J = 8.8 Hz, 1H), 7.61-7.57 (m, 4H), 7.21-7.19 (d, J = 8 Hz, 1H), 4.68 (s, 2H), 2.42 (s, 3H), 1.26 (s, 9H). |
| 216 | 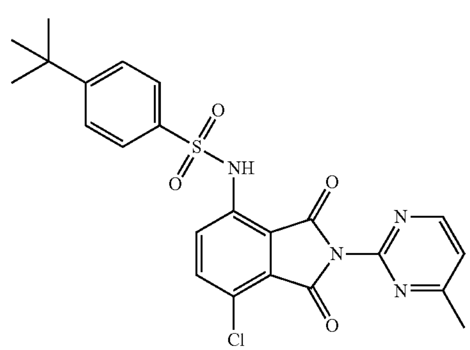 [SMILES: Cc1ccnc(N2C(=O)c3c(Cl)ccc(NS(=O)(=O)c4ccc(C(C)(C)C)cc4)c3C2=O)n1] | 485.05 | 99.04% Rt = 6.0 min (1) | ¹H NMR (400 MHz, DMSO-d6): δ 10.02 (bs, 1H), 8.86-8.84 (d, J = 5.2 Hz, 1H), 7.88-7.86 (m, 3H), 7.69-7.67 (6, J = 9.2 Hz, 1H), 7.62-7.57 (m, 3H), 2.55 (s, 3H), 1.26 (s, 9H). |

-continued

| S. No. | Structure | LCMS (M + 1) | Purity (LCMS) | 1HNMR |
|---|---|---|---|---|
| 217 | 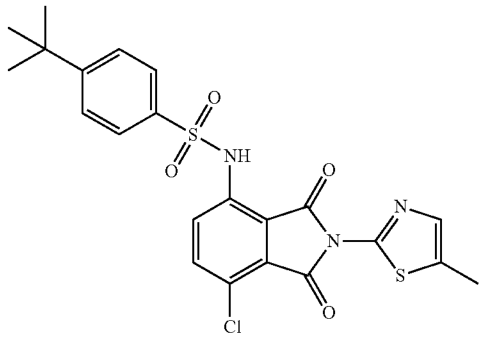 [SMILES: Cc1cnc(N2C(=O)c3c(Cl)ccc(NS(=O)(=O)c4ccc(C(C)(C)C)cc4)c3C2=O)s1] | 490.00 | 96.66% Rt = 4.72 min (2) | ¹H NMR (400 MHz, DMSO-d6): δ 10.08 (bs, 1H), 7.93-7.91 (d, J = 8 Hz, 2H), 7.83-7.81 (d, J = 8.8 Hz, 1H), 7.67-7.62 (m, 3H), 7.52 (s, 1H), 2.45 (s, 3H), 1.27 (s, 9H). |
| 218 | 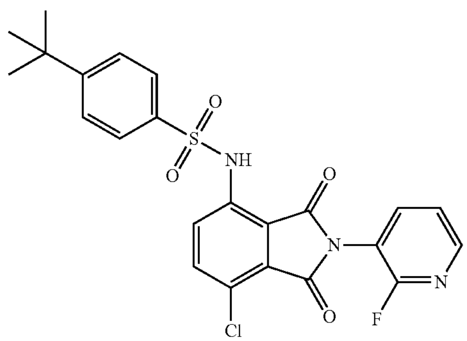 [SMILES: CC(C)(C)c1ccc(S(=O)(=O)Nc2ccc(Cl)c3c2C(=O)N(c2cccnc2F)C3=O)cc1] | 485.97 (M − 1) | 99.36% Rt = 6.20 min (1) | ¹H NMR (400 MHz, DMSO-d6): δ 10.10 (bs, 1H), 8.39-8.38 (d, J = 2.8 Hz, 1H), 8.12-8.10 (m, 1H), 7.91-7.89 (d, J = 8.4 Hz, 2H), 7.87-7.84 (d, J = 9.2 Hz, 1H), 7.72-7.69 (m, 1H), 7.63-7.58 (m, 3H), 1.27 (s, 9H). |
| 219 | 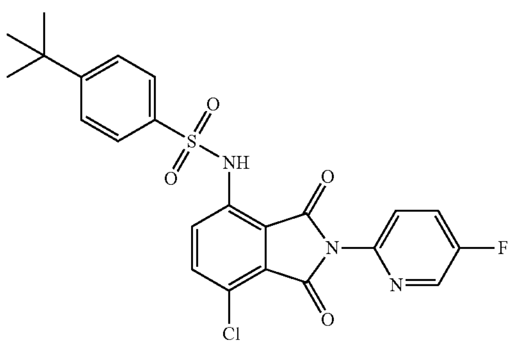 | 488.02 | 98.21% Rt = 6.27 min (1) | ¹H NMR (400 MHz, DMSO-d6): δ 9.98 (bs, 1H), 8.66 (m, 1H), 8.01-7.74 (m, 4H), 7.69-7.53 (m, 4H), 1.27 (s, 9H). |
| 220 | 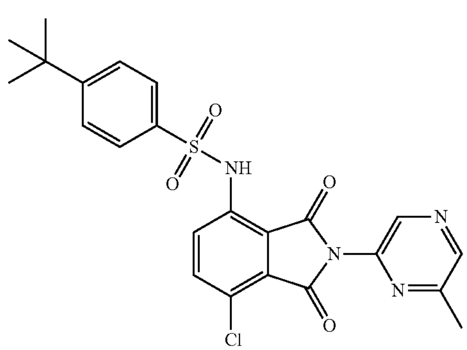 | 485.04 | 99.85% Rt = 6.06 min (1) | ¹H NMR (400 MHz, DMSO-d6): δ 10.07 (bs, 1H), 8.69 (s, 1H), 8.57 (s, 1H), 7.92-7.90 (d, J = 8.4 Hz, 2H), 7.86-7.84 (d, J = 8.4 Hz, 1H), 7.70-7.68 (d, J = 8.4 Hz, 1H), 7.64-7.62 (d, J = 8.4 Hz, 2H), 2.56 (s, 3H), 1.27 (s, 9H). |

| S. No. | Structure | LCMS (M + 1) | Purity (LCMS) | 1HNMR |
|---|---|---|---|---|
| 221 | 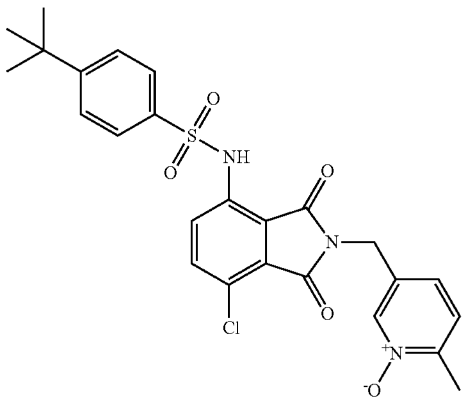 | 514.05 | 98.39% Rt = 5.55 min (1) | $^1$H NMR (400 MHz, DMSO-d6): δ 9.91 (bs, 1H), 8.30 (s, 1H), 7.93-7.90 (d, J = 8.4 Hz, 2H), 7.75-7.73 (d, J = 8.8 Hz, 1H), 7.63-7.58 (m, 3H), 7.44-7.42 (d, J = 8 Hz, 1H), 7.22-7.20 (d, J = 7.6 Hz, 1H), 4.67 (s, 2H), 2.31 (s, 3H), 1.26 (s, 9H). |
| 222 | 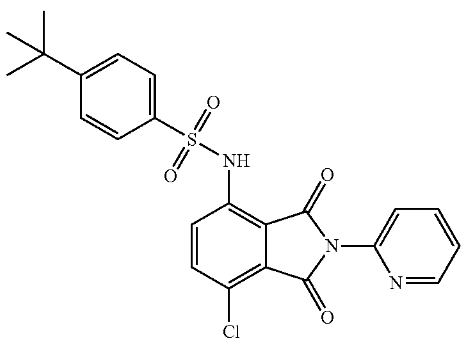 [SMILES: CC(C)(C)c1ccc(S(=O)(=O)Nc2ccc(Cl)c3c2C(=O)N(c2ccccn2)C3=O)cc1] | 470.02 | 97.71% Rt = 6.12 min (1) | $^1$H NMR (400 MHz, DMSO-d6): δ 9.98 (bs, 1H), 8.64-8.63 (d, J = 4.4 Hz, 1H), 8.06-8.02 (m, 1H), 7.93-7.90 (d, J = 8.4 Hz, 2H), 7.84-7.82 (d, J = 9.2 Hz, 1H), 7.69-7.67 (d, J = 8.8 Hz, 1H), 7.64-7.62 (d, J = 8.4 Hz, 2H), 7.55-7.49 (m, 2H), 1.27 (s, 9H). |
| 223 | 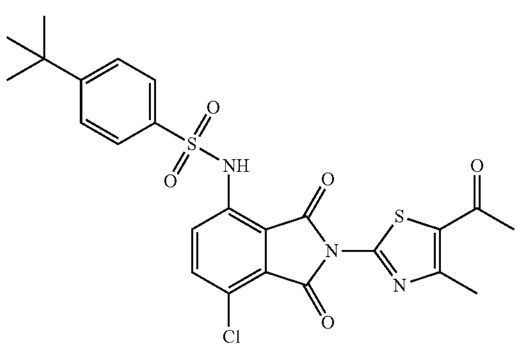 [SMILES: CC(=O)c1sc(N2C(=O)c3c(Cl)ccc(NS(=O)(=O)c4ccc(C(C)(C)C)cc4)c3C2=O)nc1C] | 532.02 | 92.58% Rt = 7.07 min (2) | $^1$H NMR (400 MHz, DMSO-d6): δ 10.17 (bs, 1H), 7.93-7.91 (d, J = 8 Hz, 2H), 7.81-7.77 (d, J = 9.2 Hz, 1H), 7.70-7.67 (d, J = 8.8 Hz, 1H), 7.63-7.61 (d, J = 8 Hz, 2H), 2.67 (s, 3H), 2.57 (s, 3H), 1.27 (s, 9H). |
| 224 | 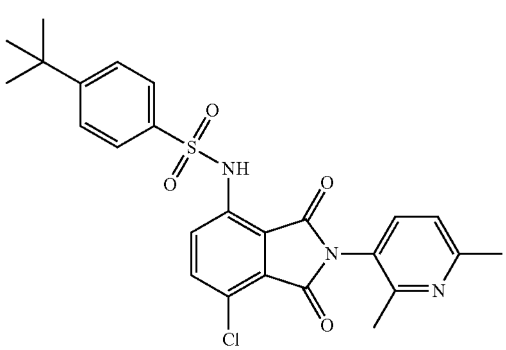 [SMILES: Cc1ccc(N2C(=O)c3c(Cl)ccc(NS(=O)(=O)c4ccc(C(C)(C)C)cc4)c3C2=O)c(C)n1] | 498.07 | 99.02% Rt = 6.22 min (1) | $^1$H NMR (400 MHz, DMSO-d6): δ 9.99 (bs, 1H), 7.92-7.90 (d, J = 8.4 Hz, 2H), 7.83-7.81 (d, J = 8.8 Hz, 1H), 7.69-7.66 (d, J = 9.2 Hz, 1H), 7.64-7.62 (m, 3H), 7.26-7.24 (d, J = 8 Hz, 1H), 2.48 (s, 3H), 2.24 (s, 3H), 1.27 (s, 9H). |

| S. No. | Structure | LCMS (M + 1) | Purity (LCMS) | 1HNMR |
|---|---|---|---|---|
| 225 | 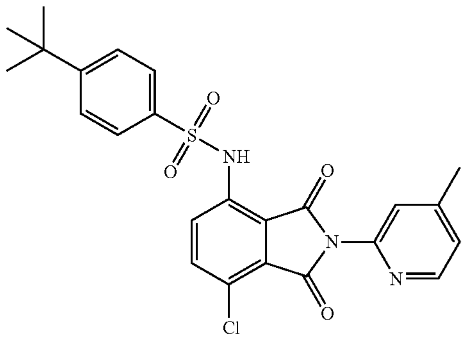 [SMILES: Cc1ccnc(N2C(=O)c3c(Cl)ccc(NS(=O)(=O)c4ccc(C(C)(C)C)cc4)c3C2=O)c1] | 484.06 | 97.84% Rt = 6.29 min (1) | ¹H NMR (400 MHz, DMSO-d6): δ 9.97 (bs, 1H), 8.48-8.47 (d, J = 4.8 Hz, 1H), 7.91-7.89 (d, J = 8.4 Hz, 2H), 7.84-7.82 (d, J = 8.4 Hz, 1H), 7.69-7.67 (d, J = 8.8 Hz, 1H), 7.64-7.62 (d, J = 8.4 Hz, 2H), 7.38-7.36 (d, J = 4.8 Hz, 1H), 7.32 (s, 1H), 2.40 (s, 3H), 1.27 (s, 9H). |
| 226 | 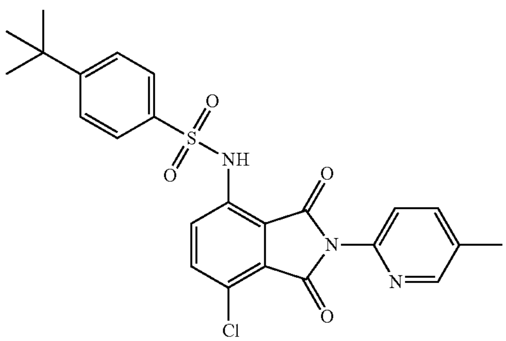 [SMILES: Cc1ccc(N2C(=O)c3c(Cl)ccc(NS(=O)(=O)c4ccc(C(C)(C)C)cc4)c3C2=O)nc1] | 484.06 | 99.58% Rt = 6.32 min (1) | ¹H NMR (400 MHz, DMSO-d6): δ 9.97 (bs, 1H), 8.46 (s, 1H), 7.92-7.90 (d, J = 8.4 Hz, 2H), 7.86-7.81 (m, 2H), 7.68-7.66 (d, J = 8.8 Hz, 1H), 7.64-7.62 (d, J = 8.4 Hz, 2H), 7.39-7.36 (d, J = 8 Hz, 1H), 2.38 (s, 3H), 1.27 (s, 9H). |
| 227 | 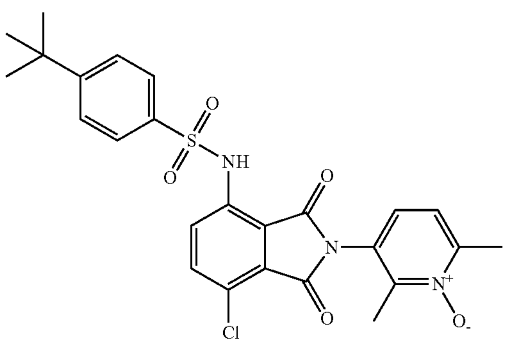 | 514.06 | 99.30% Rt = 5.57 min (1) | ¹H NMR (400 MHz, DMSO-d6): δ 10.02 (bs, 1H), 7.93-7.91 (d, J = 8.4 Hz, 2H), 7.84-7.82 (d, J = 8.8 Hz, 1H), 7.68-7.62 (m, 3H), 7.54-7.52 (d, J = 8.4 Hz, 1H), 7.33-7.31 (d, J = 8.8 Hz, 1H), 2.45 (s, 3H), 2.22 (s, 3H) 1.28 (s, 9H). |
| 228 | 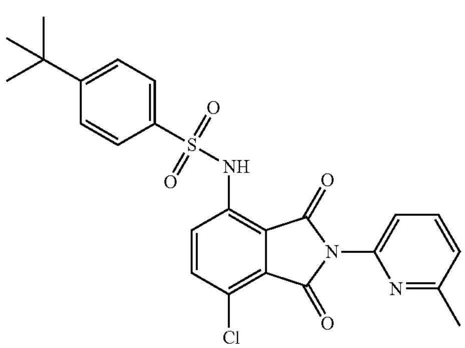 | 484.06 | 99.87% Rt = 6.32 min (1) | ¹H NMR (400 MHz, DMSO-d6): δ 9.98 (bs, 1H), 7.93-7.91 (m, 3H), 7.83-7.81 (d, J = 8.4 Hz, 1H), 7.68-7.66 (d, J = 8.4 Hz, 1H), 7.64-7.62 (d, J = 8.4 Hz, 2H), 7.40-7.39 (d, J = 7.2 Hz, 1H), 7.30-7.28 (d, J = 7.2 Hz, 1H), 2.45 (s, 3H), 1.27 (s, 9H). |

| S. No. | Structure | LCMS (M + 1) | Purity (LCMS) | 1HNMR |
|---|---|---|---|---|
| 229 | 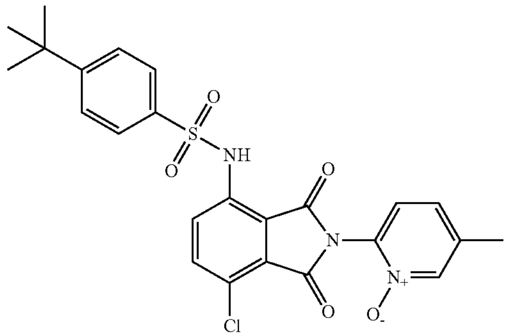 | 500.05 | 98.18% Rt = 5.50 min (1) | ¹H NMR (400 MHz, DMSO-d6): δ 10.18 (bs, 1H), 8.40 (s, 1H), 7.94-7.92 (d, J = 8.4 Hz, 2H), 7.89-7.86 (d, J = 9.2 Hz, 1H), 7.68-7.62 (m, 4H), 7.37-7.35 (d, J = 8.4 Hz, 1H), 2.33 (s, 3H), 1.28 (s, 9H). |
| 230 | 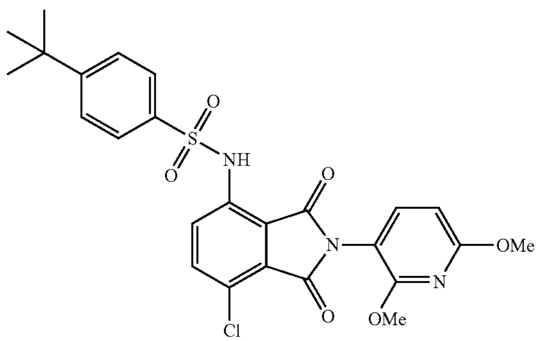 [SMILES: COc1ccc(N2C(=O)c3c(Cl)ccc(NS(=O)(=O)c4ccc(C(C)(C)C)cc4)c3C2=O)c(OC)n1] | 530.06 | 97.32% Rt = 6.74 min (1) | ¹H NMR (400 MHz, DMSO-d6): δ 10.04 (bs, 1H), 7.94-7.92 (d, J = 8.4 Hz, 2H), 7.83-7.81 (d, J = 8.8 Hz, 1H), 7.68-7.62 (m, 4H), 6.55-6.53 (d, J = 8.4 Hz, 1H), 3.92 (s, 3H), 3.84 (s, 3H), 1.28 (s, 9H). |
| 231 | 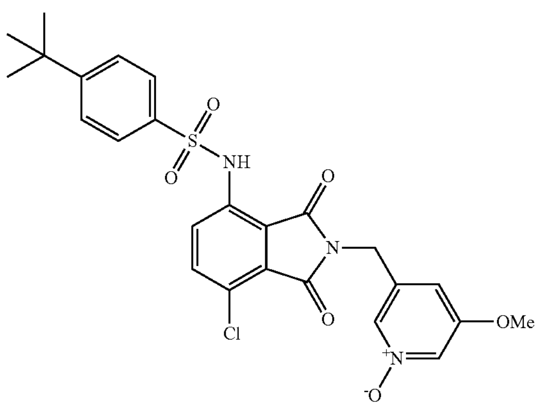 | 530.09 | 97.23% Rt = 5.59 min (1) | ¹H NMR (400 MHz, DMSO-d6): δ 9.91 (bs, 1H), 7.98-7.88 (m, 4H), 7.72-7.54 (m, 4H), 6.97 (s, 1H), 4.64 (s, 2H), 3.79 (s, 3H), 1.27 (s, 9H). |
| 232 | 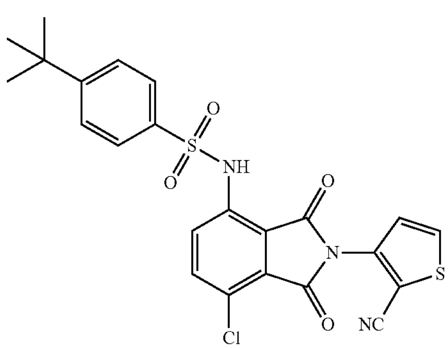 [SMILES: CC(C)(C)c1ccc(S(=O)(=O)Nc2ccc(Cl)c3c2C(=O)N(c2ccsc2C#N)C3=O)cc1] | 498.00 (M − 1) | 99.31% Rt = 6.22 min (1) | ¹H NMR (400 MHz, DMSO-d6): δ 10.11 (bs, 1H), 8.19-8.17 (d, J = 5.6 Hz, 1H), 7.93-7.91 (d, J = 8.4 Hz, 2H), 7.86-7.84 (d, J = 8.4 Hz, 1H), 7.70-7.68 (d, J = 8.4 Hz, 1H), 7.64-7.62 (d, J = 8.4 Hz, 2H), 7.30-7.29 (d, J = 5.2 Hz, 1H). 1.27 (s, 9H). |

| S. No. | Structure | LCMS (M + 1) | Purity (LCMS) | 1HNMR |
|---|---|---|---|---|
| 233 | 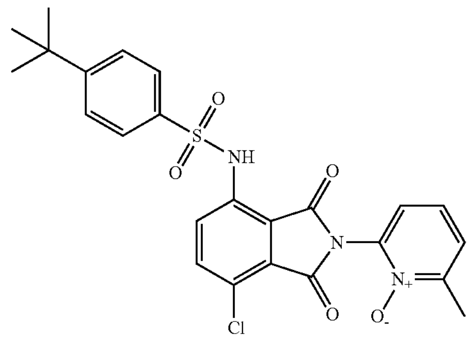 | 500.05 | 97.58% Rt = 6.59 min (2) | ¹H NMR (400 MHz, DMSO-d6): δ 10.15 (bs, 1H), 7.93-7.87 (m, 3H), 7.67-7.63 (m, 5H), 7.43 (m, 1H), 2.40 (s, 3H), 1.28 (s, 9H). |
| 234 | 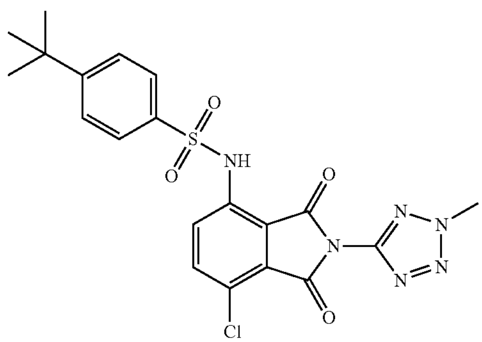 [SMILES: Cn1nnc(N2C(=O)c3c(Cl)ccc(NS(=O)(=O)c4ccc(C(C)(C)C)cc4)c3C2=O)n1] | 473.05 (M − 1) | 96.42% Rt = 5.83 min (1) | ¹H NMR (400 MHz, DMSO-d6): δ 10.14 (bs, 1H), 7.91-8.85 (m, 3H), 7.69-7.63 (m, 3H), 4.49 (s, 3H), 1.27 (s, 9H). |
| 235 | 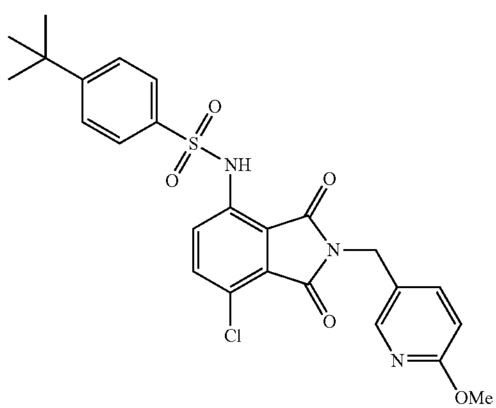 [SMILES: COc1ccc(CN2C(=O)c3c(Cl)ccc(NS(=O)(=O)c4ccc(C(C)(C)C)cc4)c3C2=O)cn1] | 514.09 | 99.34% Rt = 4.76 min (2) | ¹H NMR (400 MHz, DMSO-d6): δ 9.91 (bs, 1H), 8.13 (s, 1H), 7.90-7.88 (d, J = 8.4 Hz, 2H), 7.76-7.71 (m, 1H), 7.65-7.57 (m, 4H), 6.78-6.76 (d, J = 8.4 Hz, 1H), 4.64 (s, 2H), 3.81 (s, 3H), 1.25 (s, 9H). |
| 236 | 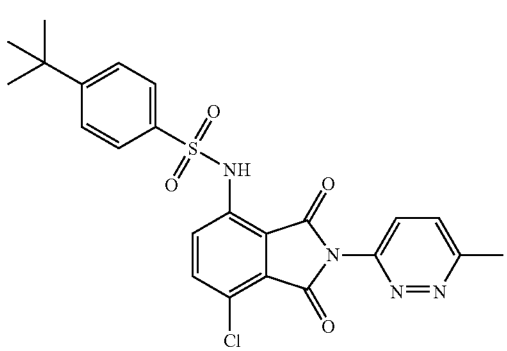 | 485.05 | 98.73% Rt = 6.64 min (2) | ¹H NMR (400 MHz, DMSO-d6): δ 10.10 (bs, 1H), 7.94-7.92 (d, J = 8.4 Hz, 2H), 7.85-7.83 (d, J = 8.4 Hz, 2H), 7.74-7.62 (m, 4H), 2.71 (s, 3H), 1.27 (s, 9H). |

| S. No. | Structure | LCMS (M + 1) | Purity (LCMS) | 1HNMR |
|---|---|---|---|---|
| 237 | 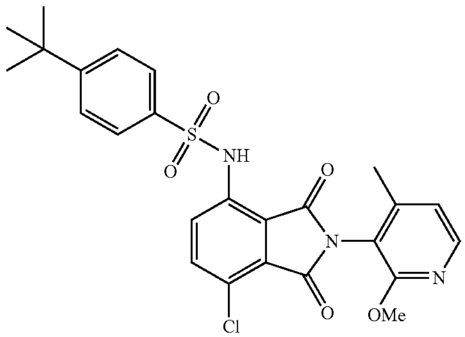 [SMILES: COc1nccc(C)c1N1C(=O)c2c(Cl)ccc(NS(=O)(=O)c3ccc(C(C)(C)C)cc3)c2C1=O] | 514.30 | 98.28% Rt = 6.52 min (1) | ¹H NMR (400 MHz, DMSO-d6): δ 10.12 (bs, 1H), 8.18-8.16 (d, J = 5.2 Hz, 1H), 7.92-7.89 (d, J = 8.4 Hz, 2H), 7.87-7.85 (d, J = 8.4 Hz, 1H), 7.69-7.67 (d, J = 8.4 Hz, 1H), 7.63-7.61 (d, J = 8.4 Hz, 2H), 7.08-7.07 (d, J = 5.2 Hz, 1H), 3.78 (s, 3H), 2.12 (s, 3H), 1.27 (s, 9H). |
| 238 | 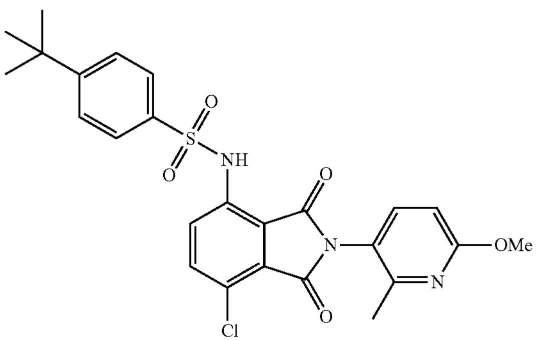 [SMILES: COc1ccc(N2C(=O)c3c(Cl)ccc(NS(=O)(=O)c4ccc(C(C)(C)C)cc4)c3C2=O)c(C)n1] | 514.29 | 97.64% Rt = 6.64 min (1) | ¹H NMR (400 MHz, DMSO-d6): δ 9.98 (bs, 1H), 7.92-7.90 (d, J = 8.4 Hz, 2H), 7.83-7.81 (d, J = 8.4 Hz, 1H), 7.68-7.57 (m, 4H), 6.80-6.78 (d, J = 8.4 Hz, 1H), 3.88 (s, 3H), 2.20 (s, 3H), 1.27 (s, 9H). |
| 239 | 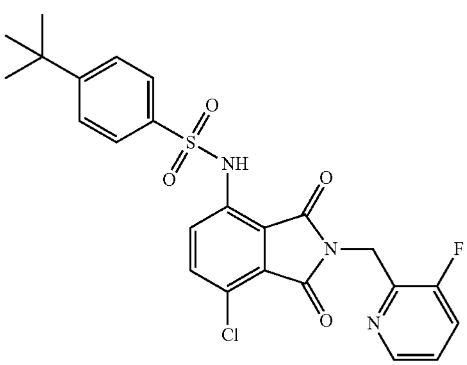 [SMILES: CC(C)(C)c1ccc(S(=O)(=O)Nc2ccc(Cl)c3c2C(=O)N(Cc2ncccc2F)C3=O)cc1] | 502.24 | 98.77% Rt = 6.51 min (1) | ¹H NMR (400 MHz, DMSO-d6): δ 10.07 (bs, 1H), 8.28-8.26 (d, J = 4.4 Hz, 1H), 7.92-7.90 (d, J = 8.4 Hz, 2H), 7.80-7.73 (m, 2H), 7.63-7.70 (m, 3H), 7.43-7.41 (m, 1H), 4.93 (s, 2H), 1.27 (s, 9H). |
| 240 | 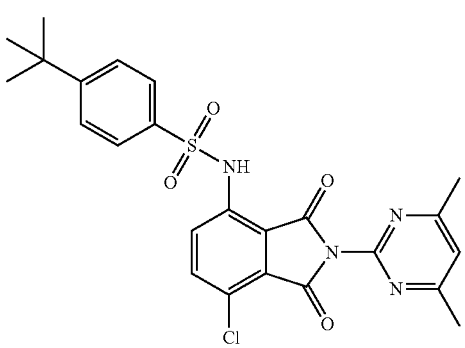 | 499.27 | 99.13% Rt = 6.13 min (1) | ¹H NMR (400 MHz, DMSO-d6): δ 10.04 (bs, 1H), 7.89-7.84 (m, 3H), 7.69-7.67 (d, J = 9.2 Hz, 1H), 7.63-7.61 (d, J = 8 Hz, 2H), 7.45 (s, 1H), 2.50 (s, 6H), 1.27 (s, 9H). |

| S. No. | Structure | LCMS (M + 1) | Purity (LCMS) | 1HNMR |
|---|---|---|---|---|
| 241 | 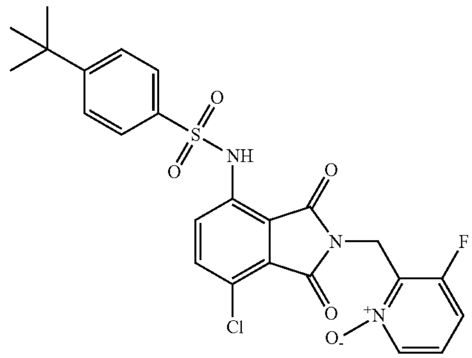 | 518.30 | 97.98% Rt = 5.82 min (1) | ¹H NMR (400 MHz, DMSO-d6): δ 10.00 (bs, 1H), 8.15-8.13 (d, J = 6.4 Hz, 1H), 7.86 (m, 2H), 7.70-7.54 (m, 4H), 7.47-7.37 (m, 2H), 4.87 (s, 2H), 1.27 (s, 9H). |
| 242 | 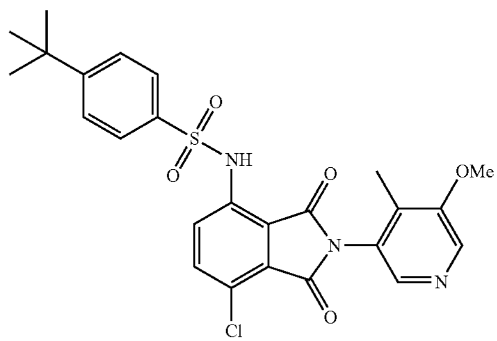 [SMILES: COc1cncc(N2C(=O)c3c(Cl)ccc(NS(=O)(=O)c4ccc(C(C)(C)C)cc4)c3C2=O)c1C] | 514.34 | 97.43% Rt = 6.21 min (1) | ¹H NMR (400 MHz, DMSO-d6): δ 10.01 (bs, 1H), 8.38 (s, 1H), 8.16 (s, 1H), 7.91-7.89 (d, J = 8.4 Hz, 2H), 7.83-7.81 (d, J = 8.8 Hz, 1H), 7.69-7.58 (m, 3H), 3.97 (s, 3H), 1.97 (s, 3H), 1.27 (s, 9H). |
| 243 | 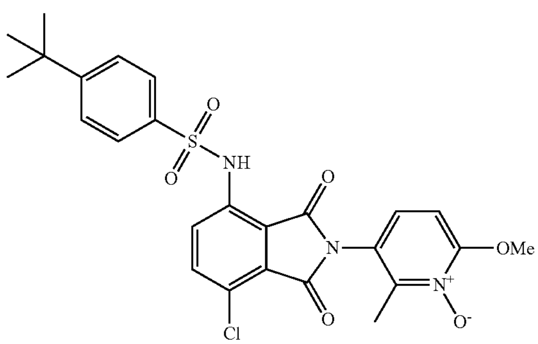 | 530.29 | 97.04% Rt = 5.22 min (1) | ¹H NMR (400 MHz, DMSO-d6): δ 10.02 (bs, 1H), 7.91-7.89 (d, J = 8 Hz, 2H), 7.75 (m, 1H), 7.66-7.60 (m, 3H), 7.41-7.39 (d, J = 9.2 Hz, 1H), 7.26-7.23 (d, J = 9.2 Hz, 1H), 4.03 (s, 3H), 2.19 (s, 3H), 1.27 (s, 9H). |
| 244 | 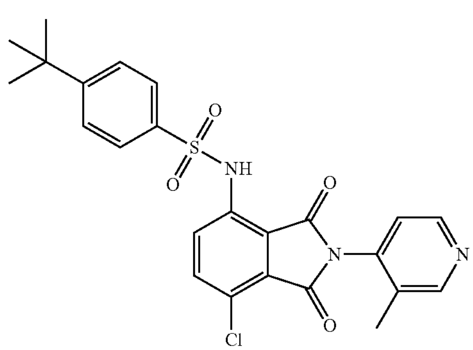 [SMILES: Cc1cnccc1N1C(=O)c2c(Cl)ccc(NS(=O)(=O)c3ccc(C(C)(C)C)cc3)c2C1=O] | 484.31 | 99.45% Rt = 6.03 min (1) | ¹H NMR (400 MHz, DMSO-d6): δ 10.03 (bs, 1H), 8.64 (s, 1H), 8.56-8.55 (d, J = 5.2 Hz, 1H), 7.92-7.90 (d, J = 8.4 Hz, 2H), 7.85-7.82 (d, J = 9.2 Hz, 1H), 7.70-7.67 (d, J = 8.8 Hz, 1H), 7.64-7.62 (d, J = 8.4 Hz, 2H), 7.39-7.37 (d, J = 5.2 Hz, 1H), 2.14 (s, 3H), 1.27 (s, 9H). |

| S. No. | Structure | LCMS (M + 1) | Purity (LCMS) | 1HNMR |
|---|---|---|---|---|
| 245 | 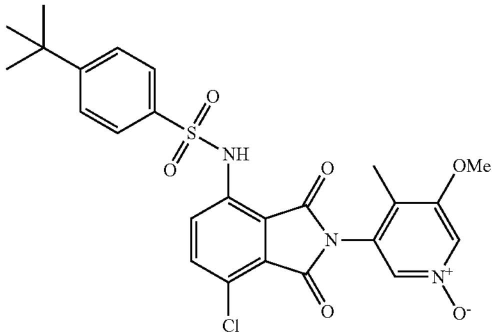 | 530.35 | 96.18% Rt = 5.53 min (1) | ¹H NMR (400 MHz, DMSO-d6): δ 10.07 (bs, 1H), 8.19 (s, 1H), 8.05 (s, 1H), 7.93-7.91 (d, J = 8.4 Hz, 2H), 7.84-7.82 (d, J = 8.4 Hz, 1H), 7.69-7.66 (d, J = 8.8 Hz, 1H), 7.64-7.62 (d, J = 8.4 Hz, 2H), 3.91 (s, 3H), 1.92 (s, 3H), 1.27 (s, 9H). |
| 246 | 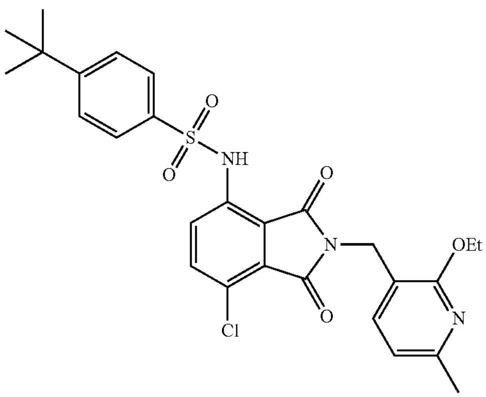 [SMILES: CCOc1nc(C)ccc1CN1C(=O)c2c(Cl)ccc(NS(=O)(=O)c3ccc(C(C)(C)C)cc3)c2C1=O] | 542.39 | 97.64% Rt = 4.87 min (1) | ¹H NMR (400 MHz, DMSO-d6): δ 9.88 (bs, 1H), 7.91-7.88 (d, J = 8.4 Hz, 2H), 7.76-7.74 (d, J = 8.4 Hz, 1H), 7.62-7.60 (m, 3H), 7.46-7.45 (d, J = 7.2 Hz, 1H), 6.76-6.74 (d, J = 7.6 Hz, 1H), 4.59 (s, 2H), 4.28-4.22 (q, J = 7.2 Hz, 6.8 Hz, 2H), 2.33 (s, 3H), 1.26 (s, 9H), 1.20-1.17 (t, J = 6.8 Hz, 3H). |
| 247 | 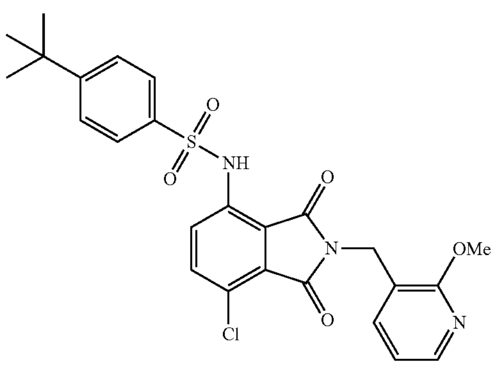 [SMILES: COc1ncccc1CN1C(=O)c2c(Cl)ccc(NS(=O)(=O)c3ccc(C(C)(C)C)cc3)c2C1=O] | 514.34 | 98.46% Rt = 6.71 min (1) | ¹H NMR (400 MHz, DMSO-d6): δ 9.94 (bs, 1H), 8.09 (m, 1H), 7.92-7.90 (d, J = 8.4 Hz, 2H), 7.76-7.74 (d, J = 8.4 Hz, 1H), 7.63-7.60 (m, 3H), 7.56-7.55 (d, J = 6.4 Hz, 1H), 6.93-6.90 (m, 1H), 4.62 (s, 2H), 3.88 (s, 3H), 1.26 (s, 9H). |
| 248 | 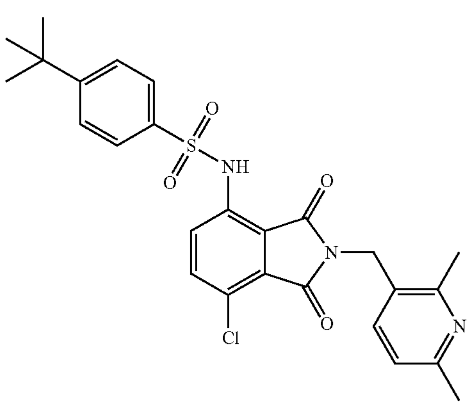 [SMILES: Cc1ccc(CN2C(=O)c3c(Cl)ccc(NS(=O)(=O)c4ccc(C(C)(C)C)cc4)c3C2=O)c(C)n1] | 512.32 | 99.27% Rt = 6.38 min (1) | ¹H NMR (400 MHz, DMSO-d6): δ 9.99 (bs, 1H), 7.91-7.89 (d, J = 8.4 Hz, 2H), 7.74-7.72 (d, J = 9.2 Hz, 1H), 7.61-7.58 (m, 3H), 7.48-7.46 (d, J = 7.6 Hz, 1H), 7.03-7.01 (d, J = 8 Hz, 1H), 4.66 (s, 2H), 2.49 (s, 3H), 2.38 (s, 3H), 1.26 (s, 9H). |

| S. No. | Structure | LCMS (M + 1) | Purity (LCMS) | 1HNMR |
|---|---|---|---|---|
| 249 | 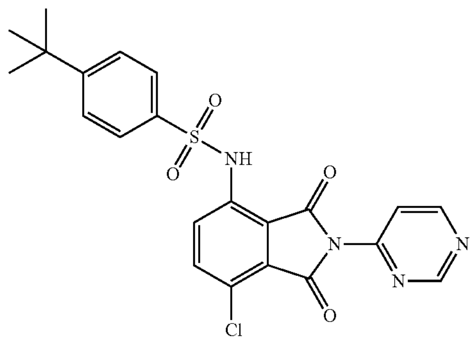 | 471.26 | 96.36% Rt = 5.64 min (1) | ¹H NMR (400 MHz, DMSO-d6): δ 10.09 (bs, 1H), 9.29 (s, 1H), 9.05-9.03 (d, J = 5.6 Hz, 1H), 7.94-7.91 (d, J = 8.4 Hz, 2H), 7.87-7.84 (d, J = 8.8 Hz, 1H), 7.70-7.68 (d, J = 8.8 Hz, 1H), 7.65-7.61 (m, 3H), 1.26 (s, 9H). |
| 250 | 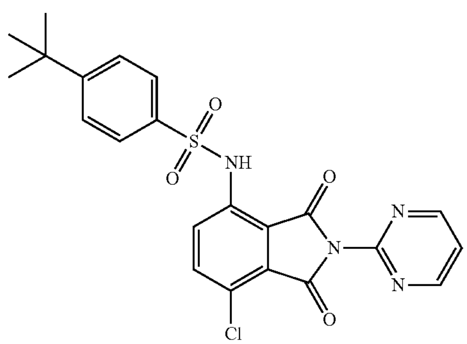 [SMILES: CC(C)(C)c1ccc(S(=O)(=O)Nc2ccc(Cl)c3c2C(=O)N(c2ncccn2)C3=O)cc1] | 471.28 | 99.25% Rt = 5.81 min (1) | ¹H NMR (400 MHz, DMSO-d6): δ 10.06 (bs, 1H), 9.04-9.03 (d, J = 4.8 Hz, 2H), 7.90-7.84 (m, 3H), 7.71-7.67 (m, 2H), 7.63-7.61 (d, J = 8.4 Hz, 2H), 1.26 (s, 9H). |
| 251 | 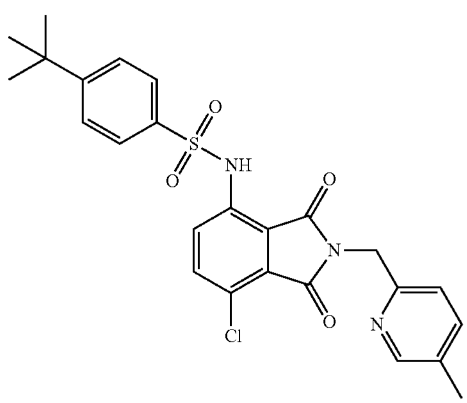 [SMILES: Cc1ccc(CN2C(=O)c3c(Cl)ccc(NS(=O)(=O)c4ccc(C(C)(C)C)cc4)c3C2=O)nc1] | 498.34 | 99.72% Rt = 6.52 min (1) | ¹H NMR (400 MHz, DMSO-d6): δ 9.98 (bs, 1H), 8.26 (s, 1H), 7.92-7.90 (d, J = 8.4 Hz, 2H), 7.78-7.76 (d, J = 8.8 Hz, 1H), 7.62-7.60 (m, 3H), 7.59-7.57 (d, J = 8 Hz, 1H), 7.30-7.29 (d, J = 7.6 Hz, 1H), 4.79 (s, 2H), 2.24 (s, 3H), 1.26 (s, 9H). |
| 252 | 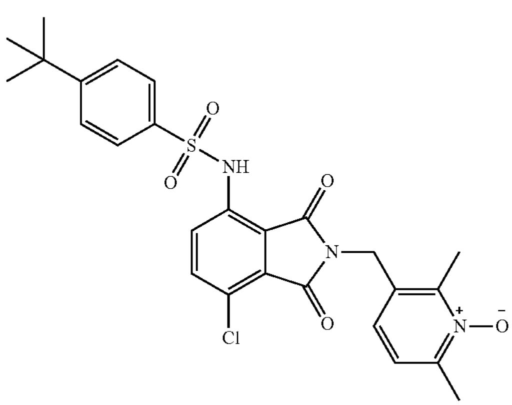 [SMILES: Cc1ccc(CN2C(=O)c3c(Cl)ccc(NS(=O)(=O)c4ccc(C(C)(C)C)cc4)c3C2=O)c(C)[n+]1[O-]] | 528.35 | 99.79% Rt = 5.70 min (1) | ¹H NMR (400 MHz, DMSO-d6): δ 9.95 (bs, 1H), 7.92-7.90 (d, J = 8.4 Hz, 2H), 7.76-7.73 (d, J = 8.8 Hz, 1H), 7.62-7.58 (m, 3H), 7.30-7.28 (d, J = 8 Hz, 1H), 7.15-7.13 (d, J = 8.4 Hz, 1H), 4.72 (s, 2H), 2.45 (s, 3H), 2.33 (s, 3H), 1.26 (s, 9H). |

-continued

| S. No. | Structure | LCMS (M + 1) | Purity (LCMS) | 1HNMR |
|---|---|---|---|---|
| 253 | 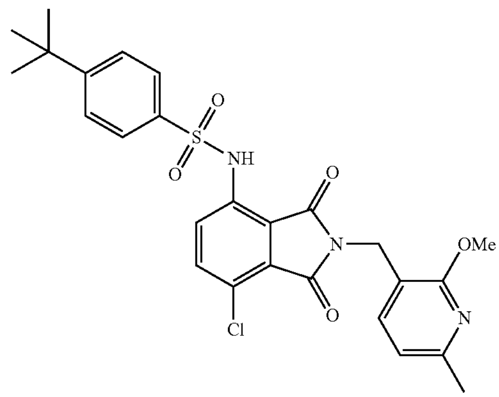 [SMILES: COc1nc(C)ccc1CN1C(=O)c2c(Cl)ccc(NS(=O)(=O)c3ccc(C(C)(C)C)cc3)c2C1=O] | 528.35 | 99.49% Rt = 5.44 min (1) | ¹H NMR (400 MHz, DMSO-d6): δ 9.92 (bs, 1H), 7.92-7.90 (d, J = 8 Hz, 2H), 7.76-7.74 (d, J = 8.8 Hz, 1H), 7.62-7.59 (m, 3H), 7.43-7.42 (d, J = 7.6 Hz, 1H), 6.77-6.75 (d, J = 7.2 Hz, 1H), 4.58 (s, 2H), 3.91 (s, 3H), 2.36 (s, 3H), 1.26 (s, 9H). |
| 254 | 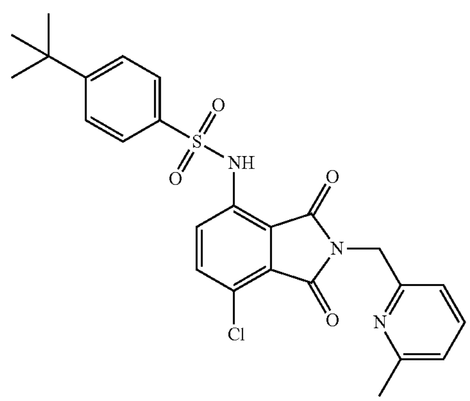 [SMILES: Cc1cccc(CN2C(=O)c3c(Cl)ccc(NS(=O)(=O)c4ccc(C(C)(C)C)cc4)c3C2=O)n1] | 498.32 | 97.29% Rt = 6.20 min (2) | ¹H NMR (400 MHz, DMSO-d6): δ 9.90 (bs, 1H), 7.92-7.90 (d, J = 8.4 Hz, 2H), 7.78-7.75 (d, J = 9.2 Hz, 1H), 7.63-7.57 (m, 4H), 7.14-7.13 (d, J = 6 Hz, 2H), 4.76 (s, 2H), 2.37 (s, 3H), 1.26 (s, 9H). |
| 255 | 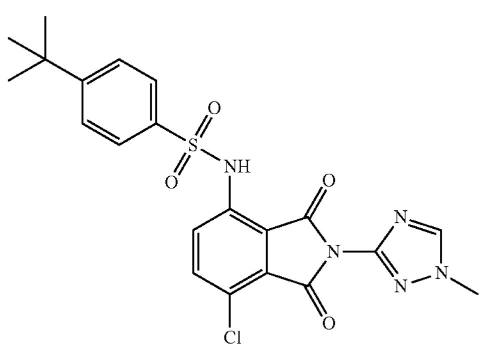 | 474.34 | 99.23% Rt = 5.63 min (1) | ¹H NMR (400 MHz, DMSO-d6): δ 10.02 (bs, 1H), 8.65 (s, 1H), 7.89-7.87 (m, 2H), 7.84-7.82 (m, 1H), 7.68-7.66 (m, 1H), 7.62-7.60 (m, 2H), 3.94 (s, 3H), 1.27 (s, 9H). |
| 256 | 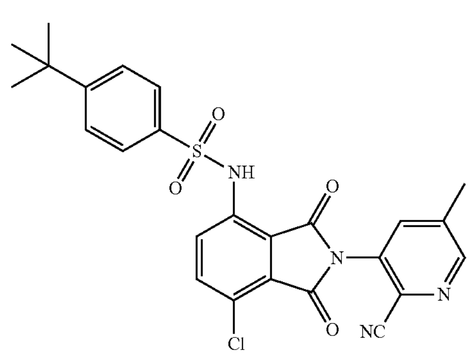 [SMILES: Cc1cnc(C#N)c(N2C(=O)c3c(Cl)ccc(NS(=O)(=O)c4ccc(C(C)(C)C)cc4)c3C2=O)c1] | 509.34 | 95.40% Rt = 6.17 min (1) | ¹H NMR (400 MHz, DMSO-d6): δ 10.20 (bs, 1H), 8.75 (s, 1H), 7.99 (s, 1H), 7.93-7.88 (m, 3H), 7.72-7.70 (d, J = 8.9 Hz, 1H), 7.64-7.62 (d, J = 8.5 Hz, 2H), 2.43 (s, 3H), 1.27 (s, 9H). |

| S. No. | Structure | LCMS (M + 1) | Purity (LCMS) | 1HNMR |
|---|---|---|---|---|
| 257 | 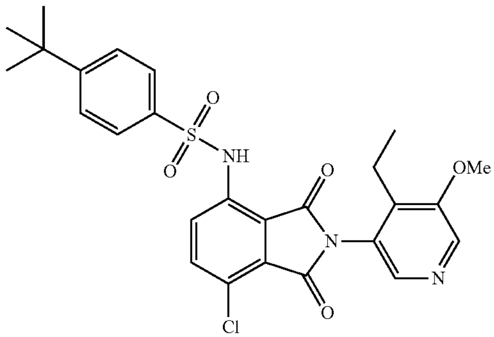 [SMILES: CCc1c(OC)cncc1N1C(=O)c2c(Cl)ccc(NS(=O)(=O)c3ccc(C(C)(C)C)cc3)c2C1=O] | 528.38 | 97.26% Rt = 6.46 min (1) | $^1$H NMR (400 MHz, DMSO-d6): δ 10.04 (bs, 1H), 8.42 (s, 1H), 8.16 (s, 1H), 7.93-7.91 (d, J = 8.5, 2H), 7.85-7.83 (d, J = 8.9 Hz 1H), 7.69-7.67 (d, J = 8.9 Hz, 1H), 7.64-7.62 (d, J = 8.9 Hz, 2H), 3.98 (s, 3H), 2.43-2.41 (q, J = 8.8 Hz, 2H), 1.27 (s, 9H), 0.97-0.93 (t, J = 7.2 Hz, 3H). |
| 258 | 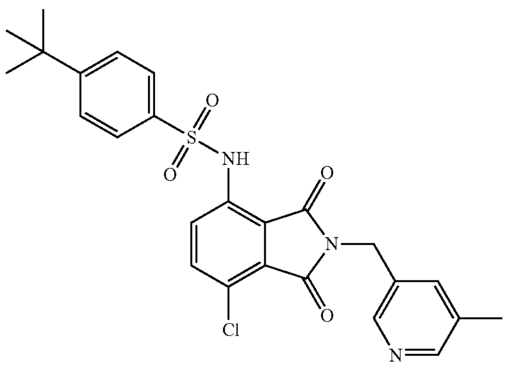 [SMILES: Cc1cncc(CN2C(=O)c3c(Cl)ccc(NS(=O)(=O)c4ccc(C(C)(C)C)cc4)c3C2=O)c1] | 498.36 | 99.50% Rt = 6.39 min (1) | $^1$H NMR (400 MHz, DMSO-d6): δ 9.95 (bs, 1H), 8.36-8.36 (d, J = 1.6 Hz, 2H), 7.92-7.90 (d, J = 8.6 Hz, 2H), 7.74-7.72 (d, J = 8.9 Hz, 1H), 7.62-7.60 (m, 3H), 7.54 (s, 1H), 4.69 (s, 2H), 2.26 (s, 3H), 1.26 (s, 9H). |
| 259 | 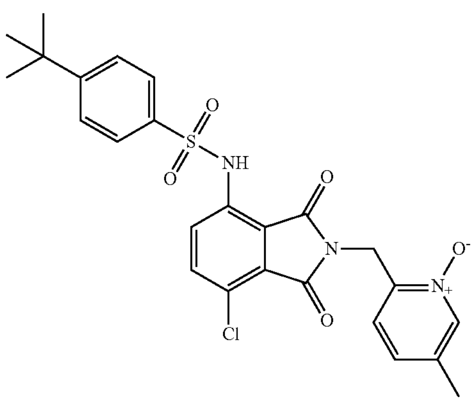 [SMILES: Cc1ccc(CN2C(=O)c3c(Cl)ccc(NS(=O)(=O)c4ccc(C(C)(C)C)cc4)c3C2=O)[n+]([O-])c1] | 514.38 | 98.04% Rt = 5.72 min (1) | $^1$H NMR (400 MHz, DMSO-d6): δ 9.97 (bs, 1H), 8.23 (s, 1H), 7.91-7.89 (d, J = 7.8 Hz, 2H), 7.70 (s, 1H), 7.61-7.59 (d, J = 7.6 Hz, 3H), 7.35-7.34 (d, J = 6.6 Hz, 1H), 7.15-7.13 (d, J = 7.7 Hz, 1H), 4.73 (s, 2H), 2.24 (s, 3H), 1.27 (s, 9H). |
| 260 | 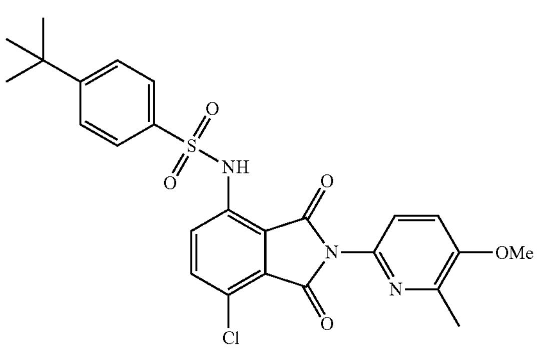 [SMILES: COc1ccc(N2C(=O)c3c(Cl)ccc(NS(=O)(=O)c4ccc(C(C)(C)C)cc4)c3C2=O)nc1C] | 514.38 | 97.80% Rt = 6.49 min (1) | $^1$H NMR (400 MHz, DMSO-d6): δ 9.94 (bs, 1H), 9.92-7.90 (d, J = 8.4 Hz, 2H), 7.82-7.80 (d, J = 8.8 Hz, 1H), 7.68-7.62 (m, 3H), 7.56-7.54 (s, 1H), 7.32-7.29 (d, J = 8.6 Hz, 1H), 3.89 (s, 3H), 2.36 (s, 3H), 1.27 (s, 9H). |

-continued

| S. No. | Structure | LCMS (M + 1) | Purity (LCMS) | 1HNMR |
|---|---|---|---|---|
| 261 | 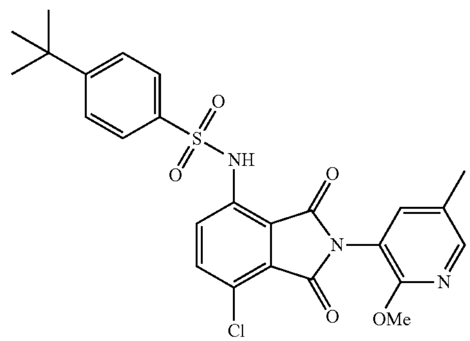 [SMILES: COc1ncc(C)cc1N1C(=O)c2c(Cl)ccc(NS(=O)(=O)c3ccc(C(C)(C)C)cc3)c2C1=O] | 514.38 | 98.58% Rt = 6.65 min (1) | $^1$H NMR (400 MHz, DMSO-d6): δ 10.04 (bs, 1H), 8.14 (s, 1H), 7.93-7.91 (d, J = 8.5 Hz, 2H), 7.84-7.26 (d, J = 8.8 Hz, 1H), 7.67-7.62 (m, 4H), 3.80 (s, 3H), 2.27 (s, 3H), 1.28 (s, 9H), |
| 262 | 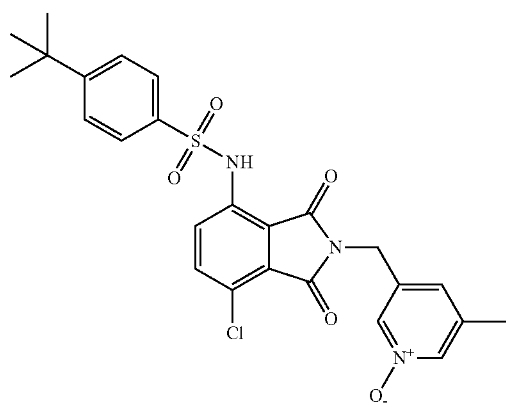 | 514.34 | 99.32% Rt = 5.55 min (1) | $^1$H NMR (400 MHz, DMSO-d6): δ 9.94 (bs, 1H), 8.10 (s, 1H), 8.04 (s, 1H), 7.94-7.92 (d, J = 8.3 Hz, 2H), 7.75-7.73 (d, J = 9.0 Hz, 1H), 7.63-7.58 (m, 3H), 7.14 (s, 1H), 4.64 (s, 2H), 2.20 (s, 3H), 1.26 (s, 9H). |
| 263 | 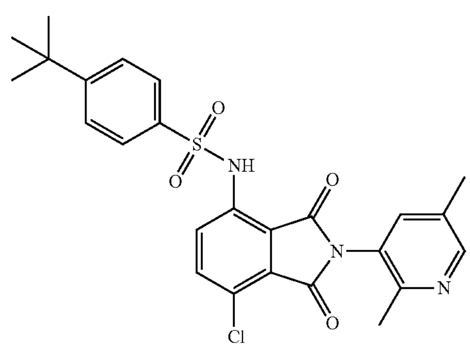 [SMILES: Cc1cnc(C)c(N2C(=O)c3c(Cl)ccc(NS(=O)(=O)c4ccc(C(C)(C)C)cc4)c3C2=O)c1] | 498.35 | 98.84% Rt = 6.31 min (1) | $^1$H NMR (400 MHz, DMSO-d6): δ 9.99 (bs, 1H), 8.41 (s, 1H), 7.91-7.89 (d, J = 8.4 Hz, 2H), 7.84-7.82 (d, J = 8.9 Hz, 1H), 7.69-7.67 (d, J = 8.9 Hz, 1H), 7.64-7.62 (d, J = 8.5 Hz, 2H), 7.58 (s, 1H), 2.30 (s, 3H), 2.25 (s, 3H), 1.27 (s, 9H) |
| 264 | 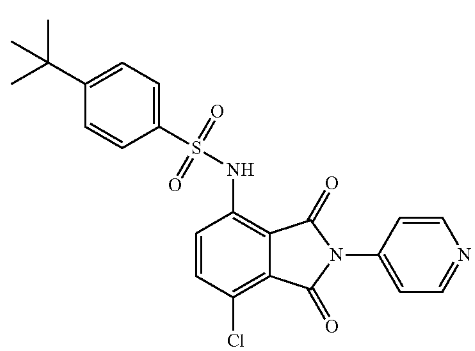 [SMILES: CC(C)(C)c1ccc(S(=O)(=O)Nc2ccc(Cl)c3c2C(=O)N(c2ccncc2)C3=O)cc1] | 470.31 | 99.76% Rt = 6.01 min (1) | $^1$H NMR (400 MHz, DMSO-d6): δ 10.03 (bs, 1H), 8.74-8.73 (d, J = 4.8 Hz, 2H), 7.94-7.92 (d, J = 8.4 Hz, 2H), 7.84-7.82 (d, J = 9.2, 1H), 7.69-7.63 (m, 3H), 7.50-7.49 (d, J = 5.2, 2H), 1.27 (s, 9H). |

-continued

| S. No. | Structure | LCMS (M + 1) | Purity (LCMS) | 1HNMR |
|---|---|---|---|---|
| 265 | 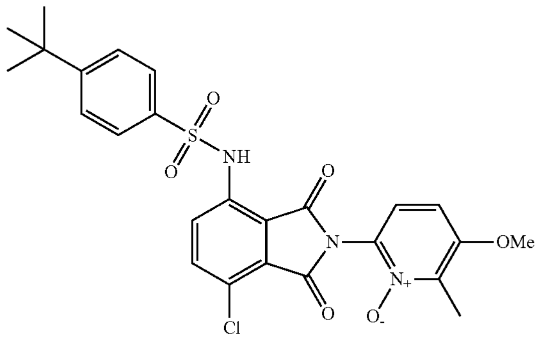 | 530.35 | 98.09% Rt = 5.76 min (1) | $^1$H NMR (400 MHz, DMSO-d6): δ 10.14 (bs, 1H), 7.94-7.91 (d, J = 8.5 Hz, 2H), 7.88-7.86 (d, J = 8.9 Hz, 1H), 7.69 (s, 1H), 7.67-7.61 (m, 2H), 7.58 (s, 1H), 7.26-7.23 (d, J = 9 Hz, 1H), 3.95 (s, 3H), 2.30 (s, 3H), 1.28 (s, 9H). |
| 266 | 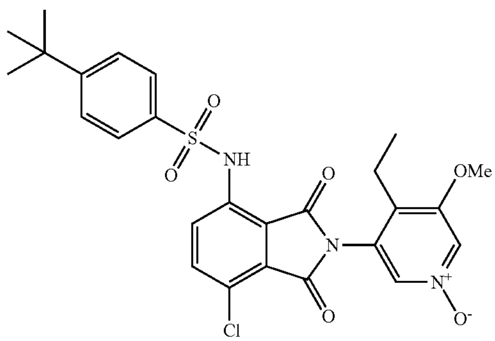 [SMILES: CCc1c(OC)c[n+]([O-])cc1N1C(=O)c2c(Cl)ccc(NS(=O)(=O)c3ccc(C(C)(C)C)cc3)c2C1=O] | 544.37 | 97.57% Rt = 5.71 min (1) | $^1$H NMR (400 MHz, DMSO-d6): δ 10.07 (bs, 1H), 8.22 (s, 1H), 8.09 (s, 1H), 7.94-7.92 (q, J = 8.8 Hz, 2H), 7.84-7.82 (d, J = 9.2 Hz, 1H), 7.69-7.67 (d, J = 9.2 Hz, 1H), 7.64-7.62 (d, J = 8.4 Hz, 2H), 3.92 (s, 3H), 2.41-2.32 (m, 2H), 1.28 (s, 9H), 0.95-0.92 (m, 3H). |
| 267 | 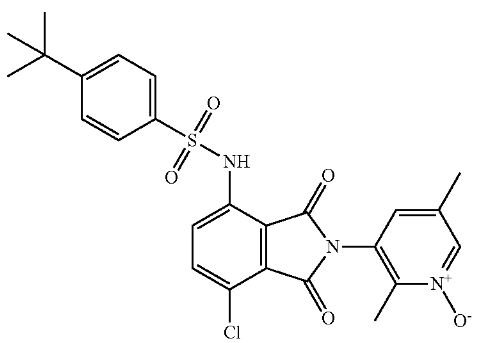 [SMILES: Cc1cc(N2C(=O)c3c(Cl)ccc(NS(=O)(=O)c4ccc(C(C)(C)C)cc4)c3C2=O)c(C)[n+]([O-])c1] | 514.38 | 99.27% Rt = 5.49 min (1) | $^1$H NMR (400 MHz, DMSO-d6): δ 10.04 (bs, 1H), 8.37 (s, 1H), 7.93-7.91 (d, J = 8.4 Hz, 2H), 7.84-7.82 (d, J = 8.8 Hz, 1H), 7.68-7.66 (d, J = 9.2 Hz, 1H), 7.64-7.62 (d, J = 8.8 Hz, 2H), 7.26 (s, 1H), 2.26 (s, 3H), 2.15 (s, 3H), 1.27 (s, 9H). |
| 268 | 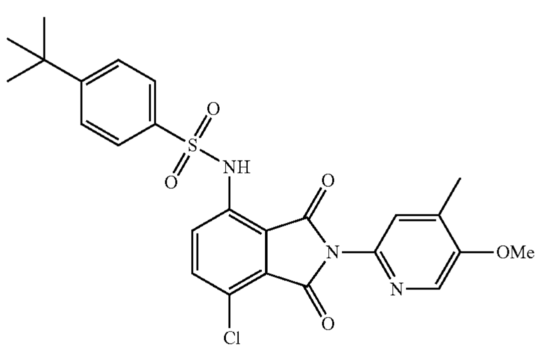 [SMILES: COc1cnc(N2C(=O)c3c(Cl)ccc(NS(=O)(=O)c4ccc(C(C)(C)C)cc4)c3C2=O)cc1C] | 514.38 | 95.83% Rt = 6.47 min (1) | $^1$H NMR (400 MHz, DMSO-d6): δ 9.96 (bs, 1H), 8.25 (s, 1H), 7.92-7.90 (d, J = 8.4 Hz, 2H), 7.83-7.81 (d, J = 8.8 Hz, 1H), 7.68-7.62 (m, 3H), 7.29 (s, 1H), 3.96 (s, 3H), 2.22 (s, 3H), 1.27 (s, 9H). |

| S. No. | Structure | LCMS (M + 1) | Purity (LCMS) | 1HNMR |
|---|---|---|---|---|
| 269 | 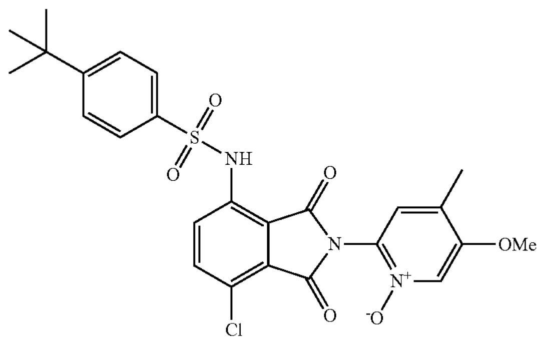 | 530.33 | 98.49% Rt = 5.67 min (1) | ¹H NMR (400 MHz, DMSO-d6): δ 10.15 (bs, 1H), 8.30 (s, 1H), 7.94-7.92 (d, J = 8.4 Hz, 2H), 7.89-7.86 (d, J = 9.2 Hz, 1H), 7.69-7.66 (d, J = 8.8 Hz, 1H), 7.65-7.63 (d, J = 8.4 Hz, 2H), 7.49 (s, 1H), 3.91 (s, 3H), 2.18 (s, 3H), 1.28 (s, 9H). |
| 270 | 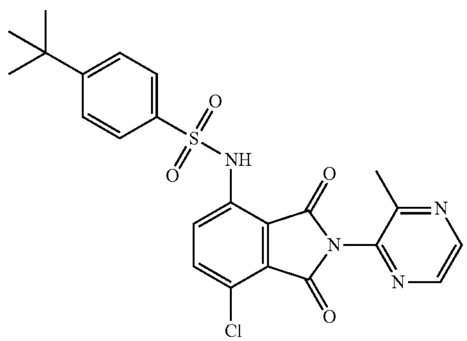 [SMILES: Cc1nccnc1N1C(=O)c2c(Cl)ccc(NS(=O)(=O)c3ccc(C(C)(C)C)cc3)c2C1=O] | 485.31 | 97.53% Rt = 6.04 min (1) | ¹H NMR (400 MHz, DMSO-d6): δ 10.08 (bs, 1H), 8.74 (d, J = 1.6 Hz, 1H), 8.61 (d, J = 1.6 Hz, 1H), 7.89-7.84 (m, 3H), 7.70-7.67 (d, J = 9.2 Hz, 1H), 7.62-7.60 (d, J = 8.4 Hz, 2H), 2.44 (s, 3H), 1.27 (s, 9H). |
| 271 | 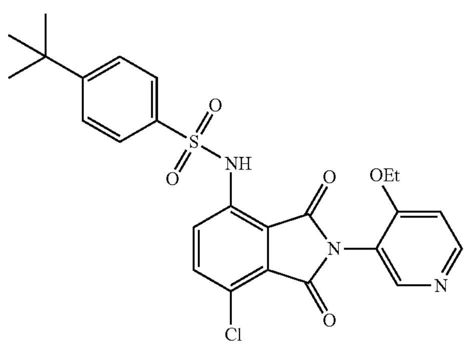 [SMILES: CCOc1ccncc1N1C(=O)c2c(Cl)ccc(NS(=O)(=O)c3ccc(C(C)(C)C)cc3)c2C1=O] | 514.33 | 99.57% Rt = 6.15 min (1) | ¹H NMR (400 MHz, DMSO-d6): δ 10.09 (bs, 1H), 8.55-8.54 (d, J = 5.6 Hz, 1H), 8.38 (s, 1H), 7.93-7.91 (d, J = 8.8 Hz, 2H), 7.85-7.83 (d, J = 8.8 Hz, 1H), 7.69-7.67 (d, J = 9.2 Hz, 1H), 7.64-7.62 (d, J = 8.8 Hz, 2H), 7.30-7.28 (d, J = 6.0 Hz, 1H), 4.19-4.14 (q, J = 6.8 Hz, 2H), 1.27 (s, 9H), 1.22-1.18 (t, J = 6.8 Hz, 3H). |
| 272 | 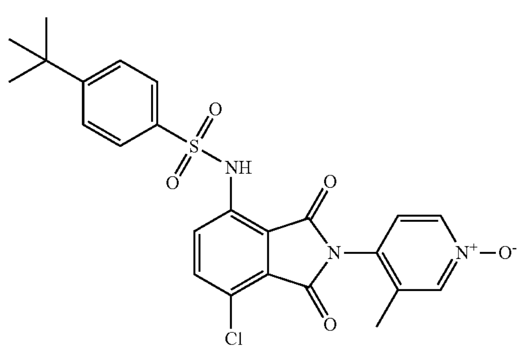 [SMILES: Cc1c[n+]([O-])ccc1N1C(=O)c2c(Cl)ccc(NS(=O)(=O)c3ccc(C(C)(C)C)cc3)c2C1=O] | 500.30 | 97.44% Rt = 5.33 min (1) | ¹H NMR (400 MHz, DMSO-d6): δ 10.04 (bs, 1H), 8.36 (s, 1H), 8.23-8.22 (d, J = 6.4 Hz, 1H), 7.93-7.91 (d, J = 8.4 Hz, 2H), 7.84-7.81 (d, J = 8.8 Hz, 1H), 7.69-7.67 (d, J = 8.8 Hz, 1H), 7.64-7.52 (d, J = 8.4 Hz, 2H), 7.41-7.40 (d, J = 6.8 Hz, 1H), 2.06 (s, 3H), 1.27 (s, 9H). |

| S. No. | Structure | LCMS (M + 1) | Purity (LCMS) | 1HNMR |
|---|---|---|---|---|
| 273 | 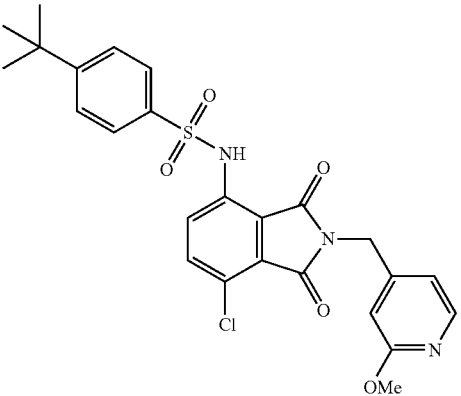 [SMILES: COc1cc(CN2C(=O)c3c(Cl)ccc(NS(=O)(=O)c4ccc(C(C)(C)C)cc4)c3C2=O)ccn1] | 514.34 | 99.73% Rt = 6.60 min (1) | $^1$H NMR (400 MHz, DMSO-d6): δ 9.93 (bs, 1H), 8.10-8.08 (d, J = 5.2 Hz, 1H), 7.92-7.90 (m, 2H), 7.76-7.74 (d, J = 8.8 Hz, 1H), 7.62-7.59 (m, 3H), 6.92-6.90 (d, J = 5.2 Hz, 1H), 6.74 (s, 1H), 4.68 (s, 2H), 3.81 (s, 3H), 1.26 (s, 9H). |
| 274 | 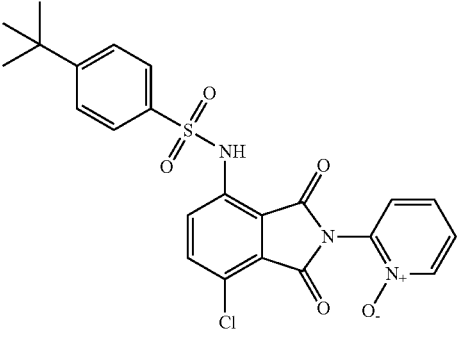 | 486.08 | 99.08% Rt = 5.34 min (1) | $^1$H NMR (400 MHz, DMSO-d6): δ 10.18 (bs, 1H), 8.49-8.48 (d, J = 6 Hz, 1H), 7.93-7.87 (m, 3H), 7.74-7.73 (d, J = 7.2 Hz, 1H), 7.69-7.61 (m, 4H), 7.54-7.50 (m, 1H), 1.28 (s, 9H). |
| 275 | 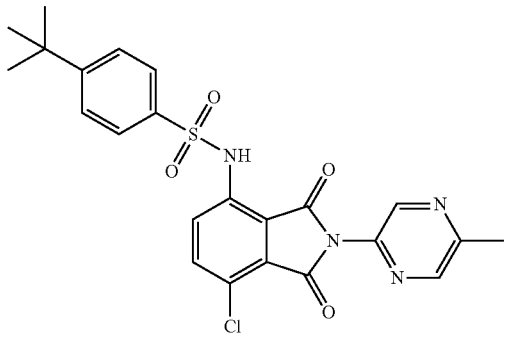 [SMILES: Cc1cnc(N2C(=O)c3c(Cl)ccc(NS(=O)(=O)c4ccc(C(C)(C)C)cc4)c3C2=O)cn1] | 485.32 | 99.59%, Rt = 6.08 min (1) | $^1$H NMR (400 MHz, DMSO-d6): δ 10.06 (bs, 1H), 8.64 (s, 1H), 8.63 (s, 1H), 7.93-7.91 (d, J = 8.4 Hz, 2H), 7.86-7.84 (d, J = 9.2 Hz, 1H), 7.69-7.67 (d, J = 9.2 Hz, 1H), 7.64-7.62 (d, J = 8.4 Hz, 2H), 2.59 (s, 3H), 1.27 (s, 9H). |
| 276 | 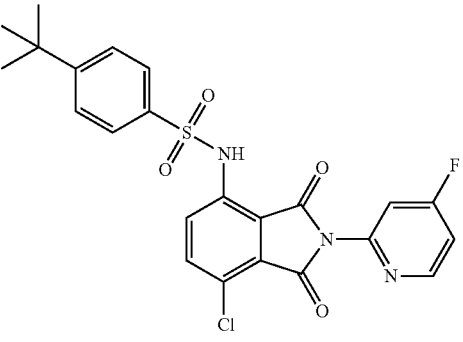 [SMILES: CC(C)(C)c1ccc(S(=O)(=O)Nc2ccc(Cl)c3c2C(=O)N(c2cc(F)ccn2)C3=O)cc1] | 488.27 | 99.27%, Rt = 6.18 min (1) | $^1$H NMR (400 MHz, DMSO-d6): δ 10.05 (bs, 1H), 8.71-8.67 (m, 1H), 7.92-7.90 (d, J = 8.4 Hz, 2H), 7.86-7.84 (d, J = 8.8 Hz, 1H), 7.70-7.67 (d, J = 8.8 Hz, 1H), 7.64-7.62 (d, J = 8.4 Hz, 2H), 7.54-7.51 (m, 1H), 7.48-7.45 (m, 1H), 1.27 (3, 9H). |

The following compounds were prepared essentially as in the methodology described in Example 10 using Compound 156 as the precursor to Compound 277, Compound 90 as the precursor to Compound 278, Compound 191 as the precursor to Compound 279 and Compound 65 as the precursor to Compound 280.

| S. No. | Structure | LCMS (M + 1) | Purity (LCMS) | 1HNMR |
|---|---|---|---|---|
| 277 | 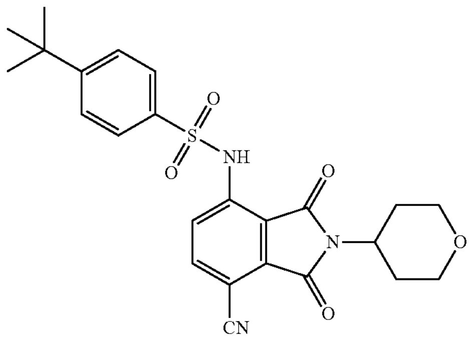 [SMILES: CC(C)(C)c1ccc(S(=O)(=O)Nc2ccc(C#N)c3c2C(=O)N(C2CCOCC2)C3=O)cc1] | 466.10 (M − 1) | 99.70% Rt = 5.32 (1) | ¹H NMR (400 MHz, DMSO-d6): δ 10.28 (bs, 1H), 8.07-8.05 (d, J = 7.6 Hz, 1H), 8.01-7.99 (d, J = 8 Hz, 2H), 7.68-7.63 (m, 3H), 4.2 (m, 1H), 3.93 (M, 2H), 3.39 (m, 2 H), 2.27 (m, 2H), 1.64 (m, 2H), 1.26 (s, 9H). |
| 278 | 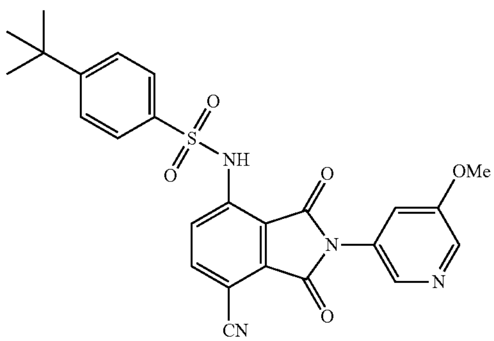 [SMILES: COc1cncc(N2C(=O)c3c(C#N)ccc(NS(=O)(=O)c4ccc(C(C)(C)C)cc4)c3C2=O)c1] | 491.08 | 96.92% Rt = 5.29 min (1) | ¹H NMR (400 MHz, DMSO-d6): δ 10.48 (bs, 1H), 8.40-8.39 (d, J = 2.4 Hz, 1H), 8.25 (s, 1H), 8.09 (s, 1H), 8.00-7.99 (d, J = 6.8 Hz, 2H), 7.75-7.73 (d, J = 8.4 Hz, 1H), 7.64-7.62 (d, J = 7.6 Hz, 2H), 7.54-7.50 (d, J = 14.8 Hz, 1H), 3.86 (s, 3H), 1.28 (s, 9H). |
| 279 | 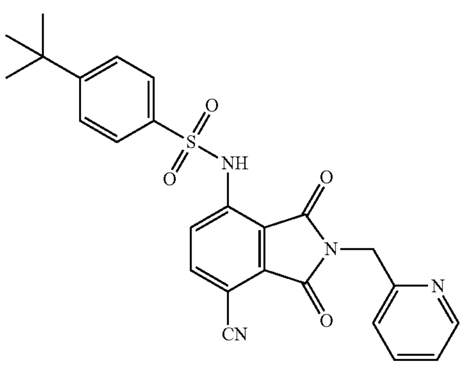 [SMILES: CC(C)(C)c1ccc(S(=O)(=O)Nc2ccc(C#N)c3c2C(=O)N(Cc2ccccn2)C3=O)cc1] | 475.12 | 92.53%, Rt = 5.30 min (1) | ¹H NMR (400 MHz, DMSO-d6): δ 10.49 (bs, 1H), 8.44 (m, 1H), 8.11-8.09 (d, J = 7.2 Hz, 1H), 8.03-8.00 (d, J = 8.4 Hz, 2H), 7.78 (m, 1H), 7.71-7.69 (d, J = 7.6 Hz, 1H), 7.65-7.63 (d, J = 8.4 Hz, 2H), 7.46-7.44 (d, J = 7.6 Hz, 1H), 7.30-7.28 (m, 1H), 4.87 (s, 2 H), 1.28 (s, 9H). |
| 280 | 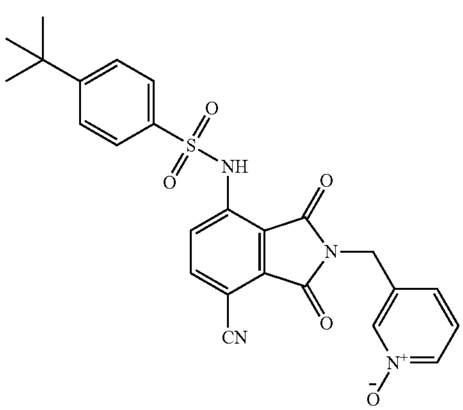 | 491.08 | 98.67%, Rt = 4.77 min (1) | ¹H NMR (400 MHz, DMSO-d6): δ 10.49 (bs, 1H), 8.28 (s, 1H), 8.14-8.13 (d, J = 6 Hz, 1H), 7.99-7.97 (m, 3H), 7.67-7.61 (m, 3H), 7.39-7.35 (m, 1H), 7.31-7.29 (d, J = 8 Hz, 1H), 4.72 (s, 2 H), 1.27 (s, 9H). |

Example 29

Synthesis of Compound 281 [4-(tert-butyl)-N-(7-chloro-1,3-dioxo-2-(2-oxo-1,2-dihydropyridin-3-yl)isoindolin-4-yl)benzenesulfonamide] and Compounds 282 to 285

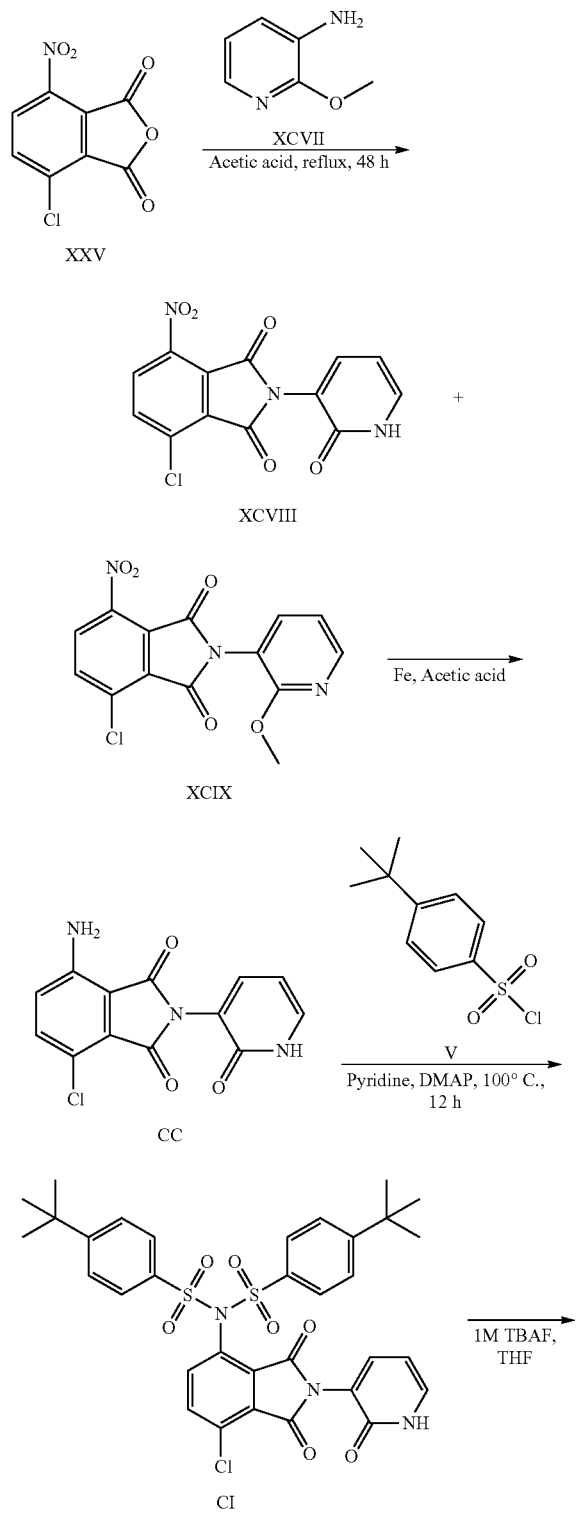

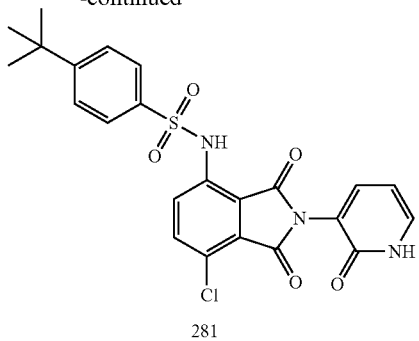

281

Synthesis of XCVIII:

To a stirred solution of compound XXV (5 g, 0.022 mol) in acetic acid (15 ml) was added 2-methoxypyridin-3-amine (XCVII, 2.18 g, 0.017 mol) and the reaction mixture was heated at 120° C. for 48 h. The reaction mixture was cooled to room temperature and the acetic acid was removed under reduced pressure to obtain crude product, a mixture of XCVIII and XCIX. The crude material obtained was triturated with ethanol to provide the desired product, 4-chloro-7-nitro-2-(2-oxo-1,2-dihydropyridin-3-yl)isoindoline-1,3-dione, as a black solid (XCVIII; 2.3 g; 32% yield). $^1$H NMR (400 MHz, DMSO-d6): δ 12.00 (bs, 1H), 8.36-8.34 (d, J=8.8 Hz, 1H), 8.21-8.19 (d, J=8.4 Hz, 1H), 7.68-7.65 (dd, J=2 Hz, 5.2 Hz, 1H), 7.60-7.59 (t, J=4.4 Hz, 1H), 6.39-7.35 (t, J=6.8 Hz, 1H). MS (M+1): 319.98

Synthesis of CC:

To a solution of compound XCVIII (4.1 g, 0.055 mol) in acetic acid (80 ml) under nitrogen atmosphere was added iron powder (3.5 g). The reaction mixture was stirred at room temperature for 12 h. This was filtered through a celite bed which was washed with ethyl acetate before the solvent was evaporated under reduced pressure to afford 4-amino-7-chloro-2-(2-oxo-1,2-dihydropyridin-3-yl)isoindoline-1,3-dione, as a yellow solid (C; 2.83 g; 76% yield). $^1$H NMR (400 MHz, DMSO-d6): δ 12.17 (bs, 1H), 7.64-7.62 (d, J=6.8 Hz, 1H), 7.54-7.53 (d, J=4.4 Hz, 1H), 7.48-7.46 (d, J=8.8 Hz, 1H), 7.06-7.04 (d, J=9.2 Hz, 1H), 6.68 (bs, 2H), 6.34-6.31 (t, J=6.8 Hz, 1H). MS (M+1): 289.97

Synthesis of 281: 4-(tert-butyl)-N-(7-chloro-1,3-dioxo-2-(2-oxo-1,2-dihydropyridin-3-yl)isoindolin-4-yl)benzenesulfonamide A solution of compound CC (2 g, 0.006 mol) in pyridine (40 ml) was stirred and cooled to 0° C. 4-(tert-butyl)benzenesulfonyl chloride (V; 6.41 g, 0.027 mmol) was added. The reaction mixture was stirred at 110° C. for 12 h and concentrated under reduced pressure before dilution with water. The resulting aqueous layer was extracted with ethyl acetate. The organic layer was washed successively with brine solution, dried over anhydrous Na$_2$SO$_4$, filtered and the organic solvent was evaporated under reduced pressure to obtain the crude compound CI. To this material was added 1M TBAF in THF solution (22 ml) and the resulting mixture was stirred for 3 h at room temperature. The reaction mixture was concentrated and diluted with ethyl acetate. The organic layer was washed with water, dried over anhydrous Na$_2$SO$_4$, filtered and the organic solvent was evaporated under reduced pressure to obtain the crude compound, which was purified by column chromatography using 45% ethyl acetate in hexane to afford the title compound, 4-(tert-butyl)-N-(7-chloro-1,3-dioxo-2-(2-oxo-1,2-dihydropyridin-3-yl)isoindolin-4-yl)benzenesulfonamide, as an off-white solid (281; 0.34 g, 16% yield). $^1$H NMR (400 MHz, DMSO-d6): $^1$H NMR (400 MHz, DMSO-d6): δ 12.25 (bs, 1H), 10.02 (bs, 1H), 7.93-7.91 (d, J=8.4 Hz, 2H), 7.83-7.81 (d, J=8 Hz, 1H), 7.66-7.57 (m, 5H), 6.36-6.33 (t, J=5.6 Hz, 1H), 1.27 (s, 9H). MS (M+1): 486.19. (LCMS purity 98.45%, RT=5.50 min) (1).

The following compounds were prepared in a similar manner as mentioned in above scheme using the appropriate amines in the first step:

| S. No. | Structure | LCMS (M + 1) | Purity (LCMS) | 1HNMR |
|---|---|---|---|---|
| 282 | 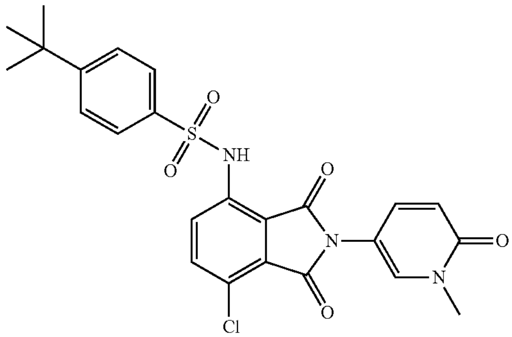 [SMILES: Cn1cc(N2C(=O)c3c(Cl)ccc(NS(=O)(=O)c4ccc(C(C)(C)C)cc4)c3C2=O)ccc1=O] | 500.33 | 99.50% Rt = 5.59 min (1) | $^1$H NMR (400 MHz, DMSO-d6): δ 9.95 (bs, 1H), 7.94-7.92 (d, J = 8.8 Hz, 2H), 7.88-7.87 (d, J = 2.4 Hz, 1H), 7.82-7.80 (d, J = 8 Hz, 1H), 7.67-7.63 (m, 3H), 7.45-7.42 (m, 1H), 6.50-6.48 (d, J = 5.6 Hz, 1H), 3.46 (s, 3H), 1.27 (s, 9H). |
| 283 | 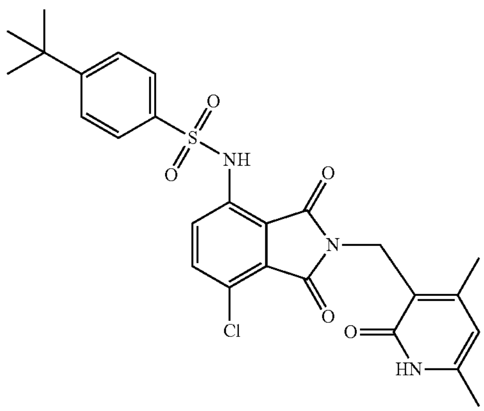 [SMILES: Cc1cc(C)c(CN2C(=O)c3c(Cl)ccc(NS(=O)(=O)c4ccc(C(C)(C)C)cc4)c3C2=O)c(=O)[nH]1] | 528.31 | 97.31% Rt = 6.08 min (1) | $^1$H NMR (400 MHz, DMSO-d6): δ 11.35 (bs, 1H), 9.93 (bs, 1H), 7.92-7.90 (d, J = 8.4 Hz, 2H), 7.71-7.69 (d, J = 8.8 Hz, 1H), 7.62-7.60 (d, J = 8.4 Hz, 2H), 7.56-7.53 (d, J = 8.8 Hz, 1H), 5.84 (s, 1H), 4.51 (s, 2H), 2.19 (s, 3H), 2.08 (s, 3H), 1.27 (s, 9H). |
| 284 | 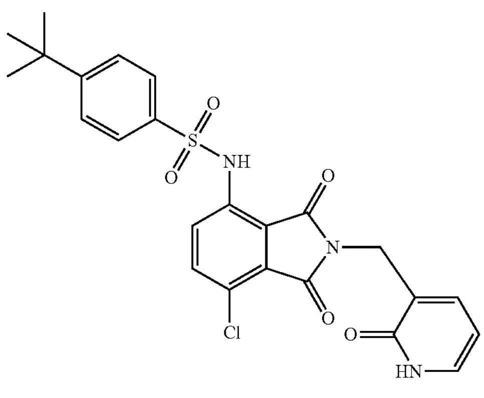 [SMILES: CC(C)(C)c1ccc(S(=O)(=O)Nc2ccc(Cl)c3c2C(=O)N(Cc2ccc[nH]c2=O)C3=O)cc1] | 500.31 | 97.59% Rt = 5.71 min (1) | $^1$H NMR (400 MHz, DMSO-d6): δ 11.74 (bs, 1H), 9.94 (bs, 1H), 7.93-7.91 (d, J = 8 Hz, 2H), 7.75-7.73 (d, J = 8.8 Hz, 1H), 7.63-7.59 (m, 3H), 7.32-7.27 (m, 2H), 6.12-6.09 (m, 1H), 4.44 (s, 2H), 1.26 (s, 9H). |
| 285 | 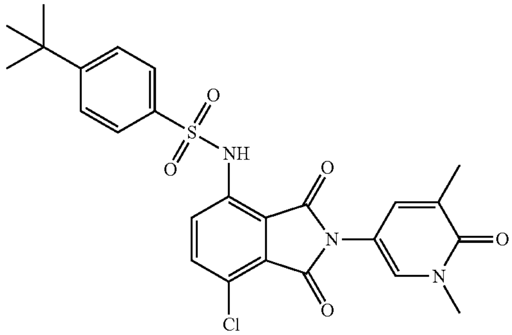 [SMILES: Cc1cc(N2C(=O)c3c(Cl)ccc(NS(=O)(=O)c4ccc(C(C)(C)C)cc4)c3C2=O)cn(C)c1=O] | 514.34 | 96.76% Rt = 5.83 min (1) | $^1$H NMR (400 MHz, DMSO-d6): δ 9.93 (bs, 1H), 7.93-7.91 (d, J = 8.24 Hz, 2H), 7.81-7.79 (d, J = 8.64 Hz, 1H), 7.73 (s, 1H), 7.67-7.63 (m, 3H), 7.32 (s, 1H), 3.47 (s, 3H), 2.02 (s, 3H), 1.27 (s, 9H). |

Example 30
Synthesis of Compound 286 [ethyl 3-(4-((4-(tert-butyl)phenyl)sulfonamido)-7-chloro-1,3-dioxoisoindolin-2-yl)picolinate]; Compound 287 [3-(4-((4-(tert-butyl)phenyl)sulfonamido)-7-chloro-1,3-dioxoisoindolin-2-yl)picolinic acid] and Compounds 288 to 292
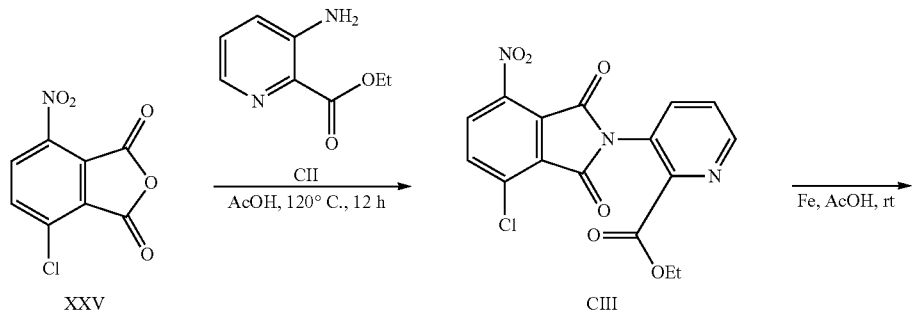
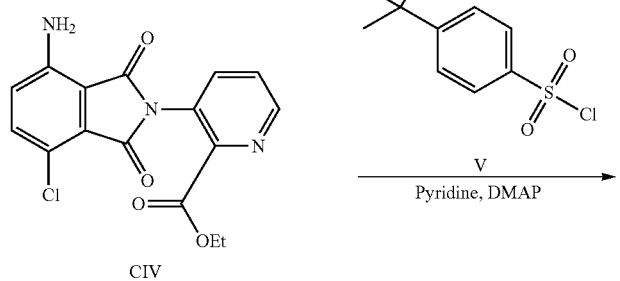
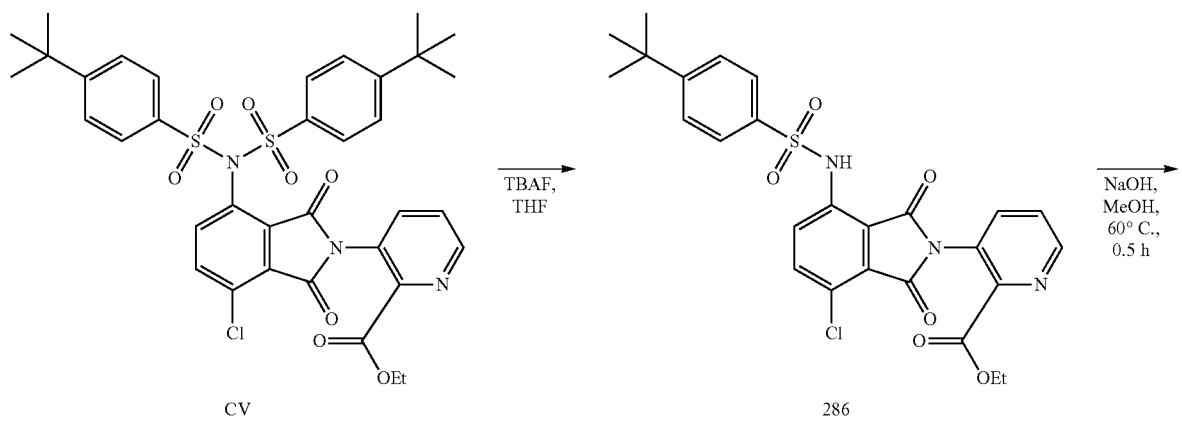

-continued

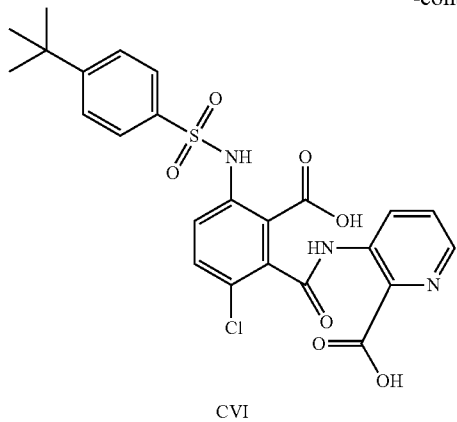

CVI

+

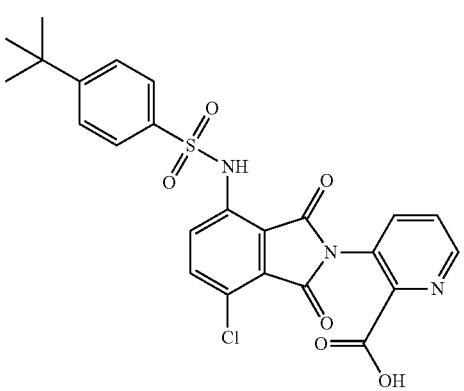

287

PTSA, Toluene, 90° C., 1 h

Synthesis of CIII:

To a stirred solution of compound XXV (5 g, 0.02 mol) in acetic acid (15 ml) was added ethyl 3-aminopicolinate (CII, 1.69 g, 0.01 mol) and the reaction mixture was heated at 120° C. for 12 h. The reaction mixture was cooled to room temperature and the acetic acid removed under reduced pressure. This was followed by washing with hexane to leave crude product ethyl 3-(4-chloro-7-nitro-1,3-dioxoisoindolin-2-yl)picolinate as an off white solid (CIII) pure enough for use in the next step. $^1$H NMR (400 MHz, DMSO-d6): δ 8.88-8.86 (d, J=4.4 Hz, 1H), 8.10-8.08 (d, J=8.4 Hz, 1H), 7.91-7.89 (d, J=8.8 Hz, 1H), 7.82-7.80 (d, J=8 Hz, 1H), 7.69-7.66 (m, 1H), 4.40-4.35 (q, J=7.2 Hz, 6.8 Hz, 2H), 1.37-1.31 (t, J=6.8 Hz, 3H). MS (M+1): 376.03

Synthesis of CIV:

To a solution of crude compound CIII (2.1 g, 0.055 mol) in acetic acid (30 ml) under a nitrogen atmosphere was added iron powder (2 g). The reaction mixture was stirred at room temperature for 5 h. The reaction mass was filtered through a celite bed which was washed with ethyl acetate and the solvent was evaporated under reduced pressure to afford ethyl 3-(4-amino-7-chloro-1,3-dioxoisoindolin-2-yl) picolinate as a yellow solid (CIV; 1.8 g; 93% yield). $^1$H NMR (400 MHz, DMSO-d6): δ 8.78-8.76 (m, 1H), 8.07-8.05 (m, 1H), 7.88-7.82 (m, 1H), 7.53-7.50 (d, J=8.8 Hz, 1H), 7.10-7.08 (d, J=8.8 Hz, 1H), 6.78 (bs, 2H), 4.20-4.15 (q, J=7.2 Hz, 6.8 Hz, 2H), 1.10-1.06 (t, J=7.2 Hz, 3H). MS (M+1): 346.03

Synthesis of 286: ethyl 3-(4-((4-(tert-butyl)phenyl) sulfonamido)-7-chloro-1,3-dioxoisoindolin-2-yl) picolinate A stirred solution of CIV (1.8 g, 0.005 mol) in pyridine (20 ml) was cooled to 0° C. and 4-(tert-butyl) benzenesulfonyl chloride (V, 3.63 g, 0.015 mmol) was added. The reaction mixture was stirred at 90° C. for 8 h and was then cooled, concentrated and diluted with water. The reaction mixture was extracted with ethyl acetate. The organic layer was washed with brine solution, dried over anhydrous Na$_2$SO$_4$, filtered and the organic solvent was evaporated under reduced pressure to obtain the crude compound CV. To this was added 1M TBAF in THF solution (15 ml) and the resulting solution was stirred for 5 h at room temperature. The reaction mixture was concentrated and diluted with ethyl acetate. The organic layer was washed with water, dried over anhydrous Na$_2$SO$_4$, filtered and evaporated under reduced pressure to obtain the crude compound which was purified by column chromatography using 20% ethyl acetate in hexane to afford the title compound, ethyl 3-(4-((4-(tert-butyl)phenyl)sulfonamido)-7-chloro-1,3-dioxoisoindolin-2-yl)picolinate as an off white solid (286; 1.2 g, 42.8% yield). $^1$H NMR (400 MHz, DMSO-d6): δ 10.16 (bs, 1H), 8.82-8.81 (d, J=3.6 Hz, 1H), 8.04-8.03 (d, J=7.6 Hz, 1H), 7.91-7.85 (m, 4H), 7.72-7.70 (d, J=9.2 Hz, 1H), 7.63-7.61 (d, J=8.4 Hz, 2H), 4.16 (q, J=7.2 Hz, 6.8 Hz, 2H), 1.27 (s, 9H), 0.99-0.95 (t, J=7.2 Hz, 3H). MS (M+1): 542.10. (LCMS purity 96.98%, RT=6.11 min) (1).

Synthesis of 287; 3-(4-((4-(tert-butyl)phenyl)sulfonamido)-7-chloro-1,3-dioxoisoindolin-2-yl)picolinic acid To a stirred solution of (286; 0.2 g, 0.37 mmol) in methanol (5 ml), was added a sodium hydroxide (0.04 g, 1.1 mmol) solution in water. The reaction was stirred at room temperature for 0.5 h whereupon the solvent was concentrated under reduced pressure and the residue diluted with water followed by acidification with aqueous citric acid till pH 5. The aqueous layer was extracted with ethyl acetate. The organic layer was washed with brine, dried over Na$_2$SO$_4$, filtered and concentrated under reduced pressure to obtained the crude compound as a mixture of CVI and 287. To a stirred solution of this mixture in toluene (3 ml) was added a catalytic quantity of para-toluene sulfonic acid and the reaction mixture heated at 90° C. for 1 h. The reaction mixture was concentrated and then diluted with ethyl acetate. The organic layer was washed with water, dried over anhydrous Na$_2$SO$_4$, filtered and the organic solvent was evaporated under reduced pressure to obtain the crude compound which was purified by preparative HPLC to afford the title compound, 3-(4-((4-(tert-butyl)phenyl)sulfonamido)-7-chloro-1,3-dioxoisoindolin-2-yl)picolinic acid as a white solid (287; 0.05 g, 26.5% yield). $^1$H NMR (400 MHz, DMSO-d6): δ 13.42 (bs, 1H), 10.18 (bs, 1H), 8.80 (m, 1H), 8.02-8.00 (d, J=8 Hz, 1H), 7.95-7.93 (d, J=8.4 Hz, 2H), 7.87-7.82 (m, 2H), 7.67-7.63 (m, 3H), 1.27 (s, 9H). MS (M+1): 514.30 (LCMS purity 98.28%).

The following compounds were prepared in a similar manner as mentioned in above reaction using appropriate amines instead of CII at step-1 with the final step described only used where necessary to generate an acid functionality:

| S. No. | Structure | LCMS (M + 1) | Purity (LCMS) | 1HNMR |
|---|---|---|---|---|
| 288 | 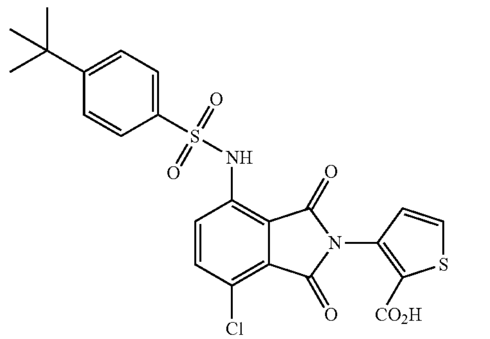 [SMILES: CC(C)(C)c1ccc(S(=O)(=O)Nc2ccc(Cl)c3c2C(=O)N(c2ccsc2C(=O)O)C3=O)cc1] | 516.98 (M − 1) | 99.30% Rt = 5.22 min (1) | ¹H NMR (400 MHz, DMSO-d6): δ 13.39 (bs, 1H), 10.08 (bs, 1H), 8.01-7.99 (d, J = 5.6 Hz, 1H), 7.94-7.91 (d, J = 8.8 Hz, 2H), 7.85-7.83 (d, J = 8.8 Hz, 1H), 7.67-7.62 (m, 3H), 7.20-7.19 (d, J = 4.8 Hz, 1H), 1.27 (s, 9H). |
| 289 | 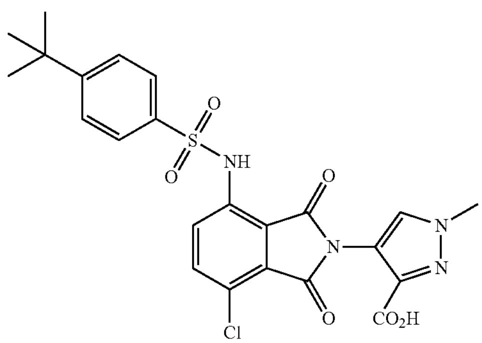 [SMILES: Cn1cc(N2C(=O)c3c(Cl)ccc(NS(=O)(=O)c4ccc(C(C)(C)C)cc4)c3C2=O)c(C(=O)O)n1] | 517.00 | 97.90% Rt = 4.84 min (1) | ¹H NMR (400 MHz, DMSO-d6): δ 12.88 (bs, 1H), 10.08 (bs, 1H), 8.03 (s, 1H), 7.94-7.92 (d, J = 8.8 Hz, 2H), 7.83-7.81 (d, J = 8.8 Hz, 1H), 7.65-7.62 (m, 3H), 3.98 (s, 3H), 1.28 (s, 9H). |
| 290 | 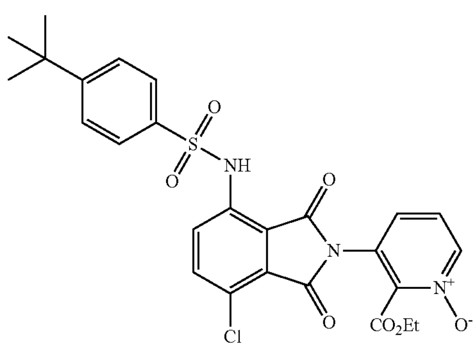 [SMILES: CCOC(=O)c1c(N2C(=O)c3c(Cl)ccc(NS(=O)(=O)c4ccc(C(C)(C)C)cc4)c3C2=O)ccc[n+]1[O-]] | 558.05 | 98.01% Rt = 5.47 min (1) | ¹H NMR (400 MHz, DMSO-d6): δ 10.24 (bs, 1H), 8.53-8.51 (d, J = 6.4 Hz, 1H), 7.93-7.91 (d, J = 8 Hz, 2H), 7.88-7.85 (d, J = 8.4 Hz, 1H), 7.76-7.72 (m, 1H), 7.65-7.59 (m, 4H), 4.18-4.17 (q, J = 6.8 Hz, 7.2 Hz, 2H), 1.28 (s, 9H), 0.97-0.95 (t, J = 6.8 Hz, 3H). |
| 291 | 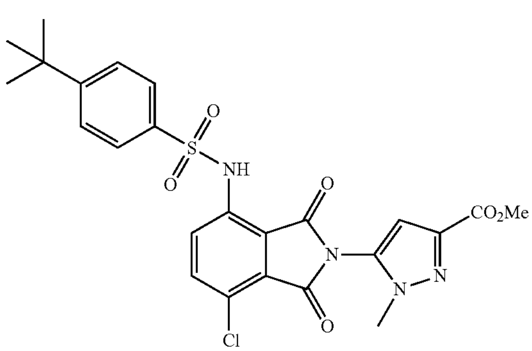 [SMILES: COC(=O)c1cc(N2C(=O)c3c(Cl)ccc(NS(=O)(=O)c4ccc(C(C)(C)C)cc4)c3C2=O)n(C)n1] | 531.05 | 98.26% Rt = 5.85 min (1) | ¹H NMR (400 MHz, DMSO-d6): δ 10.09 (bs, 1H), 7.95-7.93 (d, J = 8.4 Hz, 2H), 7.86-7.84 (d, J = 8.8 Hz, 1H), 7.70-7.67 (d, J = 8.8 Hz, 1H), 7.65-7.63 (d, J = 8.4 Hz, 2H), 6.83 (s, 1H), 3.82 (s, 3H), 3.80 (s, 3H), 1.28 (s, 9H). |

| S. No. | Structure | LCMS (M + 1) | Purity (LCMS) | 1HNMR |
|---|---|---|---|---|
| 292 | 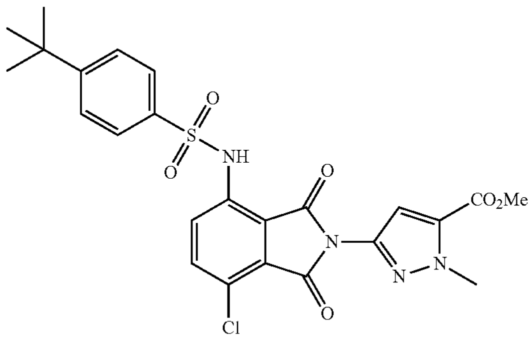 [SMILES: COC(=O)c1cc(N2C(=O)c3c(Cl)ccc(NS(=O)(=O)c4ccc(C(C)(C)C)cc4)c3C2=O)nn1C] | 531.07 | 99.00% Rt = 6.33 min (1) | $^1$H NMR (400 MHz, DMSO-d6): δ 9.97 (bs, 1H), 7.91-7.88 (d, J = 8.4 Hz, 2H), 7.84-7.81 (d, J = 9.2 Hz, 1H), 7.68-7.62 (m, 3H), 6.90 (s, 1H), 4.13 (s, 3H), 3.86 (s, 3H), 1.27 (s, 9H). |

Example 31

Biological Activity: FLIPR Assay Using hCCR9 Over Expressed Cells

A calcium flux assay was used to determine the ability of the compounds to interfere with the binding between CCR9 and its chemokine ligand (TECK) in Chem1-hCCR9 over-expressing cells. hCCR9 overexpressing cells were seeded (25,000 cells/well) into black Poly-D-Lysine coated clear bottom 96-well plates (BD Biosciences, Cat #356640) and incubated overnight at 37° C./5% $CO_2$ in a humidified incubator. Media was aspirated and cells washed twice with 100 μL assay buffer (1×HBSS, 20 mM HEPES) containing 2.5 mM Probenecid. A 0.3× Fluo-4 NW calcium dye was prepared in assay buffer containing 5 mM Probenecid and stored in the dark. Each well was loaded with 100 μL of 0.3× Fluo-4 NW calcium dye and incubated at 37° C./5% $CO_2$ for 60 minutes and then at room temperature for 30 minutes. A half-log serially diluted concentration response curve was prepared at a 3× final assay concentration for each compound (10 μM-0.1 nM final assay concentration) and 50 μL of the compound then transferred to the cells (150 μL final volume) for 60 minutes prior to stimulation (30 minutes at 37° C./5% $CO_2$ and 30 minutes at room temperature). TECK was diluted to 4× its $EC_{80}$ in assay buffer (containing 0.1% [w/v] bovine serum albumin [BSA]) and 50 μL dispensed through the fluorometric imaging plate reader (FLIPR) instrument to stimulate the cells (200 μL final volume). The increase in intracellular calcium levels was measured with the FLIPR instrument. The potency of the compound as a CCR9 antagonist was calculated as an $IC_{50}$ using GraphPad Prism software (variable slope four parameter). The Ki of the compound was determined from the $IC_{50}$ values using the following equation.

$IC_{50}/1+$(Agonist (TECK) conc. used in assay/$EC_{50}$ of agonist (TECK) generated on day of experiment)     Ki calculation:

| Compound number | Structure | Ki (nM) |
|---|---|---|
| 1 | 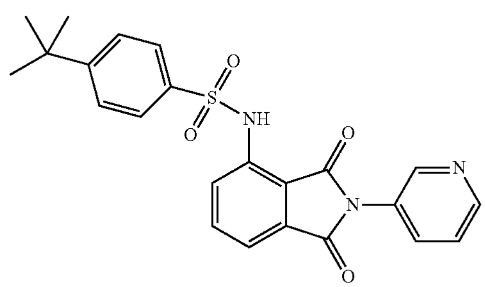 [SMILES: CC(C)(C)c1ccc(S(=O)(=O)Nc2cccc3c2C(=O)N(c2cccnc2)C3=O)cc1] | 1244 |
| 6 | 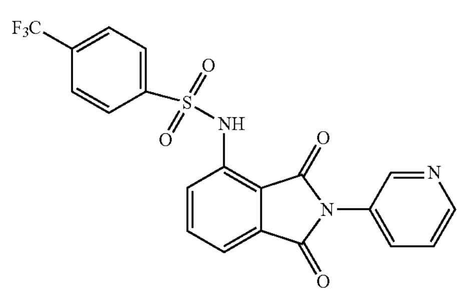 [SMILES: O=C1c2cccc(NS(=O)(=O)c3ccc(C(F)(F)F)cc3)c2C(=O)N1c1cccnc1] | 5632 |

| Compound number | Structure | Ki (nM) |
|---|---|---|
| 43 | 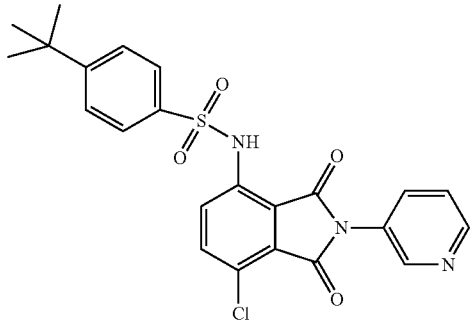 [SMILES: CC(C)(C)c1ccc(S(=O)(=O)Nc2ccc(Cl)c3c2C(=O)N(c2cccnc2)C3=O)cc1] | 42 |
| 44 | 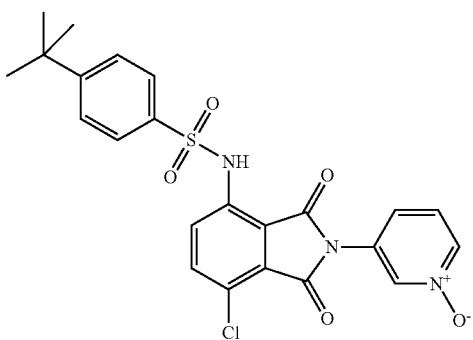 [SMILES: CC(C)(C)c1ccc(S(=O)(=O)Nc2ccc(Cl)c3c2C(=O)N(c2ccc[n+]([O-])c2)C3=O)cc1] | 179 |
| 45 | 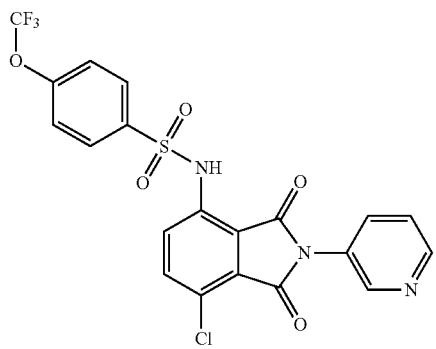 [SMILES: O=C1c2c(Cl)ccc(NS(=O)(=O)c3ccc(OC(F)(F)F)cc3)c2C(=O)N1c1cccnc1] | 314 |
| 47 | 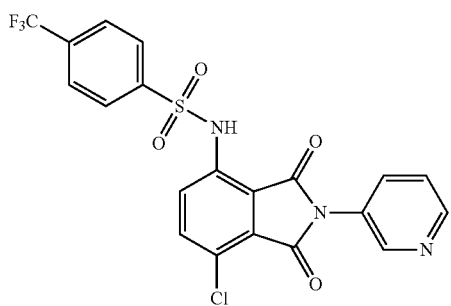 | 309 |

-continued

| Compound number | Structure | Ki (nM) |
|---|---|---|
| 64 | 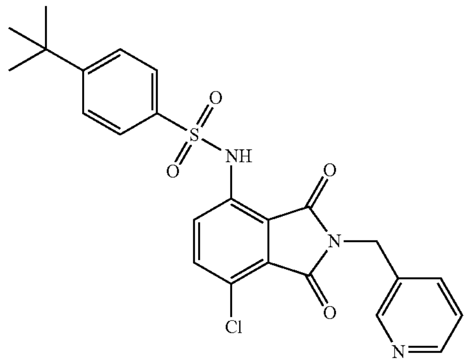 | 27 |
| 65 | 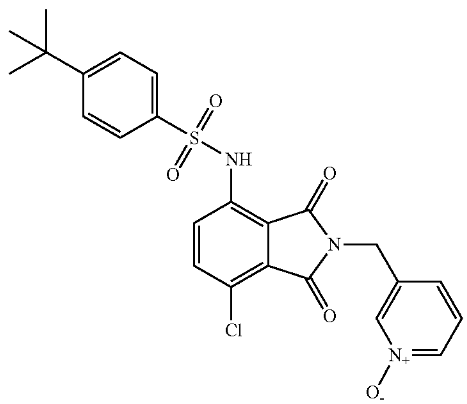 | 74 |
| 66 | 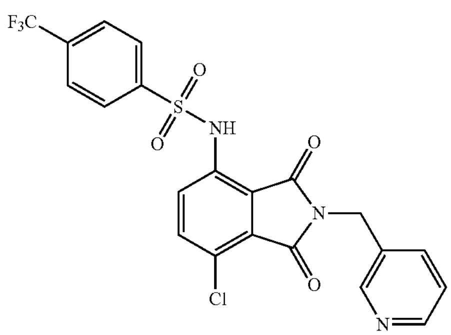 | 269 |
| 82 | 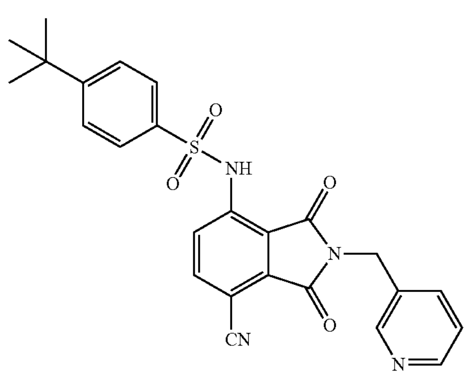 | 98 |

-continued
| Compound number | Structure | Ki (nM) |
|---|---|---|
| 90 | 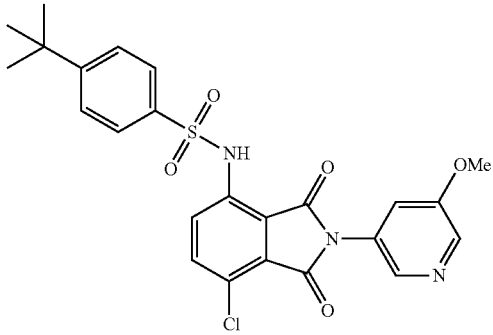 | 174 |
| 103 | 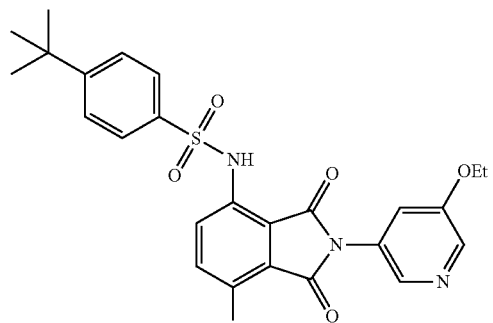 | 242 |
| 104 | 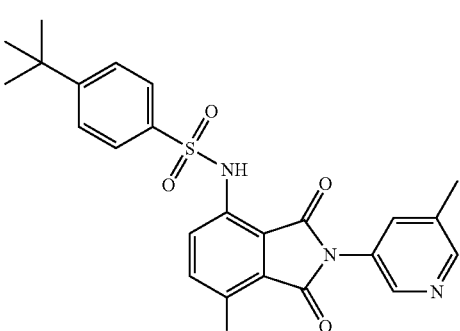 | 239 |
| 119 | 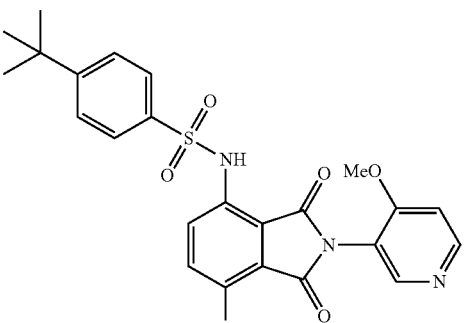 | 35 |

-continued
| Compound number | Structure | Ki (nM) |
|---|---|---|
| 120 | 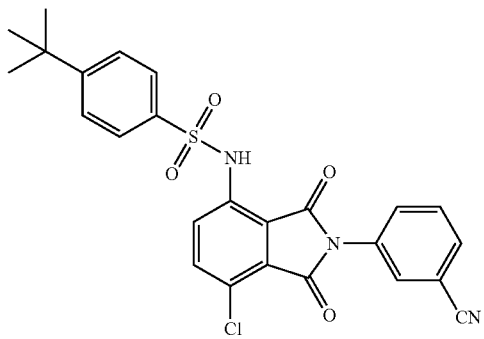 [SMILES: CC(C)(C)c1ccc(S(=O)(=O)Nc2ccc(Cl)c3c2C(=O)N(c2cccc(C#N)c2)C3=O)cc1] | 90 |
| 121 | 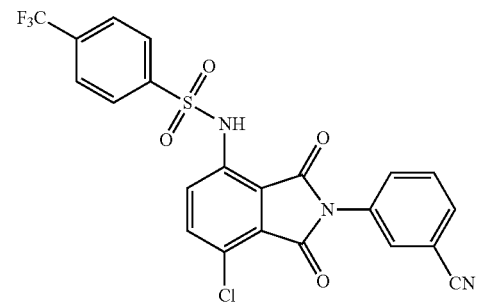 [SMILES: N#Cc1cccc(N2C(=O)c3c(Cl)ccc(NS(=O)(=O)c4ccc(C(F)(F)F)cc4)c3C2=O)c1] | 337 |
| 126 | 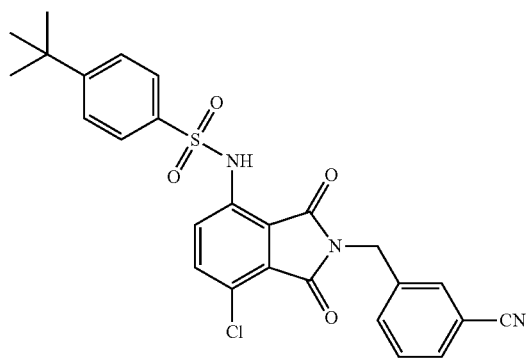 [SMILES: CC(C)(C)c1ccc(S(=O)(=O)Nc2ccc(Cl)c3c2C(=O)N(Cc2cccc(C#N)c2)C3=O)cc1] | 343 |
| 128 | 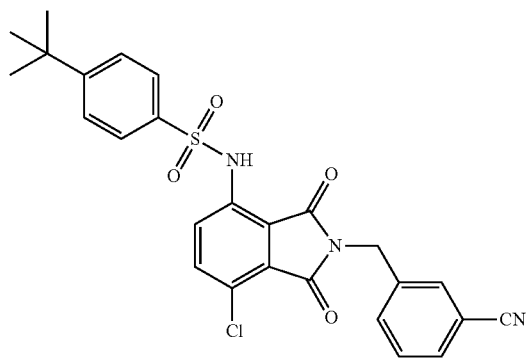 | 447 |

-continued
| Compound number | Structure | Ki (nM) |
|---|---|---|
| 133 | 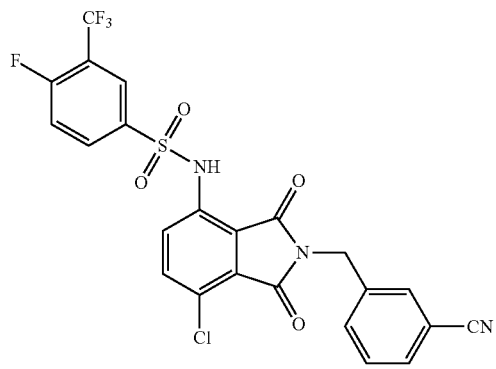 [SMILES: N#Cc1cccc(CN2C(=O)c3c(Cl)ccc(NS(=O)(=O)c4ccc(F)c(C(F)(F)F)c4)c3C2=O)c1] | 158 |
| 138 | 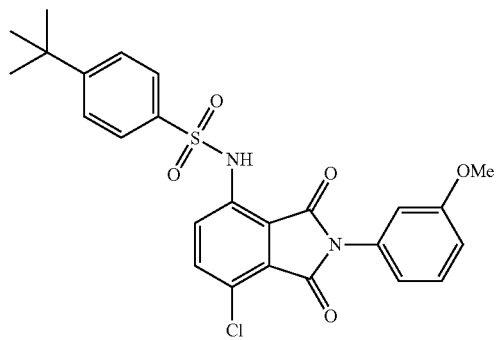 | 138 |
| 144 | 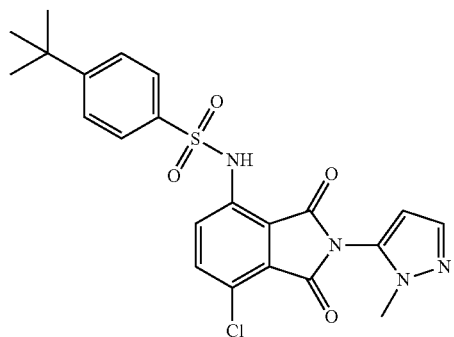 [SMILES: Cn1nccc1N1C(=O)c2c(Cl)ccc(NS(=O)(=O)c3ccc(C(C)(C)C)cc3)c2C1=O] | 23 |
| 145 | 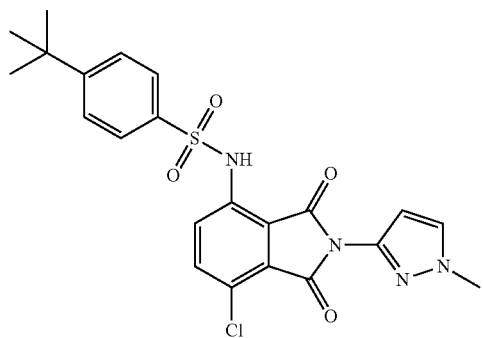 | 73 |

-continued

| Compound number | Structure | Ki (nM) |
|---|---|---|
| 148 | 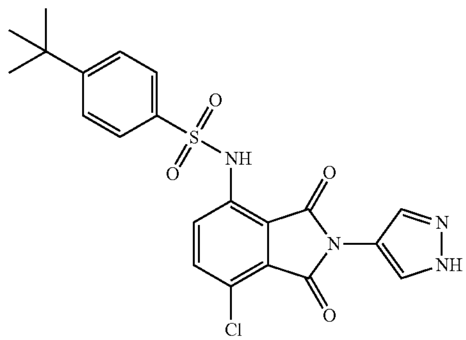 [SMILES: CC(C)(C)c1ccc(S(=O)(=O)Nc2ccc(Cl)c3c2C(=O)N(c2cn[nH]c2)C3=O)cc1] | 94 |
| 149 | 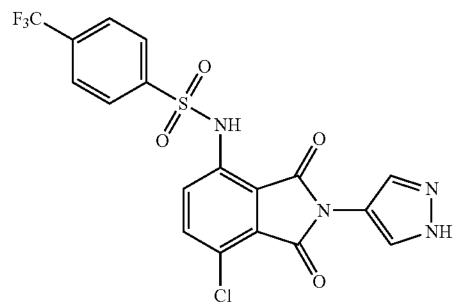 [SMILES: O=C1c2c(Cl)ccc(NS(=O)(=O)c3ccc(C(F)(F)F)cc3)c2C(=O)N1c1cn[nH]c1] | 397 |
| 153 | 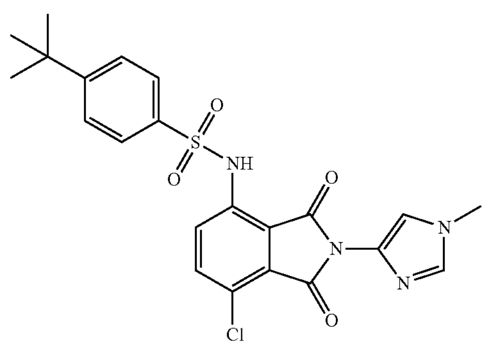 [SMILES: Cn1cnc(N2C(=O)c3c(Cl)ccc(NS(=O)(=O)c4ccc(C(C)(C)C)cc4)c3C2=O)c1] | 43 |
| 155 | 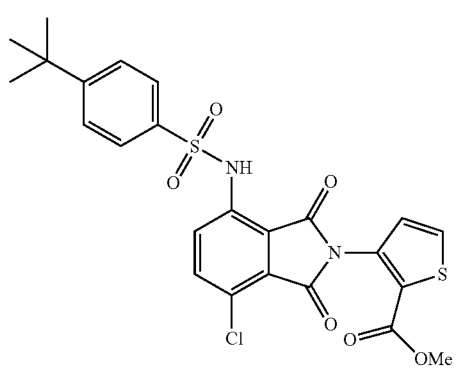 [SMILES: COC(=O)c1sccc1N1C(=O)c2c(Cl)ccc(NS(=O)(=O)c3ccc(C(C)(C)C)cc3)c2C1=O] | 135 |

-continued

| Compound number | Structure | Ki (nM) |
|---|---|---|
| 160 | 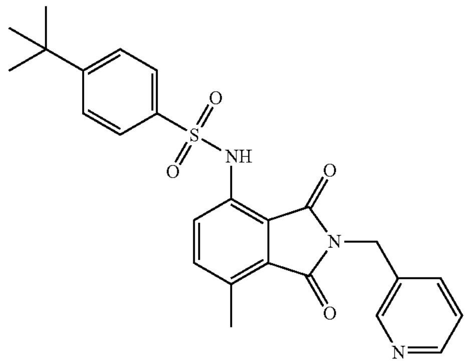 [SMILES: Cc1ccc(NS(=O)(=O)c2ccc(C(C)(C)C)cc2)c2c1C(=O)N(Cc1cccnc1)C2=O] | 776 |
| 175 | 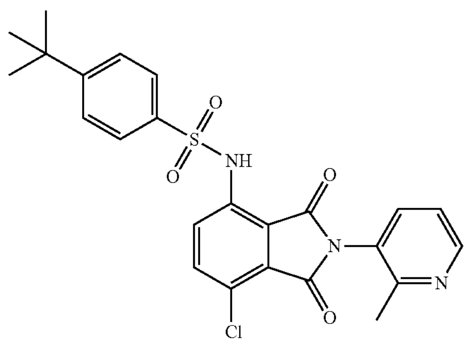 | 12 |
| 176 | 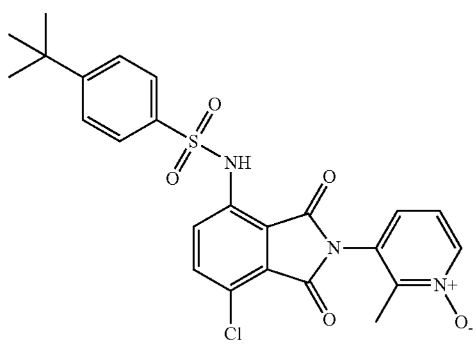 | 13 |
| 179 | 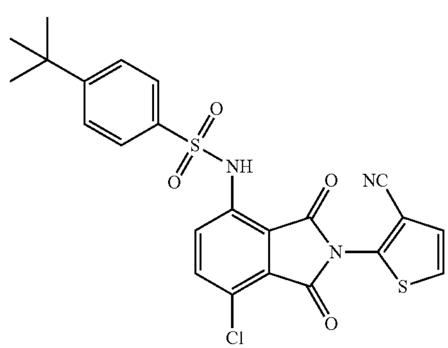 [SMILES: CC(C)(C)c1ccc(S(=O)(=O)Nc2ccc(Cl)c3c2C(=O)N(c2sccc2C#N)C3=O)cc1] | 57 |

-continued

| Compound number | Structure | Ki (nM) |
|---|---|---|
| 182 | 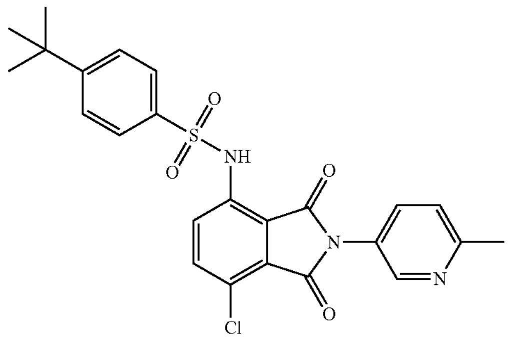 | 58 |
| 183 | 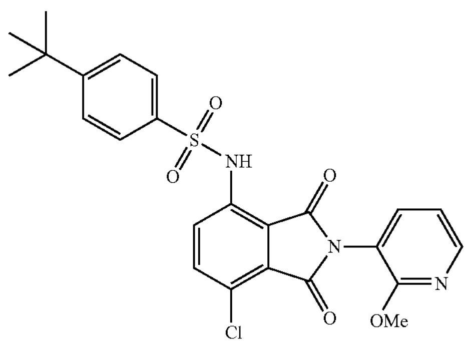 [SMILES: COc1ncccc1N1C(=O)c2c(Cl)ccc(NS(=O)(=O)c3ccc(C(C)(C)C)cc3)c2C1=O] | 3 |
| 184 | 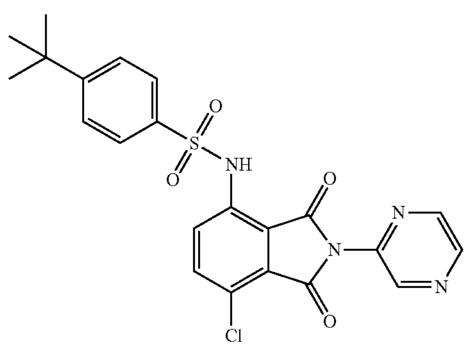 | 24 |
| 185 | 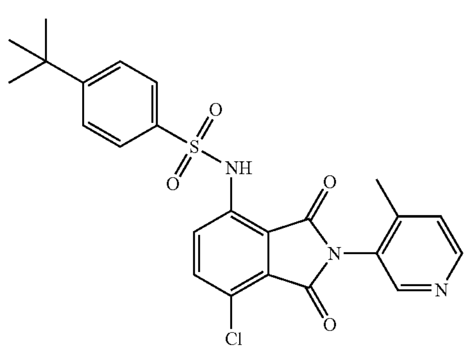 [SMILES: Cc1ccncc1N1C(=O)c2c(Cl)ccc(NS(=O)(=O)c3ccc(C(C)(C)C)cc3)c2C1=O] | 23 |

-continued
| Compound number | Structure | Ki (nM) |
|---|---|---|
| 188 | 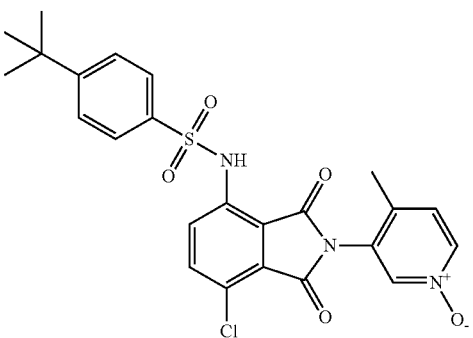 | 89 |
| 189 | 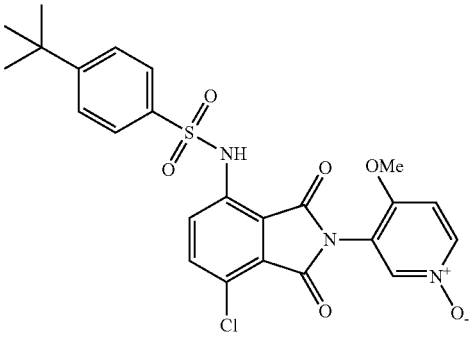 | 34 |
| 190 | 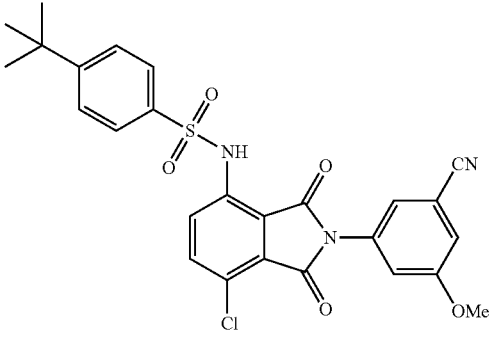 [SMILES: COc1cc(C#N)cc(N2C(=O)c3c(Cl)ccc(NS(=O)(=O)c4ccc(C(C)(C)C)cc4)c3C2=O)c1] | 81 |
| 191 | 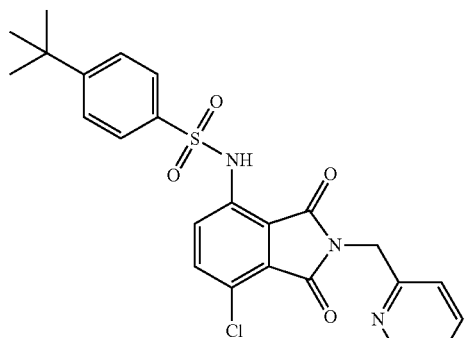 | 33 |

-continued

| Compound number | Structure | Ki (nM) |
|---|---|---|
| 192 | 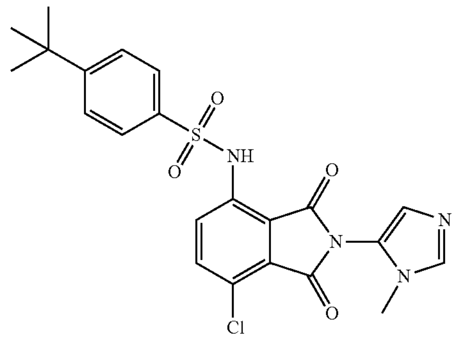 | 12 |
| 193 | 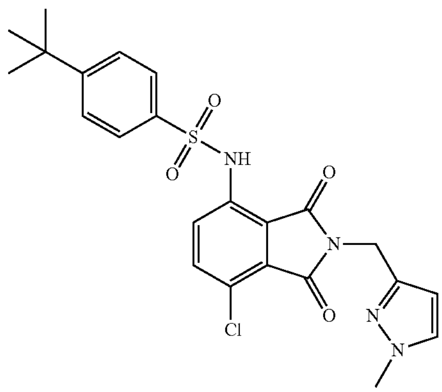 [SMILES: Cn1ccc(CN2C(=O)c3c(Cl)ccc(NS(=O)(=O)c4ccc(C(C)(C)C)cc4)c3C2=O)n1] | 21 |
| 194 | 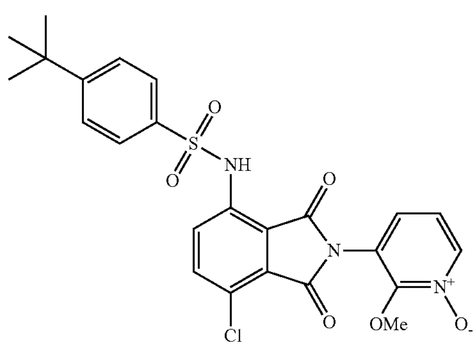 | 6 |
| 195 | 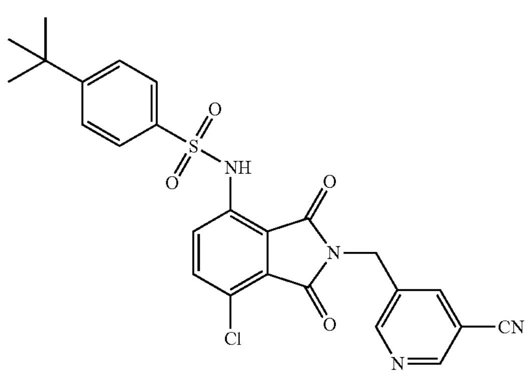 [SMILES: CC(C)(C)c1ccc(S(=O)(=O)Nc2ccc(Cl)c3c2C(=O)N(Cc2cncc(C#N)c2)C3=O)cc1] | 42 |

| Compound number | Structure | Ki (nM) |
|---|---|---|
| 196 | 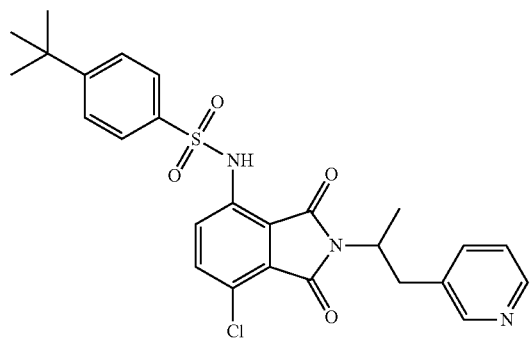 [SMILES: CC(Cc1cccnc1)N1C(=O)c2c(Cl)ccc(NS(=O)(=O)c3ccc(C(C)(C)C)cc3)c2C1=O] | 103 |
| 197 | 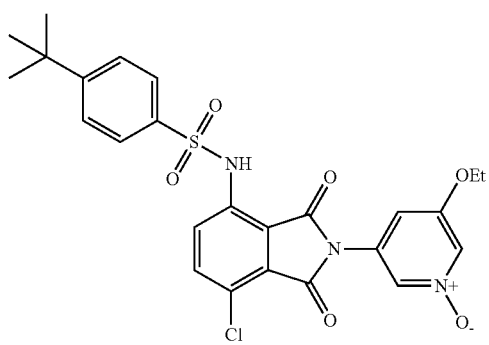 | 40 |
| 199 | 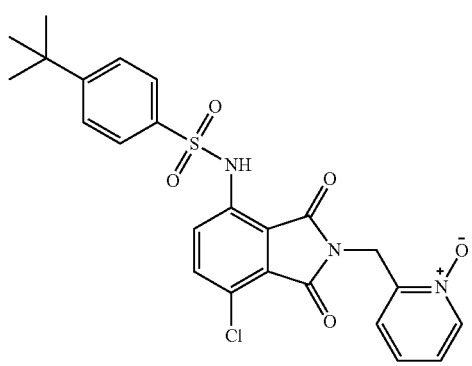 [SMILES: CC(C)(C)c1ccc(S(=O)(=O)Nc2ccc(Cl)c3c2C(=O)N(Cc2cccc[n+]2[O-])C3=O)cc1] | 10 |
| 200 | 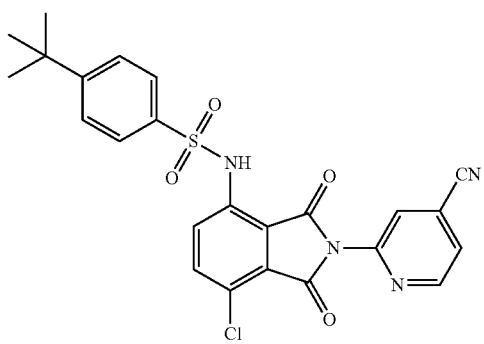 | 92 |

| Compound number | Structure | Ki (nM) |
|---|---|---|
| 201 | 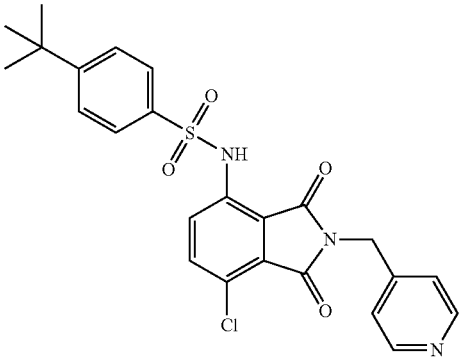 [SMILES: CC(C)(C)c1ccc(S(=O)(=O)Nc2ccc(Cl)c3c2C(=O)N(Cc2ccncc2)C3=O)cc1] | 17 |
| 202 | 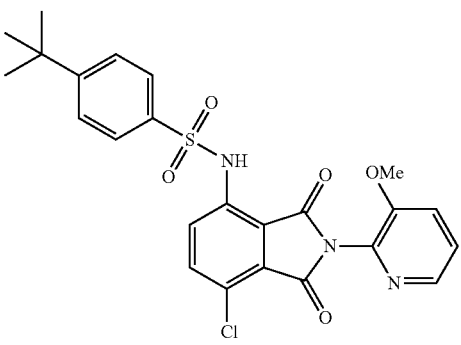 [SMILES: COc1cccnc1N1C(=O)c2c(Cl)ccc(NS(=O)(=O)c3ccc(C(C)(C)C)cc3)c2C1=O] | 49 |
| 203 | 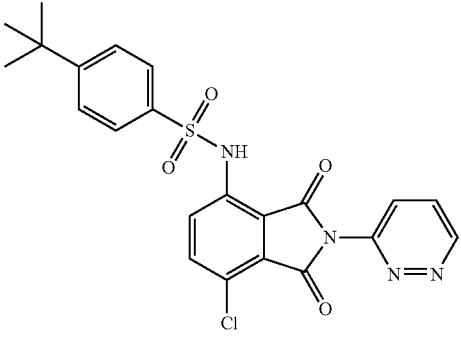 | 59 |
| 204 | 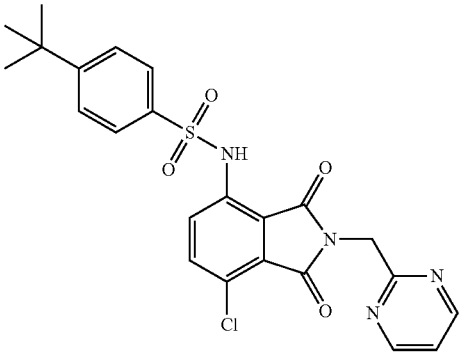 [SMILES: CC(C)(C)c1ccc(S(=O)(=O)Nc2ccc(Cl)c3c2C(=O)N(Cc2ncccn2)C3=O)cc1] | 30 |

-continued

| Compound number | Structure | Ki (nM) |
|---|---|---|
| 207 | 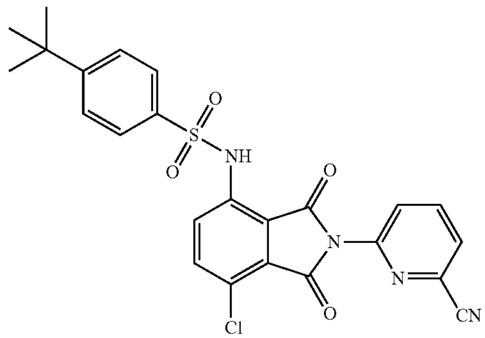 [SMILES: CC(C)(C)c1ccc(S(=O)(=O)Nc2ccc(Cl)c3c2C(=O)N(c2cccc(C#N)n2)C3=O)cc1] | 36 |
| 208 | 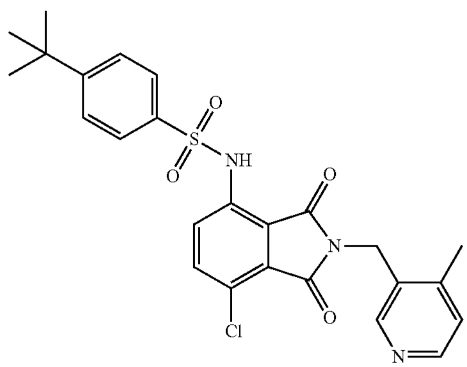 | 16 |
| 209 | 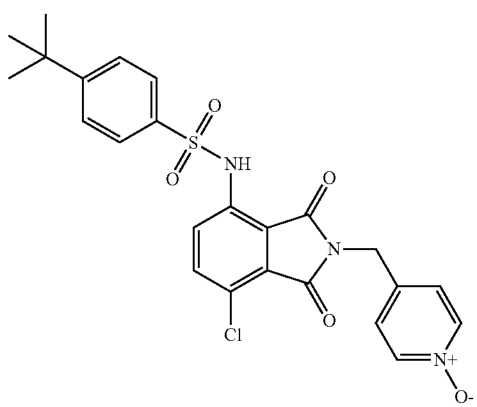 [SMILES: CC(C)(C)c1ccc(S(=O)(=O)Nc2ccc(Cl)c3c2C(=O)N(Cc2cc[n+]([O-])cc2)C3=O)cc1] | 77 |
| 211 | 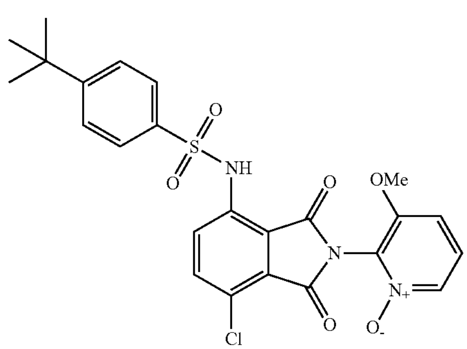 | 61 |

-continued
| Compound number | Structure | Ki (nM) |
|---|---|---|
| 212 | 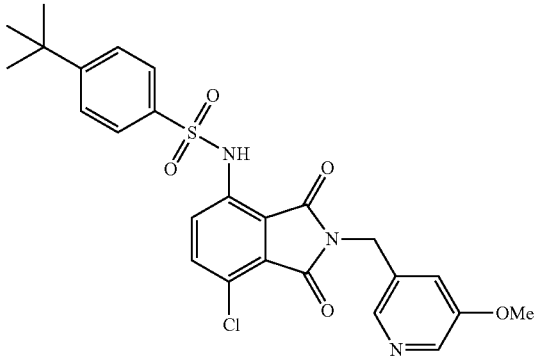 [SMILES: COc1cncc(CN2C(=O)c3c(Cl)ccc(NS(=O)(=O)c4ccc(C(C)(C)C)cc4)c3C2=O)c1] | 60 |
| 213 | 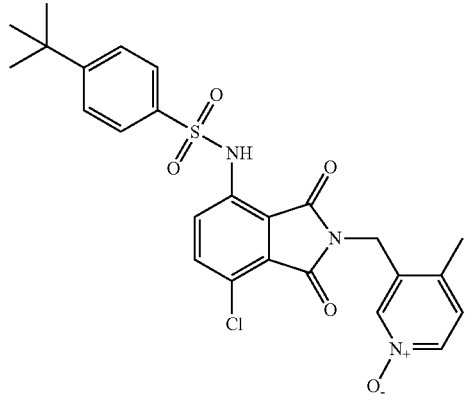 | 23 |
| 214 | 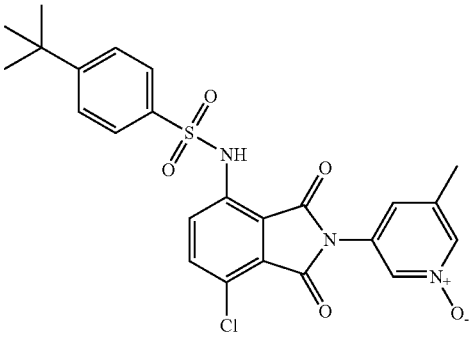 | 53 |
| 216 | 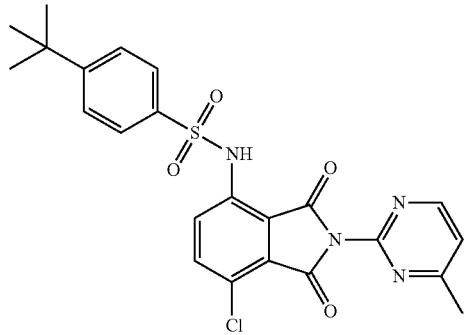 | 49 |

| Compound number | Structure | Ki (nM) |
|---|---|---|
| 217 | 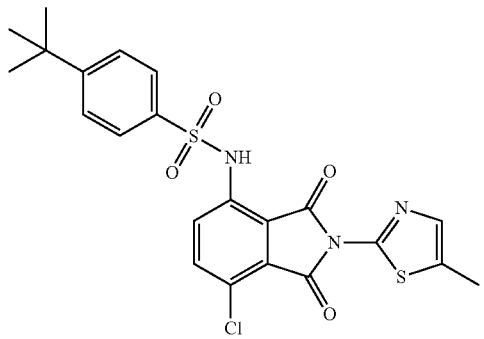 [SMILES: Cc1cnc(N2C(=O)c3c(Cl)ccc(NS(=O)(=O)c4ccc(C(C)(C)C)cc4)c3C2=O)s1] | 39 |
| 218 | 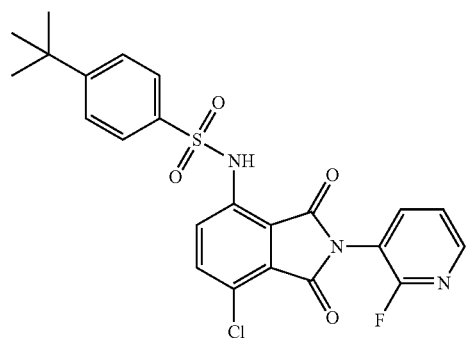 | 26 |
| 219 | 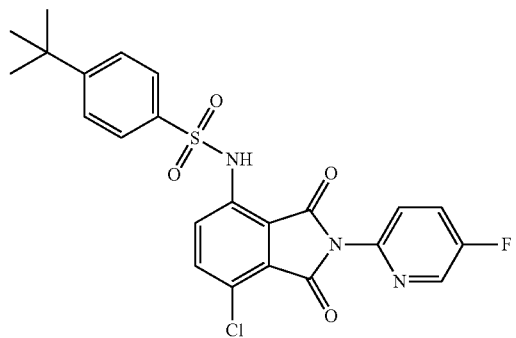 | 30 |
| 220 | 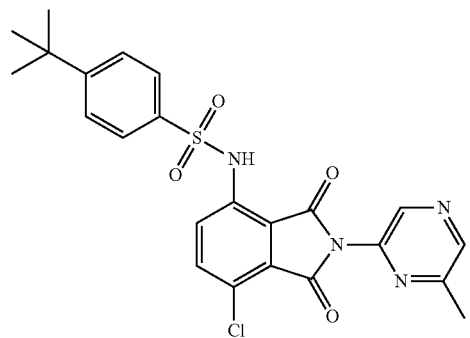 [SMILES: Cc1cncc(N2C(=O)c3c(Cl)ccc(NS(=O)(=O)c4ccc(C(C)(C)C)cc4)c3C2=O)n1] | 42 |

-continued
| Compound number | Structure | Ki (nM) |
|---|---|---|
| 222 | 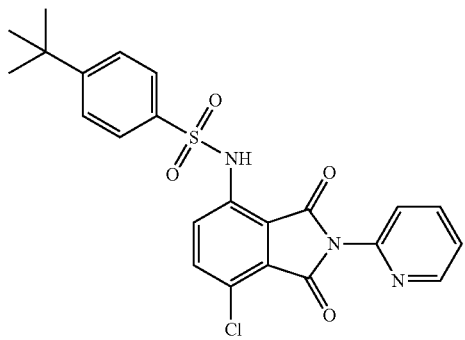 | 12 |
| 224 | 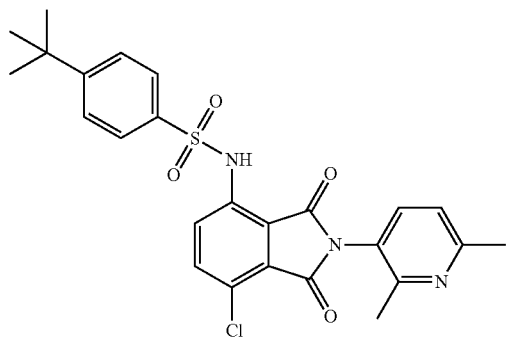 [SMILES: Cc1ccc(N2C(=O)c3c(Cl)ccc(NS(=O)(=O)c4ccc(C(C)(C)C)cc4)c3C2=O)c(C)n1] | 6 |
| 225 | 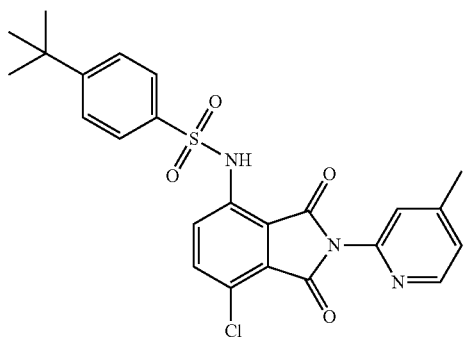 [SMILES: Cc1ccnc(N2C(=O)c3c(Cl)ccc(NS(=O)(=O)c4ccc(C(C)(C)C)cc4)c3C2=O)c1] | 51 |
| 226 | 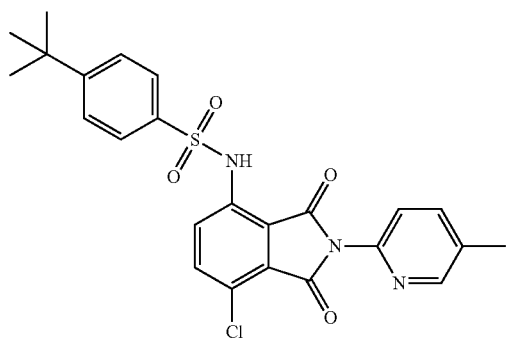 | 23 |

-continued

| Compound number | Structure | Ki (nM) |
|---|---|---|
| 227 | 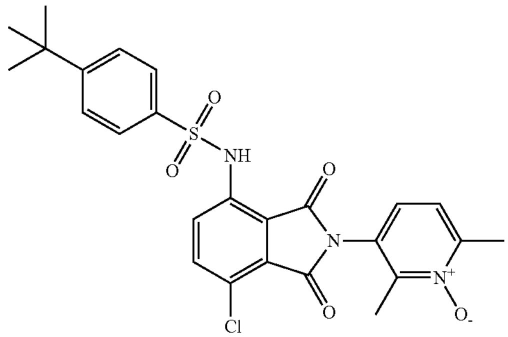 | 32 |
| 228 | 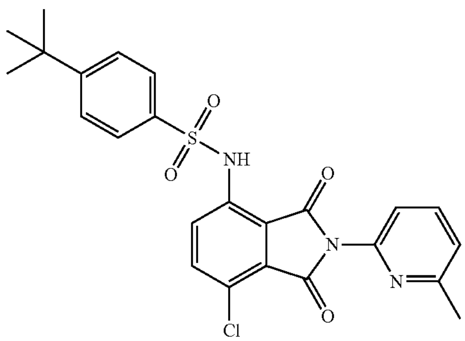 | 6 |
| 229 | 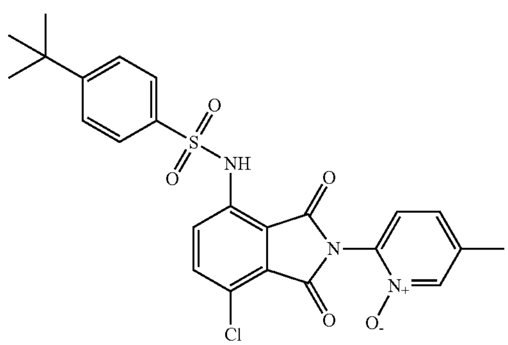 | 63 |
| 230 | 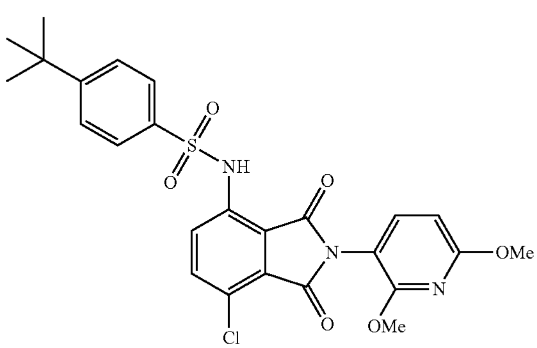 [SMILES: COc1ccc(N2C(=O)c3c(Cl)ccc(NS(=O)(=O)c4ccc(C(C)(C)C)cc4)c3C2=O)c(OC)n1] | 6 |

-continued
| Compound number | Structure | Ki (nM) |
|---|---|---|
| 231 | 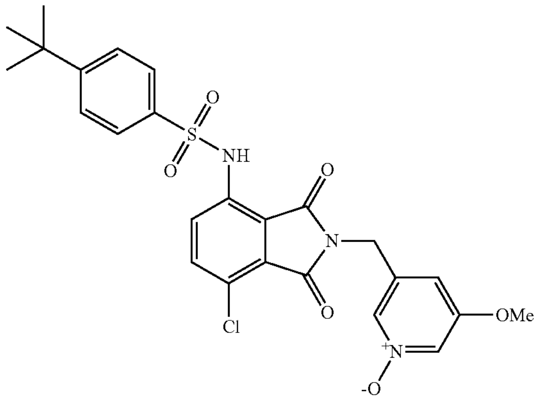 | 89 |
| 232 | 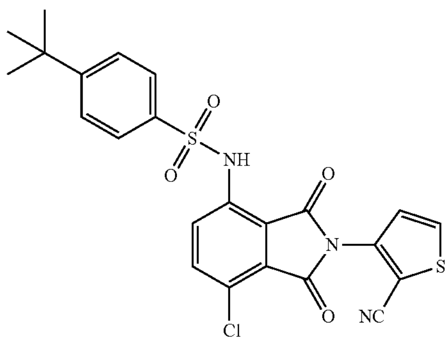 [SMILES: CC(C)(C)c1ccc(S(=O)(=O)Nc2ccc(Cl)c3c2C(=O)N(c2ccsc2C#N)C3=O)cc1] | 3 |
| 233 | 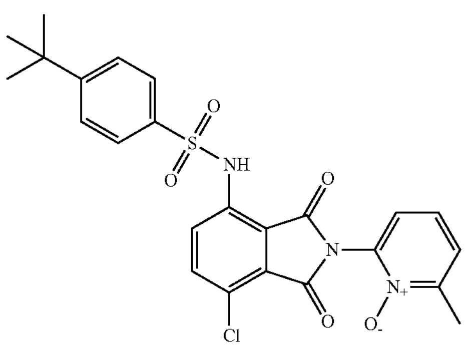 | 21 |
| 234 | 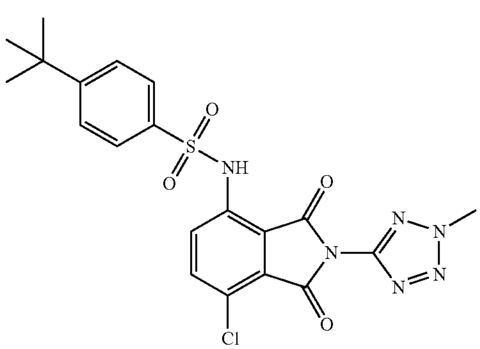 [SMILES: Cn1nnc(N2C(=O)c3c(Cl)ccc(NS(=O)(=O)c4ccc(C(C)(C)C)cc4)c3C2=O)n1] | 43 |

-continued
| Compound number | Structure | Ki (nM) |
| --- | --- | --- |
| 235 | 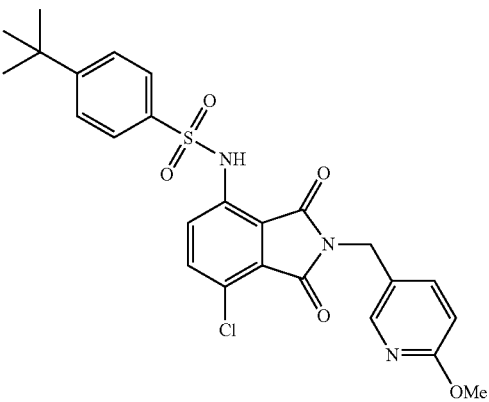 [SMILES: COc1ccc(CN2C(=O)c3c(Cl)ccc(NS(=O)(=O)c4ccc(C(C)(C)C)cc4)c3C2=O)cn1] | 94 |
| 236 | 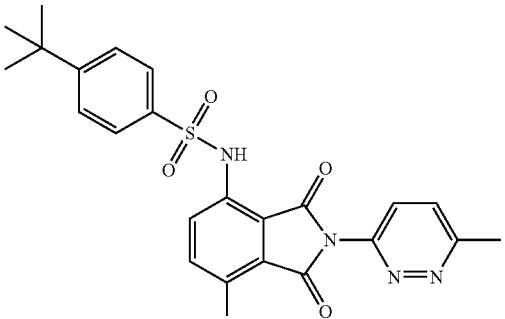 | 32 |
| 237 | 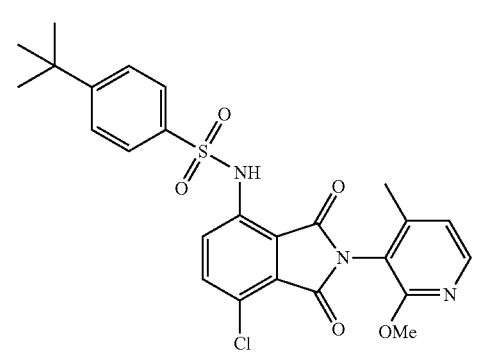 [SMILES: COc1nccc(C)c1N1C(=O)c2c(Cl)ccc(NS(=O)(=O)c3ccc(C(C)(C)C)cc3)c2C1=O] | 9 |
| 238 | 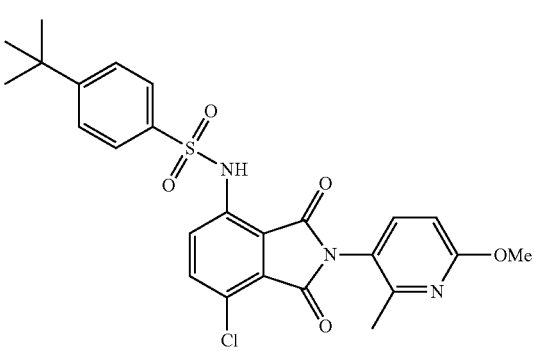 [SMILES: COc1ccc(N2C(=O)c3c(Cl)ccc(NS(=O)(=O)c4ccc(C(C)(C)C)cc4)c3C2=O)c(C)n1] | 13 |

-continued
| Compound number | Structure | Ki (nM) |
|---|---|---|
| 239 | 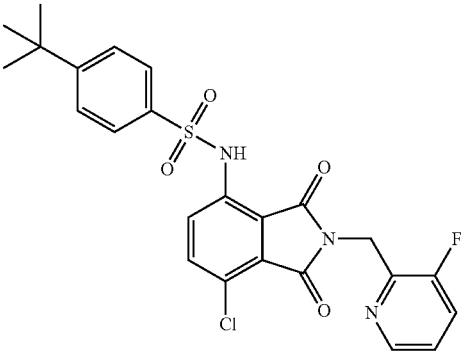 [SMILES: CC(C)(C)c1ccc(S(=O)(=O)Nc2ccc(Cl)c3c2C(=O)N(Cc2ncccc2F)C3=O)cc1] | 23 |
| 241 | 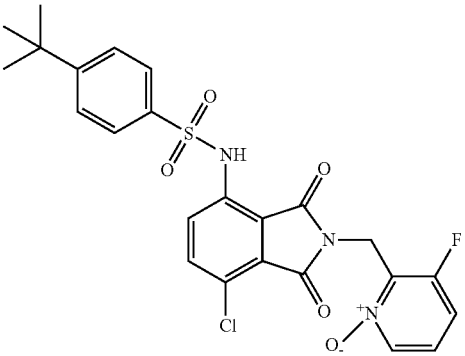 | 7 |
| 242 | 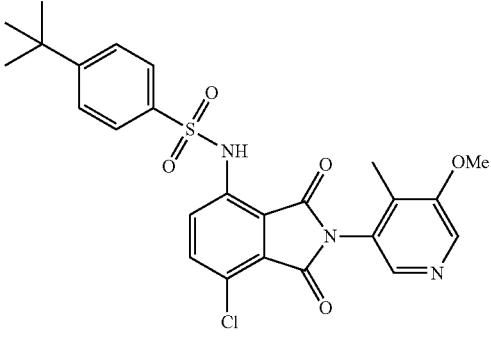 [SMILES: COc1cncc(N2C(=O)c3c(Cl)ccc(NS(=O)(=O)c4ccc(C(C)(C)C)cc4)c3C2=O)c1C] | 56 |
| 243 | 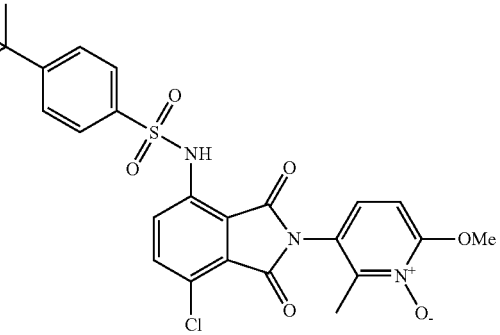 | 115 |

| Compound number | Structure | Ki (nM) |
|---|---|---|
| 244 | 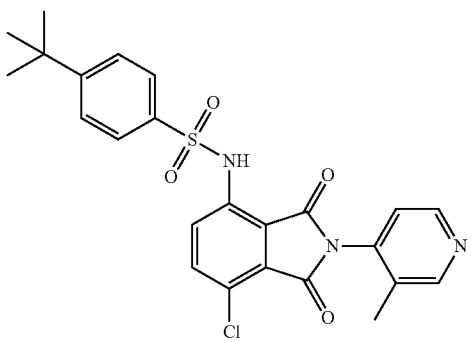 [SMILES: Cc1cnccc1N1C(=O)c2c(Cl)ccc(NS(=O)(=O)c3ccc(C(C)(C)C)cc3)c2C1=O] | 3 |
| 245 | 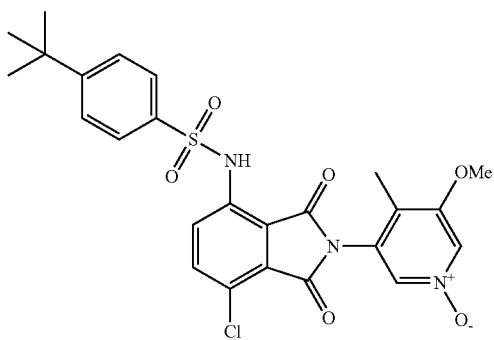 | 54 |
| 247 | 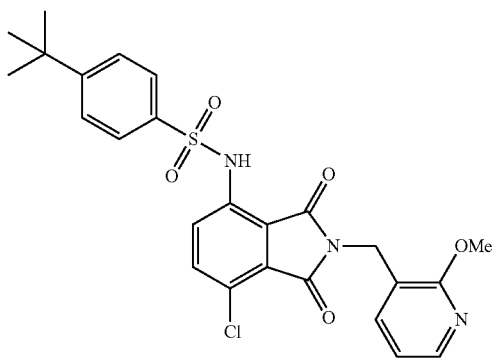 [SMILES: COc1ncccc1CN1C(=O)c2c(Cl)ccc(NS(=O)(=O)c3ccc(C(C)(C)C)cc3)c2C1=O] | 51 |
| 249 | 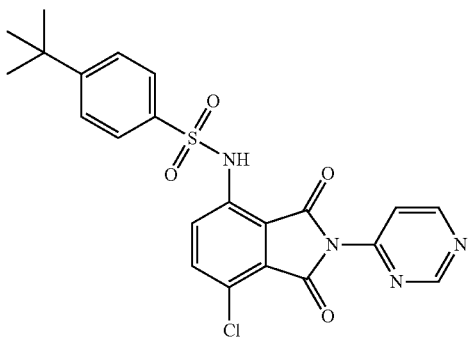 | 60 |

-continued

| Compound number | Structure | Ki (nM) |
|---|---|---|
| 250 | 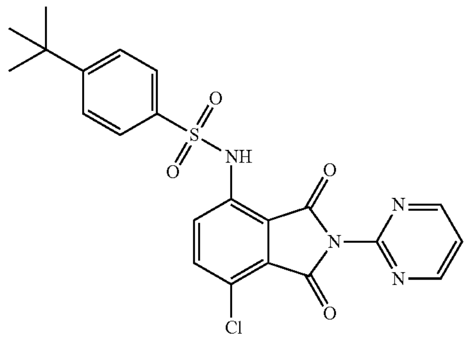 [SMILES: CC(C)(C)c1ccc(S(=O)(=O)Nc2ccc(Cl)c3c2C(=O)N(c2ncccn2)C3=O)cc1] | 56 |
| 251 | 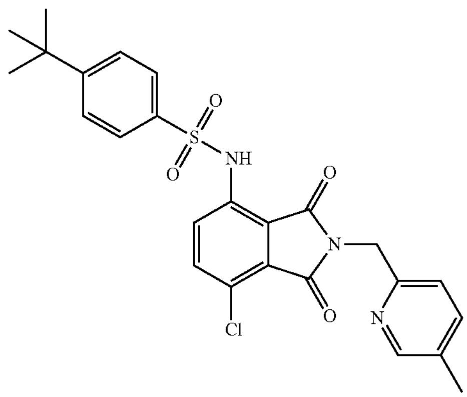 [SMILES: Cc1ccc(CN2C(=O)c3c(Cl)ccc(NS(=O)(=O)c4ccc(C(C)(C)C)cc4)c3C2=O)nc1] | 148 |
| 254 | 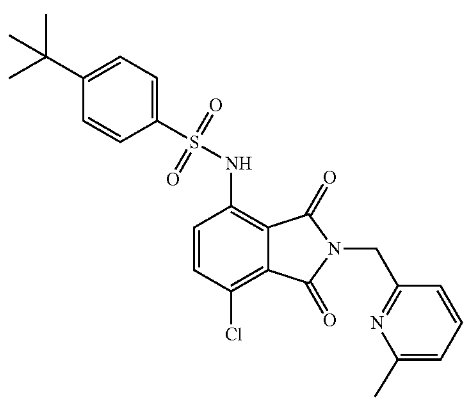 [SMILES: Cc1cccc(CN2C(=O)c3c(Cl)ccc(NS(=O)(=O)c4ccc(C(C)(C)C)cc4)c3C2=O)n1] | 68 |
| 255 | 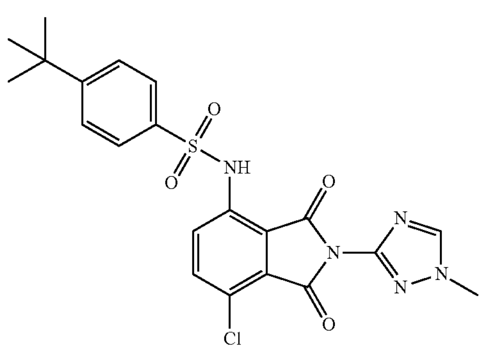 | 72 |

-continued

| Compound number | Structure | Ki (nM) |
|---|---|---|
| 256 | 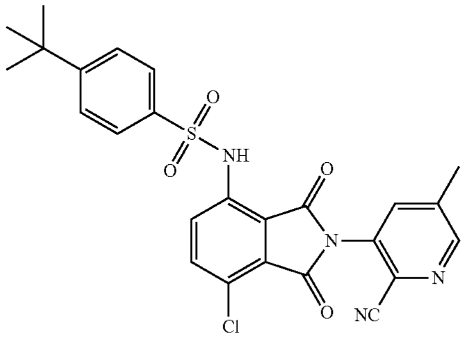 [SMILES: Cc1cnc(C#N)c(N2C(=O)c3c(Cl)ccc(NS(=O)(=O)c4ccc(C(C)(C)C)cc4)c3C2=O)c1] | 18 |
| 257 | 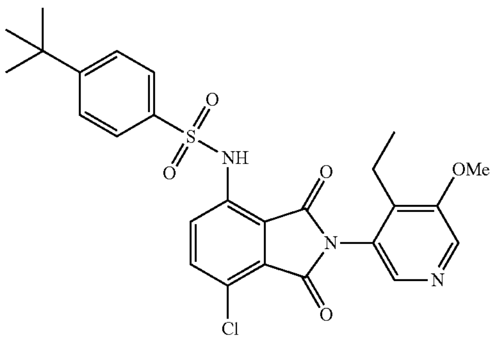 [SMILES: CCc1c(OC)cncc1N1C(=O)c2c(Cl)ccc(NS(=O)(=O)c3ccc(C(C)(C)C)cc3)c2C1=O] | 21 |
| 258 | 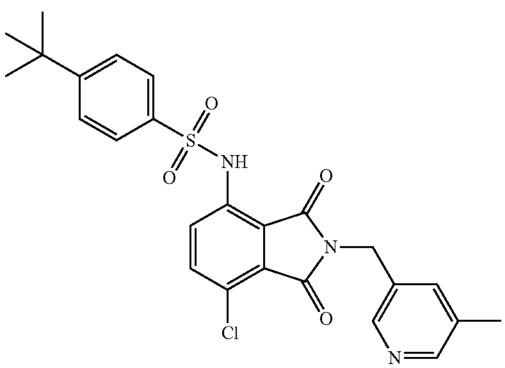 [SMILES: Cc1cncc(CN2C(=O)c3c(Cl)ccc(NS(=O)(=O)c4ccc(C(C)(C)C)cc4)c3C2=O)c1] | 67 |
| 259 | 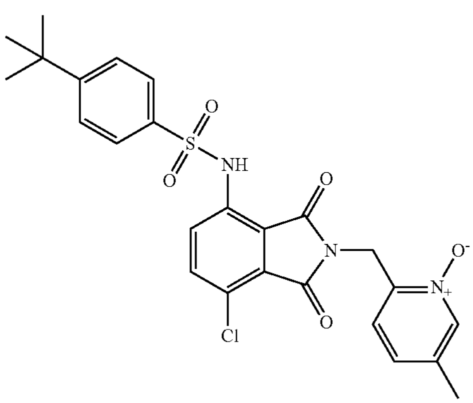 [SMILES: Cc1ccc(CN2C(=O)c3c(Cl)ccc(NS(=O)(=O)c4ccc(C(C)(C)C)cc4)c3C2=O)[n+]([O-])c1] | 45 |

-continued

| Compound number | Structure | Ki (nM) |
|---|---|---|
| 260 | 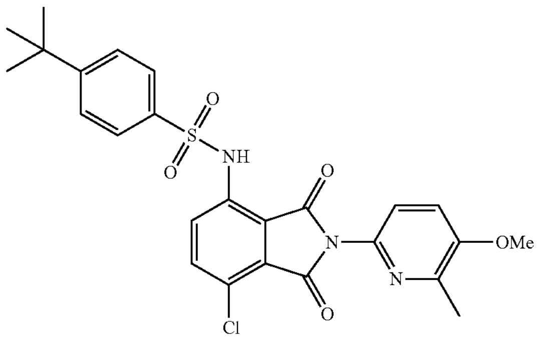 [SMILES: COc1ccc(N2C(=O)c3c(Cl)ccc(NS(=O)(=O)c4ccc(C(C)(C)C)cc4)c3C2=O)nc1C] | 22 |
| 261 | 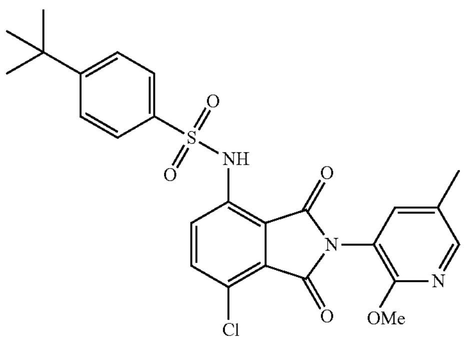 [SMILES: COc1ncc(C)cc1N1C(=O)c2c(Cl)ccc(NS(=O)(=O)c3ccc(C(C)(C)C)cc3)c2C1=O] | 11 |
| 262 | 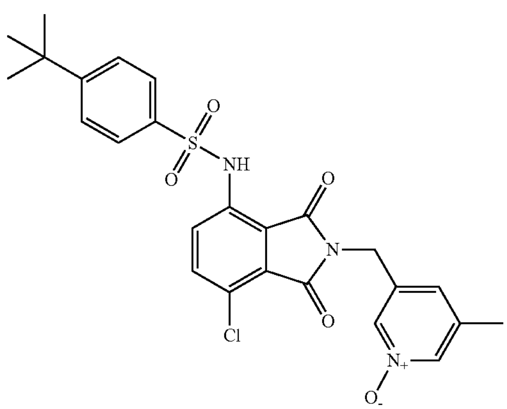 | 119 |
| 263 | 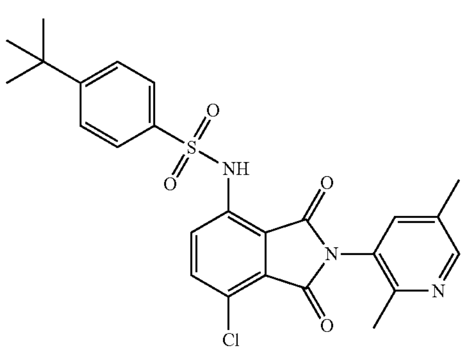 | 25 |

-continued
| Compound number | Structure | Ki (nM) |
|---|---|---|
| 264 | 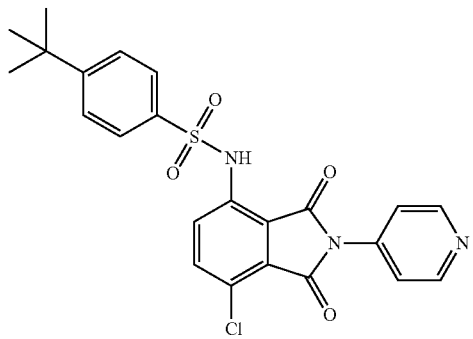 [SMILES: CC(C)(C)c1ccc(S(=O)(=O)Nc2ccc(Cl)c3c2C(=O)N(c2ccncc2)C3=O)cc1] | 18 |
| 266 | 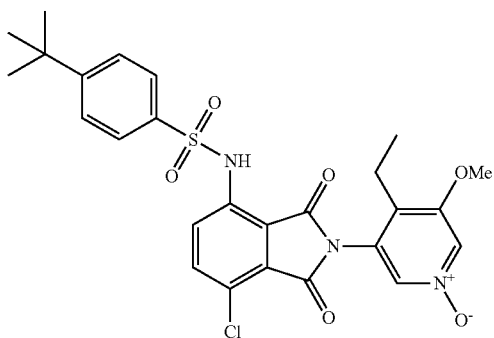 | 25 |
| 267 | 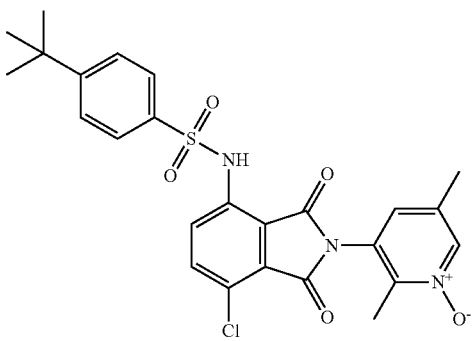 [SMILES: Cc1cc(N2C(=O)c3c(Cl)ccc(NS(=O)(=O)c4ccc(C(C)(C)C)cc4)c3C2=O)c(C)[n+]([O-])c1] | 59 |
| 270 | 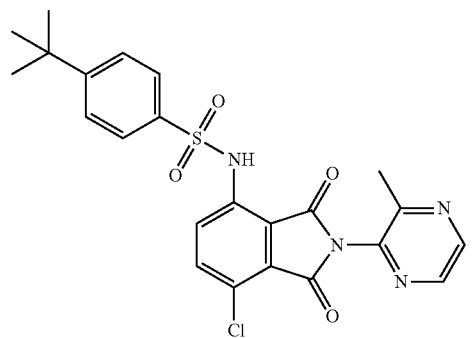 [SMILES: Cc1nccnc1N1C(=O)c2c(Cl)ccc(NS(=O)(=O)c3ccc(C(C)(C)C)cc3)c2C1=O] | 61 |

| Compound number | Structure | Ki (nM) |
|---|---|---|
| 271 | 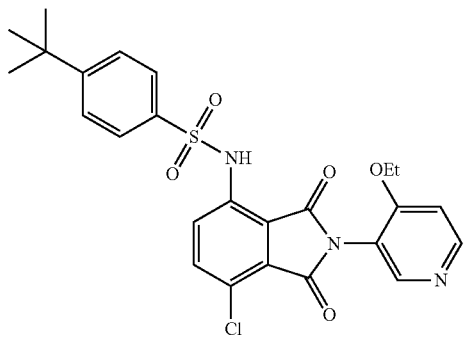 [SMILES: CCOc1ccncc1N1C(=O)c2c(Cl)ccc(NS(=O)(=O)c3ccc(C(C)(C)C)cc3)c2C1=O] | 35 |
| 272 | 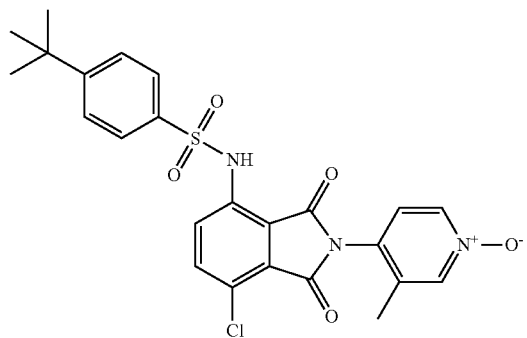 [SMILES: Cc1c[n+]([O-])ccc1N1C(=O)c2c(Cl)ccc(NS(=O)(=O)c3ccc(C(C)(C)C)cc3)c2C1=O] | 29 |
| 274 | 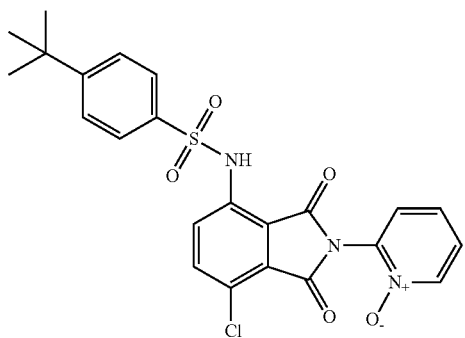 | 50 |
| 275 | 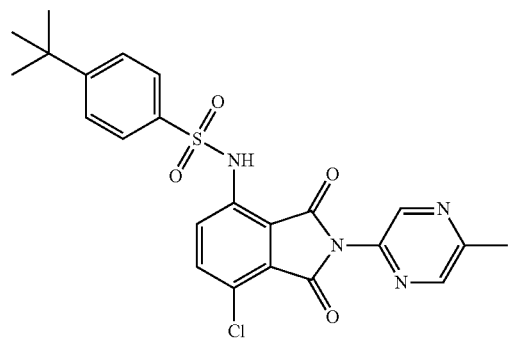 [SMILES: Cc1cnc(N2C(=O)c3c(Cl)ccc(NS(=O)(=O)c4ccc(C(C)(C)C)cc4)c3C2=O)cn1] | 54 |

-continued

| Compound number | Structure | Ki (nM) |
|---|---|---|
| 276 | 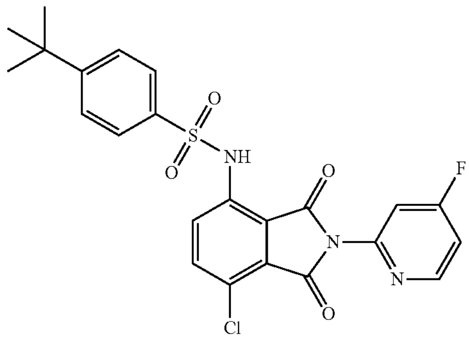 [SMILES: CC(C)(C)c1ccc(S(=O)(=O)Nc2ccc(Cl)c3c2C(=O)N(c2cc(F)ccn2)C3=O)cc1] | 91 |
| 278 | 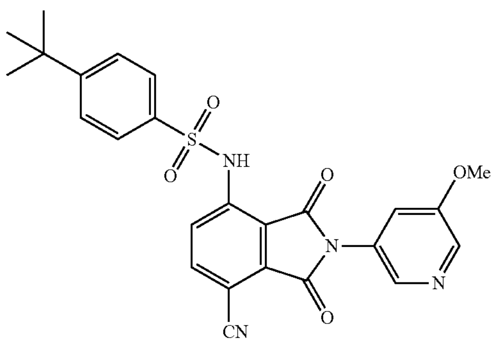 [SMILES: COc1cncc(N2C(=O)c3c(C#N)ccc(NS(=O)(=O)c4ccc(C(C)(C)C)cc4)c3C2=O)c1] | 17 |
| 279 | 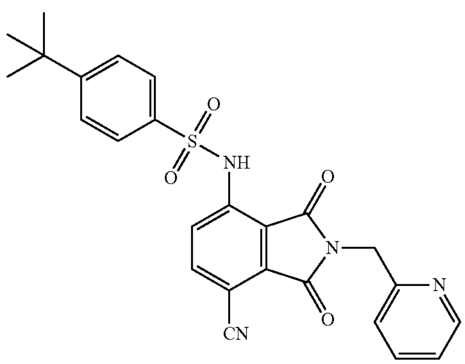 [SMILES: CC(C)(C)c1ccc(S(=O)(=O)Nc2ccc(C#N)c3c2C(=O)N(Cc2ccccn2)C3=O)cc1] | 17 |
| 280 | 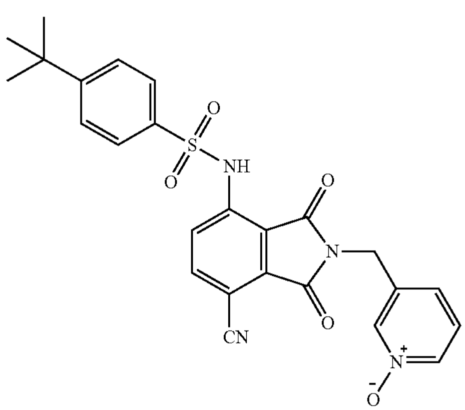 | 84 |

-continued
| Compound number | Structure | Ki (nM) |
|---|---|---|
| 281 | 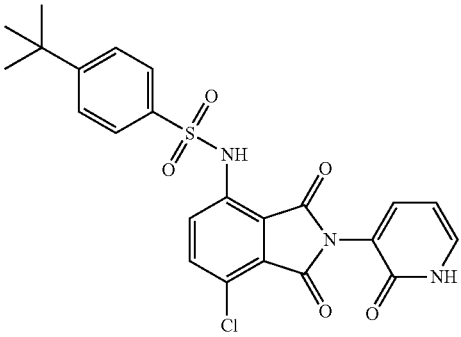 [SMILES: CC(C)(C)c1ccc(S(=O)(=O)Nc2ccc(Cl)c3c2C(=O)N(c2ccc[nH]c2=O)C3=O)cc1] | 4 |
| 282 | 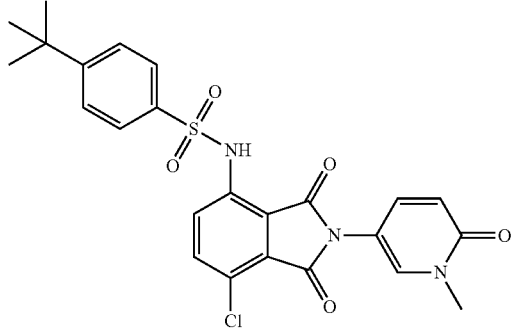 [SMILES: Cn1cc(N2C(=O)c3c(Cl)ccc(NS(=O)(=O)c4ccc(C(C)(C)C)cc4)c3C2=O)ccc1=O] | 23 |
| 283 | 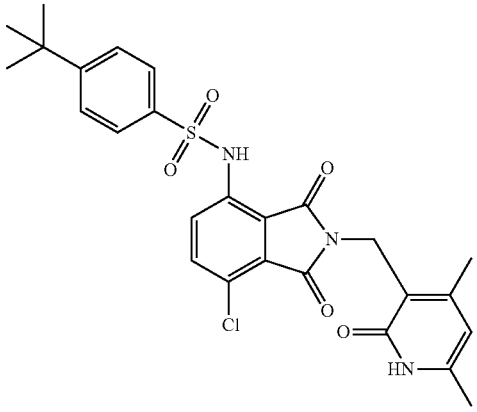 [SMILES: Cc1cc(C)c(CN2C(=O)c3c(Cl)ccc(NS(=O)(=O)c4ccc(C(C)(C)C)cc4)c3C2=O)c(=O)[nH]1] | 20 |
| 284 | 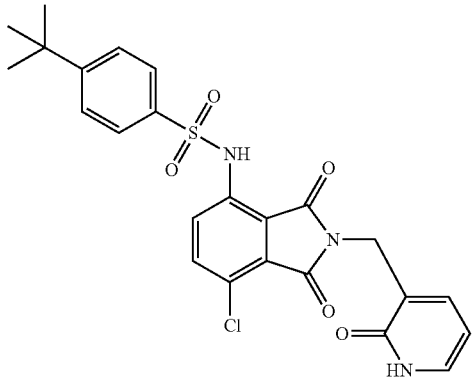 [SMILES: CC(C)(C)c1ccc(S(=O)(=O)Nc2ccc(Cl)c3c2C(=O)N(Cc2ccc[nH]c2=O)C3=O)cc1] | 12 |

-continued

| Compound number | Structure | Ki (nM) |
|---|---|---|
| 285 | 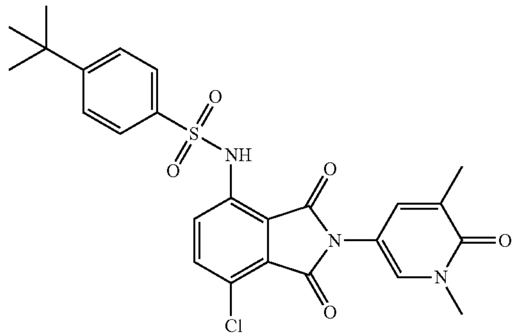 [SMILES: Cc1cc(N2C(=O)c3c(Cl)ccc(NS(=O)(=O)c4ccc(C(C)(C)C)cc4)c3C2=O)cn(C)c1=O] | 78 |
| 286 | 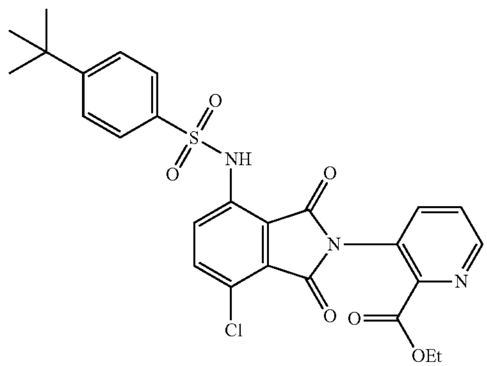 [SMILES: CCOC(=O)c1ncccc1N1C(=O)c2c(Cl)ccc(NS(=O)(=O)c3ccc(C(C)(C)C)cc3)c2C1=O] | 14 |
| 287 | 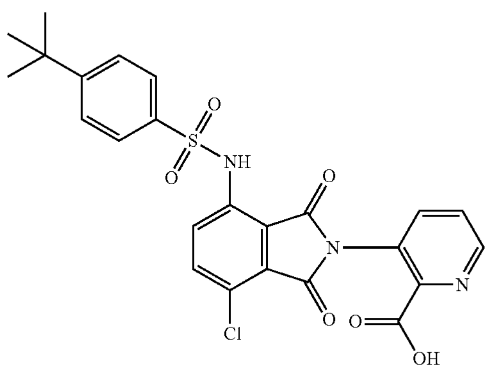 | 10 |
| 288 | 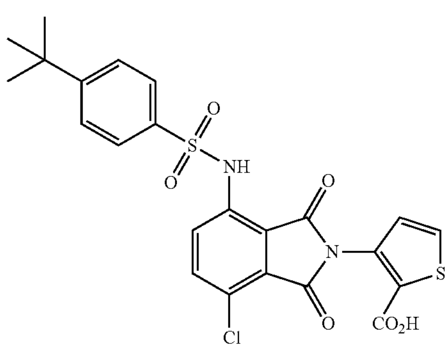 [SMILES: CC(C)(C)c1ccc(S(=O)(=O)Nc2ccc(Cl)c3c2C(=O)N(c2ccsc2C(=O)O)C3=O)cc1] | 23 |

| Compound number | Structure | Ki (nM) |
| --- | --- | --- |
| 289 | 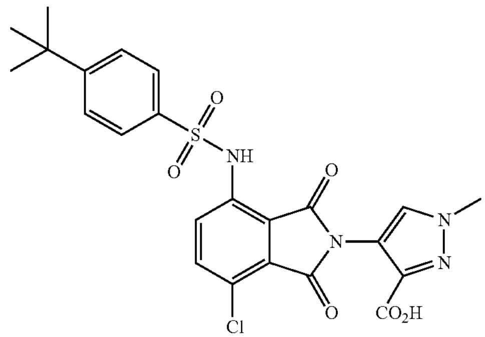 [SMILES: Cn1cc(N2C(=O)c3c(Cl)ccc(NS(=O)(=O)c4ccc(C(C)(C)C)cc4)c3C2=O)c(C(=O)O)n1] | 109 |
| 290 | 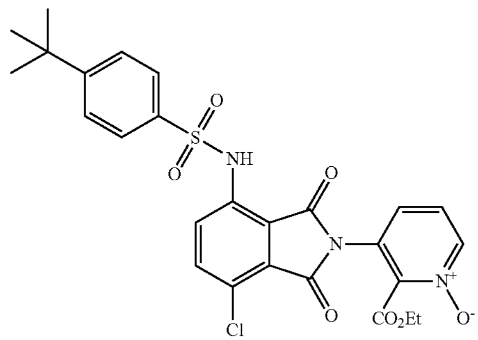 [SMILES: CCOC(=O)c1c(N2C(=O)c3c(Cl)ccc(NS(=O)(=O)c4ccc(C(C)(C)C)cc4)c3C2=O)ccc[n+]1[O-]] | 14 |
| 291 | 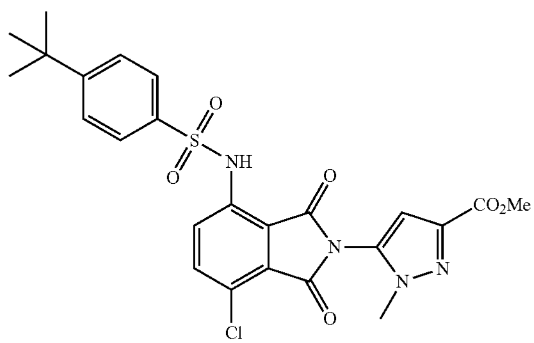 [SMILES: COC(=O)c1cc(N2C(=O)c3c(Cl)ccc(NS(=O)(=O)c4ccc(C(C)(C)C)cc4)c3C2=O)n(C)n1] | 15 |
| 292 | 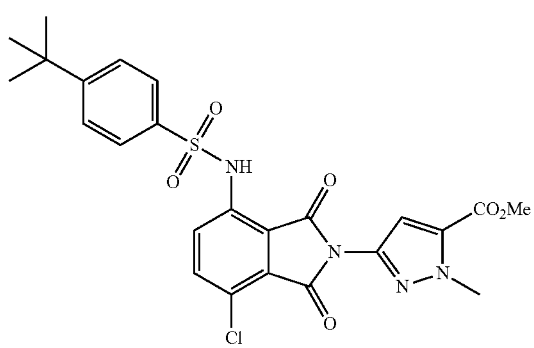 [SMILES: COC(=O)c1cc(N2C(=O)c3c(Cl)ccc(NS(=O)(=O)c4ccc(C(C)(C)C)cc4)c3C2=O)nn1C] | 16 |

Example 32

Biological Activity: FLIPR Assay Using MOLT4 Cells

A calcium flux assay was used to determine the ability of the compounds to interfere with the binding between CCR9 and its chemokine ligand (TECK) in MOLT4 cells (a human T-cell line). MOLT4 cells were seeded (100,000 cells/well) in corning cell culture plates (Cat #3603) in assay buffer (1×HBSS, 20 mM HEPES) containing 2.5 mM Probenecid. The plate was centrifuged at 1200 rpm for 3 minutes and incubated at 37° C./5% $CO_2$ for 2 hours. A 0.3× Fluo-4 NW calcium dye was prepared in assay buffer containing 5 mM Probenecid and stored in the dark. Each well was loaded with 25 µl of 0.3× Fluo-4 NW calcium dye and incubated at 37° C./5% $CO_2$ for 60 minutes and then at room temperature for 30 minutes. A half-log serially diluted concentration response curve was prepared at a 4× concentration for each (10 μM-0.1 nM final assay concentration) and 25 μL of the compound then transferred to the cells (100 μL final volume) for 60 minutes prior to stimulation (30 minutes at 37° C./5% $CO_2$ and 30 minutes at room temperature). TECK was diluted to 5× its $EC_{50}$ in assay buffer (containing 0.1% [w/v] bovine serum albumin [BSA]) and 25 μL dispensed through the FLIPR instrument to stimulate the cells (125 μL final volume). The increased in intracellular calcium levels was measured with the FLIPR instrument. The potency of the compound as CCR9 antagonist was calculated as an $IC_{50}$ using GraphPad Prism software (variable slope four parameter). The Ki of the compound was determined from the $IC_{50}$ values using the following equation.

$IC_{50}/1+$(Agonist (TECK) conc. used in assay/$EC_{50}$ of agonist (TECK) generated on day of experiment) Ki calculation:

| Compound number | Structure | Ki (nM) |
|---|---|---|
| 1 | 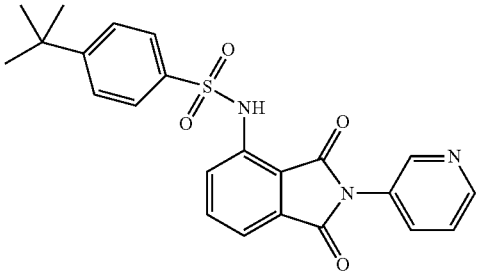 [SMILES: CC(C)(C)c1ccc(S(=O)(=O)Nc2cccc3c2C(=O)N(c2cccnc2)C3=O)cc1] | 479 |
| 4 | 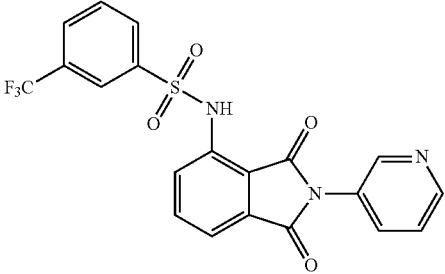 [SMILES: O=C1c2cccc(NS(=O)(=O)c3cccc(C(F)(F)F)c3)c2C(=O)N1c1cccnc1] | 2713 |
| 5 | 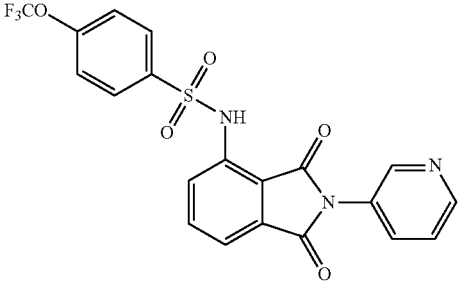 [SMILES: O=C1c2cccc(NS(=O)(=O)c3ccc(OC(F)(F)F)cc3)c2C(=O)N1c1cccnc1] | 123 |
| 7 | 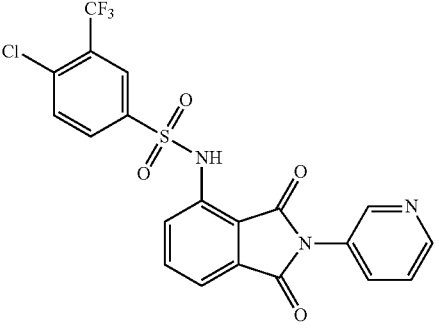 [SMILES: O=C1c2cccc(NS(=O)(=O)c3ccc(Cl)c(C(F)(F)F)c3)c2C(=O)N1c1cccnc1] | 206 |

-continued

| Compound number | Structure | Ki (nM) |
| --- | --- | --- |
| 8 | 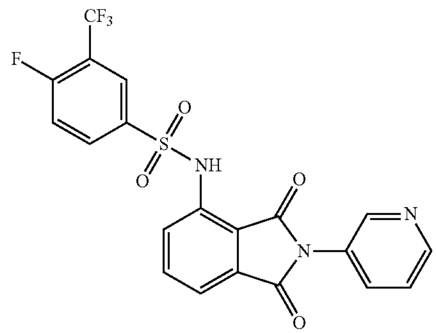 [SMILES: O=C1c2cccc(NS(=O)(=O)c3ccc(F)c(C(F)(F)F)c3)c2C(=O)N1c1cccnc1] | 1322 |
| 12 | 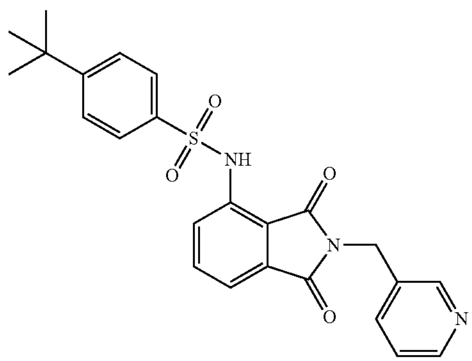 [SMILES: CC(C)(C)c1ccc(S(=O)(=O)Nc2cccc3c2C(=O)N(Cc2cccnc2)C3=O)cc1] | 618 |
| 14 | 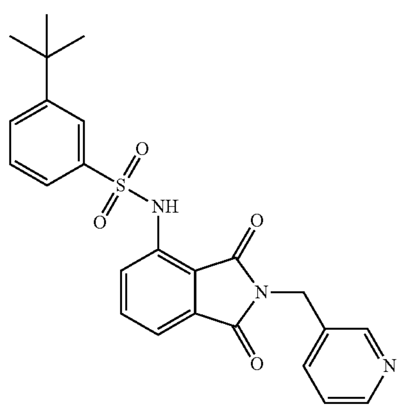 [SMILES: CC(C)(C)c1cccc(S(=O)(=O)Nc2cccc3c2C(=O)N(Cc2cccnc2)C3=O)c1] | 1555 |
| 19 | 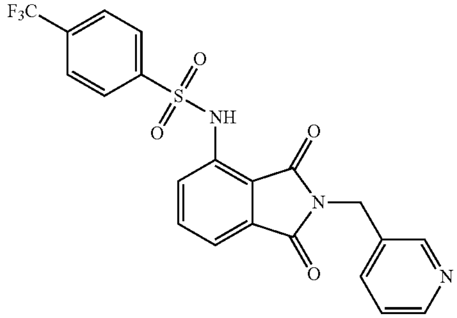 [SMILES: O=C1c2cccc(NS(=O)(=O)c3ccc(C(F)(F)F)cc3)c2C(=O)N1Cc1cccnc1] | 758 |

-continued

| Compound number | Structure | Ki (nM) |
|---|---|---|
| 36 | 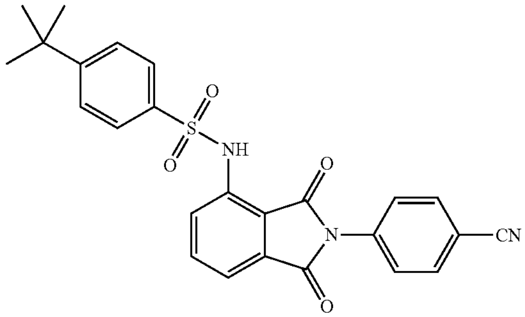 [SMILES: CC(C)(C)c1ccc(S(=O)(=O)Nc2cccc3c2C(=O)N(c2ccc(C#N)cc2)C3=O)cc1] | 1210 |
| 39 | 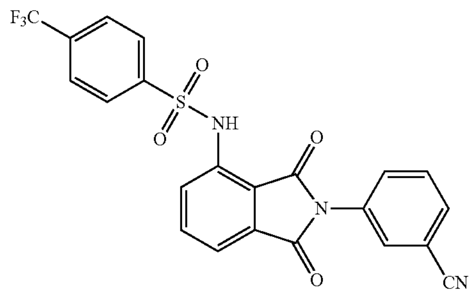 [SMILES: N#Cc1cccc(N2C(=O)c3cccc(NS(=O)(=O)c4ccc(C(F)(F)F)cc4)c3C2=O)c1] | 611 |
| 40 | 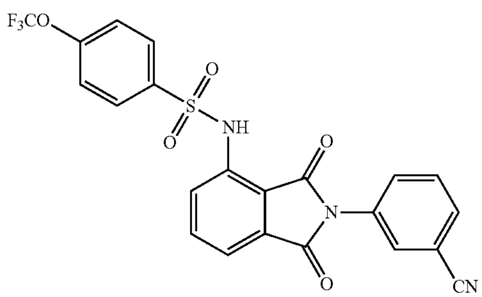 [SMILES: N#Cc1cccc(N2C(=O)c3cccc(NS(=O)(=O)c4ccc(OC(F)(F)F)cc4)c3C2=O)c1] | 1355 |
| 41 | 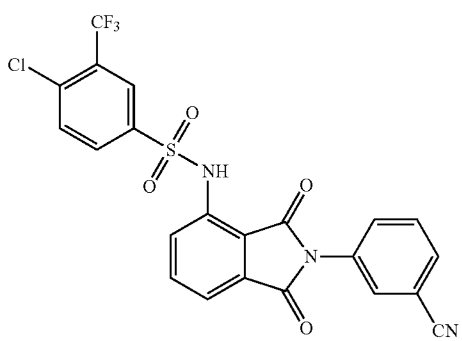 [SMILES: N#Cc1cccc(N2C(=O)c3cccc(NS(=O)(=O)c4ccc(Cl)c(C(F)(F)F)c4)c3C2=O)c1] | 167 |
| 43 | 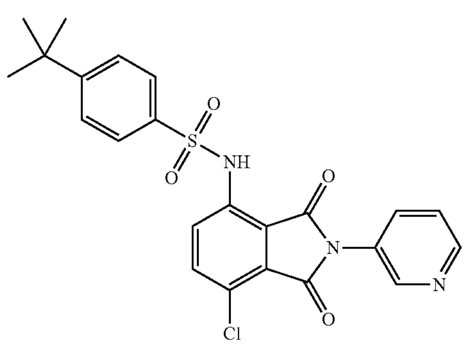 [SMILES: CC(C)(C)c1ccc(S(=O)(=O)Nc2ccc(Cl)c3c2C(=O)N(c2cccnc2)C3=O)cc1] | 25 |

-continued

| Compound number | Structure | Ki (nM) |
|---|---|---|
| 44 | 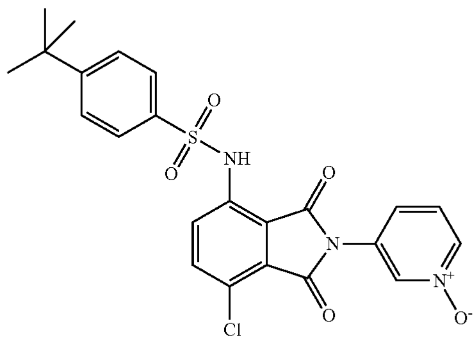 [SMILES: CC(C)(C)c1ccc(S(=O)(=O)Nc2ccc(Cl)c3c2C(=O)N(c2ccc[n+]([O-])c2)C3=O)cc1] | 16 |
| 45 | 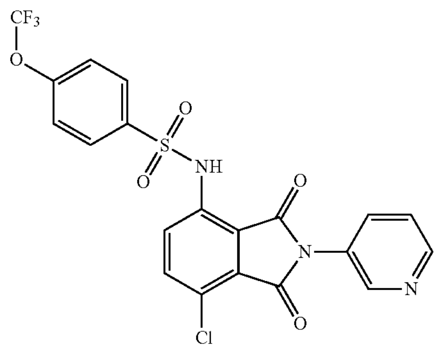 [SMILES: O=C1c2c(Cl)ccc(NS(=O)(=O)c3ccc(OC(F)(F)F)cc3)c2C(=O)N1c1cccnc1] | 52 |
| 47 | 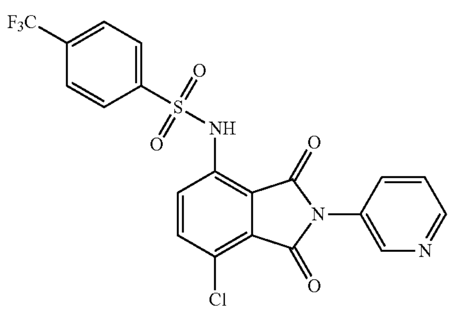 | 34 |
| 48 | 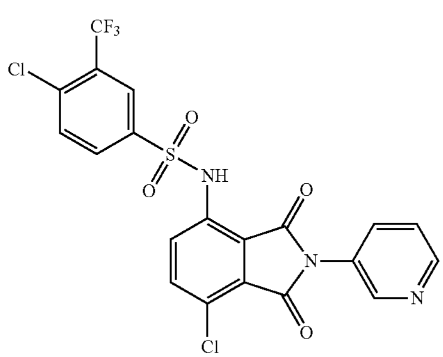 [SMILES: O=C1c2c(Cl)ccc(NS(=O)(=O)c3ccc(Cl)c(C(F)(F)F)c3)c2C(=O)N1c1cccnc1] | 171 |

-continued

| Compound number | Structure | Ki (nM) |
|---|---|---|
| 52 | 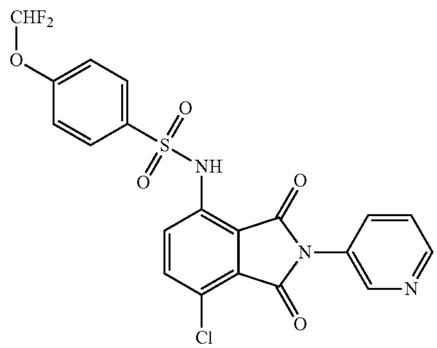 [SMILES: O=C1c2c(Cl)ccc(NS(=O)(=O)c3ccc(OC(F)F)cc3)c2C(=O)N1c1cccnc1] | 187 |
| 57 | 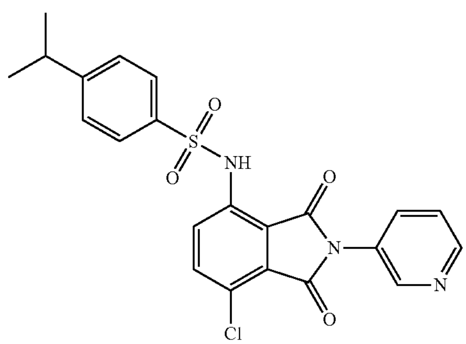 | 38 |
| 64 | 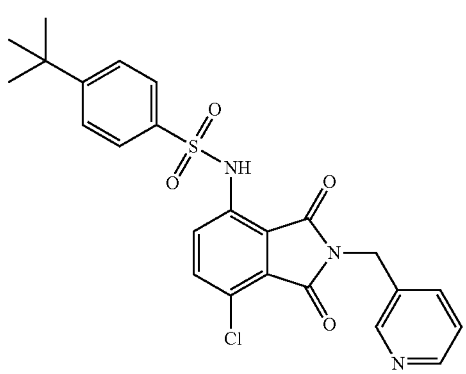 | 22 |
| 65 | 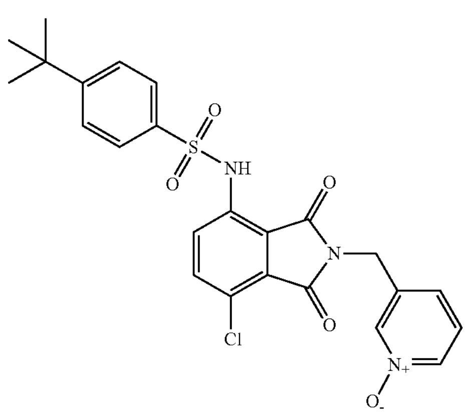 | 13 |

-continued

| Compound number | Structure | Ki (nM) |
|---|---|---|
| 66 | 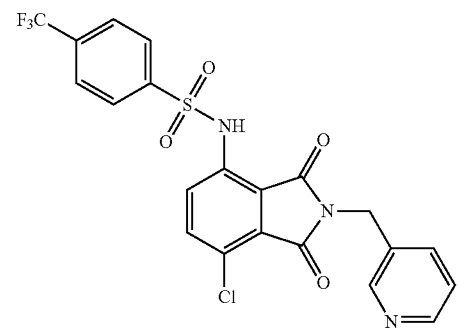 | 115 |
| 79 | 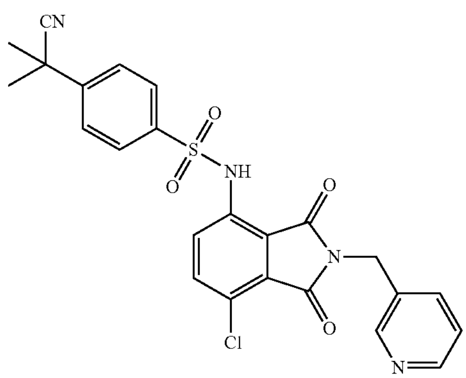 [SMILES: CC(C)(C#N)c1ccc(S(=O)(=O)Nc2ccc(Cl)c3c2C(=O)N(Cc2cccnc2)C3=O)cc1] | 33 |
| 80 | 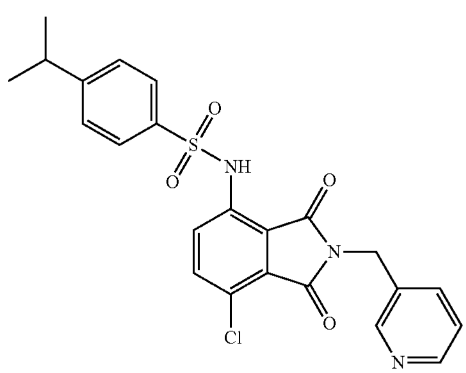 [SMILES: CC(C)c1ccc(S(=O)(=O)Nc2ccc(Cl)c3c2C(=O)N(Cc2cccnc2)C3=O)cc1] | 173 |
| 81 | 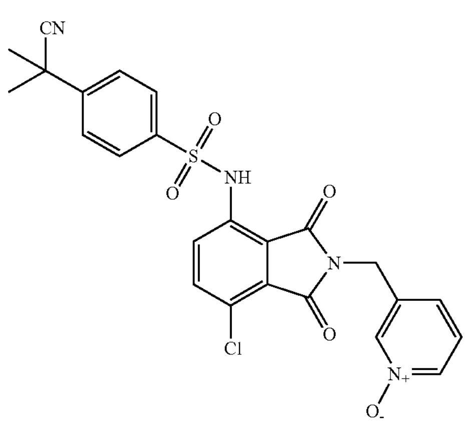 | 148 |

-continued

| Compound number | Structure | Ki (nM) |
| --- | --- | --- |
| 82 | 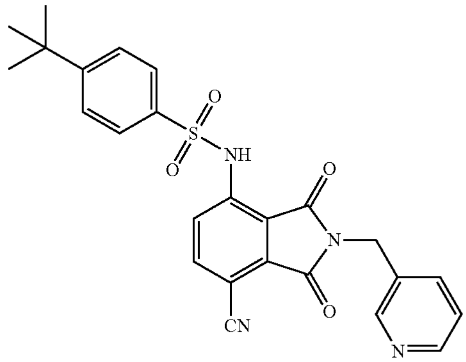 [SMILES: CC(C)(C)c1ccc(S(=O)(=O)Nc2ccc(C#N)c3c2C(=O)N(Cc2cccnc2)C3=O)cc1] | 19 |
| 90 | 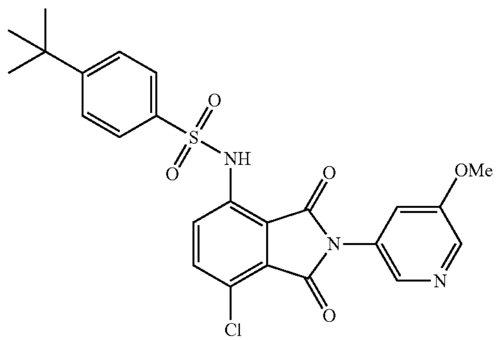 | 22 |
| 91 | 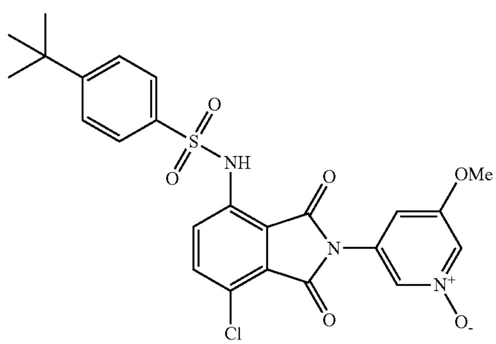 | 50 |
| 92 | 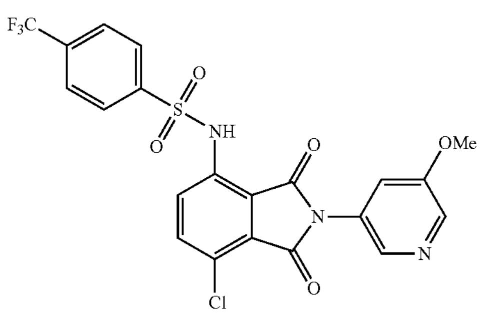 [SMILES: COc1cncc(N2C(=O)c3c(Cl)ccc(NS(=O)(=O)c4ccc(C(F)(F)F)cc4)c3C2=O)c1] | 255 |

-continued

| Compound number | Structure | Ki (nM) |
|---|---|---|
| 93 | 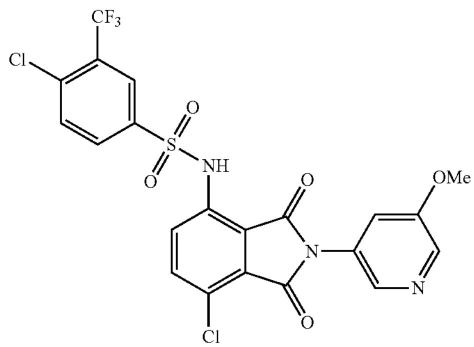 [SMILES: COc1cncc(N2C(=O)c3c(Cl)ccc(NS(=O)(=O)c4ccc(Cl)c(C(F)(F)F)c4)c3C2=O)c1] | 217 |
| 94 | 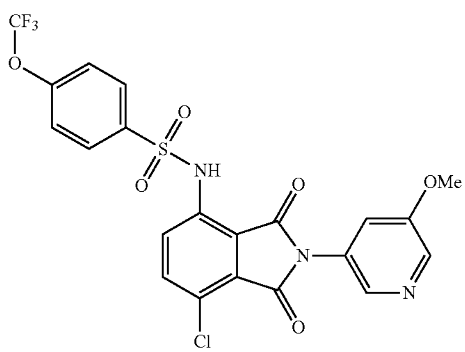 [SMILES: COc1cncc(N2C(=O)c3c(Cl)ccc(NS(=O)(=O)c4ccc(OC(F)(F)F)cc4)c3C2=O)c1] | 244 |
| 103 | 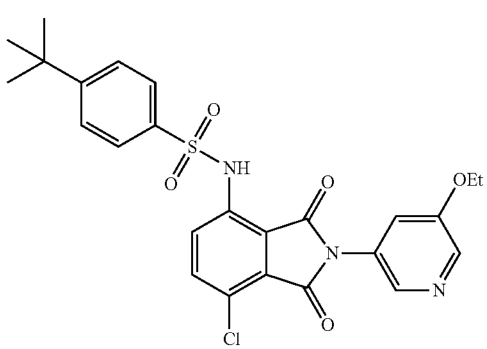 [SMILES: CCOc1cncc(N2C(=O)c3c(Cl)ccc(NS(=O)(=O)c4ccc(C(C)(C)C)cc4)c3C2=O)c1] | 128 |
| 104 | 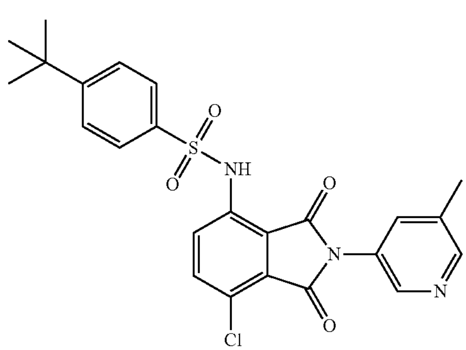 | 30 |

-continued

| Compound number | Structure | Ki (nM) |
| --- | --- | --- |
| 105 | 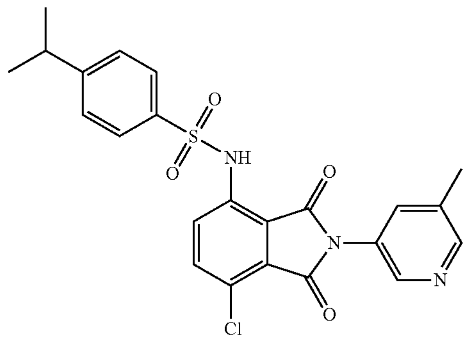 | 311 |
| 107 | 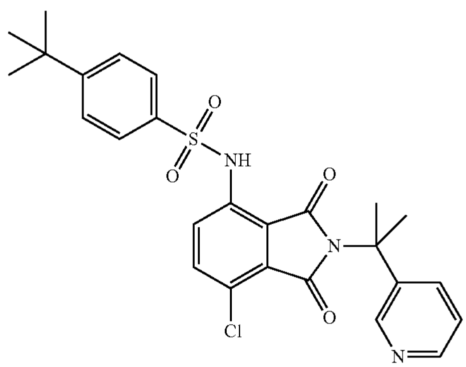 [SMILES: CC(C)(C)c1ccc(S(=O)(=O)Nc2ccc(Cl)c3c2C(=O)N(C(C)(C)c2cccnc2)C3=O)cc1] | 318 |
| 116 | 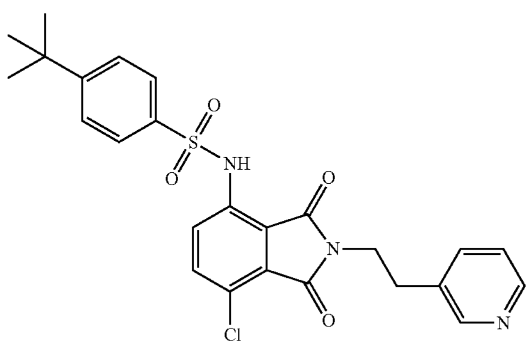 | 100 |
| 117 | 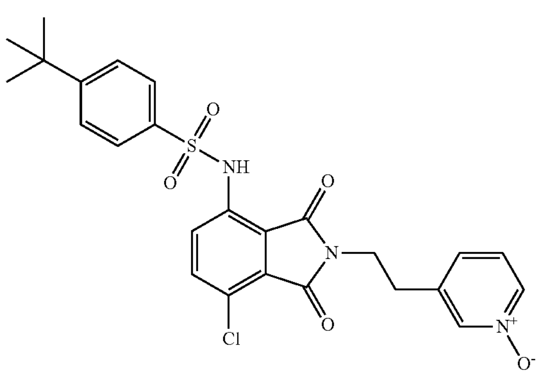 [SMILES: CC(C)(C)c1ccc(S(=O)(=O)Nc2ccc(Cl)c3c2C(=O)N(CCc2ccc[n+]([O-])c2)C3=O)cc1] | 184 |

-continued

| Compound number | Structure | Ki (nM) |
|---|---|---|
| 118 | 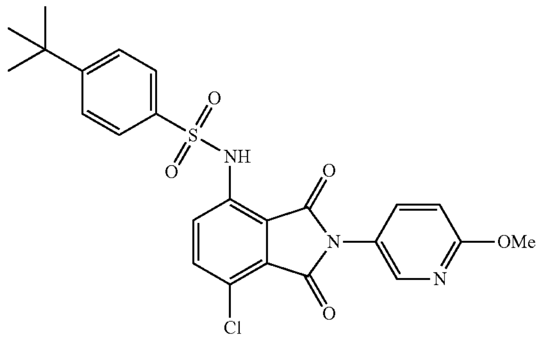 [SMILES: COc1ccc(N2C(=O)c3c(Cl)ccc(NS(=O)(=O)c4ccc(C(C)(C)C)cc4)c3C2=O)cn1] | 78 |
| 119 | 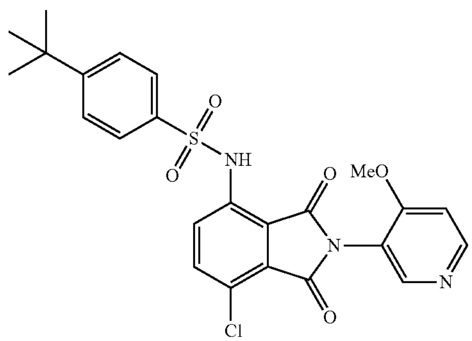 [SMILES: COc1ccncc1N1C(=O)c2c(Cl)ccc(NS(=O)(=O)c3ccc(C(C)(C)C)cc3)c2C1=O] | 2 |
| 120 | 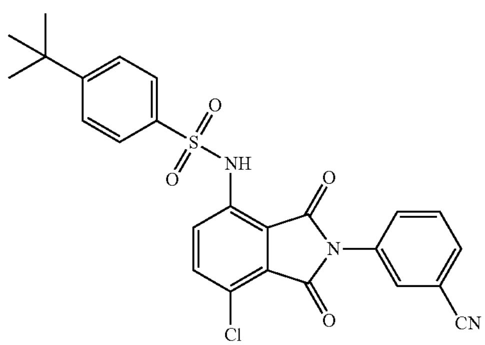 [SMILES: CC(C)(C)c1ccc(S(=O)(=O)Nc2ccc(Cl)c3c2C(=O)N(c2cccc(C#N)c2)C3=O)cc1] | 74 |
| 121 | 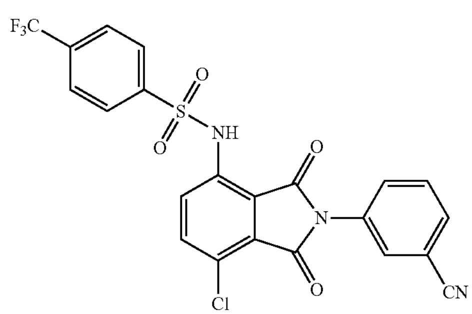 [SMILES: N#Cc1cccc(N2C(=O)c3c(Cl)ccc(NS(=O)(=O)c4ccc(C(F)(F)F)cc4)c3C2=O)c1] | 192 |

-continued

| Compound number | Structure | Ki (nM) |
|---|---|---|
| 122 | 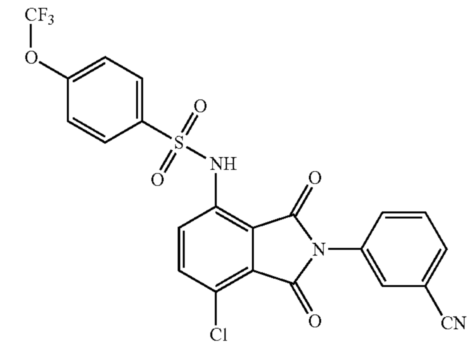 [SMILES: N#Cc1cccc(N2C(=O)c3c(Cl)ccc(NS(=O)(=O)c4ccc(OC(F)(F)F)cc4)c3C2=O)c1] | 175 |
| 124 | 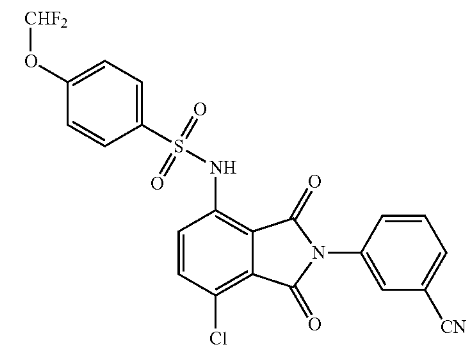 [SMILES: N#Cc1cccc(N2C(=O)c3c(Cl)ccc(NS(=O)(=O)c4ccc(OC(F)F)cc4)c3C2=O)c1] | 224 |
| 125 | 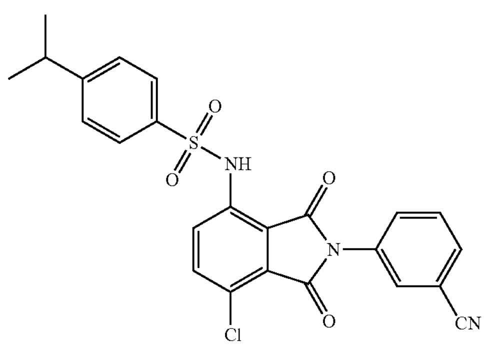 [SMILES: CC(C)c1ccc(S(=O)(=O)Nc2ccc(Cl)c3c2C(=O)N(c2cccc(C#N)c2)C3=O)cc1] | 243 |
| 126 | 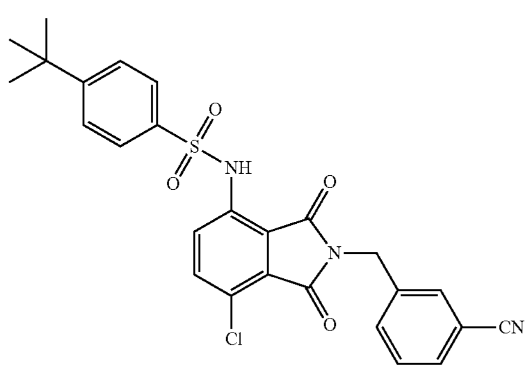 [SMILES: CC(C)(C)c1ccc(S(=O)(=O)Nc2ccc(Cl)c3c2C(=O)N(Cc2cccc(C#N)c2)C3=O)cc1] | 158 |

-continued
| Compound number | Structure | Ki (nM) |
|---|---|---|
| 127 | 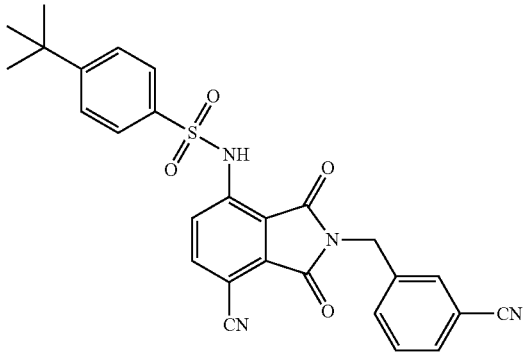 | 153 |
| 128 | 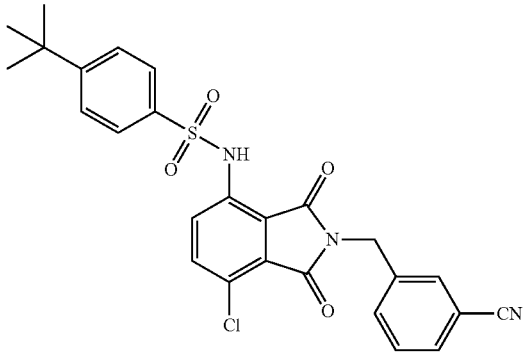 | 244 |
| 132 | 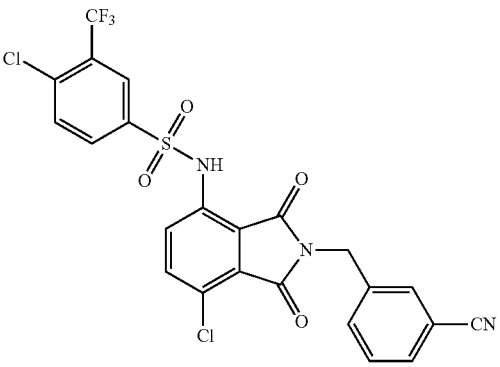 [SMILES: N#Cc1cccc(CN2C(=O)c3c(Cl)ccc(NS(=O)(=O)c4ccc(Cl)c(C(F)(F)F)c4)c3C2=O)c1] | 252 |
| 133 | 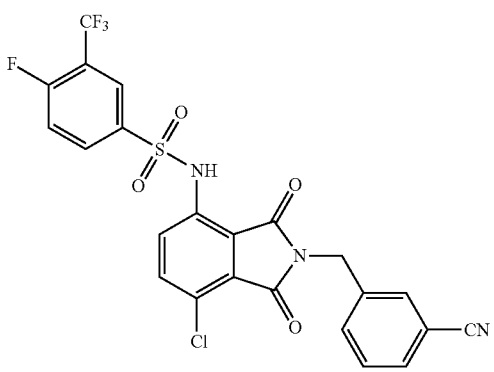 [SMILES: N#Cc1cccc(CN2C(=O)c3c(Cl)ccc(NS(=O)(=O)c4ccc(F)c(C(F)(F)F)c4)c3C2=O)c1] | 220 |

-continued

| Compound number | Structure | Ki (nM) |
|---|---|---|
| 138 | 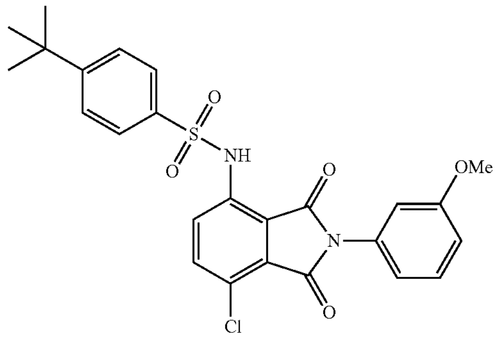 [SMILES: COc1cccc(N2C(=O)c3c(Cl)ccc(NS(=O)(=O)c4ccc(C(C)(C)C)cc4)c3C2=O)c1] | 83 |
| 140 | 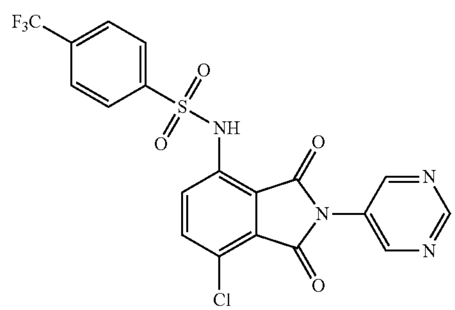 | 216 |
| 142 | 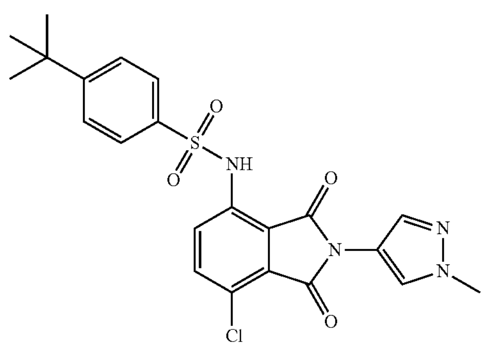 | 41 |
| 143 | 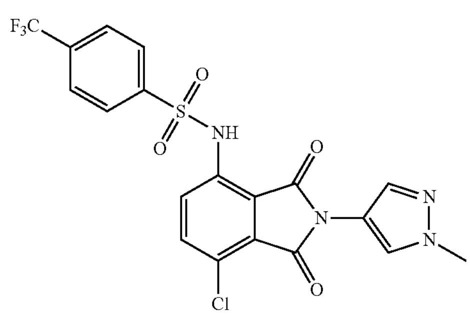 [SMILES: Cn1cc(N2C(=O)c3c(Cl)ccc(NS(=O)(=O)c4ccc(C(F)(F)F)cc4)c3C2=O)cn1] | 64 |

| Compound number | Structure | Ki (nM) |
|---|---|---|
| 144 | 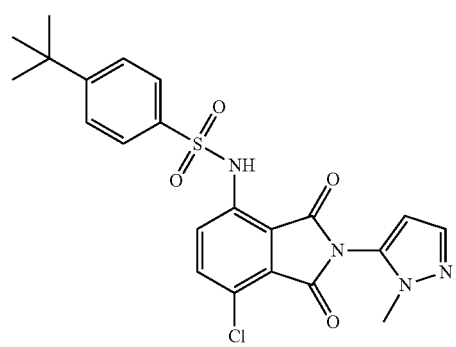 | 3 |
| 145 | 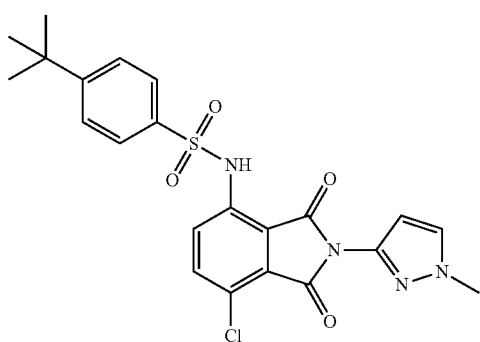 [SMILES: Cn1ccc(N2C(=O)c3c(Cl)ccc(NS(=O)(=O)c4ccc(C(C)(C)C)cc4)c3C2=O)n1] | 129 |
| 146 | 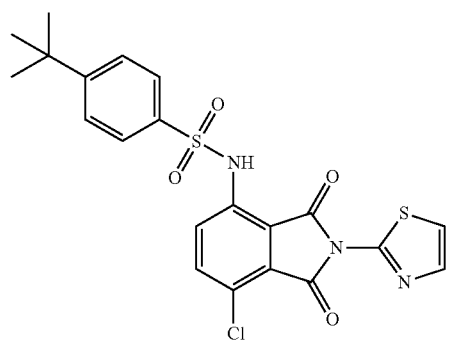 [SMILES: CC(C)(C)c1ccc(S(=O)(=O)Nc2ccc(Cl)c3c2C(=O)N(c2nccs2)C3=O)cc1] | 154 |
| 148 | 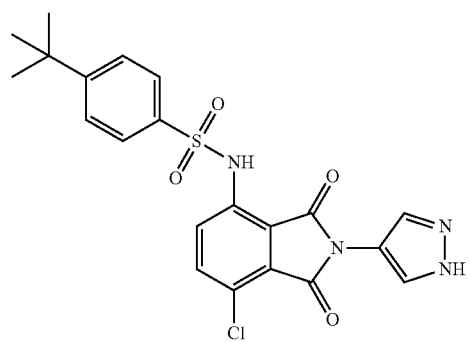 | 36 |

-continued

| Compound number | Structure | Ki (nM) |
|---|---|---|
| 149 | 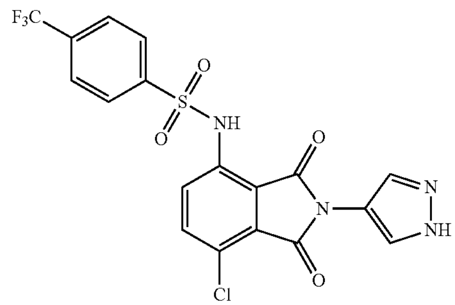 [SMILES: O=C1c2c(Cl)ccc(NS(=O)(=O)c3ccc(C(F)(F)F)cc3)c2C(=O)N1c1cn[nH]c1] | 53 |
| 151 | 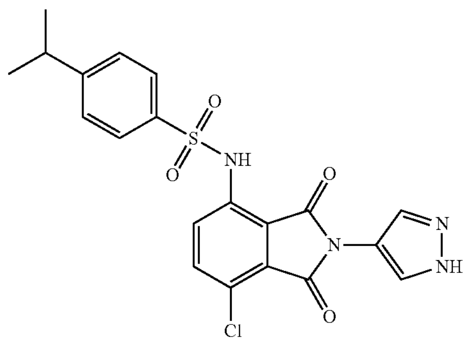 [SMILES: CC(C)c1ccc(S(=O)(=O)Nc2ccc(Cl)c3c2C(=O)N(c2cn[nH]c2)C3=O)cc1] | 42 |
| 152 | 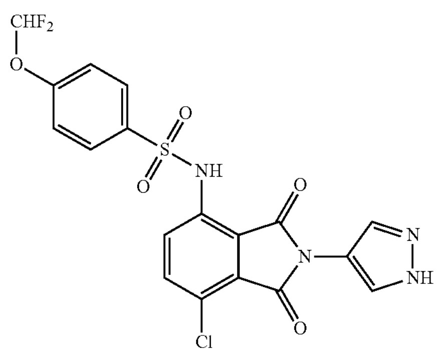 [SMILES: O=C1c2c(Cl)ccc(NS(=O)(=O)c3ccc(OC(F)F)cc3)c2C(=O)N1c1cn[nH]c1] | 245 |
| 153 | 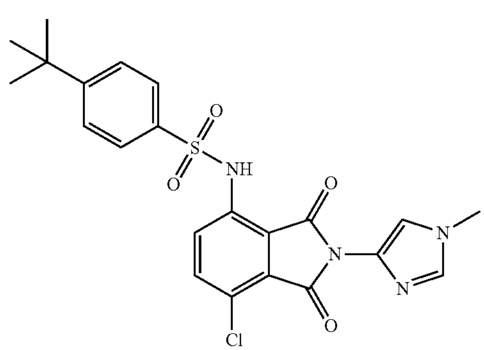 | 7 |

-continued
| Compound number | Structure | Ki (nM) |
|---|---|---|
| 154 | 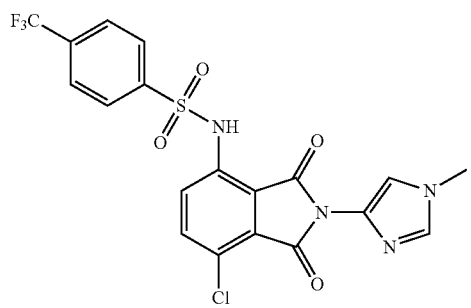 [SMILES: Cn1cnc(N2C(=O)c3c(Cl)ccc(NS(=O)(=O)c4ccc(C(F)(F)F)cc4)c3C2=O)c1] | 32 |
| 155 | 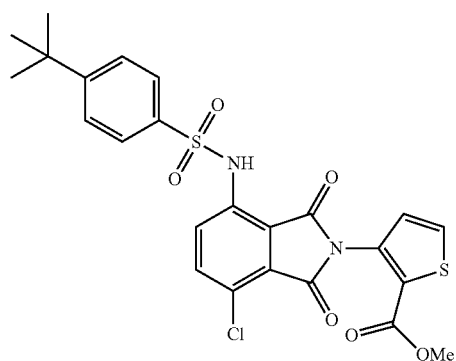 [SMILES: COC(=O)c1sccc1N1C(=O)c2c(Cl)ccc(NS(=O)(=O)c3ccc(C(C)(C)C)cc3)c2C1=O] | 44 |
| 157 | 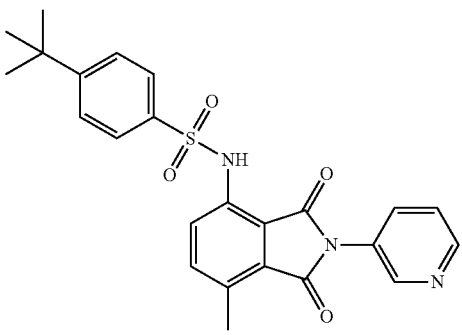 [SMILES: Cc1ccc(NS(=O)(=O)c2ccc(C(C)(C)C)cc2)c2c1C(=O)N(c1cccnc1)C2=O] | 189 |
| 160 | 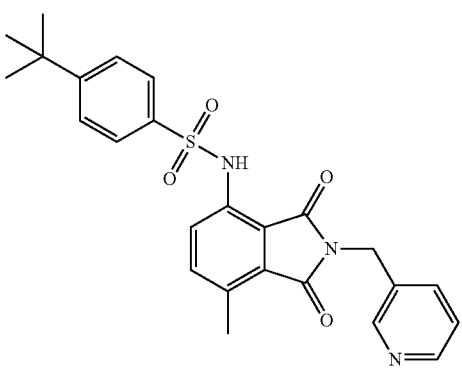 | 456 |

-continued
| Compound number | Structure | Ki (nM) |
|---|---|---|
| 161 | 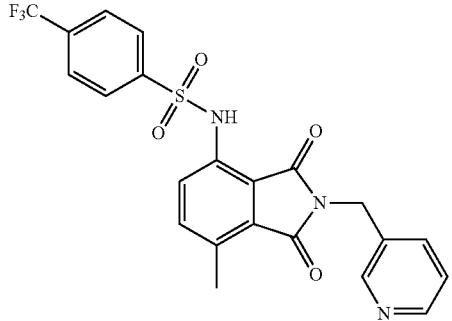 [SMILES: Cc1ccc(NS(=O)(=O)c2ccc(C(F)(F)F)cc2)c2c1C(=O)N(Cc1cccnc1)C2=O] | 568 |
| 162 | 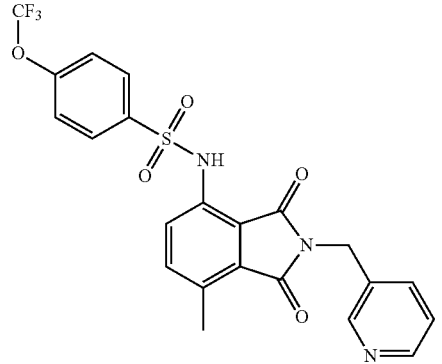 [SMILES: Cc1ccc(NS(=O)(=O)c2ccc(OC(F)(F)F)cc2)c2c1C(=O)N(Cc1cccnc1)C2=O] | 1000 |
| 175 | 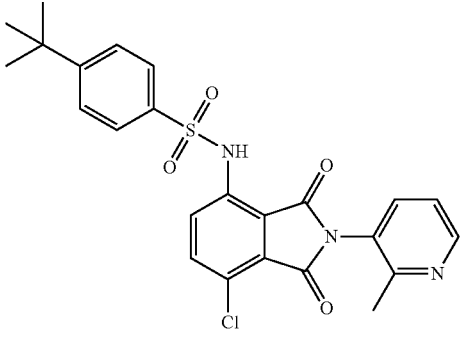 | 3 |
| 176 | 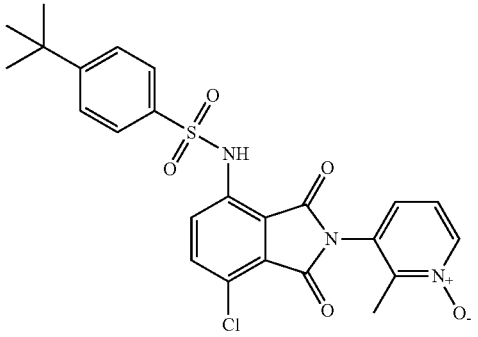 | 6 |

-continued
| Compound number | Structure | Ki (nM) |
|---|---|---|
| 177 | 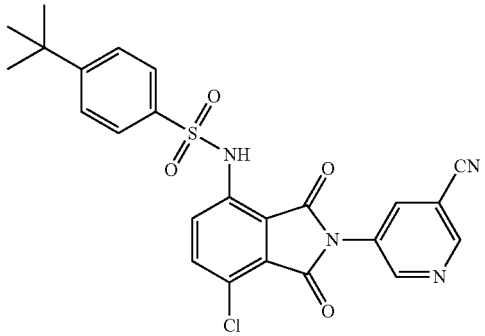 | 73 |
| 178 | 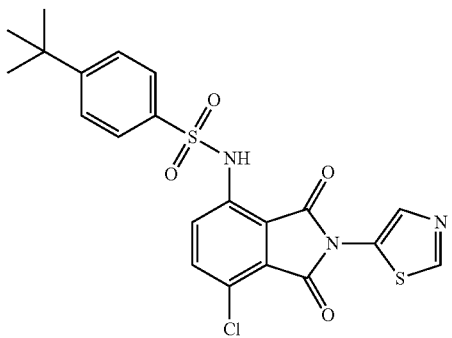 | 164 |
| 179 | 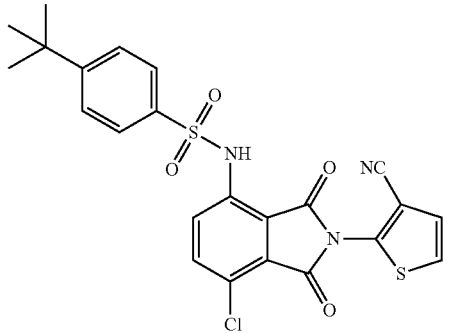 [SMILES: CC(C)(C)c1ccc(S(=O)(=O)Nc2ccc(Cl)c3c2C(=O)N(c2sccc2C#N)C3=O)cc1] | 16 |
| 180 | 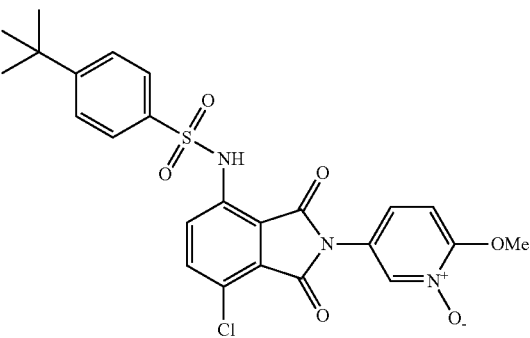 | 78 |

-continued

| Compound number | Structure | Ki (nM) |
|---|---|---|
| 182 | 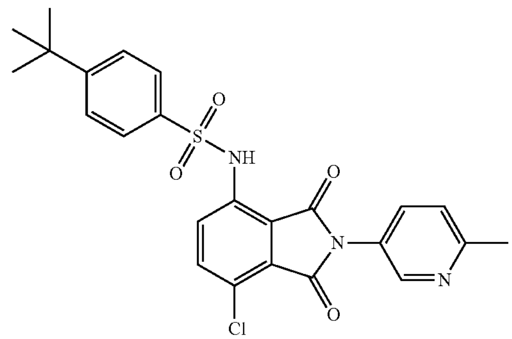 | 19 |
| 183 | 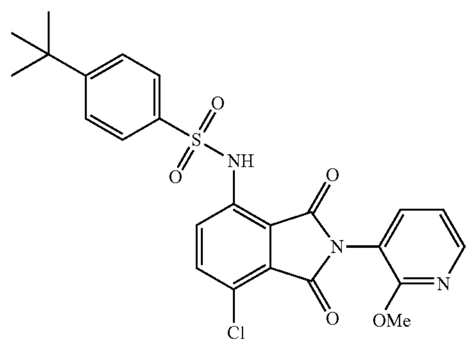 | 3 |
| 184 | 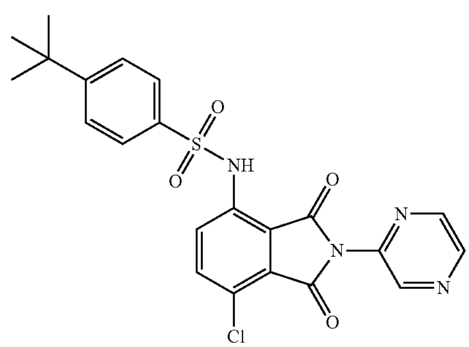 [SMILES: CC(C)(C)c1ccc(S(=O)(=O)Nc2ccc(Cl)c3c2C(=O)N(c2cnccn2)C3=O)cc1] | 16 |
| 185 | 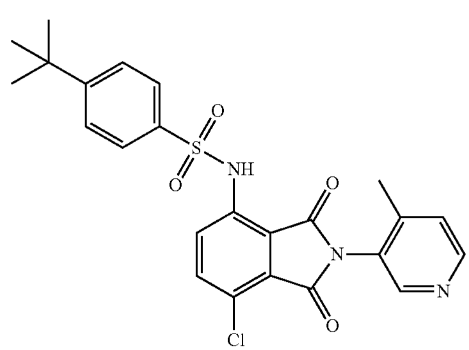 [SMILES: Cc1ccncc1N1C(=O)c2c(Cl)ccc(NS(=O)(=O)c3ccc(C(C)(C)C)cc3)c2C1=O] | 7 |

-continued

| Compound number | Structure | Ki (nM) |
|---|---|---|
| 187 | 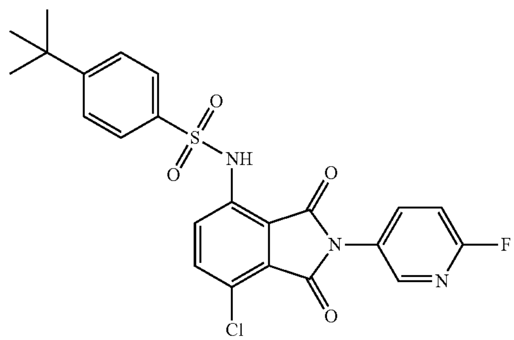 [SMILES: CC(C)(C)c1ccc(S(=O)(=O)Nc2ccc(Cl)c3c2C(=O)N(c2ccc(F)nc2)C3=O)cc1] | 33 |
| 188 | 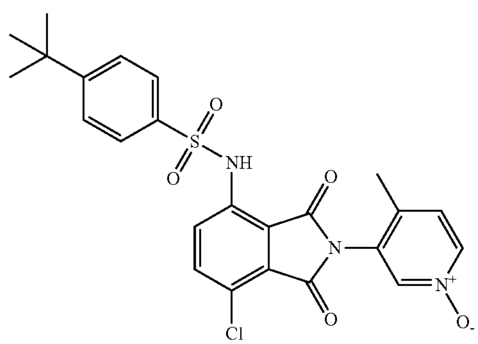 | 15 |
| 189 | 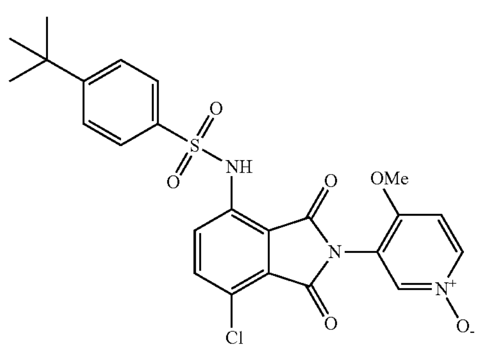 | 8 |
| 190 | 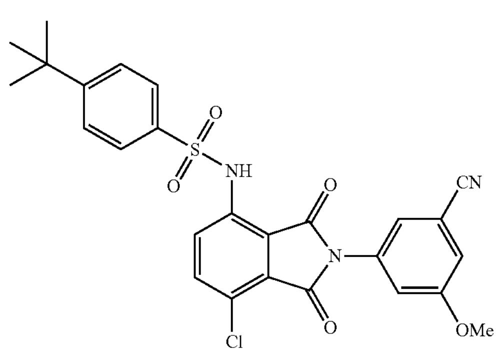 [SMILES: COc1cc(C#N)cc(N2C(=O)c3c(Cl)ccc(NS(=O)(=O)c4ccc(C(C)(C)C)cc4)c3C2=O)c1] | 24 |

-continued

| Compound number | Structure | Ki (nM) |
|---|---|---|
| 191 | 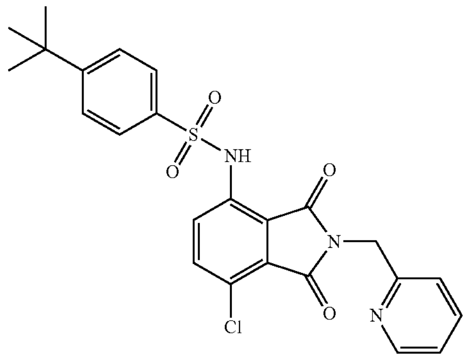 [SMILES: CC(C)(C)c1ccc(S(=O)(=O)Nc2ccc(Cl)c3c2C(=O)N(Cc2ccccn2)C3=O)cc1] | 20 |
| 192 | 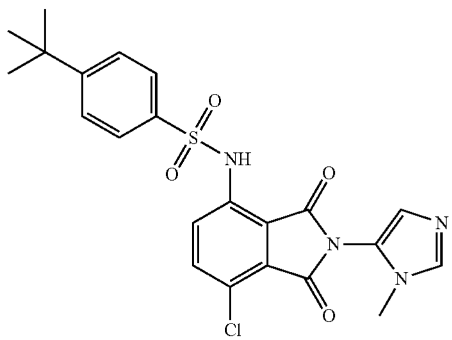 | 4 |
| 193 | 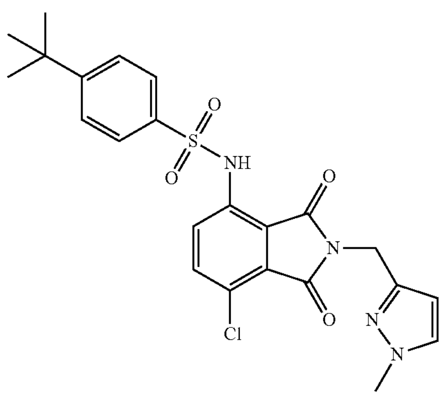 [SMILES: Cn1ccc(CN2C(=O)c3c(Cl)ccc(NS(=O)(=O)c4ccc(C(C)(C)C)cc4)c3C2=O)n1] | 16 |
| 194 | 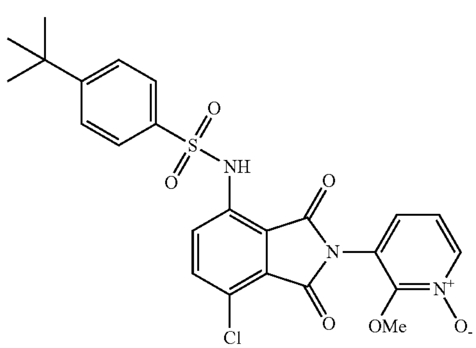 | 4 |

-continued

| Compound number | Structure | Ki (nM) |
|---|---|---|
| 195 | 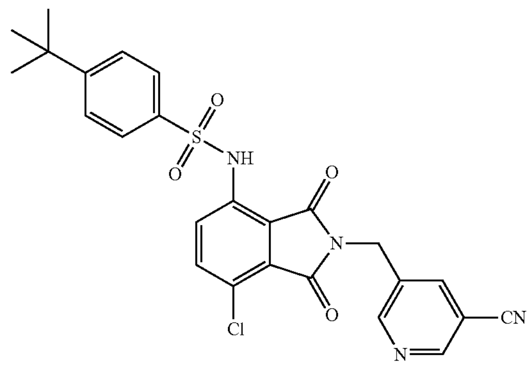 [SMILES: CC(C)(C)c1ccc(S(=O)(=O)Nc2ccc(Cl)c3c2C(=O)N(Cc2cncc(C#N)c2)C3=O)cc1] | 31 |
| 196 | 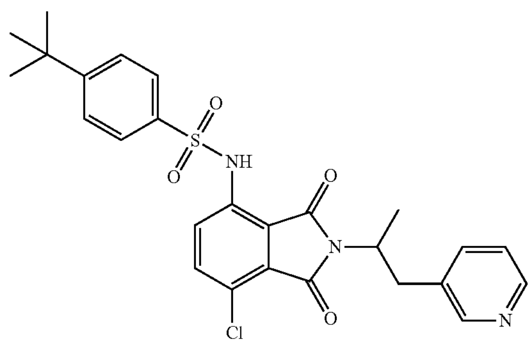 [SMILES: CC(Cc1cccnc1)N1C(=O)c2c(Cl)ccc(NS(=O)(=O)c3ccc(C(C)(C)C)cc3)c2C1=O] | 46 |
| 197 | 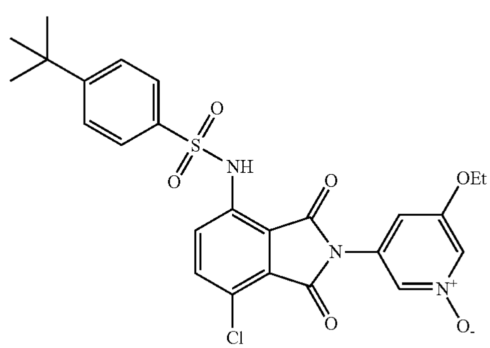 | 21 |
| 198 | 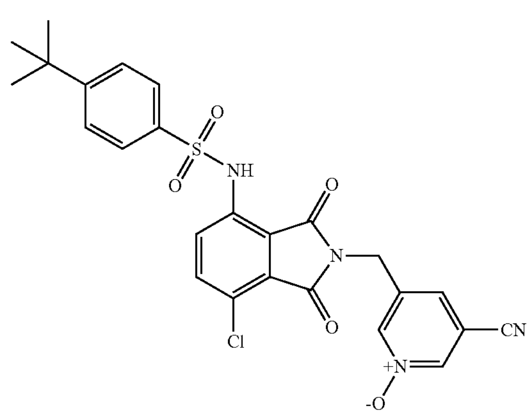 | 76 |

-continued

| Compound number | Structure | Ki (nM) |
|---|---|---|
| 199 | 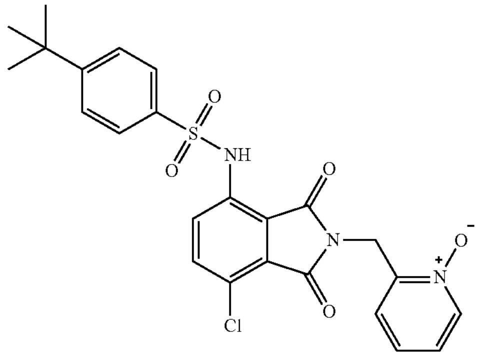 [SMILES: CC(C)(C)c1ccc(S(=O)(=O)Nc2ccc(Cl)c3c2C(=O)N(Cc2cccc[n+]2[O-])C3=O)cc1] | 6 |
| 200 | 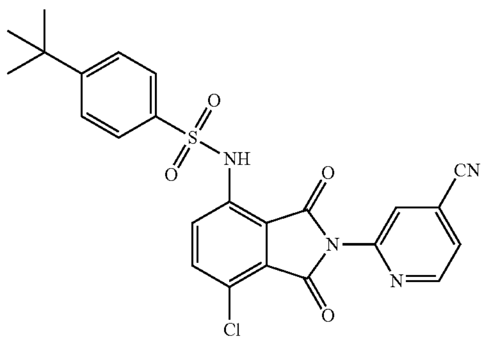 [SMILES: CC(C)(C)c1ccc(S(=O)(=O)Nc2ccc(Cl)c3c2C(=O)N(c2cc(C#N)ccn2)C3=O)cc1] | 45 |
| 201 | 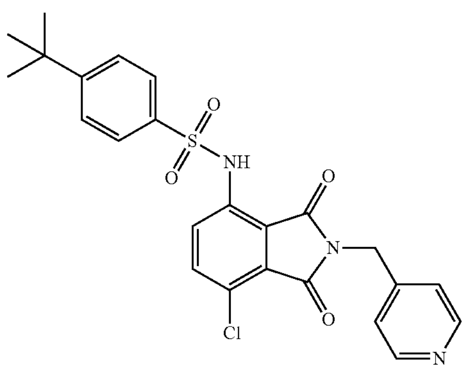 | 8 |
| 202 | 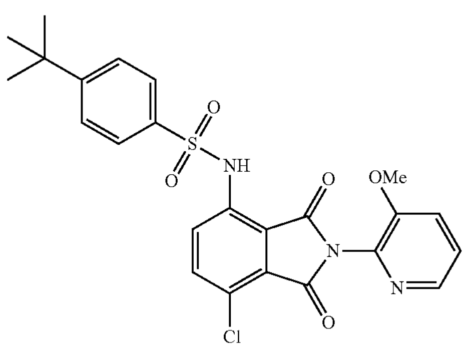 [SMILES: COc1cccnc1N1C(=O)c2c(Cl)ccc(NS(=O)(=O)c3ccc(C(C)(C)C)cc3)c2C1=O] | 22 |

-continued

| Compound number | Structure | Ki (nM) |
|---|---|---|
| 203 | 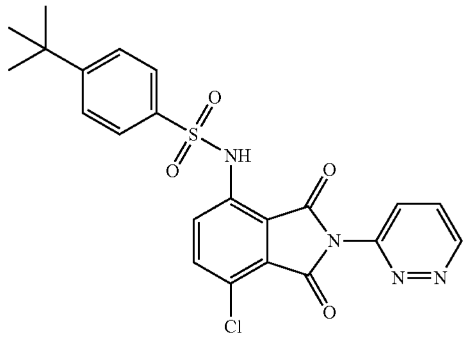 | 38 |
| 204 | 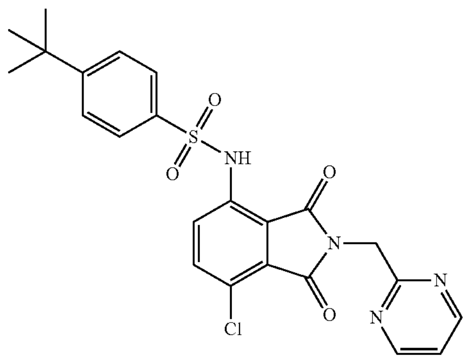 | 7 |
| 205 | 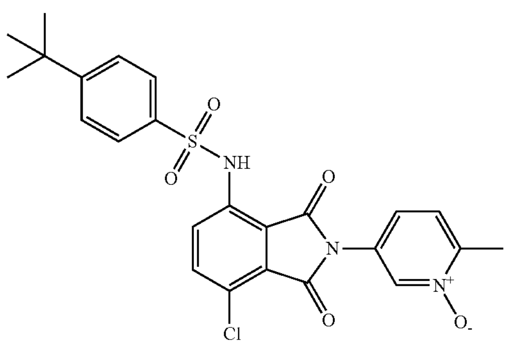 | 46 |
| 207 | 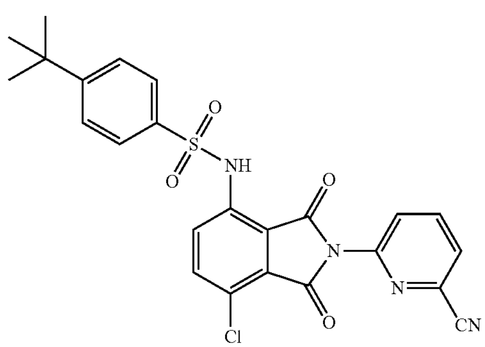 [SMILES: CC(C)(C)c1ccc(S(=O)(=O)Nc2ccc(Cl)c3c2C(=O)N(c2cccc(C#N)n2)C3=O)cc1] | 30 |

-continued

| Compound number | Structure | Ki (nM) |
|---|---|---|
| 208 | 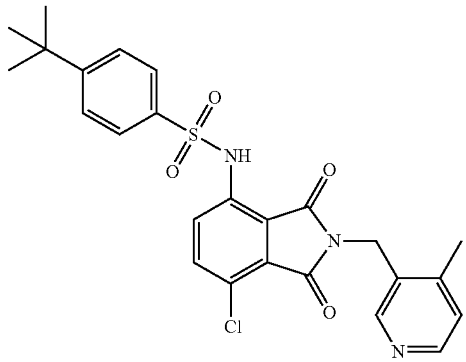 [SMILES: Cc1ccncc1CN1C(=O)c2c(Cl)ccc(NS(=O)(=O)c3ccc(C(C)(C)C)cc3)c2C1=O] | 24 |
| 209 | 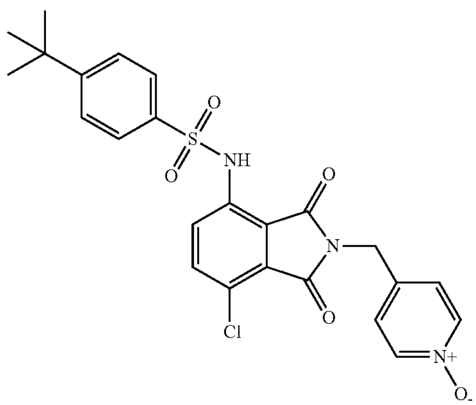 | 30 |
| 210 | 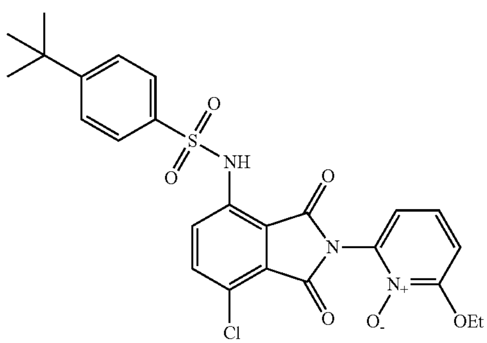 | 44 |
| 211 | 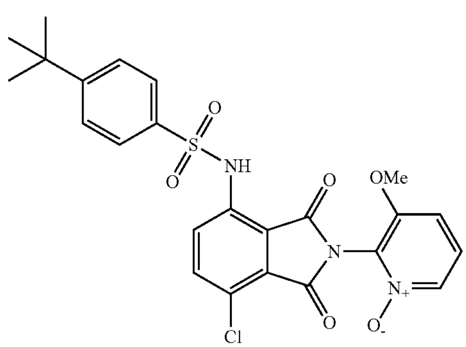 | 33 |

-continued
| Compound number | Structure | Ki (nM) |
|---|---|---|
| 212 | 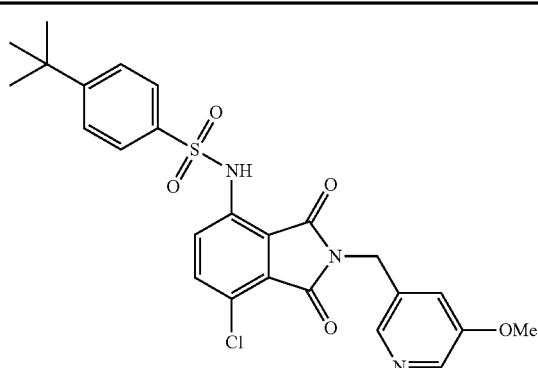 | 59 |
| 213 | 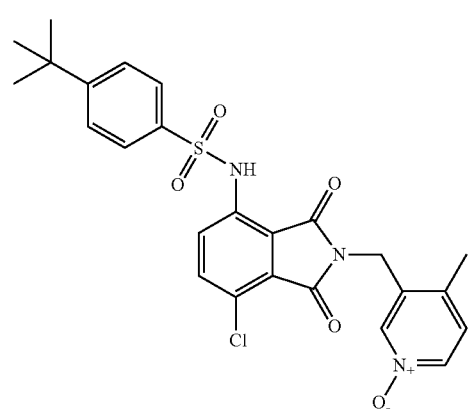 | 12 |
| 214 | 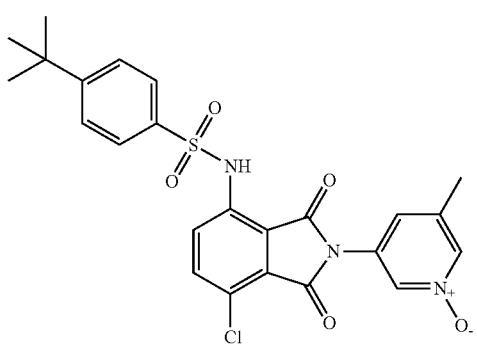 | 20 |
| 215 | 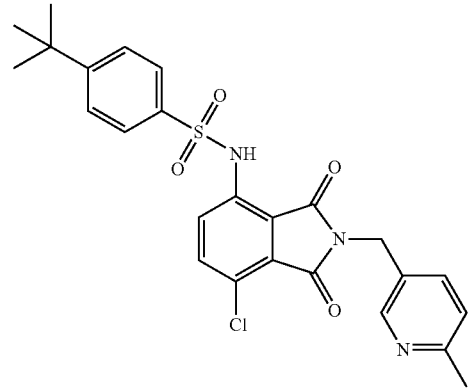 [SMILES: Cc1ccc(CN2C(=O)c3c(Cl)ccc(NS(=O)(=O)c4ccc(C(C)(C)C)cc4)c3C2=O)cn1] | 85 |

-continued
| Compound number | Structure | Ki (nM) |
|---|---|---|
| 216 | 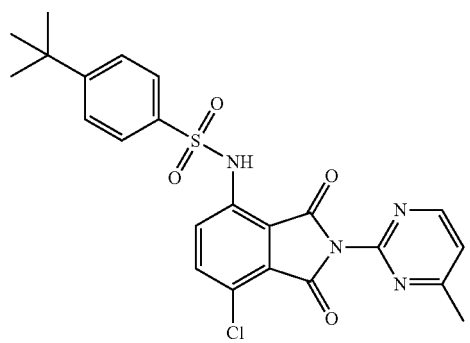 [SMILES: Cc1ccnc(N2C(=O)c3c(Cl)ccc(NS(=O)(=O)c4ccc(C(C)(C)C)cc4)c3C2=O)n1] | 23 |
| 217 | 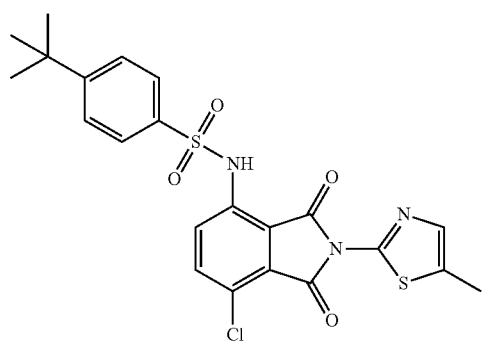 [SMILES: Cc1cnc(N2C(=O)c3c(Cl)ccc(NS(=O)(=O)c4ccc(C(C)(C)C)cc4)c3C2=O)s1] | 35 |
| 218 | 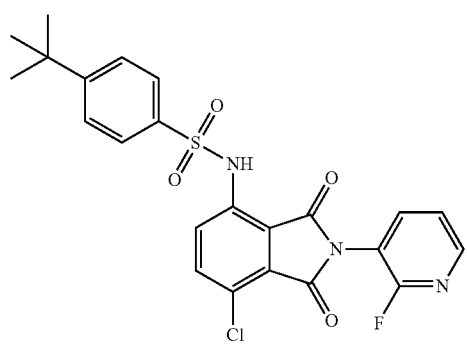 | 7 |
| 219 | 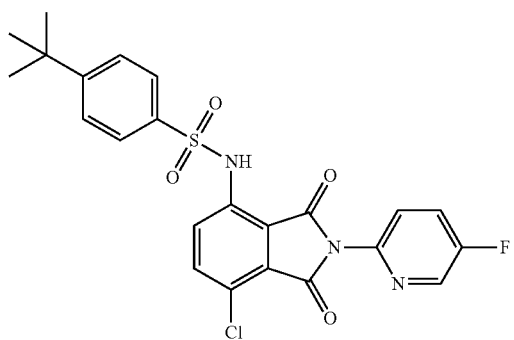 [SMILES: CC(C)(C)c1ccc(S(=O)(=O)Nc2ccc(Cl)c3c2C(=O)N(c2ccc(F)cn2)C3=O)cc1] | 10 |

US 9,969,687 B2
479                                                                                         480
-continued
| Compound number | Structure | Ki (nM) |
|---|---|---|
| 220 | 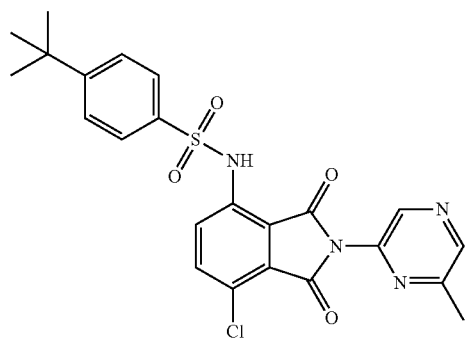 | 12 |
| 221 | 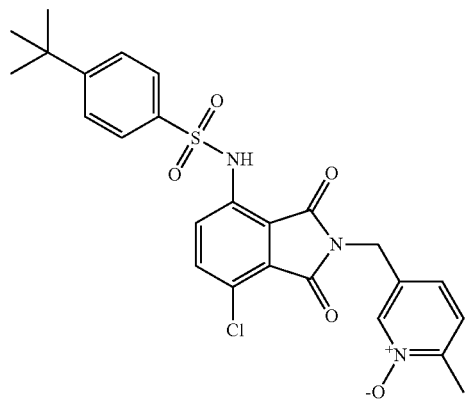 | 212 |
| 222 | 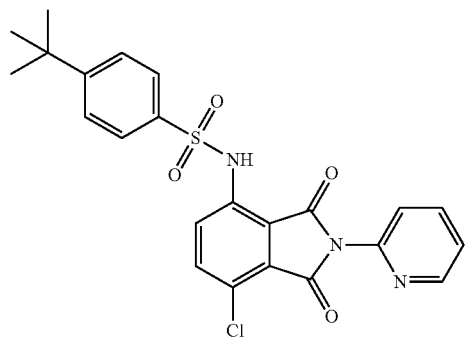 | 6 |
| 224 | 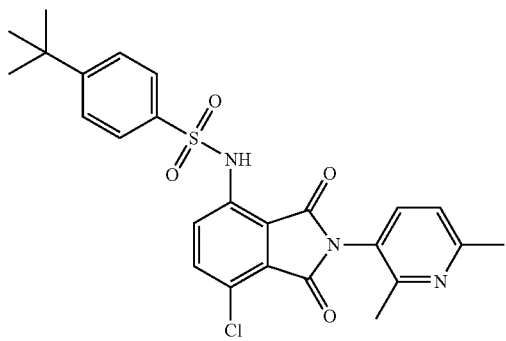 [SMILES: Cc1ccc(N2C(=O)c3c(Cl)ccc(NS(=O)(=O)c4ccc(C(C)(C)C)cc4)c3C2=O)c(C)n1] | 5 |

-continued

| Compound number | Structure | Ki (nM) |
|---|---|---|
| 225 | 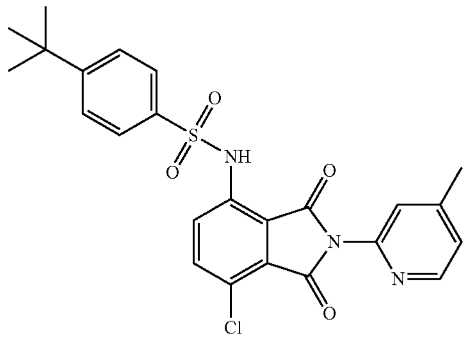 [SMILES: Cc1ccnc(N2C(=O)c3c(Cl)ccc(NS(=O)(=O)c4ccc(C(C)(C)C)cc4)c3C2=O)c1] | 54 |
| 226 | 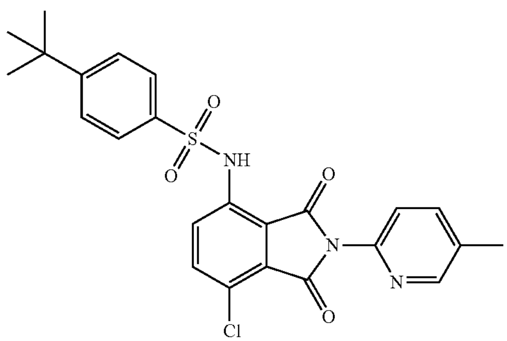 | 21 |
| 227 | 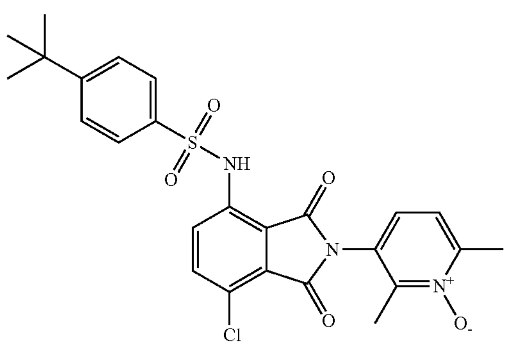 | 14 |
| 228 | 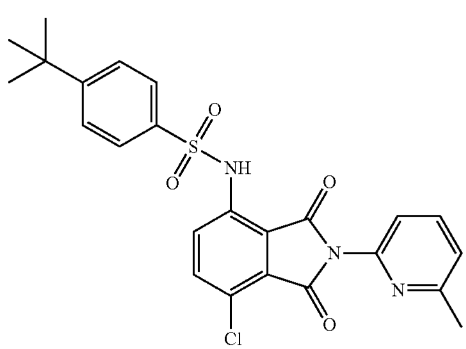 [SMILES: Cc1cccc(N2C(=O)c3c(Cl)ccc(NS(=O)(=O)c4ccc(C(C)(C)C)cc4)c3C2=O)n1] | 5 |

-continued

| Compound number | Structure | Ki (nM) |
|---|---|---|
| 229 | 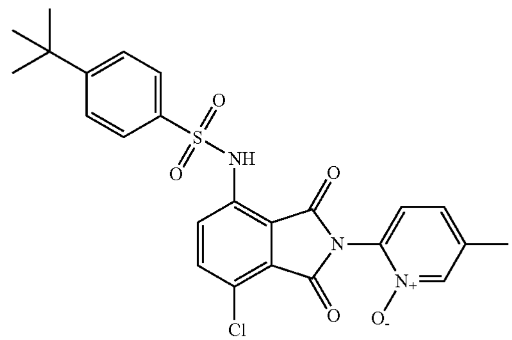 | 46 |
| 230 | 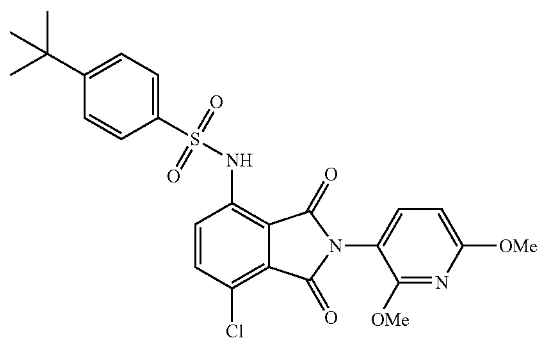 [SMILES: COc1ccc(N2C(=O)c3c(Cl)ccc(NS(=O)(=O)c4ccc(C(C)(C)C)cc4)c3C2=O)c(OC)n1] | 8 |
| 231 | 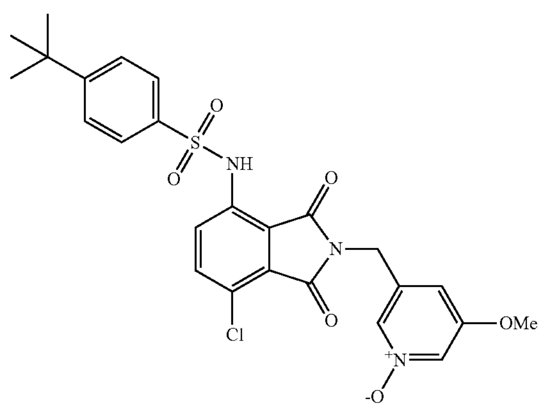 | 50 |
| 232 | 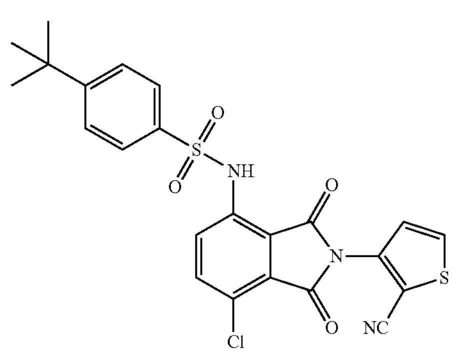 [SMILES: CC(C)(C)c1ccc(S(=O)(=O)Nc2ccc(Cl)c3c2C(=O)N(c2ccsc2C#N)C3=O)cc1] | 7 |

-continued
| Compound number | Structure | Ki (nM) |
|---|---|---|
| 233 | 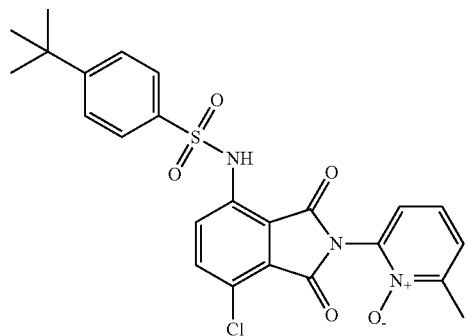 | 19 |
| 234 | 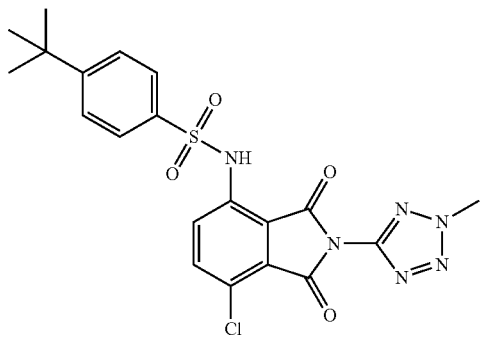 [SMILES: Cn1nnc(N2C(=O)c3c(Cl)ccc(NS(=O)(=O)c4ccc(C(C)(C)C)cc4)c3C2=O)n1] | 45 |
| 235 | 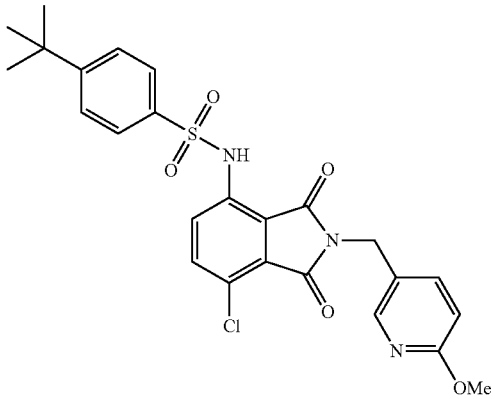 [SMILES: COc1ccc(CN2C(=O)c3c(Cl)ccc(NS(=O)(=O)c4ccc(C(C)(C)C)cc4)c3C2=O)cn1] | 123 |
| 236 | 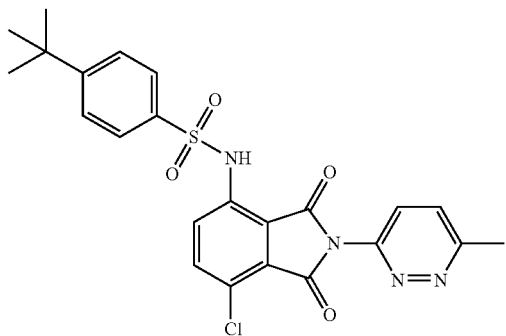 | 51 |

-continued
| Compound number | Structure | Ki (nM) |
|---|---|---|
| 237 | 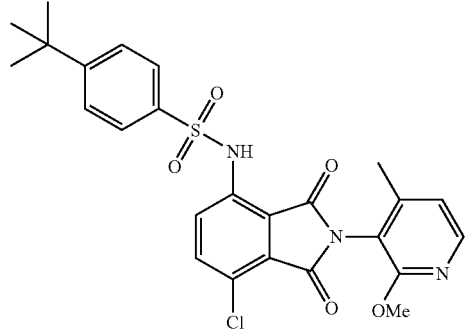 [SMILES: COc1nccc(C)c1N1C(=O)c2c(Cl)ccc(NS(=O)(=O)c3ccc(C(C)(C)C)cc3)c2C1=O] | 28 |
| 238 | 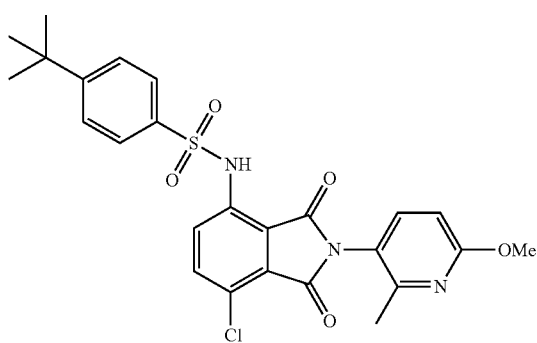 [SMILES: COc1ccc(N2C(=O)c3c(Cl)ccc(NS(=O)(=O)c4ccc(C(C)(C)C)cc4)c3C2=O)c(C)n1] | 14 |
| 239 | 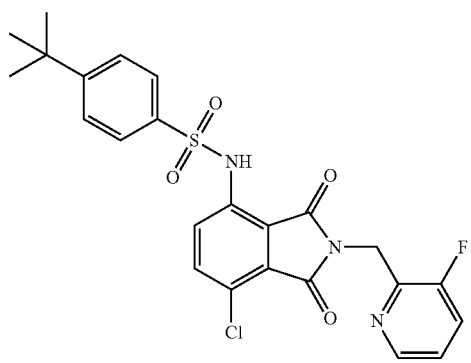 [SMILES: CC(C)(C)c1ccc(S(=O)(=O)Nc2ccc(Cl)c3c2C(=O)N(Cc2ncccc2F)C3=O)cc1] | 13 |
| 240 | 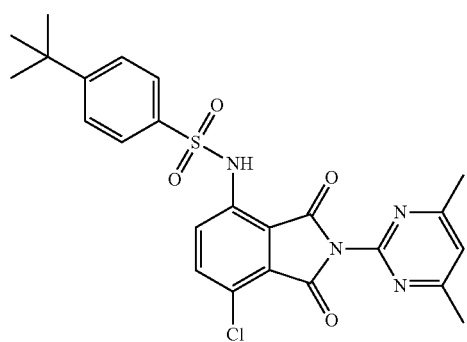 | 84 |

-continued
| Compound number | Structure | Ki (nM) |
|---|---|---|
| 241 | 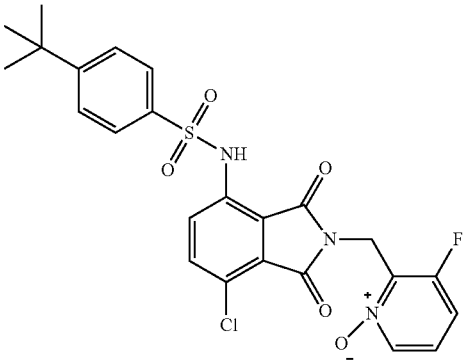 [SMILES: CC(C)(C)c1ccc(S(=O)(=O)Nc2ccc(Cl)c3c2C(=O)N(Cc2c(F)ccc[n+]2[O-])C3=O)cc1] | 5 |
| 242 | 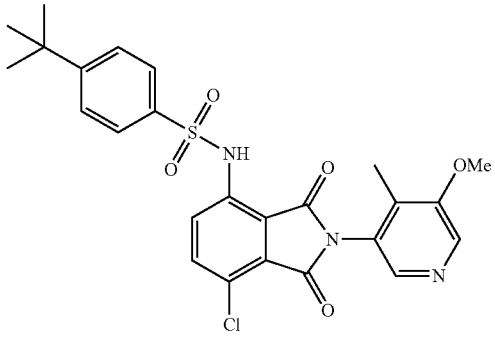 [SMILES: COc1cncc(N2C(=O)c3c(Cl)ccc(NS(=O)(=O)c4ccc(C(C)(C)C)cc4)c3C2=O)c1C] | 18 |
| 243 | 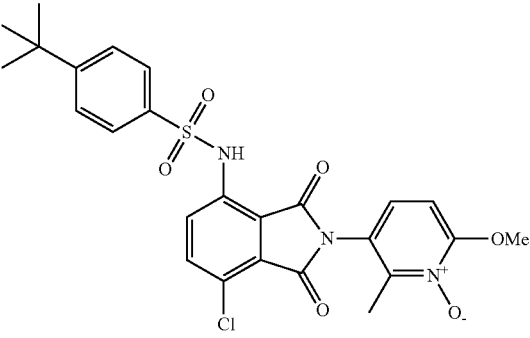 | 34 |
| 244 | 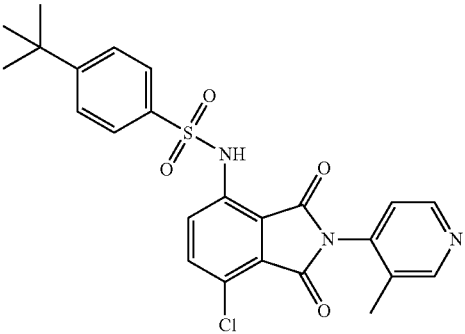 [SMILES: Cc1cnccc1N1C(=O)c2c(Cl)ccc(NS(=O)(=O)c3ccc(C(C)(C)C)cc3)c2C1=O] | 6 |

-continued
| Compound number | Structure | Ki (nM) |
|---|---|---|
| 245 | 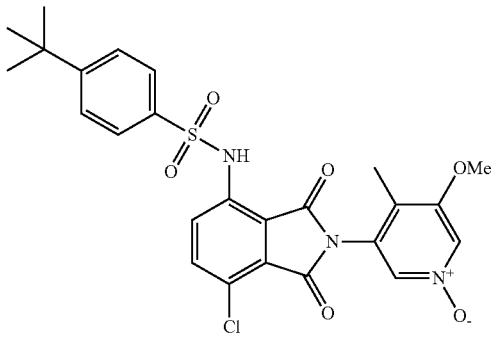 | 47 |
| 246 | 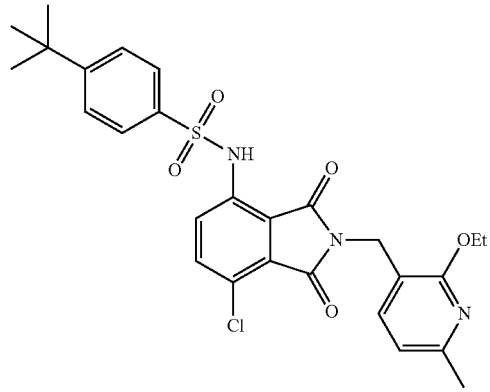 [SMILES: CCOc1nc(C)ccc1CN1C(=O)c2c(Cl)ccc(NS(=O)(=O)c3ccc(C(C)(C)C)cc3)c2C1=O] | 125 |
| 247 | 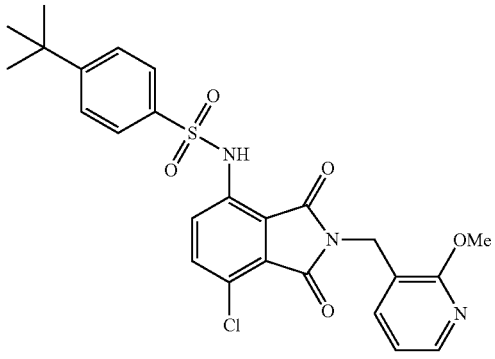 [SMILES: COc1ncccc1CN1C(=O)c2c(Cl)ccc(NS(=O)(=O)c3ccc(C(C)(C)C)cc3)c2C1=O] | 78 |
| 248 | 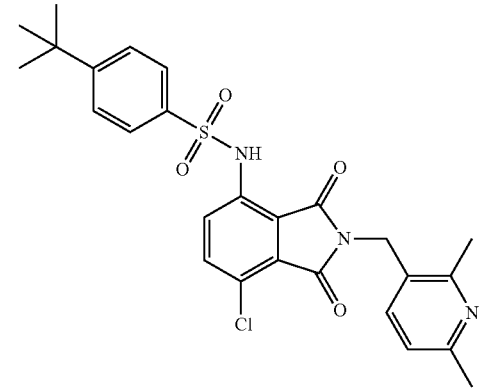 [SMILES: Cc1ccc(CN2C(=O)c3c(Cl)ccc(NS(=O)(=O)c4ccc(C(C)(C)C)cc4)c3C2=O)c(C)n1] | 70 |

-continued

| Compound number | Structure | Ki (nM) |
|---|---|---|
| 249 | 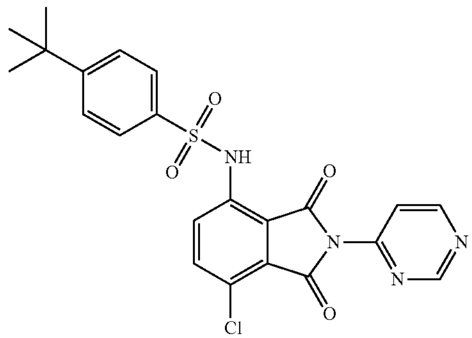 | 33 |
| 250 | 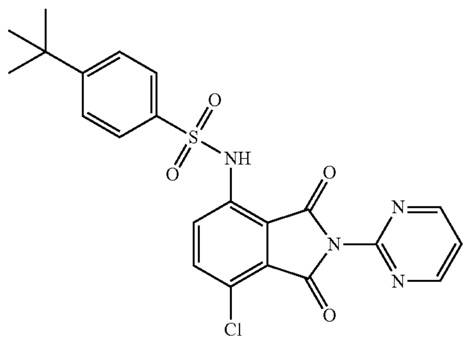 [SMILES: CC(C)(C)c1ccc(S(=O)(=O)Nc2ccc(Cl)c3c2C(=O)N(c2ncccn2)C3=O)cc1] | 23 |
| 251 | 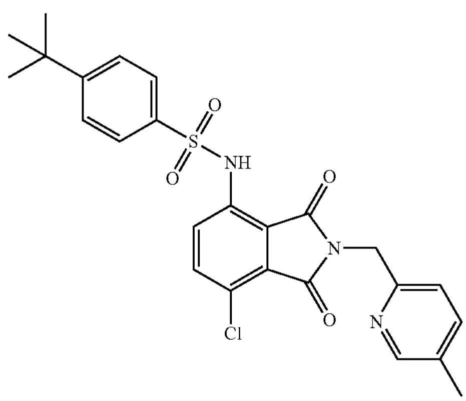 [SMILES: Cc1ccc(CN2C(=O)c3c(Cl)ccc(NS(=O)(=O)c4ccc(C(C)(C)C)cc4)c3C2=O)nc1] | 51 |
| 252 | 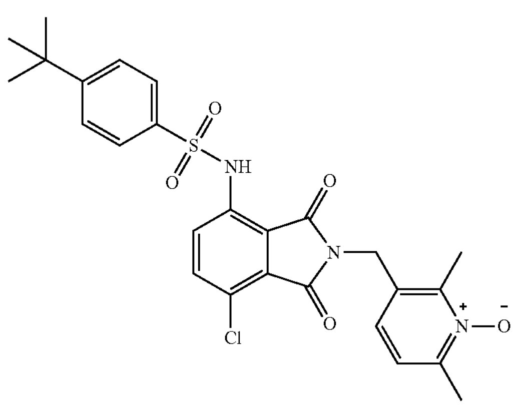 [SMILES: Cc1ccc(CN2C(=O)c3c(Cl)ccc(NS(=O)(=O)c4ccc(C(C)(C)C)cc4)c3C2=O)c(C)[n+]1[O-]] | 33 |

-continued
| Compound number | Structure | Ki (nM) |
|---|---|---|
| 253 | 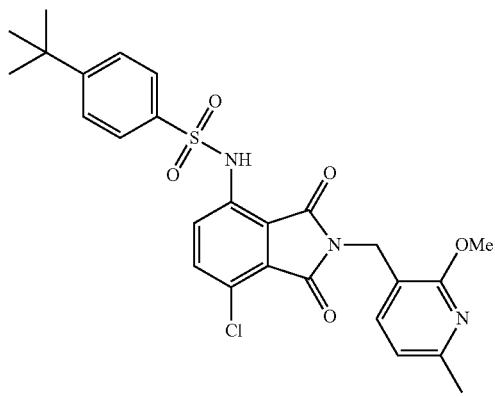 [SMILES: COc1nc(C)ccc1CN1C(=O)c2c(Cl)ccc(NS(=O)(=O)c3ccc(C(C)(C)C)cc3)c2C1=O] | 41 |
| 254 | 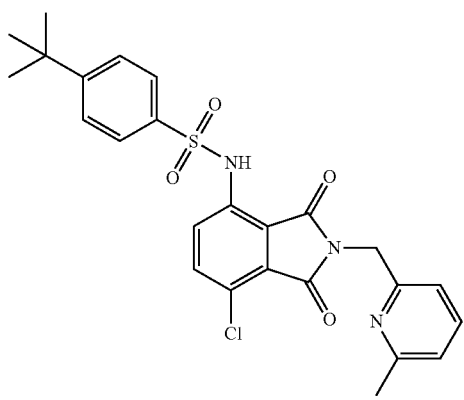 [SMILES: Cc1cccc(CN2C(=O)c3c(Cl)ccc(NS(=O)(=O)c4ccc(C(C)(C)C)cc4)c3C2=O)n1] | 58 |
| 255 | 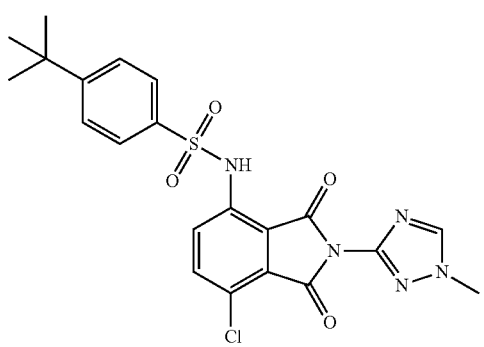 | 17 |
| 256 | 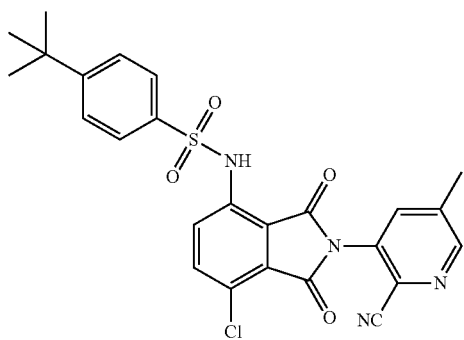 [SMILES: Cc1cnc(C#N)c(N2C(=O)c3c(Cl)ccc(NS(=O)(=O)c4ccc(C(C)(C)C)cc4)c3C2=O)c1] | 18 |

-continued
| Compound number | Structure | Ki (nM) |
|---|---|---|
| 257 | 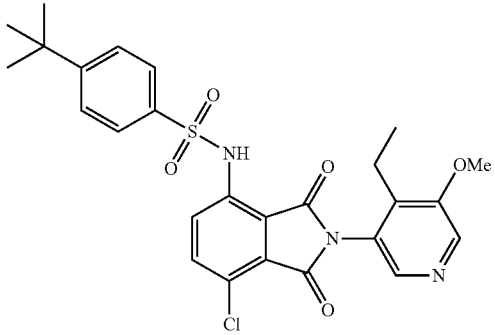 [SMILES: CCc1c(OC)cncc1N1C(=O)c2c(Cl)ccc(NS(=O)(=O)c3ccc(C(C)(C)C)cc3)c2C1=O] | 25 |
| 258 | 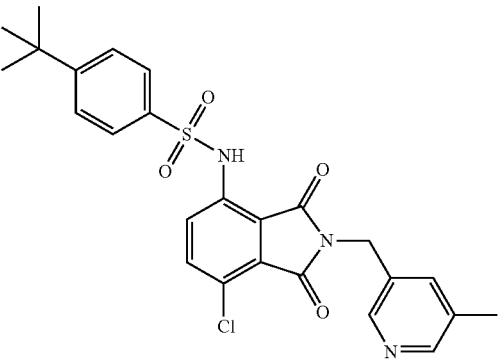 [SMILES: Cc1cncc(CN2C(=O)c3c(Cl)ccc(NS(=O)(=O)c4ccc(C(C)(C)C)cc4)c3C2=O)c1] | 23 |
| 259 | 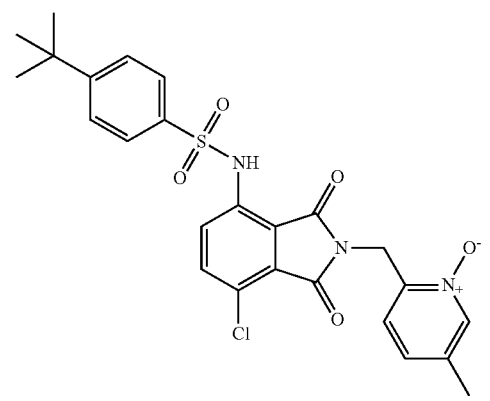 [SMILES: Cc1ccc(CN2C(=O)c3c(Cl)ccc(NS(=O)(=O)c4ccc(C(C)(C)C)cc4)c3C2=O)[n+]([O-])c1] | 13 |
| 260 | 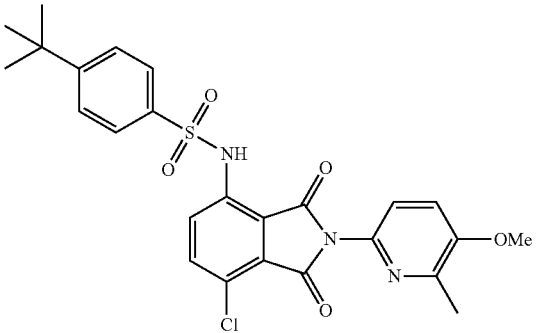 [SMILES: COc1ccc(N2C(=O)c3c(Cl)ccc(NS(=O)(=O)c4ccc(C(C)(C)C)cc4)c3C2=O)nc1C] | 16 |

-continued

| Compound number | Structure | Ki (nM) |
|---|---|---|
| 261 | 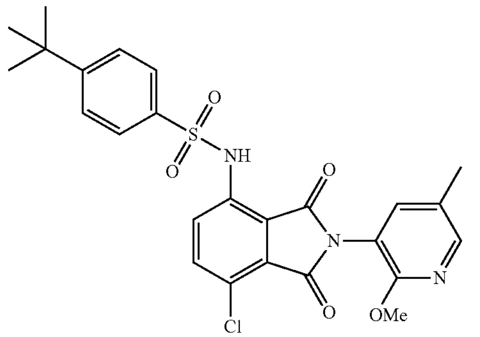 [SMILES: COc1ncc(C)cc1N1C(=O)c2c(Cl)ccc(NS(=O)(=O)c3ccc(C(C)(C)C)cc3)c2C1=O] | 16 |
| 262 | 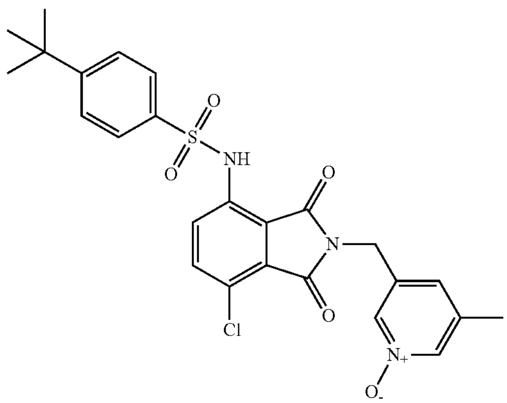 | 46 |
| 263 | 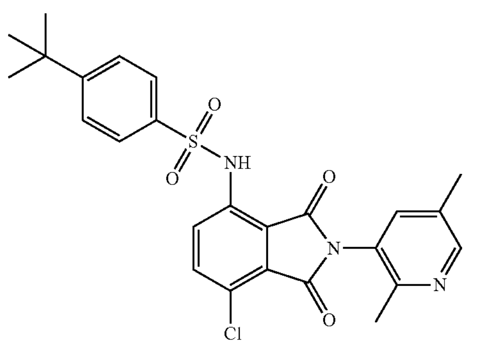 | 11 |
| 264 | 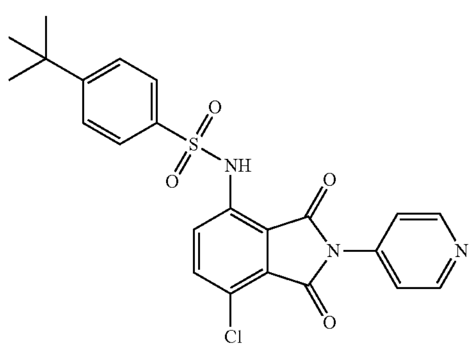 | 11 |

-continued
| Compound number | Structure | Ki (nM) |
|---|---|---|
| 265 | 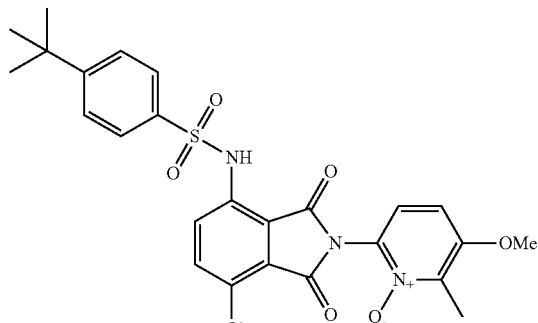 | 41 |
| 266 | 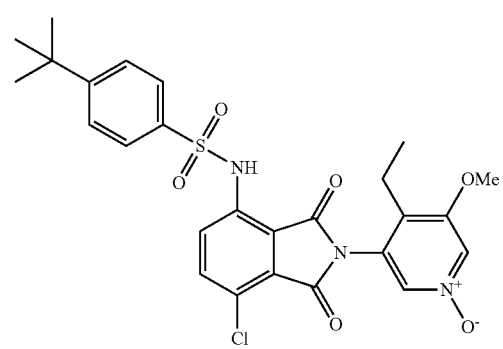 | 10 |
| 267 | 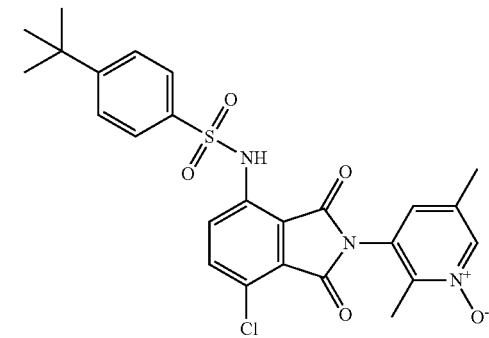 [SMILES: Cc1cc(N2C(=O)c3c(Cl)ccc(NS(=O)(=O)c4ccc(C(C)(C)C)cc4)c3C2=O)c(C)[n+]([O-])c1] | 27 |
| 268 | 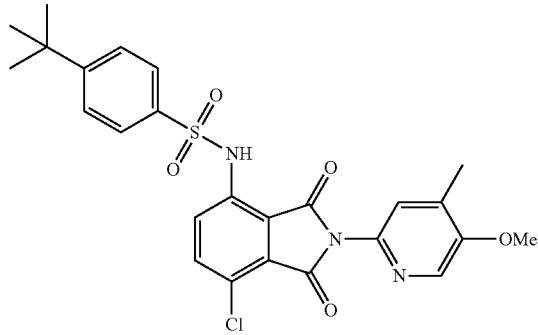 [SMILES: COc1cnc(N2C(=O)c3c(Cl)ccc(NS(=O)(=O)c4ccc(C(C)(C)C)cc4)c3C2=O)cc1C] | 54 |

-continued
| Compound number | Structure | Ki (nM) |
|---|---|---|
| 269 | 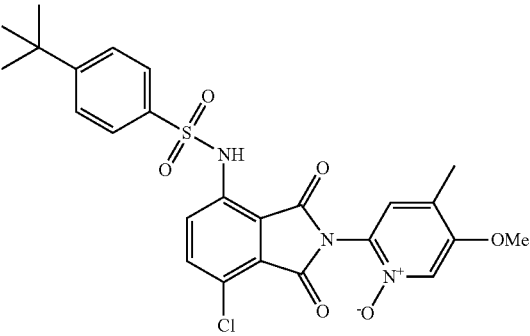 | 76 |
| 270 | 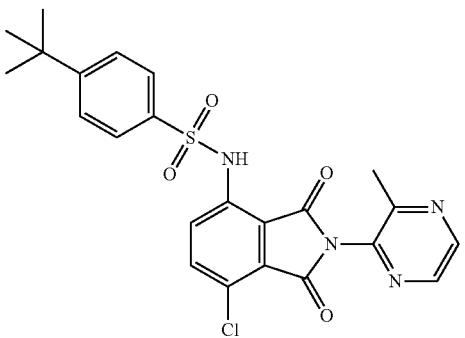 [SMILES: Cc1nccnc1N1C(=O)c2c(Cl)ccc(NS(=O)(=O)c3ccc(C(C)(C)C)cc3)c2C1=O] | 23 |
| 271 | 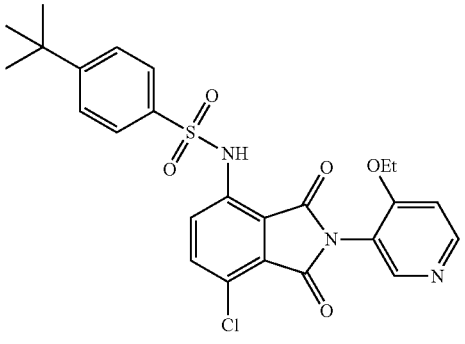 [SMILES: CCOc1ccncc1N1C(=O)c2c(Cl)ccc(NS(=O)(=O)c3ccc(C(C)(C)C)cc3)c2C1=O] | 9 |
| 272 | 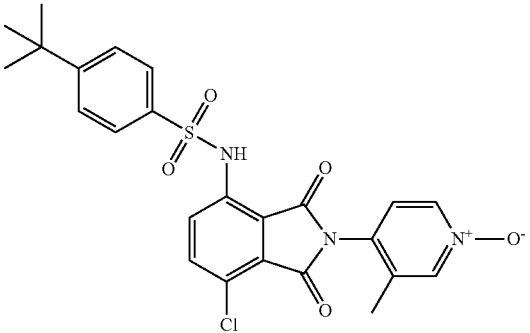 [SMILES: Cc1c[n+]([O-])ccc1N1C(=O)c2c(Cl)ccc(NS(=O)(=O)c3ccc(C(C)(C)C)cc3)c2C1=O] | 9 |

-continued
| Compound number | Structure | Ki (nM) |
| --- | --- | --- |
| 273 | 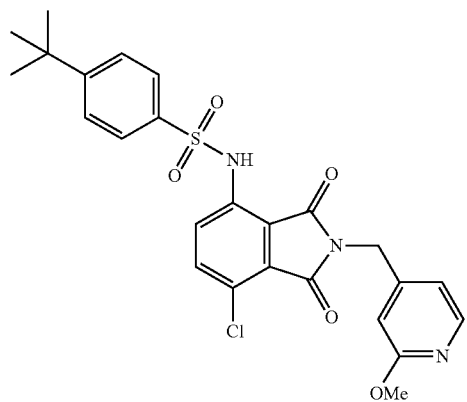 [SMILES: COc1cc(CN2C(=O)c3c(Cl)ccc(NS(=O)(=O)c4ccc(C(C)(C)C)cc4)c3C2=O)ccn1] | 108 |
| 274 | 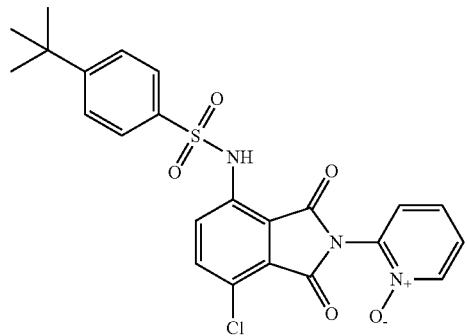 | 34 |
| 275 | 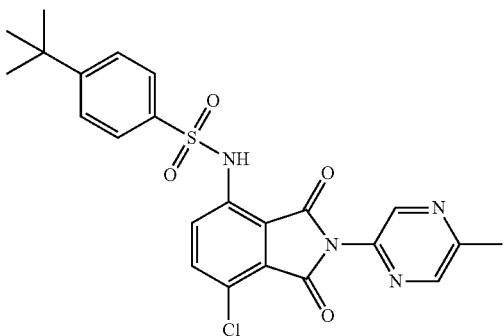 [SMILES: Cc1cnc(N2C(=O)c3c(Cl)ccc(NS(=O)(=O)c4ccc(C(C)(C)C)cc4)c3C2=O)cn1] | 32 |
| 276 | 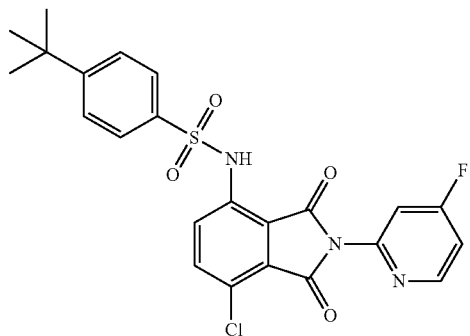 [SMILES: CC(C)(C)c1ccc(S(=O)(=O)Nc2ccc(Cl)c3c2C(=O)N(c2cc(F)ccn2)C3=O)cc1] | 22 |

-continued
| Compound number | Structure | Ki (nM) |
|---|---|---|
| 277 | 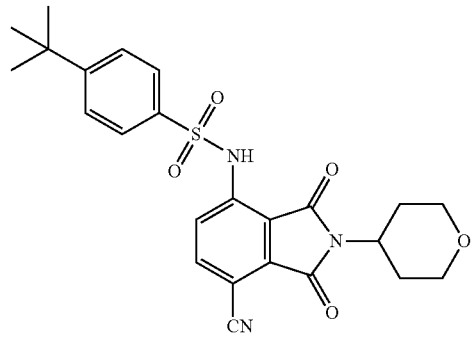 [SMILES: CC(C)(C)c1ccc(S(=O)(=O)Nc2ccc(C#N)c3c2C(=O)N(C2CCOCC2)C3=O)cc1] | 28 |
| 278 | 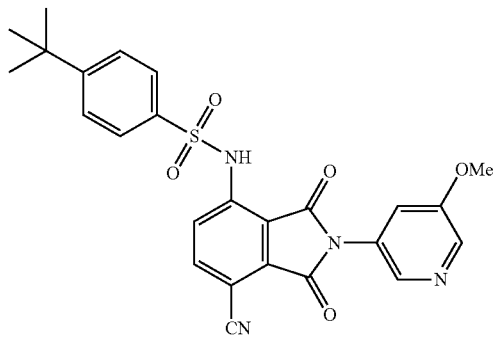 [SMILES: COc1cncc(N2C(=O)c3c(C#N)ccc(NS(=O)(=O)c4ccc(C(C)(C)C)cc4)c3C2=O)c1] | 10 |
| 279 | 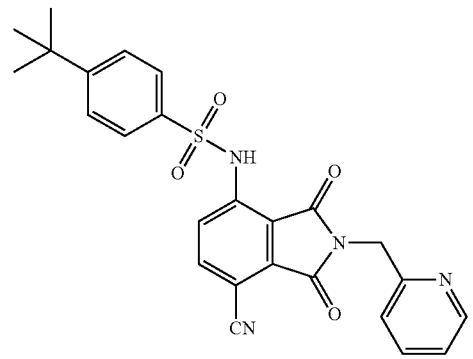 [SMILES: CC(C)(C)c1ccc(S(=O)(=O)Nc2ccc(C#N)c3c2C(=O)N(Cc2ccccn2)C3=O)cc1] | 18 |
| 280 | 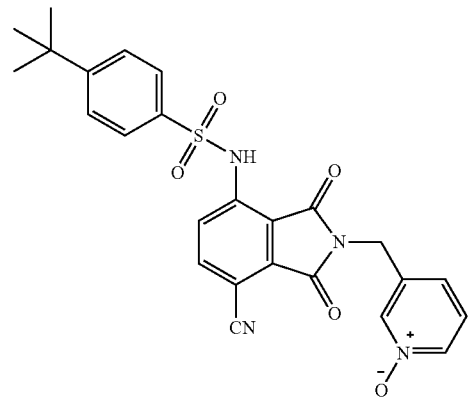 [SMILES: CC(C)(C)c1ccc(S(=O)(=O)Nc2ccc(C#N)c3c2C(=O)N(Cc2ccc[n+](O)c2)C3=O)cc1] | 37 |

-continued
| Compound number | Structure | Ki (nM) |
|---|---|---|
| 281 | 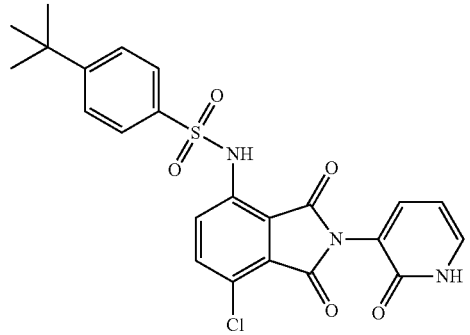 [SMILES: CC(C)(C)c1ccc(S(=O)(=O)Nc2ccc(Cl)c3c2C(=O)N(c2ccc[nH]c2=O)C3=O)cc1] | 5 |
| 282 | 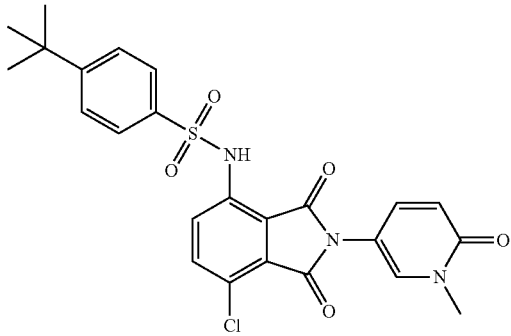 | 9 |
| 283 | 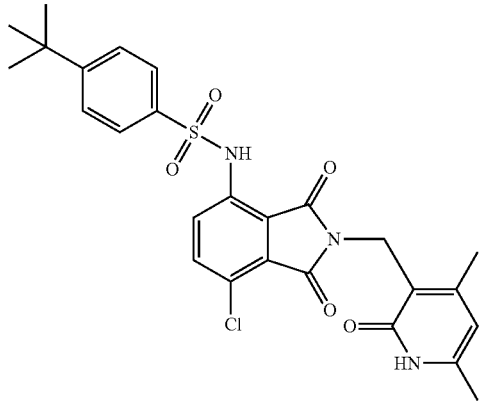 [SMILES: Cc1cc(C)c(CN2C(=O)c3c(Cl)ccc(NS(=O)(=O)c4ccc(C(C)(C)C)cc4)c3C2=O)c(=O)[nH]1] | 15 |
| 284 | 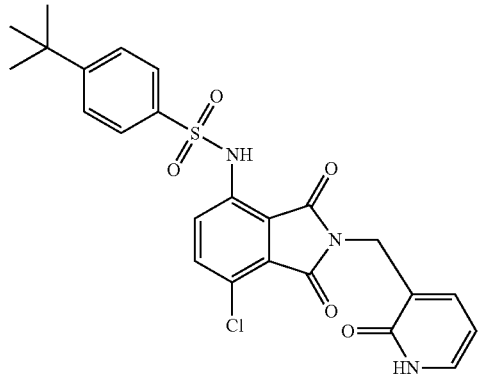 [SMILES: CC(C)(C)c1ccc(S(=O)(=O)Nc2ccc(Cl)c3c2C(=O)N(Cc2ccc[nH]c2=O)C3=O)cc1] | 7 |

-continued

| Compound number | Structure | Ki (nM) |
|---|---|---|
| 285 | 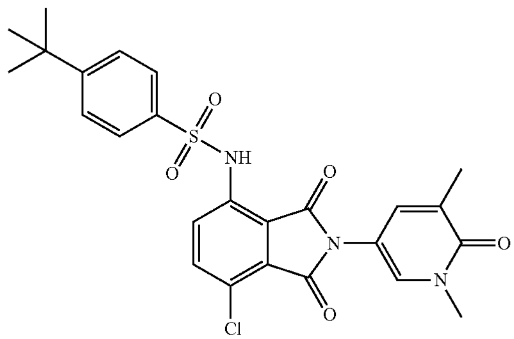 [SMILES: Cc1cc(N2C(=O)c3c(Cl)ccc(NS(=O)(=O)c4ccc(C(C)(C)C)cc4)c3C2=O)cn(C)c1=O] | 16 |
| 286 | 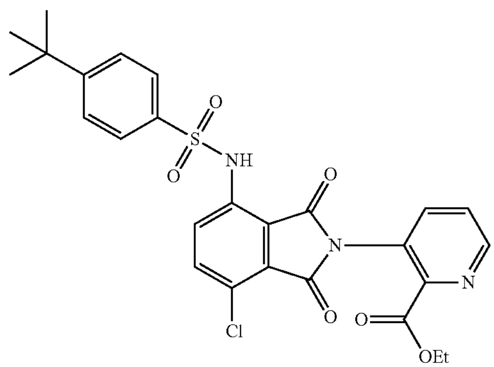 | 10 |
| 287 | 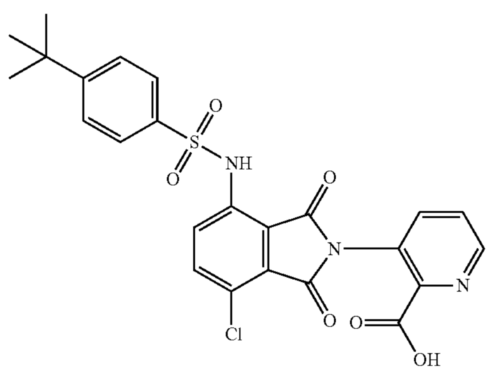 | 22 |
| 288 | 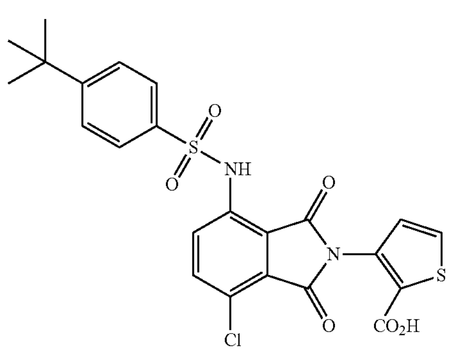 [SMILES: CC(C)(C)c1ccc(S(=O)(=O)Nc2ccc(Cl)c3c2C(=O)N(c2ccsc2C(=O)O)C3=O)cc1] | 3 |

-continued
| Compound number | Structure | Ki (nM) |
|---|---|---|
| 289 | 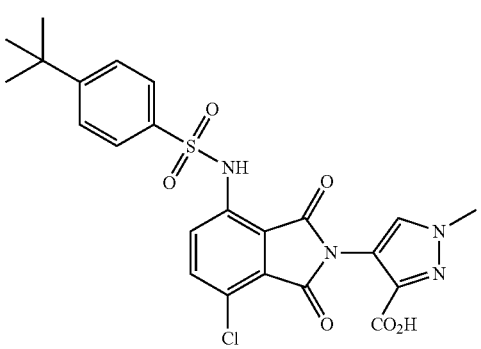 [SMILES: Cn1cc(N2C(=O)c3c(Cl)ccc(NS(=O)(=O)c4ccc(C(C)(C)C)cc4)c3C2=O)c(C(=O)O)n1] | 104 |
| 290 | 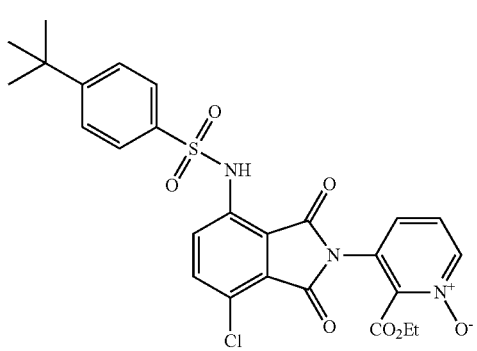 [SMILES: CCOC(=O)c1c(N2C(=O)c3c(Cl)ccc(NS(=O)(=O)c4ccc(C(C)(C)C)cc4)c3C2=O)ccc[n+]1[O-]] | 7 |
| 291 | 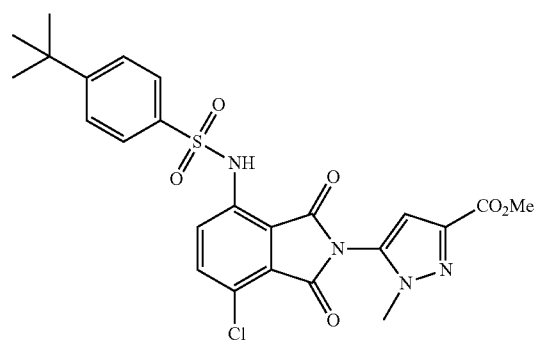 [SMILES: COC(=O)c1cc(N2C(=O)c3c(Cl)ccc(NS(=O)(=O)c4ccc(C(C)(C)C)cc4)c3C2=O)n(C)n1] | 5 |
| 292 | 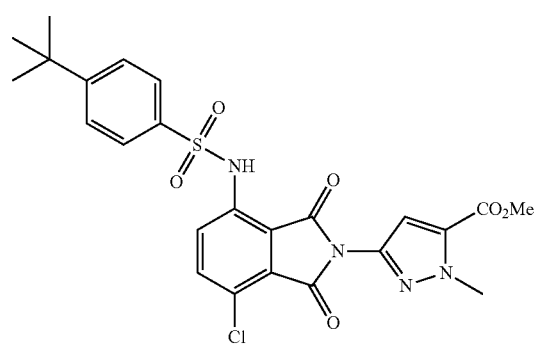 [SMILES: COC(=O)c1cc(N2C(=O)c3c(Cl)ccc(NS(=O)(=O)c4ccc(C(C)(C)C)cc4)c3C2=O)nn1C] | 11 |

What we claim is:

1. A compound of Formula (I), or a salt, solvate, or solvate of a salt thereof:

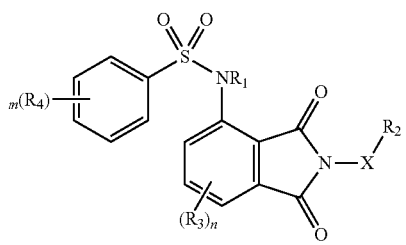

in which:
R₁ is selected from hydrogen, methyl, and ethyl;
X is selected from a direct bond and (CR₅R₆)ₚ;
p is 1, 2, 3, 4, or 5;
each R₅ is independently selected from hydrogen, methyl, and fluoro;
each R₆ is independently selected from hydrogen, methyl, and fluoro;
R₂ is selected from optionally substituted aryl, optionally substituted heteroaryl, and optionally substituted C₃₋₇heterocycloalkyl;
each R₃ is independently selected from halo, cyano, C₁₋₆alkyl, methanesulfonyl, C₁₋₆alkoxy, haloalkyl, haloalkoxy, and C₃₋₇cycloalkyl;
n is 0, 1 or 2;
each R₄ is Z_{q1}B;
m is 0, 1, 2 or 3;
q₁ is 0, 1, 2, 3, 4, 5 or 6;
each Z is independently selected from CR₇R₈, O, C=O, SO₂, and NR₉;
each R₇ is independently selected from hydrogen, methyl, ethyl, and halo;
each R₈ is independently selected from hydrogen, methyl, ethyl, and halo;
each R₉ is independently selected from hydrogen, methyl, and ethyl;
each B is independently selected from hydrogen, halo, CN, optionally substituted aryl, optionally substituted heteroaryl, optionally substituted cycloalkyl, and A;
A is

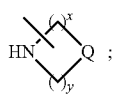

Q is selected from CH₂, O, NH, and NCH₃;
x is 0, 1, 2, 3 or 4, and y is 1, 2, 3, 4 or 5, the total of x and y being greater or equal to 1 and less than or equal to 5 (1≤x+y≤5).

2. The compound of claim 1, or a salt, solvate, or solvate of a salt thereof, wherein R₁ is hydrogen.

3. The compound of claim 1, or a salt, solvate, or solvate of a salt thereof, wherein X is a direct bond.

4. The compound of claim 1, or a salt, solvate, or solvate of a salt thereof, wherein X is CH₂.

5. The compound of claim 1, or a salt, solvate, or solvate of a salt thereof, wherein R₂ is selected from optionally substituted aryl and optionally substituted heteroaryl.

6. The compound of claim 5, or a salt, solvate, or solvate of a salt thereof, wherein R₂ is selected from optionally substituted phenyl, optionally substituted pyridyl, optionally substituted thiophenyl, optionally substituted pyrazolyl, optionally substituted pyrimidinyl, optionally substituted imidazolyl, and optionally substituted thiazolyl.

7. The compound of claim 5, or a salt, solvate, or solvate of a salt thereof, wherein R₂ is selected from cyanophenyl, acetylphenyl, methoxy-phenyl, pyridine N-oxide, methyl-pyridine N-oxide, methoxy-pyridine N-oxide, ethoxy-pyridine N-oxide, pyridyl, methoxy-pyridyl, ethoxy-pyridyl, methyl-pyridyl, cyano-pyridyl, thiophenyl, carboxy-thiophenyl, carboxymethyl-thiophenyl, pyrazolyl, methyl-pyrazolyl, imidazolyl, and methyl-imidazolyl.

8. The compound of claim 1, or a salt, solvate, or solvate of a salt thereof, wherein each R₃ is independently selected from halo, cyano, C₁₋₃alkyl, C₁₋₃alkoxy, C₁₋₃haloalkyl, and cyclopropyl.

9. The compound of claim 8, or a salt, solvate, or solvate of a salt thereof, wherein each R₃ is independently selected from chloro, cyano, methyl, methoxy, propoxy, isopropoxy, trifluoromethyl, and cyclopropyl.

10. The compound of claim 1, or a salt, solvate, or solvate of a salt thereof, wherein n is 0 or 1.

11. The compound of claim 1, or a salt, solvate, or solvate of a salt thereof, wherein R₄ is Z_{q1}B and q₁ is 0, and each B is independently selected from halo, CN, optionally substituted aryl, optionally substituted heteroaryl, and A.

12. The compound of claim 1, or a salt, solvate, or solvate of a salt thereof, wherein R₄ is Z_{q1}B and q₁ is 1, 2 or 3, each Z is independently C₁₋₃alkyl, and each B is independently selected from halo, CN, optionally substituted aryl, optionally substituted heteroaryl, and A.

13. The compound of claim 1, or a salt, solvate, or solvate of a salt thereof, wherein R₄ is Z_{q1}B and q₁ is 1, 2, 3, 4, 5, or 6, each Z is independently selected from CR₇R₈, O, C=O, and SO₂, each R₇ is independently selected from hydrogen, methyl, and halo, each R₈ is independently selected from hydrogen, methyl, and halo, and B is selected from hydrogen, halo, and cyano.

14. The compound of claim 13, or a salt, solvate, or solvate of a salt thereof, wherein each R₄ is independently selected from butyl, tert-butyl, propyl, iso-propyl, methyl, COCH₃, C(CH₃)(CH₃)CN, trifluoromethyl, trifluoromethoxy, difluoromethoxy, and methoxy.

15. The compound of claim 1, or a salt, solvate, or solvate of a salt thereof, wherein m is 1 or 2.

16. The compound of claim 15, or a salt, solvate, or solvate of a salt thereof, wherein m is 1 and R₄ is para to the sulfonamide, or m is 2 and one R₄ group is meta to the sulfonamide and the other R₄ group is para to the sulfonamide.

17. The compound of claim 15, or a salt, solvate, or solvate of a salt thereof, wherein R₁ is hydrogen, X is CH₂, R₂ is an optionally substituted heteroaryl, n is 0, m is 1, and R₄ is trifluoromethoxy.

18. The compound of claim 15, or a salt, solvate, or solvate of a salt thereof, wherein $R_1$ is hydrogen, X is a direct bond, $R_2$ is selected from optionally substituted aryl and optionally substituted heteroaryl, n is 0, m is 2, one $R_4$ group is halo and the other $R_4$ group is trifluoromethyl.

19. The compound of claim 15, or a salt, solvate, or solvate of a salt thereof, wherein $R_1$ is hydrogen, X is a direct bond, $R_2$ is selected from optionally substituted aryl and optionally substituted heteroaryl, n is 0, m is 1, and $R_4$ is selected from butyl, tert-butyl, trifluoromethyl, trifluoromethoxy, and difluoromethoxy.

20. The compound of claim 1, or a salt, solvate, or solvate of a salt thereof, wherein $R_1$ is hydrogen, X is a direct bond or $CH_2$, $R_2$ is selected from optionally substituted aryl and optionally substituted heteroaryl, n is 1, $R_3$ is halo or cyano, m is 1, and $R_4$ is butyl or tert-butyl.

21. The compound of claim 20, or a salt, solvate, or solvate of a salt thereof, wherein $R_2$ is selected from optionally substituted pyridyl, optionally substituted phenyl, optionally substituted pyrazolyl, optionally substituted imidazolyl, and optionally substituted thiophenyl, wherein optional substituents are selected from $O^-$, $OCH_3$, $OC_2H_5$, $CH_3$, carboxy, carboxymethyl, and CN, $R_3$ is chloro, and $R_4$ is tert-butyl.

22. The compound of claim 1, or a salt, solvate, or solvate of a salt thereof, selected from the group consisting of:

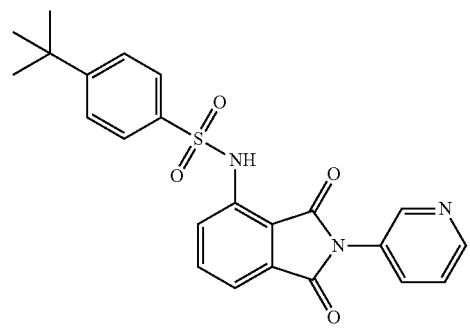

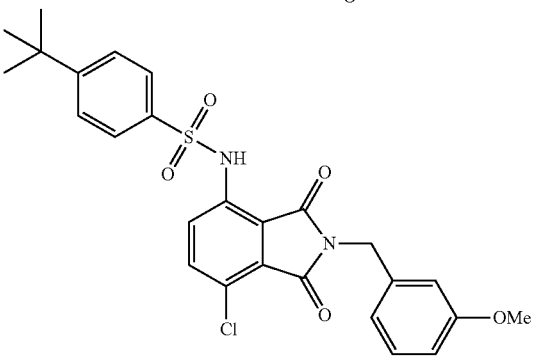

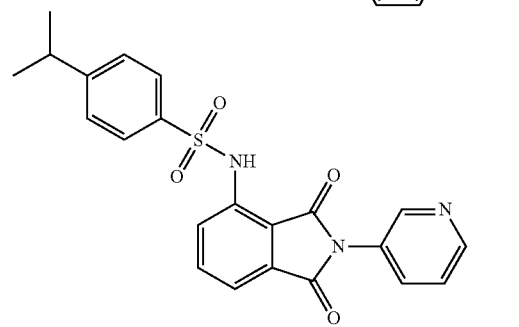

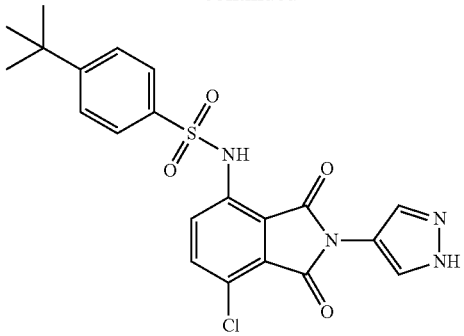

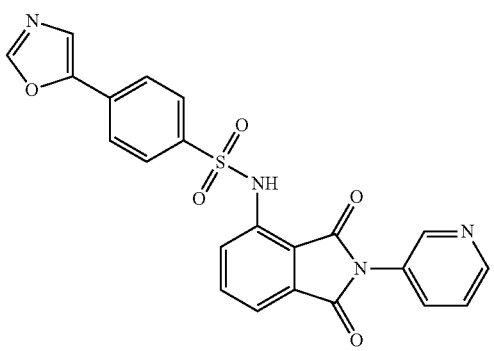

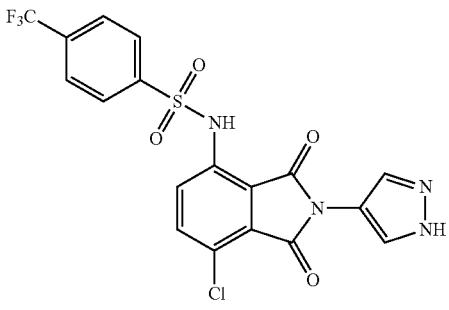

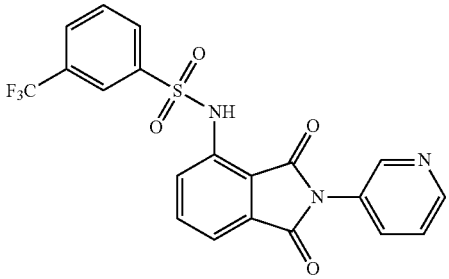

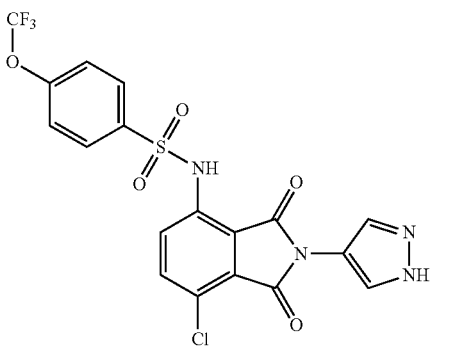

519
-continued
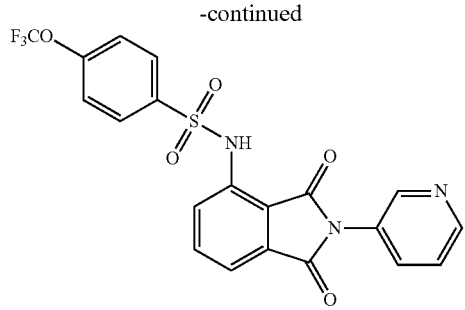
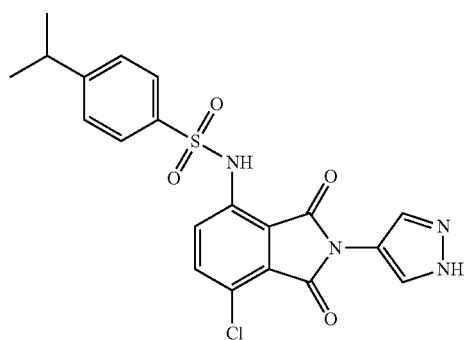
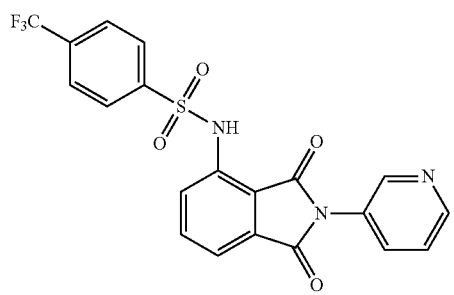
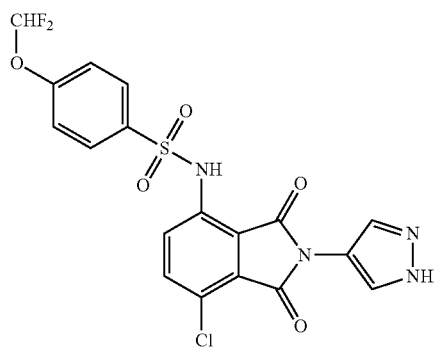
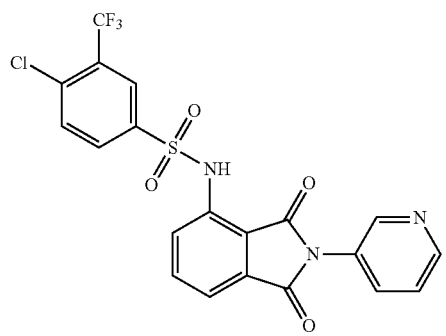
520
-continued
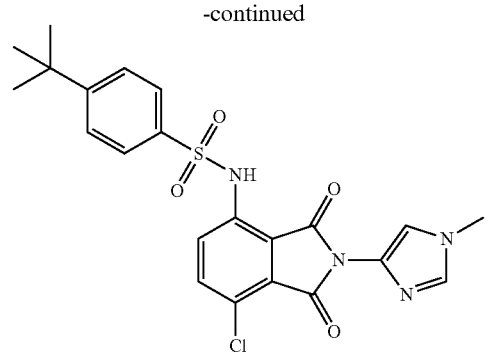
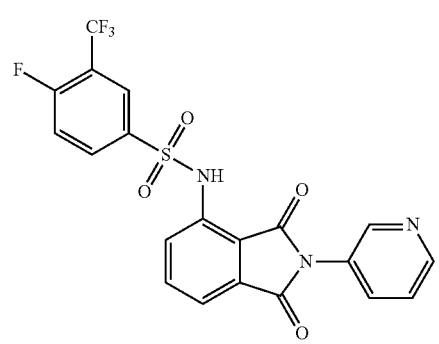
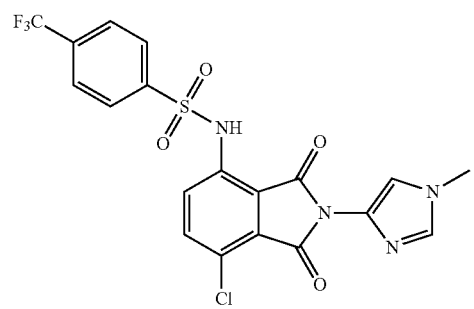
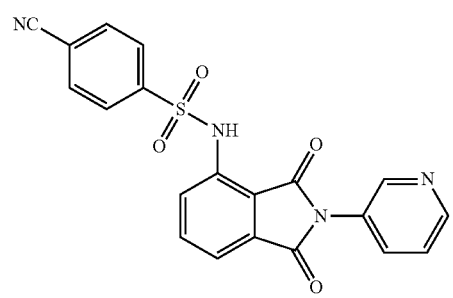
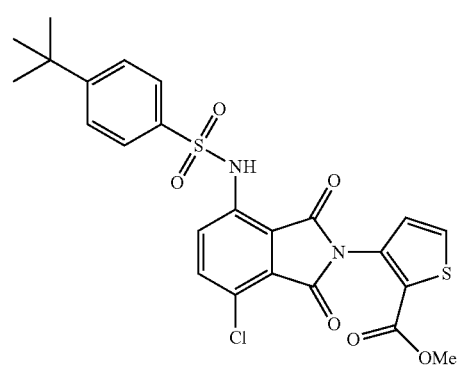

521
-continued
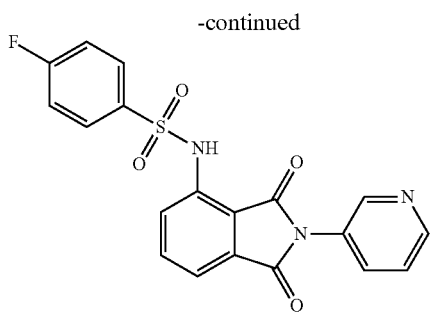
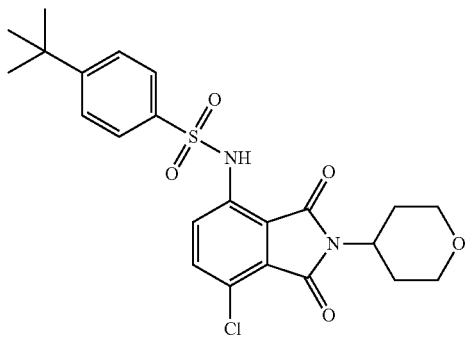
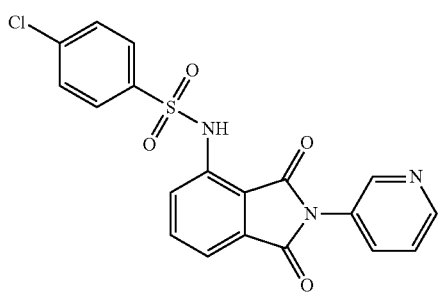
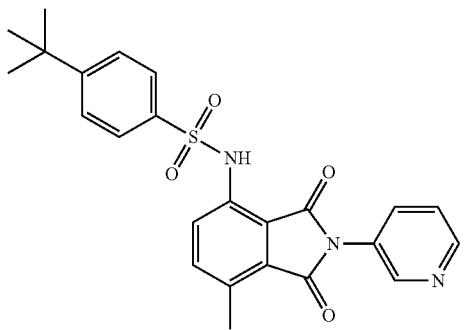
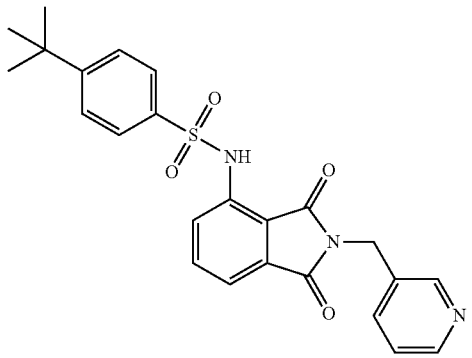
522
-continued
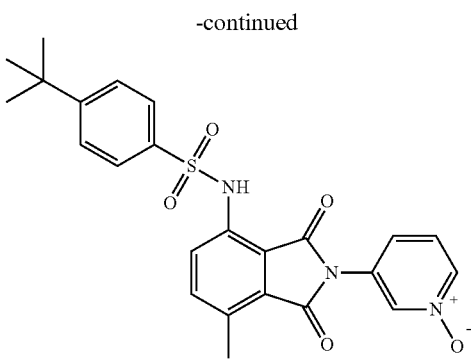
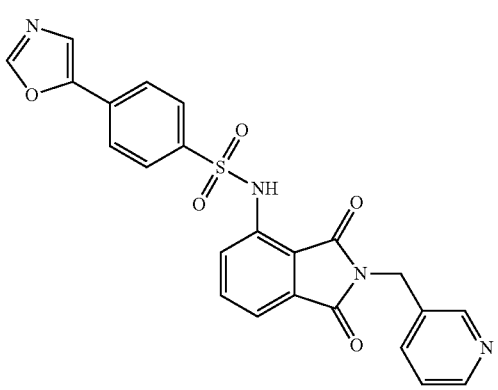
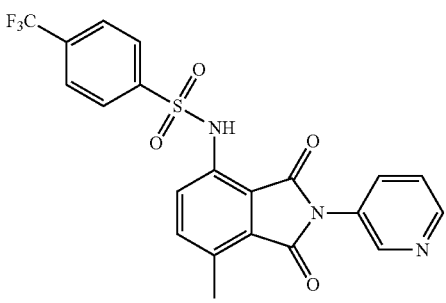
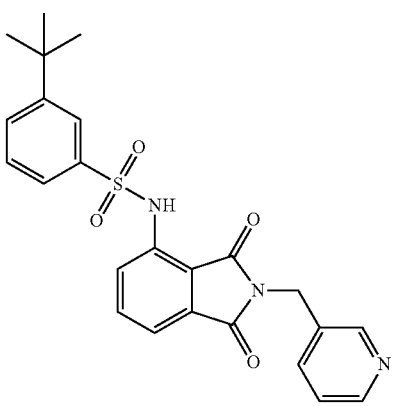

523
-continued
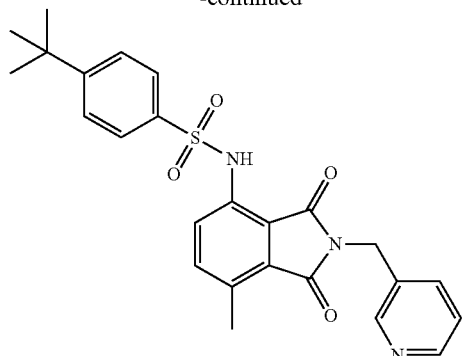
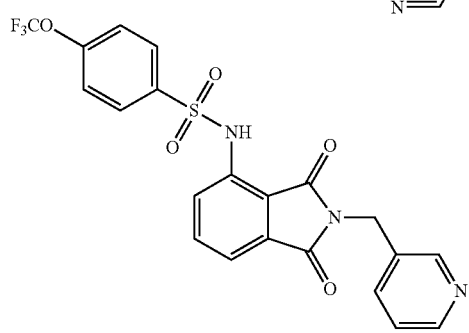
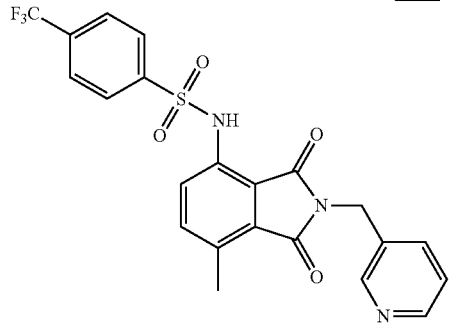
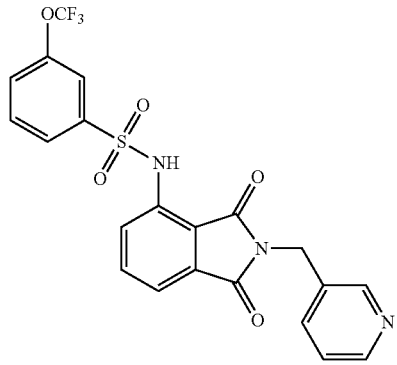
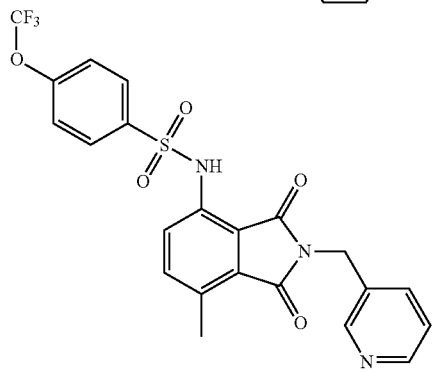
524
-continued
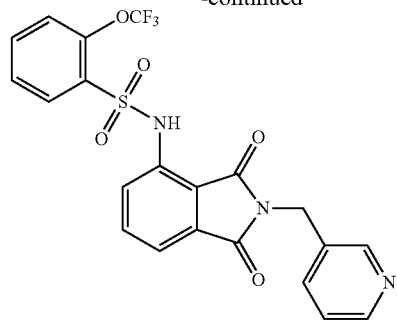
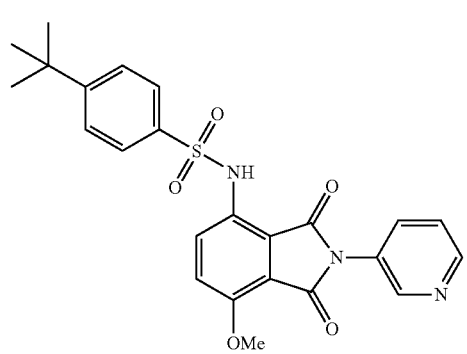
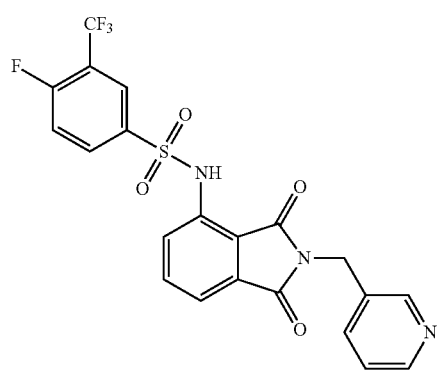
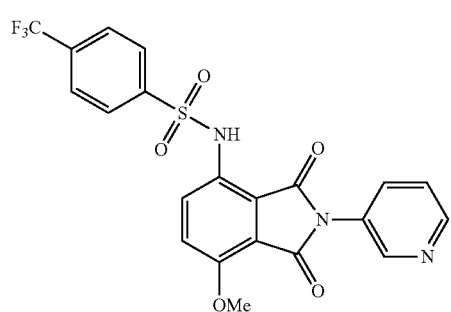
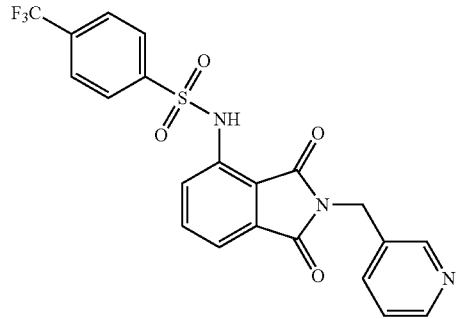

525
-continued
526
-continued
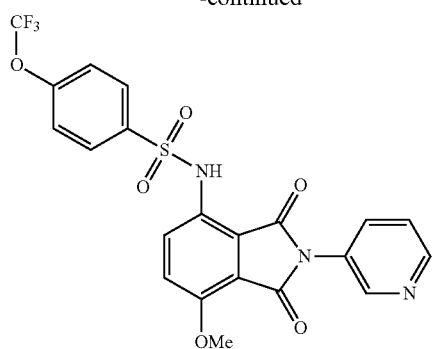
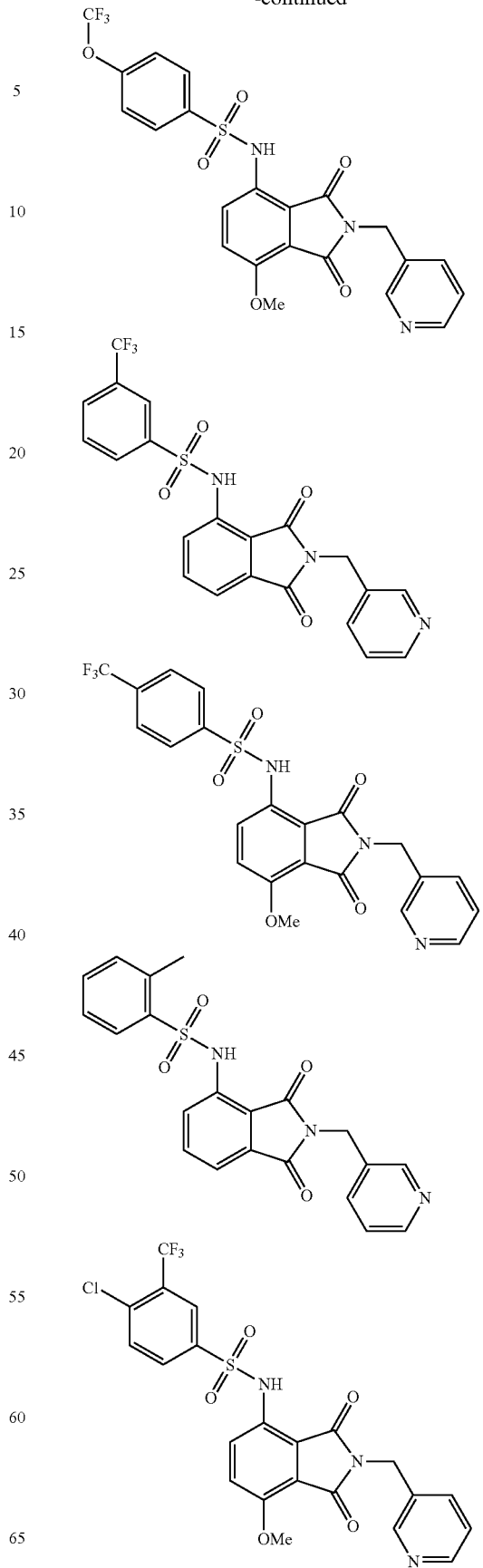

527
-continued
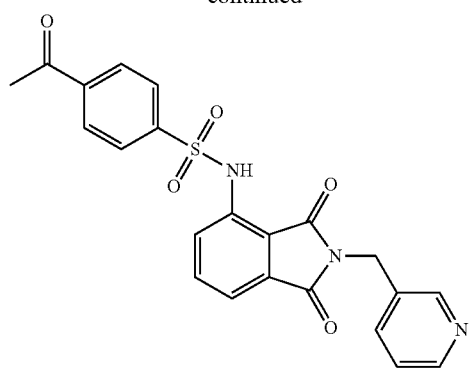
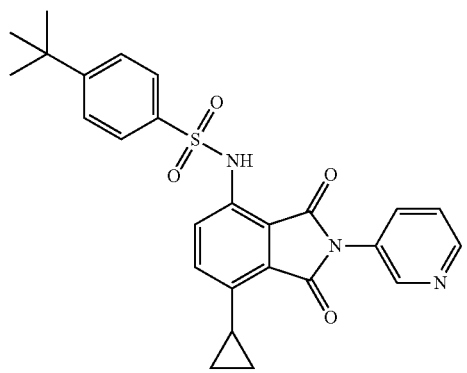
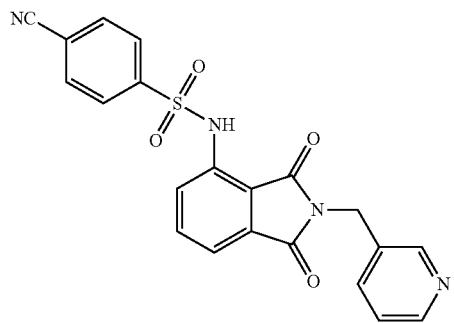
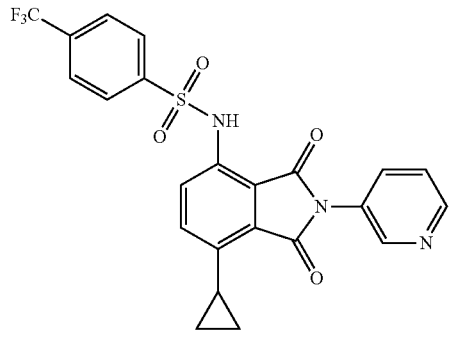
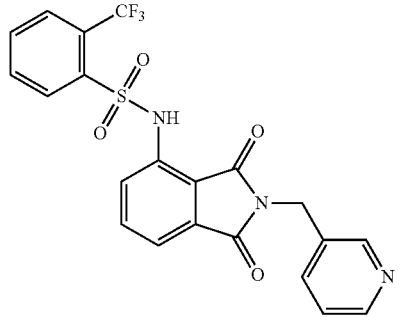
528
-continued
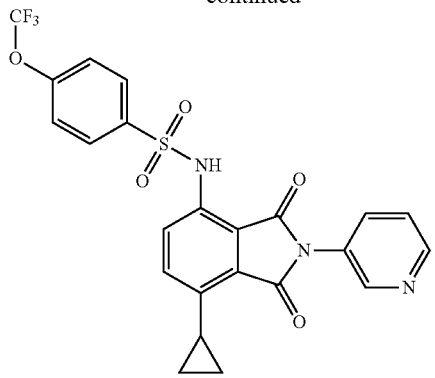
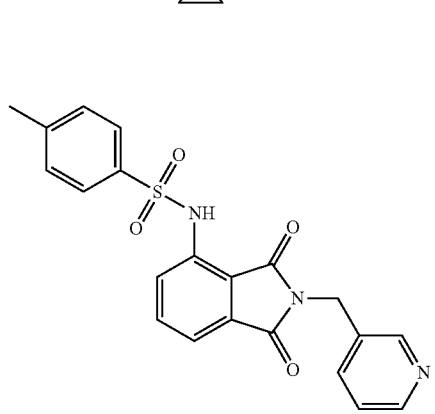
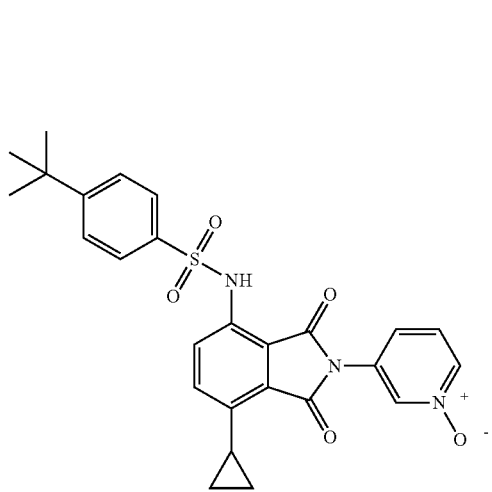
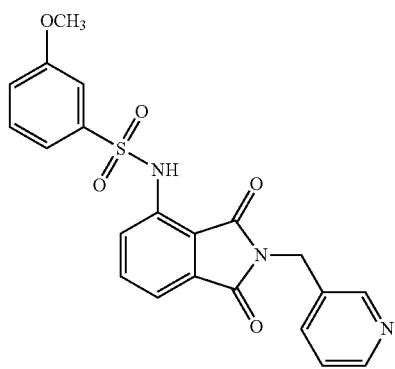

529
-continued
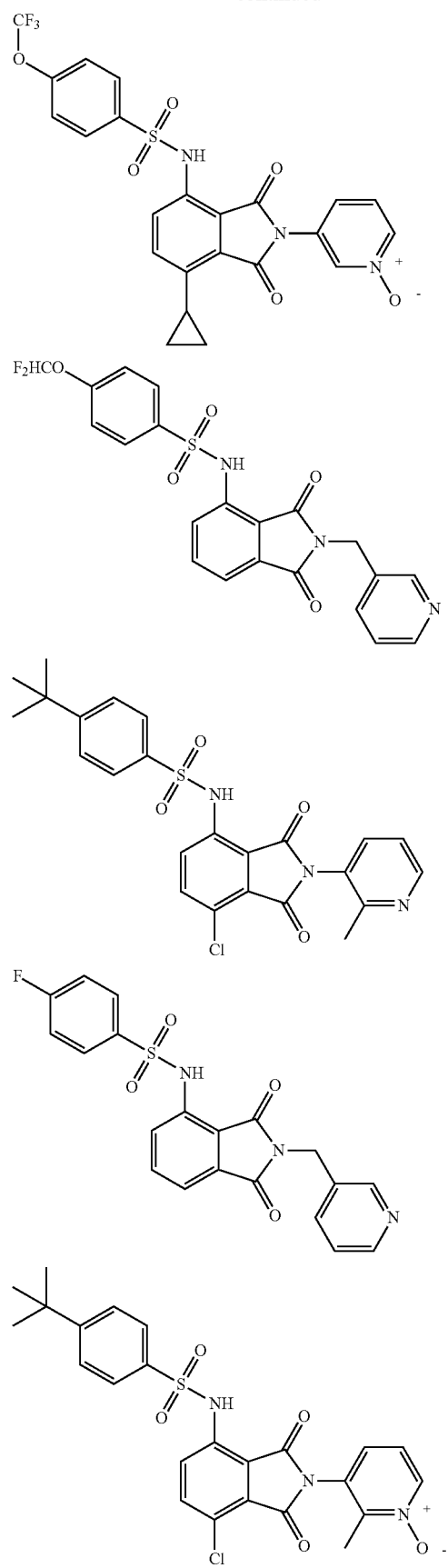
530
-continued
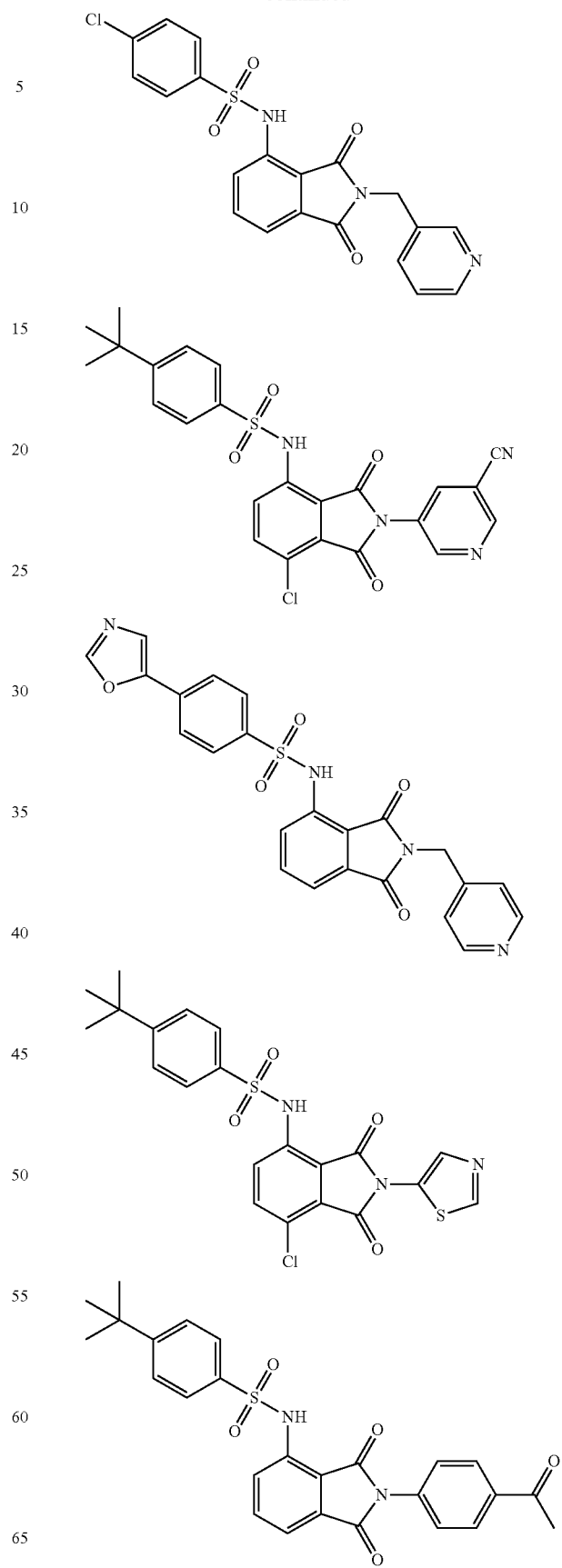

531
-continued
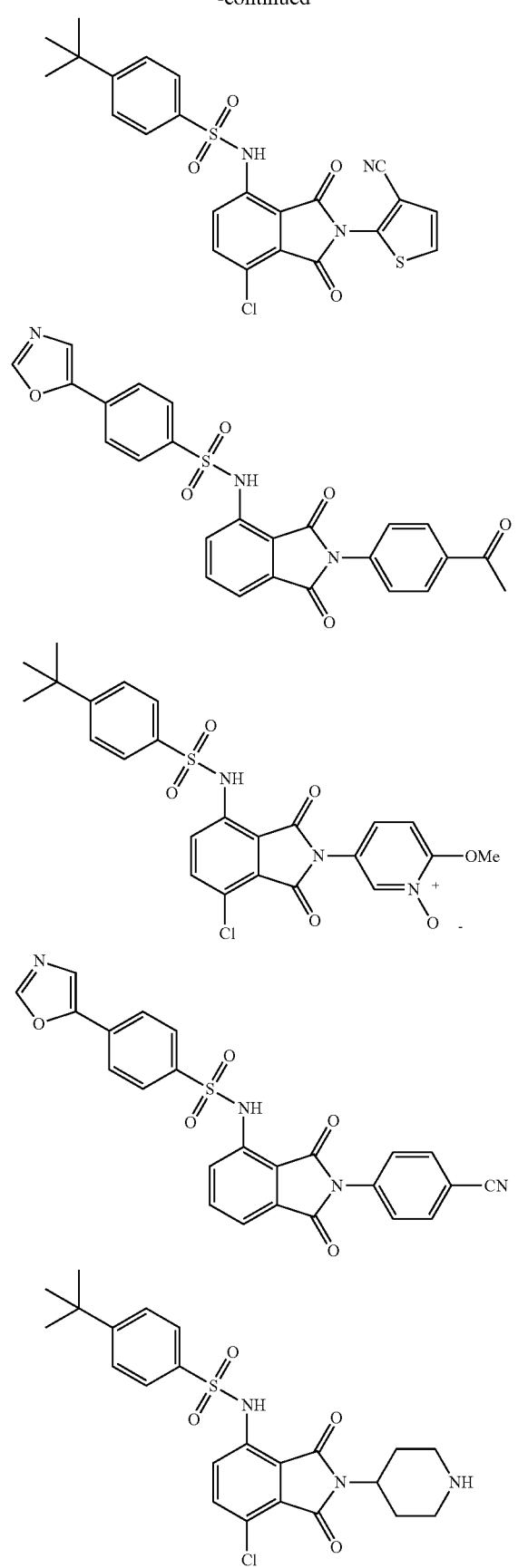
532
-continued
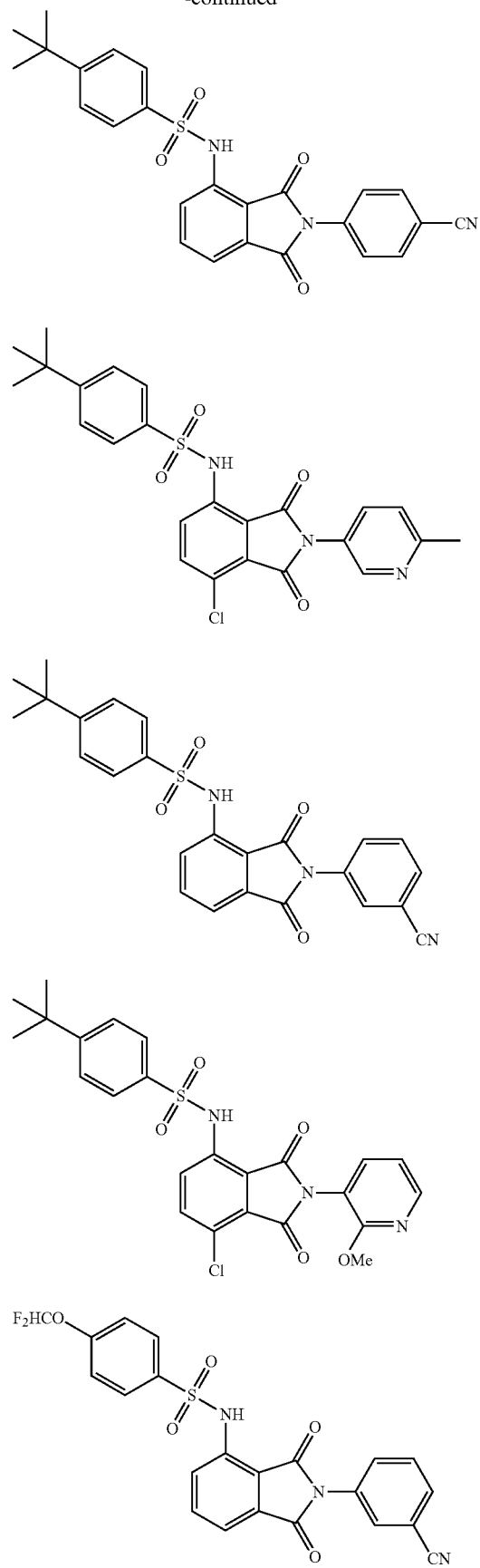

533
-continued
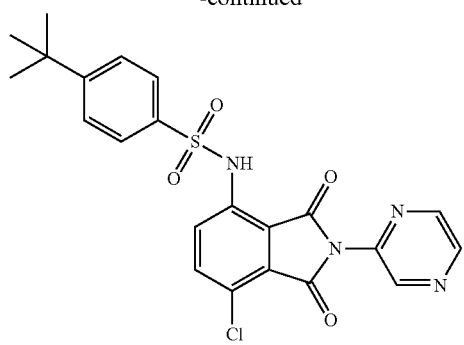
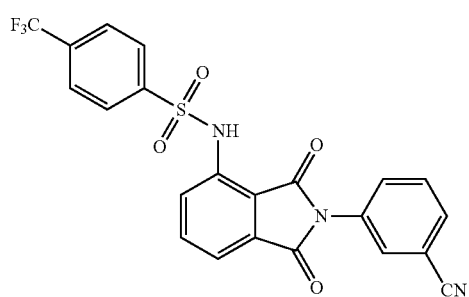
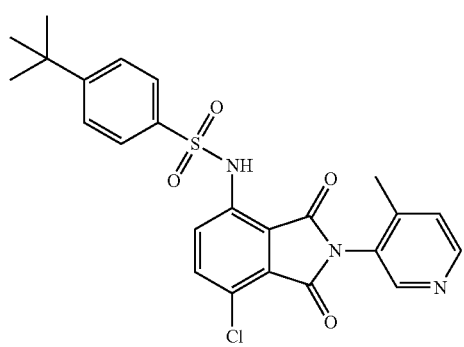
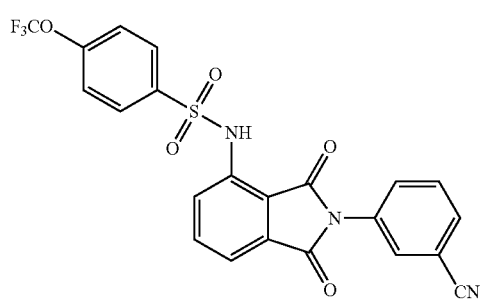
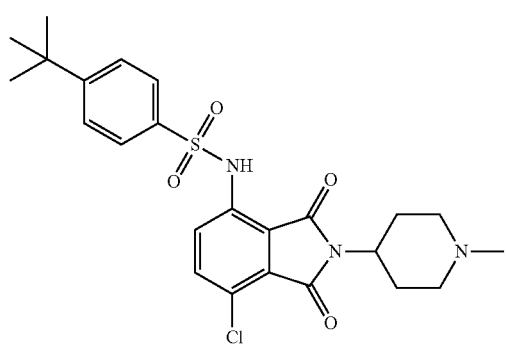
534
-continued
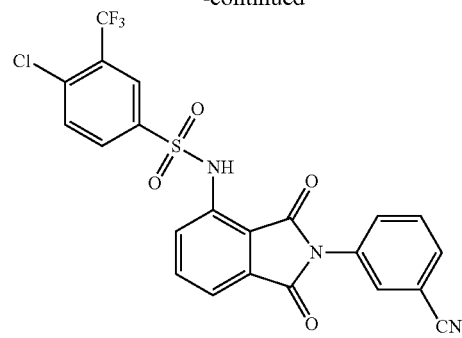
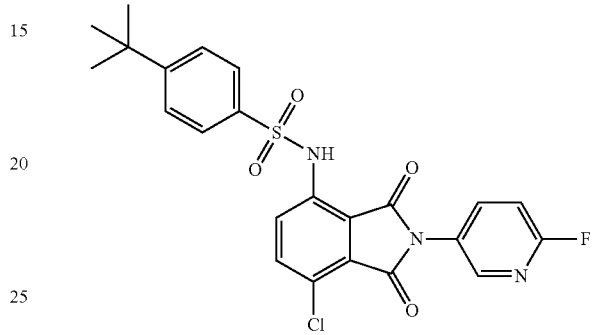
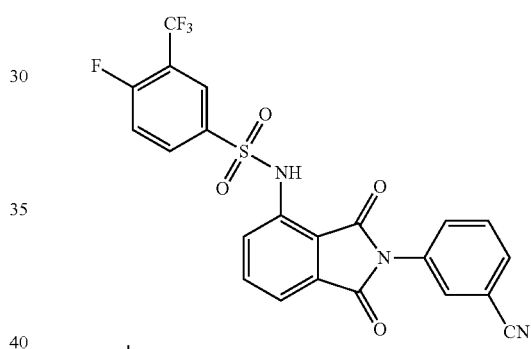
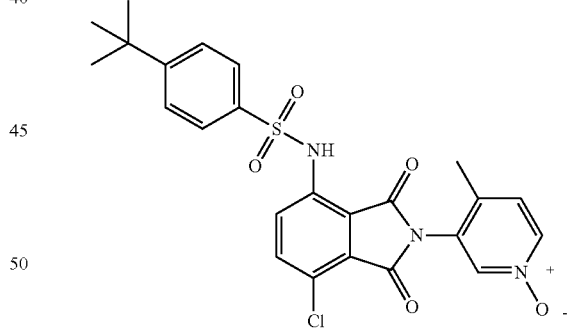
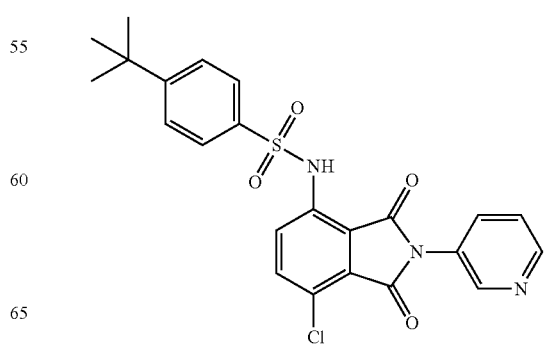

535
-continued
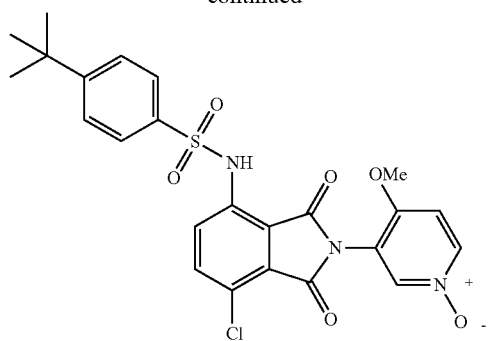
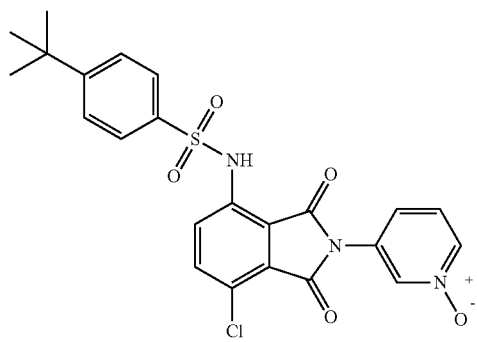
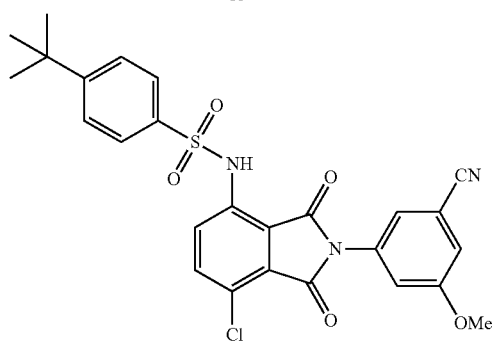
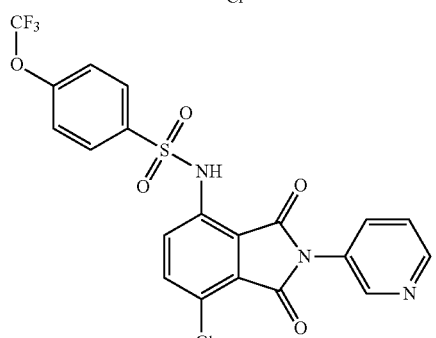
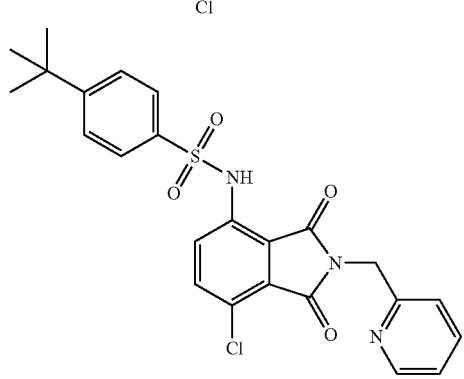
536
-continued
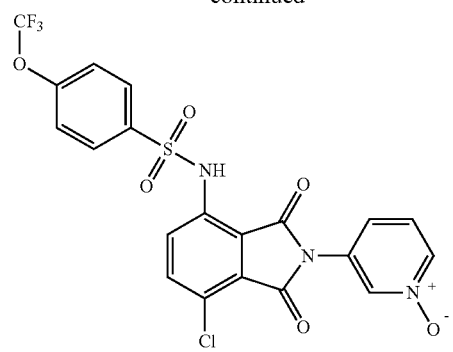
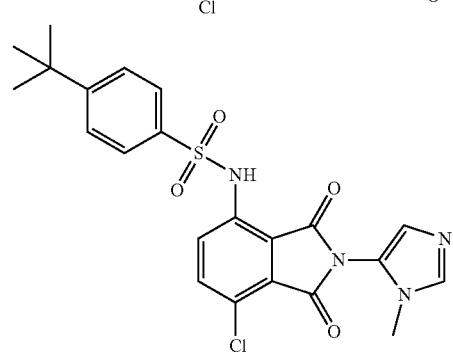
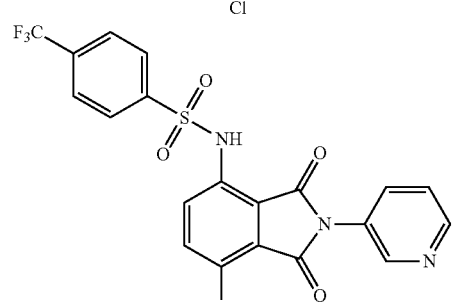
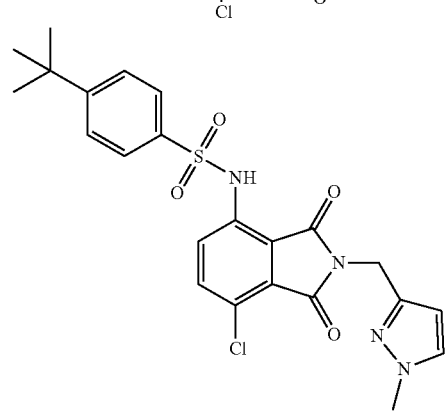
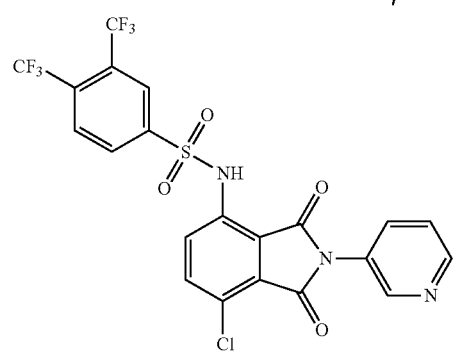

537
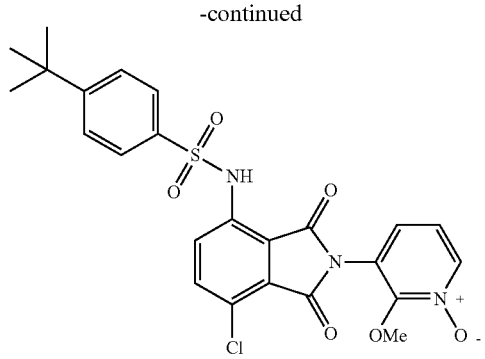
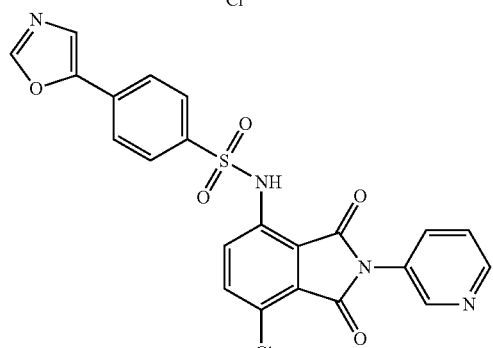
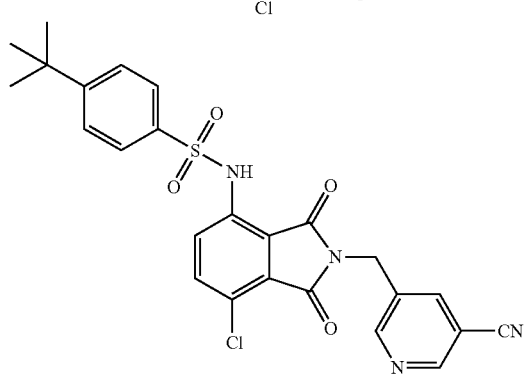
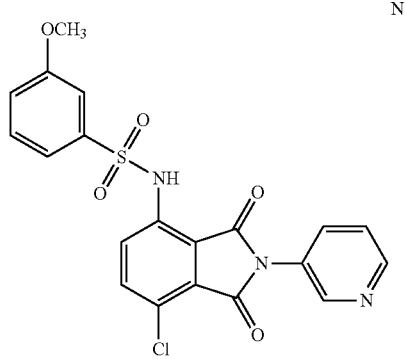
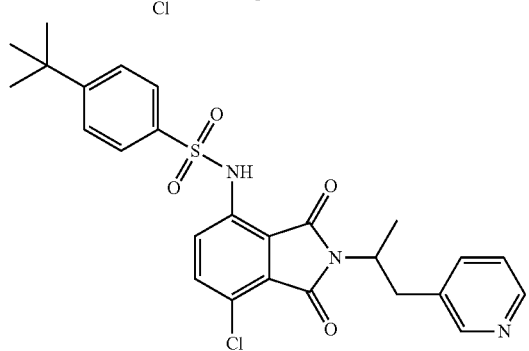
538
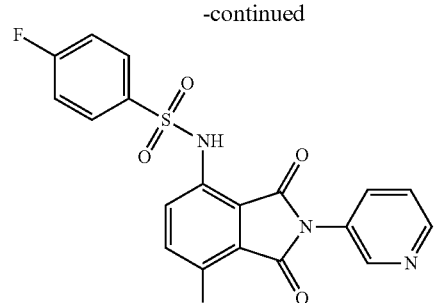
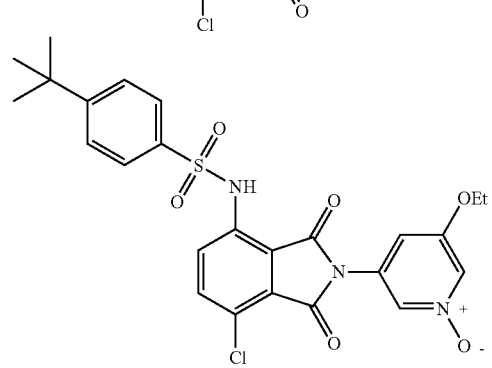
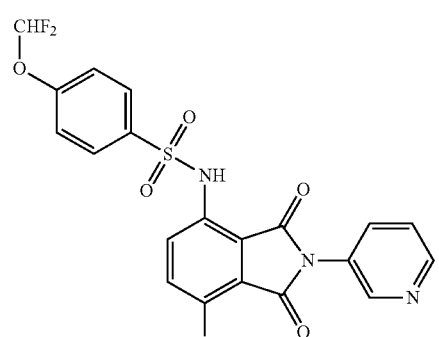
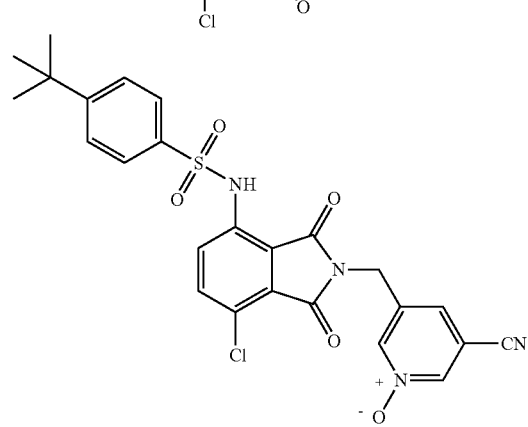
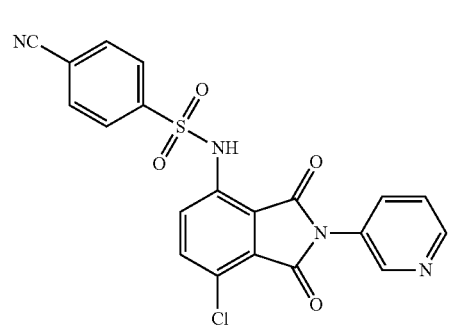

539
-continued
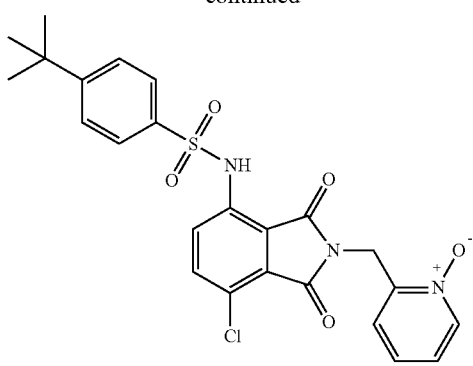
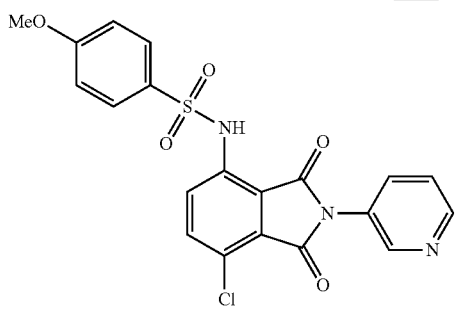
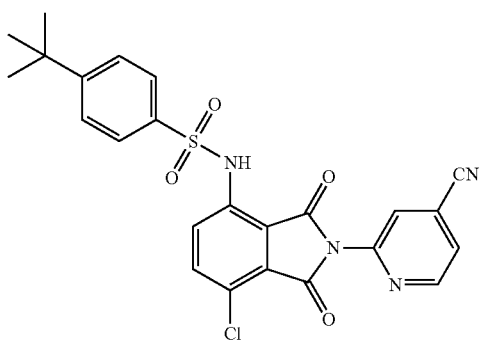
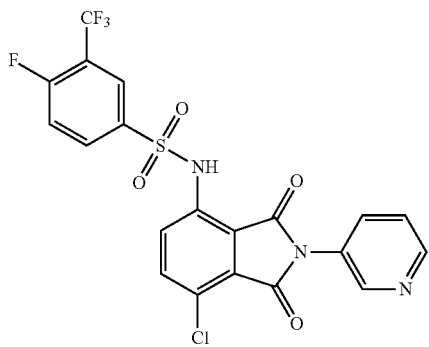
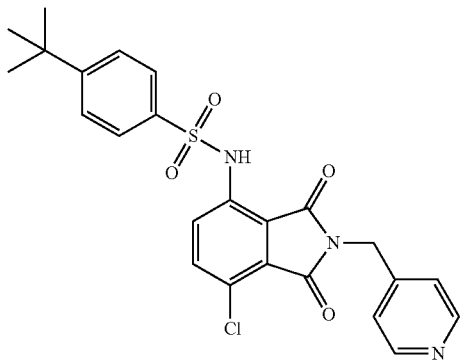
540
-continued
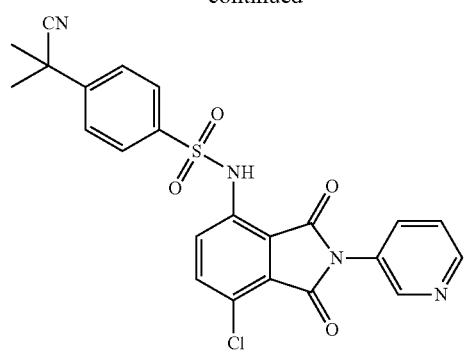
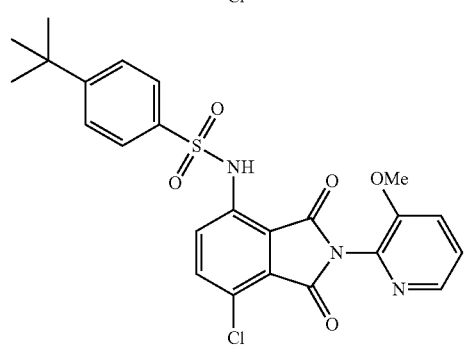
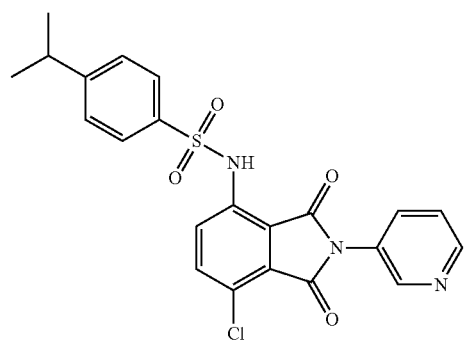
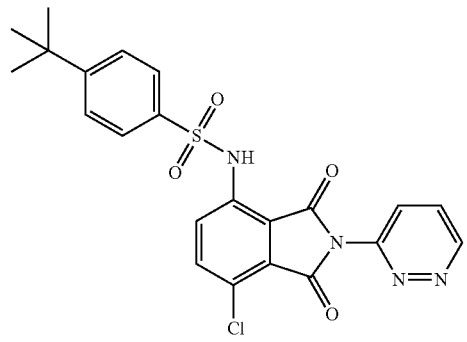
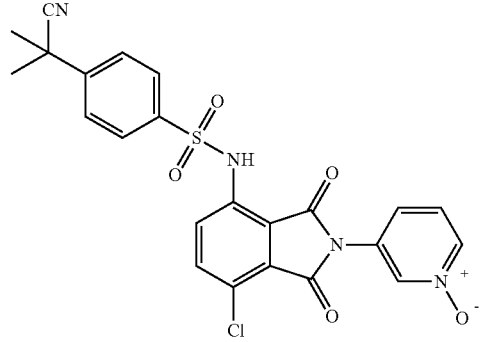

541
-continued
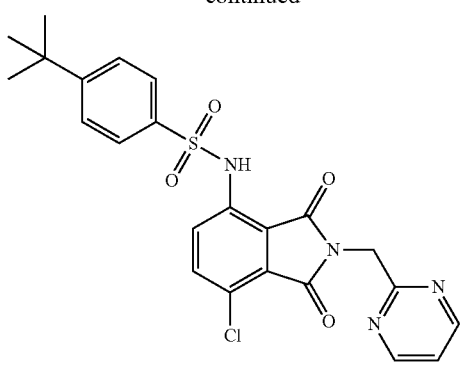
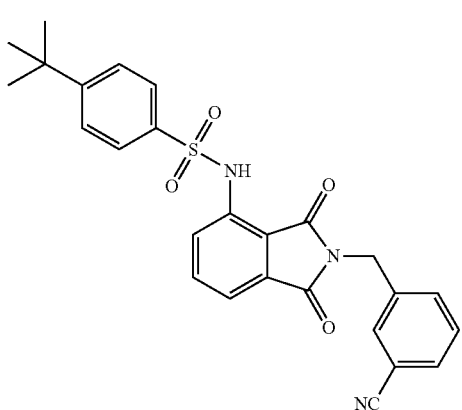
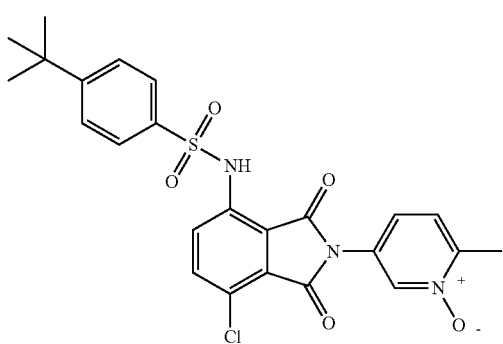
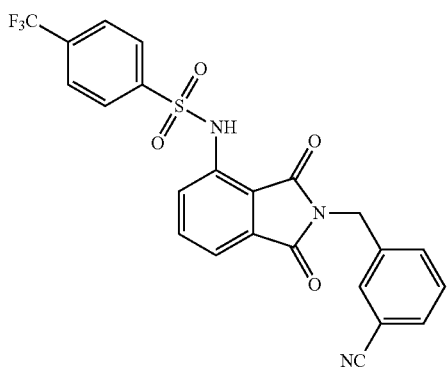
542
-continued
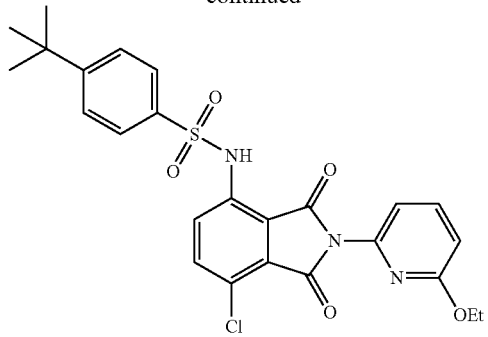
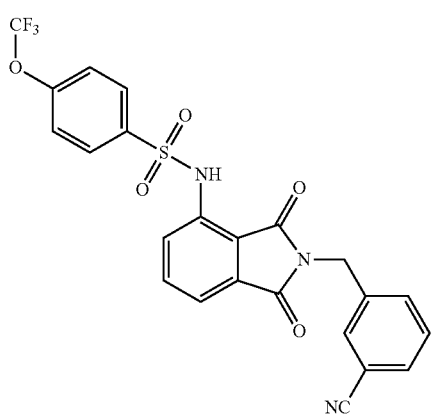
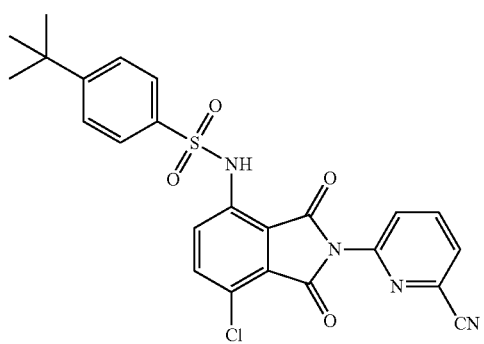
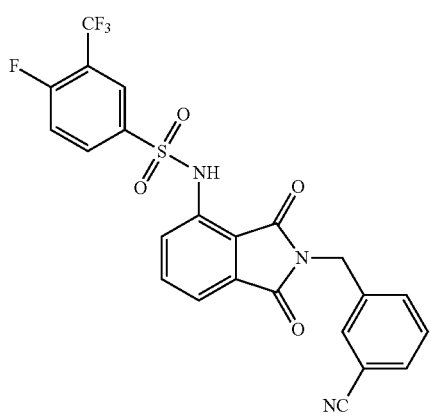

543
-continued
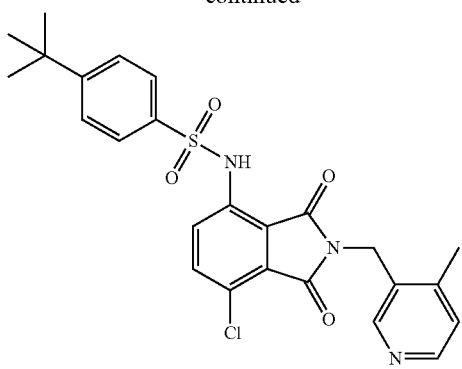
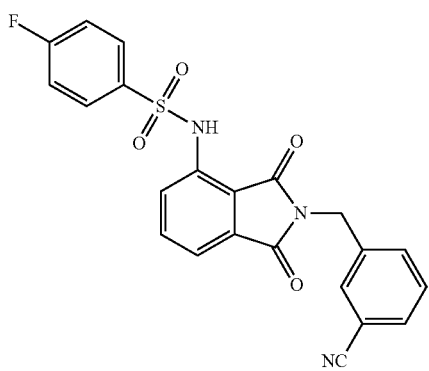
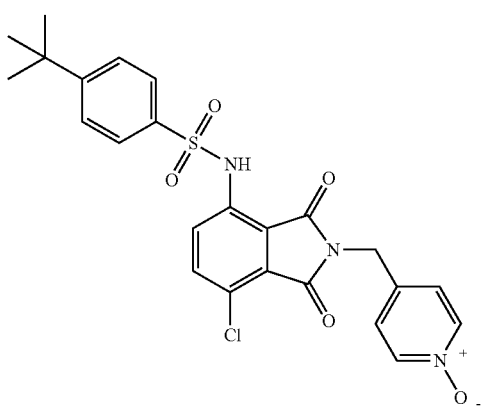
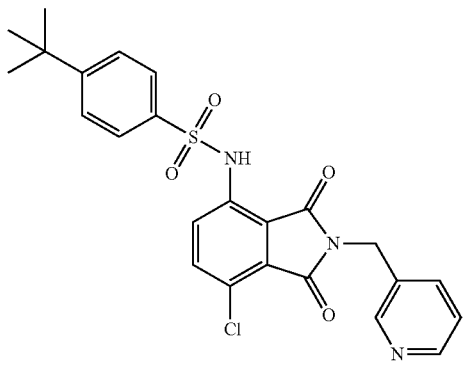
544
-continued
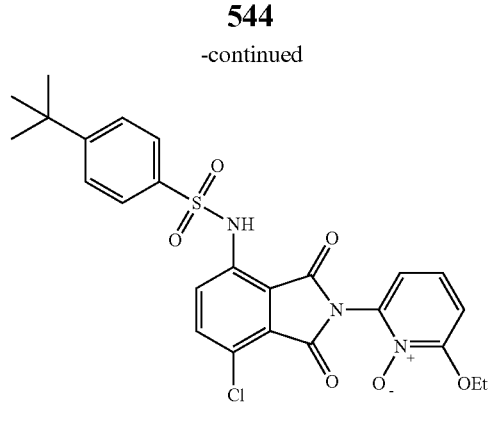
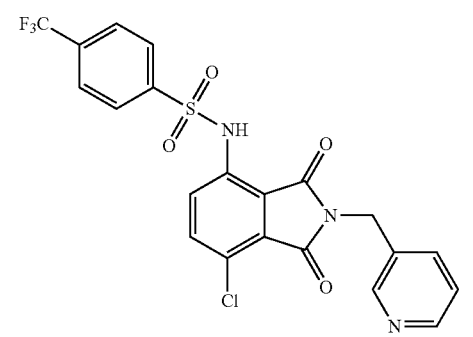

545
-continued
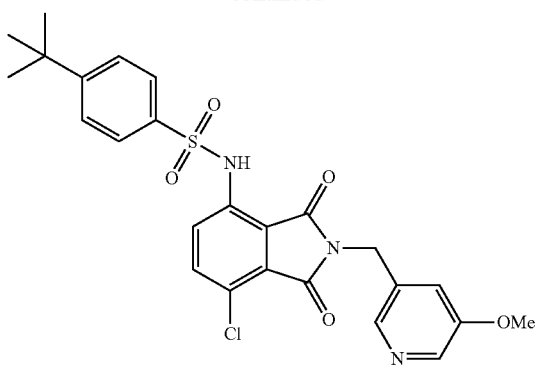
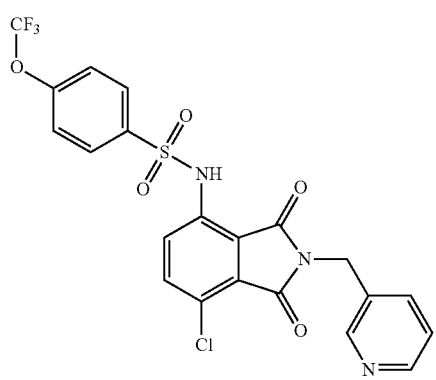
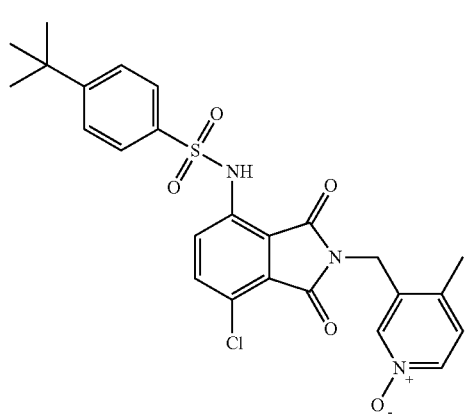
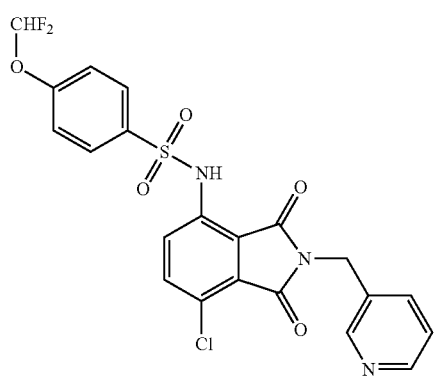
546
-continued
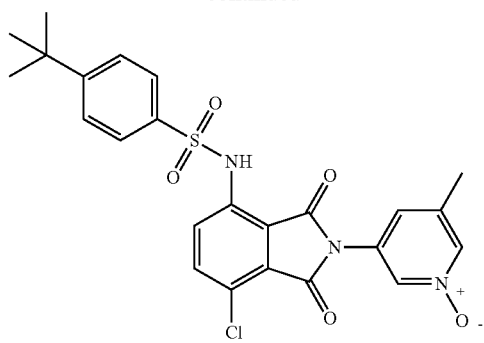
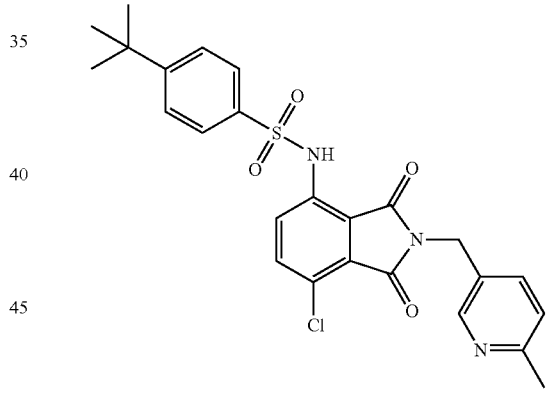
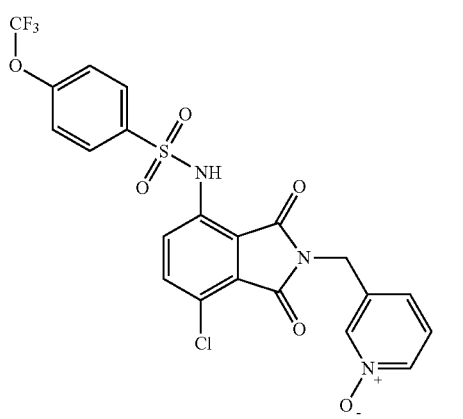

547
-continued
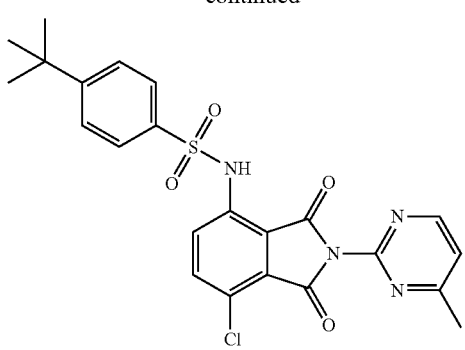
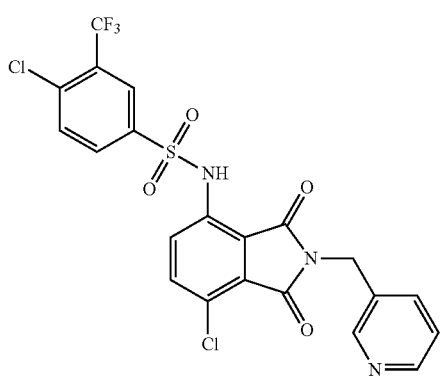
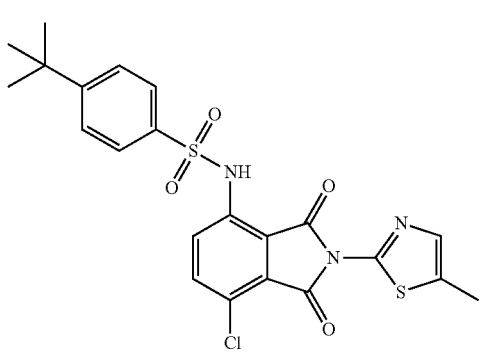
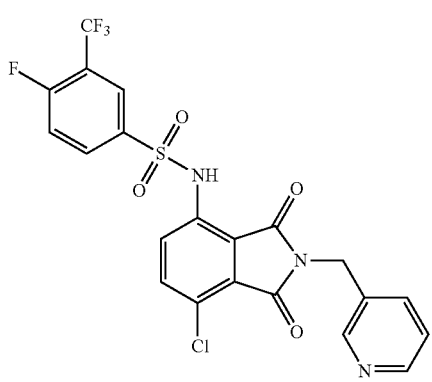
548
-continued
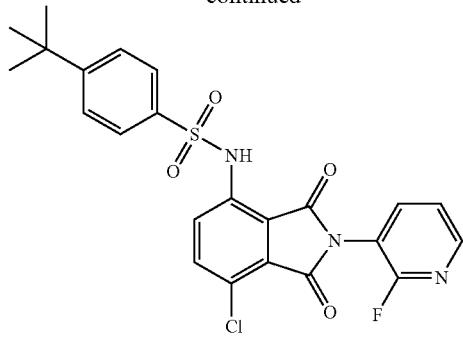
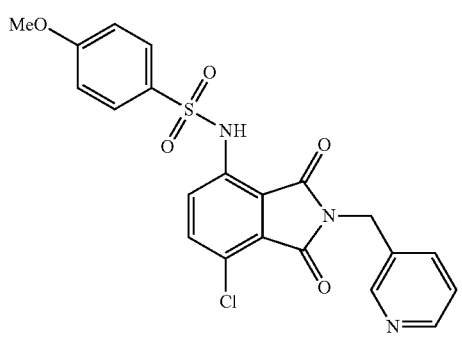
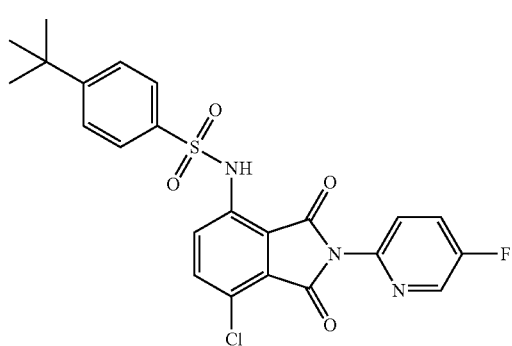
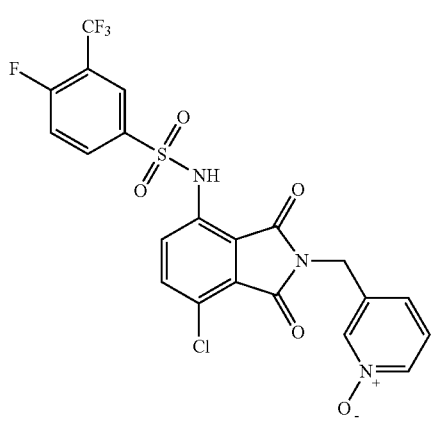

549
-continued
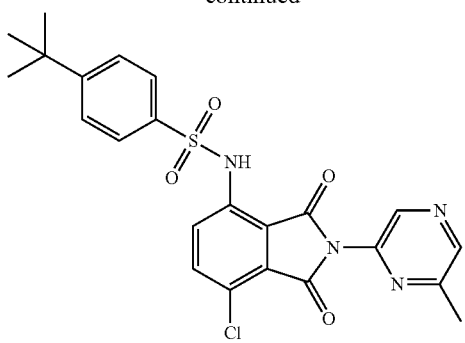
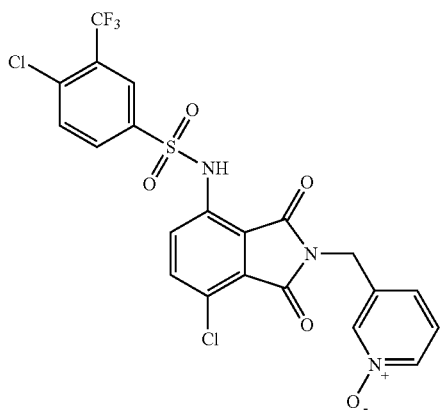
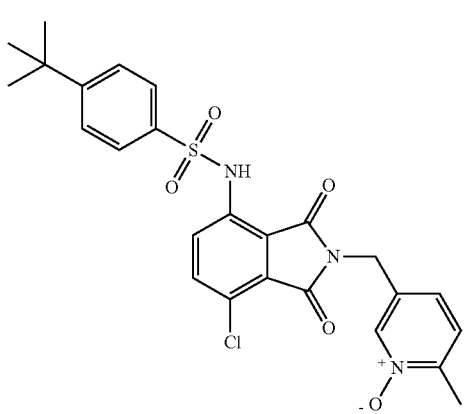
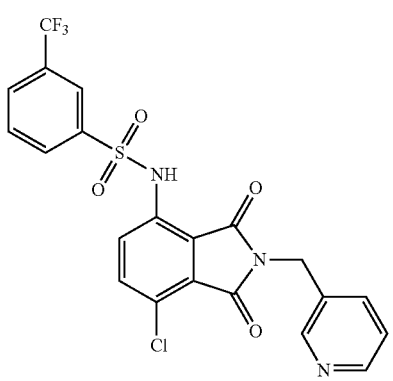
550
-continued
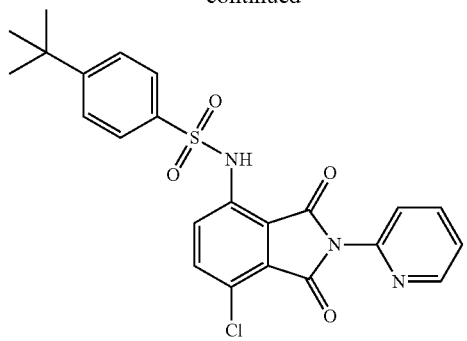
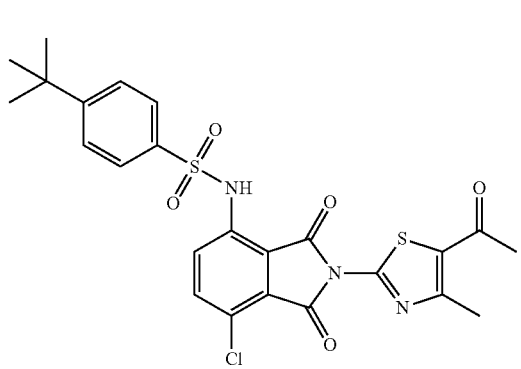
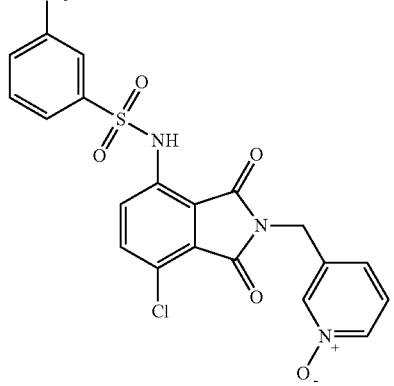

551
-continued
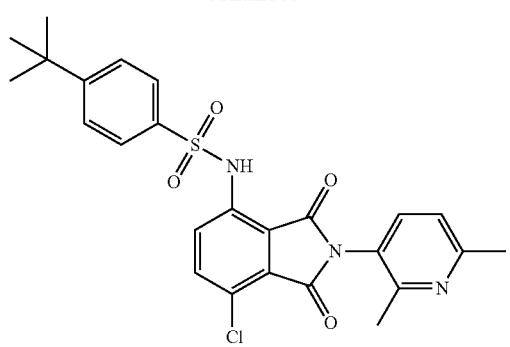
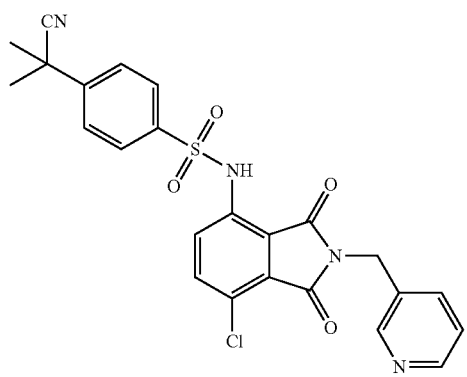
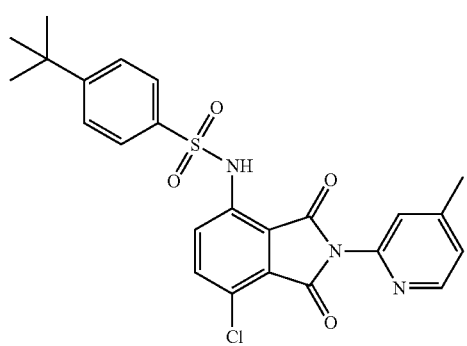
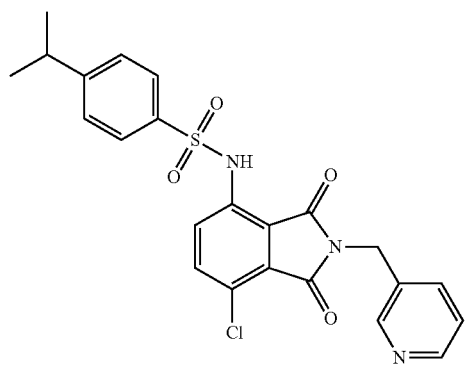
552
-continued
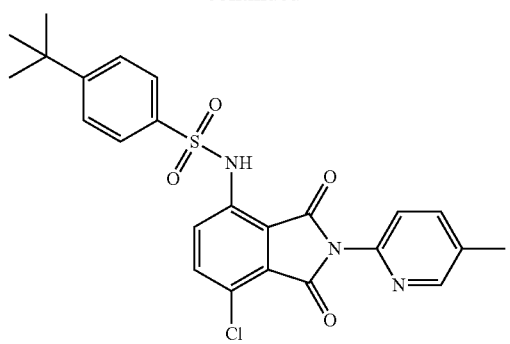
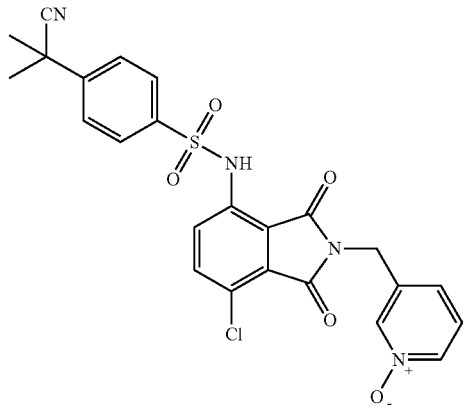
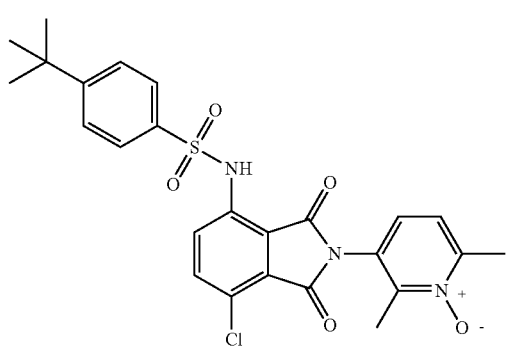
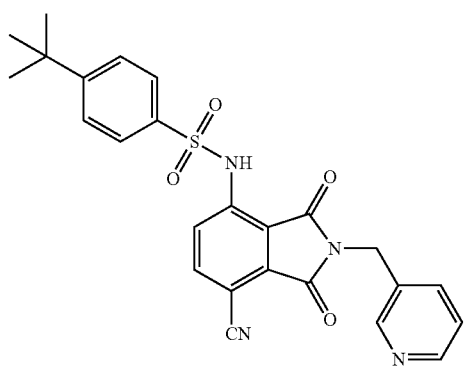

553
-continued
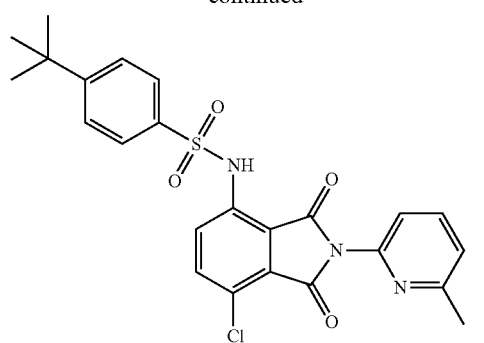
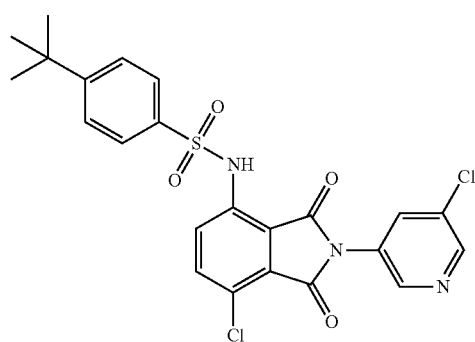
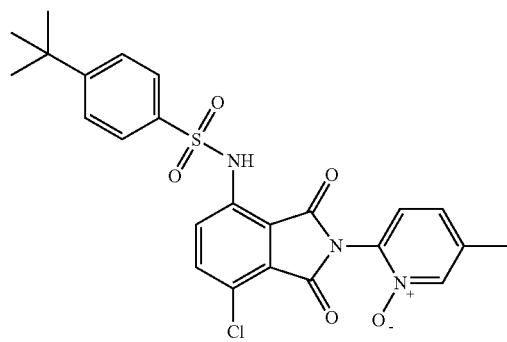
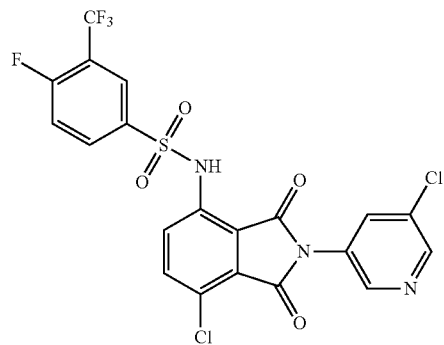
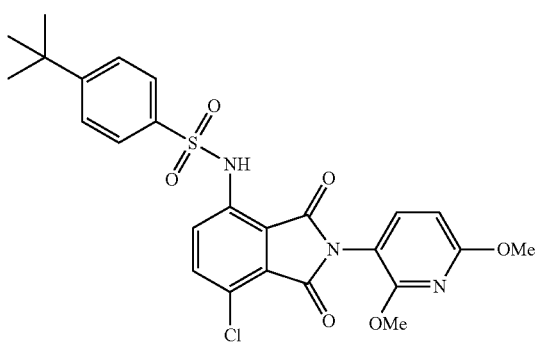
554
-continued
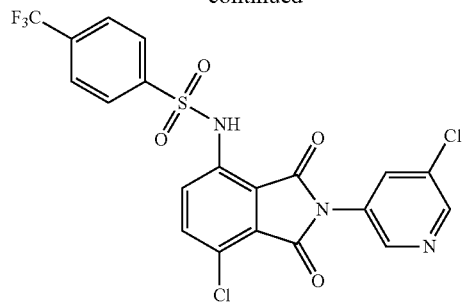
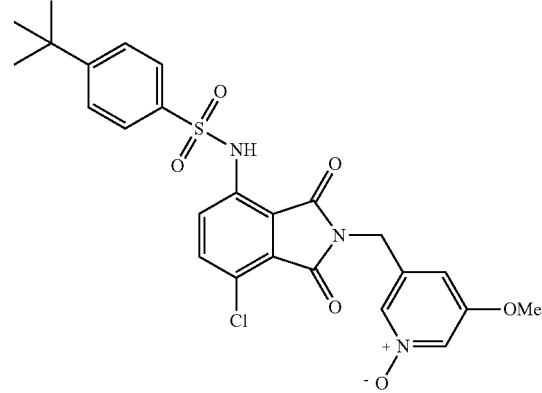
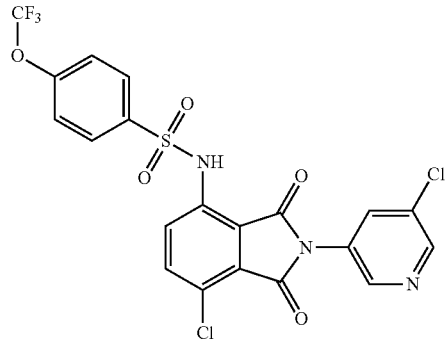
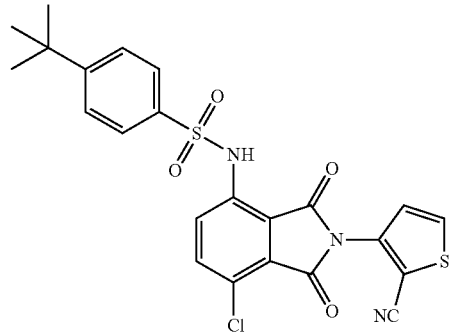
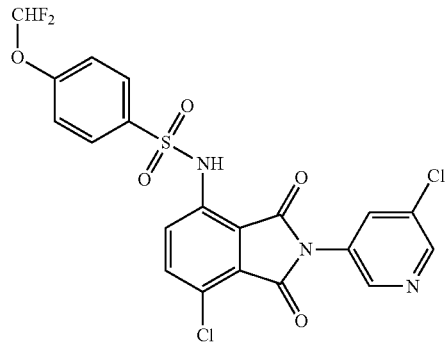

555
-continued
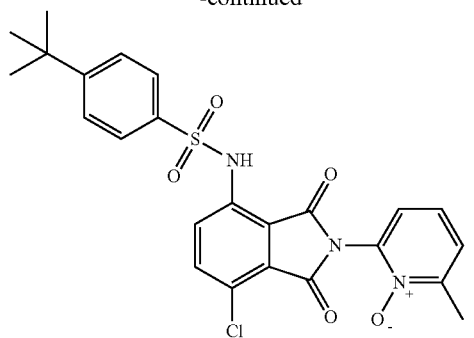
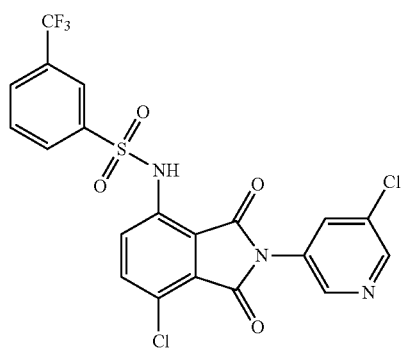
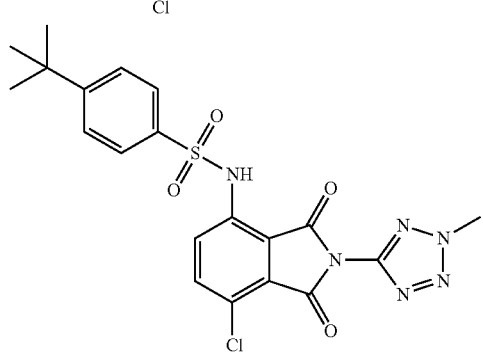
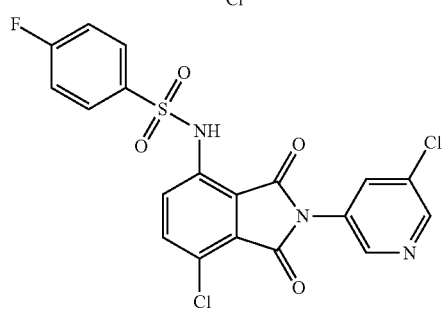
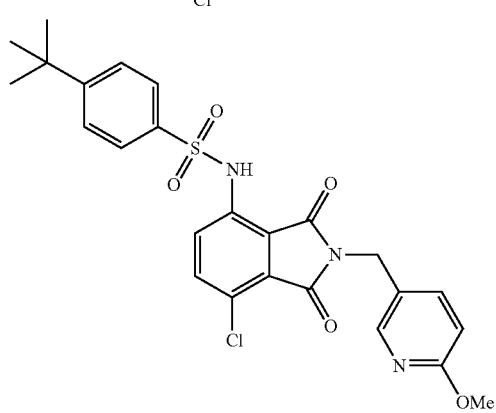
556
-continued
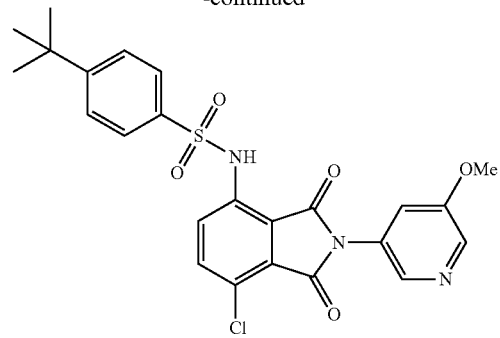
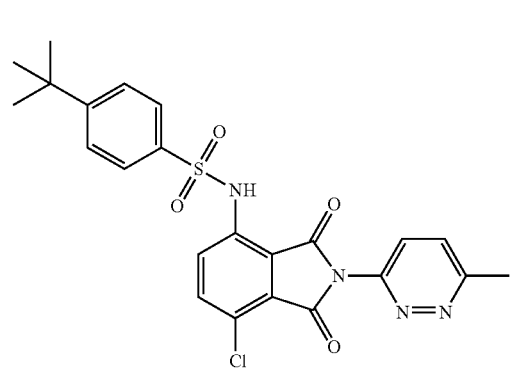
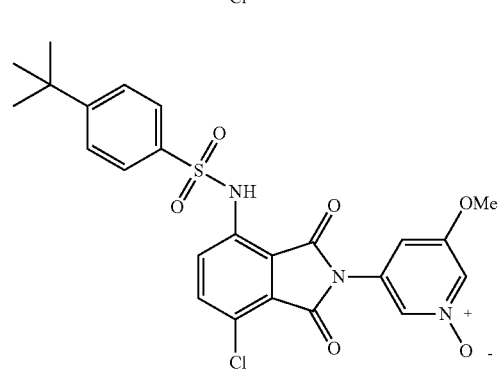
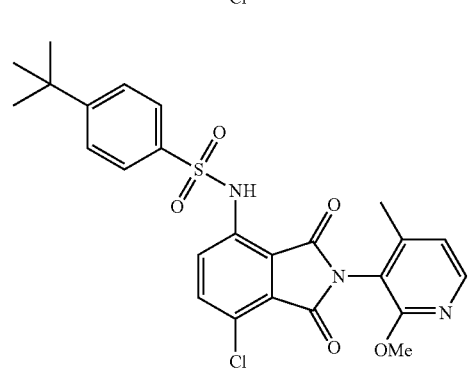
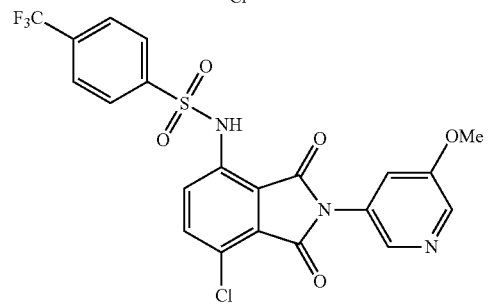

557
-continued
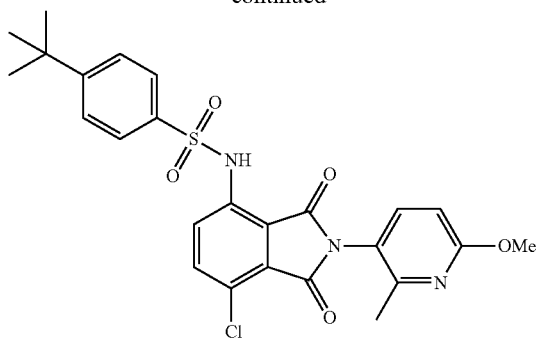
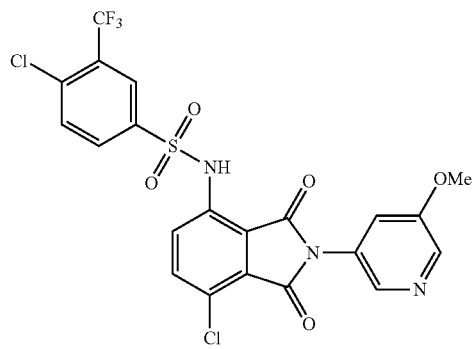
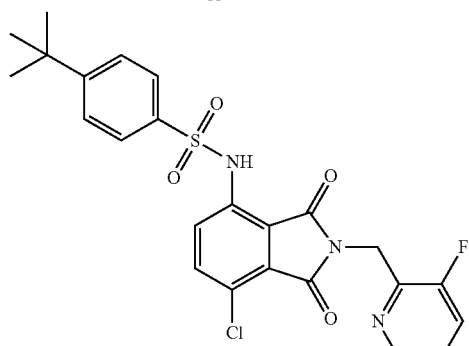
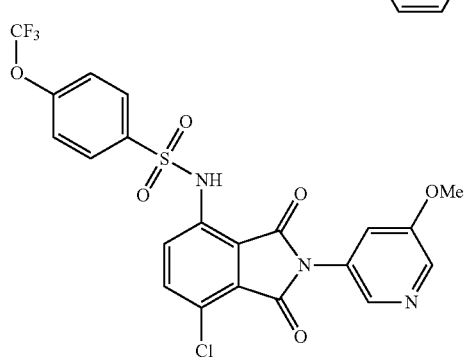
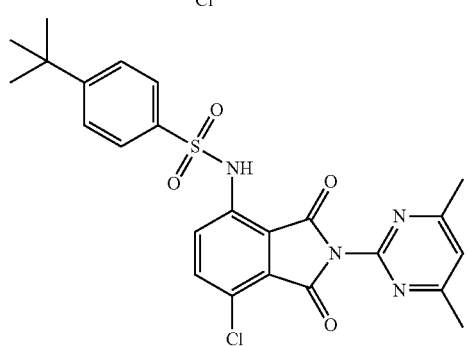
558
-continued
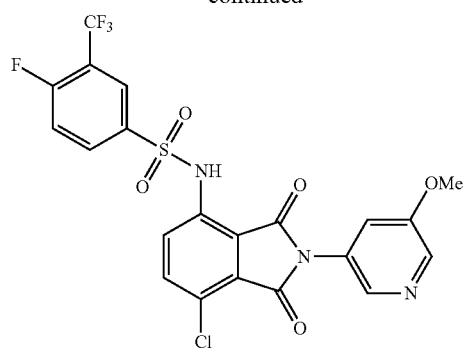
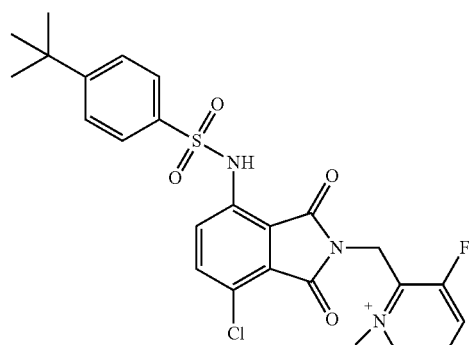
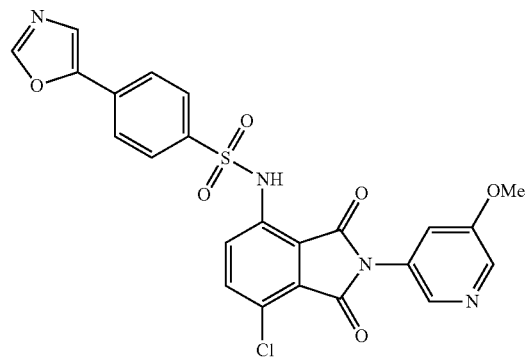
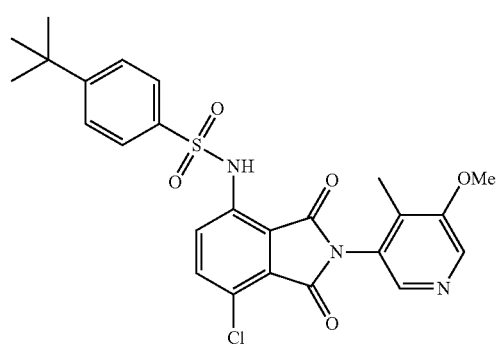

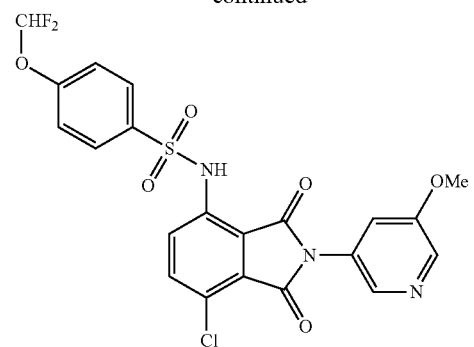
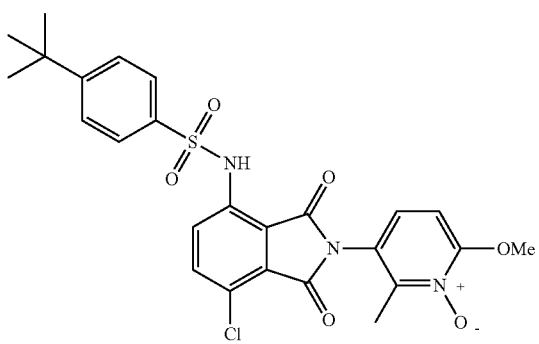
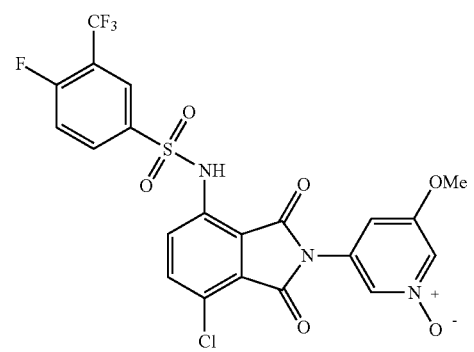
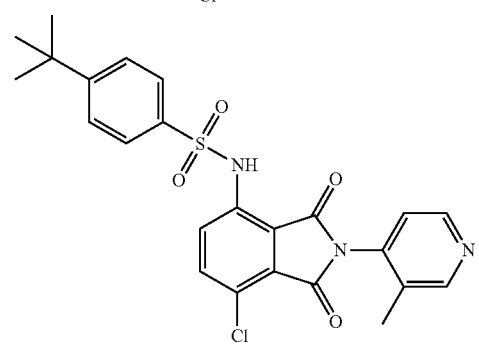
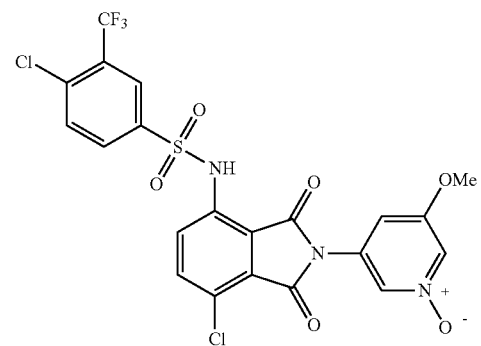
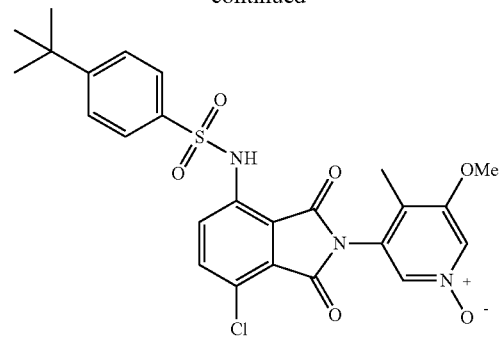
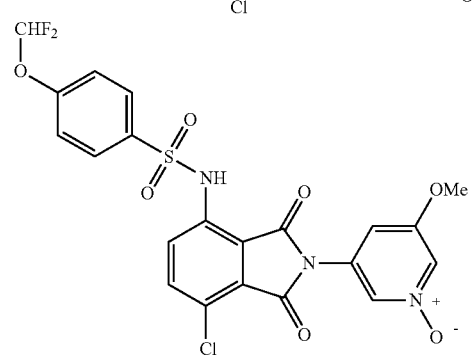
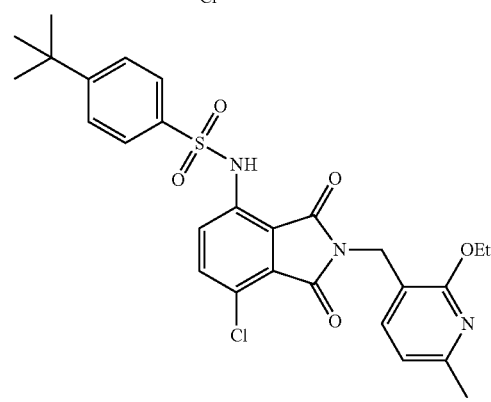
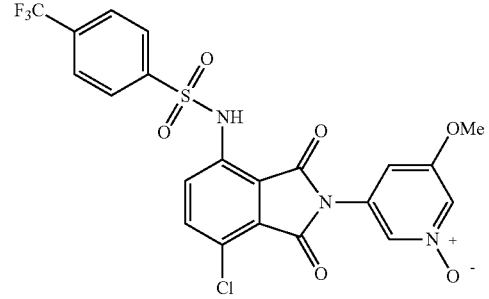
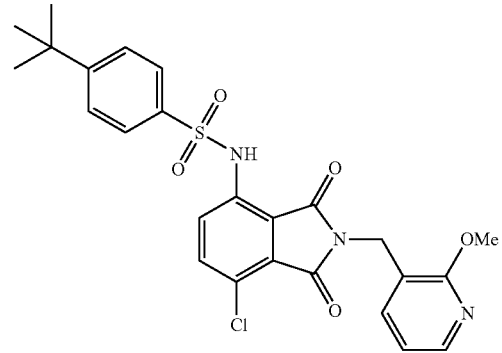

561
-continued
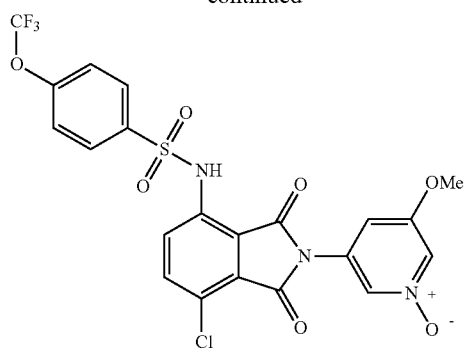
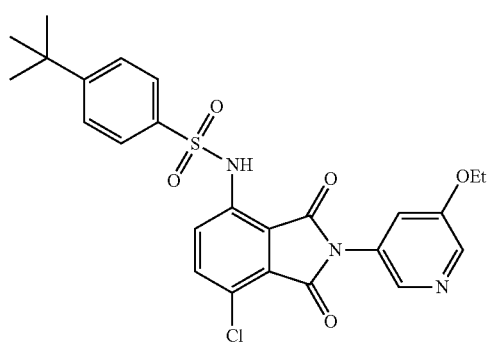
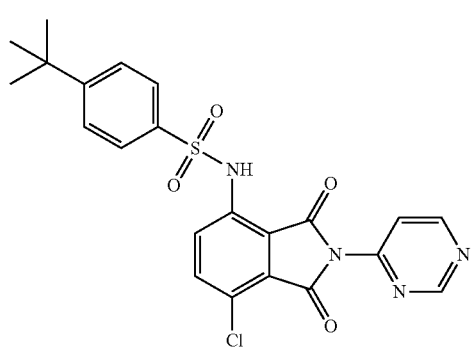
562
-continued
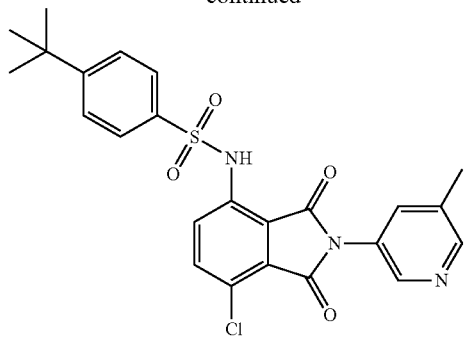
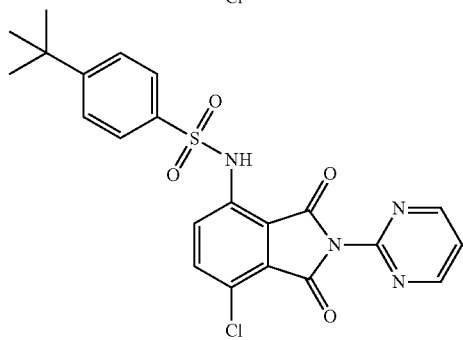
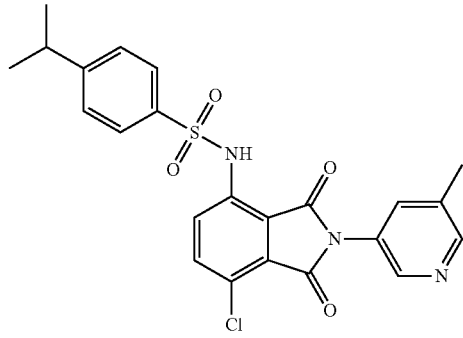
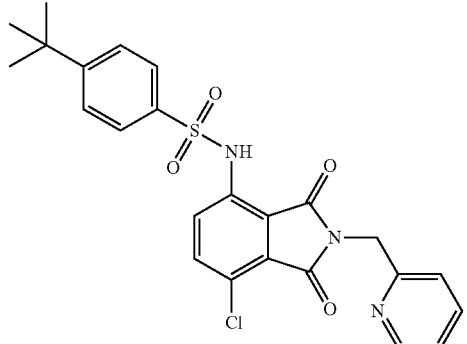
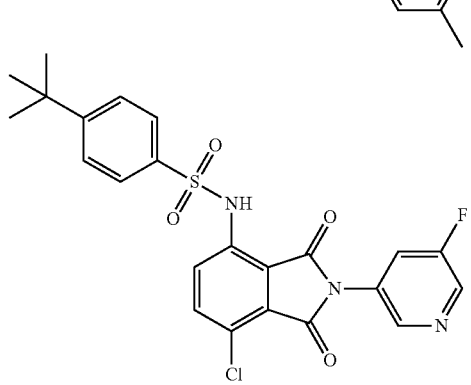

563
-continued
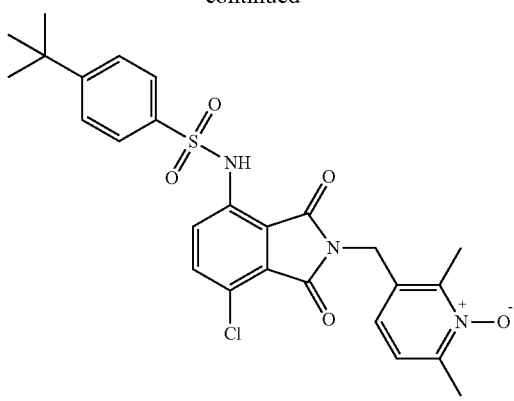
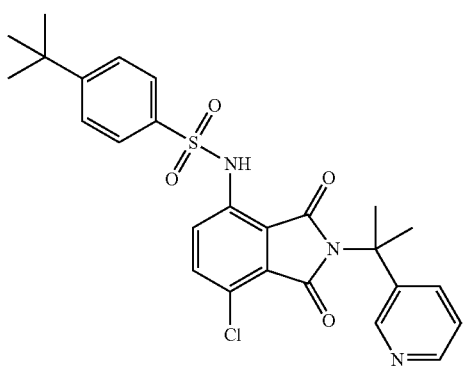
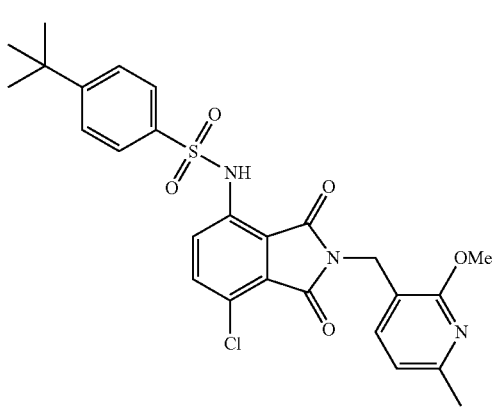
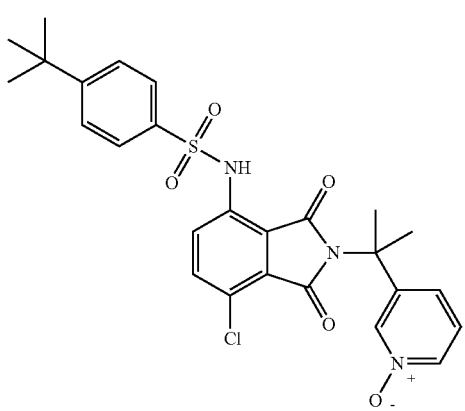
564
-continued
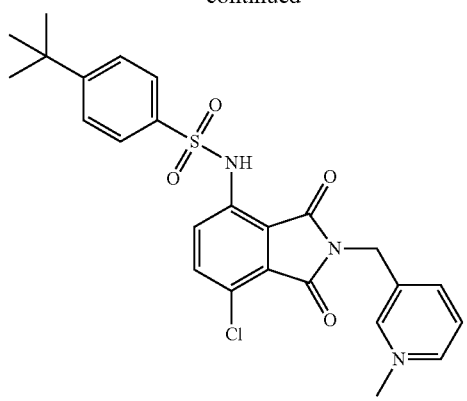
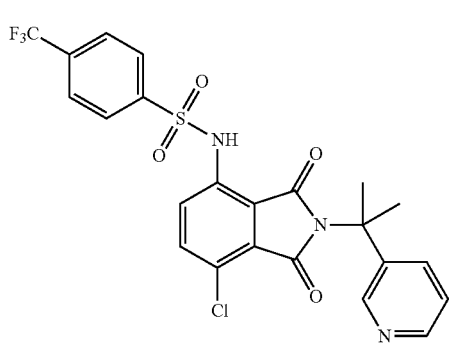
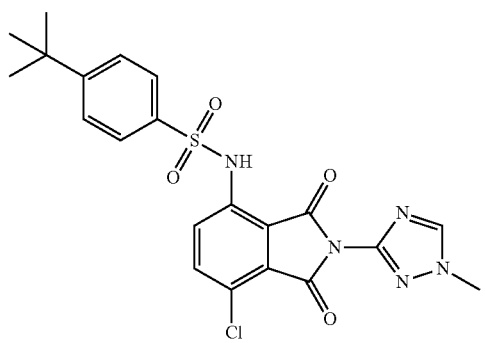
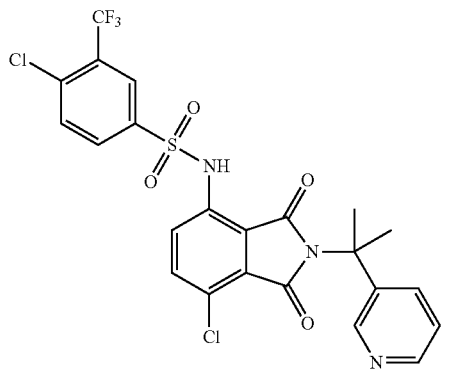

565
-continued
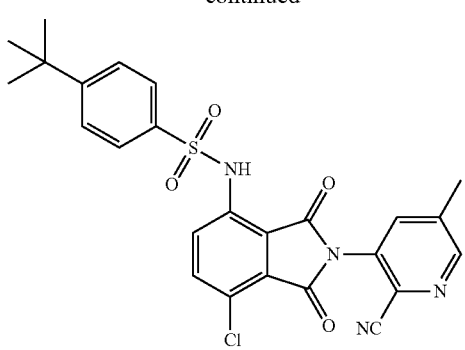
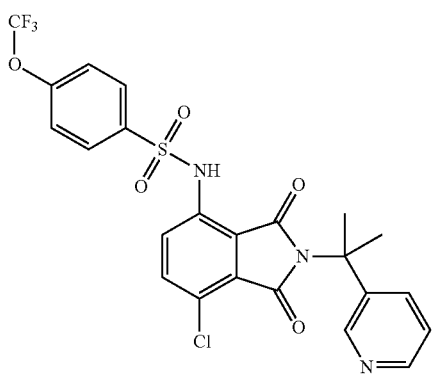
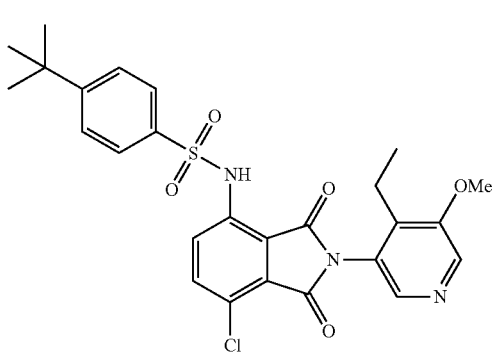
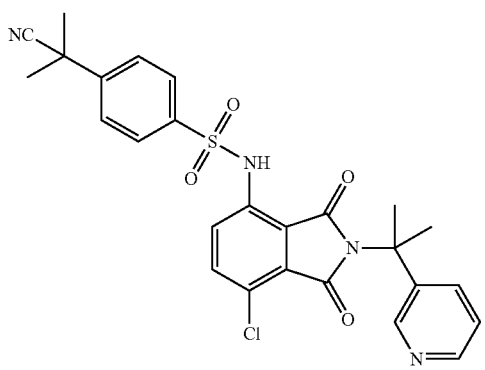
566
-continued
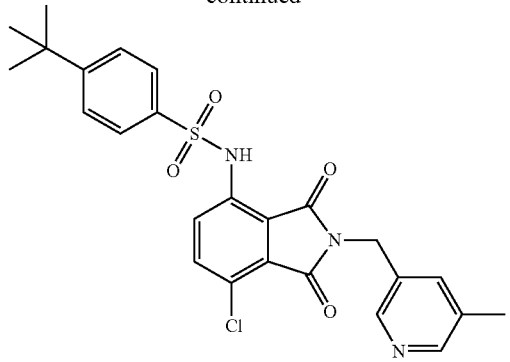
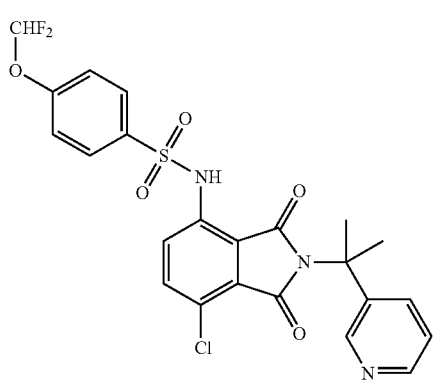
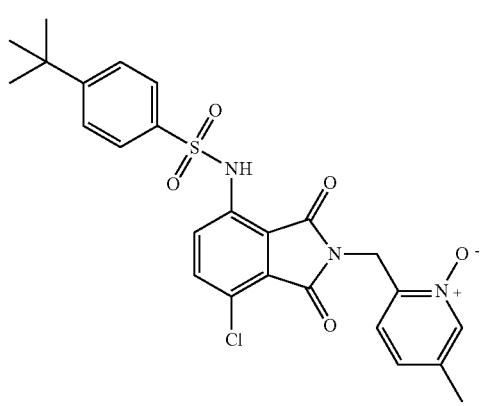
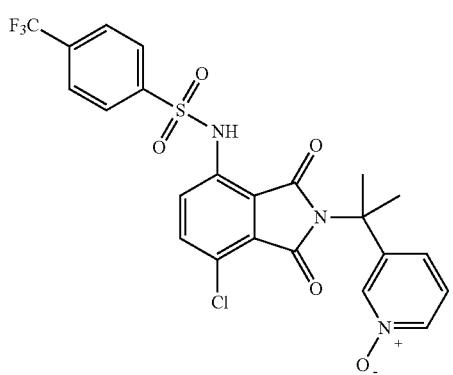

567
-continued
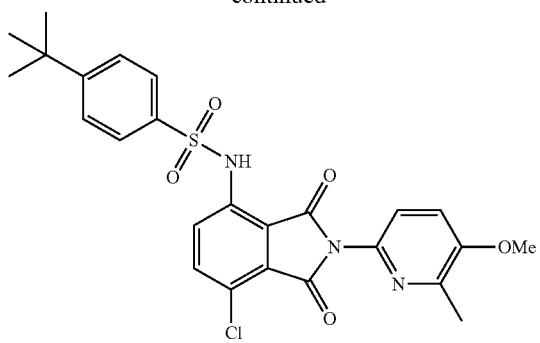
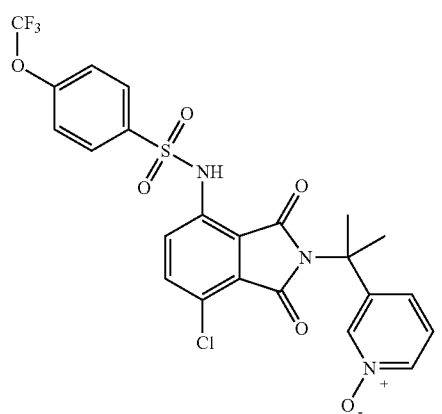
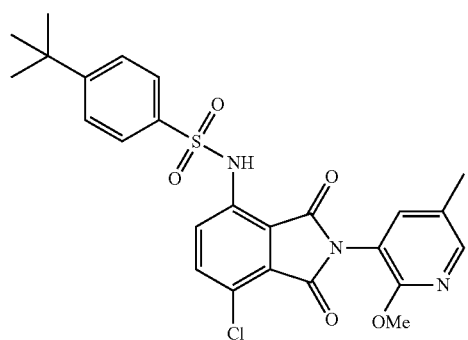
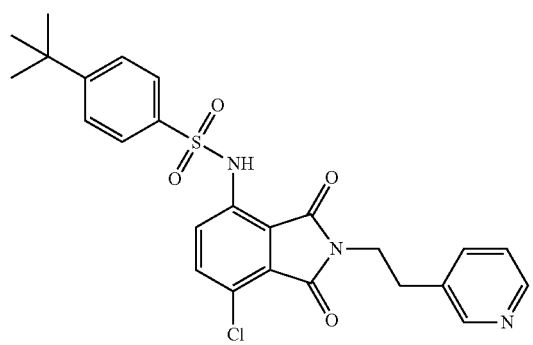
568
-continued
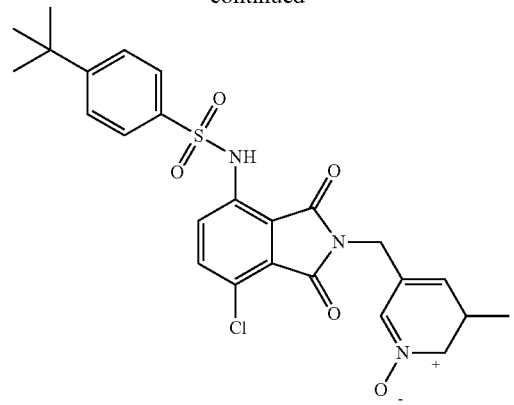
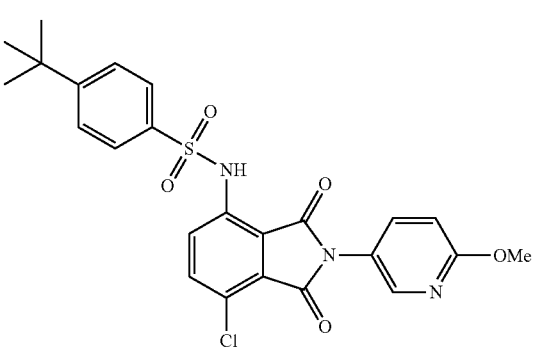

| 569 -continued | 570 -continued |
|---|---|
| 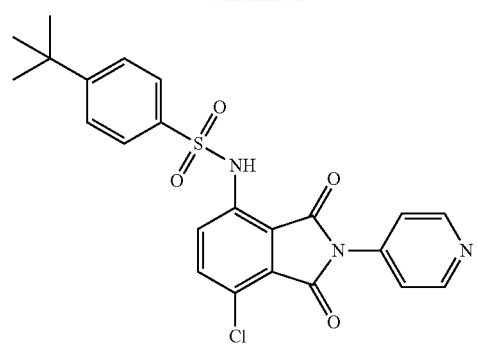 | 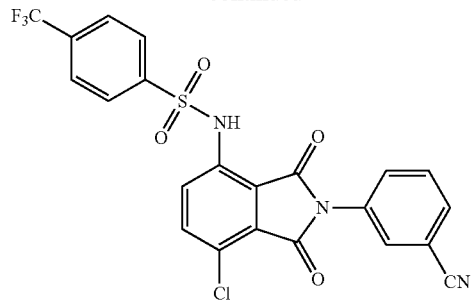 |
| 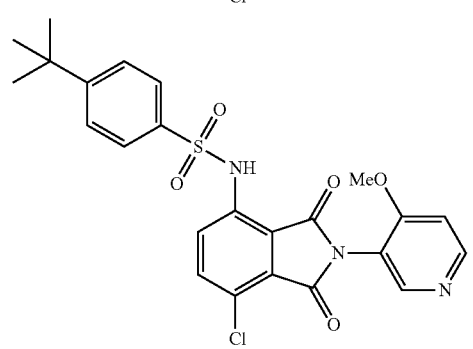 | 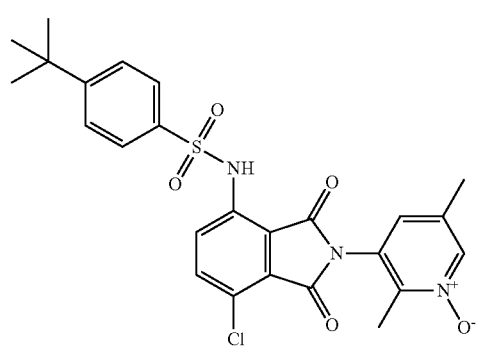 |
| 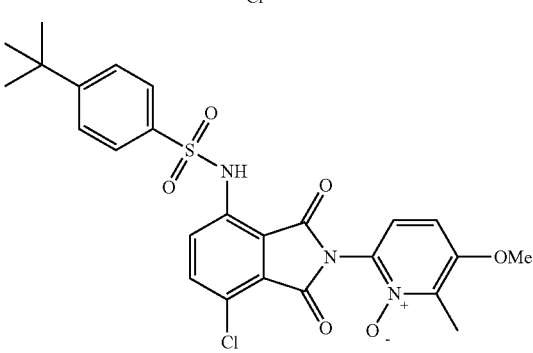 | 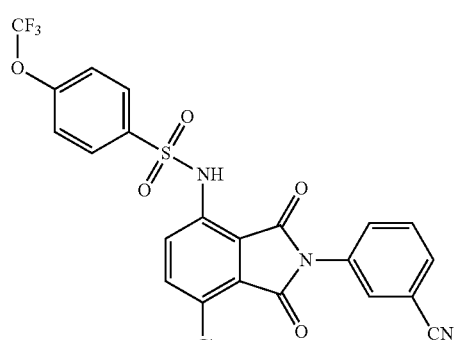 |
| 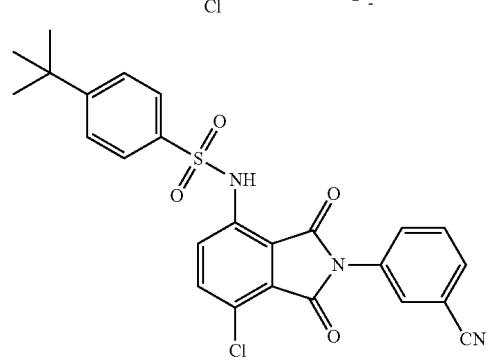 | 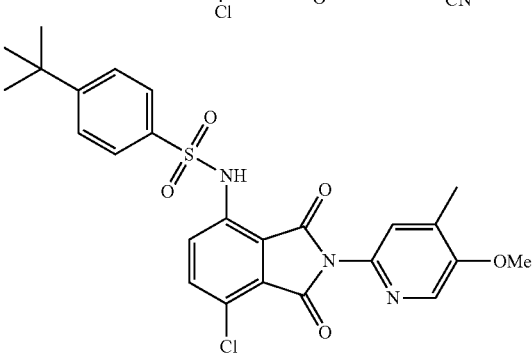 |
| 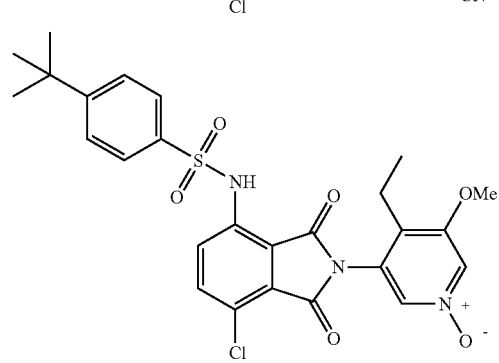 | 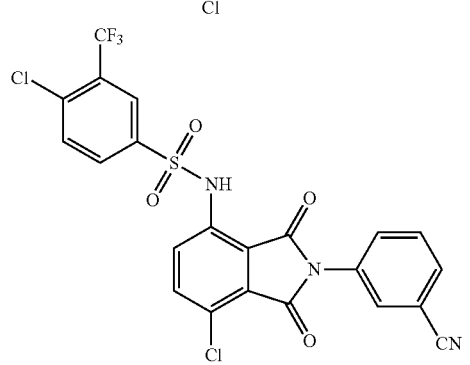 |

571
-continued
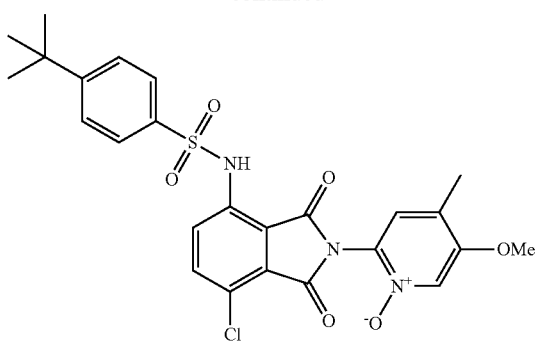
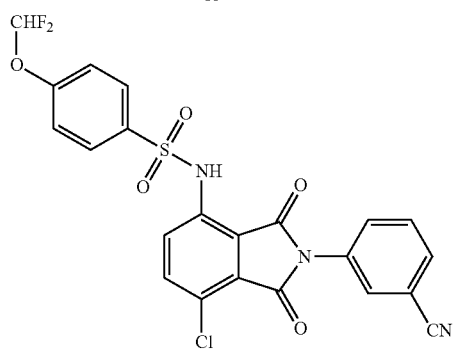
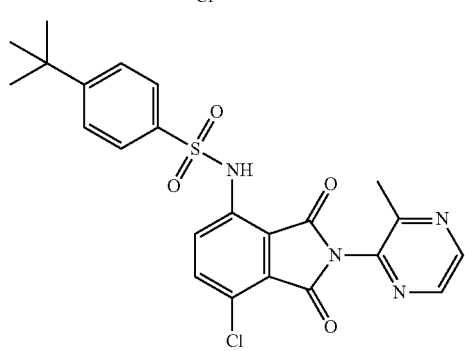
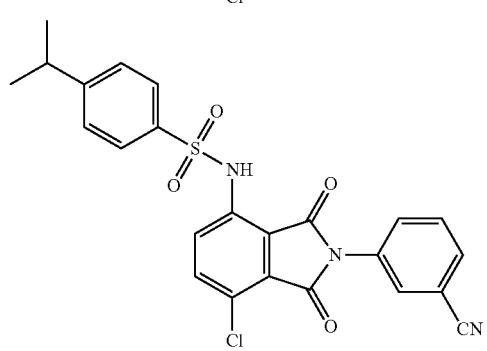
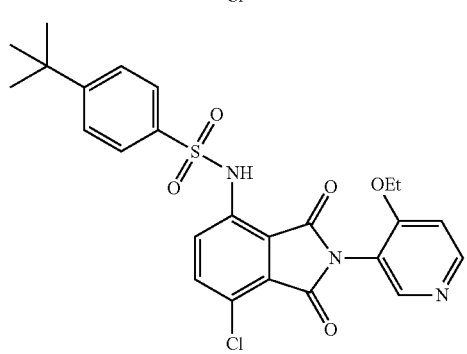
572
-continued
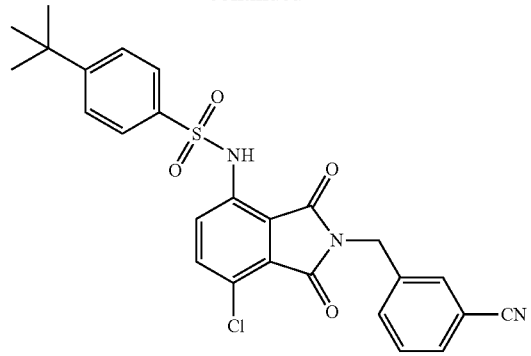
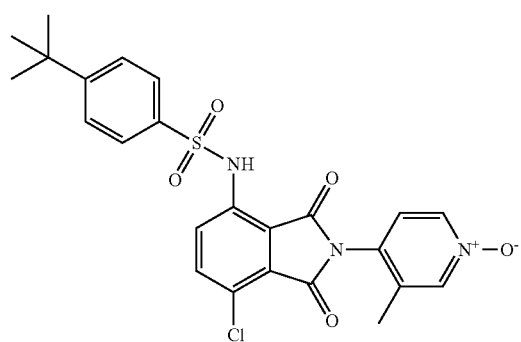
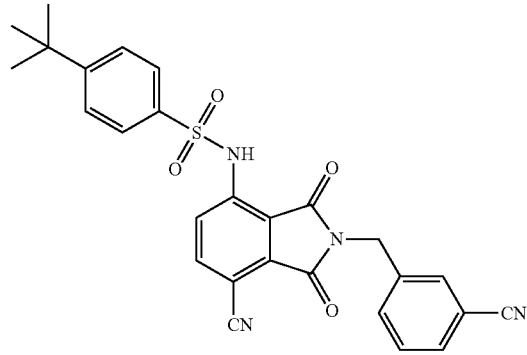
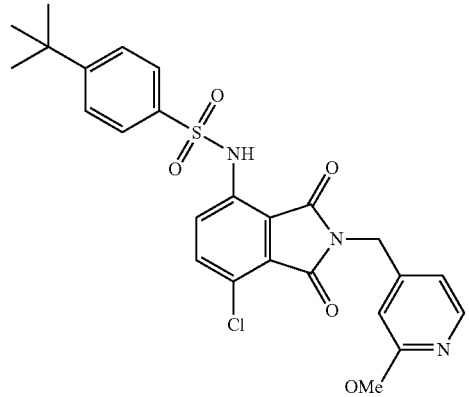

573
-continued
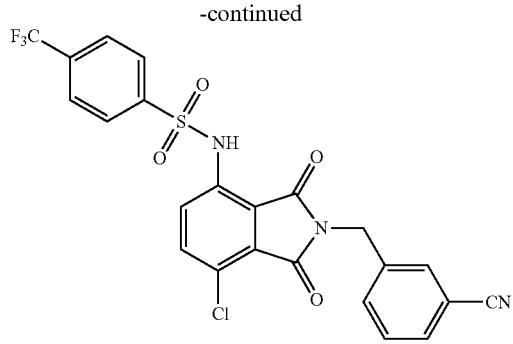
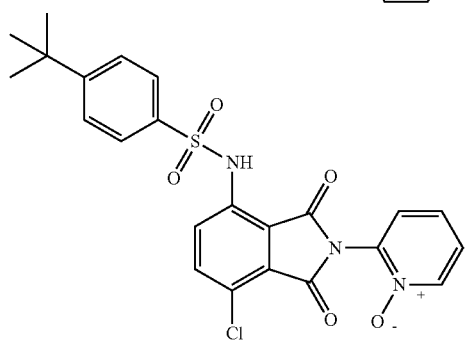
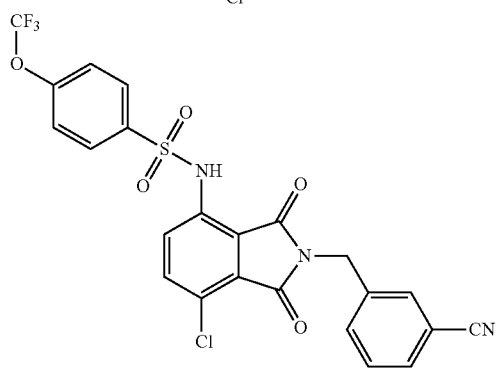
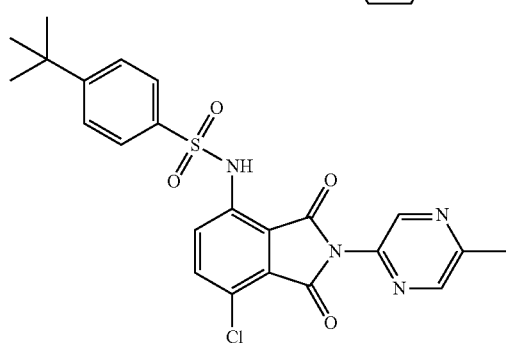
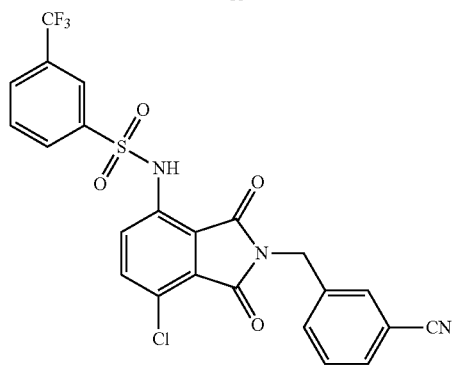
574
-continued
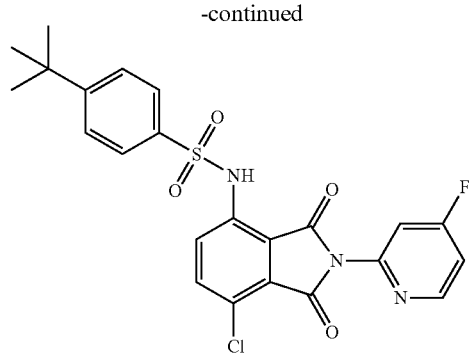
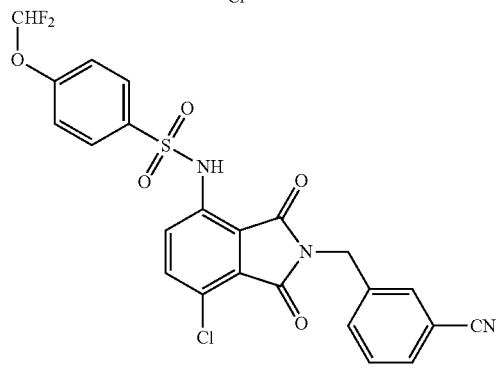
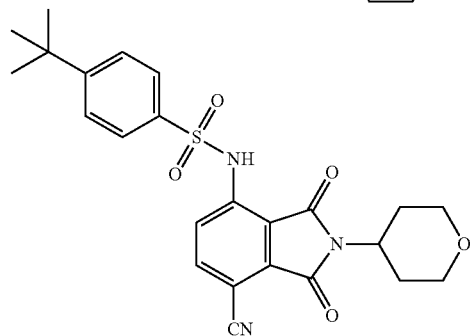
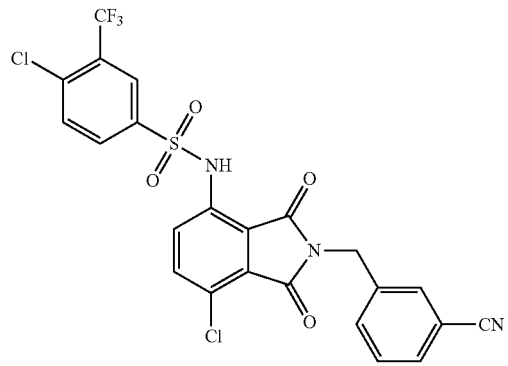
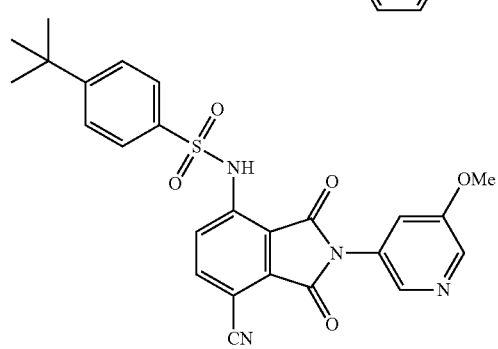

575
-continued
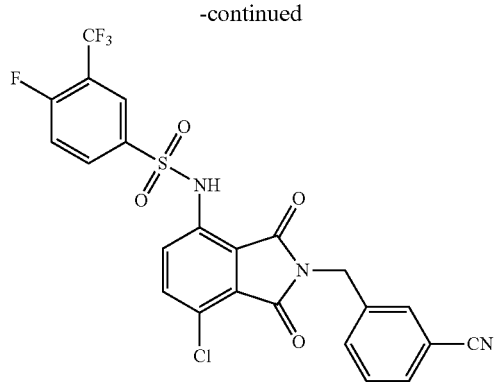
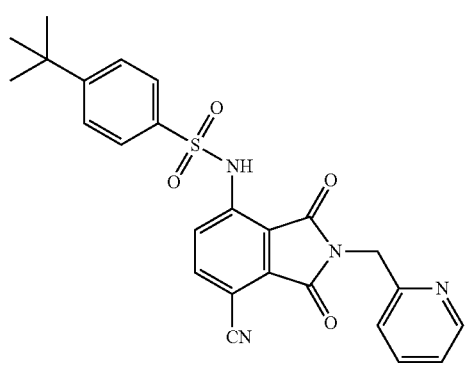
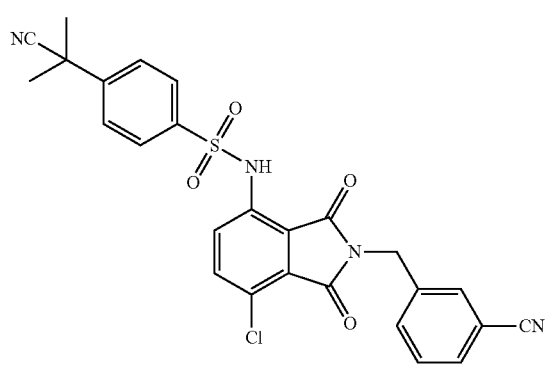
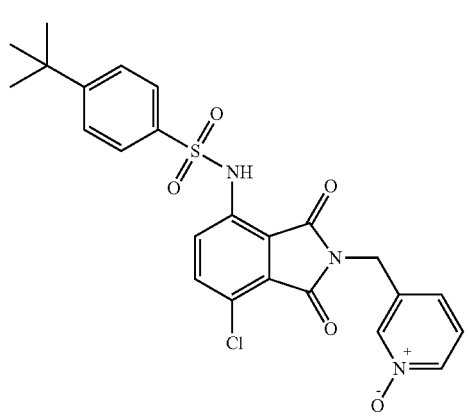
576
-continued
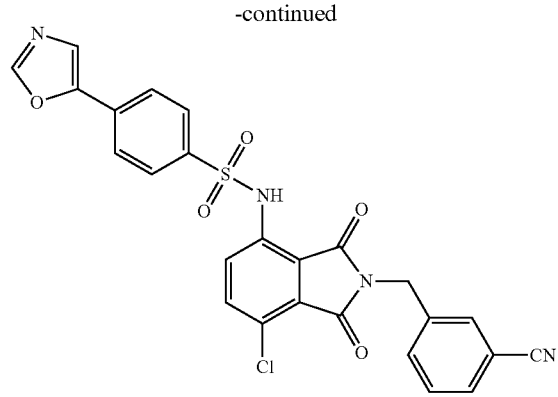
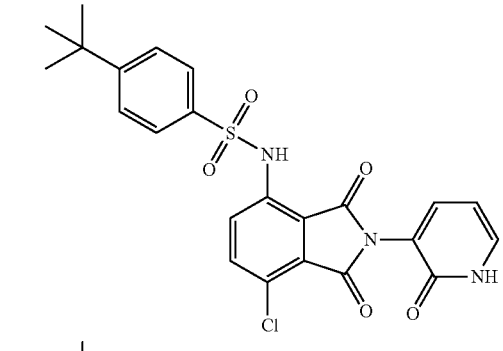
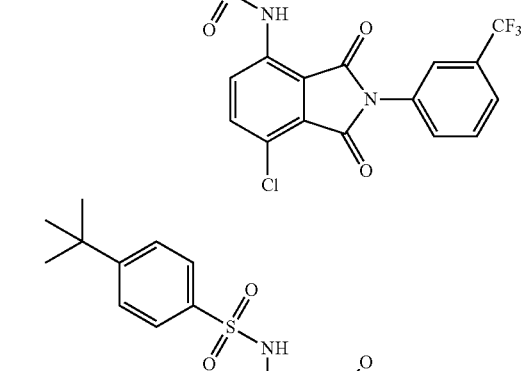
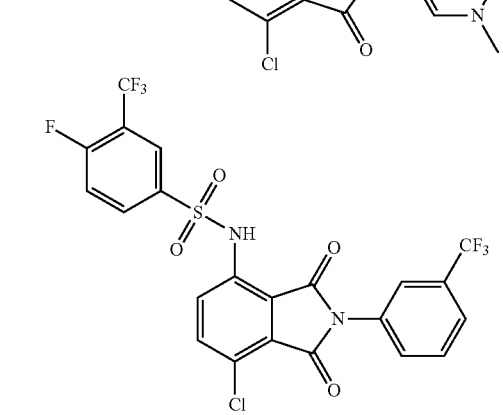
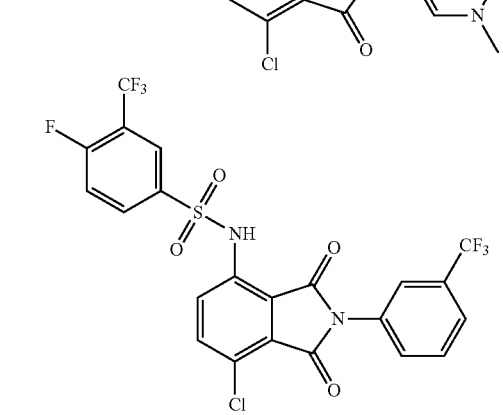

577
-continued
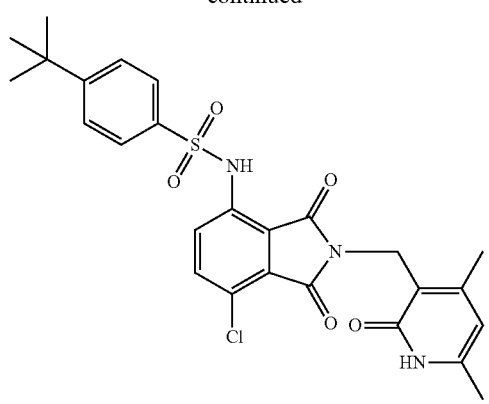
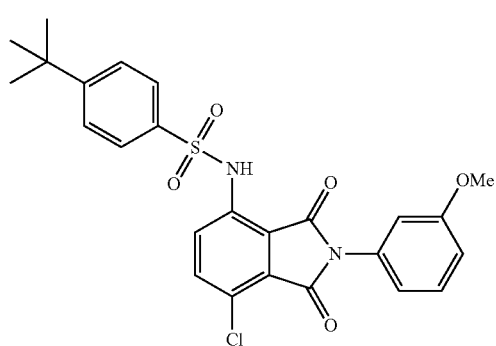
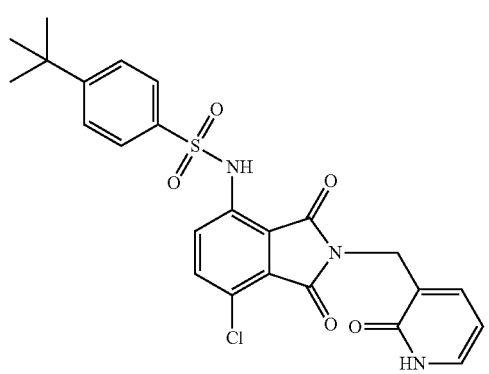
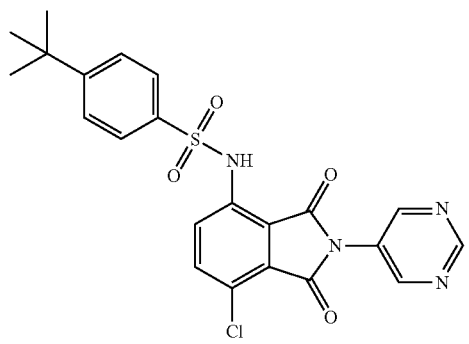
578
-continued
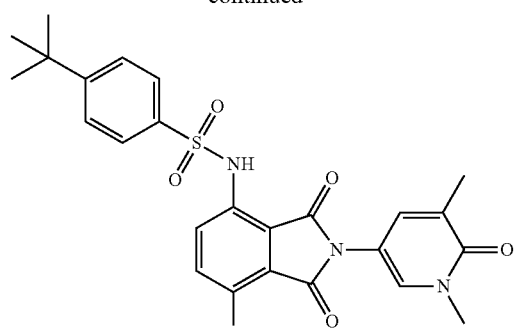
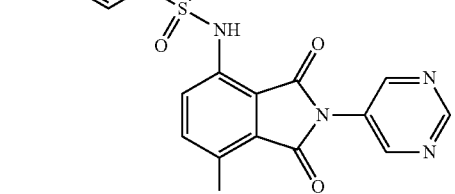
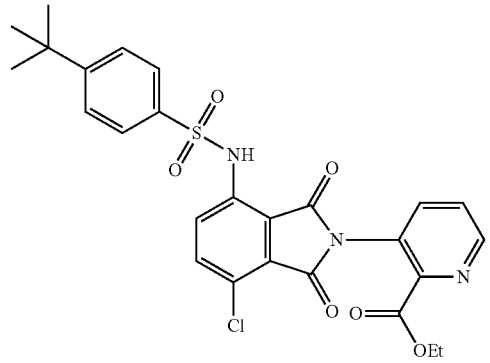
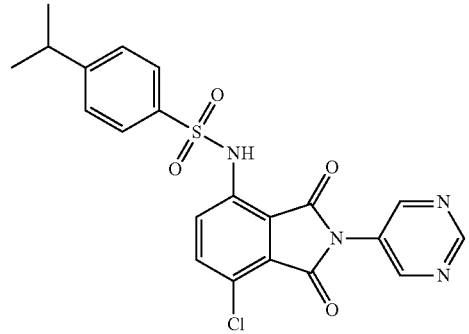
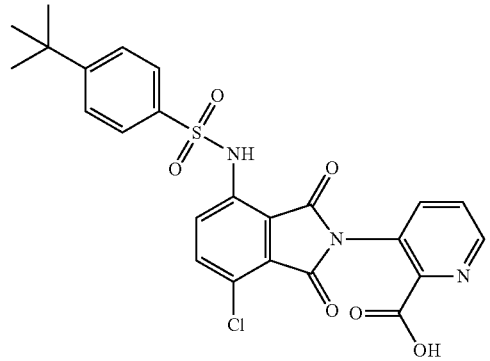

579
-continued
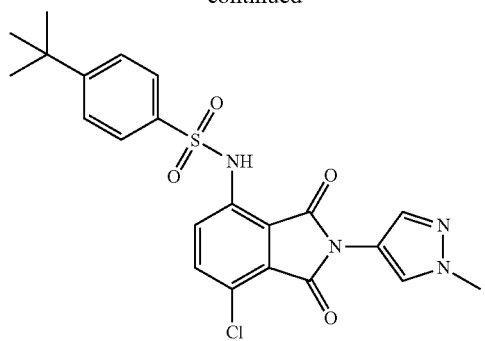
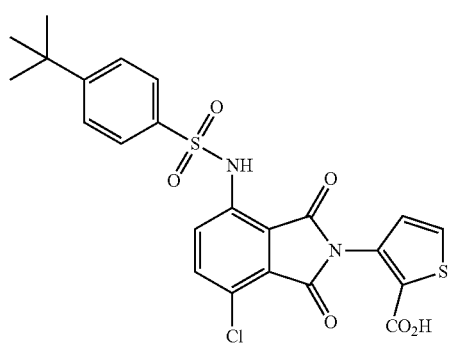
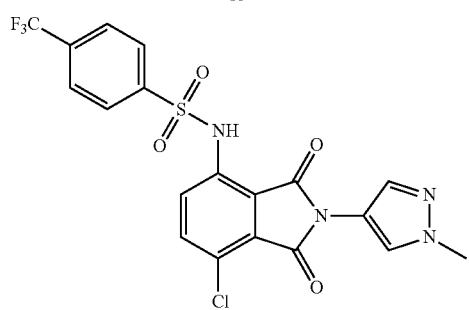
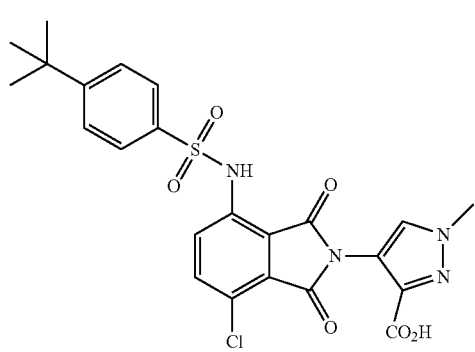
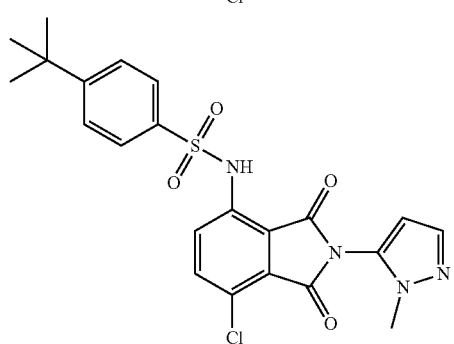
580
-continued
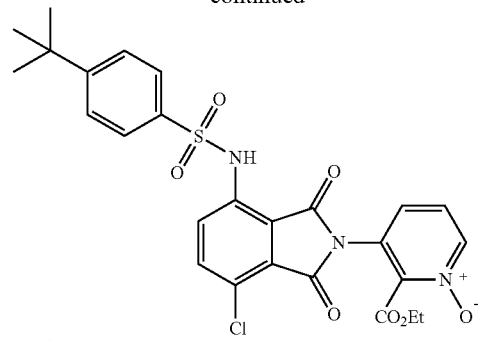
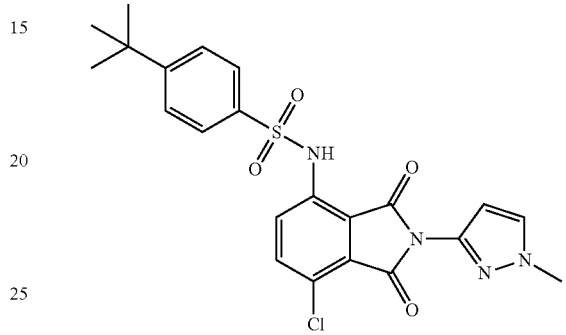
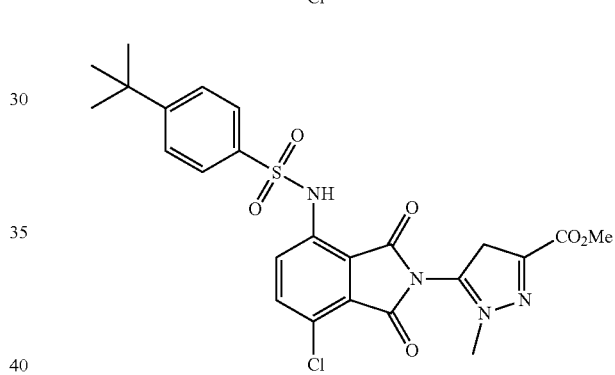
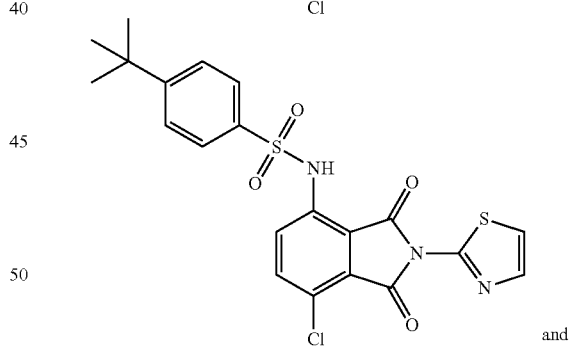
and
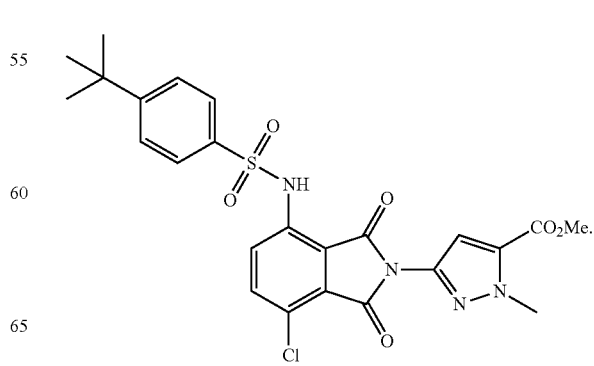

23. A composition comprising a compound of claim 1, or a salt, solvate, or solvate of a salt thereof, together with an acceptable carrier.

\* \* \* \* \*

UNITED STATES PATENT AND TRADEMARK OFFICE
CERTIFICATE OF CORRECTION

PATENT NO. : 9,969,687 B2
APPLICATION NO. : 15/107397
DATED : May 15, 2018
INVENTOR(S) : Rajagopal Bakthavatchalam et al.

It is certified that error appears in the above-identified patent and that said Letters Patent is hereby corrected as shown below:

In Claim 22, at Column 575, Lines 52-65, formula:

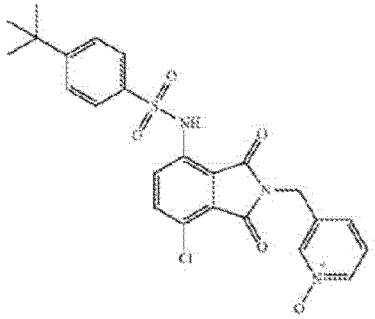

Should be replaced with the formula:

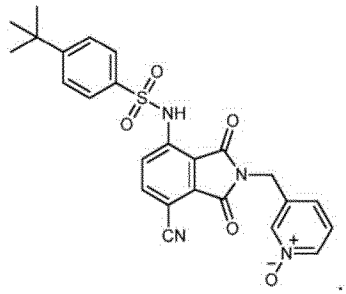

Signed and Sealed this
Twenty-first Day of August, 2018

Andrei Iancu
*Director of the United States Patent and Trademark Office*